US012268727B2

(12) United States Patent
Thompson et al.

(10) Patent No.: US 12,268,727 B2
(45) **Date of Patent: *Apr. 8, 2025**

(54) BIOACTIVE POLYPEPTIDES FOR IMPROVEMENTS IN PLANT PROTECTION, GROWTH AND PRODUCTIVITY

(71) Applicant: Spogen Biotech Inc., St. Louis, MO (US)

(72) Inventors: Brian Thompson, Creve Coeur, MO (US); Michelle Leslie, Webster Groves, MO (US)

(73) Assignee: Spogen Biotech Inc., Saint Louis, MO (US)

( * ) Notice: Subject to any disclaimer, the term of this patent is extended or adjusted under 35 U.S.C. 154(b) by 869 days.

This patent is subject to a terminal disclaimer.

(21) Appl. No.: 17/350,746

(22) Filed: Jun. 17, 2021

(65) Prior Publication Data

US 2023/0016543 A1 Jan. 19, 2023

Related U.S. Application Data

(62) Division of application No. 16/929,422, filed on Jul. 15, 2020, now Pat. No. 11,046,735, which is a division of application No. 16/041,059, filed on Jul. 20, 2018, now Pat. No. 10,717,767.

(60) Provisional application No. 62/534,710, filed on Jul. 20, 2017.

(51) Int. Cl.

| | |
|---|---|
| ***A61K 38/16*** | (2006.01) |
| ***A01N 37/46*** | (2006.01) |
| ***A01N 63/10*** | (2020.01) |
| ***A01N 63/22*** | (2020.01) |
| ***A01N 63/25*** | (2020.01) |
| ***A01N 63/50*** | (2020.01) |
| ***C07K 14/195*** | (2006.01) |
| ***C07K 14/21*** | (2006.01) |
| ***C07K 14/245*** | (2006.01) |
| ***C07K 14/27*** | (2006.01) |
| ***C07K 14/32*** | (2006.01) |
| ***C12N 1/20*** | (2006.01) |
| ***C12N 15/82*** | (2006.01) |
| ***C12P 21/02*** | (2006.01) |

(52) U.S. Cl.

CPC .............. *A61K 38/16* (2013.01); *A01N 37/46* (2013.01); *A01N 63/10* (2020.01); *A01N 63/50* (2020.01); *C07K 14/195* (2013.01); *C07K 14/21* (2013.01); *C07K 14/245* (2013.01); *C07K 14/27* (2013.01); *C07K 14/32* (2013.01); *C12N 1/20* (2013.01); *C12N 15/82* (2013.01); *C12P 21/02* (2013.01); *A01N 63/22* (2020.01); *A01N 63/25* (2020.01); *C12N 2510/02* (2013.01)

(58) Field of Classification Search

CPC ........ A01N 37/46; A01N 63/50; A01N 63/22; A01N 63/25; A01N 63/23; A01N 63/20; A61K 38/16; C07K 14/195; C07K 14/21; C07K 14/245; C07K 14/27; C07K 14/32; C12N 1/20; C12N 2510/02; C12P 21/02

See application file for complete search history.

(56) References Cited

U.S. PATENT DOCUMENTS

| | | | |
|---|---|---|---|
| 5,631,007 | A | 5/1997 | Ryals et al. |
| 5,668,007 | A | 9/1997 | Spencer et al. |
| 5,851,953 | A | 12/1998 | Pehu et al. |
| 5,922,649 | A | 7/1999 | Pehu et al. |
| 5,952,267 | A | 9/1999 | Mottram |
| 5,972,840 | A | 10/1999 | Mottram |
| 6,083,876 | A | 7/2000 | Jokinen et al. |
| 6,281,411 | B1 | 8/2001 | Adams et al. |
| 6,413,908 | B1 | 7/2002 | Reekmans et al. |
| 6,460,290 | B1 | 10/2002 | Moore et al. |
| 6,593,275 | B1 | 7/2003 | Unkefer et al. |
| 6,831,040 | B1 | 12/2004 | Unkefer et al. |
| 6,927,322 | B2 | 8/2005 | Stewart et al. |

(Continued)

FOREIGN PATENT DOCUMENTS

| | | | |
|---|---|---|---|
| CN | 105950312 | A | 9/2016 |
| CN | 107208072 | A | 9/2017 |

(Continued)

OTHER PUBLICATIONS

Penn State Extension, Agricultural Alternatives, Pepper Production, extension.psu.edu, 2010, 6 pages.

(Continued)

*Primary Examiner* — Mina Haghighatian

*Assistant Examiner* — Nathan W Schlientz

(74) *Attorney, Agent, or Firm* — Lewis Rice LLC

(57) ABSTRACT

Bioactive priming polypeptides are provided that are useful when applied to plants in agricultural formulations. Methods of using the formulations containing the bioactive priming polypeptides are also provided which are applied exogenously to the surface of a plant or a plant cell membrane or endogenously to the interior of a plant or to a plant cell. The bioactive priming polypeptides when applied to a plant, a plant part, or a plant growth medium or a rhizosphere in an area surrounding the plant or the plant part increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture.

25 Claims, 12 Drawing Sheets

Specification includes a Sequence Listing.

(56) References Cited

U.S. PATENT DOCUMENTS

| | | | | |
|---|---|---|---|---|
| 7,410,800 | B2 | 8/2008 | Bensen et al. | |
| 7,517,684 | B2 | 4/2009 | Rubenfield et al. | |
| 7,914,802 | B2 | 3/2011 | Rhee et al. | |
| 7,915,381 | B2 | 3/2011 | Anderem et al. | |
| 8,007,812 | B2 * | 8/2011 | Gudkov | A61P 31/04 424/234.1 |
| 8,263,078 | B2 | 9/2012 | Rachamim et al. | |
| 8,618,059 | B2 | 12/2013 | Gudkov et al. | |
| 8,703,146 | B2 | 4/2014 | Aderem et al. | |
| 8,883,174 | B2 | 11/2014 | Dickey et al. | |
| 9,006,180 | B2 | 4/2015 | Gudkov et al. | |
| 9,061,002 | B2 | 6/2015 | Gomez Casado | |
| 9,085,616 | B2 | 7/2015 | Aderem et al. | |
| 9,101,144 | B2 | 8/2015 | Doktycz et al. | |
| 9,186,400 | B2 | 11/2015 | Dickey et al. | |
| 9,205,095 | B2 | 12/2015 | Gudkov | |
| 9,222,103 | B2 | 12/2015 | Zipfel et al. | |
| 9,314,484 | B2 | 4/2016 | Blander et al. | |
| 9,457,061 | B2 | 10/2016 | Gudkov et al. | |
| 9,463,230 | B2 | 10/2016 | Emery et al. | |
| 9,499,823 | B2 | 11/2016 | De Lorenzo et al. | |
| 10,034,926 | B2 | 7/2018 | Gleiberman et al. | |
| 10,306,895 | B2 | 6/2019 | Chen et al. | |
| 10,336,793 | B2 | 7/2019 | Gudkov et al. | |
| 10,717,767 | B2 | 7/2020 | Thompson et al. | |
| 11,046,735 | B2 | 6/2021 | Thompson et al. | |
| 2003/0044429 | A1 | 3/2003 | Aderem et al. | |
| 2007/0065902 | A1 | 3/2007 | Dicosimo et al. | |
| 2007/0128183 | A1 | 6/2007 | Meinke et al. | |
| 2008/0120740 | A1 | 5/2008 | Frank et al. | |
| 2009/0297552 | A1 | 12/2009 | Aderem et al. | |
| 2010/0015170 | A1 | 1/2010 | Takeshita et al. | |
| 2010/0239583 | A1 | 9/2010 | Murthy et al. | |
| 2010/0285532 | A1 | 11/2010 | Berger et al. | |
| 2011/0008383 | A1 | 1/2011 | Powell et al. | |
| 2012/0082700 | A1 | 4/2012 | Dickey et al. | |
| 2012/0137392 | A1 | 5/2012 | De Lorenzo et al. | |
| 2012/0151636 | A1 | 6/2012 | Ronald et al. | |
| 2013/0108661 | A1 | 5/2013 | Blander et al. | |
| 2013/0324462 | A1 | 12/2013 | Gudkov et al. | |
| 2013/0331548 | A1 | 12/2013 | Nakaar et al. | |
| 2014/0255441 | A1 | 9/2014 | Compans et al. | |
| 2014/0274707 | A1 | 9/2014 | Thompson et al. | |
| 2014/0295012 | A1 | 10/2014 | Kutsch et al. | |
| 2015/0064219 | A1 | 3/2015 | Blander et al. | |
| 2015/0110827 | A1 | 4/2015 | Song et al. | |
| 2015/0125492 | A1 | 5/2015 | Dickey et al. | |
| 2015/0165009 | A1 | 6/2015 | Gewirtz et al. | |
| 2015/0182587 | A1 | 7/2015 | Gudkov et al. | |
| 2015/0191742 | A1 | 7/2015 | Zimmerli et al. | |
| 2015/0216926 | A1 | 8/2015 | Kutsch | |
| 2016/0022767 | A1 | 1/2016 | Neish et al. | |
| 2016/0031948 | A1 | 2/2016 | Thompson et al. | |
| 2016/0073640 | A1 | 3/2016 | Curtis et al. | |
| 2016/0074508 | A1 | 3/2016 | Dickey et al. | |
| 2016/0108096 | A1 | 4/2016 | Thompson et al. | |
| 2016/0165890 | A1 | 6/2016 | Matsuzaki | |
| 2016/0166671 | A1 | 6/2016 | Tussey et al. | |
| 2016/0193319 | A1 | 7/2016 | Mizel et al. | |
| 2016/0193329 | A1 | 7/2016 | Song et al. | |
| 2016/0206690 | A1 | 7/2016 | Gleiberman et al. | |
| 2016/0220660 | A1 | 8/2016 | Song et al. | |
| 2016/0302416 | A1 | 10/2016 | Fefer et al. | |
| 2017/0292108 | A1 | 10/2017 | Wei | |
| 2017/0332645 | A1 | 11/2017 | Chen et al. | |
| 2018/0099999 | A1 | 4/2018 | Thompson et al. | |
| 2018/0325103 | A1 | 11/2018 | Thompson | |

FOREIGN PATENT DOCUMENTS

| | | | | |
|---|---|---|---|---|
| EA | 23386 | B1 | 5/2016 | |
| RU | 2444880 | C2 | 3/2012 | |
| RU | 2563930 | C1 | 9/2015 | |
| WO | 96/07319 | A1 | 3/1996 | |
| WO | 98/26081 | A1 | 6/1998 | |
| WO | 9949047 | A2 | 9/1999 | |
| WO | 20000066740 | A | 11/2000 | |
| WO | 2002/072782 | A2 | 9/2002 | |
| WO | 2005/070455 | A1 | 8/2005 | |
| WO | 2006/069198 | A1 | 6/2006 | |
| WO | 2006/097482 | A1 | 9/2006 | |
| WO | 2009/102818 | A1 | 8/2009 | |
| WO | 2010/111485 | A1 | 9/2010 | |
| WO | 2010/117978 | A1 | 10/2010 | |
| WO | 2011/097573 | A2 | 8/2011 | |
| WO | 2011/146612 | A2 | 11/2011 | |
| WO | 2012/097012 | A1 | 7/2012 | |
| WO | 2013/144579 | A1 | 10/2013 | |
| WO | 2016/007606 | A2 | 1/2016 | |
| WO | 2016/011179 | A2 | 1/2016 | |
| WO | 2016/044542 | A1 | 3/2016 | |
| WO | 2016/044768 | A1 | 3/2016 | |
| WO | 2016044661 | A1 | 3/2016 | |
| WO | WO-2016039961 | A1 * | 3/2016 | A01N 37/46 |
| WO | 2017/001927 | A1 | 1/2017 | |
| WO | 2017/161091 | A1 | 9/2017 | |
| WO | 2019/018768 | A1 | 1/2019 | |

OTHER PUBLICATIONS

Penn State Extension, Agricultural, Tomato Production, extension.psu.edu, 2016, 8 pages.

Corn Growth and Management Quick Guide, North Dakota State University, www.ag.ndsu.edu, 2013, 8 pages.

Saline and Sodic Soils, North Dakota State University Extension Service, www.ag.ndsu.edu, Date Unknown, 8 pages.

Examination Report in AU2018304469, mailed Jun. 21, 2022, 6 pages.

Flg22 peptide (30-51 aa, Flic, *P. aeruginosa*,) Product Specification Sheet from Alpha Diagnostic International, Retrieved from the Internet: <URL: https://www.4adi.com/product/pdf/FLG22-P-1.pdf,> 1 page.

Garcia et al., "*Salmonella enterica* induces and subverts the plant immune system," Frontiers in Microbiology, Apr. 4, 2015, vol. 5, Article 141, 6 pages.

Accession WP_097951446, "flagellin [*Bacillus cereus*]," NCBI Reference Sequence WP_097951446.1, Jun. 20, 2022, 2 pages.

Gomez-Gomez, L., et al, "Flagellin perception: a paradigm for innate immunity,"Trends in Plant Science, 2002, pp. 251-256, vol. 7 No. 6.

Dill, G. M., "Glyphosate-resistant Crops: History, Status and Future," Pest Management Science, 2005, pp. 219-224, vol. 61.

Duan, P., et al, "Naturally ocuring betaine grafted on cotton fabric for achieving antibacterial and anti-protein adsorption functions" Cellulose, 2020, pp. 6603-6615, vol. 27.

Fosternic, V., et al, "The role of the C-terminal D0 domain of flagellin in activation of Toll like receptor 5," PLOS Pathogens, 2017, 20 pages.

Schulz, T., et al, "Soybean Seed Inoculent and Fungicidal Seed Treatment Effects on Soybean," Crop Science, 2008, pp. 1975-1983, vol. 48.

Hao, G., et al, "Induction of innate immune responses by flagellin from the intracellular bacterium, 'Candidatus Liberibacter solanacearum'," BMC Plant Biology, 2014, pp. 1471-2229, vol. 14:211.

Felitsky, D., et al, "The Exclusion of Glycine Betaine from Anionic Biopolumer Surface Why Glycine Betaine Is am Effective Osmoprotectant but Also a Compatibke Solute", Biochemistry, 2004, pp. 14732-14743, vol. 43.

Accession WP_064449846, "flagellin [*Bacillus wiedmannii*]," NCBI Reference Sequence WP_064449846.1, Jun. 20, 2022, 1 page.

Berger, Eldie, et al., "Extracellular secretion of a recombinant therapeutic peptide by Bacillus halodrans utilizing a modified flagellin type III secretion system", Microbial Cell Factories, 2011, vol. 10, issue 62.

Meng, Qingfeng, et al., "A proteomic insight into the MSP1 and flg22 induced signaling in *Oryza sativa* leaves", Journal of Proteomics, Jun. 30, 2018, pp. 120-130, vol. 196.

(56) References Cited

OTHER PUBLICATIONS

Xu, Dong, et al., “Sequence Diversity of the Bacillus thuringiensis and B. cereus Sensu Lato Flagellin (H Antigen) Protein: Comparison with H Serotype Diversity” Applied and Environmental Microbiology, Jul. 2006, pp. 4653-4662.
European Patent Office, Partial European Search Report issued Dec. 12, 2022 Application No. 20745065.1.
Chinchilla, D., et al., “The *Arabidopsis* Receptor Kinase FLS2 Binds flg22 and Determines the Specificity of Flagellin Perception,” The Plant Cell, Feb. 2006, pp. 465-476, vol. 18.
Choi, M.-S., et al., “Harpins, Multifunctional Proteins Secreted by Gram-Negative Plant-Pathogenic Bacteria,” Molecular Plant-Microbe Interactions, 2013, pp. 1115-1122, vol. 26, No. 10.
Engelhardt, S., et al., “Separable Roles of the *Pseudomonas syringae* pv. *phaseolicola* Accessory Protein HrpZ1 in Ion-Conducting Pore Formation and Activation of Plant Immunity,” The Plant Journal, 2009, pp. 706-717, vol. 57, No. 4.
Felix, G., et al., “Plants Have A Sensitive Perception System for the Most Conserved Domain of Bacterial Flagellin,” The Plant Journal, 1999, pp. 265-276, vol. 18, No. 3.
Garcia, AV., et al. “*Salmonella enterica* Flagellin Is Recongnized via FLS2 and Activates PAMP-Triggered Immunity in *Arabidopsis thaliana*,” Molecular Plan, 2014, pp. 657-674, vol. 7(4).
Gohre, V., et al., “Molecular crosstalk between PAMP-triggered immunity and photosynthesis.” Molecular Plant-Microbe Interactions, 2012, pp. 1083-1092, vol. 8.
Gomez-Gomez, L., et al., “FLS2: An LRR Receptor-like Kinase Involved in the Perception of the Bacterial Elicitor Flagellin in *Arabidopsis*,” Molecular Cell, Jun. 2000, pp. 1003-1011, vol. 5, No. 6.
Gottwald, T. R., et al., “Citrus Canker,” The Plant Health Instructor, 2005, 10 pages.
Guptasarma, P., “Reversal of Peptide Backbone Direction May Result in the Mirroring of Protein Structure,” FEBS Letters, Oct. 1992, pp. 205-210, vol. 310, No. 3.
Halbert, S.E., et al., “Asian Citrus Psyllids (*Sternorrhyncha*: *Psyllidae*) and Greening Disease of Citrus: A Literature Review and Assessment of Risk in Florida,” Florida Entomologist, Sep. 2004, pp. 330-353, vol. 87, No. 3.
Hu, H., et al., “Quantification of Live ‘Candiatus Liberibacter asiaticus’ Populations Using Real-Time PCR and Propidium Monoazide,” Plant Disease, Sep. 2013, pp. 1158-1167, vol. 97, No. 9.
International Search Report and Written Opinion issued for PCT/US2018/043092 dated Nov. 15, 2018, 18 pages.
JBT FoodTech, “Procedures for Analysis of Citrus Products,” Laboratory Manual,, Sixth Edition, 2011, 193 pages.
Kim, J.-G., et al., “Mutational Analysis of Xanthomonas Harpin HpaG Identifies A Key Functional Region that Elicits the Hypersensitive Response in Nonhost Plants,” Journal of Bacteriology, Sep. 2004, pp. 6239-6247, vol. 186, No. 18.
Kutschmar, A., et al., “PSK-alpha Promotes Root Growth in *Arabidopsis*,” New Phytologist, 2009, pp. 820-831, vol. 181, No. 4.
Lorbiecke, R., et al., “Comparative Analysis of PSK Peptide Growth Factor Precursor Homologs,” Plant Science, 2002, pp. 321-332, vol. 163, No. 2.
Matsubayashi, Y., et al., “Phytosulfonkine-alpha, A sulfated Pentapeptide, Stimulates the Proliferation of Rice Cells by Means of Specific High- and Low-Affinity Binding Sites,” Proceedings of the National Academy of Sciences of the United States of America, Nov. 1997, pp. 13357-13362, vol. 94, No. 24.
Matsubayashi, Y., et al., “The Endogenous Sulfated Pentapeptide Phytosulfokine-alpha Stimulates Tracheary Element Differentiation of Isolated Mesophyll Cells of Zinnia,” Plant Physiology, Aug. 1999, pp. 1043-1048, vol. 120, No. 4.
Matsumiya, Y., et al., “Soybean Peptide: Novel Plant Growth Promoting Peptide from Soybean,” Soybean and Nutrition, Chapter 11, Intech, 2011, pp. 215-230.
Meindl, T., et al., “The Bacterial Elicitor Flagellin Activates Its Receptor in Tomato Cells According to the Address-Message Concept,” The Plant Cell, Sep. 2000, pp. 1783-1794, vol. 12.
Nawrot, R., et al., “Plant Antimicrobial Peptides,” Folia Microbiologica, 2014, pp. 181-196, vol. 59, No. 3.
Pond, L., et al., “A Role of Acidic Residues in Di-leucine Motif-based Targeting to the Endocytic Pathway,” The Journal of Biological Chemistry, Aug. 1995, pp. 19989-19997, vol. 270, No. 34.
Ryan, C.A., et al., “Polypeptide Hormones,” The Plant Cell, 2002, pp. S251-S264, Supplement 2002.
Sauter, M., “Phytosulfokine Peptide Signalling,” Journal of Experimental Botany, 2015, pp. 5161-5169, vol. 66, No. 17.
Takai, R., et al., “Analysis of Flagellin Perception Mediated by flg22 Receptor OsFLS2 in Rice,” Molecular Plant-Microbe Interactions, 2008, pp. 1635-1642, vol. 21, No. 12.
Tam, J. P., et al., “Antimicrobial Peptides from Plants,” Pharmaceuticals, 2015, pp. 711-757, vol. 8, No. 4.
Yoshiki, M., et al., “Soybean as a Nitrogen Supplier,” Chapter 3, Intech, 2013, pp. 49-60.
Zhang, C., et al., “Harpin-Induced Expression and Transgenic Overexpression of the Phloem Protein Gene AtPP2-A1 in *Arabidopsis* Repress Phloem Feeding of the Green Peach Aphid Myzus persicae,” BMC Plant Biology, 2011, pp. 1-19, vol. 11, No. 11.
Zhang, W., et al., “The plant innate immunity response in stomatal guard cells invokes G-protein-dependent ion channel regulation,” The Plant Journal, 2008, pp. 984-996, vol. 56.
Zeigler, D., et al., Bacillus Genetic Stock Center Catalog of Strains, Seventh Edition, Part 2: Bacillus thuringiensis and Bacillus cereus, 1999, 58 pages.
Zipfel, C., et al., “Bacterial Disease Resistance in *Arabidopsis* Through Flagellin Perception,” Nature, Apr. 2004, pp. 764-767, vol. 428, No. 6984.
Zipfel, C., et al., “Perception of the Bacterial PAMP EFa-Tu by the Receptor EFS Restricts Agrobacterium-Mediated Transformation,” Cell, May 2006, pp. 749-760, vol. 125.
International Search Report and Written Opinion issued for PCT/US2020/014591 dated Jun. 1, 2020, 10 pages.
Aroca, A., et al., “S-Sulfhydration: A Cysteine Posttranslational Modification in Plant Systems,” Plant Physiology, 2015, pp. 334-342, vol. 168, No. 1.
Gottwald, T. R., “Current Epidemiological Understanding of Citrus Huanglongbing,” Annual Review of Phytopathology, 2010, pp. 119-139, vol. 48.
Jaffe, M. J., et al., “Callose Deposition During Gravitropism of *Zea mays* and Pisum sativum and its Inhibition by 2-deoxy-D-glucose,” Planta, 1984, pp. 20-26, vol. 161, No. 1.
Keppler, B. D., et al., “3-Aminobenzamide Blocks MAMP-Induced Callose Deposition Independently of Its Poly (ADPribosyl)ation Inhibiting Activity,” Frontiers in Plant Science, 2018, pp. 1-13, vol. 9, Article 1907.
Koh, E. J., et al., “Callose Deposition in the Phloem Plasmodesmata and Inhibition of Phloem Transport in Citrus Leaves Infected with “Candidatus Liberibacter asiaticus”,” Protoplasma, 2012, pp. 687-697, vol. 249, No. 3.
El Sabagh, A., et al., “Alleviation of Adverse Effects of Salt Stress on Soybean (*Glycine max*. L.) by Using Osmoprotectants and Organic Nutrients,” International Journal of Biological, Biomolecular, Agricultural, Food and Biotechnological Engineering, 2015, pp. 1003-1007, vol. 9, No. 9.
Mcneil, S. D., et al., “Betaines and Related Osmoprotectants. Targets for Metabolic Engineering of Stress Resistance,” Plant Physiology, Aug. 1999, pp. 945-949, vol. 120.
Moghaieb, R. E. A., et al., “Effect of Salinity on Osmotic Adjustment, Glycinebetaine Accumulation and the Betaine Aldehyde Dehydrogenase Gene Expression in Two Halophytic Plants, Salicornia europaea and Suaeda maritima,” Plant Science, 2004, pp. 1345-1349, vol. 166.
Molazem, D., et al., Role of Proline, Na and Chlorophyll Content in Salt Tolerance of Corn (*Zea mays* L.), American-Eurasian J. Agric. & Environ. Sci., 9 (3): 319-324 (2010).

(56) References Cited

OTHER PUBLICATIONS

Molla, R., et al., "Exogenous Proline and Betaine-induced Upregulation of Glutathione Transferase and Glyoxalase I in Lentil (*Lens culinaris*) under Drought Stress," Not Bot Horti Agrobo, 2014, pp. 73-80, vol. 42, No. 1.
Naeve, S., "Soybean Production—Growth Stages," [https://www.extension.umn.edu/agriculture/soybean/growth-and-development], Mar. 23, 2018, 3 pages.
Phillips, D. A., et al., "Trigonelline and Stachydrine Released from Alfalfa Seeds Activate NodD2 Protein in Rhizobium meliloti," Plant Physiology, 1992, pp. 1526-1531, vol. 99, Number.
Rossi, A. M. et al., "Nitrogen Contents in Food: A Comparison Between the Kjeldahl and Hach Methods," The Journal of the Argentine Chemical Society, 2004, pp. 99-108, vol. 92, Nos. 4/6.
Siddique, A. B., et al., "Mitigation of Salt Stress by Foliar Application of Proline in Rice," Universal Journal of Agricultural Research, 2015, pp. 81-88, vol. 3, No. 3.
Slama, I., et al., "Diversity, Distribution and Roles of Osmoprotective Compounds Accumulated in Halophytes Under Abiotic Stress," Annals of Botany, 2014, 15 pages.
Sobahan, M. A., et al., Exogenous Proline and Glycinebetaine Suppress Apoplastic Flow to Reduce Na+ Uptake in Rice Seedlings, Bioscience, Biotechnology, and Biochemistry, 2009, pp. 2037-2042, vol. 73, No. 9.
Zhang, L., et al., "Exogenous Glycinebetaine and Humic Acid Improve Growth, Nitrogen Status, Photosynthesis, and Antioxidant Defense System and Confer Tolerance to Nitrogen Stress in Maize Seedlings," Journal of Plant Interactions, 2014, pp. 159-166, vol. 9, No. 1.

* cited by examiner

BIOACTIVE POLYPEPTIDES FOR IMPROVEMENTS IN PLANT PROTECTION, GROWTH AND PRODUCTIVITY

CROSS REFERENCE TO RELATED APPLICATIONS

This application is a divisional of U.S. application Ser. No. 16/929,422, filed on Jul. 15, 2020, which is a divisional of U.S. application Ser. No. 16/041,059, filed on Jul. 20, 2018, issued as U.S. Pat. No. 10,717,767 on Jul. 21, 2020, which claims the benefit of U.S. Provisional Application No. 62/534,710, filed on Jul. 20, 2017. Each of the above-cited applications is incorporated herein by reference in its entirety.

FIELD OF THE INVENTION

Bioactive priming polypeptides are provided which can be delivered in agricultural formulations. The polypeptides can be applied to crops to achieve agronomically desirable outcomes such as enhanced phenotypes in plants (e.g., those that exhibit protection against pest, disease agents and abiotic stress), increased plant growth, productivity and yield.

BACKGROUND OF THE INVENTION

Conventional methods to achieve desired agronomic phenotypes such as increased yield, disease prevention, disease resistance, and improved abiotic stress tolerance have utilized mostly selective breeding, grafting, transgenic and agrochemical approaches.

Bioactive Priming Polypeptides Involved in Plant Defense Responses

Plants possess an immune system that detects and protects against microbes that can cause disease. Antimicrobial peptides (AMPs) in plants are often the first line of defense against invading pathogens and are involved in the initiation of defense responses that can impart innate immunity to a plant. Many AMPs are generically active against various kinds of infectious agents. They are generally classified as antibacterial, anti-fungal, anti-viral and/or anti-parasitic.

The resistance of given plant species against certain pathogenic organisms that can contact a plant surface and colonize it, is based on highly specialized recognition systems for molecules produced only by certain microbes (for example, specific bacterial or fungal strains). Plants sense potential microbial invaders by using pattern-recognition receptors (PRRs) to recognize the pathogen-associated molecular patterns (PAMPs) associated with them.

Flagellin/Flagellin-Associated Polypeptides

Flagellins and flagellin-associated polypeptides derived from those flagellins have been reported primarily to have functional roles in innate immune responses in plants. These polypeptides are derived from highly conserved domains of eubacterial flagellin. Flagellin is the main building block of the bacterial flagellum. The flagellin protein subunit building up the filament of bacterial flagellum can act as a potent elicitor in cells to mount defense-related responses in various plant species.

“Flagellin” is a globular protein that arranges itself in a hollow cylinder to form the filament in a bacterial flagellum. Flagellin is the principal substituent of bacterial flagellum, and is present in flagellated bacteria. Plants can perceive, combat infection and mount defense signaling against bacterial microbes through the recognition of conserved epitopes, such as the stretch of 22 amino acids (Flg22) located in the N-terminus of a full length flagellin coding sequence. The elicitor activity of Flg22 polypeptide is attributed to this conserved domain within the N-terminus of the flagellin protein (Felix et al., 1999). Plants can perceive bacterial flagellin through a pattern recognition receptor (PRR) at the plant’s cell surface known as flagellin sensitive receptor, which is a leucine-rich repeat receptor kinase located in the plasma membrane and available at the plant cell surface. In plants, the best-characterized PRR is FLAGELLIN SENSING 2 (FLS2), which is highly conserved in both monocot and dicot plants.

In *Arabidopsis*, the innate immune response to Flg22 involves a host recognition protein complex that contains the FLS2 leucine rich repeat (LRR) receptor kinase (Gomez-Gomez L. and Boller T., “FLS2: An LRR receptor-like kinase involved in the perception of the bacterial elicitor flagellin in *Arabidopsis*,” Molecular Cell 5: 1003-1011, 2000). In *Arabidopsis thaliana*, FLS2 is a PRR that determines flagellin perception and is specific for the binding of the flagellin-associated polypeptide(s). For example, the binding of Flg22 to the outer plant FLS2 membrane-bound receptor triggers a signaling cascade that is involved in the innate immune response that induces the plant to mount a highly specific signaling-associated cascade that is involved in the activation of pattern-triggered immunity (Chinchilla et al., “The *Arabidopsis* receptor kinase FLS2 binds Flg22 and determines the specificity of flagellin perception,” Plant Cell 18: 465-476, 2006). Thus, the binding of Flg22 to the *Arabidopsis* FLS2 membrane-bound receptor promotes the first step of activation in which the binding elicits an activation cascade for defense responses in the plant. The Flg22-FLS2 interaction can also lead to the production of reactive oxygen species (ROS) that contribute to the induction of an oxidative burst, cellular medium alkalinization, downstream induction of pathogen-responsive genes and defense-related responses which then can impart disease resistance to a plant (Felix G. et al., “Plants have a sensitive perception system for the most conserved domain of bacterial flagellin,” The Plant Journal 18: 265-276, 1999, Gómez-Gómez L. and Boller T., “FLS2: An LRR receptor-like kinase involved in the perception of the bacterial elicitor flagellin in *Arabidopsis*,” Molecular Cell 5: 1003-1011, 2000, Meindi et al., “The bacterial elicitor flagellin activates its receptor in tomato cells according to the address-message concept,” The Plant Cell 12: 1783-1794, 2000). In tomato, high affinity binding of Flg22 to a FLS receptor was observed using both intact cells as well as to microsomal membrane preparations. In this study, the binding of Flg22 to the FLS2 receptor(s) at the plasma membrane surface was nonreversible under physiological conditions, which reflects an uptake process of the Flg22 elicitor with import into the tomato cells (Meindi et al., “The bacterial elicitor flagellin activates its receptor in tomato cells according to the address-message concept,” The Plant Cell 12: 1783-1794, 2000). Recognition of Flg22 by FLS2 triggers both local and systemic plant immune responses. The Flg22-bound, activated FLS2 receptor complex is internalized into plant cells by endocytosis and moves systemically throughout the plant (Jelenska et al., “Flagellin peptide flg22 gains access to long-distance trafficking in *Arabidopsis* via its receptor, FLS2,” Journal of Experimental Botany 68: 1769-1783, 2017), which may contribute towards systemic Flg22 immune responses.

Flagellin receptor perception mediation involving Flg22 is highly conserved across divergent plant taxa (Taki et al., “Analysis of flagellin perception mediated by flg22 receptor OsFLS2 in rice," Molecular Plant Microbe Interactions 21: 1635-1642, 2008). Submicromolar concentrations of synthetic polypeptides comprising between 15-22 or 28 amino acids from conserved domains of a flagellin protein, act as elicitors to initiate defense responses in a variety of plant species.

Generation of transgenic plants has been used to confirm the flagellin-specific PAMPs that bind to the flagellin-specific PRRs. Ectopic expression of FLS2 in *Arabidopsis* plants showed a direct correlation between the flagellin responses and FLS2 expression levels, which indicate that FLS2 is involved in the recognition of flagellin (a signal of bacterial presence) and leads to the activation of defense responses in plants (Gómez-Gómez L. and Boller T., "FLS2: An LRR receptor-like kinase involved in the perception of the bacterial elicitor flagellin in *Arabidopsis*," Molecular Cell 5: 1003-1011, 2000). Transgenic plants expressing the flagellin binding receptor have shown efficacy against certain pathogens. Flagellin binding to FLS2 was involved in the initiation of expression of specific MAP kinase transcription factors that function downstream of the flagellin receptor FLS2. Mutant plants (fls2) lacking in the FLS2 receptor are insensitive to Flg22 (Gómez-Gómez L. and Boller T., "FLS2: An LRR receptor-like kinase involved in the perception of the bacterial elicitor flagellin in *Arabidopsis*," Molecular Cell 5: 1003-1011, 2000), and impaired in Flg22 binding to the FLS2 receptor. Mutant plants (fls2) also exhibited enhanced susceptibility to infection and disease when treated with pathogenic bacteria (Zipfel et al., "Bacterial disease resistance in *Arabidopsis* through flagellin perception," Nature 428: 764-767, 2004).

Traditionally, methods to improve disease resistance have capitalized on these and other such findings and have taken a transgenic approach. Transgenic plants and seeds transformed with a Flagellin-Sensing (FLS) receptor protein (WO2016007606A2 incorporated herein by reference in its entirety) or with transcription factors involved in downstream signaling of FLS (WO2002072782A2 incorporated herein by reference in its entirety) have produced plants that confer disease resistance to certain pathogenic microorganisms. In another example, transgenic plants expressing Flagellin-Sensing (FLS3) receptor also have exhibited enhanced resistance to disease compared to non-transgenic plants not expressing the FLS3 receptor (WO2016007606A2 incorporated herein by reference in its entirety).

Plant Defensins/Thionins

Plant defensins are also characterized as anti-microbial peptides (AMPs). Plant defensins contain several conserved cysteinyl residues that form disulphide bridges and contribute to their structural stability. Defensins are among the best characterized cysteine-rich AMPs in plants. Members of the defensin family have four disulfide bridges that fold into a globular structure. This highly conserved structure bestows highly specialized roles in protecting plants against microbial pathogenic organisms (Nawrot et al., "Plant antimicrobial peptides," Folia Microbiology 59: 181-196, 2014).

Thionins are cystine-rich plant AMPs classified in the defensin family and typically comprise 45-48 amino acid residues, in which 6-8 of these amino acids are cysteine that form 3-4 disulfide bonds in higher plants. Thionins have been found to be present in both monocot and dicot plants and their expression can be induced by infection with various microbes (Tam et. al., "Antimicrobial peptides from plants," Pharmaceuticals 8: 711-757, 2015). Particular amino acids of thionins such as Lys1 and Tyr13, which are highly conserved, have been found to be vital to the functional toxicity of these AMPs.

Harpin and Harpin-Like (HpaG-Like)

Similar to the flagellins or the flagellin-associated polypeptides, harpins comprise a group of bacterial-derived elicitors that are derived from larger precursor proteins. Harpins are critical for the elicitation of a hypersensitive response (HR) when infiltrated into the intercellular space or apoplast of plant cells (Kim et al., "Mutational analysis of *Xanthomonas* harpin HpaG identifies a key functional region that elicits the hypersensitive response in nonhost plants," Journal of Bacteriology 186: 6239-6247, 2004). Application of the distant harpin-like (HpaG-like) bioactive priming polypeptide(s) to a plant provides an alternative conduit to protect a plant from disease and insect pressure. Harpins utilize a type III secretion system that enable the transport of proteins across the lipid bilayers that makeup the plant plasma cell membrane. The binding of harpins to the surface of the plasma cell membrane can trigger an innate immune response that resembles those triggered by pathogen-associated molecular patterns (PAMPs) and are known to activate PAMP-triggered immunity (Engelhardt et al., "Separable roles of the *Pseudomonas syringae* pv. *phaseolicola* accessory protein HrpZ1 in ion-conducting pore formation and activation of plant immunity," The Plant Journal 57: 706-717, 2009). Mutational analysis of a harpin-like HpaG derived polypeptide showed that the 12 amino acid residues between Leu-39 and Leu50 of the original 133 amino acid harpin elicitor precursor protein was critical to the elicitation of a hypersensitive (HR) and subsequent innate immune responses in tobacco (Kim et al., "Mutational analysis of *Xanthomonas* harpin HpaG identifies a key functional region that elicits the hypersensitive response in nonhost plants," Journal of Bacteriology 186: 6239-6247, 2004). This indicates that a specific amino acid region of harpins (similar to the other AMPs) is responsible for the elicitation responses. Harpins, such as HpaG-like can be used to enhance resistance to not only plant pathogens but also to insects (Choi et al., "Harpins, multifunctional proteins secreted by gram-negative plant pathogenic bacteria," Molecular Plant Microbe Interactions 26: 1115-1122, 2013). Harpin has been used to induce disease resistance in plants and protect plants from colonization and feeding by insect phloem-feeding insects, such as aphids (Zhang et al., "Harpin-induced expression and transgenic overexpression of phloem protein gene At.PP2A1 in *Arabidopsis* repress phloem feeding of the green peach aphid *Myzus persicae*," BMC Plant Biology 11: 1-11, 2011).

Elongation Factor Tu (EF-Tu)

Elongation factor Tu is an abundant protein found in bacteria and acts as a pathogen-associated molecular pattern (PAMP) to initiate signaling cascades that are involved in plant disease resistance and plant innate immunity to microbial pathogenic organisms. Interestingly, some EF-Tu polypeptides are also found to exist in plants. The first 18 amino acid residues of the N-terminus of EF-Tu from *Escherichia coli*, termed elf18, is known to be a potent inducer of PAMP-triggered immune responses in plants (Zipfel et al., "Perception of the bacterial PAMP EF-Tu by the Receptor EFR restricts *Agrobacterium*-mediated transformation," Cell 125: 749-760, 2006). Polypeptides derived from *E. coli* EF-Tu are perceived by the plant cell-surface localized receptor EF-Tu receptor (EFR) (Zipfel et al., 2006). EF-Tu binding and activation of EFR follow a similar mode of action compared to that of the Flg peptide-FLS2 receptor complex (Mbengue et al., "Clathrin-dependent endocytosis is required for immunity mediated by pattern recognition receptor kinases," Proc Natl Acad Sci U.S.A. 113: 11034-9, 2016).

Growth Altering Bioactive Priming Polypeptides Phytosulfokines (PSKα)

Phytosulfokines (PSK) belong to a group of sulfated plant polypeptides that are encoded by precursor genes that are ubiquitously present and highly conserved in higher plants (Sauter M., "Phytosulfokine peptide signaling," Journal of Experimental Biology 66: 1-9, 2015). PSK genes are encoded by small gene families that are present in both monocots and dicots and encode a PSK polypeptide(s) that can be active as either a pentapeptide or a C-terminally truncated tetrapeptide (Lorbiecke R, Sauter M, "Comparative analysis of PSK peptide growth factor precursor homologs," Plant Science 163: 348-357, 2002).

The phytosulfokine protein is targeted to the secretory pathway in plants by a conserved signal polypeptide (Lorbiecke R, Sauter M, "Comparative analysis of PSK peptide growth factor precursor homologs," Plant Science 163: 348-357, 2002). Processing of the phytosulfokine precursor protein involves sulfonylation by a tyrosylprotein sulfotransferase within the plant secretory pathway, specifically the trans-Golgi followed by secretion and proteolytic cleavage in the apoplast in order to produce PSK (Sauter M., "Phytosulfokine peptide signaling," Journal of Experimental Biology 66: 1-9, 2015). After PSK is processed from the larger precursor polypeptide, the polypeptide undergoes tyrosine sulphation (Ryan et al., "Polypeptide hormones," The Plant Cell Supplement, S251-S264, 2002). The secreted polypeptide is then perceived at the cell surface by a membrane-bound receptor kinase of the leucine-rich repeat family (Sauter M., "Phytosulfokine peptide signaling," Journal of Experimental Biology 66: 1-9, 2015 where PSK can then bind to the specialized PSK receptor (for example, PSK1 from *Arabidopsis*) which has a leucine-rich repeat region located on the plant plasma membrane surface. Specific binding of PSK was detected in plasma membrane fractions from cell suspension cultures derived from rice and maize and the binding to the receptor was shown to initiate and stimulate cell proliferation (Matsubayashi et al., "Phytosulfokine-α, a sulfated pentapeptide, stimulates the proliferation of rice cells by means of specific high- and low-affinity binding sites," Proceedings National Academy of Science USA 94:13357-13362, 1997).

Phytosulfokines (PSK) serve as sulfated growth factors with biostimulant activities and are involved in the control of the development of root and shoot apical meristems, growth regulation and reproductive processes. PSKs have also been reported to initiate cell proliferation, differentiation of quiescent tissues and are involved in the formation and stimulation and differentiation of tracheary elements (Matsubayashi et al., "The endogenous sulfated pentapeptide phytosulfokine-α stimulates tracheary element differentiation of isolated mesophyll cells of *zinnia*, Plant Physiology 120: 1043-1048, 1999). PSK signaling has also been reported to be involved in the regulation of root and hypocotyl elongation that occurs in *Arabidopsis* seedlings (Kutschmar et al., "PSK-α promotes root growth in *Arabidopsis*," New Phytologist 181: 820-831, 2009).

Root Hair Promoting Polypeptide (RHPP)

Root hair promoting polypeptide (RHPP) is a 12 amino acid fragment derived from soybean Kunitz trypsin inhibitor (KTI) protein, which was detected from soybean meal that was subjected to degradation using an alkaline protease from *Bacillus circulans* $HA_{12}$ (Matsumiya Y. and Kubo M. "Soybean and Nutrition, Chapter 11: Soybean Peptide: Novel plant growth promoting peptide from soybean," Agricultural and Biological Sciences, Sheny H. E. (editor), pgs. 215-230, 2011). When applied to soybean roots, RHPP was shown to accumulate in the roots and promote root growth through the stimulation of cell division and root hair differentiation in *Brassica*.

SUMMARY OF THE INVENTION

A polypeptide is provided for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture. The polypeptide comprises either:

(a) a flagellin or flagellin-associated polypeptide and an amino acid sequence of the flagellin or flagellin-associated polypeptide comprises any one of SEQ ID NOs: 226, 1-225, 227-375, 526, 528, 530, 532, 534, 536, 538, 540, 541, 751 and 752; or (b) a mutant flagellin or flagellin-associated polypeptide and an amino acid sequence of the mutant flagellin or flagellin-associated polypeptide comprises any one of SEQ ID NOs: 571-579 and 753; or (c) a mutant flagellin or flagellin-associated polypeptide and an amino acid sequence of the mutant flagellin or flagellin-associated polypeptide comprises any one of SEQ ID NOs: 580-585; or (d) a retro inverso Flg22 polypeptide and an amino acid sequence of the retro inverso Flg22 polypeptide comprises any one of SEQ ID NOs: 376-450, 527, 531, 533, 535, 537 and 539; or (e) a retro inverso FlgII-28 polypeptide and an amino acid sequence of the retro inverso FlgII-28 polypeptide comprises any one of SEQ ID NOs: 451-525; or (f) a retro inverso Flg15 polypeptide and an amino acid sequence of the retro inverso Flg15 polypeptide comprises SEQ ID NO: 529; or (g) a harpin or harpin-like polypeptide and an amino acid sequence of the harpin or harpin-like polypeptide comprises any one of SEQ ID NOs: 587, 589, 591, 593, 594 and 595; or (h) a retro inverso harpin or harpin-like polypeptide and an amino acid sequence of the retro inverso harpin or harpin-like polypeptide comprises any one of SEQ ID NOs: 588, 590, 592, 596 and 597; or (i) a root hair promoting polypeptide (RHPP) and an amino acid sequence of the RHPP comprises any one of SEQ ID Nos: 600, 603 and 604; or (j) a Kunitz Trypsin Inhibitor (KTI) polypeptide and an amino acid sequence of the KTI polypeptide comprises SEQ ID No: 602; or (k) a retro inverso root hair promoting polypeptide (RI RHPP) and an amino acid sequence of the RI RHPP comprises any one of SEQ ID NO: 601, 605 and 606; or (l) an elongation factor Tu (EF-Tu) polypeptide and an amino acid sequence of the EF-Tu polypeptide comprises any one of SEQ ID NOs: 607-623; or (m) a retro inverso elongation factor Tu (RI EF-Tu) polypeptide and an amino acid sequence of the RI EF-Tu polypeptide comprises any one of SEQ ID NOs: 624-640; or (n) a fusion polypeptide comprising SEQ ID NO: 750; or (o) a phytosulfokine (PSK) polypeptide and an amino acid sequence of the PSK polypeptide comprises SEQ ID NO: 598; or (p) a retro inverso phytosulfokine (RI PSK) polypeptide and an amino acid sequence of the RI PSK polypeptide comprises SEQ ID NO: 599; or (q) a thionin or thionin-like polypeptide and an amino acid sequence of the thionin or thionin-like polypeptide comprises any one of SEQ ID NOs: 650-749, and optionally, wherein the flagellin or flagellin-associated polypeptide of (a), the mutant flagellin or flagellin-associated polypeptide of (c), the harpin or harpin-like polypeptide of (g), the PSK polypeptide of (o), and the thionin or thionin-like polypeptide of (q) either: contains a chemical modification; is a variant having an amino acid insertion, deletion, inversion, repeat, duplication, extension, or substitution within the amino acid sequence; is part of a fusion protein; or contains a protease recognition sequence.

A composition is provided for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture. The composition comprises either: the polypeptide as described above or any combination thereof, and an agrochemical or a carrier; or any combination of the polypeptides.

A seed coated with the polypeptide or the composition as described herein is also provided.

A recombinant microorganism that expresses or overexpresses a polypeptide is also provided. The polypeptide comprises the polypeptides as described above for the composition.

Methods are provided for increasing growth, yield, health, longevity, productivity, and/or vigor of a plant or a plant part and/or decreasing abiotic stress in the plant or the plant part and/or protecting the plant or the plant part from disease, insects and/or nematodes, and/or increasing the innate immune response of the plant or the plant part and/or changing plant architecture. The method can comprise applying the polypeptide or the composition as described herein to a plant, a plant part, or a plant growth medium or a rhizosphere in an area surrounding the plant or the plant part to increase growth, yield, health, longevity, productivity, and/or vigor of the plant or the plant part and/or decrease abiotic stress in the plant or the plant part and/or protect the plant or the plant part from disease, insects and/or nematodes, and/or increase the innate immune response of the plant or the plant part and/or change the plant architecture.

Alternatively, the method can comprise applying the polypeptide or the composition as described herein to a plant growth medium to increase growth, yield, health, longevity, productivity, and/or vigor of a plant or a plant part to be grown in the plant growth medium and/or decrease abiotic stress in the plant or the plant part to be grown in the plant growth medium and/or protect the plant or the plant part to be grown in the plant growth medium from disease, insects and/or nematodes, and/or increase the innate immune response and/or change plant architecture of the plant or the plant part to be grown in the plant growth medium.

Another method comprises applying the recombinant microorganism as described herein to a plant, a plant part, or a plant growth medium or a rhizosphere in an area surrounding the plant or the plant part to increase growth, yield, health, longevity, productivity, and/or vigor of the plant or the plant part and/or decrease abiotic stress in the plant or the plant part and/or protect the plant or the plant part from disease, insects and/or nematodes, and/or increase the innate immune response of the plant or the plant part and/or change the plant architecture. The recombinant microorganism expresses the polypeptide and expression of the polypeptide is increased as compared to the expression level the polypeptide in a wild-type microorganism of the same kind under the same conditions.

A method of producing a polypeptide comprising producing a fusion protein comprising any polypeptide as described herein and an enterokinase (EK) cleavage site via fermentation, the enterokinase cleavage site enhancing activity and stability of the polypeptide.

DEFINITIONS

Figure 1:
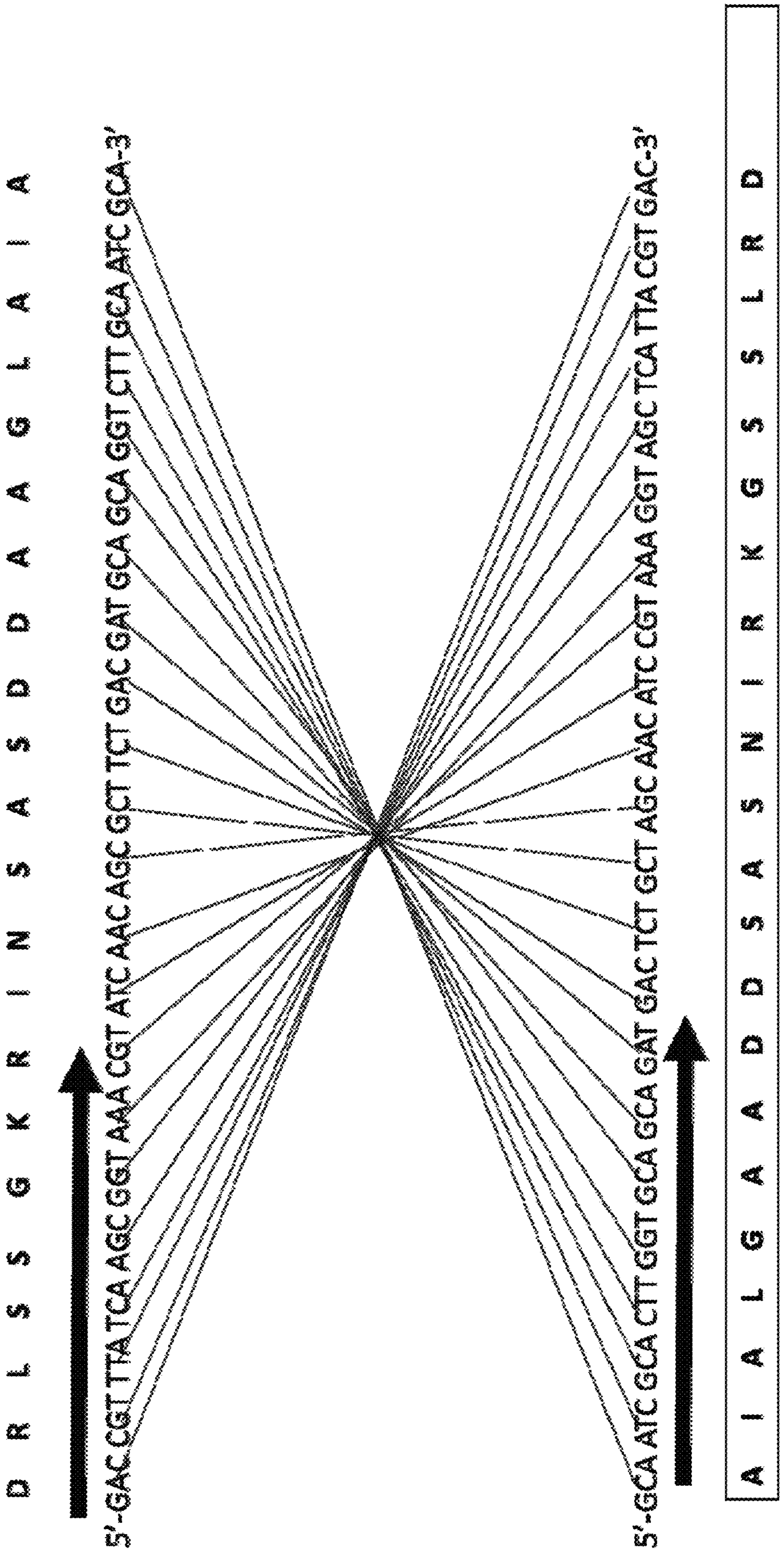
FIG. 1 shows the Bt.4Q7Flg22 bioactive priming polypeptide in its native L configuration (SEQ ID NO: 226) and the corresponding retro inverso or D configuration form (SEQ ID NO: 375).

When the articles "a," "an," "one," "the," and "said" are used herein, they mean "at least one" or "one or more" unless otherwise indicated.

The terms "comprising," "including," and "having" are intended to be inclusive and mean that there may be additional elements other than the listed elements.

"Abiotic stress" as used herein is defined as an environmental condition that can have a negative impact on a plant. Abiotic stress can include: temperature (high or low) stress, radiation stress (visible or UV), drought stress, cold stress, salt stress, osmotic stress, nutrient-deficient or high metal stress, or water stress that results in water deficit, flooding or anoxia. Other abiotic stress factors include dehydration, wounding, ozone, and high or low humidity.

"Bioactive priming" refers to an effect of the polypeptides as described herein to improve a plant or a plant part. Bioactive priming can increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture.

A "bioactive priming polypeptide" as used herein may be used interchangeably with the term "priming agent(s)" and as described for the classes of polypeptides of the: flagellin and flagellin-associated polypeptides, harpin and harpin-like polypeptide (HpaG-like), thionins, elongation factor Tu (EF-Tu) and its polypeptides, phytosulfokine α (PSKα), kunitz trypsin inhibitor (KTI), and root hair promoting polypeptide (RHPP), as well as any retro inverso polypeptides thereof.

A "colorant" as used herein acts as a visual product identifier for product branding and application. Colorants can include, but are not limited to, dyes and pigments, inorganic pigments, organic pigments, polymeric colorants, and formulated pigment coating dispersions available in a variety of highly concentrated shades.

"Endogenously" applied as used herein refers to an application to the inside of a plant surface. Small bioactive priming polypeptides are particularly suited for signalling and communication within a plant. Inside a plant surface refers to a surface internal to any plant membrane or plant cell. Internal could be used to mean either extracellular or intracellular to a plant cell and is inclusive of xylem, phloem, tracheids, etc. Endogenous can refer to movement systemically or through a plant such as referring to cell to cell movement in a plant. Endogenous application can include delivery of bioactive priming polypeptides using recombinant endophytic bacteria or fungi, wherein the endophytic microorganism is delivered externally to the plant and through natural mechanisms moves internally to the plant.

"Exogenously" applied as used herein refers to an application to the outside of a plant surface. A plant surface can be any external plant surface, for example a plasma membrane, a cuticle, a trichome, a leaf, a root hair, seed coat, etc.

"-associated" or "-like" polypeptides as used herein refers to polypeptides derived from or structurally similar to the recited polypeptide but having an amino acid sequence and/or source distinct from the recited polypeptide. For example, the thionin-like protein from *Brassica rapa* (SEQ ID NO: 694) has a different sequence than thionin from *Brassica napus* (SEQ ID NOs 693) but is structurally and functionally similar.

A "foliar treatment" as used herein refers to a composition that is applied to the above ground parts or foliage of a plant or plant part and may have leaves, stems, flowers, branches, or any aerial plant part, for example, scion.

"Injection" as described herein can be used interchangeably with vaccination or immunization and provides a process whereby the bioactive priming polypeptides are delivered endogenously to a plant or plant part.

"Inoculation" means to deliver-bacteria or living microorganisms that produce the priming polypeptide to a plant or plant part. Inoculation can also refer to the delivery of the priming polypeptide for passive entry through the stomata or any opening in or on a plant or plant part. A "plant" refers to but is not limited to a monocot plant, a dicot plant, or a gymnosperm plant. The term "plant" as used herein includes whole plants, plant organs, progeny of whole plants or plant organs, embryos, somatic embryos, embryo-like structures, protocorms, protocorm-like bodies, and suspensions of plant cells. Plant organs comprise, shoot vegetative organs/structures (e.g., leaves, stems and tubers), roots, flowers and floral organs/structures (e.g., bracts, sepals, petals, stamens, carpels, anthers and ovules), seed including embryo, endosperm, and seed coat and fruit (the mature ovary), plant tissue (e.g., phloem tissue, vascular tissue, ground tissue, and the like) and cells (e.g., guard cells, egg cells, trichomes and the like). The class of plants that can be used in the methods described herein is generally as broad as the class of higher plants, specifically angio-sperms monocotyledonous (monocots) and dicotyledonous (dicots) plants and gymnosperms. It includes plants of a variety of ploidy levels, including aneuploid, polyploid, diploid, haploid, homozygous and hemizygous. The plants described herein can be monocot crops, such as, *sorghum*, maize, wheat, rice, barley, oats, rye, millet, and triticale. The plants described herein can also be dicot crops, such as apple, pear, peach, plum, orange, lemon, lime, grapefruit, kiwi, pomegranate, olive, peanut, tobacco, tomato, etc. Also, the plants can be horticultural plants such as rose, marigold, primrose, dogwood, pansy, geranium, etc.

A plant "biostimulant" is any substance or microorganism applied to a plant or a plant part that is used to enhance nutrition efficiency, abiotic stress tolerance and/or any other plant quality trait(s).

A "plant cell" as used herein refers to any plant cell and can comprise a cell at the plant surface or internal to the plant plasma membrane, for example, an epidermal cell, a trichome cell, a xylem cell, a phloem cell, a sieve tube element, or a companion cell.

A "plant part" as described herein refers to a plant cell, a leaf, a stem, a flower, a floral organ, a fruit, pollen, a vegetable, a tuber, a corm, a bulb, a pseudobulb, a pod, a root, a rhizome, a root ball, a root stock, a scion, or a seed.

A "polypeptide" as described herein refers to any protein, peptide or polypeptide.

"Priming" or "peptide priming" as used herein refers to a technique used to improve plant performance. In particular priming is a process whereby the bioactive priming polypeptides are applied either exogenously or endogenously to a plant, plant part, plant cell or to the intercellular space of a plant that results in outcomes that provide benefits to a plant, such as enhanced growth, productivity, abiotic stress tolerance, pest and disease tolerance or prevention.

A "retro-inverso" polypeptide as used herein refers to a polypeptide chain of a natural derived polypeptide from a normal-all-L chain reconfigured and built using non-naturally occurring D-amino acids in reverse order of the naturally occurring L-amino acids. The all-D-amino acid form and the parent chain containing all L-form are topological mirrorings of the protein structure.

A "seed treatment" as used herein refers to a substance or composition that is used to treat or coat a seed. Sample seed treatments include an application of biological organisms, chemical ingredients, inoculants herbicide safeners, micronutrients, plant growth regulators, seed coatings, etc. provided to a seed to suppress, control or repel plant pathogens, insects, or other pests that attack seeds, seedlings or plants or any useful agent to promote plant growth and health.

A "synergistic" effect refers to an effect arising between the interaction or cooperation of two or more bioactive priming polypeptides, substances, compounds, or other agents to produce a combined effect greater than the sum of their separate effects.

A "synergistic effective concentration" refers to the concentration(s) of two or more bioactive priming polypeptides, substances, compounds or other agents that produces an effect greater than the sum of the individual effects.

DESCRIPTION OF THE PREFERRED EMBODIMENTS

There is a growing need for bioactive polypeptides that act as "priming agents" to provide benefits to agriculture. The use of bioactive "priming" polypeptides in agricultural practices provides a paradigm shift for integrated crop management practices for example, to manage disease, abiotic stress and yield programs. Bioactive (naturally occurring, recombinant or synthetic) priming polypeptides are delivered in agricultural formulations. Compositions and methods of using the bioactive priming polypeptides are described to supply a multi-tiered treatment regime to apply to crops to achieve agronomically desirable outcomes. Such desirable outcomes include enhanced phenotypes in plants such as those that exhibit protection against pest, disease agents and abiotic stress, as well as increased plant growth, productivity and yield. More specifically, the bioactive priming polypeptides or formulations of the bioactive priming polypeptides can be applied using various treatment regimes, exogenously and/or endogenously to a plant or plant part, and have been discovered to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture.

Specific classes of synthetically derived or naturally occurring bioactive priming polypeptides including flagellins and flagellin-associated polypeptides (including those conserved among the *Bacillus* genera), thionins, harpin-like polypeptide (HpaG-like), elongation factor Tu (EF-Tu), phytosulfokine (PSKα) and root hair promoting polypeptide (RHPP) were selected for their distinct modes of action and can be used individually or in combination with other polypeptides to accommodate the specific agricultural needs described above. They can be used in the place of or in addition to commercially available agrochemicals, biostimulants, supplemental bioactives and/or pesticidal compounds.

Combinations of the bioactive priming polypeptides are also provided that are applied in synergistically effective amounts to provide control of pests, pathogens and additionally provide benefits to enhance plant growth and promote plant health.

I. Polypeptides

The bioactive priming polypeptides are provided as naturally occurring, recombinant or chemically synthesized forms derived from bacteria or plants. The bioactive priming polypeptides are provided in both the normal L and non-natural retro-inverso D amino-acid forms. In addition, bioactive priming polypeptides are provided that contain non-natural modifications, including N-terminal and C-terminal modifications, cyclization, β-amino and D-amino acid containing, and other chemical modifications that enhance stability or performance of the polypeptides. For example, flagellin and the Flg-associated polypeptides comprising 22 amino acids in length and derived from the full coding region of flagellin were initially isolated and identified from a proprietary genome assembled for bacterial strain, *Bacillus thuringiensis* 4Q7. These Flg22 derived polypeptides were provided in the standard (L) and retro-inverso (D) forms. They are described as Bt.4Q7Flg22 and retro-inverso (RI) Bt.4Q7Flg22. Other bacterial derived bioactive priming polypeptides are Ec.Flg22 (*Escherichia coli*), HpaG-like (*Xanthomonas* spp.), while the plant derived polypeptides include thionins (*Citrus* spp. and other plant species), PSKα (*Arabidopsis thaliana* and other plants), EF-Tu (both bacterial or plant derived) and RHPP (*Glycine max*).

The bioactive priming polypeptides can include full-length proteins and are provided as naturally occurring, synthetic or recombinant forms derived from bacteria or plants. For example, flagellin, EF-Tu, KTI, and HpaG can all be delivered to plants.

The bioactive priming polypeptides can also be delivered as fusion partners to other protein sequences, including protease cleavage sites, binding proteins, and targeting proteins for specific delivery to plants or plant parts.

Also provided are signature, signal anchor sorting and secretion sequences that can be naturally or chemically synthesized and targeting sequences, such as phloem-targeting sequences that are produced along with the bioactive priming polypeptide(s) using recombinant microorganisms and either used as fusion or assistance polypeptides with the bioactive priming polypeptides as described herein.

Non-naturally occurring polypeptides are also described herein. More specifically, a polypeptide is provided for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture. The polypeptide comprises either:

(a) a flagellin or flagellin-associated polypeptide and an amino acid sequence of the flagellin or flagellin-associated polypeptide comprises any one of SEQ ID NOs: 226, 1-225, 227-375, 526, 528, 530, 532, 534, 536, 538, 540, and 541; or (b) a mutant flagellin or flagellin-associated polypeptide and an amino acid sequence of the mutant flagellin or flagellin-associated polypeptide comprises any one of SEQ ID NOs: 571-579; or (c) a mutant flagellin or flagellin-associated polypeptide and an amino acid sequence of the mutant flagellin or flagellin-associated polypeptide comprises any one of SEQ ID NOs: 580-585; or (d) a retro inverso Flg22 polypeptide and an amino acid sequence of the retro inverso Flg22 polypeptide comprises any one of SEQ ID NOs: 376-450, 527, 531, 533, 535, 537 and 539; or (e) a retro inverso FlgII-28 polypeptide and an amino acid sequence of the retro inverso FlgII-28 polypeptide comprises any one of SEQ ID NOs: 451-525; or (f) a retro inverso Flg15 polypeptide and an amino acid sequence of the retro inverso Flg15 polypeptide comprises SEQ ID NO: 529; or (g) a harpin or harpin-like polypeptide and an amino acid sequence of the harpin or harpin-like polypeptide comprises any one of SEQ ID NOs: 587, 589, 591, 593, 594 and 595; or (h) a retro inverso harpin or harpin-like polypeptide and an amino acid sequence of the retro inverso harpin or harpin-like polypeptide comprises any one of SEQ ID NOs: 588, 590, 592, 596 and 597; or (i) a root hair promoting polypeptide (RHPP) and an amino acid sequence of the RHPP comprises any one of SEQ ID Nos: 600, 603 and 604; or (j) a Kunitz Trypsin Inhibitor (KTI) polypeptide and an amino acid sequence of the KTI polypeptide comprises SEQ ID No: 602; or (k) a retro inverso root hair promoting polypeptide (RI RHPP) and an amino acid sequence of the RI RHPP comprises any one of SEQ ID NO: 601, 605 and 606; or (l) an elongation factor Tu (EF-Tu) polypeptide and an amino acid sequence of the EF-Tu polypeptide comprises any one of SEQ ID NOs: 607-623; or (m) a retro inverso elongation factor Tu (RI EF-Tu) polypeptide and an amino acid sequence of the RI EF-Tu polypeptide comprises any one of SEQ ID NOs: 624-640; or (n) a fusion polypeptide comprising SEQ ID NO: 750; or (o) a phytosulfokine (PSK) polypeptide and an amino acid sequence of the PSK polypeptide comprises SEQ ID NO: 598; or (p) a retro inverso phytosulfokine (RI PSK) polypeptide and an amino acid sequence of the RI PSK polypeptide comprises SEQ ID NO: 599; or (q) a thionin or thionin-like polypeptide and an amino acid sequence of the thionin or thionin-like polypeptide comprises any one of SEQ ID NOs: 650-749, and optionally, wherein the flagellin or flagellin-associated polypeptide of (a), the mutant flagellin or flagellin-associated polypeptide of (c), the harpin or harpin-like polypeptide of (g), the PSK polypeptide of (o), and the thionin or thionin-like polypeptide of (q) either: contains a chemical modification; is a variant having an amino acid insertion, deletion, inversion, repeat, duplication, extension, or substitution within the amino acid sequence; is part of a fusion protein; or contains a protease recognition sequence.

Flagellins and Flagellin-Associated Polypeptides

The polypeptide can include a flagellin or flagellin-associated polypeptide.

The flagellin or flagellin-associated polypeptide can be derived from a *Bacillus*, a *Lysinibacillus*, a *Paenibacillus*, an *Aneurinibacillus* genus bacterium, or any combination thereof.

One of the main classes of bioactive priming polypeptides as described herein are the flagellin(s) and the flagellin-associated priming polypeptide(s). Conserved full and partial length amino acid flagellin coding sequences were identified from various species of *Bacillus* and non-*Bacillus* bacteria using methods as described herein.

Flagellin is a structural protein that forms the main portion of flagellar filaments from flagellated bacterial species that can show conservation in the N-terminal and C-terminal regions of the protein but can be variable in the central or mid part (Felix G. et al., "Plants have a sensitive perception system for the most conserved domain of bacterial flagellin," The Plant Journal 18: 265-276, 1999). The N- and C-terminal conserved regions from flagellins that form the inner core of the flagellin protein may have roles in the polymerization of the protein into a filament, in the motility and transport of the protein and in the surface attachment of a peptide fragment to the plant cell membrane/cell surface receptors of a plant.

Full or partial flagellins (Table 1-2) and the flagellin-associated polypeptides derived from those *Bacillus* and non-*Bacillus* flagellins (Tables 3 and 5) are provided.

The amino acid sequence of the flagellin or flagellin-associated polypeptide can comprise any one of SEQ ID NOs: 1-768, or any combination thereof.

Flagellin-associated bioactive priming polypeptides are produced from flagellin coding polypeptides (such as the precursor proteins of Flg22). More specifically, a polypeptide or a cleaved fragment derived from the polypeptide is provided to achieve a bioactive priming Flg polypeptide that can be used to prime or treat a plant. The cleavage of the FIG. 22 fragment from larger precursors can be accomplished through introduction of proteolytic cleavage sites near the FIG. 22 to facilitate processing of the active biopeptide from the larger polypeptide.

The flagellin-associated bioactive priming polypeptides can be derived from full length flagellin proteins (or precursor proteins from Flg-associated polypeptides from a *Bacillus*, a *Lysinibacillus*, a *Paenibacillus*, or an *Aneurinibacillus* or other non-related genera bacterium). For example, PCR purified DNA from the flagellin-associated polypeptides such as Flg22 and FlgII-28 (*Bacillus* genera) and Flg15 and Flg22 (*E. coli*) are cloned into a recombinant vector, amplified to achieve adequate amounts of purified DNA that is then sequenced using conventional methods known and used by one of ordinary skill in the art. The same methods can be used with the flagellin coding or the flagellin partial sequences (Table 1), N- or C-terminal flagellin polypeptides (Table 2) and any of the Flg-associated polypeptides (Tables 3-5).

The flagellin or flagellin-associated polypeptide can be derived from any member of Eubacteria that contains the conserved 22 amino acid region that is recognized by the plants. Preferred flagellin or flagellin-associated polypeptides can be derived from a *Bacillus*, a *Lysinibacillus*, a *Paenibacillus*, an *Aneurinibacillus* genus bacterium, or any combination thereof. Additional preferred flagellin and Flg22 sequences can be obtained from the gammaproteobacteria, which contain conserved 22 amino acid sequences of >68% identity.

Conserved Flagellin Sequences from *Bacillus*

The flagellin-associated bioactive priming polypeptides correspond to the N-terminal conserved domains of *Bacillus* spp. and other Eubacterial flagellin and are provided as synthetic, recombinant or naturally occurring forms. The flagellin bioactive priming polypeptides of Flg22, Flg15 and FlgII-28 (Table 3) were identified and act as potent elicitors on a wide range of crops and vegetables to prevent and treat the spread of select disease(s) while synergistically stimulating and promoting growth responses in plants.

The flagellin and flagellin-associated bioactive priming polypeptides as described herein are provided for use individually or in combination with other bioactive priming polypeptides as described herein, and include conserved full and partial flagellins from *Bacillus* (Table 1), conserved N- and C-terminal regions from flagellin polypeptides (Table 2), *Bacillus* derived Flg22 and FlgII-28-derived bioactive priming polypeptides (Table 3) and retro-inverso sequences that are mirror images derived from the *Bacillus* Flg22 and FlgII-28 (Table 4). The underlined portion of the sequences in Tables 1 and 3 represent identified signal anchor sorting or secretion sequences, and signal anchoring sequences, respectively. Other non-*Bacillus* derived polypeptide and proteins are also described that are functional equivalents and can be utilized in similar fashion (Table 5).

TABLE 1

Conserved flagellin sequences from *Bacillus*

| SEQ ID NO: | Full or Partial Flagellin Coding Sequence - Amino Acid |
|---|---|
| Flagellin<br>SEQ ID NO: 1<br>*Bacillus thuringiensis*<br>strain 4Q7 | MRINTNINSMRTQEYMRQNQAKMSNAMDRLSSGKRINSASDDAAGLAIATRMKAR<br>EGGLNVAGRNTQDGMSLIRTADSALNSVSNILLRMRDLANQSANGTNTKGNQASL<br>QKEFAQLTEQIDYIAKNTQFNDQQLLGTADKKIKIQTLDTGSTNPAQIEITLNSV<br>KSADLGLDVQIGDEGDAESTAAADPTSAKQAIDAIDAAITTVAGQRATLGATLNR<br>FEFNANNLKSQETSMADAASQIEDADMAKEMSEMTKFKILNEAGISMLSQANQTP<br>QMVSKLLQ |
| Flagellin<br>SEQ ID NO: 2<br>*Bacillus thuringiensis*,<br>strain<br>HD1002 | MRINTNINSMRTQEYMRQNQAKMSNAMDRLSSGKRINSASDDAAGLAIATRMKAR<br>EGGLNVAGRNTQDGMSLIRTADSALNSVSNILLRMRDLANQSANGTNTKGNQASL<br>QKEFAQLTEQIDYIAKNTQFNDQQLLGTADKKIKIQTLDTGSTNPAQIEITLNSV<br>KSADLGLDVQIGDEGDAESTAAADPTSAKQAIDAIDAAITTVAGQRATLGATLNR<br>FEFNANNLKSQETSMADAASQIEDADMAKEMSEMTKFKILNEAGISMLSQANQTP<br>QMVSKLLQ |
| Flagellin<br>SEQ ID NO: 3<br>*Bacillus thuringiensis*,<br>strain HD-789 | MRINTNINSMRTQEYMRQNQAKMSNAMDRLSSGKRINSASDDAAGLAIATRMKAR<br>EGGLNVAGRNTQDGMSLIRTADSALNSVSNILLRMRDLANQSANGTNTKGNQASL<br>QKEFAQLTEQIDYIAKNTQFNDQQLLGTADKKIKIQTLDTGSTNPAQIEITLNSV<br>KSADLGLDVQIGDEGDAESTAAADPTSAKQAIDAIDAAITTVAGQRATLGATLNR<br>FEFNANNLKSQETSMADAASQIEDADMAKEMSEMTKFKILNEAGISMLSQANQTP<br>QMVSKLLQ |
| Flagellin<br>SEQ ID NO: 4<br>*Bacillus cereus*<br>strain G9842 | MRINTNINSMRTQEYMRQNQAKMSNAMDRLSSGKRINSASDDAAGLAIATRMKAR<br>EGGLNVAGRNTQDGMSLIRTADSALNSVSNILLRMRDLANQSANGTNTKGNQASL<br>QKEFAQLTEQIDYIAKNTQFNDQQLLGTADKKIKIQTLDTGSTNPAQIEITLNSV<br>KSADLGLDVQIGDEGDAESTAAADPTSAKQAIDAIDAAITTVAGQRATLGATLNR<br>FEFNANNLKSQETSMADAASQIEDADMAKEMSEMTKFKILNEAGISMLSQANQTP<br>QMVSKLLQ |
| Flagellin<br>SEQ ID NO: 5<br>*Bacillus thuringiensis*<br>serovar *indiana* strain<br>HD521 | MRIGTNVLSMNARQSLYENEKHMNVAMEHLATGKKLNNASDNPANIAIVTRMHAR<br>ASGMRVAIRNNEDAISMLRTAEAALQTVTNILQRMRDLAVQSANGTNSNKNRHSL<br>NKEFQSLTEKIGYIGETTEFNDLSVFEGQNRPITLDDIGHTINMMKHIPPSPTQH<br>DIKISTEQEARAAILKIEDALQSVSLHRADLGAMINRLQFNIENLNSQSMALTDA<br>ASLIEDADMAQEMSDFLKFKLLTEVALSMVSQANQIPQMVSKLLQS |
| Flagellin<br>SEQ ID NO: 6<br>*Bacillus thuringiensis*<br>strain CTC | MRINTNINSMRTQEYMRQNQAKMSNSMDRLSSGKRINNASDDAAGLAIATRMRAR<br>ESGLGVAADNTQNGMSLIRTADSAMNSVSNILLRMRDIANQSANGTNTNENKSAL<br>QKEFAQLQKQITYIAENTQFNDKNLLNEDSEVKIQTLDSSKGEQQITIDLKAVTL<br>EKLNIKDIAIGKADAADKPVTPGATVDQKDLDSVTDKIAALTETSSKADIDAIQS<br>SLDNFKASMTPEDVKTLEDALKGFKTGQANPADAGVDAIQDALSKVKLPTATAAA<br>PAADADKSDALAAIAAIDAALTKVADNRATLGATLNRLDFNVNNLKSQSSSMASA<br>ASQIEDADMAKEMSEMTKFKILNEAGISMLSQANQTPQMVSKLLQ |
| Flagellin<br>SEQ ID NO: 7<br>*Bacillus*<br>*thuringiensis*<br>seroyar *yunnanensis*<br>strain IEBC-T20001 | MTGITINLEIDFFAYYRFSICRKVNIKKWGFLNMRINTNINSMRTQEYMRQNQAK<br>MSNAMDRLSSGKRINNASDDAAGLAIATRMRARENGLGVAANNTQDGMSLIRTAD<br>SAMNSVSNILLRMRDLANQSANGTNTDDNQKALDKEFSALKEQIDYISKNTEFND<br>KKLLNGENKTIAIQTLDNADTTKQININLADSSTSALQIDKLTISGKTTDTTKTE<br>TITVTDDEIKAAKTDIDEFNDAKKALADLKAETSAGKADGSTDDEIKTAVSNFTK<br>SFEKIQKFMNDSDIKTVQTEIEKFDAAAPALDKAKGMGIAFTSAMDPKAGTITKA<br>ATRQNASDAIKSIDAALETIASNRATLGATLNRLDFNVNNLKSQSSSMAAAASQI<br>EDADMAKEMSEMTKFKILNEAGISMLSQANV |
| Flagellin<br>SEQ ID NO: 8<br>*Bacillus thuringiensis*<br>serovar *tolworthi* | MRINTNINSMRTQEYMRQNQAKMSNAMDRLSSGKRINNASDDAAGLAIATRMRAR<br>ENGLGVAANNTQDGMSLIRTADSALQSVSNILLRMRDLANQSANGTNTDENKAAM<br>EKEFGQLKDQIKYITDNTQFNDKNLLDAASGTTKSIAIQTLDSDQASTQIEIKIA<br>GSSLAALGLDKVQIGQETVAQKDLDVLTKAMGRLAAPDADATTRDLDVQVAKDAF<br>DKVKGFIADPAQAKAVERAFEDYTAAEAGKEEDAAKAIDAAYKKVTGLTAGTTGT<br>VDAHNAVNKIDAALKTVADNRATLGATLNRLDFNVNNLKSQSASMASAASQIEDA<br>DMAKEMSEMTKFKILNEAGISMLSQANQTPQMVSKLLQ |

TABLE 1-continued

Conserved flagellin sequences from *Bacillus*

| SEQ ID NO: | Full or Partial Flagellin Coding Sequence - Amino Acid |
|---|---|
| Flagellin<br>SEQ ID NO: 9<br>*Bacillus cereus* strain<br>FM1 | MRINTNINSMRTQEYMRQNQAKMSNSMDRLSSGKRINNASDDAAGLAIATRMRAR<br>ESGLGVAANNTQDGMSLIRTADSAMNSVSNILLRMRDIANQSANGTNTDKNQVAL<br>QKEFGELQKQIDYIAKNTQFNDKNLLSGKAGAPDQALEINIQTLDSSDPNQQIKI<br>SLDSVSTAQLGVKDLQIGSSSITQQQLDTLDNAMKRLETASTTAAVRDQDVADAK<br>AAFENVKGFFSEGNVDSINRAFTDFANETTNKDDKAEAIYALYNNATLITKPTPD<br>ASNPASVDPANAIKKIDQAIEKIASSRATLGATLNRLDFNVNNLKSQQSSMASAA<br>SQVEDADMAKEMSEMTKFKILNEAGISMLSQANQTPQMVSKLLQ |
| Flagellin<br>SEQ ID NO: 10<br>*Bacillus cereus* strain<br>FM1 | MRIGTNVLSMNARQSFYENEKRMNVAIEHLATGKKLNHASDNPANVAIVTRMHAR<br>TSGIHVAIRNNEDAISMLRTAEAALQTVTNILQRMRDVAVQSANGTNSNKNRDSL<br>NKEFQSLTEQIGYIDETTEFNDLSVFDRQNCPVTLDDIGHTVNVTKHIPPSPTQH<br>DINISTEQEARAAIRKIEETLQNVSLHRADLGAMINQLQFNIENLNSQSTALTDA<br>ASRIEDADMAQEMSDFLKFKLLTEVALSMVSQANQIPQMVYKLLQS |
| Flagellin<br>SEQ ID NO: 11<br>Bacillus *thuringiensis*<br>strain MC28 | MDRLSSGKRINNASDDAAGLAIATRMRARESGLGVAANNTQDGMSLIRTADSALN<br>SVSNILLRMRDIANQSANGTNTADNQQALQKEFGQLKEQISYIADNTEFNDKTLL<br>KADNSVKIQTLDSADTNKQISIDLKGVTLNQLGLDTVNIGSEKLSAESLNVAKAT<br>MARLVKADQNADPSTFALDVNTAKESFDKIKGFIANKTNVQNVENAFNDYAVADP<br>AADKADKADAIQAFNTAITGLTAGTPNTSNPSSAVDSIDAALKTVASNRATLGAT<br>LNRLDFNVNNLKSQSASMASAASQIEDADMAKEMSEMTKFKILNEAGISMLSQAN<br>QTPQMVSKLLQ |
| Flagellin<br>SEQ ID NO: 12<br>*Bacillus*<br>*bombysepticus*<br>strain Wang | MRINTNINSMRTQEYMRQNQAKMSNSMDRLSSGKRINNASDDAAGLAIATRMRSR<br>EGGLNVAARNTEDGMSLIRTADSALNSVSNILLRMRDLANQSASGTNTDKNQAAM<br>QKEFDQLKEQIQYIADNTEFNDKKLLDGSNSTINIQTLDSHDKNKQITISLDSAS<br>LKNLDIKDLAIGSATINQTDLDTATNSMKRLATPATDGKVLAQDIADAKAAFNKV<br>QSAYTPAEVDKIQDAFKAYDKLAADPASKATDIADAAKNVNTVFGTLATPTATKF<br>DPSSAVEKIDKAIETIASSRATLGATLNRLDFNVTNLKSQENSMAASASQIEDAD<br>MAKEMSEMTKFKILNEAGISMLSQANQTPQMVSKLLQ |
| Flagellin<br>SEQ ID NO: 13<br>*Bacillus thuringiensis*<br>serovar *kenyae* | MTGITINLEIDFFAYYRFSICRKVNIKKWGFLNMRINTNINSMRTQEYMRQNQAK<br>MSNSMDRLSSGKRINNASDDAAGLAIATRMRSREGGLNVAARNTEDGMSLIRTAD<br>SALNSVSNILLRMRDLANQSASGTNTDKNQAAMQKEFDQLKEQIQYIADNTEFND<br>KKLLDGSNSTINIQTLDSHDKNKQITISLDSASLKNLDIKDLAIGSATINQTDLD<br>TATNSMKRLATPATDGKVLAQDIADAKAAFNKVQSAYTPAEVDKIQDAFKAYDKL<br>AADPASKDTDIADAAKNVNTVFGTLATPTATKFDPSSAVEKIDKAIETIASSRAT<br>LGATLNRLDFNVTNLKSQENSMAASASQIEDADMAKEMSEMTKFKILNEAGISML<br>SQANQTPQMVSKLLQ |
| Flagellin<br>SEQ ID NO: 14<br>*Bacillus thuringiensis*<br>serovar *kenyae* | MRINTNINSMRTQEYMRQNQAKMSNSMDRLSSGKRINNASDDAAGLAIATRMRSR<br>EGGLNVAARNTEDGMSLIRTADSALNSVSNILLRMRDLANQSASGTNTDKNQAAM<br>QKEFDQLKEQIQYIADNTEFNDKKLLDGSNSTINIQALDSHDKNKQITISLDSAS<br>LKNLDIKDLAIGSATINQTDLDTATNSMKRLATPATDGKVLAQDIADAKAAFNKV<br>QSAYTPAEVDKIQDAFKAYDKLAADPASKDTDIADAAKNVNTVFGTLATPTATKF<br>DPSSAVEKIDKAIETIASSRATLGATLNRLDFNVTNLKSQENSMAASASQIEDAD<br>MAKEMSEMTKFKILNEAGISMLSQANQTPQMVSKLLQ |
| Flagellin (A-type)<br>SEQ ID NO: 15<br>*Bacillus cereus* | MRINTNINSMRTQEYMRQNQAKMSNAMDRLSSGKRINNASDDAAGLAIATRMRAR<br>ENGLGVAANNTQDGMSLIRTADSALNSVSNILLRMRDLANQSANGTNTGDNQKAL<br>DKEFSALKEQIDYISKNTEFNDKKLLNGDNKTIAIQTLDNADTSKQININLADSS<br>TSALKIEKLTISGSTAIAGKTEKVTITAEDIKAAEEDIKAFTQAQEGLANLVKEV<br>KDTDGSVKTPGSTPDDIKKAVTAFTESFEKMKKFMNDEDITKVEEKIKAFDAASP<br>DLDAAKEMGTAFTAAMKPAAGEITKAAMKPNASDAIKSIDEALETIASNRATLGA<br>TLNRLDFNVNNLKSQSSSMASAASQIEDADMAKEMSEMTKFKILNEAGISMLSQA<br>NQTPQMVSKLLQ |
| Flagellin (A-type)<br>SEQ ID NO: 16<br>*Bacillus cereus* | MRIGTNVLSMNARQSLYENEKRMNVAMEHLATGKKLNNASDNPANIAIVTRMHAR<br>ASGMRLAIRNNEDTISMLRTAEAALQTLTNILQRMRDLAVQSANGTNSNKNRDSL<br>NKEFQSLTEQIGYIGETTEFNDLSVFDGQNRPVTLDDIDHTINMTKHIPPSPTQH<br>DIKISTEQEARAAILKIEEALQSVSIHRADLGSMINRLQFNIENLNSQSMALTDA<br>ASRIEDADMAQEMSDFLKFKLLTEVALSMVSQANQIPQMVSKLLQS |
| Flagellin<br>SEQ ID NO: 17<br>*Bacillus thuringiensis*<br>serovar *finitimus*<br>strain YBT-020 | MRIGTNVLSMNARQSLYENEKRMNVAMEHLATGKKLNHASDNPANVAIVTRMHAR<br>ASGMRVAIRNNEDAISMLRTAEAALQTVTNVLQRMRDVAVQSANGTNLNKNRDSL<br>NNEFQSLTEQIGYIDETTAFNDLSVFDGQNRPVTLDDIGHTVNVTKHISPSPTQH<br>DINISTEQEARAAIRKIEEALQNVSLYRADLGAMINRLQFNIENLNSQSTALTDA<br>ASRIEDADMAQEMSDFLKFKLLTEVALSMVSQANQIPQMVYKLLQS |
| Flagellin<br>SEQ ID NO: 18<br>*Bacillus thuringiensis*<br>serovar *finitimus*<br>strain YBT-020 | MRINTNINSMRTQEYMRQNQAKMSNAMDRLSSGKRINNASDDAAGLAIATRMRAR<br>ESGLNVAADNTQNGMSLIRTADSAMNSVSNILLRMRDIANQSANGTNTDSNKSAL<br>QKEFAELQKQITYIADNTQFNDKNLLKEDSEVKIQTLDSSKGEQQIGIDLKAVTL<br>EKLGINNISIGKADGTTEGTKADLTALQAAAKKLEKPDTGTMEKDVKDAKEEFDK<br>VKASLSDEDVKKIEAAFGEFDKDKTNTTKASDIFNAIKDVKLADKAAAAPAPADL<br>TKFKAALDKLQTPNAGTMVDDVKDAKDEFEKIKGSLSDADAQKIQAAFEEFEKAN |

TABLE 1-continued

| Conserved flagellin sequences from *Bacillus* | |
|---|---|
| SEQ ID NO: | Full or Partial Flagellin Coding Sequence - Amino Acid |
| | TDDSKASAIYNLAKDVKVNATDTTTGTDKDTTTSTDKDAALAAIAAIDAALTKVA DNRATLGATLNRLDFNVNNLKSQSSSMASAASQIEDADMAKEMSEMTKFKILNEA GISMLSQANQTPQMVSKLLQ |
| Flagellin SEQ ID NO: 19 *Bacillus cereus* strain B4264 | MRINTNINSMRTQEYMRQNQAKMSNAMDRLSSGKRINNASDDAAGLAIATRMRAR ESGLGVAANNTQDGMSLIRTADSALNSVSNILLRMRDLANQSANGTNTAENKAAM QKEFGELKDQIKYISENTQFNDQHLLNAAKGSTNEIAIQTLDSDSSSKQIKITLQ GASLDSLDIKDLQIGSGSTVSQTDLDVLDATMTRVKTATGATRDVDVQAAKSAFD KVKGLMTKPAEVKAIERAFEDYNAGKTDALATAIEAAYTANKTGLPAPAAAAGTV DALGAITKIDAALKTVADNRATLGATLNRLDFNVNNLKSQSASMASAASQIEDAD MAKEMSEMTKFKILNEAGISMLSQANQTPQMVSKLLQ |
| Flagellin SEQ ID NO: 20 *Bacillus thuringiensis* serovar *nigeriensis* | MRINTNINSMRTQEYMRQNQAKMSNAMDRLSSGKRINNASDDAAGLAIATRMRAR ESGLGVAANNTQDGMSLIRTADSALNSVSNILLRMRDIANQSANGTNTSDNQKAL DKEFSALKEQIDYISKNTEFNDKKLLNGDNKSIAIQTLDNADTTKQININLADSS TTALNIDKLSIEGTGNKTITLTAADIAKDKANIDAVGTAKTALAGLTGTPAAAAI NSAVADFKTAFAKADKNLMSDAQIKAVTDAITAFEADATPDLTKAKAIGTAYTAP AAGDITKASPNASEAIKSIDAALDTIASNRATLGATLNRLDFNVNNLKSQSSSMA SAASQIEDADMAKEMSEMTKFKILNEAGISMLSQANQTPQMVSKLLQ |
| Flagellin SEQ ID NO: 21 *Bacillus thuringiensis* | MRINTNINSMRTQEYMRQNQAKMSNAMDRLSSGKRINNASDDAAGLAIATRMRAR ESGLGVAANNTQDGMSLIRTADSALNSVSNILLRMRDIANQSANGTNTADNQQAL QKEFGQLKEQISYIADNTEFNDKTLLKADNSVKIQTLDSADTNKQISIDLKGVTL NQLGLDTVNIGSETLSAESLNVAKATMARLVKADQNADPSTFALDVNTAKESFDK IKGFITNKTNVQNVENAFNDYTVADPADKADKADAIQAAFNTAITGLTAGTPNTS NPSSAVDAIDAALKTVASNRATLGATLNRLDFNVNNLKSQSASMASAASQIEDAD MAKEMSEMTKFKILNEAGISMLSQANQTPQMVSKLLQ |
| Flagellin SEQ ID NO: 22 *Bacillus thuringiensis* serovar *konkukian* strain 97-27 | MRIGTNVLSMNARQSLYENEKRMNVAMEHFATGKKLNHASDNPANVAIVTRMHAR ASGMRVAIRNNEDAISMLRTAEAALQTVMNILQRMRDLAVQSANGTNSNKNRDSL NKEFQSLTEQIGYIGETTEFNDLSVFDGQNRPVTLDDIGHTVNVTKHTSPSPTKH DIKISTEQEARAAIRKIEEALQNVSLHRADFGAMINRLQFNIENLNSQSMALTDA ASRIEDADMAQEMSDFLKFKLLTEVALSMVSQANQIPQMVSKLLQS |
| Flagellin SEQ ID NO: 23 *Bacillus thuringiensis* serovar *konkukian* strain 97-27 | MRINTNINSMRTQEYMRQNQAKMSNAMDRLSSGKRINNASDDAAGLAIATRMRAR ESGLGVAANNTQDGMSLIRTADSALNSVSNILLRMRDIANQSANGTNTADNQQAL QKEFGQLKEQISYIADNTEFNDKTLLKADNSVKIQTLDSADTNKQISIDLKGVTL NQLGLDTVNIGSETLSAESLNVAKATMARLVKADQNADPSTFALDVNTAKESFDK IKGFITNKTNVQNVENAFNDYTVADPADKADKADAIQAAFNTAITGLTAGTPNTS NPSSAVDAIDAALKTVASNRATLGATLNRLDFNVNNLKSQSASMASAASQIEDAD MAKEMSEMTKFKILNEAGISMLSQANQTPQMVSKLLQ |
| Flagellin protein FlaA SEQ ID NO: 24 *Bacillus thuringiensis* serovar *thuringiensis* strain IS5056 | MRIGTNVLSMNARQSLYENEKRMNVAMEHLATGKKLNHASDNPANIVIVTRMYAR ASGMRVAIRNNEDAISMLRTAEAALQTVTNILQHMRDFAIQSANGTNSNTNRDSL NKEFQSLTEPIGYIGETTEFNDLSVFDGQNRPITLDDIGHTINMTKHIPPSPTQH DIKISTEQEARAAIRKIEEALQNVSLHRADLGSMINRLQFNIENLNSQSMALIDT ASQVEDADMAQEISDFLKFKLLTAVALSVVSQANQIPQIVSKLLQS |
| Flagellin protein FlaA SEQ ID NO: 25 *Bacillus thuringiensis* serovar *thuringiensis* strain IS5056 | MRINTNINSMRTQEYMRQNQAKMSNAMDRLSSGKRINNASDDAAGLAIATRMRAR ESGLGVAANNTQDGMSLIRTADSAMNSVSNILLRMRDISNQSANGTNTDKNQSAL DKEFAALKDQIDYISKNTEFNDQKLLDGSKKSIAIQTLDNADTNKQIDIQLSNVS TKELKLDTLSIEGSSSKTFTITADDMLAVGTANATAKAKAGTLKGLNVTTGDLTA AKTDVQDFRAAFDKVKGFMGSTEVTNIEKALTKFDGDQSLANAKAIGDALTSDLA TTIAKDQTYSKNVSNASSAIASIDAALESIASNRATLGATLNRLDFNVNNLKSQS SSMASAASQIEDADMAKEMSEMTKFKILNEAGISMLSQANQTPQMVSKLLQ |
| Flagellin B SEQ ID NO: 26 *Bacillus thuringiensis* strain Bt407 | MRINTNINSMRTQEYMRQNQAKMSNAMDRLSSGKRINNASDDAAGLAIATRMRAR ESGLGVAANNTQDGMSLIRTADSAMNSVSNILLRMRDISNQSANGTNTDKNQSAL DKEFAALKDQIDYISKNTEFNDQKLLDGSKKSIAIQTLDNADTNKQIDIQLSNVS TKELKLDTLSIEGSSSKTFTITADDMLAVGTANATAKAKAGTLKGLNVTTGDLTA AKTDVQDFRAAFDKVKGFMGSTEVTNIEKALTKFDGDQSLANAKAIGDALTSDLA TTIAKDQTYSKNVSNASSAIASIDAALESIASNRATLGATLNRLDFNVNNLKSQS SSMASAASQIEDADMAKEMSEMTKFKILNEAGISMLSQANQTPQMVSKLLQ |
| Flagellin SEQ ID NO: 27 *Bacillus thuringiensis* serovar *chinensis* CT-43 | MRINTNINSMRTQEYMRQNQAKMSNAMDRLSSGKRINNASDDAAGLAIATRMRAR ESGLGVAANNTQDGMSLIRTADSAMNSVSNILLRMRDISNQSANGTNTDKNQSAL DKEFAALKDQIDYISKNTEFNDQKLLDGSKKSIAIQTLDNADTNKQIDIQLSNVS TKELKLDTLSIEGSSSKTFTITADDMLAVGTANATAKAKAGTLKGLNVTTGDLTA AKTDVQDFRAAFDKVKGFMGSTEVTNIEKALTKFDGDQSLANAKAIGDALTSDLA TTIAKDQTYSKNVSNASSAIASIDAALESIASNRATLGATLNRLDFNVNNLKSQS SSMASAASQIEDADMAKEMSEMTKFKILNEAGISMLSQANQTPQMVSKLLQ |
| Flagellin SEQ ID NO: 28 *Bacillus thuringiensis* serovar *canadensis* | MTGITINLEIDFFAYYRFSICRKVNIKKWGFLNMRINTNINSMRTQEYMRQNQAK MSNAMDRLSSGKRINNASDDAAGLAIATRMRARESGLGVAANNTQDGISLIRTAD SAMNSVSNILLRMRDLANQSANGTNTNENQAALNKEFDALKEQIDYISTNTEFND KKLLDGSNKTIAVQTLDNADTSKQININLSNVSTKELGLDTLSIGTDKVEKTVYD |

TABLE 1-continued

Conserved flagellin sequences from *Bacillus*

| SEQ ID NO: | Full or Partial Flagellin Coding Sequence - Amino Acid |
|---|---|
| | ATTKAFADLGATGADKAAFDADVTAAMKEFDKVKPFMSADDVKKIETKLEDYNKA<br>NDAGAQTAAQALGKEFATLTKLETTDLKANASGAIASIDTALKNIASNRATLGAT<br>LNRLDFNVNNLKSQSSSMASAASQIEDADMAKEMSEMTKFKILNEAGISMLSQAN<br>QTPQMVSKLLQ |
| Flagellin<br>SEQ ID NO: 29<br>*Bacillus thuringiensis*<br>serovar *galleriae* | MTGITINLEIDFFAYYRFSICRKVNIKKWGFLNMRINTNINSMRTQEYMRQNQAK<br>MSNAMDRLSSGKRINNASDDAAGLAIATRMRARESGLGVAANNTQDGISLIRTAD<br>SAMNSVSNILLRMRDLANQSANGTNTNENQAALNKEFDALKEQIDYISTNTEFND<br>KKLLDGSNKTIAVQTLDNADTSKQININLSNVSTKELGLSTLSIGTDKVEKTVYD<br>ATTKAFADLGAKTGTDKAAFAADVTAAMKEFDKVKPFMSADDVKKIETKLEDYNK<br>ANDAGAEAAAQALGKEFATLTKLETTDLKANASGAIASIDTALKNIASNRATLGA<br>TLNRLDFNVNNLKSQSSSMASAASQIEDADMAKEMSEMTKFKILNEAGISMLSQA<br>NQTPQMVSKLLQ |
| Flagellin N-terminal<br>helical region<br>SEQ ID NO: 30<br>*Bacillus*<br>*weihenstephanensis* | MRINTNINSMRTQEYMRQNQAKMSNAMDRLSSGKRINNASDDAAGLAIATRMRAR<br>ESGLSVAANNTQDGMSLIRTADSAMNSVSNILLRMRDLSNQSANGTNTDENQQAL<br>NKEFAALKDQIDYISKNTEFNDKKLLDGSNKSIAIQTLDNADTTKQINIDLSNVS<br>TDTLNISGLTINGKKDITVTISDKDIANAATDIGKATSAQQGLADLTDTTPAVPD<br>TPAVIGTGTAGNPQFPAVKGTPEIPGSSPAEIAKAVDDFKQAFNKVKGLMSDSAV<br>SAMEQKFATFEKDKSLANAKDIGTAFSAPIAGNITKGEQNASGAIKSIDAALEKI<br>ASNRATLGATLNRLDFNVNNLKSQSSSMASAASQIEDADMAKEMSEMTKFKILNE<br>AGISMLSQANQTPQMVSKLLQ |
| Flagellin<br>SEQ ID NO: 31<br>*Bacillus thuringiensis*<br>serovar *ostriniae* | MTGITINLEIDFFAYYRFSICRKVNIKKWGFLNMRINTNINSMRTQEYMRQNQAK<br>MSNAMDRLSSGKRINNASDDAAGLAIATRMRARESGLGVAANNTQDGMSLIRTAD<br>SALNSVSNILLRMRDIANQSANGTNTGDNQKALDKEFSALKEQIDYISKNTEFND<br>KKLLNGDNKSIAIQTLDNADTAKQININLADSSTKALNIDTLSIAGTTDKTITIT<br>AKDLTDNKTTLDALKTAKDDLAKLDDKSDQATIDKAVDAFKTAFNNVDKNLLSDK<br>AIEGITEKMTAFDGTHTAAAAIGAAYTEPTAADIKKSAPNASGAIKSIDAALETI<br>ASNRATLGATLNRLDFNVNNLKSQSSSMASAASQIEDADMAKEMSEMTKFKILNE<br>AGISMLSQANQTPQMVSKLLQ |
| Flagellin<br>SEQ ID NO: 32<br>*Bacillus thuringiensis* | MRIGTNVLSMNARQSLYENEKRMNVAMEHLATGKKLNHASDNPANVAIVTRMHAR<br>ASGMRVAIRNNEDALSMLRTAEATLQTVANILQRMRDLAVQSSNDTNSNKNRDSL<br>NKEFQSLTEQISYIGETTEFNDLSVFDGQNRPVTLDDIGHTVNVTKHISPSPTQH<br>DIKISTEQEARAAIRKIEEALQNVLLHRADLGAMINRLQFNIENLNSQSMALTDA<br>ASRIEDADMAQEMSDFLKFKLLSEVALSMVSQANQIPQMVSELLQS |
| Flagellin<br>SEQ ID NO: 33<br>*Bacillus thuringiensis* | MRINTNINSMRTQEYMRQNQTKMSNAMDRLSSGKRINNASDDAAGLAIATRMRAR<br>ENGLGVAANNTQDGMSLIRTADSAMNSVSNILLRMRDLANQSANGTNTDDNQKAL<br>DKEFSALKEQIDYISKNTEFNDKKLLNGENKTIAIQTLDNADTTKQININLADSS<br>TSALQIDKLTISGKTTDTTKTQTITVTDDEIKAAKTDIDEFNDAKKALADLKAES<br>APSKGDGSSDDEIKEAVSNFKKSFEKIQKFMNDSDIKTVQTEIEKFDAAAPALDK<br>AKGMGIAFTSAMDPKAGTITKAATRQNASDAIKSIDAALETIASNRATLGATLNR<br>LDFNVNNLKSQSSSMAAAASQIEDADMAKEMSEMTKFKILNEAGISMLSQANQTP<br>QMVSKLLQ |
| Flagellin<br>SEQ ID NO: 34<br>*Bacillus thuringiensis*<br>serovar<br>*pondicheriensis* | MTGITINLEIDFFAYYRFSICRKVNIKKWGFLIMRINTNINSMRTQEYMRQNQTK<br>MSNAMDRLSSGKRINNASDDAAGLAIATRMRARENGLGVAANNTQDGMSLIRTAD<br>SAMNSVSNILLRMRDLANQSANGTNTDDNQKALDKEFSALKEQIDYISKNTEFND<br>KKLLNGENKTIAIQTLDNADTTKQININLADSSTSALQIDKLTISGKTTDTTKTQ<br>TITVTDDEIKAAKTDIDEFNDAKKALADLKAESAPSKGDGSSDDEIKEAVSNFKK<br>SFEKIQKFMNDSDIKTVQTEIEKFDAAAPALDKAKGMGIAFTSAMDPKAGTITKA<br>ATRQNASDAIKSIDAALETIASNRATLGATLNRLDFNVNNLKSQSSSMAAAASQI<br>EDADMAKEMSEMTKFKILNEAGISMLSQANQTPQMVSKLLQ |
| Flagellin B<br>SEQ ID NO: 35<br>*Bacillus thuringiensis*<br>serovar *Berliner* | MSIMRIGTNVLSMNARQSLYENEKRMNVAMEHLATGKKLNHASDNPANIVIVTRM<br>YARASGMRVAIRNNEDAISMLRTAEAALQTVTNILQHMRDFAIQSANGTNSNTNR<br>DSLNKEFQSLTEPIGYIGETTEFNDLSVFDGQNRPITLDDIGHTINMTKHIPPSP<br>TQHDIKISTEQEARAAIRKIEEALQNVSLHRADLGSMINRLQFNIENLNSQSMAL<br>IDTASQVEDADMAQEISDFLKFKLLTAVALSVVSQANQIPQIVSKLLQS |
| Flagellin A<br>SEQ ID NO: 36<br>*Bacillus thuringiensis*<br>serovar *Berliner* | MARITINLEIDFFAYYRFSICRKVNIKKWGFLNMRINTNINSMRTQDYMRQNQAK<br>MSNAMDRLSSGKRINNASDDAAGLAIATRMRARESGLGVAANNTQDGMSLIRTAD<br>SAMNSVSNILLRMRDISNQSANGTNTDKNQSALDKEFAALKDQIDYISKNTEFND<br>QKLLDGSKKSIAIQTLDNADTNKQIDIQLSNVSTKELKLDTLSIEGSSSKTFTIT<br>ADDMLAVGTANATAKAKAGTLKGLNVTTGDLTAAKTDVQDFRAAFDKVKGFMGST<br>EVTNIEKALTKFDGDQSLANAKAIGDALTSDLATTIAKDQTYSKNVSNASSAIAS<br>IDAALESIASNRATLGATLNRLDFNVNNLKSQSSSMASAASQIEDADMAKEMSEM<br>TKFKILNEAGISMLSQANQTPQMVSKLLQ |
| Flagellin<br>SEQ ID NO: 37<br>*Bacillus cereus* strain<br>Q1 | MRIGTNVLSMNARQSLYENEKRMNVAMEHLATGKKLNHASNNPANVAIVTRMHAR<br>ASGMRVAIRNNEDAISMLRTAEAALQTVTNVLQRMRDVAVQSANGTNSSKNRDSL<br>NKEFQSLTEQIGYIDETTEFNDLSVFDGQNRTVTLDDIGHTVNVTKHIPPSPTQH<br>DINISTEQEARAAIRKIEEALQNVSLHRADLGAMINRLQFNIENLNSQSTALTDA<br>ASRIEDADMAQEMSDFLKFKLLTEVALSMVSQANQIPQMVSKLLQS |

TABLE 1-continued

| Conserved flagellin sequences from *Bacillus* | |
|---|---|
| SEQ ID NO: | Full or Partial Flagellin Coding Sequence - Amino Acid |
| Flagellin<br>SEQ ID NO: 38<br>*Bacillus cereus* strain<br>Q1 | MRINTNINSMRTQEYMRQNQAKMSNAMDRLSSGKRINNASDDAAGLAIATRMRAR<br>ESGLSVAADNTQNGMSLIRTADSAMNSVSNILLRMRDIANQSANGTNTDKNQVAL<br>QKEFAALKEQITYIADNTQFNDKNLLNGNQTINIQTLDSHDSTKQIGIDLKSATL<br>EALGIKDLTVGAVGSTEAKNYVDAKEALAKNVAANEFIDAKKALDGNAIAKGYVE<br>AKTAFDDAKPEVKALVSNYTDALAALAKDDTNDDLKKDVADTKALMDANTVAKTY<br>FEAKTAHDGADQAIKDIVTTYDSKLGALDDAANKAISDFDKAKAAFDESPAAKEL<br>VKTMDDAKQAATQNNTANAYLVAKAAAELAPNDADKKAELENATKALEKDDTAKG<br>LVKTYENAKEALNPANAMPLDAVKQIDAALKTVADNRATLGATLNRLDFNVNNLK<br>SQSSAMAASASQIEDADMAKEMSEMTKFKILNEAGISMLSQANQTPQMVSKLLQ |
| Flagellin<br>SEQ ID NO: 39<br>*Bacillus thuringiensis*<br>serovar *morrisoni* | MRIGTNFLSMNARQSLYENEKRMNVAMEHLATGKKLNHASDNPANIAIVTRMHAR<br>ANGMRVAIRNNEDAISMLRTAEAALQTVMNILQRMRDLAIQSANSTNSNKNRDSL<br>NKEFQSLTEQISYIGETTEFNDLSVFDGQNRPVTLDDIGHTVHISKSIPPPSPTQ<br>HDIKISTEQEARAAILKIEEALQSVSLHRADLGAMINRLHFNIENLNSQSMALTD<br>AASRIEDADMAQEMSDFLKFKLLTEVALSMVSQANQIPQMVSKLLQS |
| Flagellin<br>SEQ ID NO: 40<br>Bacillus *thuringiensis*<br>serovar *neoleonensis* | MRINTNINSMRTQEYMRQNQTKMSNAMDRLSSGKRINNASDDAAGLAIATRMRAR<br>ENGLGVAANNTQDGMSLIRTADSALNSVSNILLRMRDIANQSANGTNTSDNQKAL<br>DKEFSALKEQIDYISKNTEFNDKKLLNGDNKSIAIQTLDNADTTKQININLADSS<br>TSALNIDKLSIEGTGNKTITLTAADIAKDKTNIDAVGTAKTALAGLTGTPAAAAI<br>NSAVADFKTAFAKADKNLMSDAQIKSVTDAITAFEADATPDLTKAKAIGTAYTAP<br>AAGDITKASPNASEAIKSIDAALDTIASNRATLGATLNRLDFNVNNLKSQSSSMA<br>SAASQIEDADMAKEMSEMTKFKILNEAGISMLSQANQTPQMVSKLLQ |
| Flagellin<br>SEQ ID NO: 41<br>*Bacillus thuringiensis*<br>serovar *morrisoni* | MTGITINLEIDFFAYYRFSICRKVNIKKWGFLNMRINTNINSMRTQEYMRQNQAK<br>MSNAMDRLSSGKRINNASDDAAGLAIATRMRARESGLGVAANNTQDGMSLIRTAD<br>SALNSVSNILLRMRDIANQSANGTNTGDNQKALDKEFSALKEQIDYISKNTEFND<br>KKLLNGDNKSIAIQTLDNADTAKQININLADSSTKALNIDTLSIAGTTDKTITIT<br>AKDLTDNKATLDALKTAKADLAKLDDKSDQATIDKAVDAFKTAFNNVDKNLLSDK<br>AIEGITDKMTAFDGTHTAAAAIGTAYTEPTAGDITKSAPNASGAIKSIDAALETI<br>ASNRATLGATLNRLDFNVNNLKSQSSSMASAASQIEDADMAKEMSEMTKFKILNE<br>AGISMLSQANQTPQMVSKLLQ |
| Flagellin<br>SEQ ID NO: 42<br>*Bacillus thuringiensis*<br>serovar *morrisoni* | MRINTNINSMRTQEYMRQNQAKMSNAMDRLSSGKRINNASDDAAGLAIATRMRAR<br>ESGLGVAANNTQDGMSLIRTADSALNSVSNILLRMRDIANQSANGTNTGDNQKAL<br>DKEFSALKEQIDYISKNTEFNDKKLLNGDNKSIAIQTLDNADTAKQININLADSS<br>TKALNIDTLSIAGTTDKTITITAKDLTDNKATLDALKTAKADLAKLDDKSDQATI<br>DKAVDAFKTAFNNVDKNLLSDKAIEGITDKMTAFDGTHTAAAAIGTAYTEPTAGD<br>ITKSAPNASGAIKSIDAALETIASNRATLGATLNRLDFNVNNLKSQSSSMASAAS<br>QIEDADMAKEMSEMTKFKILNEAGISMLSQANQTPQMVSKLLQ |
| Flagellin<br>SEQ ID NO: 43<br>*Bacillus thuringiensis*<br>serovar *jegathesan* | MRINTNINSMRTQEYMRQNQAKMSNAMDRLSSGKRINNASDDAAGLAIATRMRAR<br>ESGLGVAANNTQDGMSLIRTADSAMNSVSNILLRMRDIANQSANGTNTNGNQAAL<br>NKEFDALKQQINYISTNTEFNDKKLLDGSNKTIAIQTLDNADTSKKIDIQLADVS<br>TKSLNIDKLKIGGVSKETTDAVGDTFTKLSTTATTDMGALKIEVEAAMKEFDKVK<br>GAMSAEDAKAVTDKLDAFNTAAAATNDAATIAAAKALGAAFDKTKVEMADPNASV<br>AAIDSALENIASNRATLGATLNRLDFNVNNLKSQQSSMASAASQIEDADMAKEMS<br>EMTKFKILNEAGISMLSQANQTPQMVSKLLQ |
| Flagellin<br>SEQ ID NO: 44<br>*Bacillus cereus* stain<br>ATCC 10987 | MRINTNINSMRTQEYMRQNQAKMSNAMDRLSSGKRINNASDDAAGLAIATRMRAR<br>ESGLGVAANNTQDGMALIRTADSAMNSVSNILLRMRDIANQSANGTNTDKNQAAL<br>QKEFGELQKQIDYIAGNTQFNDKNLLDGSNPSISIQTLDSADQSKQISIDLKSAT<br>LEALGIKDLTVGATENTLAKATITAKDAFDAAKDASDAAKKEIDAAAKDTPSKND<br>AQLAKEYIEAKATLATLKPTDATYAAKAAELDAATTALNDNAKVLVDGYEKKLTT<br>TKTKEAEYTAAKEQSTKSTAAADLVTKYETAKSNALGNDIAKEYLEAKTAYEANK<br>NDISSKSRFEAAETELNKDITANKAAKVLVETYEKAKTAGTTEKSLVAVDKIDEA<br>LKTIADNRATLGATLNRLDFNVNNLKSQSASMASAASQIEDADMAKEMSEMTKFK<br>ILNEAGISMLSQANQTPQMVSKLLQ |
| Flagellin<br>SEQ ID NO: 45<br>*Bacillus thuringiensis*<br>serovar *monterrey* | MTGITINLEIDFFAYYRFSICRKVNIKKWGFLIMRINTNINSMRTQEYMRQNQAK<br>MSNAMDRLSSGKRINNASDDAAGLAIATRMRARESGLGVAANNTQDGMSLIRTAD<br>SAMNSVSNILLRMRDLANQSANGTNTNENQAALNKEFDALKEQINYISTNTEFND<br>KKLLDGSNKTIAIQTLDNADTSKKIDIKLADVSTESLKIDKLKIGGVSKETTDAV<br>SETFTKLSTTKTTDKDALKAEVEAAMKEFDKVKGAMSTEDAKAVTDKLGLFNTAA<br>AGTDDTAIATAAKNLGAAFDKTKVNMADPNASVAAIDSALENIASNRATLGATLN<br>RLDFNVNNLKSQQSSMASAASQIEDADMAKEMSEMTKFKILNEAGISMLSQANQT<br>PQMVSKLLQ |
| Flagellin<br>SEQ ID NO: 46<br>*Bacillus cereus* strain<br>NC7401 | MRIGTNVLSLNARQSLYENEKRMNVAMEHLATGKKLNNASDNPANIAIVTRMHAR<br>ASSMRVAIRNNEDAISMLRTAEAALQTVTNVLQRMRDLAVQSANDTNSNKNRDSL<br>NKEFQSLTEQIGYIDETTDFNDLSVFDGQNRTVTLDDIGHTVNVTKHIPPSPTQH<br>DINISTEQEARAAIRKIEEALQNVSLHRADLGAMINRLQFNIENLNSQSTALTDA<br>ASRIEDADMAQEMSDFLKFKLLTEVALSMVSQANQIPQMVSKLLQS |

TABLE 1-continued

Conserved flagellin sequences from *Bacillus*

| SEQ ID NO: | Full or Partial Flagellin Coding Sequence - Amino Acid |
|---|---|
| Flagellin<br>SEQ ID NO: 47<br>*Bacillus cereus* strain<br>NC7401 | MRINTNINSMRTQEYMRQNQAKMSNAMDRLSSGKRINNASDDAAGLAIATRMRAR<br>ESGLGVASNNTQDGMSLIRTADSALNSVSNILLRMRDLANQSANGTNTNENKAAM<br>QKEFGELKEQIKYIAENTQFNDQHLLNADKGITKEIAIQTLDSDSDSKQIKIKLQ<br>GSSLEALDIKDLQIGNTELAQKDLDLLNATMDRLDATVPGTRDVDVQAAKDAFDK<br>VKGFYTNSDSVKAIERAFEDYATASTAGTAKADAATAIKAAFDLAANKVGKPATG<br>GAQGSANSLGAITKIDAALKTVADNRATLGATLNRLDFNVNNLKSQASSMAAAAS<br>QVEDADMAKEMSEMTKFKILNEAGISMLSQANQTPQMVSKLLQ |
| Flagellin (A-type)<br>SEQ ID NO: 48<br>*Bacillus cereus* strain<br>AH820 | MRINTNINSLRTQEYMRQNQAKMSNSMDRLSSGKRINNASDDAAGLAIATRMRAR<br>ESGLNVAANNTQDGMSLIRTADSALGSVSNILLRMRDLANQSANGTNTSDNQAAM<br>QKEFAELQKQITYIADNTQFNDKNLLQSNSSINIQTLDSSDGNQQIGIELKSASL<br>KSLGIEDLAIGASVNPLAKATVEASEAYDKAKADTAAFAKSIADTAATGTGAAKA<br>DAAAVDAYIKEADPTAKGNLYTGLTADQKKLADEHNTLKAAEDGKKAELTMATTK<br>STADGTAKGLVDAYDNAKSDAMNDPKAKAYLEAKMAYEKDTSNVANKQKLDSTKE<br>AMEKDPASKDLVVKLDAAKAAATNGTPLDAVSKIDAALKTVADNRATLGATLNRL<br>DFNVNNLKSQSSSMASAASQIEDADMAKEMSEMTKFKILNEAGISMLSQANQTPQ<br>MVSKLLQ |
| Flagellin<br>SEQ ID NO: 49<br>Bacillus *cereus* AH187 | MRINTNINSMRTQEYMRQNQAKMSNAMDRLSSGKRINNASDDAAGLAIATRMRAR<br>ESGLGVASNNTQDGMSLIRTADSALNSVSNILLRMRDLANQSANGTNTNENKAAM<br>QKEFGELKEQiKYIAENTQFNDQHLLNADKGITKEIAIQTLDSDSDSKQIKIKLQ<br>GSSLEALDIKDLQIGNTELAQKDLDLLNATMDRLDATVPGTRDVDVQAAKDAFDK<br>VKGFYTNSDSVKAIERAFEDYATASTAGTAKADAATAIKAAFDLAANKVGKPATG<br>GAQGSANSLGAITKIDAALKTVADNRATLGATLNRLDFNVNNLKSQASSMAAAAS<br>QVEDADMAKEMSEMTKFKILNEAGISMLSQANQTPQMVSKLLQ |
| Flagellin<br>SEQ ID NO: 50<br>*Bacillus cereus* | MDFFAYYRFSICRKVNIKKWGFFYMRINTNINSMRTQEYMRQNQAKMSNAMDRLS<br>SGKRINNASDDAAGLAIATRMRARESGLGVASNNTQDGMSLIRTADSALNSVSNI<br>LLRMRDLANQSANGTNTNENKAAMQKEFGELKEQIKYIAENTQFNDQHLLNADKG<br>ITKEIAIQTLDSDSDSKQIKIKLQGSSLEALDIKDLQIGNTELAQKDLDLLNATM<br>DRLDATVPGTRDVDVQAAKDAFDKVKGFYTNSDSVKAIERAFEDYATASTAGTAK<br>ADAATAIKAAFDLAANKVGKPATGGAQGSANSLGAITKIDAALKTVADNRATLGA<br>TLNRLDFNVNNLKSQASSMAAAASQVEDADMAKEMSEMTKFKILNEAGISMLSQA<br>NQTPQMVSKLLQ |
| Flagellin protein Fla<br>SEQ ID NO: 51<br>*Bacillus cereus* | MRINTNINSMRTQEYMRQNQAKMSNAMDRLSSGKRINNASDDAAGLAIATRMRAR<br>ESGLGVAANNTQDGMSLIRTADSALNSVSNILLRMRDIANQSANGTNTGDNQKAL<br>DKEFSALKEQIDYISKNTEFNDKKLLNGENTSIAIQTLDSADTAKQININLADSS<br>TSALLIDKLSISGAGAGTALAGVATADINAAGTKQAALSGLTGSKTTDELDDAVK<br>EFKTEFDKVKSGLSAENADKITAAMDKYTNNKTLDNAKAIGDLYKTMAPADSTVV<br>GTAGTKGQALIDLNATATGDTAQKRQVAVDAFKDDFDKIKGGLNAQDAAKVTAAL<br>DKFNKADGSGNTLENAQEIGKVFAEVAAGSTKSNASDAIKSIDKALETIASNRAT<br>LGATLNRLDFNVNNLKSQSSSMASAASQIEDADMAKEMSEMTKFKILNEAGISML<br>SQANQTPQMVSKLLQ |
| Flagellin<br>SEQ ID NO: 52<br>*Bacillus thuringiensis*<br>Strain HD-771<br>[51] | MRINTNINSMRTQEYMRQNQTKMSNAMDRLSSGKRINNASDDAAGLAIATRMRSR<br>EGGLNVAARNTEDGMSLIRTADSALNSVSNILLRMRDLANQSASETNTSKNQAAM<br>QKEFDQLKEQIQYIADNTEFNDKKLLDGSNSTINIQTLDSHDKNKQITISLDSAS<br>LKNLDITDLAIGSNTVNKNDLDTLNNSMKRLETAAADAAVQAQDVTDAKNAFNKV<br>KSGYTPAEVEKMEDAFKAYDKVVADPAKTDALLKAAAEKINTEFKTLTAPTATAF<br>DPSSSVEKIDKAIETIASSRATLGATLNRLDFNVTNLKSQENSMAASASQIEDAD<br>MAKEMSEMTKFKILNEAGISMLSQANQTPQMVSKLLQ |
| Flagellin<br>SEQ ID NO: 53<br>*Bacillus thuringiensis*<br>serovar *sotto*<br>[52] | MRINTNINSMRTQEYMRQNQTKMSNAMDRLSSGKRINNASDDAAGLAIATRMRSR<br>EGGLNVAARNTEDGMSLIRTADSALNSVSNILLRMRDLANQSASETNTSKNQAAM<br>KEFDQLKEQIQYIADNTEFNDKKLLDGSNSTINIQTLDSHDKNKQITISLDSASL<br>KNLDITQDLAIGSNTVNKNDLDTLNNSMKRLETAAADAAVQAQDVTDAKNAFNKV<br>KSGYTPAEVEKMEDAFKAYDKVVADPAKTDALLKAAAEKINTEFKTLTAPTATAF<br>DPSSSVEKIDKAIETIASSRATLGATLNRLDFNVTNLKSQENSMAASASQIEDAD<br>MAKEMSEMTKFKILNEAGISMLSQANQTPQMVSKLLQ |
| Flagellin<br>SEQ ID NO: 54<br>*Bacillus thuringiensis*<br>serovar *Novosibirsk* | MGVLNMRINTNINSMRTQEYMRQNQAKMSNAMDRLSSGKRINNASDDAAGLAIAT<br>RMRARENGLGVAANNTQDGMSLIRTADSALNSVSNILLRMRDIANQSANGTNTGD<br>NQKALDKEFSALKEQIDYISKNTEFNDKKLLNGDNKSIAIQTLDNADTSKQINID<br>LANTSTSSLKIDKLSIEGKGNQTIAITAADIAKDTNIAALTSAQGKLAALTGTPA<br>PAALTTAVDEFKAAFEKVDKNLMSDTQITGIENAIKAYDGATTKTLALAQAVGTA<br>YTAPTPGDITKELPNASSSIKSIDAALETIASNRATLGATLNRLDFNVNNLKSQA<br>SSMASAASQIEDADMAKEMSEMTKFKILNEAGISMLSQANQTPQMVSKLLQ |
| Flagellin<br>SEQ ID NO: 55<br>*Bacillus thuringiensis*<br>serovar *londrina* | MGVLNMRINTNINSMRTQEYMRQNQAKMSNAMDRLSSGKRINNASDDAAGLAIAT<br>RMRARESGLGVAANNTQDGISLIRTADSAMNSVSNILLRMRDLANQSANGTNTSE<br>NQAALDKEFGALKEQINYISTNTEFNDKKLLDGSNETIAIQTLDNADEGKKIDIK<br>LANVSTDSLKIDKLTIGGAAQKTVDAVADKFNALKTTTTTDKAAIQTEVDAVMKE |

TABLE 1-continued

Conserved flagellin sequences from *Bacillus*

| SEQ ID NO: | Full or Partial Flagellin Coding Sequence - Amino Acid |
|---|---|
| | FDKVKGSMSAEDAKVITDKLKDYNDAADTDTAKATAAKDLGAAFDKTKVNIANPN<br>AAVAAIDSALENIASNRATLGATLNRLDFNVNNLKSQSSSMASAASQIEDADMAK<br>EMSEMTKFKILNEAGISMLSQANQTPQMVSKLLQ |
| Flagellin<br>SEQ ID NO: 56<br>*Bacillus cereus* strain<br>E33L | MRIGTNVLSMNARQSLYENEKRMNVAMEHLATGKKLNHASNNPANIAIVTRMHAR<br>ASGMRVAIRNNEDALSMLRTAEAALQTVTNILQRMRDLAVQSANVTNSNKNRNSL<br>NKEFQSLTEQISYIGETTEFNDLSVFDGQNRPVTLDDIGYTVNVTKHTPPSPTQH<br>DIKISTEQEARAAIRKIEEALQNVSLHRADLGSMMNRLQFNIENLNSQSMALTDA<br>ASRIEDADMAQEMSDFLKFKLLTEVALSMVSQANQIPQMVSKLLQS |
| Flagellin<br>SEQ ID NO: 57<br>*Bacillus cereus* strain<br>E33L | MRINTNINSMRTQEYMRQNQAKMSTAMDRLSSGKRINNASDDAAGLAIATRMRAR<br>ESGLGVAANNTQDGISLIRTADSAMNSVSNILLRMRDLANQSANGTNTDKNQGAL<br>DKEFAALKEQIDYISKNTEFNDKKLLDGSNKAIAIQTLDSDDKGKQIDISLSDTS<br>TTALKINNLSIAANGLGIGSGKELVGVADNTIANASAEALKKLDGTTGDTDVKRS<br>NAVKAFTDQYKDLKVAMNAKDVETIDAAIKKFEGANTLENAQAIGAAFEGAAKAT<br>LTTDINNATLTSKALSDLDTDSTTETRKAAMKDFVAAFDKVKGSMNSSDVTKISD<br>AIDRFSKTDDSGNTLEAARAIGDAFKAATTNGKTSTATDANSAIKAIDEALETIA<br>SNRATLGATLNRLDFNVNNLKNQASSMASAASQVEDADMAKEMSEMTKFKILNEA<br>GISMLSQANQTPQMVSKLLQ |
| Flagellin<br>SEQ ID NO: 58<br>*Bacillus cereus*<br>strain FRI-35 | MRINTNINSMRTQEYMRQNQAKMSTAMDRLSSGKRINNASDDAAGLAIATRMRAR<br>ESGLGVAANNTQDGISLIRTADSAMNSVSNILLRMRDLANQSANGTNTDKNQAAL<br>DKEFNALKEQIDYISKNTEFNDKKLLDGSNKSIAVQTLDNADTSKQININLSNTS<br>TKALEINSLTISGTTPIAGKNETSKITAEQMTAASDALEKFKTAQEGLANLTEPT<br>KGSDGKPEAGTGSSNEDIVKAVKAFKEAFKNIQPLMSDTDITTVQNKIDLFDEDA<br>PDLSAAKLIGTTFEESMKPVADKEITKAAVKPNASDAIAAIDAALTKVADNRATL<br>GATLNRLDFNVNNLKSQASSMASAASQVEDADMAKEMSEMTKFKILNEAGISMLS<br>QANQTPQMVSKLLQ |
| Flagellin<br>SEQ ID NO: 59<br>*Bacillus cereus*<br>strain FRI-35 | MRIGTNVLSLNARQSLYENEKRMNVAMEHLATGKKLNNASDNPANIAIVTRMHAR<br>ASGMRVAIRNNEDAISMLRTAEAALQTVTNVLQRMRDLAVQSANGTNSNKNRDSL<br>NKEFQSLTEQIGYIDETTEFNNLSVFDGQNRPVTLDDIGHTVNVTKHIPPFPTQH<br>DINISTEQEARAAIRKIEEALQNVSLHRADLGAMINRLQFNIENLNSQSTALTDA<br>ASRIEDADMAQEMSDFLKFKLLTEVALSMVSQANQVPQMVSKLLQS |
| Flagellin<br>SEQ ID NO: 60<br>*Bacillus thuringiensis* | MRINTNINSMRTQEYMRQNQAKMSNAMDRLSSGKRINNASDDAAGLAIATRMRAH<br>ESGLSVAARNTSDGISLIRTADSALQSVSNILLRMRDIANQTANGTNKDTDIEAL<br>GKEFAALKEQITYVSDNTKFNGRELLKGGDDINIQTYDGSDESQQIKIKISELDL<br>SSLDTGEVTDSDTARGTVSTLDDAITNIASKRAELGATLNRLDYNTQNVNSEAAS<br>MAASASQIEDADMAKEMSEMTKFKILSEAGISMLSQANQTPQMVSKLLQ |
| Flagellin<br>SEQ ID NO: 61<br>*Bacillus cereus strain*<br>ATCC 4342 | MRINTNINSMRTQEYMRQNQAKMSNAMDRLSSGKRINNASDDAAGLAIATRMRAH<br>ESGLSVAARNTSDGISLIRTADSALQSVSNILLRMRDIANQTANGTNKDTDIEAL<br>GKEFAALKEQITYVSDNTKFNGRELLKGGDDINIQTYDGSDESQQIKIKISELDL<br>SSLDTGEVTDSDTARGTVSTLDDAITNIASKRAELGATLNRLDYNTQNVNSEAAS<br>MAASASQIEDADMAKEMSEMTKFKILSEAGISMLSQANQTPQMVSKLLQ |
| Flagellin<br>SEQ ID NO: 62<br>*Bacillus thuringiensis* | MRIGTNFLSMNARQSLYENEKRMNVAMEHLATGKKLNHASDNPANIAIVTRMHAR<br>ANGMRVAIRNNEDAISMLRTAEAALQTVMNILQRMRDLAIQSANSTNSNKNRDSL<br>NKEFQSLTEQISYIGETTEFNDLSVFDGQNRPVTLDDIGHTVHISKSIPPPSPTQ<br>HDIKISTEQEARAAILKIEEALQSVSLHRADLGAMINRLHFNIENLNSQSMALTD<br>AASRIEDADMAQEMSDFLKFKLLTEVALSMVSQANQIPQMVSKLLQS |
| Flagellin<br>SEQ ID NO: 63<br>*Bacillus thuringiensis* | MRINTNINSMRTQEYMRQNQAKMSNAMDRLSSGKRINNASDDAAGLAIATRMRAR<br>ESGLGVAANNTQDGMSLIRTADSALNSVSNILLRMRDIANQSANGTNTGDNQKAL<br>DKEFSALKEQIDYISKNTEFNDKKLLNGDNKSIAIQTLDNADTAKQININLADSS<br>TKALNIDTLSIAGTTDKTITITAKDLTDNKATLDALKTAKADLAKLDDKSDQATI<br>DKAVDAFKTAFNNVDKNLLSDKAIEGITDKMTAFDGTHTAAAAIGTAYTEPTAGD<br>ITKSAPNASGAIKSIDAALETIASNRATLGATLNRLDFNVNNLKSQSSSMASAAS<br>QIEDADMAKEMSEMTKFKILNEAGISMLSQANQTPQMVSKLLQ |
| Flagellin<br>SEQ ID NO: 64<br>*Bacillus aryabhattai* | MRINHNITALNTYRQFNNANNAQAKSMEKLSSGQRINSASDDAAGLAISEKMRGQ<br>IRGLDQASRNAQDGVSLIQTAEGALNETHDILQRMRELVVQAGNGTNKTEDLDAI<br>QDEIGSLIEEIGGETDSKGISDRAQFNGRNLLDGSLDITLQVGANAGQQVNLKIG<br>DMSAGALGADTDSDGAADAFVNSINVKDFATTSFDDQLAIIDGAINQVSEQRSGL<br>GATQNRLDHTINNLSTSSENLTASESRIRDVDYALAA |
| Flagellin<br>SEQ ID NO: 65<br>*Bacillus manliponensis* | MRINTNINSMRTQEYMRQNQDKMNTSMNRLSSGKQINSASDDAAGLAIATRMRAK<br>EGGLNVGAKNTQDGMSALRTMDSALNSVSNILLRMRDLATQSATGTNQGNDRESL<br>DLEFQQLTEEITHIAEKTNFNGNALLSGSGSAINVQLSDAAEDKLTIAAIDATAS<br>TLLKGAVDVKTEDKADAAITKIDQAIQDIADNRATYGSQLNRLDHNLNNVNSQAT<br>NMAAAASQIEDADMAKEMSEMTKFKILSEAGVSMLSQANQTPQMVSKLLQ |
| Flagellin<br>SEQ ID NO: 66<br>*Lysinibacillus* sp. strain | MRIGSWTATGMSIVNHMNRNWNAASKSMLRLSSGYRINSAADDAAGLAISEKMRG<br>QIRGLTMASKNIMDGVSLIQTAEGALNETHAIVQRMRELAVQAATDTNTDDDRAK<br>LDLEFQELKKEIDRISTDTEFNTRTLLNGDYKDNGLKIQVGANSGQAIEVKIGDA |

TABLE 1-continued

Conserved flagellin sequences from *Bacillus*

| SEQ ID NO: | Full or Partial Flagellin Coding Sequence - Amino Acid |
|---|---|
| BF-4 | GLAGIGLSTESIATREGANAALGKLDEATKNVSMERSRLGAYQNRLEHAYNVAEN<br>TAINLQDAESRIRDVDIAKEMMNMVKSQILAQVGQQVLAMHMQQAQGILRLLG |
| Flagellin<br>SEQ ID NO: 67<br>*Lysinibacillus* sp. strain<br>13S34_air | MKIGSWTATGMSIVNHMNRNWNAASKSMLRLSSGYRINSAADDAAGLAISEKMRG<br>QIRGLTMASKNIMDGVSLIQTAEGALNETHAIVQRMRELAVQAATDTNTDDDRAK<br>LDLEFQELKKEIDRISTDTAFNTRTLLNGDYKDNGLKIQVGANSGQAIEVKIGDA<br>GLAGIGLSTESIATREGANAALGKLDEATKNVSMERSRLGAYQNRLEHAYNVAEN<br>TAINLQDAESRIRDVDIAKEMMHMVKSQILAQVGQQVLAMHIQQAQGILRLLG |
| Flagellin<br>SEQ ID NO: 68<br>*Paenibacillus* sp. strain<br>HW567 | MIISHNLTALNTMNKLKQKDLAVSKSLGKLSSGLRINGASDDAAGLAISEKMRGQ<br>IRGLNQASRNIQDGISLIQVADGAMQEIHSMLQRMNELAVQASNGTYSGSDRLNI<br>QSEVEQLIEEIDEIAGNTGFNGIKLLNGNNEKTEKTEKTGSVVSVNNPPNNKLIT<br>ISSPVGTSVSEILNNLLTVFNEAKNGQVGDSDSKRVSSKFTLSINNDELSIVCDT<br>GDGFLLSGGSPNLFYQGYIGGSYKYKFTEFINENDFINIMDIGGANGGDTLKFNF<br>SSISKEPEEQKEQKGLTLQIGANSGETLNIKLPNVTTSAIGISSIDVSTIPNAES<br>SLSSISAAIDKVSAERARMGAYQNRLEHSRNNVVTYAENLTAAESRIRDVDMAKE<br>MMELMKNQIFTQAGQAMLLQTNTQPQAILQLLK |
| Flagellin<br>SEQ ID NO: 69<br>*Bacillus anthracis* | MRINTNINSMRTQEYMRQNQAKMSNAMDRLSSGKRINNASDDAAGLAIATRMRAR<br>ESGLGVAANNTQDGMSLIRTADSAMNSVSNILLRMRDLANQSANGTNTKENQDAL<br>DKEFGALKEQIDYISKNTEFNDKKLLNGDNKSIAIQTLDNADTAKQININLADSS<br>TKALNIDSLTISGSKDATITITAEDITAASAEITAAKGARTALANLKDTPADPTK<br>DPAASTPAEIKAAVDDFKGKFEKIKGLMNDTDVKAVEEKIKEFETTSTLAKAQAI<br>GTAFTTGMEPKAGNITKNVPAASSSIKAIDSALETIASNRATLGATLNRLDFNVN<br>NLKSQSSAMASAASQIEDADMAKEMSEMTKFKILNEAGISMLSQANQTPQMVSKL<br>LQ |
| Flagellin<br>SEQ ID NO: 70<br>*Bacillus anthracis* | MQKSQYKKMGVLKMRINTNINSMRTQEYMRQNQDKMNVSMNRLSSGKRINSAADD<br>AAGLAIATRMRARQSGLEKASQNTQDGMSLIRTAESAMNSVSNILTRMRDIAVQS<br>SNGTNTAENQSALQKEFAELQEQIDYIAKNTEFNDKNLLAGTGAVTIGSTSISGA<br>EISIETLDSSATNQQITIKLANTTAEKLGIDATTSNISISGAASALAAISALNTA<br>LNTVAGNRATLGATLNRLDRNVENLNNQATNMASAASQIEDADMAKEMSEMTKFK<br>ILNEAGISMLSQANQTPQMVSKLLQ |
| Flagellin<br>SEQ ID NO: 71<br>*Bacillus anthracis* | MRINTNINSMRTQEYMRQNQDKMNVSMNRLSSGKRINSAADDAAGLAIATRMRAR<br>QSGLEKASQNTQDGMSLIRTAESAMNSVSNILTRMRDIAVQSSNGTNTAENQSAL<br>QKEFAELQEQIDYIAKNTEFNDKNLLAGTGAVTIGSTSISGAEISIETLDSSATN<br>QQITIKLANTTAEKLGIDATTSNISISGAASALAAISALNTALNTVAGNRATLGA<br>TLNRLDRNVENLNNQATNMASAASQIKDADKAKEMSEMTKFKILNEAGISMLSQA<br>NQTPQMVSKLLQ |
| Flagellin<br>SEQ ID NO: 72<br>*Bacillus anthracis* | MRINTNINSMRTQEYMRQNQDKMNVSMNRLSSGKRINSAADDAAGLAIATRMRAR<br>QSGLEKASQNTQDGMSLIRTAESAMNSVSNILTRMRDIAVQSSNGTNTAENQSAL<br>QKEFAELQEQIDYIAKNTEFNDKNLLAGTGAVTIGSTSISGAEISIETLDSSATN<br>QQITIKLANTTAEKLGIDATTSNISISGAASALAAISALNTALNTVAGNRATLGA<br>TLNRLDRNVENLNNQATNMASAASQIEDADMAKEMSEMTKFKILNEAGISMLSQA<br>NQTPQMV |
| Flagellin<br>SEQ ID NO: 73<br>*Bacillus anthracis*<br>strain H9401 | MNVSMNRLSSGKRINSAADDAAGLAIATRMRARQSGLEKASQNTQDGMSLIRTAE<br>SAMNSVSNILTRMRDIAVQSSNGTNTAENQSALQKEFAELQEQIDYIAKNTEFND<br>KNLLAGTGAVTIGSTSISGAEISIETLDSSATNQQITIKLANTTAEKLGIDATTS<br>NISISGAASALAAISALNTALNTVAGNRATLGATLNRLDRNVENLNNQATNMASA<br>ASQIEDADMAKEMSEMTKFKILNEAGISMLSQANQTPQMVSKLLQ |
| Flagellin<br>SEQ ID NO: 74<br>*Bacillus megaterium*<br>strain WSH-002 | MRINHNITALNTYRQFNNANNAQAKSMEKLSSGQRINSASDDAAGLAISEKMRGQ<br>IRGLDQASRNAQDGVSLIQTAEGALNETHDILQRMRELVVQAGNGTNKTEDLDAI<br>QDEIGSLIEEIGGEADSKGISDRAQFNGRNLLDGSLDITLQVGANAGQQVNLKIG<br>DMSAGALGADTNSDGAADAFVNSINVKDFTATSFDDQLAIIDGAINQVSEQRSGL<br>GATQNRLDHTINNLSTSSENLTASESRIRDVDYALAA |
| Flagellin<br>SEQ ID NO: 75<br>*Aneurinibacillus* sp.<br>XH2 | MRINHNLPALNAYRNLAQNQIGTSKILERLSSGYRINRASDDAAGLAISEKMRGQ<br>IRGLEQGQRNTMDGVSLIQTAEGALQEIHEMLQRMRELAVQAANGTYSDKDKKAI<br>EDEINQLTAQIDQIAKTTEFNGIQLIGDSDSTSLQDVKIQYGPKKEDSLTLELTT<br>QPEADPPFAAGCKADKASLKIDNVDVISDPEGAIETFKAAIDQVSRIRSYFGAIQ<br>NRLEHVVNNLSNYTENLTGAESRIRDADMAKEMTEFTRFNIINQSATAMLAQANQ<br>LPQGVLQLLKG |

N- and C-Terminal Conserved Regions of Flagellin

The flagellin or flagellin-associated polypeptide can comprise a truncated N-terminal polypeptide and an amino acid sequence of the truncated N-terminal polypeptide can comprise SEQ ID NO: 76, 78, 80, 82, 84, 86, 88, 90, 92, 94, 96, 98, 100, 102, 104, 106, 108, 109, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 752, or any combination thereof.

The flagellin or flagellin-associated polypeptide can comprise a truncated C-terminal polypeptide and an amino acid sequence of the truncated C-terminal polypeptide can comprise SEQ ID NO: 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 141, 143, 145, 147, 149, 151, 153, 155, 157, 159, 161, 163, 165, 167, 169, 171, 173, 175, 177, 179, 181, 183, 185, 187, 189, 191, 201, 203, 205, 207, 209, 211, 213, 215, 217, 219, 221, 223, 225, or any combination thereof.

N-terminal and C-terminal conserved regions were identified from full length flagellin sequences from diverse strains of *Bacillus* spp. and other Eubacteria (Table 2). Conserved N- and C-terminal domains were identified using BLAST multiple alignment software and assigned functional annotations based on individual hits searching against *Bacillus* and other Eubacterial bacterial databases. The start site for the N-terminal region of the coding sequences is bolded methionine (M). The conserved domains are provided as amino acid sequences N-terminus (left column) and C-terminus (right column).

TABLE 2

N- and C-terminal conserved regions of flagellins

| SEQ ID NO: | Conserved N-terminus | Conserved C-terminus |
|---|---|---|
| Flagellin<br>N-SEQ ID NO: 76<br>C-SEQ ID NO: 77<br>*Bacillus thuringensis*<br>strain 4Q7<br>[CDS of SEQ ID NO: 1] | GFLN**M**RINTNINSMRTQEYMRQNQAKM<br>SNAMDRLSSGKRINSASDDAAGLAIAT<br>RMKAREGGLNVAGRNTQDGMSLIRTAD<br>SALNSVSNILLRMRDLANQSANGTNTK<br>GNQASLQKEFAQLTEQIDYIAKNTQFN<br>DQQLLGTADKKIKIQTL | IDAAITTVAGQRATLGATLN<br>RFEFNANNLKSQETSMADAA<br>SQIEDADMAKEMSEMTKFKI<br>LNEAGISMLSQANQTPQMVS<br>KLLQ |
| Flagellin<br>N-SEQ ID NO: 78<br>C-SEQ ID NO: 79<br>*Bacillus thuringiensis*,<br>strain HD1002<br>[CDS of SEQ ID NO: 2] | GFLN**M**RINTNINSMRTQEYMRQNQAKM<br>SNAMDRLSSGKRINSASDDAAGLAIAT<br>RMKAREGGLNVAGRNTQDGMSLIRTAD<br>SALNSVSNILLRMRDLANQSANGTNTK<br>GNQASLQKEFAQLTEQIDYIAKNTQFN<br>DQQLLGTADKKIKIQTL | IDAAITTVAGQRATLGATLN<br>RFEFNANNLKSQETSMADAA<br>SQIEDADMAKEMSEMTKFKI<br>LNEAGISMLSQANQTPQMVS<br>KLLQ |
| Flagellin<br>N-SEQ ID NO: 80<br>C-SEQ ID NO: 81<br>*Bacillus thuringiensis*,<br>strain HD-789<br>[CDS of SEQ ID NO: 3] | GFLN**M**RINTNINSMRTQEYMRQNQAKM<br>SNAMDRLSSGKRINSASDDAAGLAIAT<br>RMKAREGGLNVAGRNTQDGMSLIRTAD<br>SALNSVSNILLRMRDLANQSANGTNTK<br>GNQASLQKEFAQLTEQIDYIAKNTQFN<br>DQQLLGTADKKIKIQTL | IDAAITTVAGQRATLGATLN<br>RFEFNANNLKSQETSMADAA<br>SQIEDADMAKEMSEMTKFKI<br>LNEAGISMLSQANQTPQMVS<br>KLLQ |
| Flagellin<br>N-SEQ ID NO: 82<br>C-SEQ ID NO: 83<br>*Bacillus cereus*<br>strain G9842<br>[CDS of SEQ ID NO: 4] | GFLN**M**RINTNINSMRTQEYMRQNQAKM<br>SNAMDRLSSGKRINSASDDAAGLAIAT<br>RMKAREGGLNVAGRNTQDGMSLIRTAD<br>SALNSVSNILLRMRDLANQSANGTNTK<br>GNQASLQKEFAQLTEQIDYIAKNTQFN<br>DQQLLGTADKKIKIQTL | IDAAITTVAGQRATLGATLN<br>RFEFNANNLKSQETSMADAA<br>SQIEDADMAKEMSEMTKFKI<br>LNEAGISMLSQANQTPQMVS<br>KLLQ |
| Flagellin<br>N-SEQ ID NO: 84<br>C-SEQ ID NO: 85<br>*Bacillus thuringiensis*<br>*serovar indiana*<br>strain HD521<br>[CDS of SEQ ID NO: 5] | GFLN**M**RINTNINSMRTQEYMRQNQAKM<br>SNSMDRLSSGKRINSAADDAAGLAIAT<br>RMKAREGGLNVAARNTQDGMSLIRTAD<br>SALNSVSNILLRMRDLANQSATGTNTT<br>KNQVALNKEFAALKEQITYIADNTQFN<br>DKNLLKSTQEIKIQTL | QLDAALTKVADNRATLGATL<br>NRLDFNVNNLKSQENSMAAS<br>ASQIEDADMAKEMSEMTKFK<br>ILNEAGISMLSQANQTPQMV<br>SKLLQ |
| Flagellin<br>N-SEQ ID NO: 86<br>C-SEQ ID NO: 87<br>*Bacillus thuringiensis*<br>strain CTC<br>[CDS of SEQ ID NO: 6] | WGFLI**M**RINTNINSMRTQEYMRQNQAK<br>MSNSMDRLSSGKRINNASDDAAGLAIA<br>TRMRARESGLGVAADNTQNGMSLIRTA<br>DSAMNSVSNILLRMRDIANQSANGTNT<br>NENKSALQKEFAQLQKQITYIAENTQF<br>NDKNLLNEDSEVKIQTLDS | AIAAIDAALTKVADNRATLG<br>ATLNRLDFNVNNLKSQSSSM<br>ASAASQIEDADMAKEMSEMT<br>KFKILNEAGISMLSQANQTP<br>QMVSKLLQ |
| Flagellin<br>N-SEQ ID NO: 88<br>C-SEQ ID NO: 89<br>*Bacillus thuringiensis*<br>*serovar yunnanensis*<br>strain IEBC-T20001<br>[CDS of SEQ ID NO: 7] | GFLN**M**RINTNINSMRTQEYMRQNQAKM<br>SNAMDRLSSGKRINNASDDAAGLAIAT<br>RMRARENGLGVAANNTQDGMSLIRTAD<br>SAMNSVSNILLRMRDLANQSANGTNTD<br>DNQKALDKEFSALKEQIDYISKNTEFN<br>DKKLL | RATLGATLNRLDFNVNNLKS<br>QSSSMAAAASQIEDADMAKE<br>MSEMTKFKILNEAGISMLSQ<br>AN |
| Flagellin<br>N-SEQ ID NO: 90<br>C-SEQ ID NO: 91<br>*Bacillus thuringiensis*<br>*serovar tolworthi*<br>[CDS of SEQ ID NO: 8] | GFLN**M**RINTNINSMRTQEYMRQNQAKM<br>SNAMDRLSSGKRINNASDDAAGLAIAT<br>RMRARENGLGVAANNTQDGMSLIRTAD<br>SALQSVSNILLRMRDLANQSANGTNTD<br>ENKAAMEKEFGQLKDQIKYITDNTQFN<br>DKNLLDA | IDAALKTVADNRATLGATLN<br>RLDFNVNNLKSQSASMASAA<br>SQIEDADMAKEMSEMTKFKI<br>LNEAGISMLSQANQTPQMVS<br>KLLQ |
| Flagellin<br>N-SEQ ID NO: 92<br>C-SEQ ID NO: 93<br>*Bacillus cereus*<br>strain FM1<br>[CDS of SEQ ID NO: 9] | MGVLN**M**RINTNINSMRTQEYMRQNQAK<br>MSNSMDRLSSGKRINNASDDAAGLAIA<br>TRMRARESGLGVAANNTQDGMSLIRTA<br>DSAMNSVSNILLRMRDIANQSANGTNT<br>DKNQVALQKEFGELQKQIDYIAKNTQF<br>ND | RATLGATLNRLDFNVNNLKS<br>QQSSMASAASQVEDADMAKE<br>MSEMTKFKILNEAGISMLSQ<br>ANQTPQMVSKLLQ |

TABLE 2-continued

N- and C-terminal conserved regions of flagellins

| SEQ ID NO: | Conserved N-terminus | Conserved C-terminus |
|---|---|---|
| Flagellin<br>N-SEQ ID NO: 94<br>C-SEQ ID NO: 95<br>*Bacillus cereus*<br>strain FM1<br>[CDS of SEQ ID NO: 10] | MGVLNMRIGTNVLSMNARQSFYENEKR<br>MNVAIEHLATGKKLNHASDNPANVAIV<br>TRMHARTSGIHVAIRNNEDAISMLRTA<br>EAALQTVTNILQRMRDVAVQSANGTNS<br>NKNRDSLNKEFQSLTEQIGYIDETTEF<br>ND | RADLGAMINQLQFNIENLNS<br>QSTALTDAASRIEDADMAQE<br>MSDFLKFKLLTEVALSMVSQ<br>ANQIPQMVYKLLQ |
| Flagellin<br>N-SEQ ID NO: 96<br>C-SEQ ID NO: 97<br>*Bacillus thuringiensis*<br>strain MC28<br>[CDS of SEQ ID NO: 11] | GFLNMRINTNINSMRTQEYMRQNQAKM<br>SNAMDRLSSGKRINNASDDAAGLAIAT<br>RMRARESGLGVAANNTQDGMSLIRTAD<br>SALNSVSNILLRMRDIANQSANGTNTA<br>DNQQALQKEFGQLKEQISYIADNTEFN<br>DKTLL | AVDSIDAALKTVASNRATLG<br>ATLNRLDFNVNNLKSQSASM<br>ASAASQIEDADMAKEMSEMT<br>KFKILNEAGISMLSQANQTP<br>QMVSKLLQ |
| Flagellin<br>N-SEQ ID NO: 98<br>C-SEQ ID NO: 99<br>*Bacillus bombysepticus*<br>strain Wang<br>[CDS of SEQ ID NO: 12] | GFLNMRINTNINSMRTQEYMRQNQAKM<br>SNSMDRLSSGKRINNASDDAAGLAIAT<br>RMRSREGGLNVAARNTEDGMSLIRTAD<br>SALNSVSNILLRMRDLANQSASGTNTD<br>KNQAAMQKEFDQLKEQIQYI | LGATLNRLDFNVTNLKSQEN<br>SMAASASQIEDADMAKEMSE<br>MTKFKILNEAGISMLSQANQ<br>TPQMVSKLLQ |
| Flagellin<br>N-SEQ ID NO: 100<br>C-SEQ ID NO: 101<br>*Bacillus thuringiensis*<br>*serovar kenyae*<br>[CDS of SEQ ID NO: 13] | GFLNMRINTNINSMRTQEYMRQNQAKM<br>SNSMDRLSSGKRINNASDDAAGLAIAT<br>RMRSREGGLNVAARNTEDGMSLIRTAD<br>SALNSVSNILLRMRDLANQSASGTNTD<br>KNQAAMQKEFDQLKEQIQYI | RATLGATLNRLDFNVTNLKS<br>QENSMAASASQIEDADMAKE<br>MSEMTKFKILNEAGISMLSQ<br>ANQTPQMVSKLLQ |
| Flagellin<br>N-SEQ ID NO: 102<br>C-SEQ ID NO: 103<br>*Bacillus thuringiensis*<br>*serovar kenyae*<br>[CDS of SEQ ID NO: 14] | GFLNMRINTNINSMRTQEYMRQNQAKM<br>SNSMDRLSSGKRINNASDDAAGLAIAT<br>RMRSREGGLNVAARNTEDGMSLIRTAD<br>SALNSVSNILLRMRDLANQSASGTNTD<br>KNQAAMQKEFDQLKEQIQYI | RATLGATLNRLDFNVTNLKS<br>QENSMAASASQIEDADMAKE<br>MSEMTKFKILNEAGISMLSQ<br>ANQTPQMVSKLLQ |
| Flagellin (A-type)<br>N-SEQ ID NO: 104<br>C-SEQ ID NO: 105<br>*Bacillus cereus*<br>[CDS of SEQ ID NO: 15] | GFLNMRINTNINSMRTQEYMRQNQAKM<br>SNAMDRLSSGKRINNASDDAAGLAIAT<br>RMRARENGLGVAANNTQDGMSLIRTAD<br>SALNSVSNILLRMRDLANQSANGTNTG<br>DNQKALDKEFSALKEQIDYISKNTEFN<br>DKKLL | RATLGATLNRLDFNVNNLKS<br>QSSSMASAASQIEDADMAKE<br>MSEMTKFKILNEAGISMLSQ<br>ANQTPQMVSKLLQ |
| Flagellin (A-type)<br>N-SEQ ID NO: 106<br>C-SEQ ID NO: 107<br>*Bacillus cereus*<br>[CDS of SEQ ID NO: 16] | GFLNMRIGTNVLSMNARQSLYENEKRM<br>NVAMEHLATGKKLNNASDNPANIAIVT<br>RMHARASGMRLAIRNNEDTISMLRTAE<br>AALQTLTNILQRMRDLAVQSANGTNSN<br>KNRDSLNKEFQSLTEQIGYIGETTEFN<br>D | RADLGSMINRLQFNIENLNS<br>QSMALTDAASRIEDADMAQE<br>MSDFLKFKLLTEVALSMVSQ<br>ANQIPQMVSKLLQ |
| Flagellin<br>N-SEQ ID NO: 108<br>C-SEQ ID NO: 109<br>*Bacillus thuringiensis*<br>*serovar finitimus*<br>strain YBT-020<br>[CDS of SEQ ID NO: 17] | GVLNMRINTNINSMRTQEYMRQNQAKM<br>SNAMDRLSSGKRINNASDDAAGLAIAT<br>RMRARESGLNVAADNTQNGMSLIRTAD<br>SAMNSVSNILLRMRDIANQSANGTNTD<br>SNKSALQKEFAELQKQITYIADNTQFN<br>DKNLLKEDSEVKIQTLDS | AIDAALTKVADNRATLGATL<br>NRLDFNVNNLKSQSSSMASA<br>ASQIEDADMAKEMSEMTKFK<br>ILNEAGISMLSQANQTPQMV<br>SKLLQ |
| Flagellin<br>N-SEQ ID NO: 110<br>C-SEQ ID NO: 111<br>*Bacillus thuringiensis*<br>*serovar finitimus*<br>strain YBT-020<br>[CDS of SEQ ID NO: 18] | GVLNMRINTNINSMRTQEYMRQNQAKM<br>SNAMDRLSSGKRINNASDDAAGLAIAT<br>RMRARESGLNVAADNTQNGMSLIRTAD<br>SAMNSVSNILLRMRDIANQSANGTNTD<br>SNKSALQKEFAELQKQITYIADNTQFN<br>DKNLLKEDSEVKIQTLDS | AAIDAALTKVADNRATLGAT<br>LNRLDFNVNNLKSQSSSMAS<br>AASQIEDADMAKEMSEMTKF<br>KILNEAGISMLSQANQTPQM<br>VSKLLQ |
| Flagellin<br>N-SEQ ID NO: 112<br>C-SEQ ID NO: 113<br>*Bacillus cereus*<br>stain B4264<br>[CDS of SEQ ID NO: 19] | GFLNMRINTNINSMRTQEYMRQNQAKM<br>SNAMDRLSSGKRINNASDDAAGLAIAT<br>RMRARESGLGVAANNTQDGMSLIRTAD<br>SALNSVSNILLRMRDLANQSANGTNTA<br>ENKAAMQKEFGELKDQIKYISENTQFN<br>DQHLL | TVADNRATLGATLNRLDFNV<br>NNLKSQSASMASAASQIEDA<br>DMAKEMSEMTKFKILNEAGI<br>SMLSQANQTPQMVSKLLQ |
| Flagellin<br>N-SEQ ID NO: 114<br>C-SEQ ID NO: 115 | GFLNMRINTNINSMRTQEYMRQNQAKM<br>SNAMDRLSSGKRINNASDDAAGLAIAT<br>RMRARESGLGVAANNTQDGMSLIRTAD | AIKSIDAALDTIASNRATLG<br>ATLNRLDFNVNNLKSQSSSM<br>ASAASQIEDADMAKEMSEMT |

TABLE 2-continued

N- and C-terminal conserved regions of flagellins

| SEQ ID NO: | Conserved N-terminus | Conserved C-terminus |
|---|---|---|
| *Bacillus thuringiensis*<br>*serovar nigeriensis*<br>[CDS of SEQ ID NO: 20] | SALNSVSNILLRMRDIANQSANGTNTS<br>DNQKALDKEFSALKEQIDYISKNTEEN<br>DKKLL | KFKILNEAGISMLSQANQTP<br>QMVSKLLQ |
| Flagellin<br>N-SEQ ID NO: 116<br>C-SEQ ID NO: 117<br>*Bacillus thuringiensis*<br>[CDS of SEQ ID NO: 21] | WGFLIMRINTNINSMRTQEYMRQNQAK<br>MSNAMDRLSSGKRINNASDDAAGLAIA<br>TRMRARESGLGVAANNTQDGMSLIRTA<br>DSALNSVSNILLRMRDIANQSANGTNT<br>ADNQQALQKEFGQLKEQISYIADNTEF<br>ND | AVDAIDAALKTVASNRATLG<br>ATLNRLDFNVNNLKSQSASM<br>ASAASQIEDADMAKEMSEMT<br>KFKILNEAGISMLSQANQTP<br>QMVSKLLQ |
| Flagellin<br>N-SEQ ID NO: 118<br>C-SEQ ID NO: 119<br>*Bacillus thuringiensis*<br>*serovar konkukian*<br>strain 97-27<br>[CDS of SEQ ID NO: 22] | WGFLIMRINTNINSMRTQEYMRQNQAK<br>MSNAMDRLSSGKRINNASDDAAGLAIA<br>TRMRARESGLGVAANNTQDGMSLIRTA<br>DSALNSVSNILLRMetRDIANQSANGT<br>NTADNQQALQKEFGQLKEQISYIADNT<br>EENDKTLL | AVDAIDAALKTVASNRATLG<br>ATLNRLDFNVNNLKSQSASM<br>ASAASQIEDADMAKEMSEMT<br>KFKILNEAGISMLSQANQTP<br>QMVSKLLQ |
| Flagellin<br>N-SEQ ID NO: 120<br>C-SEQ ID NO: 121<br>*Bacillus thuringiensis*<br>*serovar konkukian*<br>strain 97-27<br>[CDS of SEQ ID NO: 23] | WGFLIMRINTNINSMRTQEYMRQNQAK<br>MSNAMDRLSSGKRINNASDDAAGLAIA<br>TRMRARESGLGVAANNTQDGMSLIRTA<br>DSAMNSVSNILLRMRDISNQSANGTNT<br>DKNQSALDKEFAALKDQIDYISKNTEE<br>NDQKLL | AIASIDAALESIASNRATLG<br>ATLNRLDFNVNNLKSQSSSM<br>ASAASQIEDADMAKEMSEMT<br>KFKILNEAGISMLSQANQTP<br>QMVSKLLQ |
| Flagellin protein FlaA<br>N-SEQ ID NO: 122<br>C-SEQ ID NO: 123<br>*Bacillus thuringiensis*<br>*serovar thuringiensis*<br>strain IS5056<br>[CDS of SEQ ID NO: 24] | GFLNMRINTNINSMRTQEYMRQNQAKM<br>SNAMDRLSSGKRINNASDDAAGLAIAT<br>RMRARESGLGVAANNTQDGMSLIRTAD<br>SAMNSVSNILLRMRDISNQSANGTNTD<br>KNQSALDKEFAALKDQIDYISKNTEFN<br>DQKLL | AIASIDAALESIASNRATLG<br>ATLNRLDFNVNNLKSQSSSM<br>ASAASQIEDADMAKEMSEMT<br>KFKILNEAGISMLSQANQTP<br>QMVSKLLQ |
| Flagellin protein FlaA<br>N-SEQ ID NO: 124<br>C-SEQ ID NO: 125<br>*Bacillus thuringiensis*<br>*serovar thuringiensis*<br>strain IS5056<br>[CDS of SEQ ID NO: 25] | GFLNMRINTNINSMRTQEYMRQNQAKM<br>SNAMDRLSSGKRINNASDDAAGLAIAT<br>RMRARESGLGVAANNTQDGMSLIRTAD<br>SAMNSVSNILLRMRDISNQSANGTNTD<br>KNQSALDKEFAALKDQIDYISKNTEFN<br>DQKLL | AIASIDAALESIASNRATLG<br>ATLNRLDFNVNNLKSQSSSM<br>ASAASQIEDADMAKEMSEMT<br>KFKILNEAGISMLSQANQTP<br>QMVSKLLQ |
| Flagellin B<br>N-SEQ ID NO: 126<br>C-SEQ ID NO: 127<br>*Bacillus thuringiensis*<br>strain Bt407<br>[CDS of SEQ ID NO: 26] | GFLNMRINTNINSMRTQEYMRQNQAKM<br>SNAMDRLSSGKRINNASDDAAGLAIAT<br>RMRARESGLGVAANNTQDGMSLIRTAD<br>SAMNSVSNILLRMRDISNQSANGTNTD<br>KNQSALDKEFAALKDQIDYISKNTEFN<br>DQKLL | AIASIDAALESIASNRATLG<br>ATLNRLDFNVNNLKSQSSSM<br>ASAASQIEDADMAKEMSEMT<br>KFKILNEAGISMLSQANQTP<br>QMVSKLLQ |
| Flagellin<br>N-SEQ ID NO: 128<br>C-SEQ ID NO: 129<br>*Bacillus thuringiensis*<br>*serovar chinensis* CT-43<br>[CDS of SEQ ID NO: 27] | GFLNMRINTNINSMRTQEYMRQNQAKM<br>SNAMDRLSSGKRINNASDDAAGLAIAT<br>RMRARESGLGVAANNTQDGMSLIRTAD<br>SAMNSVSNILLRMRDISNQSANGTNTD<br>KNQSALDKEFAALKDQIDYISKNTEFN<br>DQKLL | AIASIDAALESIASNRATLG<br>ATLNRLDFNVNNLKSQSSSM<br>ASAASQIEDADMAKEMSEMT<br>KFKILNEAGISMLSQANQTP<br>QMVSKLLQ |
| Flagellin<br>N-SEQ ID NO: 130<br>C-SEQ ID NO: 131<br>*Bacillus thuringiensis*<br>*serovar Canadensis*<br>[CDS of SEQ ID NO: 28] | GFLNMRINTNINSMRTQEYMRQNQAKM<br>SNAMDRLSSGKRINNASDDAAGLAIAT<br>RMRARESGLGVAANNTQDGISLIRTAD<br>SAMNSVSNILLRMRDLANQSANGTNTN<br>ENQAALNKEFDALKEQIDYISTNTEEN<br>DKKLL | RATLGATLNRLDFNVNNLKS<br>QSSSMASAASQIEDADMAKE<br>MSEMTKFKILNEAGISMLSQ<br>ANQTPQMVSKLLQ |
| Flagellin<br>N-SEQ ID NO: 132<br>C-SEQ ID NO: 133<br>*Bacillus thuringiensis*<br>*serovar galleriae*<br>[CDS of SEQ ID NO: 29] | GFLNMRINTNINSMRTQEYMRQNQAKM<br>SNAMDRLSSGKRINNASDDAAGLAIAT<br>RMRARESGLGVAANNTQDGISLIRTAD<br>SAMNSVSNILLRMRDLANQSANGTNTN<br>ENQAALNKEFDALKEQIDYISTNTEEN<br>DKKLL | RATLGATLNRLDFNVNNLKS<br>QSSSMASAASQIEDADMAKE<br>MSEMTKFKILNEAGISMLSQ<br>ANQTPQMVSKLLQ |
| Flagellin N-terminal<br>helical region | GVLNMRINTNINSMRTQEYMRQNQAKM<br>SNAMDRLSSGKRINNASDDAAGLAIAT | RATLGATLNRLDFNVNNLKS<br>QSSSMASAASQIEDADMAKE |

TABLE 2-continued

N- and C-terminal conserved regions of flagellins

| SEQ ID NO: | Conserved N-terminus | Conserved C-terminus |
|---|---|---|
| N-SEQ ID NO: 134<br>C-SEQ ID NO: 135<br>*Bacillus weihenstephanensis*<br>[CDS of SEQ ID NO: 30] | RMRARESGLSVAANNTQDGMSLIRTAD SAMNSVSNILLRMRDLSNQSANGTNTD ENQQALNKEFAALKDQIDYISKNTEFN DKKLL | MSEMTKFKILNEAGISMLSQ ANQTPQMVSKLLQ |
| Flagellin<br>N-SEQ ID NO: 136<br>C-SEQ ID NO: 137<br>*Bacillus thuringiensis serovar ostriniae*<br>[CDS of SEQ ID NO: 31] | GFLN**M**RINTNINSMRTQEYMRQNQAKM SNAMDRLSSGKRINNASDDAAGLAIAT RMRARESGLGVAANNTQDGMSLIRTAD SALNSVSNILLRMRDIANQSANGTNTG DNQKALDKEFSALKEQIDYISKNTEEN DKKLL | IDAALETIASNRATLGATLN RLDFNVNNLKSQSSSMASAA SQIEDADMAKEMSEMTKFKI LNEAGISMLSQANQTPQMVS KLLQS |
| Flagellin<br>N-SEQ ID NO: 138<br>C-SEQ ID NO: 139<br>Bacillus thuringiensis<br>[CDS of SEQ ID NO: 32] | WGFLI**M**RINTNINSMRTQEYMRQNQTK MSNAMDRLSSGKRINNASDDAAGLAIA TRMRARENGLGVAANNTQDGMSLIRTA DSAMNSVSNILLRMRDLANQSANGTNT DDNQKALDKEFSALKEQIDYISKNTEF NDKKLL | LGATLNRLDFNVNNLKSQSS SMAAAASQIEDADMAKEMSE MTKFKILNEAGISMLSQANQ TPQMVSKLLQ |
| Flagellin<br>N-SEQ ID NO: 140<br>C-SEQ ID NO: 141<br>*Bacillus thuringiensis*<br>[CDS of SEQ ID NO: 33] | WGFLI**M**RINTNINSMRTQEYMRQNQTK MSNAMDRLSSGKRINNASDDAAGLAIA TRMRARENGLGVAANNTQDGMSLIRTA DSAMNSVSNILLRMRDLANQSANGTNT DDNQKALDKEFSALKEQIDYISKNTEF NDKKLL | LGATLNRLDFNVNNLKSQSS SMAAAASQIEDADMAKEMSE MTKFKILNEAGISMLSQANQ TPQMVSKLLQ |
| Flagellin<br>N-SEQ ID NO: 142<br>C-SEQ ID NO: 143<br>*Bacillus thuringiensis serovar pondicheriensis*<br>[CDS of SEQ ID NO: 34] | WGFLI**M**RINTNINSMRTQEYMRQNQTK MSNAMDRLSSGKRINNASDDAAGLAIA TRMRARENGLGVAANNTQDGMSLIRTA DSAMNSVSNILLRMRDLANQSANGTNT DDNQKALDKEFSALKEQIDYISKNTEE NDKKLL | RATLGATLNRLDFNVNNLKS QSSSMAAAASQIEDADMAKE MSEMTKFKILNEAGISMLSQ ANQTPQMVSKLLQ |
| Flagellin B<br>N-SEQ ID NO: 144<br>C-SEQ ID NO: 145<br>*Bacillus thuringiensis serovar Berliner*<br>[CDS of SEQ ID NO: 35] | GFLN**M**RINTNINSMRTQDYMRQNQAKM SNAMDRLSSGKRINNASDDAAGLAIAT RMRARESGLGVAANNTQDGMSLIRTAD SAMNSVSNILLRMRDISNQSANGTNTD KNQSALDKEFAALKDQIDYISKNTEFN DQKLL | AIASIDAALESIASNRATLG ATLNRLDFNVNNLKSQSSSM ASAASQIEDADMAKEMSEMT KFKILNEAGISMLSQANQTP QMVSKLLQ |
| Flagellin A<br>N-SEQ ID NO: 146<br>C-SEQ ID NO: 147<br>*Bacillus thuringiensis serovar Berliner*<br>[CDS of SEQ ID NO: 36] | GFLN**M**ARITINLEIDFFAYYRFSICRK VNIKKWGFLNMRINTNINSMRTQDYMR QNQAKMSNAMDRLSSGKRINNASDDAA GLAIATRMRARESGLGVAANNTQDGMS LIRTADSAMNSVSNILLRMRDISNQSA NGTNTDKNQSALDKEFAALKDQIDYIS KNTEFNDQKLL | AIASIDAALESIASNRATLG ATLNRLDFNVNNLKSQSSSM ASAASQIEDADMAKEMSEMT KFKILNEAGISMLSQANQTP QMVSKLLQ |
| Flagellin<br>N-SEQ ID NO: 148<br>C-SEQ ID NO: 149<br>*Bacillus cereus* strain Q1<br>[CDS of SEQ ID NO: 37] | GVLY**M**RINTNINSMRTQEYMRQNQAKM SNAMDRLSSGKRINNASDDAAGLAIAT RMRARESGLSVAADNTQNGMSLIRTAD SAMNSVSNILLRMRDIANQSANGTNTD KNQVALQKEFAALKEQITYIADNTQFN DKNLLNGNQTINIQTLDSHDST | TVADNRATLGATLNRLDFNV NNLKSQSSAMAASASQIEDA DMAKEMSEMTKFKILNEAGI SMLSQANQTPQMVSKLLQ |
| Flagellin<br>N-SEQ ID NO: 150<br>C-SEQ ID NO: 151<br>*Bacillus cereus* strain Q1<br>[CDS of SEQ ID NO: 38] | GVLYM**R**INTNINSMRTQEYMRQNQAKM SNAMDRLSSGKRINNASDDAAGLAIAT RMRARESGLSVAADNTQNGMSLIRTAD SAMNSVSNILLRMRDIANQSANGTNTD KNQVALQKEFAALKEQITYIADNTQFN DKNLLNGNQTINIQTLDSHDST | TVADNRATLGATLNRLDFNV NNLKSQSSAMAASASQIEDA DMAKEMSEMTKFKILNEAGI SMLSQANQTPQMVSKLLQ |
| Flagellin<br>N-SEQ ID NO: 152<br>C-SEQ ID NO: 153<br>*Bacillus thuringiensis serovar morrisoni*<br>[CDS of SEQ ID NO: 39] | GFLN**M**RINTNINSMRTQEYMRQNQAKM SNAMDRLSSGKRINNASDDAAGLAIAT RMRARESGLGVAANNTQDGMSLIRTAD SALNSVSNILLRMRDIANQSANGTNTG DNQKALDKEFSALKEQIDYISKNTEEN DKKLL | LGATLNRLDFNVNNLKSQSS SMASAASQIEDADMAKEMSE MTKFKILNEAGISMLSQANQ TPQMVSKLLQ |
| Flagellin<br>N-SEQ ID NO: 154<br>C-SEQ ID NO: 155<br>*Bacillus thuringiensis serovar neoleonensis*<br>[CDS of SEQ ID NO: 40] | GFLN**M**RINTNINSMRTQEYMRQNQTKM SNAMDRLSSGKRINNASDDAAGLAIAT RMRARENGLGVAANNTQDGMSLIRTAD SALNSVSNILLRMRDIANQSANGTNTS DNQKALDKEFSALKEQIDYISKNTEFN DKKLL | AIKSIDAALDTIASNRATLG ATLNRLDFNVNNLKSQSSSM ASAASQIEDADMAKEMSEMT KFKILNEAGISMLSQANQTP QMVSKLLQ |

TABLE 2-continued

N- and C-terminal conserved regions of flagellins

| SEQ ID NO: | Conserved N-terminus | Conserved C-terminus |
|---|---|---|
| Flagellin<br>N-SEQ ID NO: 156<br>C-SEQ ID NO: 157<br>*Bacillus thuringiensis serovar morrisoni*<br>[CDS of SEQ ID NO: 41] | GFLNMRINTNINSMRTQEYMRQNQAKMSNAMDRLSSGKRINNASDDAAGLAIATRMRARESGLGVAANNTQDGMSLIRTADSALNSVSNILLRMRDIANQSANGTNTGDNQKALDKEFSALKEQIDYISKNTEENDKKLL | RATLGATLNRLDFNVNNLKSQSSSMASAASQIEDADMAKEMSEMTKFKILNEAGISMLSQANQTPQMVSKLLQ |
| Flagellin<br>N-SEQ ID NO: 158<br>C-SEQ ID NO: 159<br>*Bacillus thuringiensis serovar morrisoni*<br>[CDS of SEQ ID NO: 42] | GFLNMRINTNINSMRTQEYMRQNQAKMSNAMDRLSSGKRINNASDDAAGLAIATRMRARESGLGVAANNTQDGMSLIRTADSALNSVSNILLRMRDIANQSANGTNTGDNQKALDKEFSALKEQIDYISKNTEENDKKLL | RATLGATLNRLDFNVNNLKSQSSSMASAASQIEDADMAKEMSEMTKFKILNEAGISMLSQANQTPQMVSKLLQ |
| Flagellin<br>N-SEQ ID NO: 160<br>C-SEQ ID NO: 161<br>*Bacillus thuringiensis serovar jegathesan*<br>[CDS of SEQ ID NO: 43] | GFLNMRINTNINSMRTQEYMRQNQAKMSNAMDRLSSGKRINNASDDAAGLAIATRMRARESGLGVAANNTQDGMSLIRTADSAMNSVSNILLRMRDIANQSANGTNTNGNQAALNKEFDALKQQINYISTNTEFNDKKLLDGSNKTIAIQTLD | LGATLNRLDFNVNNLKSQQSSMASAASQIEDADMAKEMSEMTKFKILNEAGISMLSQANQTPQMVSKLLQ |
| Flagellin<br>N-SEQ ID NO: 162<br>C-SEQ ID NO: 163<br>*Bacillus cereus*<br>stain ATCC 10987<br>[CDS of SEQ ID NO: 44] | GVLNMRINTNINSMRTQEYMRQNQAKMSNAMDRLSSGKRINNASDDAAGLAIATRMRARESGLGVAANNTQDGMALIRTADSAMNSVSNILLRRDIANQSANGTNTDKNQAALQKEFGELQKQIDYIAGNTQFNDK | DKIDEALKTIADNRATLGATLNRLDFNVNNLKSQSASMASAASQIEDADMAKEMSEMTKFKILNEAGISMLSQANQTPQMVSKLLQ |
| Flagellin<br>N-SEQ ID NO: 164<br>C-SEQ ID NO: 165<br>*Bacillus thuringiensis serovar monterrey*<br>[CDS of SEQ ID NO: 45] | WGFLIMRINTNINSMRTQEYMRQNQAKMSNAMDRLSSGKRINNASDDAAGLAIATRMRARESGLGVAANNTQDGMSLIRTADSAMNSVSNILLRMRDLANQSANGTNTNENQAALNKEFDALKEQINYISTNTEFNDKKLL | RATLGATLNRLDFNVNNLKSQQSSMASAASQIEDADMAKEMSEMTKFKILNEAGISMLSQANQTPQMVSKLLQ |
| Flagellin<br>N-SEQ ID NO: 166<br>C-SEQ ID NO: 167<br>*Bacillus cereus*<br>strain NC7401<br>[CDS of SEQ ID NO: 46] | WGFFYMRINTNINSMRTQEYMRQNQAKMSNAMDRLSSGKRINNASDDAAGLAIATRMRARESGLGVASNNTQDGMSLIRTADSALNSVSNILLRMRDLANQSANGTNTNENKAAMQKEFGELKEQIKYIAENTQFNDQHLL | TVADNRATLGATLNRLDFNVNNLKSQASSMAAAASQVEDADMAKEMSEMTKFKILNEAGISMLSQANQTPQMVSKLLQ |
| Flagellin<br>N-SEQ ID NO: 168<br>C-SEQ ID NO: 169<br>*Bacillus cereus*<br>strain NC7401<br>[CDS of SEQ ID NO: 47] | WGFFYMRINTNINSMRTQEYMRQNQAKMSNAMDRLSSGKRINNASDDAAGLAIATRMRARESGLGVASNNTQDGMSLIRTADSALNSVSNILLRMRDLANQSANGTNTNENKAAMQKEFGELKEQIKYIAENTQFNDQHLL | TVADNRATLGATLNRLDFNVNNLKSQASSMAAAASQVEDADMAKEMSEMTKFKILNEAGISMLSQANQTPQMVSKLLQ |
| Flagellin (A-type)<br>N-SEQ ID NO: 170<br>C-SEQ ID NO: 171<br>*Bacillus cereus*<br>strain AH820<br>[CDS of SEQ ID NO: 48] | GVLNMRINTNINSLRTQEYMRQNQAKMSNSMDRLSSGKRINNASDDAAGLAIATRMRARESGLNVAANNTQDGMSLIRTADSALGSVSNILLRMRDLANQSANGTNTSDNQAAMQKEFAELQKQITYIADNTQFNDKNLL | IDAALKTVADNRATLGATLNRLDFNVNNLKSQSSSMASAASQIEDADMAKEMSEMTKFKILNEAGISMLSQANQTPQMVSKLLQ |
| Flagellin<br>N-SEQ ID NO: 172<br>C-SEQ ID NO: 173<br>*Bacillus cereus* AH187<br>[CDS of SEQ ID NO: 49] | WGFFYMRINTNINSMRTQEYMRQNQAKMSNAMDRLSSGKRINNASDDAAGLAIATRMRARESGLGVASNNTQDGMSLIRTADSALNSVSNILLRMRDLANQSANGTNTNENKAAMQKEFGELKEQIKYIAENTQFNDQHLL | TVADNRATLGATLNRLDFNVNNLKSQASSMAAAASQVEDADMAKEMSEMTKFKILNEAGISMLSQANQTPQMVSKLLQ |
| Flagellin<br>N-SEQ ID NO: 174<br>C-SEQ ID NO: 175<br>*Bacillus cereus*<br>[CDS of SEQ ID NO: 50] | WGFFYMRINTNINSMRTQEYMRQNQAKMSNAMDRLSSGKRINNASDDAAGLAIATRMRARESGLGVASNNTQDGMSLIRTADSALNSVSNILLRMRDLANQSANGTNTNENKAAMQKEFGELKEQIKYIAENTQFNDQHLL | TVADNRATLGATLNRLDFNVNNLKSQASSAAAASQVEDADMAKEMSEMTKFKILNEAGISMLSQANQTPQMVSKLLQ |
| Flagellin protein Fla<br>N-SEQ ID NO: 176 | GFLNMRINTNINSMRTQEYMRQNQAKMSNAMDRLSSGKRINNASDDAAGLAIAT | LGATLNRLDFNVNNLKSQSSSMASAASQIEDADMAKEMSE |

TABLE 2-continued

N- and C-terminal conserved regions of flagellins

| SEQ ID NO: | Conserved N-terminus | Conserved C-terminus |
|---|---|---|
| C-SEQ ID NO: 177<br>*Bacillus cereus*<br>[CDS of SEQ ID NO: 51] | RMRARESGLGVAANNTQDGMSLIRTAD<br>SALNSVSNILLRMRDIANQSANGTNTG<br>DNQKALDKEFSALKEQIDYISKNTEFN<br>DKKLL | MTKFKILNEAGISMLSQANQ<br>TPQMVSKLLQ |
| Flagellin<br>N-SEQ ID NO: 178<br>C-SEQ ID NO: 179<br>*Bacillus thuringiensis*<br>Strain HD-771<br>[CDS of SEQ ID NO: 52] | GFLNMRINTNINSMRTQEYMRQNQTKM<br>SNAMDRLSSGKRINNASDDAAGLAIAT<br>RMRSREGGLNVAARNTEDGMSLIRTAD<br>SALNSVSNILLRMRDLANQSASETNTS<br>KNQAAMQKEFDQLKEQIQYI | RATLGATLNRLDFNVTNLKS<br>QENSMAASASQIEDADMAKE<br>MSEMTKFKILNEAGISMLSQ<br>ANQTPQMVSKLLQ |
| Flagellin<br>N-SEQ ID NO: 180<br>C-SEQ ID NO: 181<br>*Bacillus thuringiensis*<br>*serovar sotto*<br>[CDS of SEQ ID NO: 53] | GFLNMRINTNINSMRTQEYMRQNQTKM<br>SNAMDRLSSGKRINNASDDAAGLAIAT<br>RMRSREGGLNVAARNTEDGMSLIRTAD<br>SALNSVSNILLRMRDLANQSASETNTS<br>KNQAAMQKEFDQLKEQIQYI | RATLGATLNRLDFNVTNLKS<br>QENSMAASASQIEDADMAKE<br>MSEMTKFKILNEAGISMLSQ<br>ANQTPQMVSKLLQ |
| Flagellin<br>N-SEQ ID NO: 182<br>C-SEQ ID NO: 183<br>*Bacillus thuringiensis*<br>*serovar Novosibirsk*<br>[CSD of SEQ ID NO: 54] | MGVLNMRINTNINSMRTQEYMRQNQAK<br>MSTAMDRLSSGKRINNASDDAAGLAIA<br>TRMRARESGLGVAANNTQDGISLIRTA<br>DSAMNSVSNILLRMRDLANQSANGTNT<br>DKNQGALDKEFAALKEQIDYISKNTEF<br>NDKKLL | AIKAIDEALETIASNRATLG<br>ATLNRLDFNVNNLKNQASSM<br>ASAASQVEDADMAKEMSEMT<br>KFKILNEAGISMLSQANQTP<br>QMVSKLLQ |
| Flagellin<br>N-SEQ ID NO: 184<br>C-SEQ ID NO: 185<br>*Bacillus thuringiensis*<br>*serovar Londrina*<br>[CDS of SEQ ID NO: 55] | MGVLNMRINTNINSMRTQEYMRQNQAK<br>MSNAMDRLSSGKRINNASDDAAGLAIA<br>TRMRARESGLGVAANNTQDGISLIRTA<br>DSAMNSVSNILLRMRDLANQSANGTNT<br>SENQAALDKEFGALKEQINYISTNTEF<br>NDKKLL | AIDSALENIASNRATLGATL<br>NRLDFNVNNLKSQSSSMASA<br>ASQIEDADMAKEMSEMTKFK<br>ILNEAGISMLSQANQTPQMV<br>SKLLQ |
| Flagellin<br>N-SEQ ID NO: 186<br>C-SEQ ID NO: 187<br>*Bacillus cereus*<br>strain E33L<br>[CDS of SEQ ID NO: 56] | MGVLNMRINTNINSMRTQEYMRQNQAK<br>MSTAMDRLSSGKRINNASDDAAGLAIA<br>TRMRARESGLGVAANNTQDGISLIRTA<br>DSAMNSVSNILLRMRDLANQSANGTNT<br>DKNQGALDKEFAALKEQIDYISKNTEF<br>NDKKLL | LGATLNRLDFNVNNLKNQAS<br>SMASAASQVEDADMAKEMSE<br>MTKFKILNEAGISMLSQANQ<br>TPQMVSKLLQ |
| Flagellin<br>N-SEQ ID NO: 188<br>C-SEQ ID NO: 189<br>*Bacillus cereus*<br>strain E33L<br>[CDS of SEQ ID NO: 57] | MGVLNMRINTNINSMRTQEYMRQNQAK<br>MSTAMDRLSSGKRINNASDDAAGLAIA<br>TRMRARESGLGVAANNTQDGISLIRTA<br>DSAMNSVSNILLRMRDLANQSANGTNT<br>DKNQGALDKEFAALKEQIDYISKNTEF<br>NDKKLL | ATLNRLDFNVNNLKNQASSM<br>ASAASQVEDADMAKEMSEMT<br>KFKILNEAGISMLSQANQTP<br>QMVSKLLQ |
| Flagellin<br>N-SEQ ID NO: 190<br>C-SEQ ID NO: 191<br>*Bacillus cereus*<br>strain FRI-35<br>[CDS of SEQ ID NO: 58] | WGFFYMRINTNINSMRTQEYMRQNQAK<br>MSTAMDRLSSGKRINNASDDAAGLAIA<br>TRMRARESGLGVAANNTQDGISLIRTA<br>DSAMNSVSNILLRMRDLANQSANGTNT<br>DKNQAALDKEFNALKEQIDYISKNTEF<br>NDKKL | AIAAIDAALTKVADNRATLG<br>ATLNRLDFNVNNLKSQASSM<br>ASAASQVEDADMAKEMSEMT<br>KFKILNEAGISMLSQANQTP<br>QMVSKLLQ |
| Flagellin<br>N-SEQ ID NO: 192<br>C-SEQ ID NO: 193<br>*Bacillus cereus*<br>strain FRI-35<br>[CDS of SEQ ID NO: 59] | WGFFYMRIGTNVLSLNARQSLYENEKR<br>MNVAMEHLATGKKLNNASDNPANIAIV<br>TRMHARASGMRVAIRNNEDAISMLRTA<br>EAALQTVTNVLQRMRDLAVQSANGTNS<br>NKNRDSLNKEFQSLTEQIGYIDETTEF<br>NN | AIRKIEEALQNVSLHRADLG<br>AMINRLQFNIENLNSQSTAL<br>TDAASRIEDADMAQEMSDFL<br>KFKLLTEVALSMVSQANQVP<br>QMVSKLLQ |
| Flagellin<br>N-SEQ ID NO: 194<br>C-SEQ ID NO: 195<br>*Bacillus thuringiensis*<br>[CDS of SEQ ID NO: 60] | LVPFAVWLAMSRIRRRILDTDCKAESA<br>VRIKEIPSDVLRAATERPLSCARIRVA<br>IARPAASSEALLIRLPLDKRSIALLIL<br>AWFWRMYSCVRMLLMFVLILMLRTP | MAASASQIEDADMAKEMSEM<br>TKFKILSEAGISMLSQANQT<br>PQMVSKLLQ |
| Flagellin<br>N-SEQ ID NO: 196<br>C-SEQ ID NO: 197<br>*Bacillus cereus* strain<br>ATCC 4342<br>[CDS of SEQ ID NO: 61] | AVWLAMSRIRRRILDTDCKAESAVRIK<br>EIPSDVLRAATERPLSCARIRVAIARP<br>AASSEALLIRLPLDKRSIALLILAWFW<br>RMYSCVRMLLMFVLILMLRTP | SMAASASQIEDADMAKEMSE<br>MTKFKILSEAGISMLSQANQ<br>TPQMVSKLLQ |
| Flagellin<br>N-SEQ ID NO: 198 | GFLNMRIGTNFLSMNARQSLYENEKRM<br>NVAMEHLATGKKLNHASDNPANIAIVT | LGAMINRLHFNIENLNSQSM<br>ALTDAASRIEDADMAQEMSD |

TABLE 2-continued

N- and C-terminal conserved regions of flagellins

| SEQ ID NO: | Conserved N-terminus | Conserved C-terminus |
|---|---|---|
| C-SEQ ID NO: 199<br>*Bacillus thuringiensis*<br>[CDS of SEQ ID NO: 62] | RMHARANGMRVAIRNNEDAISMLRTAE<br>AALQTVMNILQRMRDLAIQSANSTNSN<br>KNRDSLNKEFQSLTEQISYI | FLKFKLLTEVALSMVSQANQ<br>IPQMVSKLLQ |
| Flagellin<br>N-SEQ ID NO: 200<br>C-SEQ ID NO: 201<br>*Bacillus thuringiensis*<br>[CDS of SEQ ID NO: 63] | GFLNMRINTNINSMRTQEYMRQNQAKM<br>SNAMDRLSSGKRINNASDDAAGLAIAT<br>RMRARESGLGVAANNTQDGMSLIRTAD<br>SALNSVSNILLRMRDIANQSANGTNTG<br>DNQKALDKEFSALKEQIDYI | LGATLNRLDFNVNNLKSQSS<br>SMASAASQIEDADMAKEMSE<br>MTKFKILNEAGISMLSQANQ<br>TPQMVSKLLQ |
| Flagellin<br>N-SEQ ID NO: 202<br>C-SEQ ID NO: 203<br>*Bacillus aryabhattai*<br>[CDS of SEQ ID NO: 64] | MRINHNITALNTYRQFNNANNAQAKSM<br>EKLSSGQRINSASDDAAGLAISEKMRG<br>QIRGLDQASRNAQDGVSLIQTAEGALN<br>ETHDILQRMRELVVQAGNGTNKTEDLD<br>AIQDEIGSLIEEIGGETDSKGISDRAQ<br>FNGRNLLDGSLDITLQVGA | IDGAINQVSEQRSGLGATQN<br>RLDHTINNLSTSSENLTASE<br>SRIRDVDYALAA |
| Flagellin<br>N-SEQ ID NO: 204<br>C-SEQ ID NO: 205<br>*Bacillus manliponensis*<br>[CDS of SEQ ID NO: 65] | MRINTNINSMRTQEYMRQNQDKMNTSM<br>NRLSSGKQINSASDDAAGLAIATRMRA<br>KEGGLNVGAKNTQDGMSALRTMDSALN<br>SVSNILLRMRDLATQSATGTNQGNDRE<br>SLDLEFQQLTEEITHIAEKTNFNGNAL<br>LSGSGSAINVQLS | IDQAIQDIADNRATYGSQLN<br>RLDHNLNNVNSQATNMAAAA<br>SQIEDADMAKEMSEMTKFKI<br>LSEAGVSMLSQANQTPQMVS<br>KLLQ |
| Flagellin<br>N-SEQ ID NO: 206<br>C-SEQ ID NO: 207<br>*Lysinibacillus* sp.<br>strain BF-4<br>[CDS of SEQ ID NO: 66] | MRIGSWTATGMSIVNHMNRNWNAASKS<br>MLRLSSGYRINSAADDAAGLAISEKMR<br>GQIRGLTMASKNIMDGVSLIQTAEGAL<br>NETHAIVQRMRELAVQAATDTNTDDDR<br>AKLDLEFQELKKEIDRISTDTEFNTRT<br>LLNGDYKDNGLKIQVG | LDEATKNVSMERSRLGAYQN<br>RLEHAYNVAENTAINLQDAE<br>SRIRDVDIAKEMMNMVKSQI<br>LAQVGQQVLAMHMQQAQGIL<br>RLLG |
| Flagellin<br>N-SEQ ID NO: 208<br>C-SEQ ID NO: 209<br>*Lysinibacillus* sp.<br>strain 13S34_air<br>[CDS of SEQ ID NO: 67] | MKIGSWTATGMSIVNHMNRNWNAASKS<br>MLRLSSGYRINSAADDAAGLAISEKMR<br>GQIRGLTMASKNIMDGVSLIQTAEGAL<br>NETHAIVQRMRELAVQAATDTNTDDDR<br>AKLDLEFQELKKEIDRISTDTAFNTRT<br>LLNGDYKDNGLKIQVG | LDEATKNVSMERSRLGAYQN<br>RLEHAYNVAENTAINLQDAE<br>SRIRDVDIAKEMMHMVKSQI<br>LAQVGQQVLAMHIQQAQGIL<br>RLLG |
| Flagellin<br>N-SEQ ID NO: 210<br>C-SEQ ID NO: 211<br>*Paenibacillus* sp.<br>strain HW567<br>[CDS of SEQ ID NO: 68] | MIISHNLTALNTMNKLKQKDLAVSKSL<br>GKLSSGLRINGASDDAAGLAISEKMRG<br>QIRGLNQASRNIQDGISLIQVADGAMQ<br>EIHSMLQRMNELAVQASNGTYSGSDRL<br>NIQSEVEQLIEEIDEIAGNTGFNGIKL<br>LNGNNEKTEKTEK | ISAAIDKVSAERARMGAYQN<br>RLEHSRNNVVTYAENLTAAE<br>SRIRDVDMAKEMMELMKNQI<br>FTQAGQAMLLQTNTQPQAIL<br>QLLK |
| Flagellin<br>N-SEQ ID NO: 212<br>C-SEQ ID NO: 213<br>*Bacillus anthracis*<br>[CDS of SEQ ID NO: 69] | MRINTNINSMRTQEYMRQNQAKMSNAM<br>DRLSSGKRINNASDDAAGLAIATRMRA<br>RESGLGVAANNTQDGMSLIRTADSAMN<br>SVSNILLRMRDLANQSANGTNTKENQD<br>ALDKEFGALKEQIDYISKNTEFNDKKL<br>LNGDNKSIAIQTL | IDSALETIASNRATLGATLN<br>RLDFNVNNLKSQSSAMASAA<br>SQIEDADMAKEMSEMTKFKI<br>LNEAGISMLSQANQTPQMVS<br>KLLQ |
| Flagellin<br>N-SEQ ID NO: 214<br>C-SEQ ID NO: 215<br>*Bacillus anthracis*<br>[CDS of SEQ ID NO: 70] | MQKSQYKKMGVLKMRINTNINSMRTQE<br>YMRQNQDKMNVSMNRLSSGKRINSAAD<br>DAAGLAIATRMRARQSGLEKASQNTQD<br>GMSLIRTAESAMNSVSNILTRMRDIAV<br>QSSNGTNTAENQSALQKEFAELQEQID<br>YIAKNTEFNDKNLLAGTGAVTIGSTSI<br>SGAEISIETL | ALNTVAGNRATLGATLNRLD<br>RNVENLNNQATNMASAASQI<br>EDADMAKEMSEMTKFKILNE<br>AGISMLSQANQTPQMVSKLL<br>Q |
| Flagellin<br>N-SEQ ID NO: 216<br>C-SEQ ID NO: 217<br>*Bacillus anthracis*<br>[CDS of SEQ ID NO: 71] | MRINTNINSMRTQEYMRQNQDKMNVSM<br>NRLSSGKRINSAADDAAGLAIATRMRA<br>RQSGLEKASQNTQDGMSLIRTAESAMN<br>SVSNILTRMRDIAVQSSNGTNTAENQS<br>ALQKEFAELQEQIDYIAKNTEFNDKNL<br>LAGTGAVTIGSTSISGAEISIETL | ALNTVAGNRATLGATLNRLD<br>RNVENLNNQATNMASAASQI<br>KDADKAKEMSEMTKFKILNE<br>AGISMLSQANQTPQMVSKLL<br>Q |
| Flagellin<br>N-SEQ ID NO: 218<br>C-SEQ ID NO: 219<br>*Bacillus anthracis*<br>[CDS of SEQ ID NO: 72] | MRINTNINSMRTQEYMRQNQDKMNVSM<br>NRLSSGKRINSAADDAAGLAIATRMRA<br>RQSGLEKASQNTQDGMSLIRTAESAMN<br>SVSNILTRMRDIAVQSSNGTNTAENQS<br>ALQKEFAELQEQIDYIAKNTEFNDKNL<br>LAGTGAVTIGSTSISGAEISIETL | ALNTVAGNRATLGATLNRLD<br>RNVENLNNQATNMASAASQI<br>EDADMAKEMSEMTKFKILNE<br>AGISMLSQANQTPQMV |
| Flagellin<br>N-SEQ ID NO: 220 | MNVSMNRLSSGKRINSAADDAAGLAIA<br>TRMRARQSGLEKASQNTQDGMSLIRTA | LNTALNTVAGNRATLGATLN<br>RLDRNVENLNNQATNMASAA |

TABLE 2-continued

N- and C-terminal conserved regions of flagellins

| SEQ ID NO: | Conserved N-terminus | Conserved C-terminus |
|---|---|---|
| C-SEQ ID NO: 221 *Bacillus anthracis* strain H9401 [CDS of SEQ ID NO: 73] | ESAMNSVSNILTRMRDIAVQSSNGTNT AENQSALQKEFAELQEQIDYIAKNTEF NDKNLLAGTGAVTIGSTSISGAEISIE TL | SQIEDADMAKEMSEMTKFKI LNEAGISMLSQANQTPQMVS KLLQ |
| Flagellin N-SEQ ID NO: 222 C-SEQ ID NO: 223 *Bacillus megaterium* strain WSH-002 [CDS of SEQ ID NO: 74] | **M**RINHNITALNTYRQFNNANNAQAKSM EKLSSGQRINSASDDAAGLAISEKMRG QIRGLDQASRNAQDGVSLIQTAEGALN ETHDILQRMRELVVQAGNGTNKTEDLD AIQDEIGSLIEEIGGEADSKGISDRAQ FNGRNLLDGSLDITLQVGA | IIDGAINQVSEQRSGLGATQ NRLDHTINNLSTSSENLTAS ESRIRDVDYALAA |
| Flagellin N-SEQ ID NO: 224 C-SEQ ID NO: 225 *Aneurinibacillus* sp. XH2 [CDS of SEQ ID NO: 75] | **M**RINHNLPALNAYRNLAQNQIGTSKIL ERLSSGYRINRASDDAAGLAISEKMRG QIRGLEQGQRNTMDGVSLIQTAEGALQ EIHEMLQRMRELAVQAANGTYSDKDKK AIEDEINQLTAQIDQIAKTTEFNGIQL IGDSDSTSLQDVK | FKAAIDQVSRIRSYFGAIQN RLEHVVNNLSNYTENLTGAE SRIRDADMAKEMTEFTRFNI INQSATAMLAQANQLPQGVL QLLKG |

The amino acid sequence of the flagellin or flagellin-associated polypeptide can comprise any one of SEQ ID NOs: 226-300, or any combination thereof.

The amino acid sequence of the flagellin or flagellin-associated polypeptide can comprise SEQ ID NO: 226.

The amino acid sequence of the flagellin or flagellin-associated polypeptide can comprise any one of SEQ ID NOs: 301-375, or any combination thereof.

The amino acid sequence of the flagellin or flagellin-associated polypeptide can comprise SEQ ID NO: 301.

The flagellin-derived polypeptide sequence for Bt4Q7Flg22 (SEQ ID NO: 226) was identified from a proprietary "in house" library from *Bacillus thuringiensis* (Bt.) strain 4Q7. Conserved primers to full length flagellin from *E. coli* were used to screen the Bt.4Q7 strain library and identify a functional flagellin-associated bioactive priming Flg22 polypeptide.

TABLE 3

Flagellin polypeptides Flg22 and FlgII-28 identified from *Bacillus* spp.

| SEQ ID NO: | |
|---|---|
| | Peptide Flg22 |
| Flg22-Bt.4Q7 SEQ ID NO: 226 *Bacillus thuringiensis* strain 4Q7 | DRLSSGKRINSASDDAAGLAIA |
| Flg22 SEQ ID NO: 227 *Bacillus thuringiensis,* strain HD1002 | DRLSSGKRINSASDDAAGLAIA |
| Flg22 SEQ ID NO: 228 *Bacillus thuringiensis,* strain HD-789 | DRLSSGKRINSASDDAAGLAIA |
| Flg22 SEQ ID NO: 229 *Bacillus cereus* strain G9842 | DRLSSGKRINSASDDAAGLAIA |

TABLE 3-continued

Flagellin polypeptides Flg22 and FlgII-28 identified from *Bacillus* spp.

| SEQ ID NO: | |
|---|---|
| Flg22 SEQ ID NO: 230 *Bacillus thuringiensis serovar indiana* strain HD521 | EHLATGKKLNNASDNPANIAIV |
| Flg22 SEQ ID NO: 231 *Bacillus thuringiensis* strain CTC | DRLSSGKRINNASDDAAGLAIAT |
| Flg22 SEQ ID NO: 232 *Bacillus thuringiensis serovar yunnanensis* strain IEBC-T20001 | DRLSSGKRINNASDDAAGLAIA |
| Flg22 SEQ ID NO: 233 *Bacillus thuringiensis serovar tolworthi* | DRLSSGKRINNASDDAAGLAIA |
| Flg22 SEQ ID NO: 234 *Bacillus cereus* strain FM1 | DRLSSGKRINNASDDAAGLAIA |
| Flg22 SEQ ID NO: 235 *Bacillus cereus* strain FM1 | EHLATGKKLNHASDNPANVAIV |
| Flg22 SEQ ID NO: 236 *Bacillus thuringiensis* strain MC28 | DRLSSGKRINNASDDAAGLAIA |
| Flg22 SEQ ID NO: 237 *Bacillus bombysepticus* strain Wang | DRLSSGKRINNASDDAAGLAIA |
| Flg22 SEQ ID NO: 238 *Bacillus thuringiensis serovar kenyae* | DRLSSGKRINNASDDAAGLAIA |

TABLE 3-continued

Flagellin polypeptides Flg22 and FlgII-28 identified from *Bacillus* spp.

| SEQ ID NO: | |
|---|---|
| Flg22<br>SEQ ID NO: 239<br>*Bacillus thuringiensis serovar kenyae* | DRLSSGKRINNASDDAAGLAIA |
| Flg22<br>SEQ ID NO: 240<br>*Bacillus cereus* | DRLSSGKRINNASDDAAGLAIA |
| Flg22<br>SEQ ID NO: 241<br>*Bacillus cereus* | EHLATGKKLNNASDNPANIAIV |
| Flg22<br>SEQ ID NO: 242<br>*Bacillus thuringiensis serovar finitimus*<br>strain YBT-020 | EHLATGKKLNHASDNPANVAIV |
| Flg22<br>SEQ ID NO: 243<br>*Bacillus thuringiensis serovar finitimus*<br>strain YBT-020 | DRLSSGKRINNASDDAAGLAIA |
| Flg22<br>SEQ ID NO: 244<br>*Bacillus cereus*<br>stain B4264 | DRLSSGKRINNASDDAAGLAIA |
| Flg22<br>SEQ ID NO: 245<br>*Bacillus thuringiensis serovar nigeriensis* | DRLSSGKRINNASDDAAGLAIA |
| Flg22<br>SEQ ID NO: 246<br>*Bacillus thuringiensis* | DRLSSGKRINNASDDAAGLAIA |
| Flg22<br>SEQ ID NO: 247<br>*Bacillus thuringiensis serovar konkukian*<br>strain 97-27 | EHFATGKKLNHASDNPANVAIV |
| Flg22<br>SEQ ID NO: 248<br>*Bacillus thuringiensis serovar konkukian*<br>strain 97-27 | DRLSSGKRINNASDDAAGLAIA |
| Flg22<br>SEQ ID NO: 249<br>*Bacillus thuringiensis serovar thuringiensis*<br>strain IS5056 | EHLATGKKLNHASDNPANIVIV |
| Flg22<br>SEQ ID NO: 250<br>*Bacillus thuringiensis serovar thuringiensis*<br>strain IS5056 | DRLSSGKRINNASDDAAGLAIA |
| Flg22<br>SEQ ID NO: 251<br>*Bacillus thuringiensis*<br>strain Bt407 | DRLSSGKRINNASDDAAGLAIA |
| Flg22<br>SEQ ID NO: 252<br>*Bacillus thuringiensis serovar chinensis*<br>CT-43 | DRLSSGKRINNASDDAAGLAIA |
| Flg22<br>SEQ ID NO: 253<br>*Bacillus thuringiensis serovar canadensis* | DRLSSGKRINNASDDAAGLAIA |
| Flg22<br>SEQ ID NO: 254<br>*Bacillus thuringiensis serovar galleriae* | DRLSSGKRINNASDDAAGLAIA |
| Flg22<br>SEQ ID NO: 255<br>*Bacillus weihenstephanensis* | DRLSSGKRINNASDDAAGLAIA |
| Flg22<br>SEQ ID NO: 256<br>*Bacillus thuringiensis serovar ostriniae* | DRLSSGKRINNASDDAAGLAIA |
| Flg22<br>SEQ ID NO: 257<br>*Bacillus thuringiensis* | EHLATGKKLNHASDNPANVAIV |
| Flg22<br>SEQ ID NO: 258<br>*Bacillus thuringiensis* | DRLSSGKRINNASDDAAGLAIA |
| Flg22<br>SEQ ID NO: 259<br>*Bacillus thuringiensis serovar pondicheriensis* | DRLSSGKRINNASDDAAGLAIA |
| Flg22<br>SEQ ID NO: 260<br>*Bacillus thuringiensis serovar Berliner* | EHLATGKKLNHASDNPANIVIV |
| Flg22<br>SEQ ID NO: 261<br>*Bacillus thuringiensis serovar Berliner* | DRLSSGKRINNASDDAAGLAIA |
| Flg22<br>SEQ ID NO: 262<br>*Bacillus cereus*<br>strain Q1 | EHLATGKKLNHASNNPANVAIV |
| Flg22<br>SEQ ID NO: 263<br>*Bacillus cereus*<br>strain Q1 | DRLSSGKRINNASDDAAGLAIA |
| Flg22<br>SEQ ID NO: 264<br>*Bacillus thuringiensis serovar morrisoni* | EHLATGKKLNHASDNPANIAIV |
| Flg22<br>SEQ ID NO: 265<br>*Bacillus thuringiensis serovar neoleonensis* | DRLSSGKRINNASDDAAGLAIA |
| Flg22<br>SEQ ID NO: 266<br>*Bacillus thuringiensis serovar morrisoni* | DRLSSGKRINNASDDAAGLAIA |
| Flg22<br>SEQ ID NO: 267<br>*Bacillus thuringiensis serovar morrisoni* | DRLSSGKRINNASDDAAGLAIA |

TABLE 3-continued

Flagellin polypeptides Flg22 and FlgII-28 identified from *Bacillus* spp.

| SEQ ID NO: | |
|---|---|
| Flg22<br>SEQ ID NO: 268<br>*Bacillus thuringiensis serovar jegathesan* | DRLSSGKRINNASDDAAGLAIA |
| Flg22<br>SEQ ID NO: 269<br>*Bacillus cereus*<br>stain ATCC 10987 | DRLSSGKRINNASDDAAGLAIA |
| Flg22 from Flagellin A<br>SEQ ID NO: 270<br>*Bacillus thuringiensis serovar monterrey* | DRLSSGKRINNASDDAAGLAIA |
| Flg22<br>SEQ ID NO: 271<br>*Bacillus cereus*<br>strain NC7401 | EHLATGKKLNNASDNPANIAIV |
| Flg22<br>SEQ ID NO: 272<br>*Bacillus cereus*<br>strain NC7401 | DRLSSGKRINNASDDAAGLAIA |
| Flg22<br>SEQ ID NO: 273<br>*Bacillus cereus*<br>strain AH820 | DRLSSGKRINNASDDAAGLAIA |
| Flg22<br>SEQ ID NO: 274<br>*Bacillus cereus* AH187 | DRLSSGKRINNASDDAAGLAIA |
| Flg22<br>SEQ ID NO: 275<br>*Bacillus cereus* | DRLSSGKRINNASDDAAGLAIA |
| Flg22<br>SEQ ID NO: 276<br>*Bacillus cereus* | DRLSSGKRINNASDDAAGLAIA |
| Flg22<br>SEQ ID NO: 277<br>*Bacillus thuringiensis*<br>Strain HD-771 [51] | DRLSSGKRINNASDDAAGLAIA |
| Flg22<br>SEQ ID NO: 278<br>*Bacillus thuringiensis serovar sotto* [52] | DRLSSGKRINNASDDAAGLAIA |
| Flg22<br>SEQ ID NO: 279<br>*Bacillus thuringiensis serovar Novosibirsk* | DRLSSGKRINNASDDAAGLAIA |
| Flg22<br>SEQ ID NO: 280<br>*Bacillus thuringiensis serovar londrina* | DRLSSGKRINNASDDAAGLAIA |
| Flg22<br>SEQ ID NO: 281<br>*Bacillus cereus*<br>strain E33L | EHLATGKKLNHASNNPANIAIV |
| Flg22<br>SEQ ID NO: 282<br>*Bacillus cereus*<br>strain E33L | DRLSSGKRINNASDDAAGLAIA |

TABLE 3-continued

Flagellin polypeptides Flg22 and FlgII-28 identified from *Bacillus* spp.

| SEQ ID NO: | |
|---|---|
| Flg22<br>SEQ ID NO: 283<br>*Bacillus cereus*<br>strain FRI-35 | DRLSSGKRINNASDDAAGLAIA |
| Flg22<br>SEQ ID NO: 284<br>*Bacillus cereus*<br>strain FRI-35 | EHLATGKKLNNASDNPANIAIV |
| Flg22<br>SEQ ID NO: 285<br>*Bacillus thuringiensis* | DRLSSGKRINNASDDAAGLAIA |
| Flg22<br>SEQ ID NO: 286<br>*Bacillus cereus*<br>strain ATCC 4342 | DRLSSGKRINNASDDAAGLAIA |
| Flg22<br>SEQ ID NO: 287<br>*Bacillus thuringiensis* | EHLATGKKLNHASDNPANIAIV |
| Flg22<br>SEQ ID NO: 288<br>Bacillus *thuringiensis* | DRLSSGKRINNASDDAAGLAIA |
| Flg22<br>SEQ ID NO: 289<br>*Bacillus aryabhattai* | EKLSSGQRINSASDDAAGLAIS |
| Flg22<br>SEQ ID NO: 290<br>*Bacillus manliponensis* | NRLSSGKQINSASDDAAGLAIA |
| Flg22<br>SEQ ID NO: 291<br>*Lysinibacillus* sp.<br>strain BF-4 | LRLSSGYRINSAADDAAGLAIS |
| Flg22<br>SEQ ID NO: 292<br>*Lysinibacillus* sp.<br>strain 13S34_air | LRLSSGYRINSAADDAAGLAIS |
| Flg22<br>SEQ ID NO: 293<br>*Paenibacillus* sp.<br>strain HW567 | GKLSSGLRINGASDDAAGLAIS |
| Flg22<br>SEQ ID NO: 294<br>*Bacillus anthracis* | DRLSSGKRINNASDDAAGLAIA |
| Flg22<br>SEQ ID NO: 295<br>*Bacillus anthracis* | NRLSSGKRINSAADDAAGLAIA |
| Flg22<br>SEQ ID NO: 296<br>*Bacillus anthracis* | NRLSSGKRINSAADDAAGLAIA |
| Flg22<br>SEQ ID NO: 297<br>*Bacillus anthracis* | NRLSSGKRINSAADDAAGLAIA |
| Flg22<br>SEQ ID NO: 298<br>*Bacillus anthracis*<br>strain H9401 | NRLSSGKRINSAADDAAGLAIA |

TABLE 3-continued

| Flagellin polypeptides Flg22 and FlgII-28 identified from *Bacillus* spp. | |
|---|---|
| SEQ ID NO: | |
| Flg22<br>SEQ ID NO: 299<br>*Bacillus megaterium*<br>strain WSH-002 | EKLSSGQRINSASDDAAGLAIS |
| Flg22<br>SEQ ID NO: 300<br>*Aneurinibacillus* sp. XH2 | ERLSSGYRINRASDDAAGLAIS |
| | Peptide Flg15 |
| Flg15-Bt4Q7<br>SEQ ID NO: 752<br>Modified FLG15-Bt4Q7;<br>Syn01<br>*Bacillus thuringiensis*<br>strain 4Q7 | RINSAKDDAAGLAIA |
| | Peptide FglI-28 |
| FlgII-28-Bt.4Q7<br>SEQ ID NO: 301<br>*Bacillus thuringiensis*<br>strain 4Q7 | SVSNILLRMRDLANQSANGTNTK<br>GNQAS |
| FlgII-28<br>SEQ ID NO: 302<br>*Bacillus thuringiensis*,<br>strain HD1002 | SVSNILLRMRDLANQSANGTNTK<br>GNQAS |
| FlgII-28<br>SEQ ID NO: 303<br>*Bacillus thuringiensis*,<br>strain HD-789 | SVSNILLRMRDLANQSANGTNTK<br>GNQAS |
| FlgII-28<br>SEQ ID NO: 304<br>*Bacillus cereus*<br>strain G9842 | SVSNILLRMRDLANQSANGTNTK<br>GNQAS |
| FlgII-28<br>SEQ ID NO: 305<br>*Bacillus thuringiensis*<br>*serovar indiana*<br>strain HD521 | TVTNILQRMRDLAVQSANGTNSN<br>KNRHS |
| FlgII-28<br>SEQ ID NO: 306<br>*Bacillus thuringiensis*<br>strain CTC | SVSNILLRMRDIANQSANITNTN<br>ENKSA |
| FlgII-28<br>SEQ ID NO: 307<br>Bacillus<br>thuringiensis<br>*serovar yunnanensis*<br>strain IEBC-T20001 | SVSNILLRMRDLANQSANGTNTD<br>DNQKA |
| FlgII-28<br>SEQ ID NO: 308<br>*Bacillus thuringiensis*<br>*serovar tolworthi* | SVSNILLRMRDLANQSANGTNTD<br>ENKAA |
| FlgII-28<br>SEQ ID NO: 309<br>*Bacillus cereus*<br>strain FM1 | SVSNILLRMRDIANQSANGTNTD<br>KNQVA |
| FlgII-28<br>SEQ ID NO: 310<br>*Bacillus cereus*<br>strain FM1 | TVTNILQRMRDVAVQSANGTNSN<br>KNRDS |

TABLE 3-continued

| Flagellin polypeptides Flg22 and FlgII-28 identified from *Bacillus* spp. | |
|---|---|
| SEQ ID NO: | |
| FlgII-28<br>SEQ ID NO: 311<br>*Bacillus thuringiensis*<br>strain MC28 | SVSNILLRMRDIANQSANGTNTA<br>DNQQA |
| FlgII-28<br>SEQ ID NO: 312<br>*Bacillus bombysepticus*<br>strain Wang | SVSNILLRMRDLANQSASGTNTD<br>KNQAA |
| FlgII-28<br>SEQ ID NO: 313<br>*Bacillus thuringiensis*<br>*serovar kenyae* | SVSNILLRMRDLANQSASGTNTD<br>KNQAA |
| FlgII-28<br>SEQ ID NO: 314<br>*Bacillus thuringiensis*<br>*serovar kenyae* | SVSNILLRMRDLANQSASGTNTD<br>KNQAA |
| FlgII-28<br>SEQ ID NO: 315<br>*Bacillus cereus* | SVSNILLRMRDLANQSANGTNTG<br>DNQKA |
| FlgII-28<br>SEQ ID NO: 316<br>*Bacillus cereus* | TNILQRMRDLAVQSANGTNSNKN<br>RDSLN |
| FlgII-28<br>SEQ ID NO: 317<br>*Bacillus thuringiensis*<br>*serovar finitimus*<br>strain YBT-020 | TNVLQRMRDVAVQSANGTNLNKN<br>RDSLN |
| FlgII-28<br>SEQ ID NO: 318<br>*Bacillus thuringiensis*<br>*serovar finitimus*<br>strain YBT-020 | SVSNILLRMRDIANQSANGTNTD<br>SNKSA |
| FlgII-28<br>SEQ ID NO: 319<br>*Bacillus cereus*<br>stain B4264 | SVSNILLRMRDLANQSANGTNTA<br>ENKAA |
| FlgII-28<br>SEQ ID NO: 320<br>*Bacillus thuringiensis*<br>*serovar nigeriensis* | SVSNILLRMRDIANQSANGTNTS<br>DNQKA |
| FlgII-28<br>SEQ ID NO: 321<br>*Bacillus thuringiensis* | SVSNILLRMRDIANQSANGTNTA<br>DNQQA |
| FlgII-28<br>SEQ ID NO: 322<br>*Bacillus thuringiensis*<br>*serovar konkukian*<br>strain 97-27 | TVMNILQRMRDLAVQSANGTNSN<br>KNRDS |
| FlgII-28<br>SEQ ID NO: 323<br>*Bacillus thuringiensis*<br>*serovar konkukian*<br>strain 97-27 | SVSNILLRMRDIANQSANGTNTA<br>DNQQA |
| FlgII-28<br>SEQ ID NO: 324<br>*Bacillus thuringiensis*<br>*serovar thuringiensis*<br>strain IS5056 | TVTNILQHMRDFAIQSANGTNSN<br>TNRDS |

TABLE 3-continued

Flagellin polypeptides Flg22 and FlgII-28 identified from *Bacillus* spp.

| SEQ ID NO: | |
|---|---|
| FlgII-28 SEQ ID NO: 325 *Bacillus thuringiensis serovar thuringiensis* strain IS5056 | SVSNILLRMRDISNQSANGTNTD KNQSA |
| FlgII-28 SEQ ID NO: 326 *Bacillus thuringiensis* strain Bt407 | SVSNILLRMRDISNQSANGTNTD KNQSA |
| FlgII-28 SEQ ID NO: 327 *Bacillus thuringiensis serovar chinensis* CT-43 | SVSNILLRMRDISNQSANGTNTD KNQSA |
| FlgII-28 SEQ ID NO: 328 *Bacillus thuringiensis serovar canadensis* | SVSNILLRMRDLANQSANGTNTN ENQAA |
| FlgII-28 SEQ ID NO: 329 *Bacillus thuringiensis serovar galleriae* | SVSNILLRMRDLANQSANGTNTN ENQAA |
| FlgII-28 SEQ ID NO: 330 *Bacillus weihenstephanensis* | SVSNILLRMRDLSNQSANGTNTD ENQQA |
| FlgII-28 SEQ ID NO: 331 *Bacillus thuringiensis serovar ostriniae* | SVSNILLRMRDIANQSANGTNTG DNQKA |
| FlgII-28 SEQ ID NO: 332 *Bacillus thuringiensis* | TVANILQRMRDLAVQSSNDTNSN KNRDS |
| FlgII-28 SEQ ID NO: 333 *Bacillus thuringiensis* | SVSNILLRMRDLANQSANGTNTD DNQKA |
| FlgII-28 SEQ ID NO: 334 *Bacillus thuringiensis serovar pondicheriensis* | SVSNILLRMRDLANQSANGTNTD DNQKA |
| FlgII-28 SEQ ID NO: 335 *Bacillus thuringiensis serovar Berliner* | TVTNILQHMRDFAIQSANGTNSN TNRDS |
| FlgII-28 SEQ ID NO: 336 *Bacillus thuringiensis serovar Berliner* | SVSNILLRMRDISNQSANGTNTD KNQSA |
| FlgII-28 SEQ ID NO: 337 *Bacillus cereus* strain Q1 | TVTNVLQRMRDVAVQSANGTNSS KNRDS |
| FlgII-28 SEQ ID NO: 338 *Bacillus cereus* strain Q1 | SVSNILLRMRDIANQSANGTNTD KNQVA |
| FlgII-28 SEQ ID NO: 339 *Bacillus thuringiensis serovar morrisoni* | TVMNILQRMRDLAIQSANSTNSN KNRDS |
| FlgII-28 SEQ ID NO: 340 *Bacillus thuringiensis serovar neoleonensis* | SVSNILLRMRDIANQSANGTNTS DNQKA |
| FlgII-28 SEQ ID NO: 341 *Bacillus thuringiensis serovar morrisoni* | SVSNILLRMRDIANQSANGTNTG DNQKA |
| FlgII-28 SEQ ID NO: 342 *Bacillus thuringiensis serovar morrisoni* | SVSNILLRMRDIANQSANGTNTG DNQKA |
| FlgII-28 SEQ ID NO: 343 *Bacillus thuringiensis serovar jegathesan* | SVSNILLRMRDIANQSANGTNTN GNQAA |
| FlgII-28 SEQ ID NO: 344 *Bacillus cereus* stain ATCC 10987 | SVSNILLRMRDIANQSANGTNTD KNQAA |
| FlgII-28 from Flagellin A SEQ ID NO: 345 *Bacillus thuringiensis serovar monterrey* | SVSNILLRMRDLANQSANGTNTN ENQAA |
| FlgII-28 SEQ ID NO: 346 *Bacillus cereus* strain NC7401 | TVTNVLQRMRDLAVQSANDTNSN KNRDS |
| FlgII-28 SEQ ID NO: 347 *Bacillus cereus* strain NC7401 | SVSNILLRMRDLANQSANGTNTN ENKAA |
| FlgII-28 SEQ ID NO: 348 *Bacillus cereus* strain AH820 | SVSNILLRMRDLANQSANGTNTS DNQAA |
| FlgII-28 SEQ ID NO: 349 *Bacillus cereus* AH187 | SVSNILLRMRDLANQSANGTNTN ENKAA |
| FlgII-28 SEQ ID NO: 350 *Bacillus cereus* | SVSNILLRMRDLANQSANGTNTN ENKAA |
| FlgII-28 SEQ ID NO: 351 *Bacillus cereus* | SVSNILLRMRDIANQSANGTNTG DNQKA |
| FlgII-28 SEQ ID NO: 352 *Bacillus thuringiensis* Strain HD-771 [51] | SVSNILLRMRDLANQSASETNTS KNQAA |
| FlgII-28 SEQ ID NO: 353 *Bacillus thuringiensis serovar sotto* [52] | SVSNILLRMRDLANQSASETNTS KNQAA |
| FlgII-28 SEQ ID NO: 354 *Bacillus thuringiensis serovar Novosibirsk* | SVSNILLRMRDIANQSANGTNTG DNQKA |

TABLE 3-continued

Flagellin polypeptides Flg22 and FlgII-28 identified from *Bacillus* spp.

| SEQ ID NO: | |
|---|---|
| FlgII-28<br>SEQ ID NO: 355<br>*Bacillus thuringiensis*<br>*serovar londrina* | SVSNILLRMRDLANQSANGTNTS<br>ENQAA |
| FlgII-28<br>SEQ ID NO: 356<br>*Bacillus cereus*<br>strain E33L | TVTNILQRMRDLAVQSANVTNSN<br>KNRNS |
| FlgII-28<br>SEQ ID NO: 357<br>*Bacillus cereus*<br>strain E33L | SVSNILLRMRDLANQSANGTNTD<br>KNQGA |
| FlgII-28<br>SEQ ID NO: 358<br>*Bacillus cereus*<br>strain FRI-35 | SVSNILLRMRDLANQSANGTNTD<br>KNQAA |
| FlgII-28<br>SEQ ID NO: 359<br>*Bacillus cereus*<br>strain FRI-35 | TVTNVLQRMRDLAVQSANGTNSN<br>KNRDS |
| FlgII-28<br>SEQ ID NO: 360<br>*Bacillus thuringiensis* | SVSNILLRMRDIANQTANGTNKD<br>TDIEA |
| FlgII-28<br>SEQ ID NO: 361<br>*Bacillus cereus*<br>strain ATCC 4342 | SVSNILLRMRDIANQTANGTNKD<br>TDIEA |
| FlgII-28<br>SEQ ID NO: 362<br>*Bacillus thuringiensis* | TVMNILQRMRDLAIQSANSTNSN<br>KNRDS |
| FlgII-28<br>SEQ ID NO: 363<br>*Bacillus thuringiensis* | SVSNILLRMRDIANQSANGTNTG<br>DNQKA |
| FlgII-28<br>SEQ ID NO: 364<br>*Bacillus aryabhattai* | ETHDILQRMRELVVQAGNGTNKT<br>EDLDA |
| FlgII-28<br>SEQ ID NO: 365<br>*Bacillus manliponensis* | SVSNILLRMRDLATQSATGTNQG<br>NDRES |
| FlgII-28<br>SEQ ID NO: 366<br>*Lysinibacillus*<br>sp. strain BF-4 | ETHAIVQRMRELAVQAATDTNTD<br>DDRAK |
| FlgII-28<br>SEQ ID NO: 367<br>*Lysinibacillus* sp.<br>strain 13S34_air | ETHAIVQRMRELAVQAATDTNTD<br>DDRAK |
| FlgII-28<br>SEQ ID NO: 368<br>*Paenibacillus* sp.<br>strain HW567 | EIHSMLQRMNELAVQASNGTYSG<br>SDRLN |
| FlgII-28<br>SEQ ID NO: 369<br>*Bacillus anthracis* | SVSNILLRMRDLANQSANGTNTK<br>ENQDA |
| FlgII-28<br>SEQ ID NO: 370<br>*Bacillus anthracis* | SVSNILTRMRDIAVQSSNGTNTA<br>ENQSA |
| FlgII-28<br>SEQ ID NO: 371<br>*Bacillus anthracis* | SVSNILTRMRDIAVQSSNGTNTA<br>ENQSA |
| FlgII-28<br>SEQ ID NO: 372<br>*Bacillus anthracis* | SVSNILTRMRDIAVQSSNGTNTA<br>ENQSA |
| FlgII-28<br>SEQ ID NO: 373<br>*Bacillus anthracis*<br>strain H9401 | SVSNILTRMRDIAVQSSNGTNTA<br>ENQSA |
| FlgII-28<br>SEQ ID NO: 374<br>*Bacillus megaterium*<br>strain WSH-002 | ETHDILQRMRELVVQAGNGTNKT<br>EDLDA |
| FlgII-28<br>SEQ ID NO: 375<br>*Aneurinibacillus*<br>sp. XH2 | EIHEMLQRMRELAVQAANGTYSD<br>KDKKA |

Retro-Inverso Flagellin-Associated Polypeptides

Bioactive Flg polypeptide(s) useful for priming can be created in a non-natural isomeric or retro-inverso (RI) form.

The retro-inverso Flg polypeptides can exhibit enhanced binding affinity for the FLS receptor protein(s). Plant flagellin receptors, like FLS2, can recognize a retro inverso Flg polypeptide fragment such as either Flg22 or FlgII-28 located within the N-terminal conserved domain of flagellin. The retro-inverso forms of these Flg polypeptides are provided as biologically active forms, which can recognize and interact with the Flg-associated or FLS receptor protein on the surface of the plant cell membrane.

Retro-inverso Flg polypeptides can possess an increased activity and stability to proteolytic degradation at the plant membrane surface. For example, retro inverso forms of *Bacillus* Flg22 or FlgII-28 polypeptides can increase activity and stability of the Flg polypeptide(s) and increase protection against proteolytic degradation at the plant surface or root surface. The retro inverso forms also exhibit enhanced stability when applied in a field, or on or in a soil.

Retro-inverso polypeptides are topological mirror images of the native structures of the parent polypeptide. Retro inverso synthetic forms of the polypeptide sequences are created by reversing the polypeptide sequences and using retro-all-D or retro-enantio-peptides. The all D-chain amino acid Flg polypeptide(s) adopts a “mirror image” of the three-dimensional structure of its related L-peptide or L-chain amino.

This is further accomplished by creating a retro-inverso alteration of any of the parent Flg polypeptide derived from *Bacillus* or other Eubacteria in Table 3. Retro-inverso polypeptides that were designed to the Flg22 (RI Flg22: SEQ ID NOs: 376-450), and FlgII-28 (RI-FlgII-28: SEQ ID NOs: 451-525) are provided in Table 4. Retro inverso forms of Ec.Flg22 (SEQ ID NO: 526) and EcFlg15 (SEQ ID NO: 529) as provided in Table 5 were also created from *E. coli* derived sequences.

The polypeptide can include a retro inverso Flg22 polypeptide.

The polypeptide can comprise a retro inverso FlgII-28 polypeptide.

Any of the flagellin-associated bioactive priming polypeptides comprising *Bacillus* or from other Eubacteria Flg22 or FlgII-28 polypeptides in Table 3 can be used in their retro-inversed forms (referenced in Table 4).

Retro inverso forms of the Flg bioactive priming polypeptides as referenced herein can be provided in any of three forms where the inversion of amino acid chirality contains the normal-all-D (inverso), all-L (retro) and/or retro-all-D (retro-inverso) or a combination of these forms to achieve the desired phenotypes in a plant.

The *Bacillus*-derived L-Flg22 and L-FlgII-28 polypeptides in Table 3 and the E.c. native L-Flg22 and L-Flg15 polypeptides in Table 5 were synthetically generated via retro-inverso engineering to form retro-inverso D-Flg22 polypeptide (SEQ ID NO: 376-450), D-FlgII-28 (SEQ ID NO: 451-525), and E.c. D-Flg22 polypeptide (SEQ ID NO: 527, 529).

The inversion of amino acid chirality (all-L to all-D) for Bt.4Q7 Flg22 (SEQ ID NO: 376), which is provided as a small linear polypeptide fragment and is referred to as a retro inverso modification was achieved by a reversal of the direction of the polypeptide backbone and described below.

$({}^{D}A{}^{D}IA{}^{D}L{}^{D}G{}^{D}A{}^{D}A{}^{D}D{}^{D}D{}^{D}S{}^{D}A{}^{D}S{}^{D}N\text{-}{}^{D}I{}^{D}R{}^{D}K{}^{D}G{}^{D}S{}^{D}S{}^{D}L{}^{D}R{}^{D}D)$ The retro inverso all D-chain amino acid Flg22 polypeptide adopts a "mirror image" of the three-dimensional structure of its related native L-Bt.4Q7Flg 22 polypeptide and this all L-chain has an equivalent mirror image to the all D Bt.4Q7Flg22 polypeptide. All L-amino acid residues are replaced by their D-enantiomers leading to all D-peptides or retro all D-isomer-peptides containing amide linkages. The native L-amino acid chain form of Bt.4Q7 Flg22 polypeptide chain reversed to generate the retro-inverso synthetic all-D confirmation that is prepared by replacing all the L-amino acid residues with their corresponding D-enantiomers.

FIG. 1 provides a diagrammatic representation of a natural (all L) Bt.4Q7 Flg22 and its retro inverso or mirror image to form an all D Bt.4Q7 Flg22 enantiomeric polypeptide. The retro-inverso Flg polypeptide that corresponds to Bt.4Q7 Flg22 (SEQ ID NO: 226) is described as SEQ ID NO: 376.

In the case of short polypeptides, such as Flg22, Flg15 and FlgII-28, the mirroring of the side chain positions in a conformational change from L-to-D conversion states results in a mirroring of symmetry transformations of the side chains as well.

Retro-all-D analogues have been found to possess biological activity (Guptasarma, "Reversal of peptide backbone direction may result in mirroring of protein structure, FEBS Letters 310: 205-210, 1992). The retro-inverso D-Flg polypeptide(s) can assume a side chain topology in its extended conformation that is similar to a corresponding native L-Flg polypeptide sequence, thus emulating biological activities of the native L-parent molecule while fully resistant to proteolytic degradation thus increasing stability when the polypeptide contacts the plant or the surrounding environment.

Retro-inverso Flg bioactive priming polypeptides are described in Table 4 or Table 5. Retro inverso Flg-associated bioactive priming polypeptides provided in Table 4 were selected for their enhanced activity and stability and their ability to survive under varying conditions and environments. Based on their D enantiomer nature, they are more resistant to proteolytic degradation and can survive and exist in harsher environmental conditions.

TABLE 4

Retro-inverso flagellin polypeptides from Flg22 and FlgII-28 from *Bacillus*

| SEQ ID NO: | Peptide Flg22 |
|---|---|
| RI Bt.4Q7Flg22<br>SEQ ID NO: 376<br>*Bacillus thuringiensis*<br>strain 4Q7 | AIALGAADDSASNIRKGSSLRD |
| RI Flg22<br>SEQ ID NO: 377<br>*Bacillus thuringiensis*,<br>strain HD1002 | AIALGAADDSASNIRKGSSLRD |
| RI Flg22<br>SEQ ID NO: 378<br>*Bacillus thuringiensis*,<br>strain HD-789 | AIALGAADDASNIRKGSSLRD |
| RI Flg22<br>SEQ ID NO: 379<br>*Bacillus cereus*<br>strain G9842 | AIALGAADDSASNIRKGSSLRD |
| RI Flg22<br>SEQ ID NO: 380<br>*Bacillus thuringiensis*<br>*serovar indiana*<br>strain HD521 | VIANAPNDSANNLKKGTALHE |
| RI Flg22<br>SEQ ID NO: 381<br>*Bacillus thuringiensis*<br>strain CTC | TAIAGAADDSANNIRKGSSLRD |
| RI Flg22<br>SEQ ID NO: 382<br>*Bacillus thuringiensis*<br>*serovaryunnanensis*<br>strain IEBC-T20001 | AIALGAADDSANNIRKGSSLRD |
| RI Flg22<br>SEQ ID NO: 383<br>*Bacillus thuringiensis*<br>*serovar tolworthi* | AIALGAADDSANNIRKGSSLRD |
| RI Flg22<br>SEQ ID NO: 384<br>*Bacillus cereus*<br>strain FM1 | AIALGAADDSANNIRKGSSLRD |
| RI Flg22<br>SEQ ID NO: 385<br>*Bacillus cereus*<br>strain FM1 | VIAVNAPNDSAHNLKKGTALHE |
| RI Flg22<br>SEQ ID NO: 386<br>*Bacillus thuringiensis*<br>strain MC28 | AIALGAADDSANNIRKGSSLRD |
| RI Flg22<br>SEQ ID NO: 387<br>*Bacillus bombysepticus*<br>strain Wang | AIALGAADDSANNIRKGSSLRD |
| RI Flg22<br>SEQ ID NO: 388<br>*Bacillus thuringiensis*<br>*serovar kenyae* | AIALGAADDSANNIRKGSSLRD |
| RI Flg22<br>SEQ ID NO: 389<br>*Bacillus thuringiensis*<br>*serovar kenyae* | AIALGAADDSANNIRKGSSLRD |

TABLE 4-continued

| Retro-inverso flagellin polypeptides from Flg22 and FlgII-28 from *Bacillus* | |
|---|---|
| SEQ ID NO: | |
| RI Flg22 SEQ ID NO: 390 *Bacillus cereus* | AIALGAADDSANNIRKGSSLRD |
| RI Flg22 SEQ ID NO: 391 *Bacillus cereus* | VIAINAPNDASNNLKKGTALHE |
| RI Flg22 SEQ ID NO: 392 *Bacillus thuringiensis serovar finitimus* strain YBT-020 | VIANAPNDSAHNLKKGTALHE |
| RI Flg22 SEQ ID NO: 393 *Bacillus thuringiensis serovar finitimus* strain YBT-020 | AIALGAADDSANNIRKGSSLRD |
| RI Flg22 SEQ ID NO: 394 *Bacillus cereus* stain B4264 | AIALGAADDSANNIRKGSSLRD |
| RI Flg22 SEQ ID NO: 395 *Bacillus thuringiensis serovar nigeriensis* | AIALGAADDSANNIRKGSSLRD |
| RI Flg22 SEQ ID NO: 396 *Bacillus thuringiensis* | AIALGAADDSANNIRKGSSLRD |
| RI Flg22 SEQ ID NO: 397 *Bacillus thuringiensis* serovar konkukian strain 97-27 | VIANAPNDSAHNLKKGTAFHE |
| RI Flg22 SEQ ID NO: 398 *Bacillus thuringiensis serovar konkukian* strain 97-27 | AIALGAADDSANNRKGSSLRD |
| RI Flg22 SEQ ID NO: 399 *Bacillus thuringiensis serovar thuringiensis* strain IS5056 | VIVINAPNDSAHNLKKGTALHE |
| RI Flg22 SEQ ID NO: 400 *Bacillus thuringiensis serovar thuringiensis* strain IS5056 | AIALGAADDSANNIRKGSSLRD |
| RI Flg22 SEQ ID NO: 401 *Bacillus thuringiensis* strain Bt407 | AIALGAADDSANNIRKGSSLRD |
| RI Flg22 SEQ ID NO: 402 *Bacillus thuringiensis serovar chinensis* CT-43 | AIALGAADDSANNIRKGSSLRD |
| RI Flg22 SEQ ID NO: 403 *Bacillus thuringiensis serovar canadensis* | AIALGAADDSANNIRKGSSLRD |
| RI Flg22 SEQ ID NO: 404 *Bacillus thuringiensis serovar galleriae* | AIALGAADDSANNIRKGSSLRD |
| RI Flg22 SEQ ID NO: 405 *Bacillus weihenstephanensis* | AIALGAADDSANNIRKGSSLRD |
| RI Flg22 SEQ ID NO: 406 *Bacillus thuringiensis serovar ostriniae* | AIALGAADDSANNIRKGSSLRD |
| RI Flg22 SEQ ID NO: 407 *Bacillus thuringiensis* | VIANAPNDSAHNLKKGTALHE |
| RI Flg22 SEQ ID NO: 408 *Bacillus thuringiensis* | AIALGAADDSANNIRKGSSLRD |
| RI Flg22 SEQ ID NO: 409 *Bacillus thuringiensis serovar pondicheriensis* | AIALGAADDSANNIRKGSSLRD |
| RI Flg22 SEQ ID NO: 410 *Bacillus thuringiensis serovar Berliner* | VIVINAPNDASHNLKKGTALHE |
| RI Flg22 SEQ ID NO: 411 *Bacillus thuringiensis serovar Berliner* | AIALGAADDSANNIRKGSSLRD |
| RI Flg22 SEQ ID NO: 412 *Bacillus cereus* strain Q1 | VIAVANPNNSAHNLKKGTALHE |
| RI Flg22 SEQ ID NO: 413 *Bacillus cereus* strain Q1 | AIALGAADDSANNIRKGSSLRD |
| RI Flg22 SEQ ID NO: 414 *Bacillus thuringiensis serovar morrisoni* | VIANAPNDSAHNLKKGTALHE |
| RI Flg22 SEQ ID NO: 415 *Bacillus thuringiensis serovar neoleonensis* | AIALGAADDSANNIRKGSSLRD |
| RI Flg22 SEQ ID NO: 416 *Bacillus thuringiensis serovar morrisoni* | AIALGAADDSANNIRKGSSLRD |
| RI Flg22 SEQ ID NO: 417 *Bacillus thuringiensis serovar morrisoni* | AIALGAADDSANNIRKGSSLRD |
| RI Flg22 SEQ ID NO: 418 *Bacillus thuringiensis serovar jegathesan* | AIALGAADDSANNIRKGSSLRD |

TABLE 4-continued

| Retro-inverso flagellin polypeptides from Flg22 and FlgII-28 from *Bacillus* | |
|---|---|
| SEQ ID NO: | |
| RI Flg22<br>SEQ ID NO: 419<br>*Bacillus cereus*<br>strain ATCC 10987 | AIALGAADDSANNIRKGSSLRD |
| RI Flg22 from Flagellin A<br>SEQ ID NO: 420<br>*Bacillus thuringiensis serovar monterrey* | AIALGAADDASNNIRKGSSLRD |
| RI Flg22<br>SEQ ID NO: 421<br>*Bacillus cereus*<br>strain NC7401 | VIANAPNDSANNLKKGTALHE |
| RI Flg22<br>SEQ ID NO: 422<br>*Bacillus cereus*<br>strain NC7401 | AIALGAADDSANNIRKGSSLRD |
| RI Flg22<br>SEQ ID NO: 423<br>*Bacillus cereus*<br>strain AH820 | AIALGAADDSANNIRKGSSLRD |
| RI Flg22<br>SEQ ID NO: 424<br>*Bacillus cereus* AH187 | AIALGAADDSANNIRKGSSLRD |
| RI Flg22<br>SEQ ID NO: 425<br>*Bacillus cereus* | AIALGAADDSANNIRKGSSLRD |
| RI Flg22<br>SEQ ID NO: 426<br>*Bacillus cereus* | AIALGAADDSANNIRKGSSLRD |
| RI Flg22<br>SEQ ID NO: 427<br>*Bacillus thuringiensis*<br>Strain HD-771 [51] | AIALGAADDSANNIRKGSSLRD |
| RI Flg22<br>SEQ ID NO: 428<br>*Bacillus thuringiensis serovar sotto* [52] | AIALGAADDANNIRKGSSLRD |
| RI Flg22<br>SEQ ID NO: 429<br>*Bacillus thuringiensis serovar Novosibirsk* | AIALGAADDSANNIRKGSSLRD |
| RI Flg22<br>SEQ ID NO: 430<br>*Bacillus thuringiensis serovar londrina* | AIALGAADDSANNIRKGSSLRD |
| RI Flg22<br>SEQ ID NO: 431<br>*Bacillus cereus*<br>strain E33L | VIAINAPNNSAHNLKKGTALHE |
| RI Flg22<br>SEQ ID NO: 432<br>*Bacillus cereus*<br>strain E33L | AIALGAADDSANNIRKGSSLRD |
| RI Flg22<br>SEQ ID NO: 433<br>*Bacillus cereus*<br>strain FRI-35 | AIALGAADDSANNIRKGSSLRD |

TABLE 4-continued

| Retro-inverso flagellin polypeptides from Flg22 and FlgII-28 from *Bacillus* | |
|---|---|
| SEQ ID NO: | |
| RI Flg22<br>SEQ ID NO: 434<br>*Bacillus cereus*<br>strain FRI-35 | VIAINAPNDSANNLKKGTALHE |
| RI Flg22<br>SEQ ID NO: 435<br>*Bacillus thuringiensis* | AIALGAADDSANNIRKGSSLRD |
| RI Flg22<br>SEQ ID NO: 436<br>*Bacillus cereus*<br>strain ATCC 4342 | AIALGAADDANNIRKGSSLRD |
| RI Flg22<br>SEQ ID NO: 437<br>*Bacillus thuringiensis* | VIANAPNDSAHNLKKGTALHE |
| RI Flg22<br>SEQ ID NO: 438<br>*Bacillus thuringiensis* | AIALGAADDSANNIRKGSSLRD |
| RI Flg22<br>SEQ ID NO: 439<br>*Bacillus aryabhattai* | SIALGAADDSASNIRQGSSLKE |
| RI Flg22<br>SEQ ID NO: 440<br>*Bacillus manliponensis* | AIALGAADDSASNIQKGSSLRN |
| RI Flg22<br>SEQ ID NO: 441<br>*Lysinibacillus* sp.<br>strain BF-4 | SIALGAADDAASNIRYGSSLRL |
| RI Flg22<br>SEQ ID NO: 442<br>*Lysinibacillus* sp.<br>strain 13S34_air | SIALGAADDAASNIRYGSSLRL |
| RI Flg22<br>SEQ ID NO: 443<br>*Paenibacillus* sp.<br>strain HW567 | SIAGLAADDSAGNIRLGSSLKG |
| RI Flg22<br>SEQ ID NO: 444<br>*Bacillus anthracis* | AIALGAADDSANNIRKGSSLRD |
| RI Flg22<br>SEQ ID NO: 445<br>*Bacillus anthracis* | AIALGAADDAASNIRKGSSLRN |
| RI Flg22<br>SEQ ID NO: 446<br>*Bacillus anthracis* | AIALGAADDAASNIRKGSSLRN |
| RI Flg22<br>SEQ ID NO: 447<br>*Bacillus anthracis* | AIALGAADDAASNIRKGSSLRN |
| RI Flg22<br>SEQ ID NO: 448<br>*Bacillus anthracis*<br>strain H9401 | AIALGAADDAASNIRKGSSLRN |
| RI Flg22<br>SEQ ID NO: 449<br>*Bacillus megaterium*<br>strain WSH-002 | SIALGAADDSASNIRQGSSLKE |

TABLE 4-continued

| Retro-inverso flagellin polypeptides from Flg22 and FlgII-28 from *Bacillus* | |
|---|---|
| SEQ ID NO: | |
| RI Flg22 SEQ ID NO: 450 *Aneurinibacillus* sp. XH2 | SIALGAADDSARNIRYGSSLRE |
| | Peptide Flg15 |
| RI Flg15-Bt4Q7 SEQ ID NO: 767 Modified FLG15-Bt4Q7; Syn01 *Bacillus thuringiensis* strain 4Q7 | AIALGAADDKASNIR |
| | Peptide FlgII-28 |
| RI FlgII-28-Bt.4Q7 SEQ ID NO: 451 *Bacillus thuringiensis* strain 4Q7 | SAQNGKTNTGNASQNALDRMRL LINSVS |
| RI FlgII-28 SEQ ID NO: 452 *Bacillus thuringiensis*, strain HD1002 | SAQNGKTNTGNASQNALDRMRL LINSVS |
| RI FlgII-28 SEQ ID NO: 453 *Bacillus thuringiensis*, strain HD-789 | SAQNGKTNTGNASQNALDRMRL LINSVS |
| RI FlgII-28 SEQ ID NO: 454 *Bacillus cereus* strain G9842 | SAQNGKTNTGNASQNALDRMRL LINSVS |
| RI FlgII-28 SEQ ID NO: 455 *Bacillus thuringiensis serovar indiana* strain HD521 | SHRNKNSNTGNASQVALDRMRQ LINTVT |
| RI FlgII-28 SEQ ID NO: 456 *Bacillus thuringiensis* strain CTC | ASKNENTNTGNASQNAIDRMRL LINSVS |
| RI FlgII-28 SEQ ID NO: 457 *Bacillus thuringiensis serovaryunnanensis* strain IEBC-T20001 | AKQNDDTNTGNASQNALDRMRL LINSVS |
| RI FlgII-28 SEQ ID NO: 458 *Bacillus thuringiensis serovar tolworthi* | AAKNEDTNTGNASQNALDRMRL LINSVS |
| RI FlgII-28 SEQ ID NO: 459 *Bacillus cereus* strain FM1 | LAVQNKDTNTGNASQNAIDRMR LLINSVS |
| RI FlgII-28 SEQ ID NO: 460 *Bacillus cereus* strain FM1 | SDRNKNSNTGNASQVAVDRMRQ LINTVT |
| RI FlgII-28 SEQ ID NO: 461 *Bacillus thuringiensis* strain MC28 | AQQNDATNTGNASQNAIDRMRL LINSVS |

TABLE 4-continued

| Retro-inverso flagellin polypeptides from Flg22 and FlgII-28 from *Bacillus* | |
|---|---|
| SEQ ID NO: | |
| RI FlgII-28 SEQ ID NO: 462 *Bacillus bombysepticus* strain Wang | AAQNKDTNTGSASQNALDRMRL LINSVS |
| RI FlgII-28 SEQ ID NO: 463 *Bacillus thuringiensis serovar kenyae* | AAQNKDTNTGSASQNALDRMRL LINSVS |
| RI FlgII-28 SEQ ID NO: 464 *Bacillus thuringiensis serovar kenyae* | AAQNKDTNTGSASQNALDRMRL LINSVS |
| RI FlgII-28 SEQ ID NO: 465 *Bacillus cereus* | AKQNDGTNTGNASQNALDRMRL LINSVS |
| RI FlgII-28 SEQ ID NO: 466 *Bacillus cereus* | NLSDRNKNSNTGNASQVALDRM RQLINT |
| RI FlgII-28 SEQ ID NO: 467 *Bacillus thuringiensis serovar finitimus* strain YBT-020 | NLSDRNKNLNTGNASQVAVDRM RQLVNT |
| RI FlgII-28 SEQ ID NO: 468 *Bacillus thuringiensis serovar finitimus* strain YBT-020 | ASKNSDTNTGNASQNAIDRMRL LINSVS |
| RI FlgII-28 SEQ ID NO: 469 *Bacillus cereus* stain B4264 | AAKNEATNTGNASQNALDRMRL LINSVS |
| RI FlgII-28 SEQ ID NO: 470 *Bacillus thuringiensis serovar nigeriensis* | AKQNDSTNTGNASQNAIDRMRL LINSVS |
| RI FlgII-28 SEQ ID NO: 471 *Bacillus thuringiensis* | AQQNDATNTGNASQNAIDRMRL LINSVS |
| RI FlgII-28 SEQ ID NO: 472 *Bacillus thuringiensis serovar konkukian* strain 97-27 | SDRNKNSNTGNASQVALDRMRQ LINMVT |
| RI FlgII-28 SEQ ID NO: 473 *Bacillus thuringiensis serovar konkukian* strain 97-27 | AQQNDATNTGNASQNAIDRMRL LINSVS |
| RI FlgII-28 SEQ ID NO: 474 *Bacillus thuringiensis serovar thuringiensis* strain IS5056 | SDRNTNSNTGNASQIAFDRMHQ LINTVT |
| RI FlgII-28 SEQ ID NO: 475 *Bacillus thuringiensis serovar thuringiensis* strain IS5056 | ASQNKDTNTGNASQNSIDRMRL LINSVS |

TABLE 4-continued

Retro-inverso flagellin polypeptides from Flg22 and FlgII-28 from *Bacillus*

| SEQ ID NO: | |
|---|---|
| RI FlgII-28<br>SEQ ID NO: 476<br>*Bacillus thuringiensis*<br>strain Bt407 | ASQNKDTNTGNASQNSIDRMRL<br>LINSVS |
| RI FlgII-28<br>SEQ ID NO: 477<br>*Bacillus thuringiensis*<br>*serovar chinensis* CT-43 | ASQNKDTNTGNASQNSISRMRL<br>LINSVS |
| RI FlgII-28<br>SEQ ID NO: 478<br>*Bacillus thuringiensis*<br>*serovar canadensis* | AAQNENTNTGNASQNALDRMRL<br>LINSVS |
| RI FlgII-28<br>SEQ ID NO: 479<br>*Bacillus thuringiensis*<br>*serovar galleriae* | AQQNEDTNTGNASQNSLDRMRL<br>LINSVS |
| RI FlgII-28<br>SEQ ID NO: 480<br>*Bacillus*<br>*weihenstephanensis* | AQQNEDTNTGNASQNSLDRMRL<br>LINSVS |
| RI FlgII-28<br>SEQ ID NO: 481<br>*Bacillus thuringiensis*<br>*serovar ostriniae* | AKQNDGTNTGNASQNAIDRMRL<br>LINSVS |
| RI FlgII-28<br>SEQ ID NO: 482<br>*Bacillus thuringiensis* | SDRNKNSNTDNSSQVALDRMRQ<br>LINAVT |
| RI FlgII-28<br>SEQ ID NO: 483<br>*Bacillus thuringiensis* | AKQNDDTNTGNASQNALDRMRL<br>LINSVS |
| RI FlgII-28<br>SEQ ID NO: 484<br>Bacillus thuringiensis<br>*serovar pondicheriensis* | AKQNDDTNTGNASQNALDRMRL<br>LINSVS |
| RI FlgII-28<br>SEQ ID NO: 485<br>*Bacillus thuringiensis*<br>*serovar Berliner* | SDRNTNSNTGNASQIAFDRMHQ<br>LINTVT |
| RI FlgII-28<br>SEQ ID NO: 486<br>*Bacillus thuringiensis*<br>*serovar Berliner* | ASQNKDTNTGNASQNSIDRMRL<br>LINSVS |
| RI FlgII-28<br>SEQ ID NO: 487<br>*Bacillus cereus*<br>strain Q1 | SDRNKSSNTGNASQVAVDRMRQ<br>LVNTVT |
| RI FlgII-28<br>SEQ ID NO: 488<br>*Bacillus cereus*<br>strain Q1 | AVQKDTNTGNASQNAIDRMRLL<br>INSVS |
| RI FlgII-28<br>SEQ ID NO: 489<br>*Bacillus thuringiensis*<br>*serovar morrisoni* | SDRNKNSNTSNASQIALDRMRQ<br>LINMVT |
| RI FlgII-28<br>SEQ ID NO: 490<br>*Bacillus thuringiensis*<br>*serovar neoleonensis* | AKQNDSTNIGNASQNAIDRMRL<br>LINSVS |

TABLE 4-continued

Retro-inverso flagellin polypeptides from Flg22 and FlgII-28 from *Bacillus*

| SEQ ID NO: | |
|---|---|
| RI FlgII-28<br>SEQ ID NO: 491<br>*Bacillus thuringiensis*<br>*serovar morrisoni* | AKQNDGTNTFNASQNAIDRMRL<br>LINSVS |
| RI FlgII-28<br>SEQ ID NO: 492<br>*Bacillus thuringiensis*<br>*serovar morrisoni* | AKQNDGTNTFNASQNAIDRMRL<br>LINSVS |
| RI FlgII-28<br>SEQ ID NO: 493<br>*Bacillus thuringiensis*<br>*serovar jegathesan* | AAQNGNTNTFNASQNAIDRMRL<br>LINSVS |
| RI FlgII-28<br>SEQ ID NO: 494<br>*Bacillus cereus*<br>stain ATCC 10987 | AAQNKDTNTGNASQNAIDRMRL<br>LINSVS |
| RI FlgII-28 from<br>Flagellin A<br>SEQ ID NO: 495<br>*Bacillus thuringiensis*<br>*serovar monterrey* | AAQNENTNTGNASQNALDRMRL<br>LINSVS |
| RI FlgII-28<br>SEQ ID NO: 496<br>*Bacillus cereus*<br>strain NC7401 | SDRNKNSNTDNASQVALDRMRQ<br>LVNTVT |
| RI FlgII-28<br>SEQ ID NO: 497<br>*Bacillus cereus*<br>strain NC7401 | AAKNENTNTGNASQNALDRMRL<br>LINSVS |
| RI FlgII-28<br>SEQ ID NO: 498<br>*Bacillus cereus*<br>strain AH820 | AAQNDSTNTGNASQNALDRMRL<br>LINSVS |
| RI FlgII-28<br>SEQ ID NO: 499<br>*Bacillus cereus* AH187 | AAKNENTNTGNASQNALDRMRL<br>LINSVS |
| RI FlgII-28<br>SEQ ID NO: 500<br>*Bacillus cereus* | AAKNENTNTGNASQNALDRMRL<br>LINSVS |
| RI FlgII-28<br>SEQ ID NO: 501<br>*Bacillus cereus* | AKQNDGTNTGNASQNAIDRMRL<br>LINSVS |
| RI FlgII-28<br>SEQ ID NO: 502<br>*Bacillus thuringiensis*<br>Strain HD-771 [51] | AAQNKSTNTESASQNALDRMRL<br>LINSVS |
| RI FlgII-28<br>SEQ ID NO: 503<br>*Bacillus thuringiensis*<br>*serovar sotto* [52] | AAQNKSTNTESASQNALDRMRL<br>LINSVS |
| RI FlgII-28<br>SEQ ID NO: 504<br>*Bacillus thuringiensis*<br>*serovar Novosibirsk* | AKQNDGTNTGNASQNAIDRMRL<br>LINSVS |
| RI FlgII-28<br>SEQ ID NO: 505<br>*Bacillus thuringiensis*<br>*serovar londrina* | AAQNESTNTGNAQNALDRMRLL<br>INSVS |

TABLE 4-continued

| Retro-inverso flagellin polypeptides from Flg22 and FlgII-28 from *Bacillus* | |
|---|---|
| SEQ ID NO: | |
| RI FlgII-28 SEQ ID NO: 506 *Bacillus cereus* strain E33L | SNRNKNSNTVNASQVALDRMRQ LINTVT |
| RI FlgII-28 SEQ ID NO: 507 *Bacillus cereus* strain E33L | AGQNKDTNTNASQNALDRMRLL INSVS |
| RI FlgII-28 SEQ ID NO: 508 *Bacillus cereus* strain FRI-35 | AAQNKDTNTGNASQNALDRMRL LINSVS |
| RI FlgII-28 SEQ ID NO: 509 *Bacillus cereus* strain FRI-35 | SDRNKNSNTGNASQVALDRMRQ LVNTVT |
| RI FlgII-28 SEQ ID NO: 510 *Bacillus thuringiensis* | AEIDTDKNTGNATQNAIDRMRL LINSVS |
| RI FlgII-28 SEQ ID NO: 511 *Bacillus cereus* strain ATCC 4342 | AEIDTDKNTGNATQNAIDRMRL LINSVS |
| RI FlgII-28 SEQ ID NO: 512 *Bacillus thuringiensis* | SDRNKNSNTSNASQIALDRMRQ LINMT |
| RI FlgII-28 SEQ ID NO: 513 *Bacillus thuringiensis* | AKQNDGTNTGNASQNAIDRMRL LINSVS |
| RI FlgII-28 SEQ ID NO: 514 *Bacillus aryabhattai* | ADLDETKNTGNGAQVVLERMRQ LIDHTE |
| RI FlgII-28 SEQ ID NO: 515 *Bacillus manliponensis* | SERDNGQNTGTAQTALDRMRLL INSVS |
| RI FlgII-28 SEQ ID NO: 516 *Lysinibacillus* sp. strain BF-4 | KARDDDTNTDTAAQVALERMRQ VIAHTE |
| RI FlgII-28 SEQ ID NO: 517 *Lysinibacillus* sp. strain 13S34_air | KARDDDTNTDTAAQVALERMRQ VIAHTE |
| RI FlgII-28 SEQ ID NO: 518 *Paenibacillus* sp. strain HW567 | NLRDSGSYTGNSAQVALENMRQ LMSHIE |
| RI FlgII-28 SEQ ID NO: 519 *Bacillus anthracis* | ADQNEKTNTGNASQNALDRMRL LINSVS |
| RI FlgII-28 SEQ ID NO: 520 *Bacillus anthracis* | ASQNEATNTGNSSQVAIDRMRT LINSVS |
| RI FlgII-28 SEQ ID NO: 521 *Bacillus anthracis* | ASQNEATNTGNSSQVAIDRMRT LINSVS |

TABLE 4-continued

| Retro-inverso flagellin polypeptides from Flg22 and FlgII-28 from *Bacillus* | |
|---|---|
| SEQ ID NO: | |
| RI FlgII-28 SEQ ID NO: 522 *Bacillus anthracis* | ASQNEATNTGNSSQVAIDRMRT LINSVS |
| RI FlgII-28 SEQ ID NO: 523 *Bacillus anthracis* strain H9401 | ASQNEATNTGNSSQVIADRMRT LINSVS |
| RI FlgII-28 SEQ ID NO: 524 *Bacillus megaterium* strain WSH-002 | ADLDETKNTGNGAQVVLERMRQ LIDHTE |
| RI FlgII-28 SEQ ID NO: 525 *Aneurinibacillus* sp. XH2 | AKKDKSYTGNAAQVALERMRQL MEHIE |

Flg Sequences from Various Organisms

TABLE 5

| Flagellin-associated Flg22 and Flg15 polypeptides from other organisms | |
|---|---|
| SEQ ID NO: | Peptide - Amino Acid |
| Flagellin (Flg22) SEQ ID NO: 256 *Escherichia coli* | ERLSSGLRINSAKDDAAGQAIA |
| Flagellin (Retro-lnverso Flg22) SEQ ID NO: 527 *Escherichia coli* | AIAQGAADDKASNIRLGSSLRE |
| Flagellin (Flg15) SEQ ID NO: 528 *Escherichia coli* | RINSAKDDAAGQAIA |
| Flagellin (Retro-lnverso Flg15) SEQ ID NO: 529 *Escherichia coli* | AIAQGAADDKASNIR |
| Flagellin (Flg22) SEQID NO: 530 *Pseudomonas aeruginosa* | QRLSTGSRINSAKDDAAGLQIA |
| Flagellin (Retro Inverso Flg22) SEQ ID NO: 531 *Pseudomonas aeruginosa* | AIQLGAADDKASNIRSGTSLRQ |
| Flagellin (Flg22) SEQ ID NO: 532 Xanthomonas spp. X. campestris & X. citri | QRLSSGLRINSAKDDAAGLAIS |
| Flagellin (Retro Inverso Flg22) SEQ ID NO: 533 *Xanthomonas* spp. *X. campestris* & *X. citri* | SIALGAADDKASNIRLGSSLRQ |
| Flagellin (Flg22) SEQ ID NO: 534 *Erwinia amylovora* | QRLSSGLRINSAKDDAAGQAIS |

TABLE 5-continued

Flagellin-associated Flg22 and Flg15 polypeptides from other organisms

| SEQ ID NO: | Peptide - Amino Acid |
|---|---|
| Flagellin (Retro Inverso Flg22) SEQ ID NO: 535 *Erwinia amylovora* | SIAQGAADDKASNIRLGSSLRQ |
| Flagellin (Flg22) SEQ ID NO: 536 *Burkholderia phytofirmans* | TRLSSGKRINSAADDAAGLAIS |
| Flagellin (Retro Inverso Flg22) SEQ ID NO: 537 *Burkholderio phytofirmons* | SIALGAADDAASNIRKGSSLRT |
| Flagellin (Flg22) SEQ ID NO: 538 *Burkholderia ubonensis* | NRLSSGKRINTAADDAAGLAIS |
| Flagellin (Retro Inverso Flg22) SEQ ID NO: 539 *Burkholderia ubonensis* | SIALGAADDAATNIRKGSSLRN |
| Flagellin (Flg22) SEQ ID NO: 540 *Pseudomonas syringae* | TRLSSGLKINSAKDDAAGLQIA |
| Flagellin (Retro Inverso Flg22) SEQ ID NO: 541 *Pseudomonos syringae* | AIQLGAADDKASNIKLGSSLRT |
| Flagellin (Flgll-28) (SEQ ID NO: 751) *Pseudomonos syringae* | ESTNILQRMRELAVQSRNDSNSA TDREA |
| Flagellin (Retro Inverso Flgll-28) (SEQ ID NO: 768) *Pseudomonos syringae* | AERDTASNSDNRSQVALERMRQL INTSE |

Sequences that Assist in Directing Flagellins or Flagellin-Associated Polypeptides to the Plant The signature, signal anchor sorting and secretion sequences can be used separately or together in combination with any of the flagellin or flagellin-associated polypeptides as described herein. These assistance sequences are useful for the efficient delivery of the flagellin polypeptides to the plant cell membrane surface. Other assistance sequences can also assist with the translocation of the Flg polypeptide fragment across the plasma membrane. Delivery of flagellins and flagellin-associated polypeptides to the plasma membrane surface of a plant (or plant part) can contribute to downstream signalling processes and result in beneficial outcomes to a plant or a plant part, such as enhanced plant health and productivity.

The polypeptide can further comprise an assistance polypeptide.

The assistance polypeptide can comprise a signature polypeptide, and an amino acid sequence of the signature polypeptide can comprise any one of SEQ ID NOs: 542-548, listed in Table 6, or any combination thereof. For example, the amino acid sequence of the signature polypeptide can comprise SEQ ID NO: 542.

The assistance polypeptide can comprise a signal anchor sorting polypeptide, and an amino acid sequence of the signal anchor sorting polypeptide can comprise any one of SEQ ID NOs: 549-562, listed in Table 7, or any combination thereof. For example, the amino acid sequence of the signal anchor sorting polypeptide can comprise SEQ ID NO: 549.

The flagellin or flagellin-associated polypeptide can be produced recombinantly by a microorganism. For example, the microorganism can comprise a *Bacillus*, a *Pseudomonas*, a *Paenibacillus, Aneurinibacillus* or a *Lysinibacillus.*

The assistance polypeptide can comprise a secretion polypeptide, and an amino acid sequence of the secretion polypeptide can comprise any one of SEQ ID NOs: 563-570, or any combination thereof. For example, the amino acid sequence of the secretion polypeptide can comprise SEQ ID NO: 563.

These three types of assistance sequences are further described in Table 6 (N-terminal signature sequences), Table 7 (signal anchor sorting sequences) and Table 8 (secretion sequences).

Also provided are "assistance" sequences having conserved signature (Table 6; SEQ ID NOs: 542-548), signal anchor sorting (Table 7; SEQ ID NOs: 549-562) and secretion (Table 8; SEQ ID NOs: 563-570) sequences in combination with any of the flagellin-associated polypeptides as described herein. Particularly useful are combinations of the signature, signal anchor sorting and secretion assistance sequences with the native L-Flg polypeptides (Table 3. SEQ ID NOs: 226-375) or any of the retro inverso Flg22 polypeptides (Table 4. SEQ ID NOs: 376-525) for providing efficient delivery of the Flg polypeptides to the extracellular plant membrane surface, such as the surface of a plant or plant part.

N-Terminal Signature Sequences

Amino acid "signature" sequences conserved within *Bacillus, Lysinibacillus, Paenibacillus* or *Aneurinibacillus* bacteria (genera) and other Eubacterial generas can function in targeting flagellin polypeptides to the appropriate Flg-associated receptor protein(s), such as FLS receptors that have an exposed binding site at the plant cell membrane surface and can be used to enhance Flg polypeptide-receptor binding leading to an increased activation potential of the Flg-associated receptor(s). Flagellin signature sequences as identified in Table 6 are useful for targeting and stably delivering the Flg polypeptides for binding to the FLS or FLS-like receptor(s) therefore increasing the contact and binding between the membrane receptor and the Flg polypeptide.

Conserved N-terminal signature sequences (SEQ ID NO: 542-548) can be used in combination with any of the flagellin-associated polypeptides as described herein. Of particular utility are the signature sequences used in combination with the native L-Flg polypeptides (L-Flg22 SEQ ID NOs: 226-300; L-FlgII-28 SEQ ID NOs: 301-375) or any of the retro inverso D-Flg polypeptides (D-Flg22 SEQ ID NOs: 376-450; FlgII-28 SEQ ID NO: 451-525) or any of the other Flg-associated sequences provided in Table 5 (SEQ ID NOs: 526-541) to provide efficient delivery of the Flg-associated polypeptides to the plant membrane surface.

Signature sequences assist with Flg22 and FlgII-28 bioactive priming polypeptide sequences in binding to the appropriate Flg-associated receptor(s) in order to activate the receptor(s) making it functionally active.

TABLE 6

| Flagellin-associated N-terminal signature sequences | |
|---|---|
| SEQ ID NO: | Flagellin Signature Sequences |
| SEQ ID NO: 542 | GFLN |
| SEQ ID NO: 543 | WGFLI |
| SEQ ID NO: 544 | MGVLN |
| SEQ ID NO: 545 | GVLN |
| SEQ ID NO: 546 | WGFFY |
| SEQ ID NO: 547 | LVPFAVWLA |
| SEQ ID NO: 548 | AVWLA |

N-terminal Signal Anchor Sorting Sequences

Amino acid "signal anchor sorting" sequences conserved within *Bacillus, Lysinibacillus, Aneurinibacillus* and *Paenibacillus* genera and other Eubacterial generas' bacteria can function in anchoring and localizing the flagellin-associate polypeptides to the plant cell membrane surface and assist in high affinity binding to the appropriate Flg-associated receptor(s) thereby increasing the activation potential of the bound receptor(s).

Conserved signal anchor sequences (SEQ ID NO: 549-562; Table 7) are located downstream of the pre-cleaved or full-length coding or partial coding flagellin sequences, for example, as described herein (SEQ ID NOs: 1-75; Table 1).

The signal anchor sorting domains as described herein are useful in membrane attachment. They can be used to aid in the localization and binding of Flg-associated polypeptides to a surface membrane receptor and have some functional similarity at the amino acid level to proteins that are endosomal (vesicular) trafficked or destined for targeting to the secretory pathway. Such signal anchor sorting sequences as described herein that are useful for anchoring the Flg bioactive priming polypeptides to the plant cell membrane are also used to enhance the membrane integration of the bioactive priming Flg polypeptides into the plant cell.

Such sequences as described in Table 7 may further be functionally annotated as import receptor signal anchor sequences, which can be used to improve targeting or delivery and efficient membrane anchoring of Flg-associated polypeptides to a plant and assist with membrane integration into the cytosol of the plant cell.

Combining the signal anchor sequences (SEQ ID NOs: 549-562; Table 7) with any of the flagellins or flagellin-associated bioactive priming polypeptides as described herein is useful to facilitate the attachment and import of these flagellin-associated polypeptide(s) into the plant.

Such signal anchor sorting sequences can be used in combination with the Flg-associated polypeptides, and are useful for targeting, efficient membrane anchoring, membrane integration and Golgi-to-lysosomal/vacuolar trafficking. The signal anchor sorting sequences are used to stably deliver the Flg polypeptides to the plant membrane surface and integrally incorporate them into the plant.

Such sequences as described herein contain di-leucine amino acids that are referenced to confer endocytosis functionalities in plant systems (Pond et al. 1995, "A role for acidic residues in di-leucine motif-based targeting to the endocytic pathway", Journal of Biological Chemistry 270: 19989-19997, 1995).

Such signal anchor sorting sequences as described can also be used to efficiently deliver systemic signals to infection sites and stimulate a plant's innate immunity in plant cells.

TABLE 7

| Flagellin-associated signal anchor sorting sequences | |
|---|---|
| SEQ ID NO: | Signal Anchor Sequence |
| SEQ ID NO: 549 | LLGTADKKIKIQ |
| SEQ ID NO: 550 | LLKSTQEIKIQ |
| SEQ ID NO: 551 | LLNEDSEVKIQ |
| SEQ ID NO: 552 | LGVAANNTQ |
| SEQ ID NO: 553 | LLRMRDLANQ |
| SEQ ID NO: 554 | LQRMRDVAVQ |
| SEQ ID NO: 555 | LLRMRDISNQ |
| SEQ ID NO: 556 | LLRMRDIANQ |
| SEQ ID NO: 557 | LQKQIDYIAGNTQ |
| SEQ ID NO: 558 | LLIRLPLD |
| SEQ ID NO: 559 | QRMRELAVQ |
| SEQ ID NO: 560 | TRMRDIAVQ |
| SEQ ID NO: 561 | TRMRDIAVQ |
| SEQ ID NO: 562 | QRMRELVVQ |

C-terminal Secretion Sequences

Conserved sequences located in the C-terminus of flagellin(s) are further described as secretion sequences (SEQ ID NO: 563-570; Table 8).

Conserved sequences were identified in the C-terminus of the *Bacillus, Lysinibacillus*, and *Paenibacillus* bacteria (genera) and other Eubacterial genera derived flagellin proteins and comprise 6 amino acids, for example LGATLN, LGSMIN, or LGAMIN. These sequences were functionally annotated using BLAST against the bacterial databases as motifs that have highest homology to secretion polypeptides. The 6 amino acid conserved polypeptides identified were found most similar to those found in type III secretion systems in *E. coli*. Type III export systems have been cited to be involved in the translocation of polypeptides across the plant cell membrane. The filament assembly of flagellin is dependent on the availability of flagellins to be secreted and may require chaperones that assist in the secretory process.

These secretion polypeptides as described herein may be used in combination with any of the flagellin-associated polypeptides as described herein to deliver these polypeptides/peptides into the cytosol of the host plant thus providing beneficial outcomes to a plant.

TABLE 8

| C-terminal flagellin-associated secretion sequences | |
|---|---|
| SEQ ID NO: | Flagellin Secretion polypeptides |
| SEQ ID NO: 563 | LGATLN |
| SEQ ID NO: 564 | LGATQN |
| SEQ ID NO: 565 | LAQANQ |
| SEQ ID NO: 566 | LGAMIN |
| SEQ ID NO: 567 | LGSMIN |
| SEQ ID NO: 568 | MGAYQN |
| SEQ ID NO: 569 | LGAYQN |
| SEQ ID NO: 570 | YGSQLN |

The signature (SEQ ID NO: 542-548; Table 6), signal anchor sorting (SEQ ID NO: 549-562; Table 7) and secretion (SEQ ID NO: 563-570; Table 8) sequences as provided herein can be used with any of the flagellin polypeptides or the flagellin-associated polypeptides to promote growth and provide health and protective benefits to a plant or a plant part.

Modification of Flg Polypeptide Sequences Function

Any of the L or D Flg-associated sequences provided in Tables 3, 4 or 5 can be similarly modified as fused to any of the assistance sequences as described in Table 6-8. For one example, fusion of any of these assistance sequences will present a modification to the Bt.4Q7Flg22 bioactive priming polypeptide sequence identified as SEQ ID NO: 226.

Mutations to Flg-Associated Polypeptides to Increase Responsiveness to Reactive Oxygen Species or polypeptide Stability The polypeptide can comprise a mutant flagellin or flagellin-associated polypeptide.

The mutant flagellin or flagellin-associated polypeptide can be derived from a *Bacillus*, a *Lysinibacillus*, a *Paenibacillus*, or an *Aneurinibacillus* genus bacterium. Other polypeptides from other Eubacterial classes, including Enterobacteraciae, can also be used in the same fashion. Other generas of interest include *Pseudomonas, Escherichia, Xanthomonas, Burkholderia, Erwinia*, and others.

The amino acid sequence of the flagellin or flagellin-associated polypeptide can comprise any one of SEQ ID NOs: 226, 289, 290, 291, 293, 294, 295, 300, 437, 532, 534, 536, 538, 540, 571-586 and 751-768. For example, the amino acid sequence of the flagellin or flagellin-associated polypeptide can comprise any one of SEQ ID NOs: 226, 293, 295, 300, 540, 571, 574 and 752, or any combination thereof.

Any bioactive priming polypeptide, whether naturally occurring or non-natural, can be further modified via chemical modification to increase performance as well as stability of the polypeptides. Such bioactive priming polypeptides include flagellin polypeptides, retro inverso polypeptides, harpin derived polypeptides, harpin-like derived polypeptides, EF-Tu polypeptides, thionin polypeptides, RHPP polypeptides, and PSK polypeptides. Specific sequences that can be chemically modified include SEQ ID NOs: 226-592, 594-601, 603-749, and 751-766.

These bioactive priming polypeptides can also be conjugated to other moieties, including a plant binding domain and a polypeptide, a plant part binding domain and a polypeptide, and other carriers such as oils, plastics, beads, ceramic, soil, fertilizers, pellets, and most structural materials.

The flagellin or flagellin-associated polypeptide can be modified chemically on its N or C terminus. Common modification of the N and C-termini include: acetylation, lipid addition, urea addition, pyroglutamyl addition, carbamate addition, sulfonamide addition, alkylamide addition, biotinylation, phosphorylation, glycosylation, PEGylation, methylation, biotinylation, acid addition, amide addition, ester addition, aldehyde addition, hydrazide addition, hydroxyamic acid addition, chloromethyl ketone addition, or addition of purification tags. These tags can increase activity of the polypeptides, increase stability, add protease inhibitor abilities to the polypeptides, block proteases directly, allow for tracking, and help in binding to plant tissues.

The flagellin or flagellin-associated polypeptide can be modified via crosslinking or cyclization. Crosslinking can bind polypeptides either to each other or to a secondary surface or moiety to help in delivery or stability of the polypeptides. Cyclization can be performed, for example, to both increase activity of the polypeptide as well as prevent protease interaction with the polypeptide.

Sequence modifications or mutations can be made to any amino acid sequence(s) as described in Tables 4 and 5 and replaced with any of the 20 standard amino acid sequences known in nature or replaced with a nonstandard or non-canonical amino acid sequence, such as selenocysteine, pyrrolysine, N-formylmethione, etc. For example, modifications or mutations can be made to the internal sequences as shown in SEQ ID NO: 571, to the C-terminis as shown in SEQ ID NO: 572 or SEQ ID NO: 753, or to the N terminus as shown in SEQ ID NO: 573 to produce Flg polypeptides with enhanced ROS activates and increased functionality in a plant or plant part. Modified polypeptides also can be truncated at the N or C terminus as shown in SEQ ID NO: 752 (N-terminus truncation) to further increase functionality in a plant or plant part. Table 9A summarizes flagellin polypeptides identified that provide modified ROS activity.

TABLE 9A

| Flagellin polypeptides Flg22 identified from *Bacillus* or other bacteria with mutations that provide modified ROS activity | |
|---|---|
| SEQ ID NO: | Peptide Flg22 |
| Flg22-Bt4Q7<br>SEQ. ID NO:- 571<br>*Bacillus thuringiensis*<br>strain 40.7<br>Modified FLG22-Bt4Q7 (S13K); Syn01 | DRLSSGKRINSAKDDAAGLAIA |

TABLE 9A-continued

Flagellin polypeptides Flg22 identified from *Bacillus* or other bacteria with mutations that provide modified ROS activity

| SEQ ID NO: | Peptide Flg22 |
|---|---|
| Flg22-Bt4Q7<br>SEQ ID NO: 572<br>*Bacillus thuringiensis*<br>strain 40.7<br>Modified FLG22-Bt4Q7 (A200); Syn02 | DRLSSGKRINSASDDAAGLQIA |
| Flg22-Bt4Q7<br>SEQ ID NO: 573<br>*Bacillus thuringiensis*<br>strain 40.7<br>Modified FLG22-Bt4Q7 (D1Q); Syn03 | QRLSSGKRINSASDDAAGLAIA |
| Flg22-Bt4Q7<br>SEQ. ID NO: 574<br>*Bacillus thuringiensis*<br>strain 40.7<br>Modified FLG22-Bt4Q7 (D1N); Syn06 | NRLSSGKRINSASDDAAGLAIA |
| *Caballeronia megalochromosomata*<br>SEQ. ID NO: 575 | TRLSSGKRINSASDDAAGLAIA |
| Flg22-Bt4Q7<br>SEQ. ID NO: 576<br><br>*Bacillus thuringiensis*<br>strain 4Q7<br>Modified FLG22-Bt4Q7 (K7Y); Syn07 | DRLSSGYRINSASDDAAGLAIA |
| Flg22-Bt4Q7<br>SEQ. ID NO: 577<br>*Bacillus thuringiensis*<br>strain 40.7<br>Modified FLG22-Bt4Q7 (K7F); Syn08 | DRLSSGFRINSASDDAAGLAIA |
| Flg22-Br4Q7<br>SEQ. ID NO: 578<br>*Bacillus thuringiensis*<br>Modified FLG22-Bt4Q7 (A16P); Syn05 | DRLSSGKRINSASDDPAGLAIA |
| Flg22-Bt4Q7<br>SEQ. ID NO: 579<br>*Bacillus thuringiensis*<br>strain 4Q7<br>Modified FLG22-Bt4Q7 (K7Q); Syn09 | DRLSSGQRINSASDDAAGLAIA |
| Flg22-Br4Q7<br>SEQ. ID NO: 753<br>*Bacillus thuringiensis*<br>strain 4Q7<br>Modified FLG22-Bt4Q7 (D15P); Syn04 | DRLSSGKRINSASDPAAGLAIA |
| Flg15-Br4Q7<br>SEQ. ID NO: 752<br>*Bacillus thuringiensis*<br>N-term Truncated Syn01 | RINSAKDDAAGLAIA |
| Bm.Flg22-B1<br>*Bacillus manliponensis*<br>SEQ. ID NO: 290 | NRLSSGKQINSASDDAAGLAIA |
| Ba.Flg22-B2<br>*Bacillus anthracis*<br>SEQ. ID NO: 295 | NRLSSGKRINSAADDAAGLAIA |
| Bc.Flg22-B3<br>*Bacillus cereus*<br>SEQ. ID NO: 294 | DRLSSGKRINNASDDAAGLAIA |
| A. spp.Flg22-B4<br>*Aneurinibacillus* spp. XH2<br>SEQ. ID NO: 300 | ERLSSGYRINRASDDAAGLAIS |

TABLE 9A-continued

Flagellin polypeptides Flg22 identified from *Bacillus* or other bacteria with mutations that provide modified ROS activity

| SEQ ID NO: | Peptide Flg22 |
|---|---|
| Ba.Flg22-B5<br>*Bacillus aryabhattai*<br>SEQ. ID NO: 289 | EKLSSGQRINSASDDAAGLAIS |
| Pspp.FIg22-B6<br>*Paenibacillus* spp. strain HW567<br>SEQ. ID NO: 293 | GKLSSGLRINGASDDAAGLAIS |
| L spp.Flg22-L1<br>*Lysinibacillus* spp.<br>SEQ. ID NO: 291 | LRLSSGYRINSAADDAAGLAIS |
| L spp.Flg22-L2<br>*Lysinibacillus* spp.<br>SEQ ID NO: 580 | EKLSSGLRINRAGDDAAGLAIS |
| L spp.Flg22-L3<br>*Lysinibacillus* spp.<br>SEQ. ID NO: - 581 | EKLSSGYKINRASDDAAGLAIS |
| L spp.Flg22-L4<br>*Lysinibacillus* spp. SG9<br>SEQ ID NO: 582 | LRISSGYRINSAADDPAGLAIS |
| Lf.Flg22-L5<br>*Lysinibacillus fusiformis*<br>SEQ. ID NO: 583 | LRISTGYRINSAADDPAGLAIS |
| Lm.Flg22-L6<br>*Lysinibacillus macroides*<br>SEQ ID NO: 584 | EKLSSGFRINRAGDDAAGLAIS |
| Lx.Flg22-L6<br>*Lysinibacillus*<br>*xylanilyticus*<br>SEQ ID NO: 585 | EKLSSGYKINRAGDDAAGLAIS |
| Pa.Flg22<br>*Pseudomonas aeruginosa*<br>SEQ. ID NO: 530 | QRLSTGSRINSAKDDAAGLQIA |
| Ec.Flg22<br>*Escherichia coli*<br>SEQ. ID NO: 586 | ERLSSGLRINSAKDDAAGQAIA |
| Xcc.Flg22<br>*Xanthomonas campestris* pv<br>campestris strain 305 or<br>(*Xanthomonas citri* pv. citri)<br>SEQ. ID NO: 532 | QRLSSGLRINSAKDDAAGLAIS |
| Ea. Flg22<br>*Erwinia amylovora*<br>SEQ. ID NO: 534 | QRLSSGLRINSAKDDAAGQAIS |
| Bp. Flg22<br>*Burkholderia phytofirmans* strain Ps1A1<br>SEQ. ID NO: 536 | TRLSSGKRINSAADDAAGLAIS |
| Bu.Flg22<br>*Burkholderia ubonensis*<br>SEQ. ID NO: 538 | NRLSSGKRINTAADDAAGLAIS |
| Ps.Flg22<br>*Pseudomonas syringae* pv. actinidiae<br>ICMP 19096<br>SEQ. ID NO: 540 | TRLSSGLKINSAKDDAAGLQIA |

Core Active Domain of Flg22

The underlined portions of the sequences in Table 9A represent the core active domain of Flg22. This core domain comprises, for example, SEQ ID NO: 754 with up to one, two or three amino acid substitutions (represented by SEQ ID NOs 755-765) that can promote growth, disease reduction and/or prevention in crops and ornamental plants. For ease of reference, this core domain is represented as the consensus sequence having the SEQ ID NO: 766. The various native and mutant Flg22 polypeptides comprising SEQ ID NOs 754-765 are described along with the consensus sequence in Table 9B, below. Therefore, the polypeptides can further comprise a core sequence. The core sequence can comprise any one of SEQ ID NOs 754-766.

The polypeptide can also comprise any polypeptide comprising any one of SEQ ID NOs 1-753 or 767 to 768 wherein the polypeptide further comprises the core sequence comprising any one of SEQ ID NOs: 754-766. The inclusion of the core sequence in the polypeptide or full-length protein of dissimilar function can increase the bioactive priming activity of the polypeptide.

TABLE 9B

Flg22 core sequence with variants.

| SEQ ID NO: | FLG22 core sequence | Polypeptides comprising core sequence |
|---|---|---|
| SEQ ID NO: 754 | RINSASDD | SEQ ID NO: 226-229<br>SEQ ID NO: 289<br>SEQ ID NO: 299<br>SEQ ID NO: 536<br>SEQ ID NO: 572-579 |
| SEQ ID NO: 755 | RINNASDD | SEQ ID NO: 231-234<br>SEQ ID NO: 236-240<br>SEQ ID NO: 243-246<br>SEQ ID NO: 248<br>SEQ ID NO: 250-256<br>SEQ ID NO: 258-259<br>SEQ ID NO: 261<br>SEQ ID NO: 263<br>SEQ ID NO: 265-270<br>SEQ ID NO: 272-280<br>SEQ ID NO: 282-283<br>SEQ ID NO: 285-286<br>SEQ ID NO: 288<br>SEQ ID NO: 294 |
| SEQ ID NO: 756 | QINSASDD | SEQ ID NO: 290 |
| SEQ ID NO: 757 | RINSAADD | SEQ ID NO: 291-292<br>SEQ ID NO: 295-298<br>SEQ ID NO: 582-583<br>SEQ ID NO: 536<br>SEQ ID NO: 582-583 |
| SEQ ID NO: 758 | RINGASDD | SEQ ID NO: 293 |
| SEQ ID NO: 759 | RINRASDD | SEQ ID NO: 300 |
| SEQ ID NO: 760 | RINSAKDD | SEQ ID NO: 526<br>SEQ ID NO: 528<br>SEQ ID NO: 530<br>SEQ ID NO: 532<br>SEQ ID NO: 534<br>SEQ ID NO: 571<br>SEQ ID NO: 586 |
| SEQ ID NO: 761 | RINTAADD | SEQ ID NO: 538 |
| SEQ ID NO: 762 | KINSAKDD | SEQ ID NO: 540 |
| SEQ ID NO: 763 | RINRAGDD | SEQ ID NO: 580<br>SEQ ID NO: 584 |
| SEQ ID NO: 764 | KINRASDD | SEQ ID NO: 581 |
| SEQ ID NO: 765 | KINRAGDD | SEQ ID NO: 585 |
| SEQ ID NO: 766 | (R/Q/K)IN(S/N/G/R/T) A(S/A/K/G)DD | Consensus of SEQ ID NO: 755-765 (sequences identified in this table) |

Harpin or Harpin-Like Polypeptides

The polypeptide can include a harpin or harpin-like polypeptide.

The amino acid sequence of the harpin or harpin-like polypeptide can comprise SEQ ID NOs: 587-592 and 594-597 (Tables 10 and 11), The harpin or harpin-like polypeptides can be derived from *Xanthomonas* species or diverse bacteria genera including *Pantoea sesami, Erwinia gerudensis, Pantoea sesami*, or *Erwinia gerudensis*

Additional Harpin-like bioactive priming polypeptides can be derived from the full length HpaG-like protein from *Xanthamonas citri* comprising SEQ ID NO: 593.

Application of HpaG-like polypeptides using the native L-harpin-like sequence (SEQ ID NO: 587) or retro inverso D-harpin-like sequence (SEQ ID NO: 588) bioactive priming polypeptides forms as represented in Tables 10 or 11 are useful to increase growth and immune responses in plants when applied either exogenously or endogenously to a plant or plant part. The retro-inverso HpaG-like (e.g. SEQ ID NO: 588) bioactive priming polypeptide is particularly useful to enhance the activity and stability of the HpaG-like polypeptide when applied to plants grown under or exposed to conditions of abiotic stress. The retro-inverso HpaG-like form can be used to enhance growth and protection responses in plants grown under such environments.

TABLE 10

Harpin-like (HpaG-like)

| SEQ ID NO: | Peptide Sequence Amino Acid |
|---|---|
| Harpin-like (HpaG-like)<br>SEQ ID NO: 587<br>*Xanthomonas* species<br>MW 2626.35 Da | NQGISEKQLDQLLTQLIMALLQQ |
| Harpin-like (Retro-Inverso HpaG-like)<br>SEQ ID NO: 588<br>*Xanthomonas* species<br>MW 2626.35 Da | QQLLAMILQTLLQDLQKESIGQN |
| Harpin-like (HpaG-like)<br>SEQ ID NO: 589<br>*Xanthomonas* species<br>MW 2626.35 Da | LDQLLTQLIMAL |
| Harpin-like (Retro-Inverso HpaG-like)<br>SEQ ID NO: 590<br>*Xanthomonas* species<br>MW 2626.35 Da | LAMILQTLLQDL |
| Harpin-like (HpaG-like)<br>SEQ ID NO: 591<br>*Xanthomonas* species<br>MW 2626.35 Da | SEKQLDQLLTQLIMALLQQ |
| Harpin-like (Retro-Inverso HpaG-like)<br>SEQ ID NO: 592<br>*Xanthomonas* species<br>MW 2626.35 Da | QQLLAMILQTLLQDLQKES |
| HpaG-Like Protein<br>SEQ ID NO: 593<br>*Xanthamonas citri* | MMNSLNTQLGANSSFFQVDPSQNTQSGSNQGNQGISEK<br>QLDQLLTQLIMALLQQSNNAEQGQGQGQGGDSGGQGGN<br>RQQAGQSNGSPSQYTQMLMNIVGDILQAQNGGGFGGGF<br>GGGFGGGLGTSLGTSLGTSLASDTGSMQ |

TABLE 11

| HpaG-like Homologs from diverse bacterial genera | |
|---|---|
| SEQ ID NO: | Peptide amino acid |
| HpaG Homolog Active Fraction SEQ ID NO: 594 *Pantoea sesami* | QLEQLMTQLRARLCRLMAM |
| HpaG Homolog Active Fraction SEQ ID NO: 595 *Erwinia gerudensis* | QLECILMTQLRARLKRLMAM |
| Retro Inverso HpaG Homolog Active Fraction SEQ ID NO: 596 *Pantoea sesami* | MAMLRCLRARLQTMLQELQ |
| Retro Inverso HpaG Homolog Active Fraction SEQ ID NO: 597 *Erwinia gerudensis* | MAMLRKLRARLQTMLQELQ |

Phytosulfokine (PSKα) Polypeptides

The polypeptide can comprise the PSK polypeptide.

The amino acid sequence of the PSK polypeptide can comprise SEQ ID NOs: 598-599.

Phytosulfokine alpha (PSKα) was originally derived from *Arabidopsis thaliana* and is a sulfonated bioactive priming polypeptide. The PSKα bioactive priming polypeptide(s) are in Table 11.

PSKα is provided either as a synthetic polypeptide or a natural polypeptide that is expressed in a recombinant microorganism, purified and used in agricultural formulations for applications to plants or plant parts.

TABLE 12

| Phytosulfokine alpha (PSKα), sulfonated bioactive priming polypeptides provided as natural and retro-inverso amino acid sequences | |
|---|---|
| SEQ ID NO: | Peptide Sequence Amino Acid |
| Phytosulfokine (PSKα) SEQ. ID NO: 598 *Arabidopsis thaliana* MW 845 Da | Tyr($SO_3H$)-I-Tyr($SO_3H$)-TQ |
| Phytosulfokine (Retro Inverso PSKα) SEQ ID NO: 599 *Arabidopsis thaliana* MW 845 Da | QT-Tyr($SO_3H$)-I-Tyr($SO_3H$) |

Root Hair Promoting Polypeptide (RHPP)

The polypeptide can comprise a RHPP

The amino acid sequence of the RHPP can comprise SEQ ID NO: 600-601 and 603-606. For example, the amino acid sequence of the RHPP can comprise SEQ ID NO: 600.

A combination of the polypeptide comprising an RHPP and a polypeptide comprising a flagellin or flagellin associated polypeptide is also provided. The flagellin or flagellin associated polypeptide can comprise any one of SEQ ID NO: 226, 752, and 571. In some instances, the polypeptide comprises an RHPP comprising SEQ ID NO: 600 and a flagellin comprising SEQ ID NO: 226.

The polypeptide can comprise the PSK polypeptide, the RHPP, the harpin or harpin-like polypeptide, or a combination thereof.

Additional RHPP bioactive priming polypeptides can be derived from the full length Kunitz Trypsin Inhibitor protein from *Glycine max* comprising SEQ ID NO: 602. The RHPP polypeptide can be modified via C-terminal amidation, N-terminal acetylation or other modification. The RHPP bioactive priming polypeptide can be obtained through addition of crude protease digest of kunitz trypsin inhibitor and/or soybean meal.

RHPP originally derived for soybean (*Glycine max*) can be provided, for example, as a foliar application to produce beneficial phenotypes in corn, soybean and other vegetables.

TABLE 13

| Amino acid sequence for RHPP forward and retro-inverso sequences | |
|---|---|
| SEQ ID NO: | Peptide Sequence Amino Acid |
| Root Hair Promoting Peptide (RHPP) SEQ ID NO: 600 *Glycine max* MW 1198.20 Da | GGIRAAPTGNER |
| Root Hair Promoting Peptide (Retro Inverso RHPP) SEQ ID NO: 601 *Glycine max* MW 1198.20 Da | RENGTPAARIGG |
| Kunltz Trypsin Inhibitor SEQ ID NO: 602 *Glycine Max* | MKSTIFFALFLFCAFTTSYLPSAIADFVLDNEGNPLENGGTYYILSD ITAFGGIRAAPTGNERCPLTVVQSRNELDKGIETIISSPYRIRFIAE GHPLSLKFDSFAVIMLCVGIPTEWSVVEDLPEGPAVKIGENKDAMDG WFRLERVSDDEFNNYKLVFCPQQAEDDKCGDIGISIDHDDGTRRLVV SKNKPLVVQFQKLDKESLAKKNHGLSRSE |

TABLE 14

| Homologs of RHPP from *Glycine* spp. | |
|---|---|
| SEQ ID NO: | Peptide Sequence Amino Acid |
| Homolog RHPP SEQ ID NO: 603 *Glycine max* | GGIRATPTENER |
| Homolog RHPP SEQ ID NO: 604 *Glycine max/Glycine soja* | GGIRVAATGKER |

The polypeptide can include a retro inverso (RI) RHPP.

The retro inverso RHPP can comprise SEQ ID NOs: 601, 605 or 606.

The retro inverso (RI) RHPP can be modified via C-terminal amidation or N-terminal acetylation.

TABLE 15

| Retro inverso amino acid sequences for homologs of RHPP from *Glycine* spp. | |
|---|---|
| SEQ ID NO: | Peptide Sequence Amino Acid |
| Homolog RHPP SEQ ID NO: 605 *Glycine max* | RENETPTARIGG |
| Homolog RHPP SEQ ID NO: 606 *Glycine max/Glycine soja* | REKGTAAVRIGG |

Elongation Factor Tu (EF-Tu) Polypeptides

The polypeptide can comprise an EF-Tu polypeptide.

Peptides derived from elongation factor Tu (EF-Tu) can be used separately or in combination with the other bioactive priming polypeptides as described herein such as in combination with Flg22 polypeptides to provide multiple modes of defense against pathogenic organisms, generally bacterial and fungal microorganisms but also including other infection agents, such as viruses.

Table 16 provides preferred N-terminal polypeptides derived from various EF-Tu bioactive priming polypeptides selected from both plants and bacteria. The EF-Tu derived polypeptides can be any length from 18 to 26 amino acids or less than 26 amino acids in length. Table 17 further provides retro-inverse (all-D) versions of EF-Tu polypeptides derived from bacteria and algae.

The amino acid sequence of the EF-Tu polypeptide can comprise and one of SEQ ID NOs: 607-640.

The amino acid sequence of the EF-Tu polypeptide can comprise SEQ ID NO: 616 or 617.

The EF-Tu polypeptide can be modified via N-terminal acetylation. For example, the EF-Tu polypeptide can be modified via N-terminal acetylation and comprise any of SEQ ID NOs: 607, 608, 610, 611, 613, 614, 616, 617, 619, or 622.

TABLE 16

| N-terminal acetylated and central polypeptides derived from elongation factors (EF-Tu) existing in plant, bacterial and algae species | | |
|---|---|---|
| SEQ ID NO: | Length amino acids | Peptide amino acid |
| Chloroplastic EF-Tu SEQ ID NO: 607 (acetylated) *Arabidopsis lyrata* | 18 | Ac-ARGKFERKKPHVNIGTIG |
| Chloroplastic EF-Tu SEQ ID NO: 608 (acetylated) *Arabidopsis lyrata* | 26 | Ac-ARGKFERKKPHVNIGTIG HVDHGKTT |
| Chloroplastic EF-Tu SEQ ID NO: 609 *Arabidopsis lyrata* | 50 | EKPNVKRGENKWVDKIYELMD SVDSYIPIPTRQTELPFLLAV EDVFSITG |
| N-terminus of EF-Tu SEQ ID NO: 610 (acetylated) *Euglena gracilis* | 18 | Ac-ARQKFERTKPHINIGTIG |
| N-terminus of EF-Tu SEQ ID NO: 611 (acetylated) *Euglena gracilis* | 26 | Ac-ARQKFERTKPHINIGTIG HVDHGKTT |
| EF-Tu fragment SEQ ID NO: 612 *Euglena gracilis* | 50 | KNPKITKGENKWVDKILNLMD QVDSYIPTPTRDTEKDFLMAI EDVLSITG |
| N-terminus of EF-Tu SEQ ID NO: 613 (acetylated) *Acidovorax avenae* | 18 | Ac-AKGKFERTKPHVNVGTIG |
| N-terminus of EF-Tu SEQ ID NO: 614 (acetylated) *Acidovorax avenae* | 26 | Ac-AKGKFERTKPHVNVGTIG HVDHGKTT |
| EF-Tu fragment SEQ ID NO: 615 *Acidovorax* spp. | 50 | KLALEGDKGPLGEQAIDKLAE ALDTYIPTPERAVDGAFLMPV EDVFSISG |
| N-terminus of EF-Tu SEQ ID NO: 616 (acetylated) *Bacillus cereus* | 18 | Ac-AKAKFERSKPHVNIGTIG |
| N-terminus of EF-Tu SEQ ID NO: 617 (acetylated) *Bacillus cereus* | 26 | Ac-AKAKFERSKPHVNIGTIG HVDHGKTT |
| EF-Tu fragment SEQ ID NO: 618 *Bacillus cereus* | 50 | SALKALQGEAEWEEKIIELMA EVDAYIPTPERETDKPFLMPI EDVFSITG |
| N-terminus of EF-Tu SEQ ID NO: 619 (acetylated) *Burkholderia* spp. | 26 | Ac-AKGKFERTKPHVNVGTIG HVDHGKTT |
| EF-Tu fragment SEQ ID NO: 620 *Burkholderia* spp. | 50 | KLALEGDTGELGEVAIMNLAD ALDTYIPTPERAVDGAFLMPV EDVFSISG |
| EF-Tu fragment SEQ ID NO: 621 *Xanthomonas campestris* | 50 | RLALDGDQSEIGVPAILKLVD ALDTFIPEPTRDVDRPFLMPV EDVFSISG |

TABLE 16-continued

| N-terminal acetylated and central polypeptides derived from elongation factors (EF-Tu) existing in plant, bacterial and algae species | | |
|---|---|---|
| SEQ ID NO: | Length amino acids | Peptide amino acid |
| N-terminus of EF-Tu SEQ ID NO: 622 (acetylated) *Pseudomonas* spp. | 26 | Ac-AKEKFERSKPHVNVGTIG HVDHGKTT |
| EF-Tu SEQ ID NO: 623 *Pseudomonas* spp. | 50 | MALEGKDDNEMGTTAVKKLVE TLDSYIPEPERAIDKPFLMPI EDVFSISG |

TABLE 17

| Retro Inverso polypeptides derived from elongation factors (EF-Tu) existing in bacterial and algae species | | |
|---|---|---|
| SEQ ID NO: | Length amino acids | Peptide amino acid |
| RI Chloroplastic EF-Tu SEQ ID NO: 624 *Arabidopsis lyrata* | 18 | GITGINVHPKKREFKGRA |
| RI Chloroplastic EF-Tu SEQ ID NO: 625 *Arabidopsis lyrata* | 26 | TTKGHDVHGITGINVHPKKREFKGRA |
| RI Chloroplastic EF-Tu SEQ ID NO: 626 *Arabidopsis lyrata* | 50 | GTISFVDEVALLFPLETQRTPIPIYSDVSDMLEYIKDVWKNEGRKVN PKE |
| RI N-terminus of EF-Tu SEQ ID NO: 627 *Euglena gracilis* | 18 | GITGINIHPKTREFKQRA |
| RI N-terminus of EF-Tu SEQ ID NO: 628 *Euglena gracilis* | 26 | TTKGHDVHGITGINIHPKTREFKQRA |
| RI EF-Tu fragment SEQ ID NO: 629 *Euglena gracilis* | 50 | GTISLVDEIAMLFDKETDRTPTPIYSDVQDMLNLIKDVWKNEGKTI KPNK |
| RI N-terminus of EF-Tu SEQ ID NO: 630 *Acidovorax avenae* | 18 | GITGVNVHPKTREFKGKA |
| RI N-terminus of EF-Tu SEQ ID NO: 631 *Acidovorax avenae* | 26 | TTKGHDVHGITGVNVHPKTREFKGKA |
| RI EF-Tu fragment SEQ ID NO: 632 *Acidovorax* spp. | 50 | GSISFVDEVPMLFAGDVAREPTPIYTDLAEALKDIAQEGLPGKDGE LALK |
| RI N-terminus of EF-Tu SEQ ID NO: 633 *Bacillus cereus* | 18 | GITGINVHPKSREFKAKA |
| RI N-terminus of EF-Tu SEQ ID NO: 634 *Bacillus cereus* | 26 | TTKGHDVHGITGINVHPKSREFKAKA |

TABLE 17-continued

Retro Inverso polypeptides derived from elongation factors (EF-Tu) existing in bacterial and algae species

| SEQ ID NO: | Length amino acids | Peptide amino acid |
|---|---|---|
| RI EF-Tu fragment SEQ ID NO: 635 *Bacillus cereus* | 50 | GITSFVDEIPMLFPKDTEREPTPIYADVEAMLEIIKEEWEAEGQLAK LAS |
| RI N-terminus of EF-Tu SEQ ID NO: 636 *Burkholderia* spp. | 26 | TTKGHDVHGITGVNVHPKTREFKGKA |
| RI EF-Tu fragment SEQ ID NO: 637 *Burkholderia* spp. | 50 | GSISFVDEVPMLFAGDVAREPTPIYTDLADALNMIAVEGLEGTDGE LALK |
| RI EF-Tu fragment SEQ ID NO: 638 *Xanthomonas campestris* | 50 | GSISFVDEVPMLFPRDVDRTPEPIFTDLADVLKLIAPVGIESQDGDL ALR |
| RI N-terminus of EF-Tu SEQ ID NO: 639 *Pseudomonas* spp. | 26 | TTKGHDVHGITGVNVHPKSREFKEKA |
| RI EF-Tu SEQ ID NO: 640 *Pseudomonas* spp. | 50 | GSISFVDEIPMLFPKDIAREPEPIYSDLTEVLKKVATTGMENDDKGE LAM |

Thionins and Thionin-Targeting Polypeptides

The polypeptide can comprise the thionin or thionin-like polypeptide.

The thionin or thionin-like polypeptide can be fused to a phloem targeting sequence to form a fused polypeptide, the amino acid sequence of the phloem targeting sequence comprising any one of SEQ ID NOs: 641-649, or any combination thereof, for delivering the fused polypeptide to vascular tissue or cells and/or phloem or phloem-associated tissue or cells in the plant or plant part.

The amino acid sequence of the phloem targeting sequence can comprise SEQ ID NO: 641.

More specifically, targeting sequences useful for targeting AMP polypeptides, such as thionins or Flg polypeptides to the vascular tissues (xylem and phloem) can be extremely useful for treating diseases that colonize restricted tissues involved in the transport of fluids and nutrients (e.g., water soluble nutrients, sugars, amino acids, hormones, etc.). Vascular tissues such as the xylem transport and store water and water-soluble nutrients and the phloem cells transport sugars, proteins, amino acids, hormones and other organic molecules in plants.

Preferred vascular/phloem targeting polypeptides useful for targeting the thionins and flagellin-associated polypeptides as described herein are provided in Table 18.

TABLE 18

Phloem targeting polypeptides

| SEQ ID NO: | Vascular/Phloem targeting polypeptides |
|---|---|
| Phloem targeting peptide Synthetic SEQ ID NO: 641 | MSTATFVDIIIAILLPPLGVFLRFGCGVEFWICLVL TLLGYIPGIIYAIYVLTK |
| Salt stress induced targeting peptide *Citrus clementine* SEQ ID NO: 642 | MGSETFLEVILAILLPPVGVFLRYGCGVEFWICLL LTVLGYIPGIIYAIYVLVG |
| Hypothetical protein CICLE *Citrus trifoliata* SEQ ID NO: 643 | MGTATCVDIILAVILPPLGVFLKFGCKAEFWICLL LTILGYIPGIIYAVYVITK |
| Hypothetical protein CICLE *Citrus sinensis* SEQ ID NO: 644 | MADEGTATCIDIILAIILPPLGVFLKFGCKVEFWIC LLLTIFGYIPGIIYAVYAITKN |
| Low temperature and salt responsive protein *Citrus sinensis* SEQ ID NO: 645 | MADGSTATCVDILLAVILPPLGVFLKFGCKAEFW ICLLLTILGYIPGIIYAVYAITKK |

TABLE 18-continued

| Phloem targeting polypeptides | |
|---|---|
| SEQ ID NO: | Vascular/Phloem targeting polypeptides |
| Hypothetical protein CICLE *Citrus clementina* SEQ ID NO: 646 | FYKQKYQVQITKAVTQNPKHFFNQSSCFLTLNFI LFHFTLFKNQSKMADGSTATCVDILLAVILPPLG VFLKFGCKAEFWICLLLTILGYIPGIIYAVYAITKK |
| Low temperature and salt responsive protein *Arabidopsis thaliana* SEQ ID NO: 647 | MSTATFVDIIIAILLPPLGVFLRFGCGVEFWICLVL TLLGYIPGIIYAIYVLTK |
| Cold-inducible protein *Camelina sativa* SEQ ID NO: 648 | MSTATFVDIIIAVLLPPLGVFLRFGCGVEFWICLV LTLLGYIPGIIYAIYVLTK |
| Low temperature and salt responsive protein *Arabidopsis lyrata* SEQ ID NO: 649 | MGTATCVDIIIAILLPPLGVFLRFGCGVEFWICLV LTLLGYIPGILYALYVLTK |

A synthetic version of a phloem targeting polypeptide (SEQ ID NO: 641) is particularly useful in targeting anti-microbial polypeptides to the phloem sieve tube and companion cells.

Anti-microbial thionin polypeptides are also provided (Table 19) and are utilized with the phloem targeting sequences provided in Table 18 for targeting the thionin sequences into the phloem tissues of citrus as well as other plants.

The amino acid sequence of the thionin or thionin-like polypeptide can comprise any one of SEQ ID NOs: 650-749, such as SEQ ID NO: 651.

TABLE 19

| Thionin and thionin-like sequences | |
|---|---|
| SEQ ID NO: | Thionin or Thionin-like Sequences- Amino Acid |
| Thionin-like protein Synthetic SEQ ID NO: 650 | RTCESQSHRFKGPCSRDSNCATVCLTEGFSGGDCRGFR RRCRCTRPCVFDEK |
| Thionin-like protein *Citrus sinensis* SEQ ID NO: 651 | RVCQSQSHHFHGACFSHHNCAFVCRNEGFSGGKCRG VRRRCFCSKLC |
| Thionin-like protein *Avena sativa* SEQ ID NO: 652 | KSCCKDIMARNCYNVCRIPGTPRPVCATTCRCKIISGNK CPKDYPK |
| Thionin-like protein Synthetic SEQ ID NO: 653 | RTCESQSHRFKGPCSRDSNCATVCLTEGFSGGDCRGFR RRCRCTRPCVFDEK |
| Thionin-like protein *Citrus sinensis* SEQ ID NO: 654 | MDSRSFGLLPLLLLILLTSQMTVLQTEARLCESQSHRFH GTCVRSHNCDLVCRTEGFTGGRCRGFRRRCFCTRIC |
| Proteinase inhibitor se60-like protein *Citrus paradise* SEQ ID NO: 655 | MKSFFGIFLLLLILFASQEIMVPAEGRVCQSQSHHFHGA CFSHHNCAFVCRNEGFSGGKCRGVRRRCFCSKLC |
| Defensin precursor *Citrus clementina* SEQ ID NO: 656 | MKSFFGIFLLLLILFASQMMVPAEGRVCQSQSHHFHG ACFSHHNCAFVCRNEGFSGGKCRGARRRCFCSKLC |
| defensin precursor *Citrus clementina* SEQ ID NO: 657 | MKSFFGIFLLLLILFASQEMMVPAEGRVCQSQSHHFH GACFSHHNCAFVCRNEGFSGGKCRGARRRCFCSKLC |
| Thionin-like protein *Citrus clementina* SEQ ID NO: 658 | MKSFFGIFLLLLILFASQMMVPAEGRVCQSQSHHFHG ACFSHHNCAFVCRNEGFSGGKCRGARRRCFCSKLC |
| Thionin-like peptide *Nicotiana benthamiana* SEQ ID NO: 659 | MANSMRFFATVLLLALLVMATEMGPMTIAEARTCES QSHRFKGPCSRDSNCATVCLTEGFSGGDCRGFRRRCF CTRPC |

TABLE 19-continued

Thionin and thionin-like sequences

| SEQ ID NO: | Thionin or Thionin-like Sequences- Amino Acid |
|---|---|
| Thionin-like protein *Nicotiana sylvestris* SEQ ID NO: 660 | MAKSMRFFATVLLLALLVMATEMGPTTIAEARTCESQ SHRFKGPCSRDSNCATVCLTEGFSGGDCRGFRRRCFCT RPC |
| Thionin-like protein *Nicotiana tabaccum* SEQ ID NO: 661 | MANSMRFFATVLLLTLLVMATEMGPMTIAEARTCES QSHRFKGPCSRDSNCATVCLTEGFSGGDCRGFRRRCF CTRPC |
| Thionin-like protein *Nicotiana tomentosiformis* SEQ ID NO: 662 | MANSMRFFATVLLIALLVMATEMGPMTIAEARTCESQ SHRFKGPCSRDSNCATVCLTEGFSGGDCRGFRRRCFCT RPC |
| Thionin-like protein *Nicotiana tabaccum* SEQ ID NO: 663 | MANSMRFFATVLLIALLVTATEMGPMTIAEARTCESQ SHRFKGPCSRDSNCATVCLTEGFSGGDCRGFRRRCFCT RPC |
| Defensin class I *Nicotiana alata* SEQ ID NO: 664 | MANSMRFFATVLLLTLLFMATEMGPMTIAEARTCESQ SHRFKGPCARDSNCATVCLTEGFSGGDCRGFRRRCFCT RPC |
| Leaf thionin *Avena sativa* SEQ ID NO: 665 | MGSIKGLKSVVICVLVLGIVLEQVQVEGKSCCKDIMAR NCYNVCRIPGTPRPVCATTCRCKIISGNKCPKDYPKLHG DPD |
| Leaf thionin *Avena sativa* SEQ ID NO: 666 | MGSIKGLKSVVICVLVLGIVLEHVQVEGKSCCKDTTAR NCYNVCRIPGTPRPVCATTCRCKIISGNKCPKDYPKLHG DLD |
| Thionin Class I *Tulipa gesneriana* SEQ ID NO: 667 | LGLVVAQTQVDAKSCCPSTAARNCYNVCRFPGTPRPV CAATCGCKIITGTKCPPDYPKLGWSTFQNSDVADKALD VVDEALHVAKEVMKEAVERCNNACSEVCTKGSYAVTA |
| Thionin-like protein Class I *Vitis vinifera* SEQ ID NO: 668 | MERKSLGFFFFLLLILLASQEMVVPSEARVCESQSHKFE GACMGDHNCALVCRNEGFSGGKCKGLRRRCFCTKLC |
| Thionin-like protein Class I *Vitis vinifera* SEQ ID NO: 669 | MERKSLGFFFFLLLILLASQMVVPSEARVCESQSHKFEG ACMGDHNCALVCRNEGFSGGKCKGLRRRCFCTKLC |
| defensin Ec-AMP-D1 *Citrus sinensis* SEQ ID NO: 670 | MERSVRLFSTVLLVLLLLASEMGLRAAEARICESQSHRF KGPCVSKSNCAAVCQTEGFHGGHCRGFRRRCFCTKRC |
| Antimicrobial Protein 1 (Ah-Amp1) *Aesculus hippocastanum* SEQ ID NO: 671 | LCNERPSQTWSGNCGNTAHCDKQCQDWEKASHGAC HKRENHWKCFCYFNC |
| hypothetical protein DCAR *Dacus carota* SEQ ID NO: 672 | MAKNSTSPVSLFAISLIFFLLANSGSITEVDGKVCEKPSL TWSGKCGNTQHCDKQCQDWEGAKHGACHSRGGW KCFCYFEC |
| Cysteine-rich antimicrobial protein *Clitoria ternatea* SEQ ID NO: 673 | NLCERASLTWTGNCGNTGHCDTQCRNWESAKHGAC HKRGNWKCFCYFNC |
| hypothetical protein DCAR *Dacus carota* SEQ ID NO: 674 | MAKKSSSFCLSAIFLVLLLVANTGMVREVDGALCEKPSL TWSGNCRNTQHCDKQCQSWEGAKHGACHKRGNW KCFCYHAC |
| Thionin-like *Bupleurum kaoi* SEQ ID NO: 675 | MAKKLNAVTVSAIFLVVFLIASYSVGAAKEAGAEGEVV FPEQLCERASQTWSGDCKNTKNCDNQCIQWEKARH GACHKRGGKWMCFCYFDKC |
| defensin Dm-AMP1 = cysteine-rich antimicrobial protein *Dahlia merckii* SEQ ID NO: 676 | ELCEKASKTWSGNCGNTGHCDNQCKSWEGAAHGAC HVRNGKHMCFCYFNC |
| Thionin-like *Helianthus annuus* SEQ ID NO: 677 | MAKISVAFNAFLLLLFVLAISEIGSVKGELCEKASQTWS GTCGKTKHCDDQCKSWEGAAHGACHVRDGKHMCFC YFNCSKAQKLAQDKLRAEELAKEKIEPEKATAKP |

TABLE 19-continued

Thionin and thionin-like sequences

| SEQ ID NO: | Thionin or Thionin-like Sequences- Amino Acid |
|---|---|
| Thionin *Cynara cardunculus* var. *scolymus* SEQ ID NO: 678 | MAKNSVAFFALLLLICILTISEFAVVKGELCEKASKTWSGNCGNTRHCDDQCKAWEGAAHGACHTRNKKHMCFCYFNCPKAEKLAQDKLKAEELARDKVEAKEVPHFKHPIEPIHHP |
| Thionin *Cynara cardunculus* var. *scolymus* SEQ ID NO: 679 | MAKQWVSFFALAFIVFVLAISETQTVKGELCEKASKTWSGNCGNTKHCDDQCKSWEGAAHGACHVRNGKHMCFCYFNSCAEADKLSEDQIEAGKLAFEKAEKLDRDVKKAVPNVDHP |
| defensin-like protein 1 - DCAR-like *Daucus carota* subsp. *Sativus* SEQ ID NO: 680 | MAQKVNSALIFSAIFVLFLVASYSVTVAEGARAGAEGEVVYPEALCERASQTWTGKCQHTDHCDNQCIQWENARHGACHKRGGNWKCFCYFDHC |
| low-molecular-weight cysteine-rich defensin *Arabidopsis lyrata* SEQ ID NO: 681 | MASSYTLMLFLCLSIFLIASTEMMAVEARICERRSKTWTGFCGNTRGCDSQCKSWERASHGACHAQFPGFACFCYFNC |
| Thionin-like protein *Parthenium hysterophorus* SEQ ID NO: 682 | MAKSSTSYLVFLLLVLVVAISEIASVNGKVCEKPSKTWFGNCKDTEKCDKRCMEWEGAKHGACHQRESKYMCFCYFDCDP |
| putative defensin AMP1 protein *Arabidopsis thaliana* SEQ ID NO: 683 | MASSYTLMLFLCLSIFLIASTEMMAVEGRICERRSKTWTGFCGNTRGCDSQCKRWERASHGACHAQFPGFACFCYFNC |
| Thionin-like *Eutrema salsugineum* SEQ ID NO: 684 | MASSYTLLLFVCLSIFFIASTEMMMVEGRVCERRSKTWTGFCGNTRGCDSQCKRWERASHGACHAQFPGFACFCYFNC |
| defensin-like *Vitis vinifera* SEQ ID NO: 685 | MAKLLGYLLSYALSFLTLFALLVSTEMVMLEAKVCQRPSKTWSGFCGSSKNCDRQCKNWEGAKHGACHAKFPGVACFCYFNC |
| Knottin *Corchorus olitorius* SEQ ID NO: 686 | MAKSLSSFATFLALLCLFFLLSTPNEMKMAEAKICEKRSQTWSGWCGNSSHCDRQCKNWENARHGSCHADGLGWACFCYFNC |
| Knottin *Corchorus olitorius* SEQ ID NO: 687 | MEMKMAEGKICEKRSQTWSGWCGNSSHCDRQCKNWENARHGSCHADGLGWACFCYFNC |
| Thionin-like protein *Camelina sativa* SEQ ID NO: 688 | MASSLKLMLFLCLSIFLIASTEMMTVEGRTCERRSKTWTGFCGNTRGCDSQCRSWEGASHGACHAQFPGFACFCYFNC |
| Thionin-like protein *Cucumis sarivus* SEQ ID NO: 689 | MAKVVGNSAKMIVALLFLLALMLSMNEKQGVVEAKVCERRSKTWSGWCGNTKHCDRQCKNWEGATHGACHAQFPGRACFCYFNC |
| Thionin-like protein *Cynara cardunculus* var. *scolymus* SEQ ID NO: 690 | MIDAFNYKQFSTVKGKICEKPSKTWFGKCQDTTKCDKQCIEWEDAKHGACHERESKLMCFCYYNCGPPKNTPPGTPPSPP |
| Thionin-like *Capsella rubella* SEQ ID NO: 691 | MASSYKLILFLCLSIFLIASFEMMAVEGRICQRRSKTWTGFCGNTRGCDSQCKRWERASHGACHAQFPGFACFCYFNC |
| Thionin *Arabidopsis thaliana* SEQ ID NO: 692 | MMAVEGRICERRSKTWTGFCGNTRGCDSQCKRWERASHGACHAQFPGFACFCYFNC |
| Thionin *Brassica napus* SEQ ID NO: 693 | MASSYTRLLLLCLSIFLIASTEVMMVEGRVCQRRSKTWTGFCGNTRGCDSQCKRWERASHGACHAQFPGFACFCYFNC |
| Thionin-like protein *Brassica rapa* SEQ ID NO: 694 | MASSYARLLLLCLSIFLIASTEVMMVEGRVCQRRSKTWTGFCGNTRGCDSQCKRWERASHGACHAQFPGFACFCYFNC |
| Thionin-like protein *Camelina sativa* SEQ ID NO: 695 | MASSLKLMLFLCLSIFLIASTEMMTVEGRTCERRSKTWTGFCGNTRGCDSQCRRWEHASHGACHAQFPGFACFCYFNC |

TABLE 19-continued

Thionin and thionin-like sequences

| SEQ ID NO: | Thionin or Thionin-like Sequences- Amino Acid |
|---|---|
| defensin-like protein *Brassica napus* SEQ ID NO: 696 | MASYTRLLLLCLSIFLIASTEVMMVEGRVCQRRSKTWT GFCGNTRGCDSQCKRWERASHGACHAQFPGFACFCY FNC |
| Thionin-like protein *Vitis vinifera* SEQ ID NO: 697 | MVMLEAKVCQRPSKTWSGFCGSSKNCDRQCKNWEG AKHGACHAKFPGVACFCYFNC |
| Thionin-like protein *Brassica napus* SEQ ID NO: 698 | MTKSFILVALLCICFILLSPTEMRLTLNACLKLAEAKICEK YSQTWSGRCTKTSHCDRQCINWEDARHGACHQDKH GRACFCYFNCKK |
| Thionin-like protein *Raphanus sativus* SEQ ID NO: 699 | MASSYTVFLLLCLSIFLIASTEVMMVEGRVCQRRSKTW TGFCGNTRGCDSQCKRWEHASHGACHAQFPGFACFC YFNC |
| Thionin-like *Arabis alpine* SEQ ID NO: 700 | MASSYTLLLFLCLSIFLIVSTEMMMVEGRICERRSKTWT GFCANTRGCDSQCKRWERASHGACHAQFPGVACFCY FNC |
| Thionin-like protein *Cucumis melo* SEQ ID NO: 701 | MAKVVGNSAKMIVAFLFLLALTLSMNEKQGVVEAKVC ERRSKTWSGWCGDTKHCDRQCKNWEGAKHGACHA QFPGRACFCYFNC |
| Thionin-like protein *Erythranthe guttate* SEQ ID NO: 702 | MAASLVYRLSSVILIVLLLFIMLNNEVMVVESRLCERRS KTWTGFCGSSNNCNNQCRNWERASHGACHAQFPGF ACFCYFNC |
| Thionin-like protein *Sesamum indicum* SEQ ID NO: 703 | MAKFQVSSTIFFALFFCFLLLASNEAKICQRMSKTWSG VCLNSGNCDRQCRNWERAQHGACHRRGLGFACLCYF KC |
| Thionin-like protein *Eclipta prostrata* SEQ ID NO: 704 | MAKNSVAFFAFLLILFVLAISEIGSVKGELCEKASQTWS GTCRITSHCDNQCKSWEGAAHGACHVRGGKHMCFC YFSHCAKAEKLTQDKLKAGHLVNEKSEADQKVPVTP |
| Gamma thionin *Cynara cardunculus* var. *scolymus* SEQ ID NO: 705 | MAKNTKVSAFLFVFLFVFFLVVHSVTAFAIRFKCFDTD MLLKVIADMVVGMKGIEKVCRRRSKTWSGYCGDSKH CDQQCREWEGAEHGACHHEGLGRACFCYFNC |
| Art v 1 precursor *Ambrosia artemisiifolia* SEQ ID NO: 706 | MAAGLLVFVLAISEIASVKGKLCEKPSVTWSGKCKVKQ TDKCDKRCIEWEGAKHGACHKRDSKASCFCYFDCDPT KNPGPPPGAPKGKAPAPSPPSGGGGEGGGEGGGER |
| Art v 1 precursor *Ambrosia artemi679siifolia* SEQ ID NO: 707 | MAAGLLVFVLAISEIASVKGKLCEKPSLTWSGKCKVKQT DKCDKRCIEWEGAKHGACHKRDSKATCFCYFDCDPTK NPGPPPGAPKGKAPAPSPPSGGGAPPPSGGEGGER |
| Thionin-like protein *Jatropha curcas* SEQ ID NO: 708 | MAKLHSSALCFLIIFLFLLVSKEMAVTEAKLCQRRSKTW SGFCGDPGKCNRQCRNWEGASHGACHAQFPGFACF CYFKC |
| Thionin-like protein *Nelumbo nucifera* SEQ ID NO: 709 | MAKAPKSVSYFAFFFILFLLASSEIQKTKKLCERRSKTWS GRCTKTQNCDKQCKDWEYAKHGACHGSWFNKKCYC YFDC |
| Thionin-like protein *Pyrus* x *bretschneideri* SEQ ID NO: 710 | MAKLLSRLSIPLIVFVFLLILLASTEVAMVEARICQRRSKT WSGFCANTGNCNRQCTNWEGALHGACHAQFPGVA CFCYFRC |
| Low-molecular-weight cysteine-rich protein LCR78 precursor *Ricinus communi* SEQ ID NO: 711 | MAKLHFPTLLCLFIFLFLLVSTEMQVTQAKVCQRRSKT WSGFCGSTKNCDRQCKNWEGALHGACHAQFPGVAC FCYFKCGGER |
| homologue of Art v 1 precursor *Ambrosia artemisiifolia* SEQ ID NO: 712 | KLCEKPSVTWSGKCKVKQTDKCDKRCIEWEGAKHGAC HKRDSKASCFCYFDCDPTKNPGPPPGAPKGKAPAPSP PSGGGAPPPSGGEGGGD |
| homologue of Art v 1 precursor *Ambrosia artemisiifolia* SEQ ID NO: 713 | KLCEKPSVTWSGNKVKQTDKCDKRCIEWEGAKHGAC HKRDSKASCFCYFDCDPTKNPGPPPGAPKGKAPAPSP PSGGGAPPPSGGEGGGDGGGGRR |
| Thionin-like protein *Prunus mume* SEQ ID NO: 714 | MAKLLSHLLFYPILFLFLFIFLASTEVAILEARICQRRSKT WSGFCGNTRNCNRQCRNWEGALRGACHAQFPGFAC FCYFRC |

TABLE 19-continued

| Thionin and thionin-like sequences | |
|---|---|
| SEQ ID NO: | Thionin or Thionin-like Sequences- Amino Acid |
| Knottin<br>*Corchorus olitorius*<br>SEQ ID NO: 715 | MAKTLQLFALFFIVILLANQEIPVAEAKLCQKRSKTWTG<br>ICIKTKNCDNQCKKWEKAEHGACHRQGIGFACFCYFN<br>QKKC |
| Knottin<br>*Corchorus olitorius*<br>SEQ ID NO: 716 | MAKFVSTVALLFALFILLASFDEGMMPMAEAKVCSKR<br>SKTWSGFCNSSANCNKQCREWEDAKHGACHFEFPGF<br>ACFCYFNC |
| Thionin-li ke protein *Solanum pennellii*<br>SEQ ID NO: 717 | MNSKVILALLVCFLLIASNEMQGGEAKVCGRRSSTWS<br>GLCLNTGNCNTQCIKWEHASSGACHRDGFGFACFCYF<br>NC |
| Thionin-like protein<br>*Fragaria vesca* subsp. *Vesca*<br>SEQ ID NO: 718 | MAKLLGYHLVYPILFLFIFLLLASTEMGMLEARICQRRSK<br>TWTGLCANTGNCHRQCRNWEGAQRGACHAQFPGF<br>ACFCYFNC |
| Knottin<br>*Corchorus capsularis*<br>SEQ ID NO: 719 | MAKFVSVALLLALFILVASFDEGMVPMAEAKLCSKRSK<br>TWSGFCNSSANCNRQCREWEDAKHGACHFEFPGFAC<br>FCYFDC |
| Thionin-like protein *Solanum tuberosum*<br>SEQ ID NO: 720 | MQGGEARVCERRSSTWSGPCFDTGNCNRQCINWEH<br>ASSGACHREGIGSACFCYFNC |
| Defensin 1.2-like protein PDF1.2-1<br>*Dimocarpus longan*<br>SEQ ID NO: 721 | MAKTLKSVQFFALFFLVILLAGSEMTAVEALCSKRSKT<br>WSGPCFITSRCDRQCKRWENAKHGACHRSGWGFAC<br>FCYFNKC |
| Thionin-like protein *Camelina sativa*<br>SEQ ID NO: 722 | MAKAATIVTLLFAALVFFAALETPTMVEAQKLCERPSG<br>TWSGVCGNSNACKNQCINLEKARHGSCNYVFPAHKCI<br>CYFPC |
| Thionin-like<br>*Arabis alpine*<br>SEQ ID NO: 723 | MAKFASIIAFLFAALVLFASFEAPTMVEAQKYCEKPSGT<br>WSGVCGNSNACNNQCINLEGARHGSCNYVFPYYRCIC<br>YFQC |
| Thionin-like<br>*Theobroma cacao*<br>SEQ ID NO: 724 | MAMSLKSVHFFALFFIVVLLANQEMPVAEAKLCQKRS<br>KTWTGPCIKTKNCDHQCRKWEKAQHGACHWQWPG<br>FACFCYVNC |
| Thionin-like<br>*Amborella trichopoda*<br>SEQ ID NO: 725 | MAKLVSPKAFFVFLFVFLLISASEFSGSEAKLCQKRSRT<br>WSGFCANSNNCSRQCKNLEGARFGACHRQRIGLACF<br>CYFNC |
| low-molecular-weight cysteine-rich 67<br>*Arabidopsis thaliana*<br>SEQ ID NO: 726 | MAKSATIVTLFFAALVFFAALEAPMVVEAQKLCERPSG<br>TWSGVCGNSNACKNQCINLEKARHGSCNYVFPAHKCI<br>CYFPC |
| Thionin-like<br>*Arabis alpine*<br>SEQ ID NO: 727 | MAKFASIITLLFAALVLFASLEAPTMVEAQKLCQRPSGT<br>WSGVCGNNGACKNQCINLEKARHGSCNYVFPYHRCIC<br>YFPC |
| Thionin-like<br>*Brassica juncea*<br>SEQ ID NO: 728 | MAKVASIIALLFAALVLFAAFEAPTMVEAQKLCERPSGT<br>WSGVCGNNNACKNQCINLEKARHGSCNYVFPAHKCI<br>CYFPC |
| Thionin-like<br>*Brassica oleracea* var. *oleracea*<br>SEQ ID NO: 729 | MAKFASIIALLFAALVLFAALEAPTMVEAQKLCERPSGT<br>WSGVCGNNNACKNQCINLEKARHGSCNYVFPAHKCI<br>CYFPC |
| Thionin-like<br>*Camelina sativa*<br>SEQ ID NO: 730 | MAKPATIVTLLFAALVFFAALETPTMVEAQKLCERPSG<br>TWSGVCGNNNACKNQCINLEKARHGSCNYVFPAHKC<br>ICYFPC |
| Thionin-like<br>*Camelina sativa*<br>SEQ ID NO: 731 | MAKSATIVTLLFAALVFFAALETPTMVEAQKLCERPSG<br>TWSGVCGNNNACKNQCINLEKARHGSCNYVFPAHKC<br>ICYFPC |
| Thionin-like<br>*Brassica napus*<br>SEQ ID NO: 732 | MAKFASIIAPLFAVLVLFAAFEAPTMVEAQKLCERPSGT<br>WSGVCGNNNACKNQCINLEKARHGSCNYVFPAHKCI<br>CYFPC |
| Thionin-like<br>*Eutrema salsugineum*<br>SEQ ID NO: 733 | MAKFASIITLLFAALVLFAVFEGPTMVEAQKLCERPSGT<br>WSGVCGNNNACKNQCINLEKARHGSCNYVFPAHKCI<br>CYFPC |

TABLE 19-continued

Thionin and thionin-like sequences

| SEQ ID NO: | Thionin or Thionin-like Sequences- Amino Acid |
|---|---|
| Cysteine-rich antifungal protein *Raphanus sativus* SEQ ID NO: 734 | MAKFASIIALLFAALVLFAAFEAPTMVEAQKLCERPSGT WSGVCGNNNACKNQCINLEKARHGSCNYVFPAHKCI CYFPC |
| Thionin-like protein 1 *Raphanus sativus* SEQ ID NO: 735 | MAKFASIVSLLFAALVLFTAFEAPAMVEAQKLCERPSG TWSGVCGNNNACKNQCINLEKARHGSCNYVFPAHKC ICYFPC |
| Thionin-like protein 1 *Raphanus sativus* SEQ ID NO: 736 | MNTKVILALLFCFLLVASNEMQVGEAKVCQRRSKTWS GPCINTGNCSRQCKQQEDARFGACHRSGFGFACFCYF KC |
| Thionin-like *Brassica rapa* SEQ ID NO: 737 | MAKFASIIAPLFAALVLFAAFEAPTMVEAQKLCERPSGT WSGVCGNNNACKNQCINLEKARHGSCNYVFPAHKCI CYFPC |
| Thionin-like *Solanum pennellii* SEQ ID NO: 738 | MNTKLILALMFCFLLIASNEMQVGEAKVCQRRSKTWS GPCINTGNCSRQCKQQEDARFGACHRSGFGFACFCYF KC |
| Thionin-like *Citrus clementina* SEQ ID NO: 739 | MAKFTTTFALLFAFFILFAAFDVPMAEAKVCQRRSKTW SGLCLNTGNCSRQCKQQEDARFGACHRQGIGFACFCY FKC |
| Thionin-like *Brassica rapa* SEQ ID NO: 740 | MAKFTSIIVLLFAALVLFAGFEAPTMVEAQKLCERPSGT WSGVCGNNNACKNQCIRLEKARHGSCNYVFPARKCIC YFPC |
| Thionin-like *Eutrema salsugineum* SEQ ID NO: 741 | MAKFASIITLLFAALVLFATFAPTMVEAKLCERPSGTWS GVCGNNNACKSQCQRLEGARHGSCNYVFPAHKCICYF PC |
| Thionin-like *Eutrema salsugineum* SEQ ID NO: 742 | MAKFASIITLLFAALVLFATFEAPTMVEAKLCERPSGTW SGVCGNNNACKSQCQRLEGARHGSCNYVFPAHKCICY FPC |
| Thionin-like *Heliophila coronopifolia* SEQ ID NO: 743 | MAKFASIIAFFFAALVLFAAFEAPTIVEAQKLCERPSGT WSGVCGNNNACRNQCINLEKARHGSCNYVFPAHKCI CYFPC |
| Thionin-like *Brassica oleracea* SEQ ID NO: 744 | MAKVASIVALLFPALVIFAAFEAPTMVEAQKLCERPSG TWSGVCGNNNACKNQCIRLEKARHGSCNYVFPAHKCI CYFPC |
| Thionin-like *Cicer arietinum* SEQ ID NO: 745 | MSKFYTVFMFLCLALLLISSWEVEAKLCQRRSKTWSGP CIITGNCKNQCKNVEHATFGACHRQGFGFACFCYFNC H |
| Thionin-like *Citrus clementina* SEQ ID NO: 746 | MAKSVASITTAFALIFAFFILFASFGVPMAEAKVCQRRS KTWSGPCLNTGKCSRQCKQQEYARYGACYRQGAGYA CYCYFNC |
| Thionin-like *Citrus sinensis* SEQ ID NO: 747 | MAKSVASITTAFALIFAFFILFASFEVPMAEAKVCQRRS KTWSGPCLNTGKCSRHCKQQEDARYGACYRQGTGYA CFCYFEC |
| Thionin-like *Citrus sinensis* SEQ ID NO: 748 | MAKFTTTFALLFAFFILFAAFDVPMAEAKVCQLRSKTW SGLCLNTGNCSRQCKQQEDARFGACHRQGIGFACFCY FKC |
| Ec-AMP-D1 *Citrus sinensis* SEQ ID NO: 749 | MERSVRLFSTVLLVLLLLASEMGLRAAEARICESQSHRF KGPCVSKSNCAAVCQTEGFHGGHCRGFRRRCFCTKRC |

The polypeptide can comprise a fusion protein.

Table 20 (SEQ ID NO: 750) describes the sequences used to make a translational fusion using the nucleotide sequence that encodes the synthetic phloem targeting polypeptide (SEQ ID NO: 641) with a synthetic thionin polypeptide (SEQ ID NO: 650). The upper case (not bold) font sequence identifies the phloem targeting sequence, the upper case bold font identifies the fusion of these two peptide sequences (Table 20) that codes for the phloem targeted bioactive priming polypeptide.

TABLE 20

| Translational fusion of a phloem targeting sequence with a thionin derived polypeptide<br>Translational fusion phloem targeting sequence with thionin polypeptide (synthetic): SEQ ID NO: 750 |
|---|
| MSTATFVDIIIAILLPPLGVFLRFGCGVEFWICLVLTLLGYIPGIIYAIY VLTK**RTCESQSHRFKGPCSRDSNCATVCLTEGFSGGDCRGFRRRCRCTRP CVFDEK** |

Additional Modifications

In addition, polypeptides can be chemically synthesized with D-amino acids, β2-amino acids, β3-amino acids, homo amino acids, gamma amino acids, peptoids, N-methyl amino acids, and other non-natural amino acid mimics and derivatives.

The polypeptides may be modified by either natural processes, such as posttranslational processing, or by chemical modification techniques that are well known in the art. Modifications can occur anywhere in a polypeptide, including the polypeptide backbone, the amino acid side-chains and the amino or carboxyl termini. The same type of modification may be present in the same or varying degrees at several sites in a polypeptide. Also, a polypeptide may contain many types of modifications.

Peptides may be branched, for example, as a result of ubiquitination, and they may be cyclic, with or without branching. Cyclic, branched, and branched cyclic polypeptides may result from posttranslation natural processes or may be made by synthetic methods.

Modifications include acetylation, acid addition, acylation, ADP-ribosylation, aldehyde addition, alkylamide addition, amidation, amination, biotinylation, carbamate addition, chloromethyl ketone addition, covalent attachment of a nucleotide or nucleotide derivative, cross-linking, cyclization, disulfide bond formation, demethylation, ester addition, formation of covalent cross-links, formation of cysteine-cysteine disulfide bonds, formation of pyroglutamate, formylation, gamma-carboxylation, glycosylation, GPI anchor formation, hydrazide addition, hydroxyamic acid addition, hydroxylation, iodination, lipid addition, methylation, myristoylation, oxidation, PEGylation, proteolytic processing, phosphorylation, prenylation, palm itoylation, addition of a purification tag, pyroglutamyl addition, racemization, selenoylation, sulfonamide addition, sulfation, transfer-RNA mediated addition of amino acids to proteins such as arginylation, ubiquitination, and urea addition. (see, e.g., Creighton et al. (1993) Proteins—Structure and Molecular Properties, 2nd Ed., T. E. Creighton, W. H. Freeman and Company, New York; Johnson, ed. (1983) Posttranslational Covalent Modification Of Proteins, Academic Press, New York; Seifter et al. (1990) Meth. Enzymol., 182: 626-646; Rattan et al. (1992) Ann. N.Y. Acad. Sci., 663: 48-62; and the like).

Using known methods of protein engineering and recombinant DNA technology, variants may be generated to improve or alter the characteristics of the polypeptides described herein. Such variants include deletions, insertions, inversions, repeats, duplications, extensions, and substitutions (e.g., conservative substitutions) selected according to general rules well known in the art so as have little effect on activity.

The polypeptide can comprise an amino acid sequence having at least 70% identity to any one of SEQ ID NOs. 1-768 wherein the polypeptide has bioactive priming activity.

The polypeptide can comprise an amino acid sequence having at least 75% identity to any one of SEQ ID NOs. 1-768, wherein the polypeptide has bioactive priming activity.

The polypeptide can comprise an amino acid sequence having at least 80% identity to any one of SEQ ID NOs. 1-768, wherein the polypeptide has bioactive priming activity.

The polypeptide can comprise an amino acid sequence having at least 85% identity to any one of SEQ ID NOs. 1-768, wherein the polypeptide has bioactive priming activity.

The polypeptide can comprise an amino acid sequence having at least 90% identity to any one of SEQ ID NOs. 1-768, wherein the polypeptide has bioactive priming activity.

The polypeptide can comprise an amino acid sequence having at least 95% identity to any one of SEQ ID NOs. 1-768, wherein the polypeptide has bioactive priming activity.

The polypeptide can comprise an amino acid sequence having at least 98% identity to any one of SEQ ID NOs. 1-768, wherein the polypeptide has bioactive priming activity.

The polypeptide can comprise an amino acid sequence having at least 99% identity to any one of SEQ ID NOs. 1-768, wherein the polypeptide has bioactive priming activity.

II. Preparation of Bioactive Priming Polypeptides

Methods and approaches are provided for cloning, genetically modifying and expressing the bioactive priming polypeptides (for example, flagellins) and the bioactive priming polypeptides (for example, Bt.4Q7Flg22) using those methods well understood and commonly used by one of ordinary skill in the art. The methods described herein can be used with any of the bioactive priming polypeptides as described herein and therefore include any of the flagellins, flagellin-associated polypeptides, thionins, harpin-like (HpaG-like), EF-Tu, PSKα or RHPP and/or any combinations thereof.

Bioactive priming polypeptides can be provided as a free polypeptide, immobilized on the surface of a particle, or impregnated on or into a matrix. Several expression systems can be used for the production of free polypeptide.

The flagellin-derived full-coding, partial coding (flagellin polypeptides) and flagellin-associated polypeptides can be overexpressed in *Bacillus* strain, for example, *Bacillus thuringiensis* strain BT013A, in *Bacillus cereus* or in *Bacillus subtilis*. The flagellins and flagellin-derived polypeptides are cloned using an appropriate expression vector to allow for the abundant production of the polypeptide.

For example, in order to facilitate cloning of the target nucleotides that encode the bioactive priming polypeptide(s) as described herein, an *E. coli* compatible shuttle vector pSUPER was constructed by fusing the pBC plasmid backbone described above with the *E. coli* pUC57 cloning vector at compatible BamHI restriction endonuclease sites. The resulting, pSUPER vector carries dual selection markers (ampicillin selection in *E. coli* and tetracycline selection in *Bacillus* spp). Cloning was performed by PCR amplification of target nucleotides with specific primers synthesized with 15 bp overlapping the pSUPER insertion site. Specific gene encoding polypeptides were fused to the pSUPER vector with In-Fusion HD Cloning Kit (Clontech). Sequence verified pSUPER constructs were amplified using the pBC suitable backbone Reverse and Forward primers. The resulting PCR products were self-ligated to generate the pBC plasmid that was used to transform the B30 donor *Bacillus* spp. strain. The final construct was verified to be completely intrageneric by Sanger sequencing.

The bioactive priming polypeptides/peptides as described herein are produced in large amounts for field and grower applications by using a free expression system that can utilize a *Bacillus subtilis* and/or *Bacillus thuringiensis* strain as the designated heterologous expression strain. The base expression plasmid designated pFEe4B consists of an *E. coli* section (=e) and a *Bacillus* section (=pFE). The e section was derived from pUC19 and enables selection and amplification of the vector in *E. coli* for cloning purposes. It comprises the beta-lactamase gene (bla) conferring resistance to beta-lactam antibiotics such as ampicillin and other penicillin derivatives, as well as an *E. coli* origin of replication allowing vector multiplication. The pFE section provides selection and plasmid amplification in *Bacillus* spp. and drives expression of the heterologous polypeptide/peptide of interest. As such it contains a gene conferring resistance to tetracycline (tetL), as well as the gene for a replication protein (repU) responsible for amplifying the plasmid in *Bacillus* spp., both of which were derived from the native *Bacillus cereus* plasmid pBC16. The expression cassette of pFEe4B contains a secretion signal (amyQ), a cloning site and a terminator (rspD), the former resulting in secretion of the expressed protein/peptide from the host strain cells into the surrounding medium, and the latter preventing transcription beyond the open reading frame of interest. Expression in pFEe4B is driven by a modified autoinducible promoter, which initiates expression once the culture reaches a sufficient optical density. In the pFEe4b expression system, expression is controlled by an IPTG-inducible promoter sequence from *Bacillus subtilis*. This promoter consists of a modified constitutive promoter combined with the *E. coli* lac repressor (lacl) and a ribosome binding site. Thus, expression from pFEe4B-encoded polypeptides/peptides depends on the presence of suitable induction agents such as isopropyl beta-D-1-thiogalactopyranoside (IPTG). However other pFe systems useful for expression of the polypeptides as described herein do not rely on such induction systems for their expression. The pFEe4 plasmid further harbors the *E. coli* lacI gene under control of the *Bacillus licheniformis* penicillase promoter to prevent expression of polypeptide/peptide as described herein in absence of any induction agent.

Other commercially available expression vectors, for example, any of those derived from *Bacillus subtilis*, can also be useful. Other expression vectors were selected for producing the recombinant bioactive priming polypeptides due to the following desired criteria: the recombinant microorganism is non-pathogenic and is considered as generally regarded as safe (GRAS) organisms, it has no significant bias in codon usage and it is capable of secreting extracellular proteins directly into the culture medium providing for a cell free version(s) of the bioactive priming polypeptides.

Other expression systems common in the art can be utilized to express bioactive priming polypeptides in a similar manner.

The bioactive priming polypeptides as described herein can be produced and purified either by the use of a protein tag(s) using affinity purification or by using column protease cleavage methods which release the un-tagged polypeptide(s). Methods of using this approach to make free versions of the bioactive priming polypeptides are commonly known and understood by one of ordinary skill in the art.

Protein tags usually comprise a relatively small sequence of amino acids incorporated into a translated polypeptide, basically providing a molecular tether for the bioactive priming polypeptide of interest. They are commonly used to aid in the expression and purification of recombinant polypeptides. The polyhistidine (His) tag was selected for the purposes of affinity purification of the bioactive priming polypeptides as described. A His tag can be fused to either the N- or C-terminus of a polypeptide. His tags are frequently combined with other tags for dual-labeling. Tags for the bioactive priming polypeptides can be useful to affinity purify them. The tags can also be cleaved off of the bioactive priming polypeptides using specific proteases and column-specific protease cleavage methods to release the purified un-tagged bioactive priming polypeptide or full-length precursor protein of interest. These methods are also common and well known to one of ordinary skill in the art. Other tags that can be utilized are known in the art, and include FLAG tags, antibody epitopes, streptavidin/biotin, among other purification tools. Another useful tag is a glutathione S-transferase (GST) tag.

Protein tags can be provided within the plasmid to produce the polypeptide. Ideally, the plasmid comprises, alongside the sequence encoding the polypeptide of interest, a secretion signal (e.g., the amyE or amyQ secretion signal) to promote secretion, and a protein tag (e.g., glutathione S transferase) to enhance the stability of the polypeptide, thereby enhancing production and stability. In preferred cases, the protein tag (e.g., GST) is linked to the polypeptide using a linker sequence comprising a consensus cleavage sequence. This can allow the addition of a targeted kinase that can cleave the tag and release the purified, isolated polypeptide. A suitable consensus cleavage sequence can comprise an enterokinase cleavage sequence (SEQ ID NO: 772), which can be cleaved by simple application of a bovine enterokinase, for example.

Therefore, a method is provided for producing a polypeptide comprising producing a fusion protein comprising any polypeptide described herein and an Enterokinase (EK) cleavage site via fermentation, the EK cleavage site serving to enhance activity and stability of the polypeptide. The fusion protein encoded by the plasmid can further comprise a protein tag (e.g., a poly-histidine (His) tag, a FLAG tag, an antibody epitope, streptavidin/biotin, glutathione S-transferase (GST), or any combination thereof), wherein the enterokinase cleavage site comprises a linking region connecting the polypeptide and the protein tag. The fusion protein can also comprise a secretion signal. The secretion signal can comprise an amyE or amyQ secretion signal (e.g., SEQ ID NO: 769), or it can comprise any one of SEQ ID NOs 563-570 as described above. The polypeptide comprising the enterokinase (EK) cleavage site can be more stable and produced in higher yields using fermentation than a polypeptide lacking the enterokinase (EK) cleavage site. When desired, an enterokinase (e.g., a bovine enterokinase) can be applied to the fusion protein to activate (e.g., isolate) the polypeptide of interest. The enterokinase can be applied on-site to enable maximum stability of the bioactive priming polypeptide prior to administration.

The bioactive priming polypeptides can be provided in a synthetic form using commercially available peptide synthesis technologies to produce high purity polypeptides. Synthetic production of the bioactive priming polypeptides utilizes general solid-phase peptide synthesis methodologies that are well known to one of ordinary skill in the art. Chemical synthesis methodologies include: a stepwise assembly of peptides from amino acid precursors, whereby peptide elongation proceeds via a coupling reaction between amino acids, followed by the removal of a reversible protecting group. Solid phase peptide synthesis is used to add a covalent attachment step that links the nascent peptide chain to an insoluble polymeric support whereby the anchored peptide can be extended by a series of cycles. These extension reactions are driven to completion and then the synthesized polypeptide is removed from the solid support by filtration and washing steps. MS and HPLC analyses are performed after the completion of synthesis and purification.

Any of the bioactive priming polypeptides as described herein for flagellin-associated polypeptides (Tables 1-5), harpin-like (HpaG-like) polypeptides (Table 10 and 11), phytosulfokine (PSKα) polypeptides (Table 12), RHPP (Table 13-15), elongation factor Tu (EF-Tu polypeptides) (Tables 16 and 17), thionin and thionin-like polypeptides (Table 19) can be provided in synthetic forms.

Additionally, such methods can be used for making and using conserved assistance sequences preferably named signature (SEQ ID NOs: 542-548), signal anchor sorting (SEQ ID NOs: 549-562) and secretion (SEQ ID NOs: 563-570) sequences.

Retro inverso can also be made synthetically or chemically manufactured. Synthetic polypeptides produced in the all-D confirmation are prepared by replacing all the L-amino acid residues with their D-enantiomers resulting in a reversed or retro-all-D-isomer Flg polypeptide. Solid phase synthesis is used to prepare the retro-inverso versions of the Flg polypeptide(s). After synthesis and purification of the retro-inverso polypeptide(s), the amino acid composition is confirmed using mass spectrometry of the Flg polypeptide(s). The purity of the retro-inverso polypeptide(s) is then confirmed at a level greater or equal to 95% using HPLC analysis. The retro-inverso versions of the Flg polypeptide(s) are further characterized using HPLC retention time, relative molecular mass and amino acid composition values (IC50 μM). Retro inverso production using recombinant DNA technology generally involves the use of non-ribosomal protein synthesis mechanisms.

Retro-inverso synthetic Flg bioactive priming polypeptides prepared by solid phase synthesis are tested for their capacity to bind to the FLS2 or alternative FLS receptors, for example, FLS3 also found in plants. Competitive ELISA experiments are used to confirm the binding affinities of retro inverso Flg-associated polypeptides to plant FLS receptors.

Recombinant Bacteria that Express Bioactive Priming Polypeptides

A recombinant microorganism that expresses or overexpresses a polypeptide is also provided. The polypeptide comprises the polypeptides as described above for the composition. For example, the polypeptide can comprise: the flagellin or flagellin-associated polypeptide of (a); or the mutant flagellin or flagellin-associated polypeptide of (b); or the mutant flagellin or flagellin-associated polypeptide of (c); or the harpin or harpin-like polypeptide of (g); or the RHPP of (i); or the KTI polypeptide of (j); or the EF-Tu polypeptide of (I); or the fusion polypeptide of (n); or the PSK polypeptide of (o); or the thionin or thionin-like polypeptide of (q).

The polypeptide can be overexpressed by the microorganism. The recombinant microorganism can comprise a microorganism that is capable of making recombinant bioactive priming polypeptides or their precursors in an effective manner. The preferred microorganism would be from the genus *Bacillus*, a bacterium of the genus *Paenibacillus*, a fungus of the genus *Penicillium*, a bacterium of the genus *Glomus*, a bacterium of the genus *Pseudomonas*, a bacterium of the genus *Arthrobacter*, a bacterium of the genus *Paracoccus*, a bacterium of the genus *Rhizobium*, a bacterium of the genus *Bradyrhizobium*, a bacterium of the genus *Azosprillium*, a bacterium of the genus *Enterobacter*, a bacterium of the genus *Escherichia*, or any combination thereof.

The recombinant microorganism can comprise a bacterium of the genus *Bacillus*, a bacterium of the genus *Paenibacillus*, or any combination thereof.

For example, the microorganism can comprise *Bacillus mycoides, Bacillus pseudomycoides, Bacillus cereus, Bacillus thuringiensis, Bacillus megaterium, Bacillus subtilis, Bacillus firmus, Bacillus aryabhattai, Bacillus amyloliquefaciens, Bacillus licheniformis, Bacillus circulans, Bacillus flexus, Bacillus nealsonii, Bacillus pumulis, Paenibacillus* genus bacterium or a combination thereof.

Methods and approaches are commonly used by one of ordinary skill in the art to determine and verify the genus and species of the bacteria. A common method provides chromosomal DNA isolated from the bacteria with PCR amplification of the 16s rRNA region using universal primers (ACTCCTACGGGAGGCAGCAGT) and (GGGTTGCGCTCGTTG/AC). The PCR amplicons are then purified and sequenced for correct identification of the appropriate bacterial strain, for example a specific strain in the genera of *Bacillus*.

Sample protocols are generally known to one in the art for the preparation of chromosomal DNA, transformation of the DNA of genes encoding the polypeptides using a plasmid, producing the polypeptides in a host bacterium, for example, a *Bacillus* strain.

The *Bacillus* strains provided can produce any bioactive priming polypeptide as described herein or a combination thereof. For example, the strain can comprise:

(a) *Bacillus aryabhattai* CAP53 (NRRL No. B-50819),
(b) *Bacillus aryabhattai* CAP56 (NRRL No. B-50817),
(c) *Bacillus flexus* BT054 (NRRL No. B-50816),
(d) *Paracoccus kondratievae* NC35 (NRRL No. B-50820),
(e) *Bacillus mycoides* BT155 (NRRL No. B-50921),
(f) *Enterobacter cloacae* CAP12 (NRRL No. B-50822),
(g) *Bacillus nealsonii* BOBA57 (NRRL No. NRRL B-50821),
(h) *Bacillus mycoides* EE118 (NRRL No. B-50918),
(i) *Bacillus subtilis* EE148 (NRRL No. B-50927),
(j) *Alcaligenes faecalis* EE107 (NRRL No. B-50920),
(k) *Bacillus mycoides* EE141 (NRRL NO. B-50916),
(l) *Bacillus mycoides* BT46-3 (NRRL No. B-50922),
(m) *Bacillus cereus* family member EE128 (NRRL No. B-50917),
(n) *Paenibacillus massiliensis* BT23 (NRRL No. B-50923),
(o) *Bacillus cereus* family member EE349 (NRRL No. B-50928),
(p) *Bacillus subtilis* EE218 (NRRL No. B-50926),
(q) *Bacillus megaterium* EE281 (NRRL No. B-50925), (r) *Bacillus cereus* family member EE-B00377 (NRRL B-67119);
(s) *Bacillus pseudomycoides* EE-B00366 (NRRL B-67120),
(t) *Bacillus mycoides* EE-B00363 (NRRL B-67121),
(u) *Bacillus pumilus* EE-B00143 (NRRL B-67123),
(v) *Bacillus thuringiensis* EE-B00184 (NRRL B-67122),
(w) *Bacillus mycoides* EE116 (NRRL No. B-50919),
(x) *Bacillus cereus* family member EE417 (NRRL No. B-50974),
(y) *Bacillus subtilis* EE442 (NRRL No. B-50975),
(z) *Bacillus subtilis* EE443 (NRRL No. B-50976),
(aa) *Bacillus cereus* family member EE444 (NRRL No. B-50977),
(bb) *Bacillus subtilis* EE405 (NRRL No. B-50978),
(cc) *Bacillus cereus* family member EE439 (NRRL No. B-50979),
(dd) *Bacillus megaterium* EE385 (NRRL No. B-50980),
(ee) *Bacillus cereus* family member EE387 (NRRL No. B-50981),
(ff) *Bacillus circulans* EE388 (NRRL No. B-50982),
(gg) *Bacillus thuringiensis* EE319 (NRRL No. B-50983),
(hh) *Bacillus cereus* family member EE377 (NRRL No. B-67119),
(ii) *Bacillus mycoides* EE363 (NRRL No. B-67121),
(jj) *Bacillus pseudomycoides* EE366 (NRRL No. B-67120);
(kk) *Bacillus thuringiensis* BT013A (NRRL No. B-50924);

or any combination thereof. Each of these strains has been deposited with the United States Department of Agriculture (USDA) Agricultural Research Service (ARS), having the address 1815 North University Street, Peoria, Ill. 61604 U.S.A., and are identified by the NRRL deposit numbers provided in parentheses. Strains (a)-(d), (f), and (g) were deposited on Mar. 11, 2013. Strains (e), (h)-(q), (w), and (kk) were deposited on Mar. 10, 2014. Strains (x)-(ff) were deposited on Sep. 10, 2014. Strain (gg) was deposited on Sep. 17, 2014. Strains (r)-(v), (hh), (ii), and (jj) were deposited on Aug. 19, 2015. *Bacillus thuringiensis* BT013A is also known as *Bacillus thuringiensis* 4Q7.

The isolation and characterization of these strains are described in the Examples found within International Publication No: WO/2017/161091, incorporated herein by reference in its entirety. For ease of identification of the organism, International Publication No: WO/2017/161091 A1 also provides the partial 16S ribosomal RNA sequences for each of these strains in a sequence list and in Table 17.

Any of the recombinant microorganisms can be used to overexpress a bioactive priming polypeptide as described herein for a flagellin-associated polypeptide (Tables 1-5), a harpin or harpin-like (HpaG-like) polypeptide (Table 10 or 11), a phytosulfokine (PSKα) polypeptide (Table 12), RHPP (Table 13-15), an EF-Tu polypeptide (Table 16-17, and a thionin or thionin-like polypeptide (Table 19).

The recombinant microorganism can comprise a mixture of two or more of any of the recombinant microorganisms described herein.

The recombinant microorganism can be inactivated. Inactivation results in microorganisms that are unable to reproduce. Inactivation of microorganisms can be advantageous, for example because it allows for delivery of the microorganism to a plant or a plant growth medium while reducing or eliminating any detrimental effects that the live microorganism may have on a plant or on the environment. The recombinant microorganism can be inactivated by any physical or chemical means, e.g., by heat treatment, gamma irradiation, x-ray irradiation, UV-A irradiation, UV-B irradiation, or treatment with a solvent such as glutaraldehyde, formaldehyde, hydrogen peroxide, acetic acid, bleach, chloroform, or phenol, or any combination thereof.

III. Compositions

A composition is provided for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture. The composition comprises either: the polypeptide as described herein or any combination thereof, and an agrochemical or a carrier; or any combination of the polypeptides as described herein.

The composition can consist essentially of the bioactive priming polypeptides or polypeptides as described herein.

The composition can comprise a majority of the bioactive priming polypeptides with the remainder of the composition being agrochemicals or carriers. More specifically, the composition can comprise from about 0.00001% to about 95% of the polypeptides, from about 0.1 to about 80 wt. % of the agrochemicals, and from about 5 to about 50 wt. % carrier based on the total weight of the composition. Alternatively, the composition can comprise from about 0.01 to about 5 wt. % of the polypeptides, from about 0.2 to about 70 wt. % of the agrochemicals, and from about 10 to about 30 wt. % carrier based on the total weight of the composition, or the composition can comprise from about 0.05 wt. % to about 1 wt. % of the polypeptides, from about 30 to about 60 wt. % of the agrochemicals, and from about 40 to about 69 wt. % carrier based on the total weight of the composition. Alternatively, the composition can comprise any detectable amount of the polypeptides, and from about 0.1 to about 80 wt. % of the agrochemicals and from about 5 to about 50 wt. % of the carrier, based on the total weight of the composition.

The composition can include either an agrochemical or a carrier which is associated with the polypeptide in nature.

The agrochemical can be non-naturally occurring in combination with the polypeptide.

The agrochemical can include, but is not limited to, a preservative, a buffering agent, a wetting agent, a surfactant, a coating agent, a monosaccharide, a polysaccharide, an abrading agent, a pesticide, an insecticide, an herbicide, a nematicide, a bacteriocide, a fungicide, a miticide, a fertilizer, a biostimulant, a colorant, a humectant, an osmoprotectant, an antibiotic, an amino acid, a biological control agent, or a combination thereof.

When the composition includes an amino acid, the amino acid can be provided separately from the amino acids that comprise the polypeptide. For example, an isolated amino acid can be used. Suitable amino acids include any natural or unnatural amino acids. For example, the composition can comprise cysteine.

The agrochemical can comprise an acid such as an acid that is present from chemical synthesis of any polypeptide described herein. For example, hydrochloric acid, acetic acid, or trifluoroacetic acid can be present if the polypeptide is synthesized such as by fermentation.

When the agrochemical is an acid, it can comprise from about 0.001 to about 30 wt. %, from about 0.01 to about 20 wt. %, or from about 0.1 to about 5 wt. % of the total weight of the composition.

Unless otherwise specified, each agrochemical can comprise from about 0.1 to about 60 wt. %, from about 0.5 to about 50 wt. %, or from about 10 to about 30 wt. % of the total weight of the composition.

When the composition includes a preservative, the preservative can comprise those based on dichlorophene and benzylalcohol hemi formal (PROXEL from ICI or ACTICIDE RS from Thor Chemie and KATHON MK from Dow Chemical) and isothiazolinone derivatives such as alkylisothiazolinones and benzisothiazolinones (ACTICIDE MBS from Thor Chemie). As further examples, suitable preservatives include MIT (2-methyl-4-isothiazolin-3-one), BIT (1,2-benzisothiazolin-3-one, which can be obtained from Avecia, Inc. as PROXEL GXL as a solution in sodium hydroxide and dipropylene glycol), 5-chloro-2-(4-chlorobenzyl)-3(2H)-isothiazolone, 5-chloro-2-methyl-2H-isothiazol-3-one, 5-chloro-2-methyl-2H-isothiazol-3-one, 5-chloro-2-methyl-2H-isothiazol-3-one-hydrochloride, 4,5-dichloro-2-cyclohexyl-4-isothiazolin-3-one, 4,5-dichloro-2-octyl-2H-isothiazol-3-one, 2-methyl-2H-isothiazol-3-one, 2-methyl-2H-isothiazol-3-one-calcium chloride complex, 2-octyl-2H-isothiazol-3-one, benzyl alcohol hemiformal, or any combination thereof.

When the composition includes a buffering agent, the buffering agent can comprise potassium, phosphoric acid, a phosphate salt, citric acid, a citrate salt, a sulfate salt, MOPS, or HEPES. The buffering agent can stabilize the polypeptide in the composition.

When the composition includes a wetting agent, the wetting agent can comprise organosilicones, polyoxyethoxylates, polysorbates, polyethyleneglycol and derivatives thereof, ethoxylates, crop oils, and polysaccharides.

When the composition includes a surfactant, the surfactant can comprise a heavy petroleum oil, a heavy petroleum distillate, a polyol fatty acid ester, a polyethoxylated fatty acid ester, an aryl alkyl polyoxyethylene glycol, a polyoxyethylenepolyoxypropylene monobutyl ether, an alkyl amine acetate, an alkyl aryl sulfonate, a polyhydric alcohol, an alkyl phosphate, an alcohol ethoxylate, an alkylphenol ethoxylate, an alkyphenol ethoxylate, an alkoxylated polyol, an alky polyethoxy ether, an alkylpolyoxethylene glycerol, ethoxylated and soybean oil derivatives, an organosilicone-based surfactant or any combination thereof. Surfactants can be included in a range of compositions including those for foliar use.

When the composition includes a coating agent, the coating agent can comprise a tackifier, polymers, filling agents, or bulking agents.

The tackifier can include, but is not limited to, carboxymethylcellulose and natural and synthetic polymers in the form of powders, granules, or latexes, such as gum Arabic, chitin, polyvinyl alcohol and polyvinyl acetate, as well as natural phospholipids, such as cephalins and lecithins, and synthetic phospholipids. Tackifiers include those composed preferably of an adhesive polymer that can be natural or synthetic without phytotoxic effect on the seed to be coated. Additional tackifiers that can be included, either alone or in combination, include, for example, polyesters, polyether esters, polyanhydrides, polyester urethanes, polyester amides; polyvinyl acetates; polyvinyl acetate copolymers; polyvinyl alcohols and tylose; polyvinyl alcohol copolymers; polyvinylpyrolidones; polysaccharides, including starches, modified starches and starch derivatives, dextrins, maltodextrins, alginates, chitosanes and celluloses, cellulose esters, cellulose ethers and cellulose ether esters including ethylcelluloses, methylcelluloses, hydroxymethylcelluloses, hydroxypropylcelluloses and carboxymethylcellulose; fats; oils; proteins, including casein, gelatin and zeins; gum arabics; shellacs; vinylidene chloride and vinylidene chloride copolymers; lignosulfonates, in particular calcium lignosulfonates; polyacrylates, polymethacrylates and acrylic copolymers; polyvinylacrylates; polyethylene oxide; polybutenes, polyisobutenes, polystyrene, polybutadiene, polyethyleneamines, polyethylenam ides; acrylamide polymers and copolymers; polyhydroxyethyl acrylate, methylacrylamide monomers; and polychloroprene, or any combination thereof. Tackifiers can be used in a range of compositions including those for seed treatment.

When the composition includes an abrading agent, the abrading agent can comprise talc, graphite, or a combination of both.

A humectant is a hygroscopic substance that assists with the retention of moisture. When the composition includes a humectant, the humectant can comprise: glycerol, glycerin, a glycerol derivative (e.g. glycerol monosterate, glycerol triacetate, triacetin, propylene glycol, hexylene glycol, or butylene glycol), triethylene glycol, tripolypropylene glycol, glyceryl triacetate, sucrose, tagatose, a sugar alcohol or a sugar polyol (e.g glycerol, sorbitol, xylitol, mannitol, or mantitol), a polymeric polyol (e.g. polydextrose, a collagen, an aloe or an aloe vera gel), or an alpha hydroxy acid (e.g. lactic acid, honey, molasses, *quillaia*, sodium hexametaphosphate, lithium chloride or urea). Synthetic humectants can also comprise: butylene glycol, and tremella extract.

When the composition includes a pesticide, the pesticide can comprise an insecticide, a herbicide, a fungicide, a bacteriocide, a nematicide, a miticide, or any combination thereof.

When the composition includes an insecticide, the insecticide can comprise clothianidin, imidacloprid, an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or any combination thereof. For example, the insecticide can comprise clothianidin or imidacloprid.

The agrochemical can comprise an herbicide. The herbicide can comprise 2,4-D, 2,4-DB, acetochlor, acifluorfen, alachlor, ametryn, atrazine, aminopyralid, benefin, bensulfuron, bensulfuron methyl bensulide, bentazon, bispyribac sodium, bromacil, bromoxynil, butylate, carfentrazone, chlorimuron, 2-chlorophenoxy acetic acid, chlorsulfuron, chlorimuron ethyl, clethodim, clomazone, clopyralid, cloransulam, CMPP-P-DMA, cycloate, DCPA, desmedipham, dicamba, dichlobenil, diclofop, 2,4-dichlorophenol, dichlorophenoxyacetic acid, dichlorprop, dichlorprop-P, diclosulam, diflufenzopyr, dimethenamid, dimethyl amine salt of 2,4-dichlorophenoxyacetic acid, diquat, diuron, DSMA, endothall, EPTC, ethalfluralin, ethofumesate, fenoxaprop, fluazifop-P, flucarbazone, flufenacet, flumetsulam, flumiclorac, flumioxazin, fluometuron, fluroxypyr, fluorxypyr 1-methyleptylester, fomesafen, fomesafen sodium salt, foramsulfuron, glufosinate, glufosinate-ammonium, glyphosate, halosulfuron, halosulfuron-methyl, hexazinone, 2-hydroxyphenoxy acetic acid, 4-hydroxyphenoxy acetic acid, imazamethabenz, imazamox, imazapic, imazaquin, imazethapyr, isoxaben, isoxaflutole, lactofen, linuron, mazapyr, MCPA, MCPB, mecoprop, mecoprop-P, mesotrione, metolachlor-s, metribuzin, metsulfuron, metsulfuron-methyl, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithiobac, pyroxasulfone,quinclorac, quizalofop, rimsulfuron, sethoxydim, siduron, simazine, sulfentrazone, sulfometuron, sulfosulfuron, tebuthiuron, terbacil, thiazopyr, thifensulfuron, thifensulfuron-methyl, thiobencarb, tralkoxydim, triallate, triasulfuron, tribenuron, tribernuron-methyl, triclopyr, trifluralin, triflusulfuron, or any combination thereof.

When the composition includes a nematicide, the nematicide can comprise *Bacillus firmus*, fluopyram, antibiotic nematicides such as abamectin; carbamate nematicides such as acetoprole, *Bacillus chitonosporus*, chloropicrin, benclothiaz, benomyl, *Burholderia cepacia*, carbofuran, carbosulfan, and cleothocard; dazomet, DBCP, DCIP, alanycarb, aldicarb, aldoxycarb, oxamyl, diamidafos, fenamiphos, fosthietan, phosphamidon, cadusafos, chlorpyrifos, diclofenthion, dimethoate, ethoprophos, fensulfothion, fostiazate, harpins, heterophos, imicyafos, isamidofos, isazofos, methomyl, mecarphon, *Myrothecium verrucaria, Paecilomyces lilacinus, Pasteuria nishizawae* (including spores thereof), phorate, phosphocarb, terbufos, thionazin, triazophos, tioxazafen, dazomet, 1,2-dicloropropane, 1,3-dichloropropene, furfural, iodomethane, metam, methyl bromide, methyl isothiocyanate, xylenol, or any combination thereof. For example, the nematicide can comprise *Bacillus firmus* strain i-2580*, Pasteuria nishizawae* (including spores thereof), or fluopyram.

When the composition includes a bacteriocide, the bacteriocide can comprise streptomycin, penicillins, tetracyclines, oxytetracycline, kasugamycin, ampicillin, oxolinic acid, chlorotetracycline, copper oxide, or any combination thereof. For example, the bacteriocide can comprise oxytetracycline.

Biological control agents are broadly defined as microorganisms that can be used instead of synthetic pesticides or fertilizers. When the composition includes a biological control agent, the biological control agent can comprise *Bacillus thuringiensis, Bacillus megaterium, Bacillus mycoides* isolate J, *Bacillus methylotrophicus, Bacillus vallismortis, Chromobacterium subtsugae, Delftia acidovorans, Streptomyces lydicus, Streptomyces colombiensis, Streptomyces galbus* K61, *Penicillium bilaii*, a lipopeptide-producing *Bacillus subtilis* strain, a lipopeptide-producing *Bacillus amyloliquefaciens* strain, a *Bacillus firmus* strain or a *Bacillus pumilus* strain.

The agrochemical can include a fungicide. The fungicide can comprise aldimorph, ampropylfos, ampropylfos potassium, andoprim, anilazine, azaconazole, azoxystrobin, benalaxyl, benodanil, benomyl, benzamacril, benzamacryl-isobutyl, benzovindflupyr, bialaphos, binapacryl, biphenyl, bitertanol, blasticidin-S, boscalid, bromuconazole, bupirimate, buthiobate, calcium polysulphide, capsimycin, captafol, captan, carbendazim, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, dimethirimol, dimethomorph, dimoxystrobin, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, flumetover, fluoromide, fluoxastrobin fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metconazole, metalzxyl, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, prothiocinazole, pyrazophos, pyrifenox, pyrimethanil, pyroquilon, pyroxyfur, quinconazole, quintozene (PCNB), a strobilurin, sulphur and sulphur preparations, tebuconazole, tecloftalam, tecnazene, tetcyclasis, tetraconazole, thiabendazole, thicyofen, thifluzamide, thiophanate-methyl, tioxymid, tolclofos-methyl, tolylfluanid, triadimefon, triadimenol, triazbutil, a triazole, triazoxide, trichlamide, tricyclazole, triclopyr, tridemorph, trifloxystrobin, triflumizole, triforine, uniconazole, validamycin A, vinclozolin, viniconazole, zarilamide, zineb, ziram and also Dagger G, OK-8705, OK-8801, a-(1,1-dimethylethyl)-(3-(2-phenoxyethyl)-1H-1,2,4-triazole-1-eth anol, a-(2,4-dichlorophenyl)-[3-fluoro-3-propyl-1H-1,2,4-triazole-1-ethanol, a-(2,4-dichlorophenyl)-[3-methoxy-a-methyl-1H-1,2,4-triazol e-1-ethanol, a-(5-methyl-1,3-dioxan-5-yl)-[3-[[4-(trifluoromethyl)-phenyl]-met hylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyim ino)-N-methyl-2-phenoxy-phenylacetamide, 1-isopropyl{2-methyl-1-[[[1-(4-methylphenyl)-ethyl]-amino]-carbonyl]-propyl}carbamate, 1-(2,4-dichlorophenyl)-2-(1H-1,2,4-triazol-1-yl)-ethanone-O-(phenyl methyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2, 4-dichlorophenyl)-1, 3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1, 3-thiazole-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sul phonyl]-5-(trichloromethyl)-1,3,4-thiadiazole, 2-[[6-deoxy-4-O-(4-0-methyl-(3-D-glycopyranosyl)-a-D-glucopyranos yl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4, 5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethyl phenyl)-2-methoxy-N-(tetra hydro-2-oxo-3-furanyl)-acetamide, N-(2,6-dimethyl phenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-1V-methoxy-methanimidamide, N-formyl-N-hydroxy-DL-alanine-sodium salt, 0,0-diethyl [2-(dipropylamino)-2-oxoethyl]-ethylphosphoramidothioate, 0-methyl S-phenyl phenylpropylphosphoramidothioate, S-methyl 1,2,3-benzothiadiazole-7-carbothioate, and spiro[2H]-1-benzopyrane-2,1'(3'H)-isobenzofuran]-3'-one, N-trichloromethyl)thio-4-cyclohexane-1,2-dicarboximide, tetramethylthioperoxydicarbonic diamide, methyl N-(2,6-dimethylphenyl)-N-(methoxyacetyl)-DL-alaninate, 4-(2,2-difluoro-I,3-benzodioxol-4-yl)-I-H-pyrrol-3-carbonitril, or any combination thereof.

When the polypeptides are formulated or applied in combination with commercially available fungicides, the compositions can provide an extra layer of protection for enhancing disease prevention or spread in a plant. The combination of the polypeptides with a fungicide can protect a plant against a primary or secondary fungal infection which may occur if the plant has become compromised or weakened due to exposure to abiotic stress or disease.

The strobilurin fungicide can comprise a Strobilurin A, a Strobilurin B, a Strobilurin C, a Strobilurin D, a Strobilurin E, a Strobilurin F, a Strobilurin G, a Strobilurin H, an Azoxystrobin, a Trifloxystrobin, a Kresoxim methyl, a Fluoxastrobin, Picoxystrobin, or any combination thereof.

The strobilurin fungicide can comprise a non-naturally occurring strobilurin fungicide such as an Azoxystrobin, a Trifloxystrobin, a Kresoxim methyl, a Fluoxastrobin, or any combination thereof. For example, the strobilurin fungicide can comprise a Trifloxystrobin, Fluoxastrobin or Picoxystrobin. Strobilurin fungicides are used to control a range of fungal diseases, including water molds, downy mildews, powdery mildews, leaf spotting and blighting fungi, fruit rotters, and rusts. They are useful for treating a variety of crops, including cereals, field crops, fruits, tree nuts, vegetables, turfgrasses, and ornamentals.

The triazole fungicide can comprise prothioconazole, imidazole, imidazil, prochloraz, propiconazole, triflumizole, diniconazole, flusilazole, penconazole, hexaconazole, cyproconazole, myclobutanil, tebuconazole, difenoconazole, tetraconazole, fenbuconazole, epoxiconazole, metconazole, fluquinconazole, triticonazole, or any combination thereof.

The bioactive priming polypeptides can be delivered in combination with strobilurins and triazole fungicides, especially fluoxastrobin or trifloxystrobin in combination with prothioconazole.

In addition, the fungicide can comprise azoxystrobin, carboxin, difenoconazole, fludioxonil, fluxapyroxad, ipconazole, mefenoxam, pyraclostrobin, silthiofam, sedaxane, thiram, triticonazole or any combination thereof.

In addition to foliar applied fungicides as described herein, the bioactive priming polypeptides can be provided in combination with a fungicide, an insecticide, a nematicide, a bacteriocide, and a miticide or any agrochemical which is a biological agent.

The agrochemical can include a fertilizer. The fertilizer can comprise ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO4\text{-}Mg_2SO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or any combination thereof.

The fertilizer can comprise a liquid fertilizer or a dry fertilizer.

The agrochemical can comprise a micronutrient fertilizer material, the micronutrient fertilizer material comprising boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or any combination thereof.

The agrochemical can comprise an insecticide, the insecticide comprising an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or any combination thereof.

When the composition includes a biostimulant, the biostimulant can comprise a seaweed extract, an elicitor, a polysaccharide, a monosaccharide, a protein extract, a soybean extract, a humic acid, a plant hormone, a plant growth regulator, or any combination thereof.

A variety of colorants may be employed, including organic chromophores classified as nitroso, nitro, azo, including monoazo, bisazo, and polyazo, diphenylmethane, triarylmethane, xanthene, methane, acridine, thiazole, thiazine, indamine, indophenol, azine, oxazine, anthraquinone, phthalocyanine, or any combination thereof.

The composition can further comprise a carrier.

The carrier of the composition can include, but is not limited to, water, peat, wheat, bran, vermiculite, clay, pasteurized soil, calcium carbonate, calcium bicarbonate, dolomite, gypsum, bentonite, a clay, a rock phosphate, a phosphorous compound, titanium dioxide, humus, talc, alginate, activated charcoal, or a combination thereof.

The composition can be in the form of an aqueous solution, a slurry or dispersion, an emulsion, a solid such as a powder or granule, or any other desirable form for applying the composition to a plant or plant part.

Bioactive priming polypeptides such as the flagellin and flagellin-associated polypeptides, thionin (defensin family), harpin-like HpaG, EF-Tu or other growth promoting or altering bioactive priming polypeptides such as PSKα and RHPP can be provided as compositions that can either be exogenously and/or endogenously applied to a plant or a plant part and provide enhanced plant growth, productivity and enhanced health of that plant or plant part as described in more detail below.

The bioactive priming polypeptides can be added separately or in combination as a composition that are useful as applications to provide a benefit to plants and/or plant parts.

In combination, the polypeptides may be formulated and delivered in a purified polypeptide form either as a genetic fusion on the same recombinant vector, or separately using different recombinant vectors.

The bioactive priming polypeptides can also be created and delivered to a plant or plant part as polypeptides from multiple actives in a fusion protein. Examples of this include delivery of multiple flagellin associated polypeptides produced in series with protease cleavage sites between each polypeptide as is within the skill of one of ordinary skill in the art. Such fusion proteins can include any combination of the bioactive priming polypeptides as described herein, including bioactive priming polypeptides from different classes, such as combinations of flagellin associated polypeptides with RHPP. Bioactive priming polypeptides can also be utilized as protein fusions to plant binding domains, which can direct the polypeptides to distinct locations within the plant where they are most desired or needed for their activities to be beneficial.

Additionally, the polypeptides may be added to formulations provided in a synthetic compound form.

The flagellin and flagellin-associated bioactive priming polypeptides as described herein can be provided individually or in combination containing at least two to multiple bioactive priming polypeptides to provide a composition that meets the specific needs of a plant over a wide range of desired host responses and cropping systems.

When a composition includes the retro-inverso form of a Flg bioactive priming polypeptide (for example, RI Bt.4Q7 Flg 22 (SEQ ID NO: 376), the polypeptide exhibits enhanced stability and less degradation over time providing for more activity at the plant cell membrane surface, which enhances the ability of the polypeptide to bind to the receptor and be taken into the plant. Retro inverso forms of such Flg-associated bioactive priming polypeptides are used to provide enhanced stability of the agriculturally applied formulation whereby the Flg polypeptide(s) exhibits enhanced protection from proteolytic cleavage, which contributes to an overall greater activity and shelf life of the composition.

When the polypeptide comprises an RHPP polypeptide, the composition can further comprise a flagellin or flagellin associated polypeptide. The RHPP polypeptide can comprise SEQ ID NO: 600. The amino acid sequence of the flagellin or flagellin-associated polypeptide can comprise any one of SEQ ID NOs: 1-525, 532, 534, 536, 538, 540, 571-586, and 751-752, or any combination thereof. For example, the flagellin or flagellin associated polypeptide can comprise any one of SEQ ID NO: 226, 571, and 752. In some instances, the RHPP polypeptide can comprise SEQ ID NO: 600 and the flagellin or flagellin associated polypeptide can comprise SEQ ID NO: 226.

The polypeptides can be formulated in combination with an assistance polypeptide. The signature (SEQ ID NOs: 542-548), signal anchor sorting (SEQ ID NOs: 549-562) and secretion (SEQ ID NOs: 563-570) polypeptides can be combined with the bioactive priming polypeptides as described for targeting the polypeptides/peptides (Tables 1-5) to the plant cell membrane surface for improved binding and activation of the Flg-associated receptors. This means for efficient delivery and binding of the polypeptide to a plant provides growth promoting benefits, as well as enhanced protection to the plant or plant part.

For example, the harpin or HpaG-like bioactive priming polypeptides as described herein can be used in combination with the assistance polypeptides as described in Tables 6-8), signature polypeptides (SEQ ID NO: 542-548), signal anchor sorting (SEQ ID NO: 549-562) and/or secretion (SEQ ID NO: 563-570) polypeptides. These assistance polypeptides used in combination with the HpaG-like bioactive priming polypeptides are useful to target and deliver the harpin-like bioactive priming polypeptides to the plant cell membrane surface enhancing the contact with the plant cell membrane and provide a conduit facilitating efficient contact and entry of harpin-like (HpaG-like) into the plant or to the plant cell milieu (apoplast).

One or more of the EF-Tu polypeptides can be combined, optionally, with the flagellin or flagellin-associated polypeptide. The amino acid sequence of the EF-Tu polypeptide or polypeptides can comprise SEQ ID NOs: 616 and/or 617. The amino acid sequence of the flagellin or flagellin-associated polypeptide can comprise any one of SEQ ID NOs: 1-525, 532, 534, 536, 538, 540, 571-586, and 751-753 or any combination thereof. For example, the amino acid sequence of the flagellin or flagellin-associated polypeptide can comprise SEQ ID NO: 571. As another example, the composition can comprise an EF-Tu polypeptides comprising SEQ ID NOs: 616 and 617, and a flagellin or flagellin associated polypeptide comprising SEQ ID NO: 226, 571, 572, or combinations thereof. As another example, the EF-Tu polypeptide or polypeptides having SEQ ID NOs 616 and/or 617 can be combined with a flagellin or flagellin associated polypeptide having SEQ ID NO: 226. Alternatively, the composition can comprise one or more EF-Tu polypeptides alone (e.g., comprising SEQ ID NOs 616 and/or 617). The EF-Tu polypeptides (e.g., SEQ ID Nos 616 and 617) can be further modified via N-terminal acetylation.

Additionally, the EF-Tu polypeptide or the EF-Tu polypeptide and the flagellin or flagellin-associated polypeptide can be combined with the harpin or harpin-like polypeptide. For example, the amino acid sequence of the harpin or harpin-like polypeptide can comprise SEQ ID NO: 587.

The composition can comprise any one of the following combinations: (a) the flagellin or flagellin-associated polypeptides and the amino acid sequences of the flagellin or flagellin-associated polypeptides comprise SEQ ID NOs: 571, 295, 300, 293, and 580; or 295, 300, 293, and 580; or 571, 295, 293, and 580; or 571, 300, 293, and 580; or 571, 293 and 580; or 571, 295, 293; or (b) the flagellin or flagellin-associated polypeptide and the amino acid sequence of the flagellin or flagellin-associated polypeptide comprises SEQ ID NO: 226 and cellobiose, cellulose, chitin, chitosan or any combination thereof; or (c) the flagellin or flagellin-associated polypeptide and the amino acid sequence of the flagellin or flagellin-associated polypeptide comprises SEQ ID NO: 226 and the harpin or harpin-like polypeptide and the amino acid sequence of the harpin or harpin-like polypeptide comprises SEQ ID NO: 591; or (d) the harpin or harpin-like polypeptide and the amino acid sequence of the harpin or harpin-like polypeptide comprises SEQ ID NO: 587 and the PSK polypeptide and the amino acid sequence of the PSK polypeptide comprises SEQ ID NO: 598; or (e) the flagellin or flagellin-associated polypeptide and the amino acid sequence of the flagellin or flagellin-associated polypeptide comprises SEQ ID NO: 226, 752, or 571 or any combination thereof and the EF-Tu polypeptides and the amino acid sequences of the EF-Tu polypeptides comprise SEQ ID NOs: 616 and 617; or (f) the flagellin or flagellin-associated polypeptide and the amino acid sequence of the flagellin or flagellin-associated polypeptide comprises SEQ ID NO: 226, 540, 752, or 571 or any combination thereof; or (g) the RHPP polypeptide and the amino acid sequence of the RHPP polypeptide comprises SEQ ID NO: 600; or (h) the flagellin or flagellin-associated polypeptide and the amino acid sequences of the flagellin or flagellin-associated polypeptide comprises SEQ ID NO: 226, 540, 226, 752, or 571 or any combination thereof and the RHPP polypeptide and the amino acid sequence of the RHPP polypeptide comprises SEQ ID NO: 600; or (i) the flagellin or flagellin-associated polypeptide and the amino acid sequence of the flagellin or flagellin-associated polypeptide comprises SEQ ID NO: 226 and the RHPP polypeptide and the amino acid sequence of the RHPP polypeptide comprises SEQ ID NO: 600.

IV. Applications

The agricultural composition and methods described herein can be used with any species of plant and/or the seeds thereof. The compositions and methods are typically used with seeds that are agronomically important.

The seed can be a transgenic seed from which a transgenic plant can grow that incorporates a transgenic event that confers, for example, tolerance to a particular herbicide or combination of herbicides, increased disease resistance, enhanced tolerance to insects, drought, stress and/or enhanced yield.

The seed can comprise a breeding trait, including for example, a disease tolerant breeding trait.

In some instances, the seed includes at least one transgenic trait and at least one breeding trait.

The bioactive priming polypeptide compositions and methods for applying the polypeptides can be used for the treatment of any suitable seed type, including, but not limited to, row crops and vegetables. For example, one or more plants or plant parts or the seeds of one or more plants can comprise abaca (manila hemp) (*Musa textilis*), alfalfa for fodder (*Medicago sativa*), alfalfa for seed (*Medicago sativa*), almond (*Prunus dulcis*), anise seeds (*Pimpinella anisum*), apple (*Malus sylvestris*), apricot (*Prunus armeniaca*), *areca* (*betel* nut) (*Areca catechu*), arracha (*Arracacia xanthorrhiza*), arrowroot (*Maranta arundinacea*), artichoke (*Cynara scolymus*), *asparagus* (*Asparagus officinalis*), avocado (*Persea americana*), bajra (pearl millet) (*Pennisetum americanum*), bambara groundnut (*Vigna subterranea*), banana (*Musa paradisiaca*), barley (*Hordeum vulgare*), beans, dry, edible, for grains (*Phaseolus vulgaris*), beans, harvested green (*Phaseolus* and *Vigna* spp.), beet, fodder (mangel) (*Beta vulgaris*), beet, red (*Beta vulgaris*), beet, sugar (*Beta vulgaris*), beet, sugar for fodder (*Beta vulgaris*), beet, sugar for seeds (*Beta vulgaris*), bergamot (*Citrus bergamia*), betel nut (*Areca catechu*), black pepper (*Piper nigrum*), black wattle (*Acacia mearnsii*), blackberries of various species (*Rubus* spp.), blueberry (*Vaccinium* spp.), Brazil nut (*Bertholletia excelsa*), breadfruit (*Artocarpus altilis*), broad bean, dry (*Vicia faba*), broad bean, harvested green (*Vicia faba*), broccoli (*Brassica oleracea* var. *botrytis*), broom millet (*Sorghum bicolor*), broom sorghum (*Sorghum bicolor*), Brussels sprouts (*Brassica oleracea* var. *gemmifera*), buckwheat (*Fagopyrum esculentum*), cabbage, red, white, Savoy (*Brassica oleracea* var. *capitata*), cabbage, Chinese (*Brassica chinensis*), cabbage, for fodder (*Brassica* spp.), cacao (cocoa) (*Theobroma cacao*), cantaloupe (*Cucumis melo*), caraway seeds (*Carum carvi*), cardamom (*Elettaria cardamomum*), cardoon (*Cynara cardunculus*), carob (*Ceratonia siliqua*), carrot, edible (*Daucus carota* spp. *sativa*), carrot, for fodder (*Daucus carota sativa*), cashew nuts (*Anacardium occidentale*), cassava (manioc) (*Manihot esculenta*), castor bean (*Ricinus communis*), cauliflower (*Brassica oleracea* var. *botrytis*), celeriac (*Apium graveolens* var. *rapaceum*), celery (*Apium graveolens*), chayote (*Sechium edule*), cherry, all varieties (*Prunus* spp.), chestnut (*Castanea sativa*), chickpea (gram pea) (*Cicer arietinum*), chicory (*Cichorium intybus*), chicory for greens (*Cichorium intybus*), chili, dry (all varieties) (*Capsicum* spp. (*annuum*)), chili, fresh (all varieties) (*Capsicum* spp. (*annuum*)), cinnamon (*Cinnamomum verum*), citron (*Citrus medica*), citronella (*Cymbopogon citrates; Cymbopogon nardus*), clementine (*Citrus reticulata*), clove (*Eugenia aromatica; Syzygium aromaticum*), clover for fodder (all varieties) (*Trifolium* spp.), clover for seed (all varieties) (*Trifolium* spp.), cocoa (cacao) (*Theobroma cacao*), coconut (*Cocos nucifera*), cocoyam (*Colocasia esculenta*), coffee (*Coffea* spp.), cola nut, all varieties (Cola *acuminata*), colza (rapeseed) (*Brassica napus*), corn (maize), for cereals (*Zea mays*), corn (maize), for silage (*Zea mays*), corn (maize), for vegetable (*Zea mays*), corn for salad (*Valerianella locusta*), cotton, all varieties (*Gossypium* spp.), cottonseed, all varieties (*Gossypium* spp.), cowpea, for grain (*Vigna unguiculata*), cowpea, harvested green (*Vigna unguiculata*), cranberry (*Vaccinium* spp.), cress (*Lepidium sativum*), cucumber (*Cucumis sativus*), currants, all varieties (*Ribes* spp.), custard apple (*Annona reticulate*), dasheen (*Colocasia esculenta*), dates (*Phoenix dactylifera*), drumstick tree (*Moringa oleifera*), durra (sorghum) (*Sorghum bicolour*), durum wheat (*Triticum durum*), earth pea (*Vigna subterranea*), edo (eddoe) (*Xanthosoma* spp.; *Colocasia* spp.), eggplant (*Solanum melongena*), endive (*Cichorium endivia*), fennel (*Foeniculum vulgare*), fenugreek (*Trigonella foenum-graecum*), fig (*Ficus carica*), filbert (hazelnut) (*Corylus avellana*), fique (*Furcraea macrophylla*), flax for fiber (*Linum usitatissimum*), flax for oil seed (linseed) (*Linum usitatissimum*), formio (New Zealand flax) (*Phormium tenax*), garlic, dry (*Allium sativum*), garlic, green (*Allium sativum*), *geranium* (*Pelargonium* spp.; *Geranium* spp.), ginger (*Zingiber officinale*), gooseberry, all varieties (*Ribes* spp.), gourd (*Lagenaria* spp; *Cucurbita* spp.), gram pea (chickpea) (*Cicer arietinum*), grape (*Vitis vinifera*), grapefruit (*Citrus paradisi*), grapes for raisins (*Vitis vinifera*), grapes for table use (*Vitis vinifera*), grapes for wine (*Vitis vinifera*), grass esparto (*Lygeum spartum*), grass, orchard (*Dactylis glomerata*), grass, Sudan (*Sorghum bicolor* var. *sudanense*), groundnut (peanut) (*Arachis hypogaea*), *guava* (*Psidium guajava*), guinea corn (sorghum) (*Sorghum bicolor*), hazelnut (filbert) (*Corylus avellana*), hemp fiber (*Cannabis sativa* spp. *indica*), hemp, *manila* (abaca) (*Musa textilis*), hemp, sun (*Crotalaria juncea*), hempseed (marijuana) (*Cannabis sativa*), henequen (*Agave fourcroydes*), henna (*Lawsonia inermis*), hop (*Humulus lupulus*), horse bean (*Vicia faba*), horseradish (*Armoracia rusticana*), hybrid maize (*Zea mays*), indigo (*Indigofera tinctoria*), jasmine (*Jasminum* spp.), Jerusalem artichoke (*Helianthus tuberosus*), jowar (*sorghum*) (*Sorghum bicolor*), jute (*Corchorus* spp.), kale (*Brassica oleracea* var. *acephala*), kapok (*Ceiba pentandra*), kenaf (*Hibiscus cannabinus*), kohlrabi (*Brassica oleracea* var. *gongylodes*), lavender (*Lavandula* spp.), leek (*Allium ampeloprasum; Allium porrum*), lemon (*Citrus limon*), lemongrass (*Cymbopogon citratus*), lentil (*Lens culinaris*), *lespedeza*, all varieties (*Lespedeza* spp.), lettuce (*Lactuca sativa* var. *capitata*), lime, sour (*Citrus aurantifolia*), lime, sweet (*Citrus limetta*), linseed (flax for oil seed) (*Linum usitatissimum*), licorice (*Glycyrrhiza glabra*), litchi (*Litchi chinensis*), loquat (*Eriobotrya japonica*), lupine, all varieties (*Lupinus* spp.), *Macadamia* (*Queensland* nut) (*Macadamia* spp. *temifolia*), mace (*Myristica fragrans*), maguey (*Agave atrovirens*), maize (corn) (*Zea mays*), maize (corn) for silage (*Zea mays*), maize (hybrid) (*Zea mays*), maize, ordinary (*Zea mays*), mandarin (*Citrus reticulata*), mangel (fodder beet) (*Beta vulgaris*), mango (*Mangifera indica*), manioc (cassava) (*Manihot esculenta*), maslin (mixed cereals) (mixture of *Triticum* spp. and *Secale cereale*), medlar (*Mespilus germanica*), melon, except watermelon (*Cucumis melo*), millet broom (*Sorghum bicolor*), millet, bajra (*Pennisetum americanum*), millet, bulrush (*Pennisetum americanum*), millet, finger (*Eleusine coracana*), millet, foxtail (*Setaria italica*), millet, Japanese (*Echinochloa esculenta*), millet, pearl (bajra, bulrush) (*Pennisetum americanum*), millet, proso (*Panicum miliaceum*), mint, all varieties (*Mentha* spp.), mulberry for fruit, all varieties (*Morus* spp.), mulberry for silkworms (*Morus alba*), mushrooms (*Agaricus* spp.; *Pleurotus* spp.; *Volvariella*), mustard (*Brassica nigra; Sinapis alba*), nectarine (*Prunus persica* var. *nectarine*), New Zealand flax (formio) (*Phormium tenax*), *Niger* seed (*Guizotia abyssinica*), nutmeg (*Myristica fragrans*), oats, for fodder (*Avena* spp.), oil palm (*Elaeis guineensis*), okra (*Abelmoschus esculentus*), olive (*Olea europaea*), onion seed (*Allium cepa*), onion, dry (*Allium cepa*), onion, green (*Allium cepa*), opium (*Papaver somniferum*), orange (*Citrus sinensis*), orange, bitter (*Citrus aurantium*), ornamental plants (various), palm palmyra (*Borassus flabellifer*), palm, kernel oil (*Elaeis guineensis*), palm, oil (*Elaeis guineensis*), palm, sago (*Metroxylon sagu*), *papaya* (pawpaw) (*Carica papaya*), parsnip (*Pastinaca sativa*), pea, edible dry, for grain (*Pisum sativum*), pea, harvested green (*Pisum sativum*), peach (*Prunus persica*), peanut (groundnut) (*Arachis hypogaea*), pear (*Pyrus communis*), pecan nut (*Carya illinoensis*), pepper, black (*Piper nigrum*), pepper, dry (*Capsicum* spp.), persimmon (*Diospyros* kaki; *Diospyros virginiana*), pigeon pea (*Cajanus cajan*), pineapple (*Ananas comosus*), pistachio nut (*Pistacia vera*), plantain (*Musa sapientum*), plum (*Prunus domestica*), pomegranate (*Punica granatum*), pomelo (*Citrus grandis*), poppy seed (*Papaver somniferum*), potato (*Solamum tuberosum*), palm, kernel oil (*Elaeis guineensis*), potato, sweet (*Ipomoea batatas*), prune (*Prunus domestica*), pumpkin, edible (*Cucurbita* spp.), pumpkin, for fodder (*Cucurbita* spp.), pyrethum (*Chrysanthemum cinerariaefolium*), quebracho (*Aspidosperma* spp.), *Queensland* nut (*Macadamia* spp. *temifolia*), quince (*Cydonia oblonga*), quinine (*Cinchona* spp.), *quinoa* (*Chenopodium quinoa*), ramie (*Boehmeria nivea*), rapeseed (colza) (*Brassica napus*), raspberry, all varieties (*Rubus* spp.), red beet (*Beta vulgaris*), redtop (*Agrostis* spp.), rhea (*Boehmeria nivea*), rhubarb (*Rheum* spp.), rice (*Oryza sativa; Oryza glaberrima*), rose (*Rose* spp.), rubber (*Hevea brasiliensis*), rutabaga (swede) (*Brassica napus* var. *napobrassica*), rye (*Secale cereale*), ryegrass seed (*Lolium* spp.), safflower (*Carthamus tinctorius*), sainfoin (*Onobrychis viciifolia*), salsify (*Tragopogon porrifolius*), *sapodilla* (*Achras sapota*), satsuma (mandarin/tangerine) (*Citrus reticulata*), *scorzonera* (black salsify) (*Scorzonera hispanica*), sesame (*Sesamum indicum*), shea butter (nut) (*Vitellaria paradoxa*), sisal (*Agave sisalana*), sorghum (*Sorghum bicolor*), *sorghum*, broom (*Sorghum bicolor*), *sorghum*, durra (*Sorghum bicolor*), *sorghum*, guinea corn (*Sorghum bicolor*), *sorghum*, jowar (*Sorghum bicolor*), *sorghum*, sweet (*Sorghum bicolor*), soybean (*Glycine max*), soybean hay (*Glycine max*), spelt wheat (*Triticum spelta*), spinach (*Spinacia oleracea*), squash (*Cucurbita* spp.), strawberry (*Fragaria* spp.), sugar beet (*Beta vulgaris*), sugar beet for fodder (*Beta vulgaris*), sugar beet for seed (*Beta vulgaris*), sugarcane for fodder (*Saccharum officinarum*), sugarcane for sugar or alcohol (*Saccharum officinarum*), sugarcane for thatching (*Saccharum officinarum*), sunflower for fodder (*Helianthus annuus*), sunflower for oil seed (*Helianthus annuus*), sunhemp (*Crotalaria juncea*), swede (*Brassica napus* var. *napobrassica*), swede for fodder (*Brassica napus* var. *napobrassica*), sweet corn (*Zea mays*), sweet lime (*Citrus limetta*), sweet pepper (*Capsicum annuum*), sweet potato (*Lopmoea batatas*), sweet sorghum (*Sorghum bicolor*), tangerine (*Citrus reticulata*), tannia (*Xanthosoma sagittifolium*), tapioca (cassava) (*Manihot esculenta*), taro (*Colocasia esculenta*), tea (*Camellia sinensis*), teff (*Eragrostis abyssinica*), timothy (*Phleum pratense*), tobacco (*Nicotiana tabacum*), tomato (*Lycopersicon esculentum*), trefoil (Lotus spp.), triticale, for fodder (hybrid of *Triticum aestivum* and *Secale cereale*), tung tree (*Aleurites* spp.; *Fordii*), turnip, edible (*Brassica rapa*), turnip, for fodder (*Brassica rapa*), urena (Congo jute) (Urena *lobata*), vanilla (*Vanilla planifolia*), vetch, for grain (*Vicia sativa*), walnut (*Juglans* spp., especially *Juglans regia*), watermelon (*Citrullus lanatus*), wheat (*Triticum aestivum*), yam (*Dioscorea* spp.), or yerba mate (*Ilex paraguariensis*).

The compositions and methods disclosed herein can also be applied to turf grass, ornamental grass, flowers, ornamentals, trees, and shrubs.

The compositions comprising the bioactive priming polypeptides are also suitable for use in the nursery, lawn and garden, floriculture or the cut flower industry and provide benefits for enhanced plant productivity, protection health, vigor and longevity. For example, they can be applied to perennials, annuals, forced bulbs, or pseudo bulbs, herbs, groundcovers, trees, shrubs, ornamentals (e.g., orchids, etc.), tropicals, and nursery stock.

The compositions comprising the bioactive priming polypeptides are suitable for treating plants, plant parts and plant propagation material(s), for example, any plant or plant part, such as seeds, roots, stems, floral organs, root stocks, scions, bulb, pseudobulbs, rhizomes, tubers, etc.

The bioactive priming polypeptides can be applied as seed treatments to treat for a number of pests, diseases, nutrient deficiencies while enhancing plant growth and productivity.

Seed coating or dressing compositions can be, for example, a liquid carrier composition, a slurry composition, or a powder composition applied with conventional additives that are provided to make the seed treatment have sticky qualities to stick to and coat the seeds. Suitable additives for a seed composition comprise: talcs, graphites, gums, stabilizing polymers, coating polymers, finishing polymers, slip agents for seed flow and plantability, cosmetic agents and cellulosic materials such as carboxymethyl cellulose and the like. The bioactive priming polypeptide seed treatments can further comprise colorant agents and other such additives.

The bioactive priming polypeptides can be applied individually as seed treatments or in combination with other additives such as fungicides, insecticides, inoculants, plant growth regulators, plant growth promoting microbes, fertilizers and fertilizer enhancers, seed nutrients, biological control agents, herbicidal antidotes and seedling disease treatments and with other conventional seed treatments.

The seed treatment composition as described herein can be applied to seeds in a suitable carrier such as water or a powder that is not harmful to the seeds or the environment. The seeds are then planted in conventional fashion.

Preferred seed treatments such as Bt.4Q7Flg22 (SEQ ID NO: 226 or SEQ ID NO: 571), Ec.Flg22 (SEQ ID NO: 526) and Gm. RHPP (SEQ ID NO: 600) are useful to enhance seedling development, decrease the time for germination, increase the number of seeds that germinate, and enhance seedling survivability. In addition, the seed treatment compositions enhance seed protection from microbial-based diseases which are known to contact the seed or the soil surrounding the seed and spread during early seedling establishment.

The seed treatment composition can comprise a polypeptide as described herein and a fungicide, an insecticide, a nematocide, a biological control agent, a biostimulant, a microbe, or any combination thereof.

The seed treatment composition can comprise a polypeptide as described herein and clothianidin, *Bacillus firmus*, metalaxyl, or any combination thereof.

The seed treatment composition can comprise a polypeptide as described herein, clothianidin and fluopyram.

The seed treatment can comprise a polypeptide as described herein, metalaxyl and fluopyram.

The bioactive priming polypeptides can be applied directly to the seed as a solution or in combination with other commercially available additives. Solutions containing the water-soluble polypeptide can be sprayed or otherwise applied to the seed as a seed slurry or a seed soak. Solids or dry materials containing soluble bioactive priming polypeptides are also useful to promote effective seedling germination, growth and protection during early seedling establishment.

The bioactive priming polypeptides can be formulated with a solubilizing carrier such as water, buffer (e.g., citrate or phosphate buffer) and other treating agents (i.e., alcohol, other solvents) or any solubilizing agent. In addition, small amounts of drying agent enhancers, such as lower alcohols, etc. can be utilized in the composition. Surfactants, emulsifiers and preservatives can also be added at small (0.5% v/v or less) levels in order to enhance the stability of the seed coating product.

Seed treatments containing the bioactive priming polypeptides can be applied using any commercially available seed treatment machinery or can also be applied using any acceptable non-commercial method(s) such as the use of syringes or any other seed treatment device. General seed treatments coating procedures using bioactive priming polypeptides can be performed using a Wintersteiger HEGE 11 (Wintersteiger AG, Austria, Germany) and applied to the seed of major crops, namely corn, soybean, wheat, rice and various vegetables. The capacity of this seed treatment machinery can accommodate a large number of different seed types, sizes and amounts of seed (20-3000 grams). The seed is loaded into bowls of the seed treater machinery. The bowl selection depends on the treatment seed amount required and the size of the bowl selected: large 14.5 L bowl (500-3000 g seed per coating); medium 7L bowl (80-800 g seed per coating); and small 1 L bowl (20-100 g seed per coating). Other larger seed treatment systems are also available.

The seed is distributed toward the radial peripheries of the rotatable bowls via an application of centrifugal force with the centrifugal coating device. The spinning disc located at the bottom of the bowl distributes the seed treatment evenly over the seed. At this point, the spin cycle is started which causes the seeds to revolve around the bowl center in a circle to evenly coat the seeds. The process of seed treatment coating is initiated after the seed is evenly dispersed around the spreader. Seed treatment sample material (such as a powdered, semi-liquid, liquid or a slurry) can be applied onto the rotatable disk as the disks are spinning within the rotatable bowls used to distribute the seed treatment evenly to provide a uniform coat and dress the surface of the seed.

A constant air flow delivered using compressed air (2-6 bars) can be provided during seed coating to assist with uniformly coating the seeds in the bowl. The amount of time for the coating of the seed depends on the amount of the seed, the viscosity of the seed treatment and the type of the seed used in the treatment. A seed treatment calculator is used to adjust for all volumes, for most major and commercially grown crops and the type of seed treatment being applied.

The seeds can be coated using a variety of methods including, but not limited to, pouring or pumping, drizzling or spraying an aqueous solution containing the bioactive priming polypeptides on or over a seed, spraying or applying onto a layer of seeds either with the use or without the use of a conveyor system. Suitable mixing devices include tumblers, mixing basins or drums, or other fluid applicating devices that include basins or drums used to contain the seed while coating.

After the seed has been treated and dried, the seeds are distributed into a larger storage container(s). Seeds are either air dried or dried with a continuous air stream that passes over the seeds. Seeds are then transferred into a separate container or bag for shipment, transfer or storage.

The bioactive priming polypeptides can further be provided for delivery to a plant surface or plant plasma membrane as a foliar spray or a seed treatment to an area surrounding a plant or a plant part.

The bioactive priming polypeptide formulation(s) can also be provided as a seed treatment application or on a matrix such as immobilized or impregnated on a particle, or a granule such as used in a broadcast treatment.

The bioactive priming polypeptides as described herein can be applied to plants and plant parts using an exogenous application as a spray, soil treatment, in furrow, seed treatment, dip or wash or as an endogenous application as an injection, inoculation, irrigation, infiltration, etc.

The polypeptides can be applied directly to a plant or to the area surrounding a plant or plant part.

They can also be provided on a matrix material which is then provided to a plant or plant part.

The compositions containing the flagellin-associated bioactive priming polypeptides can also be provided for direct delivery into a plant, plant tissues or a plant cell by various delivery methods, for example, injection, inoculation or infiltration (for example, infiltration into the stomata on the leaf). These polypeptides can also be provided in a manner where they can move systemically through a plant and influence signaling cascades in the plant that subsequently produce beneficial and productive outcomes to the plant or plant part.

Retro-inverso Flg bioactive priming polypeptides as described in Table 4 or Table 5 can be applied individually or in combination with any other flagellin, flagellin-associated or other bioactive priming polypeptide sequences as described herein. Combinations of such RI flagellin and flagellin-associated bioactive priming polypeptides are useful as plant protectants as well as plant growth promoting enhancers.

The signature (SEQ ID NO: 542-548; Table 6), signal anchor sorting (SEQ ID NO: 549-562, Table 7) and secretion assistance polypeptides (SEQ ID NOs 563-570; Table 8) can be used in combination with any of the flagellin coding (Table 1), N and/or C-terminal conserved sequences from *Bacillus*-derived flagellins (Table 2), flagellin-associated polypeptides: Flg22 and FlgII-28 (Table 3), the retro inverso forms of Flg22 and FlgII-28 (Table 4) or any of the other Flgs (Table 5) as described herein.

For example, any of the Flg-associated bioactive priming polypeptides or combinations thereof can be provided in individual formulations and applied either simultaneously, sequentially in separate formulations or provided as fusion protein(s) that contain the assistance sequences as described in Tables 6-8 and applied directly or separately to a plant or plant part.

Harpin-like polypeptides or RHPP polypeptides can provide functional benefits when applied both exogenously, for example as a foliar spray to the plant surface, or provided apoplastically (to the space outside of the plant cell membrane) or endogenously (inside a plant cell/plant cell membrane). RHPP polypeptides can also provide functional benefits when applied as a seed treatment.

Foliar or in furrow applications of harpin-like, HpaG-like polypeptides are useful to enhance growth, increase biomass, and greenness or chlorophyll production of a plant.

The PSKα bioactive priming polypeptide(s) can be provided for delivery to a plant surface/plant plasma membrane as a foliar spray or, a seed treatment to an area surrounding a plant, plant part or a plant cell.

The compositions containing the PSKα bioactive priming polypeptides can also be provided for delivery into a plant, plant tissues or a plant cell by various delivery methods, for example, injection, inoculation or infiltration (for example, added directly or prerequisitely to cell culture).

V. Methods of Use

Methods are provided for increasing growth, yield, health, longevity, productivity, and/or vigor of a plant or a plant part and/or decreasing abiotic stress in the plant or the plant part and/or protecting the plant or the plant part from disease, insects and/or nematodes, and/or increasing the innate immune response of the plant or the plant part and/or changing plant architecture. The method can comprise applying the polypeptide or the composition as described herein to a plant, a plant part, or a plant growth medium or a rhizosphere in an area surrounding the plant or the plant part to increase growth, yield, health, longevity, productivity, and/or vigor of the plant or the plant part and/or decrease abiotic stress in the plant or the plant part and/or protect the plant or the plant part from disease, insects and/or nematodes, and/or increase the innate immune response of the plant or the plant part and/or change the plant architecture.

Alternatively, the method can comprise applying the polypeptide or the composition as described herein to a plant growth medium to increase growth, yield, health, longevity, productivity, and/or vigor of a plant or a plant part to be grown in the plant growth medium and/or decrease abiotic stress in the plant or the plant part to be grown in the plant growth medium and/or protect the plant or the plant part to be grown in the plant growth medium from disease, insects and/or nematodes, and/or increase the innate immune response and/or change plant architecture of the plant or the plant part to be grown in the plant growth medium.

Another method comprises applying the recombinant microorganism as described herein to a plant, a plant part, or a plant growth medium or a rhizosphere in an area surrounding the plant or the plant part to increase growth, yield, health, longevity, productivity, and/or vigor of the plant or the plant part and/or decrease abiotic stress in the plant or the plant part and/or protect the plant or the plant part from disease, insects and/or nematodes, and/or increase the innate immune response of the plant or the plant part and/or change the plant architecture. The recombinant microorganism expresses the polypeptide and expression of the polypeptide is increased as compared to the expression level the polypeptide in a wild-type microorganism of the same kind under the same conditions.

Methods using the bioactive priming polypeptides are also provided to increase the overall plant productivity in a field, orchard, planting bed, nursery, timberland, farm, lawn, garden, garden center or acreage. Applications and methods using the bioactive priming polypeptides are also useful for increasing plant growth, health and productivity in diverse crops (monocots and dicots), for example, corn, wheat, rice, sugarcane, soybean, sorghum, potatoes and a variety of vegetables.

A "bioactive polypeptide priming" approach is also provided by direct application of the polypeptides, which can be applied either exogenously to a plant cell surface or endogenously to the interior of a plant and/or a plant cell. The polypeptides are provided for delivery to the plant surface or plasma cell membrane or to the interior of a plant, plant tissue or cell and are useful for regulating developmental processes that result in enhanced growth phenotypes such as increases in overall biomass, vegetative growth, seed fill, seed size, and number of seed that contribute to increases in the total yield of crop plants.

Application of the retro-inverso Flg polypeptides provided in agricultural formulations can result in enhanced plant protection from diseases and abiotic stresses while synergistically enhancing growth, productivity and yield while maintaining increased plant health with enhanced plant performance for longer periods of time.

Selection of the native L (Table 3) or the retro-inverso D (Table 4) forms of the Flg-associated polypeptides can depend on the environment, the plant/crop, or the combination of plant/crop and environment. In addition, the timing of the treatment application (for example, a foliar spray application) during the growing season are all relevant considerations. The retro inverso Flg bioactive priming polypeptides have enhanced binding affinity to cell surface membranes. Due to these features, the RI forms of the Flg bioactive priming polypeptides can be used to improve abiotic stress tolerance in a plant or plant part.

Additionally, the retro inverso forms of RI Ec.Flg22 and RI Bt.4Q7Flg22 can be useful to stimulate the closure of stomata under conditions of drought and heat stress and improve yields under those conditions. Control of stomatal closure using Flg-associated bioactive priming polypeptide applied to a plant during periods of environmental stress can assist in the regulation of water loss and stabilize turgor pressure in a plant when environmental conditions are unfavorable.

In the methods, the polypeptide or the composition can comprise: the Flg22 polypeptide and an amino acid sequence of the Flg22 polypeptide comprising any one of SEQ ID NOs: 226-300 and 571-573; the retro inverso Flg22 polypeptide and an amino acid sequence of the retro inverso Flg22 polypeptide comprising any one of SEQ ID NO: 376-450; or any combination thereof to protect the plant or the plant part from disease and/or increase the innate immune response of the plant or the plant part.

In the methods, the polypeptide or the composition can comprise: the FlgII-28 polypeptide and an amino acid sequence of the FlgII-28 polypeptide comprising any one of SEQ ID NOs: 301-375; the retro inverso FlgII-28 polypeptide and an amino acid sequence of the retro inverso FlgII-28 polypeptide comprising any one of SEQ ID NO: 451-525; or any combination thereof to protect the plant or the plant part from disease and/or increase the innate immune response of the plant or the plant part.

In the methods, the polypeptide or the composition can comprise the FlgII-28 polypeptide and an amino acid sequence of the Flg22 polypeptide can comprise any one of SEQ ID NO: 226, 571, or 752 and/or EF-Tu polypeptides, the amino acid sequence of the EF-Tu polypeptides comprising SEQ ID NOs: 616 and 617, to protect the plant or the plant part from disease and/or increase the innate immunity of the plant or plant part. In the methods, the amino acid sequence of the flagellin or flagellin-associated polypeptide can comprise any one of SEQ ID NOs: 226, 289, 290, 291, 293, 294, 295, 300, 437, 532, 534, 536, 538, 540, 571-586, and 751-766 or any combination thereof to protect the plant or the plant part from disease, insects or nematodes. These are polypeptides with mutant sequences exhibiting increased activity to reactive oxygen species. For example, the amino acid sequence of the flagellin or flagellin-associated polypeptide can comprise any one of SEQ ID NOs: 226, 293, 295, 300, 540, 571 574, 751 and 752 or any combination thereof.

The disease can comprise Asian citrus greening, Huanglonging (HLB) disease, Asian soybean rust, *Sclerotinia* stem rot (or white mold), *Pseudomonas* leaf spot, or *Cercospora* leaf blight.

In the methods, the polypeptide or the composition can comprise the Flg22 polypeptide and an amino acid sequence of the Flg22 polypeptide comprising any one of SEQ ID NOs: 226-300 and 571-573 or any combination thereof.

In the methods, the polypeptide or the composition can comprise the FlgII-28 polypeptide and an amino acid sequence of the FlgII-28 polypeptide comprising any one of SEQ ID NOs: 301-375 or 751 or any combination thereof.

In the methods, the polypeptide or the composition can comprise the Flg22 polypeptide and the FlgII-28 polypeptide, an amino acid sequence of the Flg22 polypeptide comprising any one of SEQ ID NOs: 226-300 and 571-573 or any combination thereof and an amino acid sequence of the FlgII-28 polypeptide comprising any one of SEQ ID NOs: 301-375 or 751 or any combination thereof. The polypeptide or the composition can further comprise the retro inverso Flg22 polypeptide, the retro inverso FlgII-28 polypeptide or a combination thereof, an amino acid sequence of the retro inverso Flg22 polypeptide comprising any one of SEQ ID NO: 376-450 or any combination thereof and an amino acid sequence of the retro inverso FlgII-28 polypeptide comprising any one of SEQ ID NO: 451-525 or any combination thereof.

In the methods, the polypeptide or the composition can comprise the RHPP polypeptide and/or the RI RHPP polypeptide to increase the yield, the growth and/or the productivity of the plant or plant part and/or change the plant architecture.

When the method includes a polypeptide or composition comprising the RHPP polypeptide and/or the RI RHPP polypeptide, the growth can comprise root growth, root length, root biomass, nodulation, total biomass, above ground biomass, or any combination thereof. When the polypeptide or composition comprises the RHPP polypeptide, the amino acid sequence of the RHPP polypeptide can comprise SEQ ID NO: 600.

When the method includes a polypeptide or composition comprising the RHPP polypeptide and/or the RI RHPP polypeptide, the plant can comprise soybean, the growth can comprise overall root length, root biomass, nodulation, nodules per plant, total biomass, above ground biomass, or any combination thereof, and the productivity can comprise number of total pods or pods per node.

The plant architecture can comprise beneficial outcomes to the plant or plant part. For example, the beneficial outcomes can include increased planting density capability for a field of the plants.

In the methods, the polypeptide or the composition can comprise the harpin-like polypeptide or the RHPP polypeptide to protect the plant or the plant part from disease, insects and/or nematodes, and/or increase the innate immune response of the plant or the plant part.

In the methods, the polypeptide or the composition can comprise the PSK polypeptide to increase yield of the plant or the plant part in environments prone to heat and drought.

The polypeptide, the composition, or the recombinant microorganism can be applied just prior to floral formation or at the pre-flowering stage.

In the methods, the polypeptide or the composition can comprise the PSK polypeptide, the RHPP, the harpin or harpin-like polypeptide, or a combination thereof to increase growth of the plant or the plant part.

The growth can comprise root and floral apical meristems, floral organ production, fruit development, fruit production, number of floral organs, size of floral organs, or a combination thereof.

In the methods, the polypeptide or the composition can comprise the PSK polypeptide and the harpin or harpin-like polypeptide to increase growth and productivity of the plant or the plant part in an environment prone to both stress and non-stress conditions for plant growth.

In the methods, the polypeptide or the composition can comprise the thionin or thionin-like polypeptide.

The thionin or thionin-like polypeptide can be fused to a phloem targeting sequence to form a fused polypeptide, the amino acid sequence of the phloem targeting sequence comprising any one of SEQ ID NOs: 641-649, or any combination thereof, for delivering the fused polypeptide to vascular tissue or cells and/or phloem or phloem-associated tissue or cells in the plant or plant part.

In the methods, protecting the plant or the plant part from disease can comprise prophylactic treatment, treatment, prevention and decreased disease progression on or in the plant or plant part.

The disease can comprise Asian citrus greening disease (HLB), Citrus canker disease, *Cercospora* leaf blight or a bacteria causing disease.

The bacteria causing disease can comprise bacterial leaf blight, bacterial leaf streak, bacterial stalk rot, bacterial leaf spot, bacterial leaf scorch, bacterial top rot, bacterial stripe, chocolate spot, Goss's bacterial wilt and blight, *Holcus* spot, purple leaf sheath, seed rot, seedling blight, Stewart's disease (bacterial wilt), corn stunt, Fire Blight, Pierce's disease, citrus variegated chlorosis, citrus canker, *Pseudomonas syringae* serovars, or a combination thereof.

In the methods, the polypeptide or the composition further can comprise the flagellin or flagellin-like polypeptide, and an amino acid sequence of the flagellin or flagellin-like polypeptide comprising any one of SEQ ID NOs: 226-525 and 571-573 or any combination thereof.

In the methods, the polypeptide, the composition, or the recombinant microorganism can be applied exogenously to the plant, the plant part, or the plant growth medium.

In the methods, the polypeptide, the composition, or the recombinant microorganism can be applied endogenously to the plant or the plant part.

The plant part can include a plant cell, a leaf, a branch, a stem, a flower, a foliage, a floral organ, a fruit, pollen, a vegetable, a tuber, a rhizome, a corm, a bulb, a pseudobulb, a pod, a root, a root ball, a root stock, a scion, or a seed.

In the methods, the polypeptide, the composition, or the recombinant microorganism can be applied to a surface of the plant, a foliage of the plant or a surface of a seed of the plant.

In the methods, the polypeptide, the composition, or the recombinant microorganism can be applied to the surface of the seed and the plant or the plant part is grown from the seed.

In the methods, the polypeptide, the composition, or the recombinant microorganism can be applied as a foliar application.

The plant can be a fruit plant or a vegetable plant, and the method provides increased yield of fruits or vegetables.

In methods where the bioactive priming polypeptides are applied two or more times during a growing season, the first application can occur at or before the V2 stage of development, and subsequent applications can occur before the plant flowers. For example, the first application can occur as a seed treatments, at/or before the VE stage of development, at or before the V1 stage of development, at or before the V2 stage of development, at or before the V3 stage of development, at or before the V4 stage of development, at or before the V5 stage of development, at or before the V6 stage of development, at or before the V7 stage of development, at or before the V8 stage of development, at or before the V9 stage of development, at or before the V10 stage of development, at or before the V11 stage of development, at or before the V12 stage of development, at or before the V13 stage of development, at or before the V14 stage of development, at or before the V15 stage of development, at or before the VT stage of development, at or before the R1 stage of development, at or before the R2 stage of development, at or before the R3 stage of development, at or before the R4 stage of development, at or before the R5 stage of development, at or before the R6 stage of development, at or before the R7 stage of development, or at or before the R8 stage of development. By way of example, the first application can occur at or before the germination stage, at or before the seedling stage, at or before the tillering stage, at or before the stem elongation stage, at or before the booting stage, or at or before the heading stage. For example, where the Feekes scale is used to identify the stage of growth of a cereal crop, the first application can occur at or before stage 1, at or before stage 2, at or before stage 3, at or before stage 4, at or before stage 5, at or before stage 6, at or before stage 7, at or before stage 8, at or before stage 9, at or before stage 10, at or before stage 10.1, at or before stage 10.2, at or before stage 10.3, at or before stage 10.4, or at or before stage 10.5.

Abiotic Stress

Abiotic stress causes significant crop loss and can result in major reductions in crop production and yield potential. The bioactive priming polypeptides and compositions as described herein can be used as chemical priming agents to increase tolerance of a plant to one or more abiotic stresses. Thus, the flagellin polypeptides, flagellin-associated polypeptides of Flg22 or FlgII-28 derived from *Bacillus* species, Flg15 and Flg22 derived from *E. coli* and other organisms (Table 5) and the RHPP polypeptides derived from *Glycine max* (Tables 13 to 15) are useful for increasing the tolerance of a plant, group of plants, field of plants and/or the parts of plants to abiotic stress. The polypeptides and compositions as described herein impart abiotic stress tolerance to a plant or plant part. The abiotic stress tolerance imparted to a plant or plant part are to abiotic stresses that include, but are not limited to: temperature stress, radiation stress, drought stress, cold stress, salt stress, osmotic stress, nutrient-deficient or high metal stress, and water stress that results from water deficit, flooding or anoxia. Chemical priming using the bioactive priming polypeptides and compositions as described herein are applied to a plant or plant part offering a versatile approach to protect the plant or plant part against individual, multiple or combined abiotic stresses.

The polypeptides and compositions as described herein are effective to protect a plant against abiotic stressors when applied as an above ground foliar application to a plant, a plant part, a plant root, a plant seed, a plant growth medium, or the area surrounding a plant or the area surrounding a plant seed. For example, for trees, one or more applications can be applied at different growth timings of trees, including timings before, during or after flushes; before, during, or after fruit set; or before or after fruit harvest.

The methods described herein chemically prime the plant for protection against abiotic stress(es) in such a way that the plant has already prepared and initiated defense mechanisms that can be activated faster and increase tolerance to an abiotic stress or multiple stressors occurring simultaneously or at different times during the growing season.

The retro inverso forms of the Flg22 polypeptides as described herein can be applied externally as a foliar spray application (or using other application methods as well, for example as a root drench) during times of excessive heat, water, and drought stress and be used to protect a plant against drought, heat stress and/or other abiotic stresses that can affect stomatal aperture and oscillation that commonly occur with transpiration loss through a plant.

In the methods, the polypeptide or the composition can comprise: the Flg22 polypeptide and an amino acid sequence of the Flg22 polypeptide comprising any one of SEQ ID NOs: 226-300 and 571-573 or any combination thereof; the retro inverso Flg22 polypeptide and an amino acid sequence of the retro inverso Flg22 polypeptide comprising any one of SEQ ID NO: 376-450 or any combination thereof; or any combination thereof to decrease abiotic stress in the plant or the plant part and/or protect the plant or the plant part from disease and/or increase the innate immune response of the plant or the plant part.

In the methods, the polypeptide or the composition can comprise: the FlgII-28 polypeptide and an amino acid sequence of the FlgII-28 polypeptide comprising any one of SEQ ID NOs: 301-375 or any combination thereof; the retro inverso FlgII-28 polypeptide and an amino acid sequence of the retro inverso FlgII-28 polypeptide comprising any one of SEQ ID NO: 451-525 or any combination thereof; or any combination thereof to decrease abiotic stress in the plant or the plant part and/or protect the plant or the plant part from disease and/or increase the innate immune response of the plant or the plant part.

In the methods, the polypeptide or the composition can comprise: the retro inverso Flg22 polypeptide and an amino acid sequence of the retro inverso Flg22 polypeptide comprising any one of SEQ ID NO: 376-450 or any combination thereof; the retro inverso FlgII-28 polypeptide and an amino acid sequence of the retro inverso FlgII-28 polypeptide comprising any one of SEQ ID NO: 451-525 or any combination thereof; or any combination thereof to decrease abiotic stress in the plant or the plant part and/or protect the plant or the plant part from disease and/or increase the innate immune response of the plant or the plant part.

In the methods, the polypeptide or the composition can comprise the RHPP polypeptide and an amino acid sequence of the RHPP polypeptide comprises SEQ ID NO: 600, 603, 604 or any combination thereof; the Kunitz Trypsin Inhibitor (KTI) polypeptide and an amino acid sequence of the KTI polypeptide comprises SEQ ID NO: 602; the retro-inverso RHPP polypeptide and an amino acid sequence of the RI RHPP comprises SEQ ID NO 601, 605, 606 or any combination thereof; or any combination thereof to decrease abiotic stress in the plant or the plant part and/or protect the plant or the plant part from disease and/or increase the innate immune response of the plant or the plant part.

The abiotic stress can comprise heat stress, temperature stress, radiation stress, drought stress, cold stress, salt stress, nutrient-deficient stress, high metal stress, water stress, osmotic stress, or any combination thereof.

Balancing Immune Response with Plant Growth and Development

Although immune responses can provide protection of plants from pathogen attack, excessive immune responses may have negative impacts on plant growth. Therefore, balancing enhanced immunity or disease prevention and protection in a plant with an increased growth promoting response is a desired combination to optimize plant health.

Bioactive priming polypeptides that are useful for enhancing immune responses as described herein can be combined with polypeptides that provide positive impacts on plant growth and productivity. The polypeptide combinations are specifically selected for their distinct modes of action/regulation when applied to a plant or plant part. However, some of the bioactive priming polypeptides (Flgs, HpGa-like, PSKα, thionins) are perceived by receptor-like proteins, followed by a process that initiates their entry and transport in the plant which results in functional outcomes while others are taken into the plant by active absorption (e.g., RHPP). For example, PSKα and the Flg-associated polypeptides such as Flg22, Flg25 and FlgII-28 are perceived by a leucine-rich receptor kinase located on the surface of the plasma membrane and involve a complex signaling pathway involved in the pathogen-triggered responses leading to immunity, disease resistance or disease prevention (Kutschmar et al. "PSKα promotes root growth in *Arabidopsis*," New Phytologist 181: 820-831, 2009).

The bioactive priming polypeptides as described herein such as Flg22 HpaG-like polypeptides and thionins can act as elicitors and exhibit antimicrobial activity (e.g., anti-pesticide; bacterial, fungal, or viral activity). Specific combinations of polypeptides are provided, for example, the combination of flagellin- and harpin-associated bioactive priming polypeptides are useful for preventing and protecting plants from pathogenic diseases and serve a dual utility when they are applied together with those other polypeptides, for example, PSKα and RHPP, that enhance plant growth and productivity in a plant, plant part, and/or field of plants.

The combinations of bioactive priming polypeptides as described herein can be applied exogenously as a foliar spray, in furrow treatment, seed treatment, drench or wash or endogenously to a plant to stimulate both the immune responsiveness and growth characteristics of the plant that collectively result in improved yield performance. They can also provide protection and growth benefits to the different parts of the plant (for example, leaves, roots, tubers, corms, rhizomes, bulbs, pseudobulbs, flowers, pods, fruits, and growing meristems).

The combined foliar application or sequential applications of PSKα with HpaG-like bioactive priming polypeptides can be useful for enhancing growth of plants under standard (non-stress or optimal growth) environments or of plants exposed to abiotic stress (for example, heat, and water deficit stress).

Foliar application treatments using the X.spp HpaG-like and the At.PSKα bioactive priming polypeptides have different modes of action when applied on plants in optimal (non-stress) and in stress environments. The two classes of bioactive priming polypeptides are useful either provided sequentially or in combination in a foliar application and can improve plant growth in an environment that is with or without abiotic stress(es).

X.spp.HpGa-like provides a plant growth benefit to corn in a non-stress environment where temperature, water, nutrients and other environmental parameters were conducive to optimal plant growth. On the other hand, At.PSKα applied as a foliar spray provides a benefit to plant growth under environmental conditions of heat and drought or water deficit stress. Thus, when used in combination in formulation together as foliar applications they can span both non-stress and stress environments and provide additive benefits to the growth of corn plants grown in a variety of environmental conditions.

Increases in plant productivity and growth for At.PSKα is also seen in soybean plants grown in environments with and without abiotic stress. Soybean plants that receive a foliar application with a formulation containing the bioactive priming polypeptide At.PSKα and are grown under conditions of heat and drought stress have increased yield over control soybean plants that received water and surfactant with no bioactive priming polypeptide.

When X. spp. HpaG-like and At.PSKα are applied as a foliar spray together, they are useful to provide synergistic effects for plant production under normal and stressed environments. At.PSKα exhibits increased overall growth in corn when applied as a spray application, whereas X. spp. HpaG-like polypeptide results in the opposite trend. Thus, applying the two bioactive priming polypeptides together can act to balance plant growth in "heat stressed" environments such that the changes in plant growth compared to control plants are greater than the sum of the effects of the bioactive priming polypeptides applied individually.

The synergistic interaction of these two classes of bioactive priming polypeptides enhance plant growth under heat stressed environments (e.g., greater growth rates with increased plant biomass).

Any of the bioactive priming polypeptides as described herein can be applied one or more times to a plant either in combination or individually to enhance growth and productivity of a plant. Multiple applications can be applied to promote yield benefits over the growing season with applications tailored to the conditions in the environment, for example if a period of hot and dry weather is expected during the growth season, an additional spray of bioactive priming polypeptides that promote growth under abiotic stress can alleviate negative impacts to the plant.

Foliar Application of Phytosulfokine alpha (PSKα) to Increase Yield

A method is provided for applying At.PSKα as a foliar application to actively growing soybean plants to provide a yield advantage in environments with heat and drought stress. For example, a means of applying a composition containing bioactive priming At.PSKα polypeptide is provided as a foliar spray to soybean at V1-V4 stage using application methods as described herein. Soybean plants treated with foliar applications of At.PSKα can be grown in field environments under conditions that produced a non-stress and stress (heat and water deficit) environments. Treatment with At.PSKα can result in growth and yield benefits in plants grown in a variety of environmental conditions including abiotic stressors.

Any of the RHPP bioactive priming polypeptides provided in Tables 12-14 can be applied as a foliar, in furrow, seed treatment or root drench application to a plant surface.

Foliar application of RHPP results in the alteration of plant architecture.

A method is provided where the RHPP polypeptide is applied as a foliar application to plants and results in a distinct leaf architecture (corn) and an enhanced root system (soybean). The increase in leaf angle and root biomass using a foliar treatment with RHPP has impactful advantages for use in agriculture in two major agriculture crops (corn and soybean).

Application of RHPP to Alter Plant Architecture

Applying the bioactive priming polypeptide, RHPP, as a foliar application to V5-V8 corn results in a distinct leaf architecture phenotype with an upright leaf orientation and more erect leaves. This is particularly relevant with higher planting densities used to maximize yield in a field environment. Foliar applications of the RHPP polypeptide in maize (corn) is useful for changing the leaf angle thus contributing to a smaller leaf angle which results in an upright leaf orientation. This phenotype can be beneficial for increasing the leaf area index, reducing maize shade syndrome, and improving photosynthetic efficiency. In addition, providing RHPP as a foliar formulation to maximize canopy development and total light penetrance is key to increasing vegetative growth of the plants prior to the initiation of the grain filling stage.

Maize plants exhibit leaf curl or changes in their leaf architecture to a more upright leaf orientation to conserve water and enhance plant tolerance to drought and heat. The upright changes to the leaf phenotype for corn after application with the RHPP bioactive priming polypeptide(s) compositions are useful and provide an alternative non-breeding approach for shaping leaf architecture and enhancing tolerance to drought and heat.

An upright leaflet orientation phenotype in corn plants functions in the reduction of leaf temperatures, whole plant transpiration and in the improvement of water use efficiency, as well as provide architectural changes to the plant canopy which can allow for higher density plantings that result in substantial increases in yield.

Application of the bioactive priming polypeptide, RHPP, to soybeans can also provide benefits. For example, foliar application of RHPP to flowering soy can increase pod set. Pod set is a stage in soybean development occuring from the middle of R4 to the middle of R5 that contributes directly to yield. Initial pod set is marked by the emergence of a % inch pod at one of the four uppermost nodes on the main stem. It then progesses to the full pod stage where pod growth is rapid and seed development begins. An increase in pod set is quantified by an increase in yield (i.e the pod number per node on a plant or the overall number of pods per plant).

RHPP to Increase Root Biomass and Yield

Soybean plants treated with foliar applied RHPP (SEQ ID NO: 600) bioactive priming polypeptide(s) can exhibit increased pod filling and a more-complete pod filing compared to non-treated plants which can be the result of increases in nitrogen fixation.

Root architecture, particularly a root system with a rapid exploitation of deep soil can optimize nitrogen capture and water uptake which is especially important in drying and nitrogen depleted soils. An RHPP polypeptide(s) as described herein when applied as a foliar treatment to soybean plants results in a root phenotype that is useful for water and mineral (nitrogen) acquisition, especially in nitrogen-deficient soils. Increasing nutrient uptake efficiency by enhancing root architecture is a key factor for improving plant productivity when used with soybean cultivation practices in a wide range of soil types.

Enhanced root biomass that results from a foliar application of RHPP provided at the early vegetative stages for soybean VE-V5 or V2-V3 stage of development results in a root system with rapid exploitation of deep soil (deep roots), and greater overall increases in root biomass. For example, a root hair promoting bioactive priming polypeptide such as RHPP (SEQ ID NO: 600) can be applied as a foliar treatment to soybean plants at the V2 to V3 stage of development to result in an overall increase in root biomass. Other notable enhancements in addition to root biomass are the production of longer lateral roots, increases in root branching, root hairs and increases in the root absorptive surface area.

RHPP can be applied as a foliar treatment at key developmental stages (VE-V8 or V2-V8) or in environments where a rapid increase in root production is desired, such as dry or nutrient poor soil types. Soil types in particular may affect root development and expansion. For example, if plants have a hard time emerging in a clay soil, it may affect root formation and root proliferation. Increasing root mass may not only beneficially effect plant emergence but also contribute to plant establishment. In addition, nodule formation and number are important because the bacteria that inhabit the nodules pull nitrogen from the air allowing soybeans to convert it into the nitrogen that they need to grow and produce seeds.

The RHPP polypeptides (Tables 13-15) can be used to increase nodule formation and nodule production of soybean roots when applied using any of these treatment application methods which can be applied directly to the soil, as a soil drench, as an in furrow treatment, or as a foliar application to the above ground plant parts.

Increase in nodules can result in increased nitrogen fixation by nitrogen fixing bacteria that inhabit the root nodules, such as *Rhizobium leguminosarum* or *japonicum*. Nodule formation can be seen shortly after VE and can increase nitrogen fixation. Effective nodulation of soybean roots results in higher yields and higher quality seed production, protein and oil per seed or acre basis. Soybean plants have fully formed first trifoliate leaves at the V1-V2 stage of development which is estimated to be the peak time for nitrogen fixation.

The combination application of Gm.RHPP bioactive priming polypeptide with various fertilizer treatment(s) can provide a yield boost and is recommended especially for crop management applications in nitrogen depleted soils.

Bacterial Disease

Methods of using the bioactive priming polypeptides such as the flagellin-associated polypeptides or the thionin-like polypeptides as described herein are useful for the prevention, treatment and control of bacterial diseases in corn and particularly useful for the treatment of bacterial leaf streak disease in corn caused by *Xanthomonas vasicola* pv. *vasculorum*, also recognized as *Xanthomnas campestris* pv. *vasculorum*.

Surveys indicate that bacterial leaf streak disease has spread and may be widely distributed throughout the U.S. Corn Belt (Western Indiana, Illinois, Iowa, Missouri, Eastern Nebraska and Eastern Kansas). Disease spread is most prevalent where corn is planted on corn in crop rotation practices. The bacterial leaf streak disease can cause infection on dent corn (field) seed corn, popcorn and sweet corn. The symptoms on corn include narrow to brown yellow streaks and brown yellow strips between the leaf veins. Lesions usually develop on lower or older plant leaves and initially spread to the higher or younger leaves on the plant. Yellow discoloration also may be present around lesions.

The bacterial leaf streak disease of corn presumably survives in previously infected host debris. Bacterial exudates found on surfaces of infected leaf tissues can serve as secondary inocula. The bacterium is spread by wind, splashing rain, and possibly by irrigation water. The pathogen penetrates corn leaves through natural openings such as stomata, which can result in a banded pattern of lesions occurring across leaves. Colonization of leaf tissues apparently is restricted by main veins.

Because the disease is caused by a bacterial pathogen, the current use of bactericides is problematic to control it. For example, most bactericides act as contact products and are not systemic and thus they will not be absorbed or taken into the plant via other mechanisms. Bactericide treatments may require repeated applications as the bactericide may be washed off with rain or wind, thus rendering them uneconomical or impractical for use in some corn crops.

Current disease management practices to date recommend crop rotation practices (such as corn, soybean and then back to corn) and the implementation of sanitation practices, such as cleaning equipment between field usage to slow disease progression.

Foliar applications of the Flg (Tables 4-5) and thionin polypeptides (Table 19) or combinations of the two classes provide an alternative approach for treating the disease. Foliar applications with these bioactive priming polypeptides provided as a spray to the leaf surface of either asymptomatic or symptomatic plants provides a means to prevent, treat, and control the bacterial leaf streak disease in corn.

Alternatively, the flagellin- and thionin bioactive priming polypeptides or combinations thereof can be useful for the prevention, treatment and control of other bacterial diseases that infect corn (Table 21).

TABLE 21

Bacteria causing diseases in corn

| Corn Disease | Bacteria Causing Diseases |
|---|---|
| Bacterial leaf blight and stalk rot | *Pseudomonas avenae* subsp. *avenae* |
| Bacterial leaf spot | *Xanthomonas campestris* pv. *holcicola* |
| Bacterial leaf streak | *Xanthomonas vasicola* |
| Bacterial stalk rot | *Enterobacter dissolvens*; *Erwinia dissolvens* |
| Bacterial stalk and top rot | *Erwinia carotovora* subsp. *carotovora* *Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis*; *Corynebacterium michiganense* pv. *nebraskense* |
| Holcus spot | *Pseudomonas syringae* pv. *syringae* *van Hall* |
| Purple leaf sheath | *Hemiparasitic bacteria* |
| Seed rot-seedling blight | *Bacillus subtilis* |
| Stewart's disease (bacterial wilt) | *Erwinia stewartii* |
| Corn stunt (achapparramiento, maize stunt, Mesa Central or Rio Grande maize stunt) | *Spiroplasma kunkelii* |

*Cercospora* Leaf Blight Disease of Soybean

*Cercospora* is a fungal pathogen that causes the disease *Cercospora* leaf blight of soybean. *Cercospora* leaf blight also referred to as the purple seed stain disease infects both the leaves and seeds of soybeans. *Cercospora* infection of soybean seeds diminishes seed appearance and quality. The causal organism of *Cercospora* leaf blight is *Cercospora kikuchii*, which overwinters in soybean residue and in the seed coats. Spread of the disease occurs when the spores from the fungus are spread to soybean plants from infected residue, weeds or other infected soybean plants. Disease spread and symptom development are accelerated during periods of warm and wet weather. Symptom development usually begins after flowering and appears as circular lesions on soybean leaves as reddish brown to purple spots that can merge to form lesions. Symptoms are apparent in the upper canopy, usually in the uppermost three or four trifoliate leaves. Infected soybean plants exhibit worsening symptoms as the crop matures, and premature defoliation of affected leaves may occur during pod-fill. *Cercospora* symptom development may also appear as lesions on stems, leaf petioles and pods. Seeds are infected through the attachment to the pod. *Cercospora* infected seeds show a purple discoloration, which can appear as specks or blotches covering the entire seed coat.

Foliar applications of flagellin or flagellin-associated polypeptides (Tables 4-5) provide an alternative approach for treating the disease. Foliar applications with these bioactive priming polypeptides provided as a spray to the leaf surface of either asymptomatic or symptomatic plants provides a means to prevent, treat, and control *Cercospora* Leaf Blight in soybeans. Foliar applications of Flg22 derived from *Bacillus thuringiensis*, particularly at high use rates (e.g. 4.0 Fl. oz/Ac), can provide a means of managing early symptom development and provide healthier more vigorous soybean plants grown in field locations that have been impacted by *Cercospora*.

Specific combinations of bioactive priming polypeptides that can be useful for treating or reducing the symptoms of *Cercospora* include: a flagellin or flagellin-associated polypeptide having an amino acid sequence comprising SEQ ID NO 226, 751 or 752; an RHPP polypeptide having a sequence comprising SEQ ID NO: 600; or a combination of a flagellin associated polypeptide having an amino acid sequence comprising any one of SEQ ID NOs 226, 751 and 572 and an RHPP polypeptide haivng the amino acid sequence comprising SEQ ID NO: 600.

For example, a useful combination of bioactive priming polypeptides for treating, or reducing the symptoms of *cercospora* on a plant or plant part is a flagellin polypeptide having an amino acid sequence comprising SEQ ID NO: 226 alone or in combination with an RHPP polypeptide having an amino acid sequence comprising SEQ ID NO: 600. Additional treatments can further comprise a fungicide in combination with these bioactive priming polypeptides.

Asian Soybean Rust Disease

Asian soybean rust is a fungal disease caused by *Phakopsora pachyrhizi*. Its etiology and symptoms are similar to *Cercospora* and the bioactive priming polypeptide combinations useful for treating it are similar as well. Specifically, combinations of bioactive priming polypeptides that can be useful for treating or reducing the symptoms of Asian soybean rust include: a flagellin or flagellin-associated polypeptide having an amino acid sequence comprising SEQ ID NO 226, 751 or 752; an RHPP polypeptide having a sequence comprising SEQ ID NO: 600; or a combination of a flagellin associated polypeptide having an amino acid sequence comprising any one of SEQ ID NOs 226, 751 and 572 and an RHPP polypeptide having the amino acid sequence comprising SEQ ID NO: 600.

For example, a useful combination of bioactive priming polypeptides for treating, or reducing the symptoms of Asian soybean rust on a plant or plant part is a flagellin polypeptide having an amino acid sequence comprising SEQ ID NO: 226 alone or in combination with an RHPP polypeptide having an amino acid sequence comprising SEQ ID NO: 600. Additional treatments can further comprise a fungicide in combination with these bioactive priming polypeptides.

*Holcus* Spot

*Holcus* spot is a bacterial disease caused by *Pseudomanas syringae* pv. *actinidae*. Methods are described herein for using flagellin or flagellin associated polypeptides to restrict growth of *P. syringae* and thus prevent or treat the disease of *Holcus* spot in a plant or a plant part. Flagellin or flagellin associated polypeptides useful for the treatment of *P. syringae* include any polypeptides having amino acid sequences comprising any one of SEQ ID NOs: 226, 540, 751, and 572 or any combination thereof.

*Sclerotinia* Stem Rot (White Mold) Disease

*Sclerotinia sclerotiorum* is a plant pathogenic fungus that causes a disease caused white mold. It is also known as cottony rot, water soft rot, stem rot, drop, crown rot, and blossom blight. Diagnostic symptoms of the white rot include black resting structures known as sclerotia and white fuzzy growths of mycelium on the infected plant. The sclerotia, in turn, produce a fruiting body that produces spores in a sac. *Sclerotinia* can affect herbaceous, succulent plants, particularly fruits and vegetables, or juvenile tissue on woody ornamentals. It can also affect legumes or tuberous plants like potatoes. White mold can affect a host at any stage of growth, including seedlings, mature plants, and harvested products. It is usually found on tissues with high water content and close proximity to soil. Left untreated, pale to dark brown lesions on the stem at the soil line are covered by a white, fluffy mycelial growth. This affects the xylem which leads to chlorosis, wilting, leaf drop, and death. White mold can also occur on fruit in the field or in storage and is characterized by white fungal mycelium covering the fruit and its subsequent decay. Flagellin or flagellin associated polypeptides useful for the treatment of *S. sclerotiorum* include any polypeptides having amino acid sequences comprising any one of SEQ ID NOs: 226, 540, 571, 751, and 752.

*Pseudomonas* Leaf Spot

*Pseudomonas syringae* pv. *actinidiae* (PSA) is a devastating plant pathogen causing bacterial canker of both green-(*Actinidiae deliciosa*) and yellow-flesh (*Actinidiae chinesis*) kiwi plants throughout zones of kiwi production, causing severe harvest loss in New Zealand, China, and Italy. In New Zealand alone, cumulative revenue losses to the most devastating biovar PSA-V are predicted to approach $740 million New Zealand leaves Dollars (NZD) by 2025 (Agribusiness and Economics Research Institute of Lincoln University "The Costs of Psa-V to the New Zealand Kiwifruit Industry and the Wider Community"; May 2012). PSA-V colonizes the outer and inner surfaces of the kiwi plant and can spread through the xylem and phloem tissues. Disease symptoms of PSA-V on kiwi include bacterial leaf spot, bacterial canker of the trunk, red exudates, blossom rot, discoloration of twigs, and ultimately dieback of kiwi vines. The standard method of control for PSA-V currently employs frequent foliar applications of metallic copper to kiwi vines which is predicted to lead to the selection of copper-resistant form of the pathogen and loss of disease control. Novel methods of control are urgently needed.

Flagellin or flagellin associated peptides useful for the treatment of *Pseudomanas* syringase, particularly in kiwis, include any polypeptides having amino acid sequences comprising SEQ ID NO: 226, 540, 752, and/or 571.

Asian Citrus Greening (Huanglonging) Disease

The methods described herein incorporate a different approach to combating disease and additionally providing benefits of increasing the overall productivity of a plant. This approach is specifically directed to providing either exogenous or endogenous applications of the bioactive priming polypeptides that include thionins to combat disease in plants.

The thionin and thionin-like polypeptides (Table 19) and compositions thereof are useful for the prevention, treatment and control of Asian citrus greening also referred to as Huanglonging (HLB) disease, a devastating disease for citrus. HLB disease is widely distributed and has been found in most commercial and residential sites in all counties that have commercial citrus orchards.

Methods are described herein for using the thionin polypeptides (SEQ ID NOs: 650-749) to prevent the spread of and in the treatment of HLB disease.

Asian citrus greening disease is transmitted by the Asian citrus psyllid, *Diaphorina citri* or the two-spotted citrus psyllid, *Trioza erytreae* Del Guercio, which are both characterized as sap-sucking, hem ipteran bug(s) in the family Psyllidae and have been implicated in the spread of citrus greening, a disease caused by a highly fastidious phloem-inhabiting bacteria, *Candidatus Liberibacter asiaticus* (Halbert, S. E. and Manjunath, K. L, "Asian citrus psyllids Sternorrhyncha: Psyllidae and greening disease of citrus: A literature review and assessment of risk in Florida," Florida Entomologist 87: 330-353, 2004). Asian citrus greening or Huanglongbing disease is considered fatal for a citrus tree once the tree becomes infected.

The early symptoms of the disease on leaves are vein yellowing and an asymmetrical chlorosis referred to as blotchy mottle, which is the most diagnostic symptom of the disease. Infected trees are stunted and sparsely foliated with a blotchy mottling appearing on the foliage. Early symptoms of yellowing may appear on a single shoot or branch and with disease progression, the yellowing can spread over the entire tree. Afflicted trees may show twig dieback, and fruit drop. Fruit are often few in number, small, deformed or lopsided and fail to color properly, remaining green at the end and display a yellow stain just beneath the peduncle (stem) on a cut fruit.

The Asian citrus greening disease may also be graft transmitted when citrus rootstocks are selected for and grafted to scion varieties.

Management of citrus greening disease has proven difficult and therefore current methods for control of HLB have taken a multi-tiered integrated disease and pest management approach using 1) the implementation of disease-free nursery stock and rootstock used in grafting, 2) the use of pesticides and systemic insecticides to control the psyllid vector, 3) the use of biological control agents such as antibiotics., 4) the use of beneficial insects, such as parasitic wasps that attack the psyllid, and 5) breeding for new citrus germ plasm with increased resistance to the citrus greening causing bacteria (*Candidatus Liberibacter* spp.). The use of cultural and regulatory measures to prevent the spread of the disease is also part of the integrated management approach. Many aspects involved in the management of citrus greening are costly both monetarily and in respect to losses in citrus production.

Interveinal application of a thionin polypeptide or mixture of thionin polypeptides can be delivered directly into the phloem (e.g., phloem cells including phloem sap, phloem companion cells and phloem sieve tube elements) where *Candidatus Liberibacter* can reside.

The thionins can be produced using an expression system where they can be fused to a phloem targeting sequence(s) (Table 18) and then uniquely delivered to the same vicinity where the bacteria can reside in the citrus plant.

The phloem targeted thionin bioactive priming polypeptides are useful for treating citrus plants to prevent, reduce or eliminate the spread of the Asian citrus greening disease or Huanglonging (HLB) by directly targeting the bacterium, *Candidatus Liberibacter asiaticus*

These phloem targeted thionins can be delivered by injection into the phloem of a shrub or tree. Additionally, they can be delivered by spraying, washing, or adding as a soak or a drench to the soil or area surrounding a plant.

Any of the phloem targeting sequences (Table 18; SEQ ID NOs: 641-649) can be used in combinations with the thionin and thionin-like polypeptides (Table 19; SEQ ID NOs: 650-749).

The bacteria that cause HLB, *Candidatus Liberibacter asiaticus* is difficult to isolate and culture. In order to test individual thionins and thionins with the phloem targeting sequences to determine if they are useful for the treatment of HLB disease, *Agrobacterium tumefaciens* can be used as a model organism to test the effectiveness on reducing the cell titer or growth of *Agrobacterium* prior to using the thionin or thionin combinations in an orchard setting.

The "peptide priming" methods provided herein with the thionins and/or thionin-like polypeptides (Table 19) can also be used in combination flagellin and flagellin-associated polypeptides (Tables 1-5). Combinations of the thionin- and flagellin-associated bioactive priming polypeptides can be used to prophylactically pre-treat a citrus plant by applying the bioactive priming polypeptide or a composition containing the polypeptide prior to the onset or appearance of any infection-related symptoms on the citrus shrubs or trees. This pretreatment increases resistance to the disease pathogen that causes citrus greening (*Candidatus Liberibacter* spp.).

The thionins provided in combination with the flagellin associated bioactive priming polypeptides provide a more comprehensive approach to disease prevention and management. The thionin and flagellin associated bioactive priming polypeptides use two distinct modes of action to prevent disease and the spread of disease.

The thionin-flagellin bioactive priming polypeptide combinations can also be used with any other integrated management approach for disease control prescribed for HLB including, but are not limited to, (1) the use of disease-free nursery stock and/or rootstocks for grafting, (2) the use of pesticides and/or systemic insecticides to control the disease-causing psyllid, (3) the use of biological control agents such as injections of antibiotics or parasitic insects that controls the psyllid, (4) breeding new varieties of citrus germplasm with increased resistance to the bacteria responsible for Asian citrus greening disease, (5) controlling parasitic plants (for example, dodder) that may spread the disease, or (6) any combination thereof.

A synthetic version of a phloem targeting polypeptide (SEQ ID NO: 641) is particularly useful in targeting antimicrobial polypeptides to the phloem sieve tube and companion cells and can be useful for treating various bacterial diseases of plants, such as bacterial leaf streak, Asian citrus greening or Huanglonging and citrus canker.

In addition, flagellin or flagellin associated polypeptides are useful for treating Asian citrus greening, especially when used in combination with a bacteriocide. For instance, flagellin or flagellin associated polypeptides having amino acid sequences comprising any one of SEQ ID NOs: 226, 571, and 752 can be used. Preferably, the bacteriocide comprises oxytetracycline.

Citrus Canker

"Peptide priming" methods were developed for use with the bioactive priming thionin and flagellin-associated polypeptides as described in Table 19 (thionins) and Tables 1-5 (flagellin and flagellin-associated polypeptides) to prophylactically treat citrus plants prior to any visible symptoms of the citrus canker disease or as a treatment once the onset of disease symptoms become apparent.

Citrus canker occurs primarily in tropical and sub-tropical climates and has been reported to occur in over thirty countries including spread of infection reported in Asia, Africa, the Pacific and Indian Oceans Islands, South America, Australia, Argentina, Uruguay, Paraguay, Brazil and the United States. Citrus canker is a disease caused by the bacterium, *Xanthomonas axonopodis* pv. *citri* or pv. *aurantifolii* (also referred as *Xanthomonas citri* subsp. *citri*) that infect foliage, fruit and young stems. Symptoms of citrus canker infection on leaves, and fruit of the citrus shrubs/trees can result in leaf-spotting, leaf lesions, defoliation, die back, deformation of fruit, fruit rind-blemishing, pre-mature fruit drop, and canker formation on leaves and fruits. Diagnostic symptoms of citrus canker include a characteristic yellow halo that surrounds the leaf lesions and a water-soaked margin that develops around the necrotic tissue on the leaves of the citrus plant. The citrus canker pathogen can spread through the transport of infected fruit, plants, and equipment. Dispersal can also be facilitated by the wind and rain. Overhead irrigation systems may also facilitate movement of the citrus canker causing pathogen. Infected stems can harbor the citrus canker causing bacteria (*Xanthomonas axonopodis* pv. *citri*) in the stem lesions for transmission to other citrus plants. Insects, such as the Asian leafminer (*Phyllocnistis citrella*) also disseminate the disease.

In general, citrus plants susceptible to the citrus canker disease include orange, sweet orange, grapefruit, pummelo, mandarin tangerine, lemon, lime, swingle acid lime, palestine sweet lime, tangerine, tangelo, sour orange, rough lemon, citron, calamondin, trifoliate orange and kumquat. World-wide, millions of dollars are spent annually on prevention, sanitation, exclusion, quarantine and eradication programs to control citrus canker (Gottwald T. R. "Citrus Canker," The American Phytopathological Society, The Plant Health Instructor 2000/updated in 2005). Treatment for the disease has included application of antibiotics or disinfectants, the use of copper-based bactericidal sprays, and pesticide applications for Asian leafminer control.

The bioactive priming polypeptide combination comprising the thionin and the flagellin-associated polypeptides can 34be applied to a citrus plant or citrus plant part (e.g., rootstock, scion, leaves, roots, stems, fruit, and foliage) using application methods that can comprise: spraying, inoculating, injecting, soaking, infiltrating, washing, dipping and/or provided to the surrounding soil as an in furrow treatment.

The methods are provided using the bioactive priming polypeptides comprising the thionin and/or flagellin-associated polypeptides to pre-treat citrus plants or citrus plant parts (e.g., root stock, scion, leaves, roots, stems, fruit, and foliage) prior to any visible occurrence of symptoms. They are also useful for providing an increase in resistance to the citrus canker pathogen resulting in a reduction in disease symptoms.

Additionally, the methods of using the bioactive priming polypeptides such as the flagellin and flagellin-associated polypeptides are useful to treat citrus plants or citrus plant parts (e.g., root stock, scion, leaves, roots, stems, fruit, and foliage) once the early onset of citrus canker disease symptoms or when the symptoms of the disease become apparent.

Application of the Flg polypeptides for treating citrus plants to prevent, reduce or eliminate the spread of the citrus canker disease can be delivered by injecting into the phloem of a shrub or tree, spraying, washing, adding as a soak or a drench to the soil or soil area surrounding a plant or provided in furrow.

Thionin bioactive priming polypeptides as described herein (Table 17) can be applied individually or in combination with any of the flagellin-associated Flg polypeptides (Tables 1-5) as a foliar treatment or spray or as an injection and are useful for the prevention of infestation of citrus plants from insects such as the Asian leafminer (*Phyllocnistis citrella*) that have been identified in the dissemination of the bacteria (*Xanthomonas axonopodis* pv. *citri*) that cause the citrus canker disease.

Citrus Plants

Any of the methods described herein to provide improved plant health, disease tolerance or disease treatment applications to treat or prevent Asian citrus greening (HLB) or citrus canker are suitable for use with any citrus plants and shrubs/trees.

The thionin or flagellin-associated polypeptides or compositions comprising the thionin or flagellin-associated polypeptides as described herein can be applied to any citrus shrub and/or tree and to any agronomically-important citrus hybrid or citrus non-hybrid plant, and are useful for prophylactically treating the citrus to prevent the onset of an infection or providing treatment after an infection has occurred.

Citrus plant species for use of the methods described herein include, but are not limited to: Sweet orange (*Citrus sinensis, Citrus maxima×Citrus reticulata*), Bergamot Orange (*Citrus bergamia, Citrus limetta×Citrus aurantium*), Bitter Orange, Sour Orange or Seville Orange (*Citrus aurantium, Citrus maxima×Citrus reticulata*), Blood Orange (*Citrus sinensis*), Orangelo or Chironja (*Citrus paradisi×Citrus sinensis*), Mandarin Orange (*Citrus reticulate*), Trifoliate Orange (*Citrus trifoliata*), Tachibana Orange (*Citrus tachibana*), Clementine (*Citrus clementina*), Cherry Orange (*Citrus kinokuni*), Lemon (*Citrus limon, Citrus maxima×Citrus medica*), Indian Wild Orange (*Citrus indica*), Imperial Lemon (*Citrus limon, Citrus medica×Citrus paradisi*), Lime (*Citrus latifoli, Citrus aurantifolia*), Meyer Lemon (*Citrus meyeri*); hybrids of *Citrus xmeyeri* with *Citrus maxima, Citrus medica, Citrus paradisi* and/or *Citrus sinensis*), Rough Lemon (*Citrus jambhiri*), Volkamer Lemon (*Citrus volkameriana*), Ponderosa Lemon (*Citrus limon×Citrus medica*) Kaffir Lime (*Citrus hystrix* or *Mauritius papeda*), Sweet Lemon, Sweet Lime, or Mosambi (*Citrus limetta*), Persian Lime or Tahiti Lime (*Citrus latifolia*), Palestine Sweet Lime (*Citrus limettioides*), Winged Lime (*Citrus longispina*), Australian Finger Lime (*Citrus australasica*), Australian Round Lime (*Citrus australis*), Australian Desert or Outback Lime (*Citrus glauca*), Mount White Lime (*Citrus garrawayae*), Kakadu Lime or Humpty Doo Lime (*Citrus gracilis*), Russel River Lime (*Citrus inodora*), New Guinea Wild Lime (*Citrus warburgiana*), Brown River Finger Lime (*Citrus wintersii*), Mandarin Lime (*Citrus limonia*; (hybrids with *Citrus reticulata×Citrus maxima×Citrus medica*), Carabao Lime (*Citrus pennivesiculata*), Blood Lime (*Citrus australasica×Citrus limonia*) Limeberry (*Triphasia brassii, Triphasia grandifolia, Triphasia trifolia*), Grapefruit (*Citrus paradisi; Citrus maxima×Citrus xsinensis*), Tangarine (*Citrus tangerina*), Tangelo (*Citrus tangelo; Citrus reticulata×Citrus maxima* or *Citrus paradisi*), Minneola Tangelo (*Citrus reticulata×Citrus paradisi*), Orangelo (*Citrus paradisi×Citrus sinensis*), Tangor (*Citrus nobilis; Citrus reticulata×Citrus sinensis*), Pummelo or Pomelo (*Citrus maxima*), Citron (*Citrus medica*), Mountain Citron (*Citrus halimii*), Kumquat (*Citrus japonica* or *Fortunella* species), Kumquat hybrids (Calamondin, *Fortunella japonica*; Citranqequat, *Citrus ichangensis*; Limequat, *Citrofortunella floridana*; Orangequat, hybrid between *Satsuma mandarin×Citrus japonica* or *Fortunella* species; Procimequat, *Fortunella hirdsiie*; Sunquat, hybrid between *Citrus meyeri* and *Citrus japonica* or *Fortunella* species; Yuzuquat, hybrid between *Citrus ichangensis* and *Fortunella margarita*), Papedas (*Citrus halimii, Citrus indica, Citrus macroptera, Citrus micrantha*), Ichang Papeda (*Citrus ichangensis*), Celebes Papeda (*Citrus celebica*), Khasi Papeda (*Citrus latipes*), Melanesian Papeda (*Citrus macroptera*), Ichang Lemon (*Citrus ichangensis×Citrus maxima*), Yuzu (*Citrus ichangensis×Citrus reticulata*), Cam sành (*Citrus reticulata×Citrus maxima*), Kabosu (*Citrus sphaerocarpa*), Sudachi (*Citrus sudachi*), Alemow (*Citrus macrophylla*), Biasong (*Citrus micrantha*), Samuyao (*Citrus micrantha*), Kalpi (*Citrus webberi*), Mikan (*Citrus unshiu*), Hyuganatsu (*Citrus tamurana*), Manyshanyegan (*Citrus mangshanensis*), Lush (*Citrus crenatifolia*), Amanatsu or Natsumikan (*Citrus natsudaidai*), Kinnow (*Citrus nobilis×Citrus deliciosa*), Kiyomi (*Citrus sinensis×Citrus unshiu*), Oroblanco (*Citrus maxima×Citrus paradisi*), Ugli (*Citrus reticulata×Citrus maxima* and/or *Citrus×paradisi*), Calamondin (*Citrus reticulata×Citrus japonica*), Chinotto (*Citrus myrtifolia, Citrus aurantium* or *Citrus pumila*), Cleopatra Mandarin (*Citrus reshni*), Daidai (*Citrus aurantium* or *Citrus daidai*), Laraha (*Citrus aurantium*), Satsuma (*Citrus unshiu*), Naartjie (*Citrus reticulata×Citrus nobilis*), Rangpur (*Citrus limonia*; or hybrid with *Citrus sinensis×Citrus maxima×Citrus reticulata*), Djeruk Limau (*Citrus amblycarpa*), lyokan, anadomikan (*Citrus iyo*), Odichukuthi (*Citrus odichukuthi*), Ougonkan (*Citrus flaviculpus*), Pompia (*Citrus monstruosa*), Taiwan Tangerine (*Citrus depressa*), Shonan gold (*Citrus flaviculpus* or *Citrus unshiu*), Sunki (*Citrus sunki*), Mangshanyen (*Citrus mangshanensis, Citrus nobilis*), Clymenia (*Clymenia platypoda, Clymenia polyandra*), Jabara (*Citrus jabara*), Mandora (*Mandora cyprus*), Melogold (*Citrus grandis×Citrus paradisfil Citrus maxima/Citrus grandis*), Shangjuan (*Citrus ichangensis×Citrus maxima*), Nanfengmiju (*Citrus reticulata*), and Shīkwāsaī (*Citrus depressa*).

The thionin and/or flagellin-associated priming polypeptides can be applied to any citrus plant, shrub/tree used for medicinal or cosmetic/health and beauty purposes, such as Bergamot Orange (*Citrus bergamia*), Sour or Bitter Orange (*Citrus aurantium*), Sweet Orange (*Citrus macrophylla*), Key Lime (*Citrus aurantiifolia*), Grapefruit (*Citrus paradisi*), Citron (*Citrus medica*), Mandarin Orange (*Citrus reticulate*), Lemon (*Citrus limon*, or hybrids with *Citrus medica*×*Citrus maxima, Citrus limonia, Citrus medica*× *Citrus maxima*×*Citrus medica*), Sweet Lime (*Citrus limetta*), Kaffir Lime, (*Citrus hystrix* or *Mauritius papeda*), Lemon hybrid or Lumia (*Citrus medica*×*Citrus limon*), (*Citrus medica*×*Citrus maxima*×*Citrus medica*), Omani Lime (*Citrus aurantiifolia, Citrus medica*×*Citrus micrantha*), Jambola (*Citrus grandis*), Kakadu Lime or Humpty Doo Lime (*Citrus gracilis*), Pomelo (*Citrus retkulata*), Tangor (*Citrus nobilis*), and Sour Lime or Nimbuka (*Citrus acida*).

Exemplary important citrus hybrids for fruit production are: Sweet Orange (*Citrus sinensis*), Bitter Orange (*Citrus aurantium*), Grapefruit (*Citrus paradisi*), Lemon (*Citrus limon*), Persian Lime (Citrus *latifolia*), Key Lime (*Citrus aurantiifolia*), Tangerine (*Citrus tangerine*) and Rangpur (*Citrus limonia*).

Additionally, any of the bioactive priming polypeptides, compositions, and methods as described herein can be applied to any citrus plant, shrub/tree used as a rootstock and/or a scion germplasm. The methods are particularly useful for rootstocks commonly used in grafting of citrus to enhance the merits of the scion varieties, which can include tolerance to drought, frost, disease or soil organisms (for example, nematodes). Such citrus plants that provide useful rootstocks include: Sour or Bitter Orange (*Citrus aurantium*), Sweet Orange (Citrus *macrophylla*), Trifoliate Orange (*Poncirus trifoliata*), Rough Lemon (*Citrus jambhiri*), Volkamer Lemon (*Citrus volkameriana*), Alemow (*Citrus macrophylla*), *Cleopatra Mandarin* (*Citrus reshini*), Citrumelo (hybrids with x *citroncircus* species), Grapefruit (*Citrus paradisi*), Rangpure Lime (*Citrus limonia*), Palestine Sweet Lime (*Citrus limettioides*) and Troyer Citrange (*Citrus sinensis*×*Poncirus trifoliata* or *Citrus sinensis*×*Citrus trifoliata*) and Citrange (*Citrus sinensis*×*Poncirus trifoliata* or *C. sinensis*×*C. trifoliata*).

Use of Retro-Inverso Flg Bioactive Priming Polypeptides to Treat and Reduce Citrus Greening Combinations of flagellin-associated polypeptides paired with their retro-inverso counterparts can be used to treat and reduce the greening effect on citrus that results in Asian citrus greening or Huanglongbing disease.

An early symptom of HLB in citrus is the yellowing of leaves on an individual limb or in one sector of a tree's canopy. Leaves that turn yellow from HLB will show an asymmetrical pattern of blotchy yellowing or mottling of the leaf, with patches of green on one side of the leaf and yellow on the other side. As the HLB disease progresses, the fruit size becomes smaller, and the juice turns bitter. The fruit can remain partially green and tends to drop prematurely.

Treatment combinations of Flg polypeptides with their retro-inverso (RI) forms can be used to minimize the effect on citrus fruit greening. Such treatment combinations can be applied on HLB-infected trees. The retro-inverso forms will compete with the native forms of Flg polypeptides for binding to the FLS-associated receptor(s) at the plant surface and thus inhibit/delay the symptom formation of greening associated with HLB disease. The native Flg22 and RI Flg22 combinations assist with a fine tuned immune response to reduce and even eliminate the disease-causing bacteria, *Candidatus Liberibacter asiaticus*, while preventing acute symptom development, such as leaf yellowing and citrus fruit greening.

EXAMPLES

The following non-limiting examples are provided to further illustrate the present invention.

Example 1: Application of Bt.4Q7Flg22 and Retro-Inverso Bt.4Q7Flg22, and Ec.Flg22 and Ec. RI Flg22 to Corn The effect of Bt.4Q7Flg22 (SEQ ID NO: 226) and retro-inverso Bt.4Q7Flg22 (SEQ ID NO: 376), as well as Ec. Flg22 (SEQ ID NO 526) and Ec. RI Flg22 (SEQ ID 527) bioactive priming polypeptides on corn (BECK'S 5828 YH, 6175YE) yield was determined in 10 separate locations in the US Midwest (FIG. 2 and FIG. 3).

Field seed beds at each location were prepared using conventional or conservation tillage methods for corn plantings. Fertilizer was applied as recommended by conventional farming practices and remained consistent between the US Midwest locations. Herbicides were applied for weed control and supplemented with cultivation when necessary. Four-row plots, 17.5 feet (5.3 meters) long were planted at all locations. Corn seed was planted 1.5 to 2 inches (3.8 to 5.1 cm) deep, to ensure normal root development, at 28,000 to 36,000 plants per acre with row widths of 30 inch (76.2 cm) rows with seed spacing of approximately 1.6 to 1.8 seeds per foot. Each hybrid was grown in at least three separate plots (replicates) at each location to account for field variability.

Native Bt.4Q7Flg22 bioactive priming polypeptide (SEQ ID NO: 226) and its retro-inverso polypeptide (SEQ ID NO: 376) were chemically synthesized via solid phase peptide synthesis and formulated at 0.33 Fl. oz/Ac (24.1 mL/hectare, Ha) use rate. The final concentration in the spray tank was 25 nM after dilution in carrier rate of 10 gallons water/Ac (37.85 L/Ha). Native Bt.4Q7Flg22 bioactive priming polypeptides were applied during first and second year field trials to measure effects across a multi-year growing season. Retro-inverso polypeptides were applied during the first year field trials to compare with native Bt.4Q7Flg22. Bioactive priming polypeptides were applied as foliar spray applications at 0.33 Fl. oz/Ac (24.1 mL/Ha) use rate during the V5-V8 development stage. Each polypeptide was applied with a non-ionic surfactant at 0.5%. The effect of bioactive priming polypeptides was measured as the absolute changes in yield in bushels per acre (Bu/Ac). Additionally, the win rate was calculated: the percentage of testing locations at which one treatment has a yield advantage over other treatments (in this case, as compared to the non-treated control plants).

Figure 2:
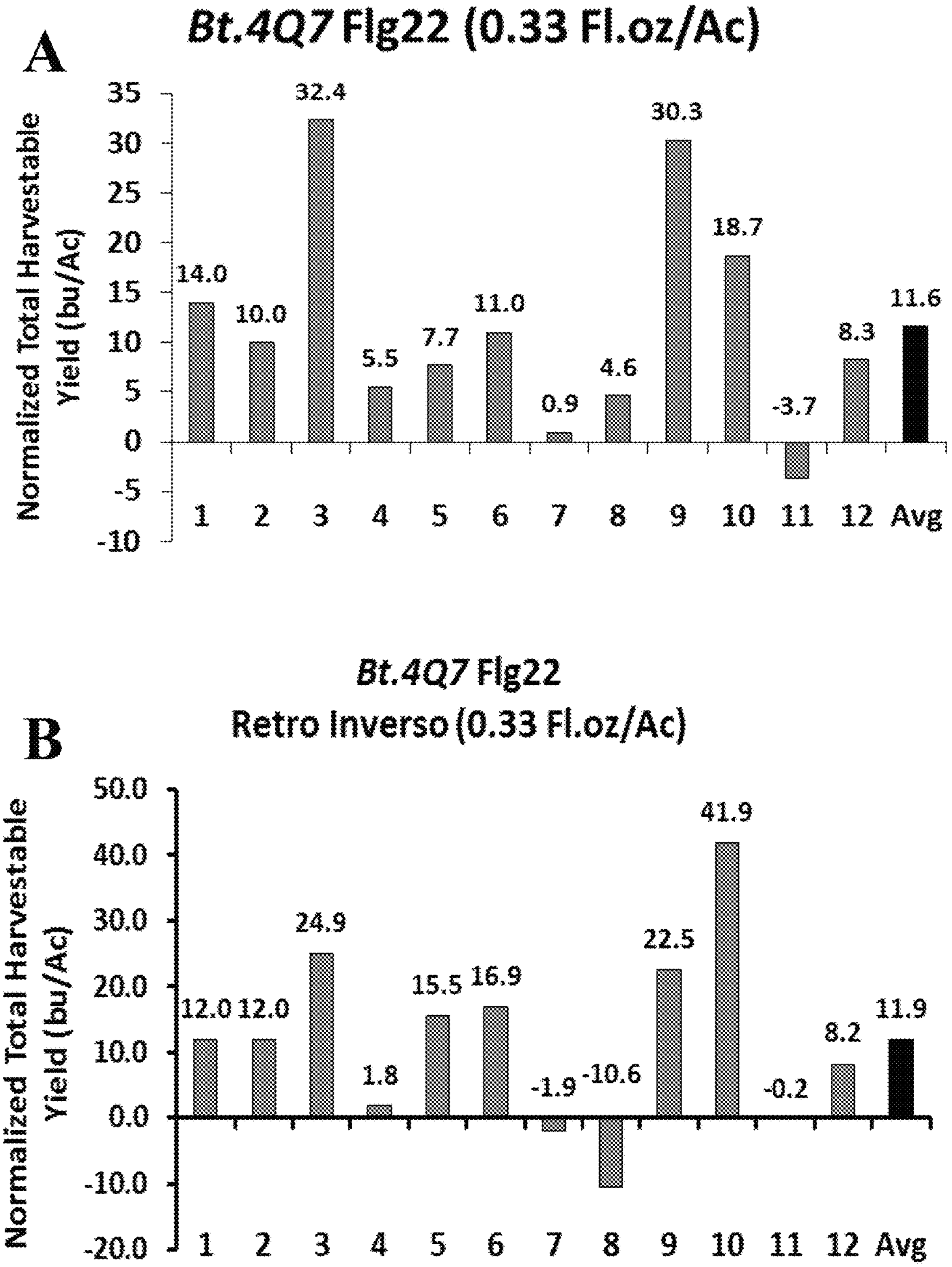
FIG. 2 illustrates total harvestable yield in corn that received foliar applications with Bt.4Q7Flg22 (SEQ ID NO:226) in 12 locations (panel A) and retro inverso (RI) version of Bt.4Q7Flg22 (SEQ ID NO: 375) bioactive priming polypeptides in 10 locations (panel B) and reported in Bu/Ac as compared to yield in the non-treated control.
Figure 3:
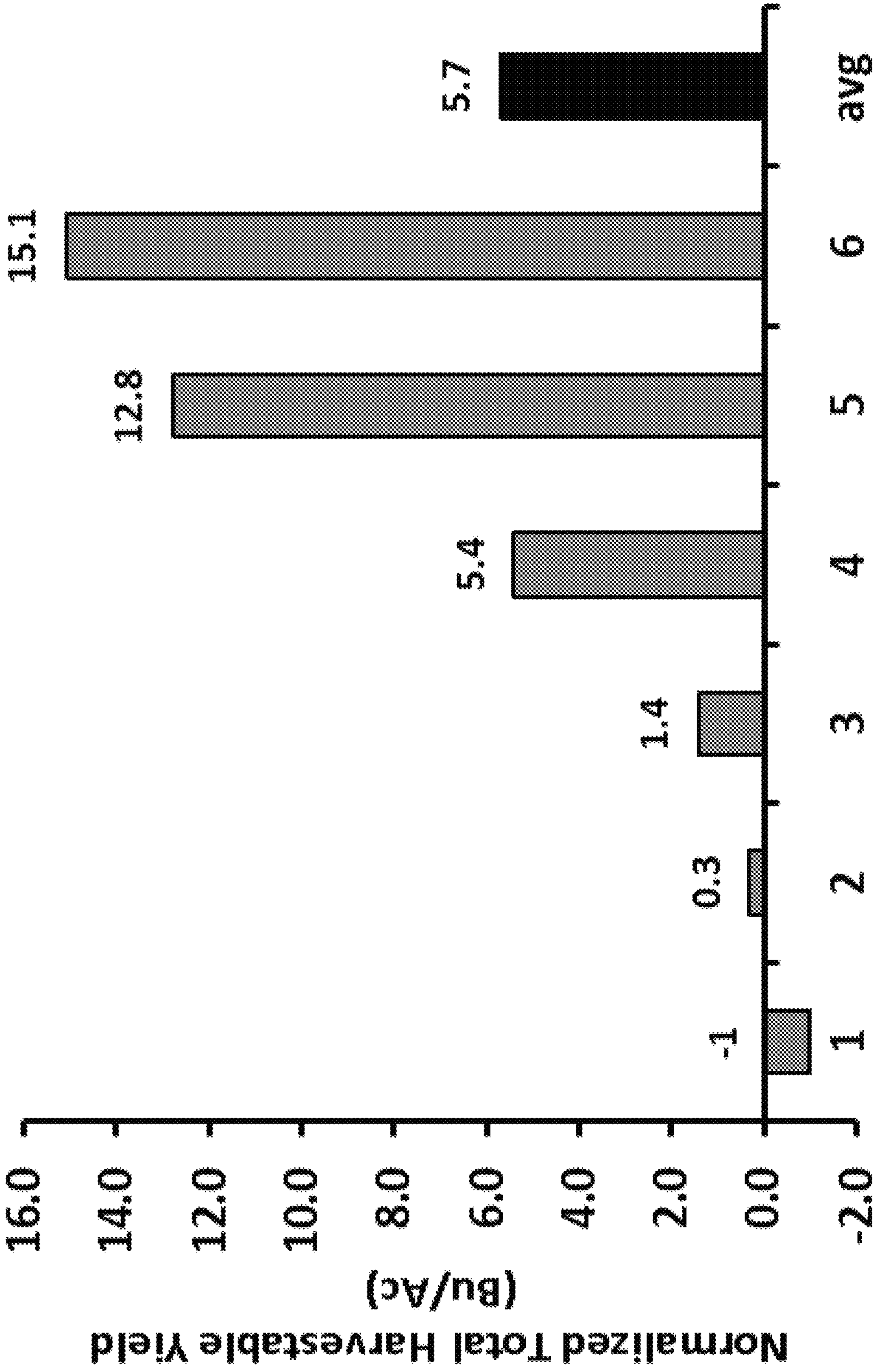
FIG. 3 illustrates total harvestable yield in corn that received foliar applications with Bt.4Q7Flg22 bioactive priming polypeptide (SEQ ID NO: 226) in 6 locations and reported in Bu/Ac as compared to yield in the non-treated control.

FIG. 2, panel A shows that during the first year field trials, foliar spray application of Bt.4Q7Flg22 (SEQ ID NO: 226) resulted in an average yield increase of 11.60 Bu/Ac (728.1 kg/Ha) and a win rate of 90% across the 10 locations compared to the non-treated control corn plants. FIG. 2, panel B shows that foliar spray applications of retro inverso Bt.4Q7Flg22 bioactive priming polypeptide (SEQ ID NO: 376) resulted in an average yield increase of +11.90 Bu/Ac (746.9 kg/Ha) and a win rate of 70% across the 10 locations in the US Midwest compared to the non-treated control corn plants. In both figures, locations (1-12) are reported on the x-axis and absolute change in yield Bu/Ac is reported on the y-axis and above or below the bar graphs at each location.

Ec. Flg22 polypeptide delivered to corn yielded 8.2 bu/Ac (514.7 kg/Ha) advantage with a 80% win rate across the 10 sites. The retro inverso version of Ec. RI Flg22 did not yield as well, giving 1.9 bu/c across the 10 sites with a 50% win rate.

The second year field trials were conducted using large acre field trials at 10-11 locations in the US MidWest (IL, IN, IA) and employed foliar spray application of the Bt.4Q7Flg22 bioactive priming polypeptide (SEQ ID NO: 226) provided to V8 corn plants (Dekalb 5064). Foliar spray application of Bt.4Q7Flg22 was applied at a use rate of 0.33 fluid ounces per acre (Fl. oz/Ac). As shown in FIG. 3, foliar application using the Bt.4Q7Flg22 bioactive priming polypeptide resulted in an average yield increase of +4.8 Bu/Ac over the control across the 11 locations with a win rate of 83%. Locations 1-6 are reported on the x-axis and absolute change in yield Bu/Ac is reported on the y-axis and above or below the bar graphs at each location.

First year field trials using foliar treatments using Bt.4Q7Flg22 bioactive priming polypeptide (SEQ ID NO: 226) applied to corn hybrid (BECK's 5828 YH) shown in FIG. 2 (panel A) resulted in over a +11 Bu/Ac (690.4 kg/Ha) increase in yield over the non-treated control plants. Second year field trials applied to V8 corn plants (Dekalb 5064) shown in FIG. 3 resulted in an almost+5 Bu/Ac (313.8 kg/Ha) increase compared to the yield of the non-treated control plants. The combined average for the two corn hybrids resulted in a 2-year average yield increase of +8.0 Bu/Ac (50.2 kg/Ha) across locations with a win rate of 86% represented for the multiple year growing season.

A third study was performed with Bt.4Q7 Flg22 bioactive priming polypeptide tested as a V5-V8 application to corn at 3 rates and applied with a non-ionic surfactant. The final use rates were 0.33 Fl. oz/Ac, 4 Fl. oz/Ac, 8 Fl. oz/Ac (24.1 mL/Ha, 292.3 mL/Ha, 584.6 mL/Ha), resulting in approximate final concentrations of 25 nM, 300 nM, 600 nM respectively. Each study was performed at between 10 and 11 sites. The end results of the study at V5-V8 at 0.33 Fl. oz/Ac (24.1 mL/Ha) was 5.75 Bu/Ac or 360.9 kg/Ha advantage, at 4 Fl. oz/Ac a 3.77 bu/Ac or 236.6 kg/Ha advantage, and at 8 Fl. oz/Ac a 5.05 Bu/Ac or 317 kg/Ha.

Example 2: Application of Bt.4Q7Flg22 to V8 Corn with Fungicide

Foliar treatments with Bt.4Q7Flg22, with and without a commercially available fungicide, STRATEGO YLD, were conducted to determine if synergistic effects resulted from the combinations of the Bt.4Q7Flg22 bioactive priming polypeptide with the fungicide. Foliar spray application of Bt.4Q7Flg22 (SEQ ID NO: 226) alone or in combination with STRATEGO YLD was assessed on corn plants (hybrid Dekalb 5064) at the V8 stage of development.

Replicated trials were conducted at 6-8 locations throughout the US Midwest (IA, IL, IN) using replicated trials. Corn plants were grown as described in Example 1. Plots were maintained using the individual grower's production practices and each plot was replicated 3-4 times. When used, STRATEGO YLD fungicide (a combination of prothioconazole and trifloxystrobin) was applied using the recommended label rates (4.0 Fl.oz/Ac or 292.3 mL/Ha)) at each location. Foliar treatment applications consisted of the following treatments: (a) non-treated control, (b) STRATEGO YLD fungicide alone, and Bt.4Q7Flg22 (SEQ ID NO: 226) delivered in a free peptide form provided with (c) and without (d) the fungicide. Bt.4Q7Flg22 was applied at a use rate of 0.33 or 4.0 fluid ounces per acre (Fl. oz/Ac) or (24.1 or 292.3 mL/Ha).

Corn yield in bushels per acre (Bu/Ac) was reported at all locations as an average yield for the replicated trials at each location. The change in yield in Bu/Ac for corn plants receiving foliar applications with the STRATEGOYLD fungicide were normalized to the average yield for the control corn plants for the 6 locations (Table 22).

Foliar treatments with Bt.4Q7Flg22 provided at 0.33 Fl. oz/Ac (24.1 mL/Ha) provided yield benefits over the non-treated control corn plants with a +4.84 Bu/Ac (303.8 kg/Ha) increase observed across the 6 locations. Foliar treatment using only the fungicide application of STRATEGO YLD also provided a yield benefit in corn of +4.88 Bu/Ac (306.3 kg/Ha) over the control plants. Application of the free peptide, Bt.4Q7Flg22, at 0.33 Fl. oz/Ac (24.1 mL/Ha) combined with STRATEGO YLD fungicide at 4.0 Fl. oz/Ac demonstrated a synergistic effect, resulting in an average of +10.72 Bu/Ac (672.9 kg/Ha) over the non-treated control plants. Therefore, the Bt.4Q7Flg22 polypeptide and fungicide treatment combination resulted in a synergistic effect at the 0.33 Fl. oz/Ac (24.1 mL/Ha) use rate for the polypeptides and 4.0 Fl. oz/Ac (292.3 mL/Ha) use rate for the fungicide.

TABLE 22

Foliar treatment of corn with Bt.4Q7Flg22 bioactive priming polypeptide applied with a fungicide to increase yield in corn

| Treatment - Corn | Application Use Rate Fl. oz/Ac | Average Total Yield Bu/Ac (6 locations) | Average Bu/Ac Increase compared to Control |
|---|---|---|---|
| Control | — | 187.37 | — |
| Bt.4Q7Flg22 | 0.33 | 192.21 | +4.84 |
| STRATEGO YLD | 4.0 | 193.80 | +4.88 |
| Bt.4Q7Flg22 + STRATEGO YLD | 0.33<br>4.0 | 207.86 | +10.72 |

A second study looking at the combination of Ec. Flg22 with STRATEGO was also performed at 8 sites as replicated trials in the same fashion as above. Ec. Flg22 at 4 Fl. oz/Ac (292.3 mL/Ha) added 1.3 (Bu/Ac) (81.6 kg/Ha) on top of STRATEGO YLD with a 63% win percentage over 8 sites. This demonstrates that both Flg22 polypeptides were able to add benefit over a commercial fungicide, STRATEGO YLD.

Figure 4:
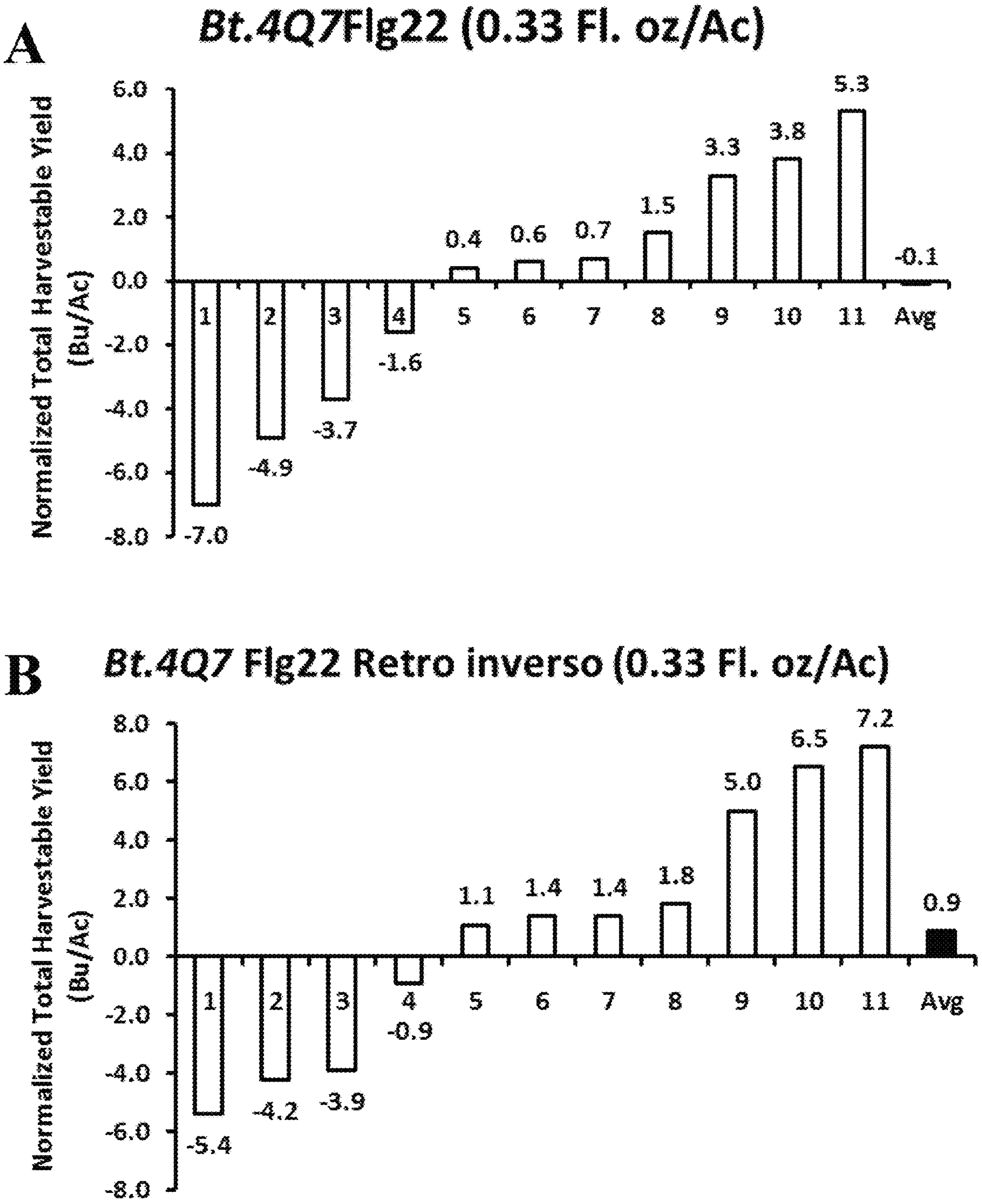
FIG. 4 illustrates total harvestable yield in soybean that received foliar applications with Bt.4Q7Flg22 (SEQ ID NO: 226) (panel A) and retro inverso (RI) Bt.4Q7Flg22 (SEQ ID NO: 375) (panel B) bioactive priming polypeptides in 11 locations and reported in Bu/Ac as compared to yield in the non-treated control.

Example 3: Application of Bt.4Q7 Flg22, Retro-Inverso Bt.4Q7Flg22, Ec.Flg22, Retro Inverso Ec.Flg22 or RHPP to R2 Soybean—Increased Yield Foliar application using, Bt.4Q7 Flg22 bioactive priming polypeptide (SEQ ID NO: 226; FIG. 4, panel A), the retro-inverso (RI) Bt.4Q7Flg22 (SEQ ID NO: 376; FIG. 4, panel B) from *Bacillus thuringiensis* strain 4Q7 and root hair promoting polypeptide (RHPP, SEQ ID NO: 600) derived from *Glycine max* were applied individually to soybean plants (commercial hybrid Beck's 294 NR) at the R2 stage of development using a use rate of 0.33 Fl. oz/Ac or 24.1 mL/Ha (Flg22 polypeptides) or 4.0 Fl. oz/Ac or 292.3 mL/Ha (RHPP). Cultivation methods employed in Example 1 were followed in growing soybean seeds. Soybean seed (commercial hybrid Beck's 294 NR) was planted 1.5 to 2 inches (3.8 to 5.1 cm) deep to assure normal root development. Soybean seed was planted at approximately on average 150,000 plants per acre with row widths of 30 inch (76.2 cm) rows with seed spacing of approximately 7 to 8 seeds per foot (0.3 meter).

Yield results in bushels per acre (Bu/Ac) are reported for soybean grown in 11 separate US Midwest locations harvested in October (FIG. 4). Soybean yield (Bu/Ac) is also reported as averaged across all of the locations as the change in yield (Bu/Ac) normalized to the control soybean plants. Soybean yield following foliar application with Bt.4Q7Flg22 (SEQ ID NO: 226) and the RI Bt.4Q7Flg22 (SEQ ID NO: 376) was compared to yield of non-treated soybean plants and plotted in FIG. 4. Locations 1-11 are reported on the x-axis. Absolute change in yield (Bu/Ac) as compared to the non-treated control soybean plants is reported on the y-axis and above or below the bar graphs at each location. Average yield across all 11 locations are reported and highlighted with the black bar. Soybean yield for the Bt4Q7Flg22 and RI Bt.4Q7Flg22 foliar treated plants showed similar trends at the 11 different locations. Spray application using RI Bt.4Q7Flg22 on soybean resulted in an average yield increase of 0.90 Bu/Ac (60.5 kg/Ha) for the 2 soybean hybrids across 11 locations compared to the soybean non-treated control plants. Yield results for the natural (all L) Bt.4Q7Flg22 in soybean was neutral (−0.1 Bu/Ac or −6.7 kg/Ha)) when compared across the locations. Yield data represented across 11 individual US Midwestern locations resulted in a win rate of 64%, for both the RI Bt.4Q7Flg22 and Bt.4Q7Flg22 spray application treatments as compared to the control or non-treated soybean plants. The addition of RHPP polypeptide at 4 Fl. oz/Ac (292.3 mL/Ha) in the same study increased yield by 1.2 Bu/Ac (80.7 kg/Ha) compared to control.

A second study was performed to test Ec. Flg22 and Ec. RI Flg22 polypeptides as R2 foliar treatments on soybeans with a carrier rate of 10 gallons/Ac (93.5 L/Ha) water and NIS surfactant. A concentration of 100 nM was obtained in the tank for each treatment. The application of the Ec. Flg22 lead to a 0.9 Bu/Ac (60.5 kg/Ha) increase with a 82% win rate for the 11 sites, and the Ec. RI Flg22 lead to a 0.6 Bu/Ac (40.3 kg/Ha) increase with a 80% win rate over 10 sites. Also included was the RHPP polypeptide as a seed treatment, with 1.2 bu/Ac (80.7 kg/Ha) over 11 sites at 73% win rate.

A third study at the same 11 sites was performed adding a foliar fertilizer alone or with RHPP at 8 fl oz/Ac (584.6 mL/Ha). The addition of RHPP on top of the foliar fertilizer gave 1 Bu/AC (67.2 kg/Ha) advantage across the 11 sites.

Example 4: Foliar Spray Application of Flg22 Polypeptides to Soybeans

Foliar treatments with Bt.4Q7Flg22, Ec.Flg22, and RHPP at 4.0 and 8.0 Fl. oz/Ac (292.3 and 584.6 mL/Ha) were tested at the R2 timing on soybean varieties over 11 sites with 10 gallons/Ac (93.5 L/Ha) water with 0.5% NIS surfactant. At the higher dose of 8 Fl. oz/Ac (584.6 mL/Ha), the Ec. Flg22 polypeptide gave a 0.74 Bu/Ac (49.8 kg/Ha) advantage and the Bt.4Q7 Flg22 gave a 0.88 Bu/Ac (59.2 kg/Ha) advantage. The lower rate of 4 Fl. oz/Ac (292.3 mL/Ha) for RHPP gave 0.31 Bu/Ac (20.9 kg/Ha) yield advantage.

Example 5: Application of *Escherichia coli* Flagellin Polypeptides to Increase Yield—Corn The effect of flagellin polypeptides derived from *Escherichia coli* on corn yield was then tested. Corn plants (Beck's 5828 YH) received an initial spray application at the V5-V8 stage of development with formulations containing the Ec. Flg22 bioactive priming polypeptide (SEQ ID NO: 526) and the retro-inverso RI Ec.Flg22 (SEQ ID NO: 527) from *Escherichia coli* applied at a use rate of 0.33 Fl. oz/Ac (24.1 mL/Ha). Yield results in bushels per acre (Bu/Ac) were determined for corn grown in the 12 separate locations harvested in October.

Figure 5:
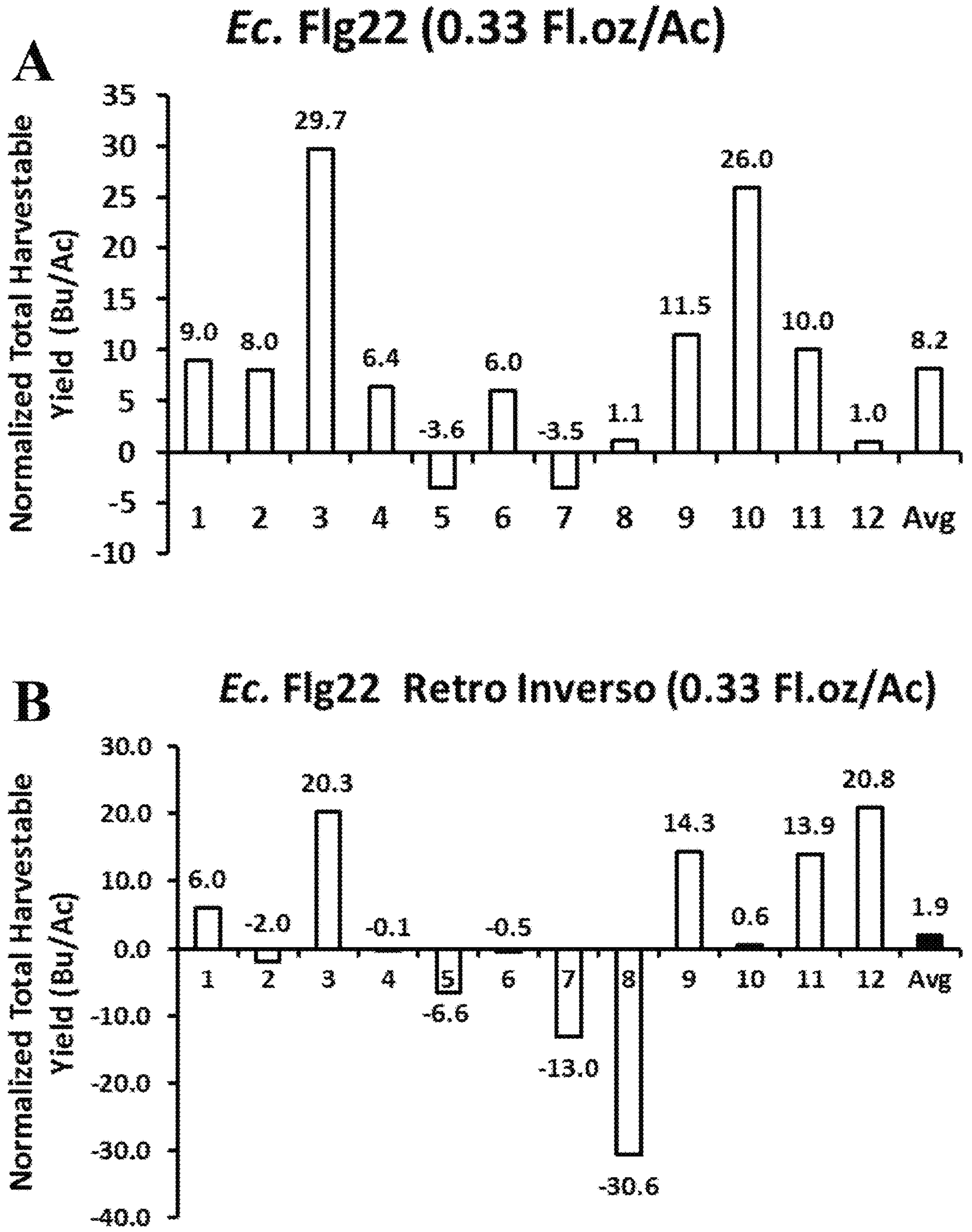
FIG. 5 illustrates total harvestable yield in corn that received foliar applications with Ec.Flg22 (SEQ ID NO: 526) (panel A) and retro inverso with Ec.Flg22 (SEQ ID NO: 527) (panel B) bioactive priming polypeptides in 12 locations and reported in Bu/Ac as compared to yield in the non-treated control.

FIG. 5 depicts yield across these 12 locations, normalized to the non-treated control plants and shown as an increase or a decrease in Bu/Ac compared to the control. Yield data represented for 12 individual locations in Illinois resulted in a win rate of 50%. Corn plants that received a foliar spray application of Ec.Flg22 bioactive priming polypeptide (FIG. 5, panel A) resulted in an average yield increase of +8.2 Bu/Ac (514.7 kg/Ha) across the 12 locations over non-treated plants. Corn plants that received the foliar spray applications of the retro inverso RI Ec.Flg22 bioactive priming polypeptide (FIG. 5, panel B) resulted in an average yield increase of +1.9 Bu/Ac 119.3 kg/Ha) across the 12 locations as compared to the non-treated control corn plants. Therefore, application of foliar sprays containing the Ec.Flg22 (SEQ ID NO: 526) bioactive priming polypeptides provided a beneficial growth response and yield benefit to corn plants when applied at the V5-V8 stage of development.

Example 6: Foliar Application of *Escherichia coli* Flagellin Polypeptides to V2-V3 Soybean to Increase Plant Height Foliar application of the Ec.Flg22 (SEQ ID NO: 526) and retro inverso RI Ec.Flg22 (SEQ ID NO: 527) was applied to soybean (Beck's 297NR). Plants were grown in an environmentally controlled growth room. Seed was planted directly into 39.7 $cm^3$ pots containing Timberline top soil at a depth of 2.54 cm, with 2 seeds per pot. After planting, 50 mL of room temperature water was added to each pot to allow for germination. The pots were kept in an artificial lighted growth room receiving approximately 300 $\mu mol\ m^{-2}\ s^{-1}$ (light photons) for a 13/11 light/day cycle and a 21° C. day/15° C. night temperature range. Plants received the same watering and fertilizer regimes.

Foliar treatments using both the native and retro inverso forms of Ec.Flg22 were applied to 3-week-old soybean plants at the V2 to V3 stage of development using a use rate of 0.33 Fl. oz/Ac (24.1 mL/Ha). Plant height (cm) was measured just prior to the foliar application delivered at 3 weeks and then again 2 weeks later when the plants were 5-weeks-old. Two replicate trials were conducted using 18 plants per trial.

As described in Table 23, foliar application of the Ec.Flg22 polypeptide to soybean at the V2-V3 stage of development increased plant height, compared to the control (water only treatment) plants (Table 23). Foliar application using the Ec.Flg22 (SEQ ID NO: 526) and the retro-inverso Ec.Flg22 (SEQ ID NO: 527) bioactive priming polypeptides resulted in +13% and +16% increases in plant height when normalized to the control non-treated soybean plants (normalized to 100%).

TABLE 23

Foliar application of flagellin polypeptide increases plant height for soybean

| Foliar Treatment | Height (cm) at 3 weeks | Height (cm) at 5 weeks | Percentage height of control |
|---|---|---|---|
| Soybean | | | |
| Ec.Flg22 (1 μM) | 40.17 (5.83) | 64.79 (8.40) | 113.2% |
| Ec.Flg22-Retro Inverso (1 μM) | 36.57 (6.00) | 66.46 (5.77) | 116.1% |

Example 7: Application of Flg22 and Retro Inverso Flg22 in Corn—Plant Height Corn (Beck's hybrid 5828 YH) plants were grown in an environmentally controlled growth room as described in Example 6. Plants were measured three weeks after emergence and then treated with foliar applications of natural (L) and retro-inverso (D) forms of Flg22 polypeptides from *Bacillus thuringiensis* (Bt.4Q7Flg22, SEQ ID Nos 226 and 376) and *Escherichia coli* (Ec.Flg22, SEQ ID NOs: 526-527). Bioactive priming polypeptides were applied as free polypeptides at a concentration of 1 μM. Control plants were treated with water alone. After an additional 2 weeks of growth, plant height was measured (at 5 weeks).

The change in plant height (Δ height cm) between the 2 week and 5 week interval time points was measured and normalized to the growth of water-treated control plants. Three replicate trials were conducted using 9 plants per trial equaling a total of 27 measurements per treatment (Table 24). There were no differences in the plant height measured between the EcFlg22, the Bt.4Q7Flg22 or the water treated control plants at the 3-week measurement time point. The greatest change in plant height from 3 to 5 weeks was reported for corn plants that received the Ec.Flg22 foliar application (A=17.60 cm). These plants also achieved a +8.3% increase in height compared to control plants at the 5 week measurement mark. The two retro inverso polypeptides (RI Ec.Flg22 and RI Bt.4Q7Flg2) and the natural Bt.4Q7Flg22 similarly increased plant height when compared to the control treatment with increases reported from approximately +2% to +4%.

TABLE 24

Foliar application of Ec.Flg22 and Bt.Flg22 polypeptides on corn resulted in increases in plant height

| Foliar Treatment Corn | Height (cm) at 3 weeks (STDEV) | Height (cm) at 5 weeks (STDEV) | Δ Height (cm) | Δ Height Normalized as a percentage of control height |
|---|---|---|---|---|
| Ec. Flg22 1 μM | 47.00 (8.30) | 64.60 (6.93) | 17.60 | +8.3% |
| Ec. Flg22 Retro inverso 1 μM | 48.62 (6.62) | 62.00 (4.07) | 13.38 | +3.9% |
| Bt 4Q7Flg 22 1 μM | 50.10 (6.79) | 61.89 (7.03) | 5.40 | +3.7% |
| Bt 4Q7Flg22 Retro inverso 1 μM | 49.05 (4.28) | 61.03 (7.13) | 11.98 | +2.3% |

Example 8: Application of Retro Inverso Flg22 Bioactive Priming Polypeptides to Promote Growth Under Stress—Corn Abiotic stress causes significant crop loss and can result in major reductions in crop production and yield potential. The flagellin compositions and flagellin-associated bioactive priming polypeptides can be used as chemical priming agents to increase tolerance of a plant to one or more abiotic stresses. Foliar treatments using the Ec.Flg22 and Bt.4Q7Flg22 and the retro inverso (RI) forms of both of these bioactive priming polypeptides were conducted to determine if these foliar applied polypeptides could provide a protective advantage against heat and drought stress.

Corn (Beck's hybrid 5828 YH) seed was planted and grown as described in Example 6 with the difference that a 16 hour day/8 hour night light-cycle was followed. Temperature was cycled from 21° C./day to 15° C./night with 75% humidity. The light cycle still provided a uniform approximately 300 μmol $m^{-2}$ $s^{-1}$, adequate light for plant growth. Plants were measured at 3 weeks after emergence and were then treated with foliar applications of natural or the retro-inverso (RI) forms of Ec.Flg22 (SEQ ID NOs 526-527) or Bt.4Q7Flg22 (SEQ ID NOs: 226 and 376) at 1 μM concentrations. Control plants were treated only with water. A week after the spray treatments were applied, the plants were subdivided into 2 groupings where one group remained in the same standard growth environment as described and the other group was transferred to an environment that provided heat and water deficit stress. In the heat stress environment, the temperature was elevated using heat maps from 21° C. to 27° C. for 18 hours per day for a period of 5 days. Plants were left un-watered for the heat stress duration to further simulate a water deficit stress. Change in plant height (cm) was measured 2 weeks later at 5 weeks and reported as a percentage of the height of the control (water) plants. Measurements are reported as the combined average of two trials with 9 replicate plants per trial (Table 25).

As shown in Table 25, both natural forms of the bioactive priming polypeptides (Ec.Flg22 and Bt.4Q7Flg22) increased plant growth, as measured by control plant height, when applied under non-stressed conditions. The two treatments resulted in plants that reached heights 103% and 108% of their respective controls. However, only corn plants treated with the retro inverso Flg22 polypeptides (both retro inverso Ec.Flg22 and Bt.4Q7Flg22) showed enhanced plant growth compared to control plants when grown in both normal and heat/water stressed environments. Plants treated with Ec, Flg22 Retro inverso reached 103% of their control heights in both conditions. Plants treated with Bt.4Q7Flg22 reached 102% and almost 108% of their counterpart control's heights in non-stressed and stressed conditions, respectively.

Therefore, corn plants that were treated with the retro inverso Flg22 polypeptides (RI-Ec.Flg22 and RI-Bt.4Q7Flg22) exhibited increased growth as indicated by increased percentage in plant height over the control plants. This result suggests that the retro-inverso forms are more stable in form and able to survive without proteolytic breakdown in harsher environments or situations conducive to abiotic stress. Thus, they may offer a protective advantage to plants that are subjected to abiotic stress environments.

TABLE 25

Foliar application of Ec.Flg22 and Bt.Flg22 to corn grown in non-stress and stress environments

| Foliar Treatment in Corn (Non-heat stressed) | Non-Stressed Δ Height (cm) Normalized as a percentage of control height | Stressed Δ Height Normalized as a percentage of control height |
|---|---|---|
| Ec. Flg22 1 μM | 108.3% | 95.8% |
| Ec. Flg22 Retro inverso 1 μM | 103.9% | 103.5% |
| Bt. 4C17Flg 22 1 μM | 103.7% | 100.1% |
| Bt.4Q7Flg22 Retro inverso 1 μM | 102.3% | 107.8% |

Example 9: Heat and Water Deficit Stress after Application of Foliar Flg22 Polypeptide to V2-V3 Corn In a separate experiment, corn plants, grown as described in Example 8, were treated with Bt.4Q7Flg22 along with a surfactant before exposure to heat and water deficit stress. Three replicate trials of 18 corn plant replicates per trial were grown in an environmentally controlled growth room until the V2-V3 stage of development. Each plant was treated with foliar sprays containing 0.1% surfactant with or without Bt.4Q7Flg22 (1 μM final concentration). A week after the spray treatments were applied, the plants were transferred to an environment that provided a heat stress and water deficit stress. Heat stress was applied using heat mats to raise the temperature in the environment from 21° C. to 27° C. During the period of heat stress, the plants were left unwatered. The corn plants remained in the simulated abiotic stress environment for one week and then plant height (cm) was re-measured (Table 26).

As shown in Table 26, in two out of the three trials, application of Bt.4Q7Flg22 polypeptide applied as a foliar spray (Trials 1 and 3) resulted in significant increased growth (height measured in cm) in corn plants as compared to the control plants treated with the surfactant alone. Foliar treatment with the Bt.4Q7Flg22 bioactive priming polypeptide resulted in an almost 13% increase in plant height in Trial 1 and more than a 33% increase in Trial 3 compared to the control (surfactant alone treated) plants.

TABLE 26

Change in plant height in corn with application of Bt.4Q7Flg22

| Treatments Corn | Height (cm) before stress 2 weeks (STDEV) | Height (cm) after stress 4 weeks (STDEV) | Δ Height (cm) | Δ Height Normalized as a percentage of control height |
|---|---|---|---|---|
| Trial 1 | | | | |
| Surfactant (0.1%) | 17.62 (2.32) | 27.96 (3.02) | +10.34 | 100.0% |
| Bt.4Q7Flg22 (1 μM) | 17.72 (2.08) | 29.39 (3.04) | +11.68 | 112.9% |
| Trial 2 | | | | |
| Surfactant (0.1%) | 15.93 (1.22) | 25.26 (1.99) | +9.32 | 100.0% |
| Bt.4Q7Flg22 (1 μM) | 16.03 (1.97) | 25.31 (6.29) | +9.28 | 99.5% |
| Trial 3 | | | | |
| Surfactant (0.1%) | 13.16 (2.28) | 21.43 (2.89) | +8.28 | 100.0% |
| Bt.4Q7Flg22 (1 μM) | 14.99 (1.97) | 26.02 (3.21) | +11.03 | 133.2% |

Example 10: Seed Treatment Using the Flg22 Polypeptides—Corn and Soy

Corn seed from two separate hybrids (hybrid BECK's 5828 AM and 4606 P2) was treated with Bt.4Q7Flg22 (SEQ ID NO: 226) bioactive priming polypeptides with final slurry concentrations of 0.25 μM or 1.0 μM (Table 27) applied to the surface of each seed. The seed applications were provided using a 40 μM polypeptide stock diluted to the appropriate concentration in a slurry containing a fungicide, insecticide, beneficial bacteria, colorant and seed finisher (EverGol Energy (0.031 mg ai/seed), PONCHON/VOTiVO (0.6 mg ai/seed), Peridium 1006 (5 fl oz/cwt or 147.9 mL/cwt) and Pro-Ized Red Colorant (normal) (0.5 fl oz/cwt). Seed treatment was applied using a Wintersteiger HEGE II (Wintersteiger AG, Austria, Germany).

Seed was planted in 12 locations in the U.S. Midwest (IA, IL, IN). Sixteen randomized replicate blocks were harvested per each of the Flg22 polypeptide treatments consisting of Bt.4Q7Flg22 applied at 0.25 μM and 1.0 μM slurry concentration.

Table 27 shows that seed treatment with the Bt.4Q7Flg22 bioactive priming polypeptide applied at what would be the equivalent of a 40 μM polypeptide solution at a rate of 0.035 or 0.14 Fl. oz (2.6 or 10.2 mL/Ha) of polypeptide solution per unit of corn seed resulted in enhanced yield with averages of +2.1Bu/Ac (131.8 kg/Ha) increases for the low rate and +5.3 Bu/Ac increases for the high rate application as compared to non-treated control seed (no seed treatment).

TABLE 27

Seed treatment on corn using Flg22 polypeptides

| Treatment Corn | Peptide concentration in seed coating slurry | Equivalent Application Rate Fl. oz/unit corn seed | Average Total Yield Bu/Ac Hybrid 1 | Average Total Yield Bu/Ac Hybrid 2 | Average Total Yield Bu/Ac Hybrid 1 and 2 | Change in Yield Bu/Ac compared to the Control Seed |
|---|---|---|---|---|---|---|
| Control | — | — | 206.65 | 184.27 | 197.32 | — |
| Bt.4Q7Flg22 | 0.25 μM | 0.035 fl oz of 40 μM peptide solution/unit | 218.36 | 182.88 | 200.62 | +2.1 |
| Bt.4Q7Flg22 | 1.0 μM | 0.14 fl oz of 40 μM peptide solution/unit | 213.44 | 187.48 | 202.62 | +5.3 |

A second study was set up to test the ability of Ec.Flg22, Ec.RI Flg22, Bt.4Q7Flg22, and Bt.4Q7R1 Flg22 to promote yield in corn. Replicated trials with 12 locations were set up as above. The Bt.4Q7 Flg22 gave 2.8 bushels or 71.1 kg at 50% win rate, the Bt.4Q7 RI Flg22 polypeptide gave 0.5 Bu/Ac. The Ec. Flg22 polypeptide gave 2.8 Bu/Ac (175.8 kg/Ha) advantage at 70% win rate, and the Ec. RI Flg22 gave no benefit.

A third study was set up to look at soybean seed treatment benefits of Bt.4Q7 Flg22, RI Bt.4Q7Flg22, Ec.RI Flg22, and RHPP as a seed treatment on soybean. Over a 12 location study, the RHPP polypeptide gave 0.4 Bu/AC (26.9 kg/Ha) at 64% win rate, the Bt.4Q7 Flg22 polypeptide gave 1.3 Bu/Ac (87.4 kg/Ha) at 64%, the Bt.4Q7 RI Bt.4Q7Flg22 polypeptide gave 0.3 Bu/Ac (20.2 kg/Ha) at 55%, and the Ec. RI Flg22 gave 1.8 Bu/Ac (121.1 kg/Ha) at 73% win rate.

Example 11: Application of Flagellin Bioactive Priming Polypeptides to Tomatoes—Increased Yield Foliar application treatments of Bt.4Q7 Flg22 (SEQ ID NO: 226) and Ec. Flg22 (SEQ ID NO: 526) were applied as an exogenous spray at the pre-bloom stage and used to increase yield in tomatoes.

Small scale plots were designed to simulate commercial growing conditions for tomatoes. Two hybrids of tomatoes, JetSetter (Trial 1) and Better Big Boy (Trial 2) were started as transplants in the greenhouse 42 to 56 days prior to planting in the raised field beds. Tomatoes were transplanted once soil temperatures three inches (7.6 cm) beneath the soil surface reach 60° F. (15.5° C.). Tomatoes were grown on raised beds covered with black plastic mulch. Plants were grown using drip irrigation and fertilizer applied following grower guidelines throughout the growing season to ensure optimum plant growth and yields. Small raised bed plots were designed to simulate the planting densities used by commercial growers that generally plant 2,600 to 5,800 plants per acre in single rows with 18 to 30 inches (46 to 76 cm) between plants in the row on 5- to 6.5-ft (1.5 to 2 m) centers.

Foliar treatments of Bt.4Q7 Flg22 and Ec. Flg22 at low and high use rates of 1 Fl. oz/Ac (73.1 mL/Ha) and 20 Fl. oz/Ac (1461.5 mL/Ha), respectively, were applied on the two hybrids at early bloom (first flower) stage. Replicated trials were conducted at the University of Missouri (Columbia, Mo.) in July. Control plants were treated with equal volumes (use rates) of water. Effects of the foliar treatments on increasing yield in tomatoes were determined and reported as normalized to the water control treatment. The average percentage change in yield over the average control yield is reported in the Table 28.

Foliar application of both the Bt.4Q7Flg22 and Ec.Flg22 bioactive priming polypeptides increased tomato fruit yield for each hybrid at both the low and high use rate. When results for the two hybrids were averaged, low and high application use rates for Bt.4Q7 Flg22 increased tomato yield +25% and +17%, respectively, over the control plants. Similarly, low and high application use rates for the Ec. Flg22 treatments resulted in an average increase in tomato yield of +43% and +46% over the control plants for the two hybrids.

TABLE 28

Foliar treatment to increase yield in different hybrids of tomato

| Foliar Treatment | Trial 1: Percent Change in Yield over Avg. Control; Hybrid: Jetsetter | Trial 2: Percent Change in Yield over Avg. Control; Hybrid: Better Big Boy | Average Trials 1 & 2 Percent Change Yield over Avg. Control |
|---|---|---|---|
| Bt.4Q7 Flg22 (1 Fl. oz/Ac) | +49% | +1% | +25% |
| Bt.4Q7 Flg22 (20 Fl. oz/Ac) | +22% | +12% | +17% |
| Ec. Flg22 (1 Fl. oz/Ac) | +61% | +25% | +43% |
| Ec. Flg22 (20 Fl. oz/Ac) | +72% | +21% | +46% |

Example 12: Foliar Treatment of Tomato Plants with a Formulation of Bt.4Q7 Flg22

In another experiment, tomato plants (hybrid: Better Boy), cultivated as described in the previous example, were treated with a formulation of Bt.4Q7 Flg22 at the first bloom stage. The formulation used consisted of the retro inverso D RI Bt.4Q7 Flg22 applied with 0.01% (v/v) non-ionic surfactant. The formulation was applied to tomato foliage using application use rates of 1 Fl. oz/Ac (73.1 mL/Ha) in two replicate winter tomato trials conducted in Florida. At harvest, the yield was measured as the number of fruits per plant, the weight (grams) per fruit and the total yield (lbs/Ac). Table 29 reports the yield as a percent comparison or change to the non-treated control (water only) plants.

Foliar treatment using the Bt.4Q7 Flg22 formulation applied at 1 Fl. oz/Ac (73.1 mL/Ha) increased yield of Better Boy tomatoes an average of 21% compared to the non-treated (water alone) control plants. This increase for Better Boy tomatoes corresponded to both an increase in number of fruits per plant and an increase in the fruit weight (Table 29).

TABLE 29

Foliar treatment with a Flg22 bioactive priming polypeptide to increase yield in tomato

| Treatment | Percent Change in Number of Fruits per Plant Compared to Control | Percent Change in Weight/Fruit Compared to Control | Percent Change in Yield (lbs/Ac) Compared to Control |
|---|---|---|---|
| Bt.4Q7 Flg22 1 Fl. oz/Ac | +12% | +9% | +21% |

Example 13: Application of Flagellin Bioactive Priming Polypeptides to Peppers—Increased Yield Foliar treatments of Bt.4Q7 Flg22 (SEQ ID NO: 226) and Ec.Flg22 (SEQ ID NO: 526) were applied as an exogenous spray at the first-bloom stage and used to increase yield in two pepper varieties.

Foliar treatments of Bt.4Q7 Flg22 and Ec.Flg22 bioactive priming polypeptides were applied using small scale plots designed to simulate commercial growing conditions for peppers (*Capsicum*). Two varieties of pepper: Red Knight (RK) and Hungarian Hot Wax (HHW) were grown from 6-week old transplants in raised beds covered with black plastic mulch that had good water-holding characteristics and a pH of 5.8-6.6. Plants were grown using drip irrigation and fertilizer applied following grower guidelines throughout the growing season to ensure optimum plant growth and yields. Small raised bed plots were designed to simulate the planting densities used by commercial growers that generally plant approximately 10,000-14,000 plants per acre in double rows 14-18 inches (35.6 to 46 cm) apart on plastic mulched beds with 16-24 inches (40.6 to 61 cm) between plants in the row and with the beds spaced 5.0-6.5 feet (40.6 to 70 cm) apart from their centers. A single row of peppers also can be planted on each bed (5,000-6,500 plants per acre or 12,355-16,062 plants per hectare).

Foliar applications with compositions containing Bt.4Q7 Flg22 and Ec.Flg22 were applied at the first flower stage at an application use rate of 1 Fl. oz/Ac (low rate) or 73.1 mL/Ha and 20 Fl. oz/Ac (high rate) or 1461.5 mL/Ha on both pepper plants and compared to the control (water applied at same use rate). Effects of the foliar applications on pepper yield were determined for two separate harvests using a once over harvest approach and normalized to the yield of the control plants. The average percentage change in yield for each treatment over the yield for the control plants is reported as pounds/acre (lbs/Ac) in Table 29.

Foliar treatment of peppers using either the Bt.4Q7 Flg22 or Ec.Flg22 bioactive priming polypeptides resulted in overall average increases in pepper yield (lbs/Ac) with both the low and high application use rates and for both the RK and HHW pepper varieties. The combined yield averages for the RK and HHW varieties were +53% higher (low rate: 1 Fl. oz/Ac or 73.1 mL/Ha) and +25% higher (high rate: 20 Fl. oz/Ac) for Bt.4Q7 Flg22 foliar treated peppers compared to the control pepper plants. Alternatively, the combined yield average increases for the RK and HHW varieties were +30% higher (low rate: 1 Fl. oz/Ac) and +47% higher (high rate: 20 Fl. oz/Ac or 1461.5 mL/Ha) for Ec. Flg22 foliar treated peppers compared to the control pepper plants.

Differences existed in how the two pepper varieties responded to the foliar treatments and in the resultant yield advantages provided to both pepper varieties (Table 30). Substantial yield increases were seen in the HHW variety as compared to the RK variety of peppers and the control or non-treated plants with yield increases of +77% (low: 1 Fl. oz/Ac or 73.1 mL/Ha) and +42% (high: 20 Fl. oz/Ac or 1461.5 mL/Ha) over the control or non-treated pepper plants for the Bt.4Q7Flg22. Additionally, low use rates of the Bt.4Q7Flg22 (1 Fl. oz/Ac) and high use rates of the Ec. Flg22 (20 Fl oz/Ac) polypeptides were the most effective at increasing yield in the HHW variety (both yielded a +72% increase over the control plants).

TABLE 30

Foliar treatment of Flg22 to increase yield in different varieties of pepper

| Foliar Treatment | Avg. Percent Change Yield Total Weight (lbs/Ac) Red Knight 2 Replicate Trials | Avg. Percent Change Yield Total Weight (lbs/Ac) (Hungarian Hot Wax) 2 Replicate Trials | Combined Avg. Percent Change Yield Total Number (lbs/Ac) RK and HHW |
|---|---|---|---|
| Bt.4Q7Flg22: 1 Fl. oz/Ac | +29% | +77% | +53% |
| Ec.Flg22: 1 Fl. oz/Ac | +30% | +29% | +30% |
| Bt.4Q7Flg22: 20 Fl. oz/Ac | +8% | +42% | +25% |

TABLE 30-continued

Foliar treatment of Flg22 to increase yield in different varieties of pepper

| Foliar Treatment | Avg. Percent Change Yield Total Weight (lbs/Ac) Red Knight 2 Replicate Trials | Avg. Percent Change Yield Total Weight (lbs/Ac) (Hungarian Hot Wax) 2 Replicate Trials | Combined Avg. Percent Change Yield Total Number (lbs/Ac) RK and HHW |
|---|---|---|---|
| Ec.Flg22: 20 Fl. oz/Ac | +22% | +72% | +47% |

Example 14: Application of Flagellin Bioactive Priming Polypeptides to Squash—Increased Yield Foliar treatment of Bt.4Q7Flg22 were applied exogenously on Ambassador squash at the first bloom stage using two separate formulations (formulation 1=F1 and formulation 2=F2). Formulation 1 (F1) consists of the native L Bt.4Q7 Flg22 bioactive priming polypeptide applied with 0.01% (v/v) non-ionic surfactant. Formulation 2 (F2) consists of the D RI Bt.4Q7 Flg22 applied with 0.01% (wv) non-ionic surfactant. Both formulations F1 and F2 were applied to squash foliage using application use rate of 1 Fl. oz/Ac (73.1 mL/Ha). Yield comparisons were made between the plants treated with the foliar Bt.4Q7Flg22 F1 and F2 spray applications compared to the control (water) or non-treated squash plants. Squash plants were cultivated in sandy loam soil as follows. 2.5 cm holes were cut in 2.5 ft. (0.76 m) wide plastic covered mounds, two rows per mound, holes spaced 1.5 ft (0.46 m) apart within each row. Rows were staggered within the mound. Mounds were spaced 4 ft (1.2 m) apart. Three squash seeds were planted per hole and thinned to a single plant per hole 14 days after planting. Drip irrigation tubing was laid in the center of each mound, and plants were watered as necessary.

Squash plants were grown from seed in raised beds until bloom, and foliar treated in the same Florida (FL) location using two replicated trials or two separate harvests. Yield for the foliar Bt.4Q7Flg22 applied F1 and F2 treated plants is reported as the number of squash per plant, the weight (grams) per squash and the total squash yield (lbs/Ac) and represented as a percentage change as compared to non-treated control plants (Table 31).

Foliar treatments of Bt.4Q7Flg22 using the two formulations F1 and F2 resulted in an increased yield advantage when foliar applied on squash (Ambassador) at the pre-bloom stage compared to the non-treated control plants. The number of squash per plant, weight per squash and overall average percent change in yield (lbs/Ac) all were increased in the Bt.4Q7Flg22 F1 and F2 treated plants compared to the control or non-treated plants. The squash plants treated with both the Bt.4Q7Flg22 F1 and F2 formulations had similar trend increases in the number of squash per plant, weight per squash and overall average percent change in yield (lbs/Ac), however squash plants that received the F1 foliar application showed increases in the number of squash per plant and in the total yield of squash over the plants that received the F2 formulation.

TABLE 31

| Foliar treatment with a composition of Flg22 polypeptides to increase yield in squash | | | |
|---|---|---|---|
| Treatment | Percent Change in Number of Squash per Plant Compared to Control | Percent Change in Weight/Squash Compared to Control | Percent Change in Yield (lbs/Ac) Compared to Control |
| Bt.4Q7Flg22 1 Fl. oz/Ac Formulation 1 | +7% | +2% | +9% |
| Bt.4Q7Flg22 1 Fl. oz/Ac Formulation 2 | +4% | +2% | +6% |

Example 15. Screening Flg Polypeptides for Reactive Oxygen Species (ROS) Production in Corn and Soybean Codon usage was performed to generate mutations in the Bt.4Q7Flg22 to better match the host organism and the binding of the Flg22 polypeptide to the FLS receptor at the plant cell surface. A probabilistic approach was used to generate three variants of the native Bt.4Q7Flg22 that were designed to have preferred amino acid signatures for corn and soybean and to perform equal to or better than the native Bt.4Q7Flg22(SEQ ID NO: 226) in ROS activity assays. These variants possessed mutations to the internal segment (SEQ ID NO: 571), or the C-terminus (SEQ ID NO: 572) or the N terminus (SEQ ID NO: 573) and were designated as Bt.4Q7Flg22-Syn01, Bt.4Q7Flg22-Syn02 and Bt.4Q7Flg22-Syn03, respectively. Bt.4Q7Flg22-Syn01 and Bt.4Q7Flg22-Syn03 were then measured in relation to their native forms at a variety of concentrations.

Fresh plant tissues from corn (hybrid 5828 YX) and soybean (hybrid 297R4) leaves were cut into uniform samples and floated on 150 μL of sterile water in a 96-well white, low luminescence plate. The plate was placed under growth lights that had a 16-hour light/8-hour dark cycles at a consistent temperature of 22° C.

For corn samples, aerial tissue from V1 to V4 stage corn plants was cut away from the plant above the soil line using a clean razor blade. The cotyledon and sheath were removed. 1-mm slices were cut through the stalk from the base of the plant until approximately 1.3 cm below the first leaf node. Each corn section was placed in an individual well of the 96-well plate.

For soybean samples, fully expanded trifoliate leaves were removed from V1-V3 stage plants. Leaf discs (12.6 $mm^2$) were cut from the leaf blades using a 4-mm diameter clean, sharpened cork borer. Discs were cut in half using a clean razor blade, and each disc half was placed in an individual well of the 96-well plate.

Native Flg22 polypeptide (SEQ ID NO: 226) or Flg22 polypeptides containing the described mutations (SEQ ID NOs 571 or 573) stocks were prepared in either sterile, deionized water or 100 mM sodium phosphate (pH 7.8-8.0) buffer with 0.1% Tween-20. After 18-24 hours, the water was removed from each well of the 96-well plate. Plant tissue samples were treated with a 100 μL elicitation solution containing 1:100 dilution of Flg22 polypeptide stock (concentration range from 250 picomolar (pM) to 10 micromolar (μM)), 34 μg/mL luminol, and 20 μg/mL horseradish peroxidase. Recognition of the Flg22 polypeptide by the plant tissue resulted in activation of immune signaling and the production of apoplastic reactive oxygen species (ROS). In the presence of ROS ($H_2O_2$), horseradish peroxidase catalyzed the oxidation of luminol and production of visible light. Relative light units (RLUs) were recorded with a GLOMAX 96 microplate luminometer (Promega Corporation) using a 0.5 s integration; 2.6 min intervals over a time course of 40 minutes.

For data analysis, total RLUs produced were calculated for each sample over the entire 40 min time course. Significant outliers beyond the interquartile range were excluded from analysis. Total RLUs in each condition (n=6-16) were normalized to the average RLU for Bt.4Q7Flg22 at 25 nM and reported as a percentage (%) of the Bt.4Q7Flg22 control (Table 32).

The synthetic mutagenized Bt.4Q7Flg22-Syn01 version had increased ROS activities at a range of concentrations (0.25–100 nM) while Bt.4Q7Flg22-Syn03 was more varied and showed increased ROS activities at 0.25 nM, 1 nM, 10 nM, 25 nM, and 100 nM concentrations as compared to the native version of Flg22 or Bt.4Q7Flg22. The synthetic version of Bt.4Q7Flg22-Syn01 treatment using 5 nM resulted in the largest change in ROS activity over the native version or Bt.4Q7Flg22. ROS activities for Bt.4Q7Flg22-Syn03 showed a more varied response over the range of concentrations added.

TABLE 32

| Flg generated synthetic mutants (Syn-01 and Syn-03) have more activity in the ROS assay than the native Bt.4Q7Flg22 over a wide range of concentrations. | | | |
|---|---|---|---|
| Concentration (nM) | Bt.4Q7Flg22 (SEQ ID NO: 226) | Bt.4Q7Flg22-Syn01 (SEQ ID NO: 571) | Bt.4Q7Flg22-Syn03 (SEQ ID NO: 573) |
| 0.25 | 8.12 | 23.56 | 14.86 |
| 0.5 | 14.86 | 55.00 | 14.86 |
| 1 | 23.85 | 57.04 | 41.47 |
| 5 | 57.00 | 113.00 | 57.00 |
| 10 | 76.85 | 116.34 | 85.70 |
| 25 | 100.00 | 118.05 | 111.40 |
| 100 | 113.74 | 120.83 | 162.29 |
| 1000 | 127.76 | 121.20 | 97.67 |

Example 16: ROS Screening Assays to Identify Functionally Active Flg Polypeptides for Corn and Soybean Based on the results from preliminary studies in Example 15, the following concentrations were chosen to screen ROS activities of a wide range of Flg22 polypeptides in corn and soybean: 5 nM in corn (hybrid 5828 YX) and 100 nM in soybean (hybrid 297R4). ROS activity assays were then used to identify the best Flg22 bioactive priming polypeptide candidates for individual treatment use of corn and soybean and to identify those candidates that were active for both corn and soybean.

Corn and soybean leaf tissues were harvested from plants and ROS assays were performed as previously described in Example 15 for the mutant polypeptides listed in Table 33. Total RLUs produced were calculated for each sample over the entire 40 min time course. Significant outliers beyond the interquartile range were excluded from analysis. Comparisons of ROS activity on corn (hybrid 5828 YX) and soybean (hybrid 297R4) were made and reported as the percentage (%) of relative light units (RLU) compared to the average RLU values at the 25 nM Bt.4Q7Flg22 treatment concentration (Table 33).

Table 33 summarizes the relative activity for a variety of mutant Flg22 polypeptides compared to native Bt.4Q7Flg22 alongside the standard deviation in for each condition (STDEV).

TABLE 33

ROS activity comparisons for various Flg22 polypeptides in corn and soybean

| SEQ ID NO: | Amino Acid Sequence | Corn (5828 YX) 5 nM polypeptide Avg. Activity (%) | Corn STDEV | Soybean (297 R4 100 nM polypeptide Avg. Activity (%) | Soybean STDEV |
|---|---|---|---|---|---|
| Bt.4Q7Flg22 *Bacillus thuringiensis* SEQ ID NO: 226 | DRLSSGKRINSA SDDAAGLAIA | 100 | — | 100 | — |
| Bt.Flg22-Syn01 Mutant S13K *Bacillus thuringiensis* SEQ ID NO: 571 | DRLSSGKRINSA KDDAAGLAIA | 142.9 | 39.3 | 112 | 3.0 |
| Bt.Flg22-Syn02 Mutant A20Q *Bacillus thuringiensis* SEQ ID NO: 572 | DRLSSGKRINSA SDDAAGLQIA | 78.3 | 26 | 68.7 | 14.0 |
| Bt.Flg22-Syn03 Mutant D1Q *Bacillus thuringiensis* SEQ ID NO: 573 | QRLSSGKRINSA SDDAAGLAIA | 122.1 | 29.5 | 113.5 | 42.6 |
| Bm.Flg22-B1 *Bacillus manliponensis* SEQ ID NO: 290 | NRLSSGKQINSA SDDAAGLAIA | 106.0 | 25.2 | 74.6 | 4.9 |
| Ba.Flg22-B2 *Bacillus anthracis* SEQ ID NO: 295 | NRLSSGKRINSA ADDAAGLAIA | 134.7 | 56.8 | 83.0 | 26.6 |
| Bc.Flg22-B3 *Bacillus cereus* SEQ ID NO: 294 | DRLSSGKRINNA SDDAAGLAIA | 80.3 | 18.4 | 90.0 | 35.5 |
| A spp.Flg22-B4 *Aneurini-bacillus* spp. XH2 SEQ ID NO: 300 | ERLSSGYRINRA SDDAAGLAIS | 78.1 | 20.1 | 133.1 | 23.9 |
| Ba.Flg22-B5 *Bacillus aryabhattai* SEQ ID NO: 289 | EKLSSGQRINSA SDDAAGLAIS | 27.1 | 2.3 | 42.2 | 7.4 |
| P spp.Flg22-B6 *Paenibacillus* spp. strain HW567 SEQ ID NO: 293 | GKLSSGLRINGA SDDAAGLAIS | 135.3 | 31.6 | 112.5 | 22.8 |
| L spp.Flg22-L1 *Lysinibacillus* spp. SEQ ID NO: 291 | LRLSSGYRINSA ADDAAGLAIS | 26.6 | 3.6 | 64.1 | 14.1 |
| L spp.Flg22-L2 *Lysinibacillus* spp. SEQ ID NO: 580 | EKLSSGLRINRA GDDAAGLAIS | 104.5 | 1.2 | 128.6 | 29.5 |
| L spp.Flg22-L3 *Lysinibacillus* spp. SEQ ID NO: 581 | EKLSSGYKINRA SDDAAGLAIS | 36.4 | 7.9 | 96.9 | 20.6 |

TABLE 33-continued

ROS activity comparisons for various Flg22 polypeptides in corn and soybean

| SEQ ID NO: | Amino Acid Sequence | Corn (5828 YX) 5 nM polypeptide Avg. Activity (%) | Corn STDEV | Soybean (297 R4 100 nM polypeptide Avg. Activity (%) | Soybean STDEV |
|---|---|---|---|---|---|
| L spp.Flg22-L4 *Lysinibacillus* spp. SG9 SEQ ID NO: 582 | LRISSGYRINSAA DDPAGLAIS | 60.1 | 5.9 | 117.9 | 25.7 |
| Lf.Flg22-L5 *Lysinibacillus fusiformis* SEQ ID NO: 583 | LRISTGYRINSAA DDPAGLAIS | 59.3 | 5.8 | 111.6 | 27.5 |
| Lm.Flg22-L6 *Lysinibacillus macroides* SEQ ID NO: 584 | EKLSSGFRINRA GDDAAGLAIS | 58.7 | 19.4 | 112.3 | 42.3 |
| Lm.Flg22-L6 *Lysinibacillus xylanilyticus* SEQ ID NO: 585 | EKLSSGYKINRA GDDAAGLAIS | 33.7 | 1.4 | 77.0 | 19.2 |
| Pa.Flg22 *Pseudomonas aeruginosa* SEQ ID NO: 530 | QRLSTGSRINSA KDDAAGLQIA | 116.0 | 32.5 | 88.6 | 22.2 |
| Ec.Flg22 *Escherichia coli* SEQ ID NO: 586 | ERLSSGLRINSA KDDAAGQAIA | 95.0 | 46.7 | 116.8 | 13.3 |
| Xcc.Flg22 *Xanthomonas campestris* pv *campestris* strain 305 or (*Xanthomonas citri* pv. *citri*) SEQ ID NO: 532 | QRLSSGLRINSA KDDAAGLAIS | 143.3 | 5.2 | 96.4 | 17.6 |
| Ea.Flg22 *Erwinia amylovora* SEQ ID NO: 534 | QRLSSGLRINSA KDDAAGQAIS | 125.2 | 9.2 | 91.9 | 10.1 |
| Bp.Flg22 *Burkholderia phytofirmans* strain PsJN SEQ ID NO: 536 | TRLSSGKRINSA ADDAAGLAIS | 111.2 | 14.0 | 67.2 | 3.0 |
| Bu.Flg22 *Burkholderia ubonensis* SEQ ID NO: 538 | NRLSSGKRINTA ADDAAGLAIS | 92.9 | 12.7 | 91.1 | 12.9 |
| Ps.Flg22 *Pseudomonas syringae* pv. *actinidiae* ICMP 19096 SEQ ID NO: 540 | TRLSSGLKINSA KDDAAGLQIA | 154.4 | 20.7 | 113.1 | 19.6 |

Based on the results from Table 33, a number of predictions could be made based on the effect of different mutations on Flg22 polypeptides on ROS activity in corn and soybean. Table 34 describes ROS activity observed or predicted for a variety of targeted mutations. Briefly, replacements at the first amino acid (D1N, D1Q or D1T) have or likely will result in strong recognition and/or activation of the Flg22 receptor in corn. Mutations in the inner segment, K7Y, K7F and A16P, will likely have similar positive results in soybean. Of the tested polypeptides, Bt.4Q7Flg22-Syn01 (S13K) and Bt.4Q7Flg22-Syn03 (D1Q) had the strongest ROS-inducing activity in corn and soybean.

TABLE 34

| Result summary of mutant versions of native Bt.4Q7Flg22 | | |
|---|---|---|
| SEQ ID NO | Amino Acid Sequence | Description of ROS activity results |
| SEQ ID NO: 226 | DRLSSGKRINSASDDA AGLAIA | Bt.4Q7Flg22 *Bacillus thuringiensis* (native version and used as the standard comparison) |
| SEQ ID NO: 571 | DRLSSGKRINSAKDDA AGLAIA | S13K mutation: Strong ROS activation in both corn and soybean |
| SEQ ID NO: 572 | DRLSSGKRINSASDDA AGLQIA | A20Q mutation: Negative ROS activation in both corn and soybean |
| SEQ ID NO: 573 | QRLSSGKRINSASDDA AGLAIA | D1Q mutation: Strong ROS activation in both corn and soybean |
| SEQ ID NO: 574 | NRLSSGKRINSASDDA AGLAIA | D1N mutation: Strong ROS activation in both corn and soybean*(predicted) |
| SEQ ID NO: 575 | TRLSSGKRINSASDDA AGLAIA | D1T mutation: Strong ROS activation in both corn and soybean*(predicted) |
| SEQ ID NO: 576 | DRLSSGYRINSASDDA AGLAIA | K7Y mutation: Strong ROS activation in only soybean*(predicted) |
| SEQ ID NO: 577 | DRLSSGFRINSASDDA AGLAIA | K7F mutation: Strong ROS activation in only soybean*(predicted) |
| SEQ ID NO: 578 | DRLSSGKRINSASDDP AGLAIA | A16P mutation: Strong ROS activation in only soybean * (predicted) |
| SEQ ID NO: 579 | DRLSSGKRINSASDDA AGLAIA | K7Q mutation: Strong reduction in ROS activation in both corn and soybean*(predicted) |

Example 17: ROS Activity Assays to Identify Combinations of Flg Polypeptides for Corn and Soybean Corn and soybean leaf tissues were harvested from plants and ROS assays were performed as previously described in Example 15. The relative ROS activity of different Flg22 variants, alone or in combination, were assessed to identify the preferred combinations of Flg22 polypeptides that when applied together provided the highest ROS activity response for both corn and soybean. Results are summarized in Table 35.

TABLE 35

| Flg22 combinations with increased ROS activities in corn and soybean | | | | | |
|---|---|---|---|---|---|
| | | Corn (5828 YX) 5 nM polypeptide | | Soybean (297 R4) 100 nM polypeptide | |
| Flagellin Composition | Amino Acid Sequence | Avg. Activity (%) | STDEV | Avg. Activity (%) | STDEV |
| Bt.4Q7Flg22 *Bacillus thuringiensis* SEQ ID NO: 226 | DRLSSGKRINS ASDDAAGLAIA | 100 | — | 100 | — |
| Bt.Flg22-Syn01 *Bacillus thuringiensis* SEQ ID NO: 571 | DRLSSGKRINS AKDDAAGLAIA | 122.48 | 31.69 | 83.54 | 36.21 |
| Ba.Flg22-B2 *Bacillus antrhacis* SEQ ID NO: 295 | NRLSSGKRINS AADDAAGLAIA | 142.53 | 7.45 | 97.59 | 68.59 |
| A spp.Flg22-B4 Aneurinbacillus spp. XH2 SEQ ID NO: 300 | ERLSSGYRINR ASDDAAGLAIS | 53.64 | 1.45 | 106.37 | 16.48 |
| P spp.Flg22-B6 *Paenibacillus* spp. strain HW567 SEQ ID NO: 293 | GKLSSGLRING ASDDAAGLAIS | 103.61 | 37.59 | 132.95 | 54.72 |

TABLE 35-continued

Flg22 combinations with increased ROS activities in corn and soybean

| Flagellin Composition | Amino Acid Sequence | Corn (5828 YX) 5 nM polypeptide Avg. Activity (%) | STDEV | Soybean (297 R4) 100 nM polypeptide Avg. Activity (%) | STDEV |
|---|---|---|---|---|---|
| L spp.Flg22-L2 *Lysinibacillus* spp. SEQ ID NO: 574 | EKLSSGLRINR AGDDAAGLAIS | 113.04 | 28.89 | 138.86 | 53.66 |
| FLG22-Syn01 +B2+B4 +B6+L2 | polypeptide combinations as described above | 148.52 | 6.30 | 132.35 | 53.99 |
| FLG22B2 +B4 +B6+L2 | polypeptide combinations as described above | 128.31 | 0.65 | 139.74 | 55.00 |
| FLG22-Syn01 +B2 +B6+L2 | polypeptide combinations as described above | 122.81 | 29.81 | 124.51 | 67.31 |
| FLG22-Syn01 +B4 +B6+L2 | polypeptide combinations as described above | 119.17 | 8.02 | 100.97 | 25.95 |
| FLG22-Syn01 +B6+L2 | polypeptide combinations as described above | 124.67 | 8.69 | 103.45 | 34.03 |
| FLG22-Syn01 +B2+B4 | polypeptide combinations as described above | 143.02 | 7.08 | 120.67 | 24.76 |

Example 18: ROS Activity Assay with Cellobiose Additive—Corn and Soybean

Cellobiose is a glucose disaccharide and a building block for cellulose polymer. Chemically, it is glucose-beta-1-4-glucose, a reducing sugar that consists of two β-glucose molecules linked by a β (1-4) bond. Cellobiose is obtained by the breakdown of cellulose or lichenin and yields glucose upon hydrolysis. Treatments using Bt.4Q7Flg22 were compared with and without cellobiose in ROS activity assays to determine if cellobiose can act an elicitor to increase ROS production in reactions containing Flg22 polypeptide. The specific treatments conducted using ROS assays with corn (FIG. 6, panel A) and soybean (FIG. 6, panel B) leaf assays were: Bt.4Q7Flg22 at 25 nM; Bt.4Q7Flg22 at 25 nM+cellobiose at 100 μM; Bt.4Q7Flg22 at 25 nM+cellobiose at 1 mM; 100 mM sodium phosphate buffer control; and cellobiose alone (100 μM).

Corn and soybean leaf tissues were harvested from plants as previously described in Example 15. Flg22 bioactive priming polypeptide stocks were prepared in either sterile, deionized water or 100 mM sodium phosphate (pH 7.8-8.0) buffer with 0.1% Tween-20. After 18-24 hours, the water was removed from each well of the 96-well plate. Samples were treated with a 100 μL solution containing Bt.4Q7Flg22 (SEQ ID NO: 226, 25 nM), cellobiose (100 μM or 1 mM), 34 μg/mL luminol, and 20 μg/mL horseradish peroxidase. Recognition of the Flg22 polypeptide by the plant tissue resulted in activation of immune signaling and the production of apoplastic reactive oxygen species (ROS). In the presence of ROS ($H_2O_2$), horseradish peroxidase catalyzed the oxidation of luminol and production of visible light. Relative Light Units (RLUs) were recorded with a GLOMAX 96 microplate luminometer (Promega Corporation) using 0.5 s integration; 2.6 min intervals over a time course of 40 minutes.

Figure 6:
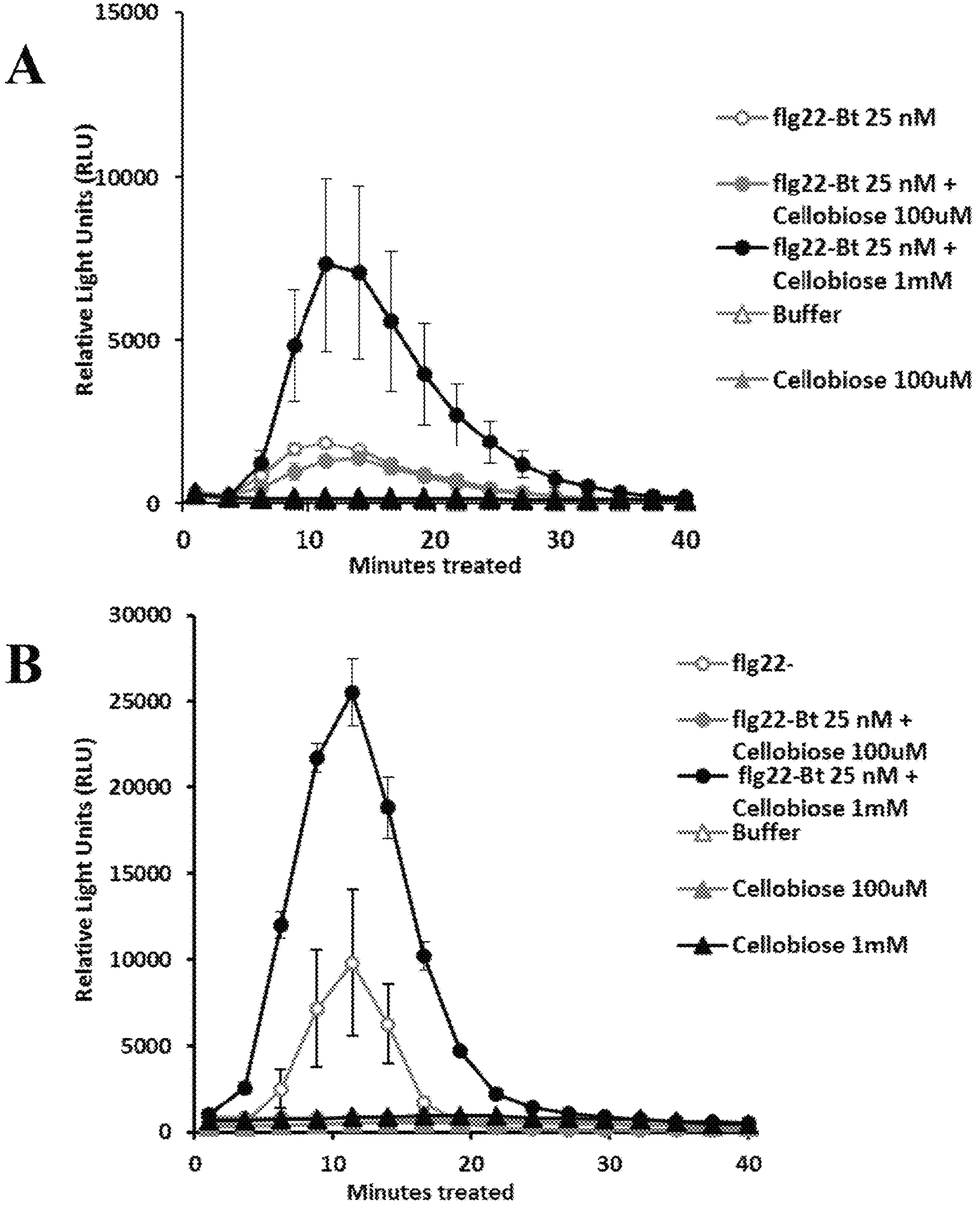
FIG. 6 is directed to a reactive oxygen species (ROS) activity assay using Bt.4Q7Flg22 in combination with different concentrations of cellobiose as an additive in corn (panel A) or in soybeans (panel B).
Figure 7:
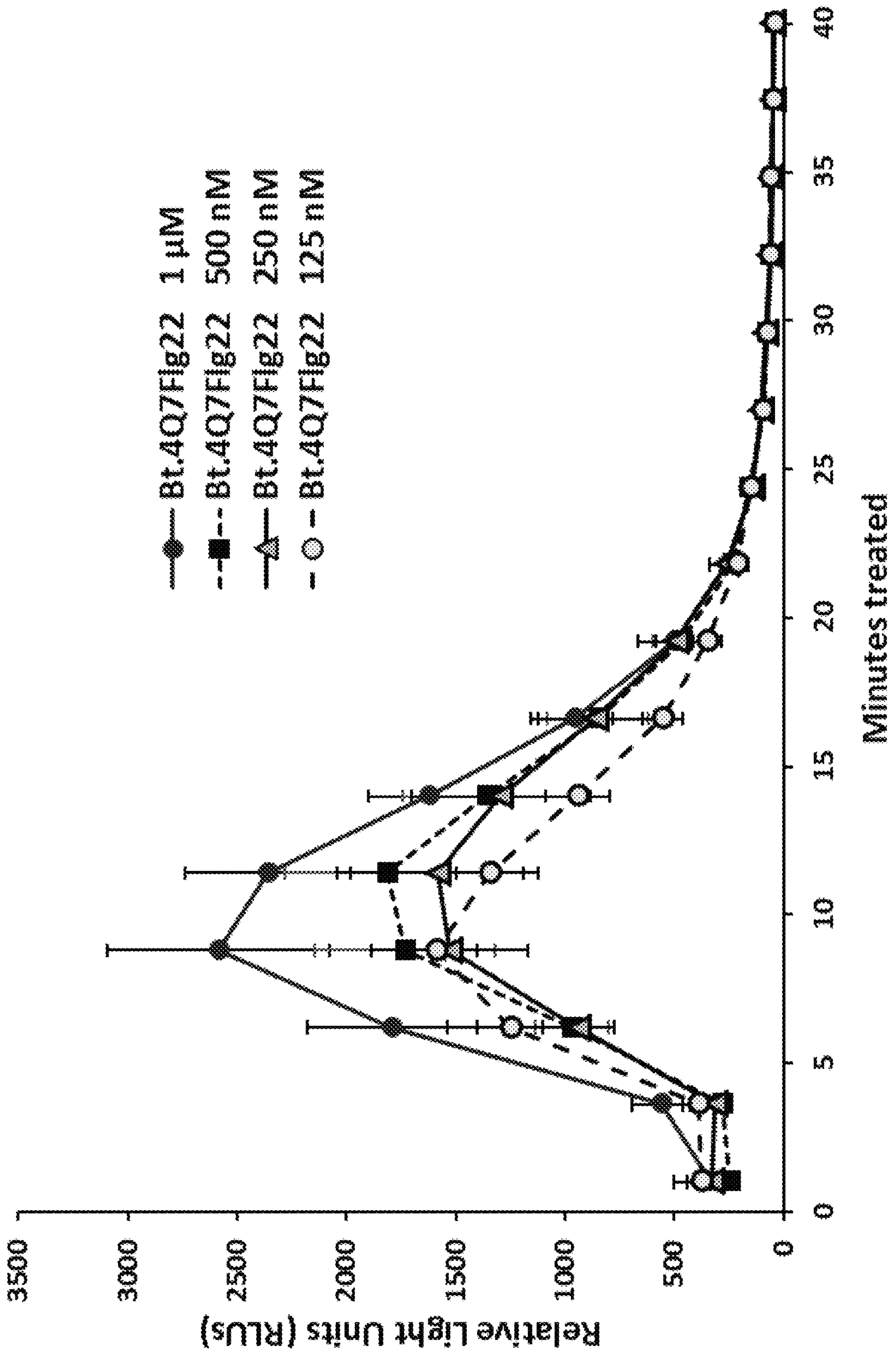
FIG. 7 is directed to a reactive oxygen species (ROS) activity assay using Bt.4Q7Flg22 at different concentrations to identify the peak activity and timing for the assay.

For data analysis, the average RLU per treatment (n=6-16 samples, +/−standard error of the means) was graphed over the time course (FIG. 6). Significant outliers beyond the interquartile range were excluded from analysis.

The average RLU across the experiment for each treatment is graphed in FIG. 6, panel A (corn) and panel B (soybeans). While ROS production was observed in both plant tissue in treatments only containing the Flg22 polypeptide (white circles), the addition of cellobiose at 1 mM resulted in significant ROS activity in both plant tissues (black circles). Addition of cellobiose at lower concentrations (100 uM) did not alter ROS activity compared to Bt.4Q7Flg22 alone (comparison of white and grey circles in FIG. 6, panel A) and did not lead to any ROS production in soybean (grey circles in FIG. 6, panel B). Notably the combination of Bt.4Q7Flg22 at 25 nM and cellobiose at 1 mM resulted in more ROS production in soybean (ROS peak at approximately 25,000 RLU) as compared to corn leaves (ROS peak at approximately 75,000 RLU).

Example 20: Application of Phytosulfokine (PSKα) to Increase Yield—Corn and Soybean The effect of Phytosulfokine alpha (PSKα), a sulfonated bioactive priming polypeptide derived from *Arabidopsis thaliana*, on corn and soybean yield was tested. Corn and soybeans were cultivated in the field as described in Example 1 and 3. *Arabidopsis thaliana* PSKα (SEQ ID NO: 598) was applied at a final concentration of 1 μM in foliar spray with a surfactant and provided using a uniform application to the above ground plant parts of corn (hybrid 5140RR) and soybean (hybrid 375 NR). At.PSKα formulations were applied at the V5-V8 stage of development in corn and the V1-V4 stage of development in soybean. Corn and soybean plants treated with At. PSKα were compared to non-treated control plants (water). Treated plants were randomized at one location in four replicate blocks for comparisons to the controls. Yield was reported in Bushels per acre (Bu/Ac).

Table 36 depicts how foliar application of At.PSKα resulted in yield increases in both corn and soybean yield trials. Both corn and soybean had positive yield increases in the field with foliar formulations containing At.PSKα applied at the V5-V8 stage of development in corn and the V1-V4 stage of development in soybean. On average, corn had a +3 Bu/Ac (188.3 kg/Ha) increase in overall yield in the field and soybean had a +0.8 Bu/Ac (53.8 kg/Ha) yield increase.

TABLE 36

Foliar application of At.PSKα to corn and soybean result in yield increases (Bu/Ac)

| Bu/Ac Foliar Corn | Bu/Ac Foliar Soybean |
|---|---|
| 3.0 | 0.8 |

Example 21: Foliar Application of Phytosulfokine Alpha (PSKα) to Increase Yield—Soybean A method is provided wherein applying At.PSKα as a foliar application to actively growing soybean plants provides a yield advantage in environments with heat and drought stress.

Soybean plants were grown as described in Example 6. The At.PSKα polypeptide (SEQ ID NO: 598) was applied as a foliar spray to the plants at the V1-V4 stage. Soybean plants treated with foliar applications of At.PSKα and control plants treated with water and surfactant alone were then grown in conditions described in Examples 7-9 that produced a non-stress and stress (heat and water deficit) environments. Table 37 describes the percentage change or increase in height reported for soybean plants treated with At.PSKα as a foliar spray at the V1-V4 growth stage. At.PSKα application resulted in a +3.5% increase in height in the non-stress environment and a +4.3% increase in height in stress environments reported in Bushels per acre (Bu/Ac) as compared to the non-treated control soybean plants.

TABLE 37

Yield increases in soybean treated with a foliar application of At.PSKα and grown in non-stress and stress environments

| Percentage (%) change in Height in Non-Stress Environment Soybean with At.PSKα over control | Percentage (%) change in Height in Stress Environment Soybean with At.PSKα over control |
|---|---|
| 3.5% | 4.3% |

Example 22: Application of RHPP to Alter Plant Architecture—Corn

Root hair promoting polypeptide (RHPP, SEQ ID NO: 600) originally derived for soybean (*Glycine max*) is provided as a foliar application to produce beneficial phenotypes in corn.

Native and retro inverso RHPP (SEQ ID NOs 600-601) will be applied to corn plants at the V5-V8 stages. Retro inverso RHPP may be modified with C-terminal amidation prior to application. Treatment with RHPP in this way is expected to result in a distinct leaf architecture phenotype with an upright leaf orientation and more erect leaves. The increase in leaf angle has impactful advantages for use in agriculture in this area. This is particularly relevant with higher planting densities used to maximize yield in a field environment. Foliar applications of the RHPP polypeptide in maize (corn) is useful for changing the leaf angle thus contributing to a smaller leaf angle which results in an upright leaf orientation. This phenotype can be beneficial for increasing the leaf area index, reducing maize shade syndrome, and improving photosynthetic efficiency. In addition, providing RHPP as a foliar formulation to maximize canopy development and total light penetrance is key to increasing vegetative growth of the plants prior to the initiation of the grain filling stage.

Example 23: Application of RHPP to Increase Root Biomass and Yield Parameter-Soybean Effective nodulation of soybean roots result in higher yields and higher quality seed production, protein and oil per seed or acre basis. This could be due to increased nitrogen fixation since nodulale formation increases nitrogen fixation. To determine whether root hair promoting bioactive priming polypeptide, RHPP (SEQ ID NO: 600) could modulate root biomass and nodulation and thereby improve nitrogen fixation, soybean plants (hybrid Morsoy 38X52 and Beck's hybrid 297R4) were treated with foliar application of RHPP (300 nM) at the R1-R2 stage of development.

Increased Plant Biomass and Nodulation

RHPP bioactive priming polypeptide (SEQ ID NO: 600, originally derived from *Glycine max*) was applied as foliar treatment to 4-week-old hybrid soybean (Morsoy variety) with 0.1% (v/v) non-ionic surfactant (ALLIGARE SURFACE™) using a spray bottle and delivering approximately 1.25 ml/plant. The experiment was conducted using a total of 8 plants per trial per treatment group. The pots were kept in an artificial lighted growth room receiving a light level of approximately 300 μmol $m^{-2}$ $s^{-1}$ for a 16/8 light/day cycle and a 21° C. day/15° C. night temperature range. Growth parameters of nodule counts, root biomass and total biomass per plant were measured at 15 days post the foliar application and compared between the foliar treatments consisting of ALLIGARE SURFACE surfactant (0.1% v/v) as a control and the RHPP polypeptide (300 nM) containing the ALLIGARE SURFACE surfactant (0.1% v/v). Average growth parameters as described were normalized to the control plants that received the surfactant alone treatment (Table 38).

Nodulation counts on the roots of each plant treated with a foliar application of RHPP were compared to the number of nodules on the control plants treated with 0.1% (v/v) surfactant alone. RHPP treatment resulted in approximately two times the number of nodules on the roots of each soybean plant compared to control (surfactant) treatment. Soybean plants receiving the foliar application of the RHPP polypeptide also exhibited an increase in root biomass and total overall plant biomass which when normalized to the control resulted in an increase of more than 20% in root biomass and 8% in total biomass.

TABLE 38

Increases in plant biomass and nodulation in soybean (Morsoy variety) after foliar application with RHPP bioactive priming polypeptide (n = 8 replicate plants)

| Growth Parameters | Control (surfactant 0.1% v/v ALLIGARE SURFACE) | RHPP (300 nM + 0.1% v/v ALLIGARE SURFACE) | RHPP treatment normalized as a percentage of the surfactant control |
|---|---|---|---|
| Average nodule count per plant | 8.88 | 15.13 | 170.42% |
| Root biomass (g) | 1.76 | 2.13 | 120.57% |
| Total biomass (g) | 42.64 | 46.24 | 108.44% |

Increased Plant Growth

RHPP bioactive priming polypeptide (SEQ ID NO: 600) was also applied as foliar treatment to R1 stage hybrid soybean (Beck's 297R4) with 0.1% (v/v) non-ionic surfactant (ALLIGARE SURFACE) using a spray bottle delivering approximately 1.2 ml/plant. This experiment was performed to look at the effects of RHPP on plant growth and was conducted using a total of 18 plants per treatment group. The pots were kept in an artificial lighted growth room receiving a light level of approximately 300 μmol $m^{-2}$ $s^{-1}$ for a 18/6 light/day cycle and a 21° C. day/15° C. night temperature range. R1 stage soybean plants were treated with nothing (non-treated control), ALLIGARE SURFACE surfactant applied at a concentration of 0.1% (v/v) or the RHPP polypeptide (300 nM) applied in combination with ALLIGARE SURFACE surfactant (0.1% v/v). Height for each plant was recorded at the time of spray and again at 16 days post foliar application and average growth parameters were compared between foliar treatments (Table 39).

Soybean plants that received the foliar application of RHPP polypeptide (300 nM+0.1% ALLIGARE SURFACE) had increased plant growth (plant height) and an increased change in plant height as compared to the plants that received the surfactant alone and non-treated control (Table 39).

TABLE 39

Increases in plant growth in soybean (Beck's 297R4) with foliar application with RHPP bioactive priming polypeptide (n = 18 replicate plants)

| Growth Parameters | Non-treated Control | Control (surfactant 0.1% ALLIGARE SURFACE) | RHPP (300 nM + 0.1% ALLIGARE SURFACE) |
|---|---|---|---|
| Height (cm) | 19.3 | 19.4 | 19.9 |
| Change in height (cm) | 4.0 | 3.7 | 4.6 |

Example 24: Application of RHPP in Combination with a Fertilizer—Soybean

The Gm. RHPP bioactive priming polypeptide (SEQ ID NO: 600) was applied as a foliar application with a liquid foliar fertilizer, N-RAGE MAX (21-1-3 N—P-K), to two soybean varieties (AG3536 and AG3832). Foliar application of RHPP was applied at 1 Fl. oz/Ac or 73.1 mL/Ha (300 nM concentration) with the recommended use rate of the fertilizer for soybeans (1 to 2 gal/Ac (9.4 to 18.8 L/Ha), or equal to Nitrogen 2.16 lbs/gal (0.29 kg/L); Phosphate $P_2O_5$ 0.10 lbs/gal and soluble potash ($K_2O$ 0.31 lbs/gal or 0.4 kg/L).

Foliar application of the combination RHPP, fertilizer treatment was provided to two soybean varieties (AG3536 and AG3832) at the R2 stage (recommended stages R1 to R6) of development in 5 locations across the US Midwest (IA, IL, IN). Foliar application of Gm. RHPP with the N-RAGE MAX provided a yield advantage of 1.9 Bu/Ac (127.8 kg/Ha) compared to the control treatment and on average a 1.4 Bu/Ac (94.2 kg/Ha) increase compared to those plants that received the fertilizer alone treatment for variety 1 (AG3536) (Table 40).

TABLE 40

Application of RHPP plus a fertilizer

| Treatment Soybean | Application Use Rate Fl. oz/Ac | Average Total Yield Bu/Ac Variety 1 | Average Total Yield Bu/Ac Variety 2 | Average Total Yield Bu/Ac Variety 1 and 2 | Average Bu/Ac Change compared to Control Variety 1 and 2 |
|---|---|---|---|---|---|
| Control | — | 62.50 | 62.16 | 62.33 | — |
| N-rage Max | 128 | 63.04 | 60.29 | 61.66 | −0.67 |
| RHPP | 4.0 | 65.42 | 61.04 | 63.23 | +0.9 |
| RHPP + N-RAGE MAX | 4.0<br>128 | 64.40 | 60.96 | 62.68 | +0.35 |

Example 25: Application of RHPP Bioactive Priming Polypeptides to Tomatoes—Increased Yield Foliar application treatments of Gm.RHPP (SEQ ID NO: 600) was applied as an exogenous spray at the pre-bloom stage and used to increase yield in tomatoes. Two tomato hybrids (JetSetter and Better Big Boy) were planted in small scale plots as described in Example 12. Foliar treatment of Gm.RHPP was applied at an application use rate of 1 Fl. oz/Ac (73.1 mL/Ha) and 20 Fl. oz/Ac(1461.5 mL/Ha) to the two hybrids, JetSetter (Trial 1) and Better Big Boy (Trial 2), at early bloom (first flower) stage. Replicated trials were conducted at the US Midwest (Missouri) in July. The foliar treatment of Gm.RHPP on tomato plants was compared to the control (water applied at same use rate). Effects of the foliar treatments on increasing yield in tomatoes were determined and reported as normalized to the water control treatment and reported as the average percentage change in yield over the average control yield in Table 41.

The average yield represented as a percent change over the control plants was reported separately for the two trials and as the average for the two tomato hybrids. Foliar application using Gm.RHPP resulted in an increase in tomato fruits for each of the two trials when applied at a use rate of 1 Fl. oz/Ac (73.1 mL/Ha). Application of Gm.RHPP resulted in an average increase in tomato yield of +52% over the control plants for the two hybrids with individual average increases of +93% for the Jetsetter hybrid and +10% for the Better Big Boy compared to the control plants.

TABLE 41

| Foliar treatment of RHPP to increase yield in different hybrids of tomato | | | |
|---|---|---|---|
| Foliar Treatment | Trial 1: Percent Change in Yield over Avg. Control; Hybrid: Jetsetter | Trial 2: Percent Change in Yield over Avg. Control; Hybrid: Better Big Boy | Average Trials 1 & 2 Percent Change Yield over Avg. Control |
| Gm.RHPP (1 Fl. oz/Ac) | +93% | +10% | +52% |

Example 26: Application of RHPP to Peppers—Increased Yield

Foliar treatment of Gm.RHPP (SEQ ID NO: 600) was applied as an exogenous spray at the first-bloom stage to increase yield in two pepper varieties. Foliar treatment of Gm.RHPP was applied using small scale plots designed to simulate commercial growing conditions for peppers (*Capsicum*) as described in Example 13. Foliar applications with the Gm.RHPP bioactive priming polypeptide were applied at the first flower stage, on two varieties of pepper, Red Knight (RK) and Hungarian Hot Wax (HHW). The foliar Gm.RHPP treatments were applied using an application use rate of 1 Fl. oz/Ac (73.1 mL/Ha) on the RK and HHW pepper plants and compared to the control (water applied at same use rate). Effects of the foliar applications on pepper yield were determined for two separate harvests using a once over harvest approach and normalized to the yield of the control plants. The average percentage change in yield over the yield for the control plants is reported in Table 42, as the percent change per total weight (lbs/Ac) of peppers harvested. Average percent change in yield is reported for the 2 replicate harvests (trials) for the RK and HHW pepper varieties and then as a combined average for both varieties.

TABLE 42

| Foliar treatment of RHPP to increase yield in different varieties of pepper | | | |
|---|---|---|---|
| Foliar Treatment | Avg. Percent Change Yield Total Weight (lbs/Ac) Red Knight | Avg. Percent Change Yield Total Weight (lbs/Ac) Hungarian Hot Wax | Combined Avg. Percent Change Yield Total Number (lbs/Ac) RK and HHW |
| Gm.RHPP 1 Fl. oz/Ac | +87% | +46% | +67% |

Percent average yield for RK and HHW peppers that received the Gm.RHPP applied at the use rate of 1 Fl. oz/Ac (73.1 mL/Ha) was increased by 87% for RK and 46% for HHW peppers compared to the control plants. The combined average for both pepper varieties was reported as an average 67% increase for the percent change in yield in the foliar Gm.RHPP treated peppers over the non-treated (water) control pepper plants (Table 42).

Example 27: Application of Harpin-like and ALPSKα Polypeptides to Corn

Harpins can provide functional benefits when applied both exogenously, for example as a foliar spray to the plant surface, or provided apoplastically (the space outside of the plant cell membrane) or endogenously (inside a plant cell/plant cell membrane). Synthetic harpin bioactive priming polypeptide, HpaG-like (*Xanthomonas* spp., SEQ ID NO: 587) was applied exogenously to the surface of corn plants at the V2-V3 stage of development. Additionally, the effect of exogenous application of Phytosulfokine alpha (PSKα), a sulfonated bioactive priming polypeptide derived from *Arabidopsis thaliana*, on corn growth was tested.

Corn (Beck's hybrid 5828 YH) plants were grown in an environmentally controlled growth room. Corn seed was planted directly into 39.7 $cm^3$ pots containing Timberline top soil at a depth of 2.54 cm, with 2 seeds per pot. After planting, 50 mL of room temperature water was added to each pot to allow for germination. The pots were kept in an artificial lighted growth room receiving approximately 300 $\mu mol\ m^{-2}\ s^{-1}$ (light photons) for a 16/8 light/day cycle and a 21° C. day/15° C. night temperature range. Plants received the same watering and fertilizer regimes.

Plant height (cm) was measured at 3 weeks after emergence. Bioactive priming polypeptides for HpaG-like (SEQ ID NO: 587), provided as a synthetic 23 amino acid polypeptide, and At.PSKα (SEQ ID NO: 598) were then applied to the corn plants as a foliar spray at final concentrations of 1 μM for HpaG-like and 100 mM for PSKα bioactive priming polypeptides. Control plants were treated with surfactant (0.01% v/v) alone. A week after the spray treatments were applied, the plants were subdivided into 2 groupings where one group remained in the same standard growth environment described above and the other group was transferred to an environment that provided heat and water deficit stress. For the heat and water deficit treatments, the growth room environment (with the exception of temperature and watering/fertilizer cycles) remained similar to the standard growth environment). Heat stress was applied using heat mats to raise the temperature in the environment from 21° C. to 27° C. During the period of heat stress, the plants were left unwatered to simulate a water deficit stress. Change in plant height (cm) was measured at 5 weeks and reported as normalized to or as a percentage of the height of the control (water) plants. Measurements are reported as the combined average of two trials with 9 replicate plants per trial (Table 43) and are presented as a percentage of growth over control corn plants that received water plus surfactant (0.01% v/v) standardized to measure 100% (Table 43).

TABLE 43

| Changes in Plant height of corn plants treated with X. spp. HpaG-like and At. PSKα | | | | | |
|---|---|---|---|---|---|
| Treatment Corn | Height (cm) and (STDEV) 3 weeks | Height (cm) after non-stress 5 weeks | Height (cm) after stress 5 weeks | Plant Height Normalized as a percentage of control height Non-stress | Plant Height Normalized as a percentage of control height Stress |
| X, spp. HpaG-like (1 μM) | 47.23 (6.11) | 64.10 (5.53) | 45.50 (4.37) | 107.4% | 89.4% |
| At.PSKα (100 nM) | 49.36 (8.00) | 58.62 (4.84) | 54.88 (2.79) | 98.2% | 107.8% |

Foliar application using the HpaG-like polypeptide showed an improved growth phenotype in normal environments, but not stressed environments, when compared to the control plants, while foliar application of PSKα exhibited an improved growth phenotype when grown under conditions of heat and water deficit stress but not in the non-stressed environment.

In a separate set of replicated trials, similar changes in growth rates resulted from the foliar applications of HpaG-like (SEQ ID NO: 587) and PSKα (SEQ ID NO: 598). Table 44 shows the percentage change in plant growth for corn receiving X. spp. HpaG-like polypeptide (1 μM final concentration) and At. PSKα (100 nM final concentration) applied as foliar treatments and measured by changes in plant height compared to control (water plus 0.01% v/v surfactant) plants grown in optimal (non-stress) and in stress environments. This suggests that the combined foliar application or sequential applications of PSKα with HpaG-like bioactive priming polypeptides may be useful for enhancing growth of plants growth under standard (non-stress or optimal growth) environments or of plants exposed to abiotic stress (for example, heat, and water deficit stress).

TABLE 44

Foliar application treatments using the Xspp HpaG-like and the At. PSKα polypeptides on corn grown under non-stress and stress conditions

| Treatment | Plant Height (cm) Percentage Change Compared to Control (0.01% surfactant) Non-Stress | Plant Height (cm) Percentage Change Compared to Control (0.01% surfactant) Stress |
|---|---|---|
| Xspp. HpaG-like (1 μM) | +5.0% | −6.1% |
| At. PSKα (100 nM) | −11.8% | +6.1% |

Example: 28 Combination of Bt.4Q7Flg22 or Ec.Flg22 with RHPP

The bioactive priming polypeptides, Bt.4Q7Flg22 and Ec.Flg22, were combined with RHPP and accessed for yield benefits in soybean. The combination of either Bt.4Q7Flg22 (SEQ ID NO: 226) or Ec.Flg22 (SEQ ID NO: 526) and RHPP (SEQ ID NO: 600) were foliar applied to two varieties of soybean (AG2836, Variety 1; AG3536, Variety 2) in 7 locations across the US Midwest (IA, IL and IA).

Foliar application using Bt.4Q7 Flg22 bioactive priming polypeptide (SEQ ID NO: 226; FIG. 4, panel A) and Ec.Flg22 (SEQ ID NO: 526; FIG. 4, panel B) and RHPP (SEQ ID NO: 600) were applied individually to soybean plants (commercial hybrid Beck'S 294 NR) at the R2 stage of development using varying use rates of 0.33, 4.0, 8.0, and 16.0 Fl. oz/Ac or (24.1 mL/Ha, 292.3 mL/Ha, 584.6 mL/Ha, 1169.2 mL/Ha). Average yield (harvested in September) in bushels per acre (Bu/Ac) is reported for soybean grown in 7 separate locations and reported individually for both soybean varieties and as a combined average yield (Table 45). Soybean yield (Bu/Ac) is also reported as the change in yield (Bu/Ac) normalized to the control soybean plants for both varieties.

TABLE 45

Flg polypeptides and RHPP polypeptides increase yield in soybean

| Treatment Soybean | Application Use Rate Fl. oz/Ac | Average Total Yield Bu/Ac Variety 1 | Average Total Yield Bu/Ac Variety 2 | Average Total Yield Bu/Ac Variety 1 and 2 | Average Bu/Ac Increase compared to Control Variety 1 and 2 |
|---|---|---|---|---|---|
| Control | — | 59.53 | 61.61 | 60.57 | — |
| Bt.4Q7Flg22 | 0.33 | 60.33 | 61.61 | 61.02 | +0.45 |
| Bt.4Q7Flg22 | 4.0 | 57.61 | 64.19 | 60.90 | +0.33 |
| Bt.4Q7Flg22 | 8.0 | 59.05 | 63.86 | 61.45 | +0.88 |
| Ec.Flg22 | 0.33 | 58.62 | 63.58 | 61.10 | +0.53 |
| Ec.Flg22 | 4.0 | 58.02 | 63.91 | 60.74 | +0.17 |
| Ec.Flg22 | 8.0 | 58.27 | 64.35 | 61.31 | +0.74 |
| Gm.RHPP | 0.33 | 59.15 | 62.44 | 60.92 | +0.35 |
| Gm RHPP | 4.0 | 58.61 | 66.35 | 61.83 | +1.26 |
| Gm RHPP | 8.0 | 59.47 | 62.46 | 61.08 | +0.51 |
| Bt.4Q7Flg22 + Gm.RHPP | 4.0 4.0 | 61.14 | 64.88 | 63.18 | +2.61 |
| Ec.Flg22 + Gm.RHPP | 4.0 16 | 59.56 | 62.46 | 61.08 | +0.51 |

Soybean variety AG3536 (Variety 2) consistently outperformed AG3536 (Variety 1) for yield Bu/Ac in all 7 locations across the US Midwest. Foliar applications with the Bt.4Q7Flg22, Ec.Flg22 and RHPP applied individually at the 3 different use rates (0.33, 4.0 and 8.0 Fl. oz/Ac) or (24.1 mL/Ha, 292.3 mL/Ha, 584.6 mL/Ha) all resulted in a yield advantage over the non-treated control plants. The RHPP applied foliarly using a 4.0 Fl. oz/Ac (292.3 mL/Ha) use rate resulted in the largest yield increase of +1.26 Bu/Ac (84.7 kg/Ha) over the control plants compared to the other bioactive priming polypeptides applied separately. However, the combination of Bt.4Q7Flg22 with RHPP provided an additional yield advantage resulting in a +2.61 Bu/Ac (175.5 kg/Ha) over the non-treated soybean control plants. This increase in yield seen from soybean plants treated with foliar applications of Bt.4Q7Flg22 combined with RHPP illustrates a synergistic effect achieved by combining the bioactive priming polypeptides where the increase in yield of the combination was greater than the sum of the two polypeptides applied separately.

Example 29: Use of *Agrobacterium tumefaciens* to Test Effectiveness of Thionins in Treating HLB Disease

*Agrobacterium tumefaciens* strain GV3101 was inoculated into Luria broth medium (LB) and grown for 20 hours. Initially the optical density (OD) of the culture was measured at a wavelength of 600 nm using a spectrophotometer and normalized to a low starting density. The cultures were then divided equally and treated with similar proportions of thionins that are representative of mixtures used to treat citrus trees. The ratios of Cs.thionin (SEQ ID NO: 651), As.thionin (SEQ ID NO: 652) and Mt.thionin (SEQ ID NO: 653) used were 10.0%, 2.0%, 0.40%, 0.08%, and 0.02% and were prepared to match the 20 mL total volume of filtrate of each of the thionin mixtures that is used as a treatment per tree. Each thionin mixture was also compared to control mixtures containing only: filtrate, minimal media (LB), or a tetracycline (Tet) antibiotic (10 μg/mL per culture). Each bar represents a combined OD measure of 3 replicates. After incubation with the thionin and antibiotic mixtures, the optical density (OD 600) was measured again to determine if growth of the *Agrobacterium* cultures was reduced or inhibited.

Figure 8:
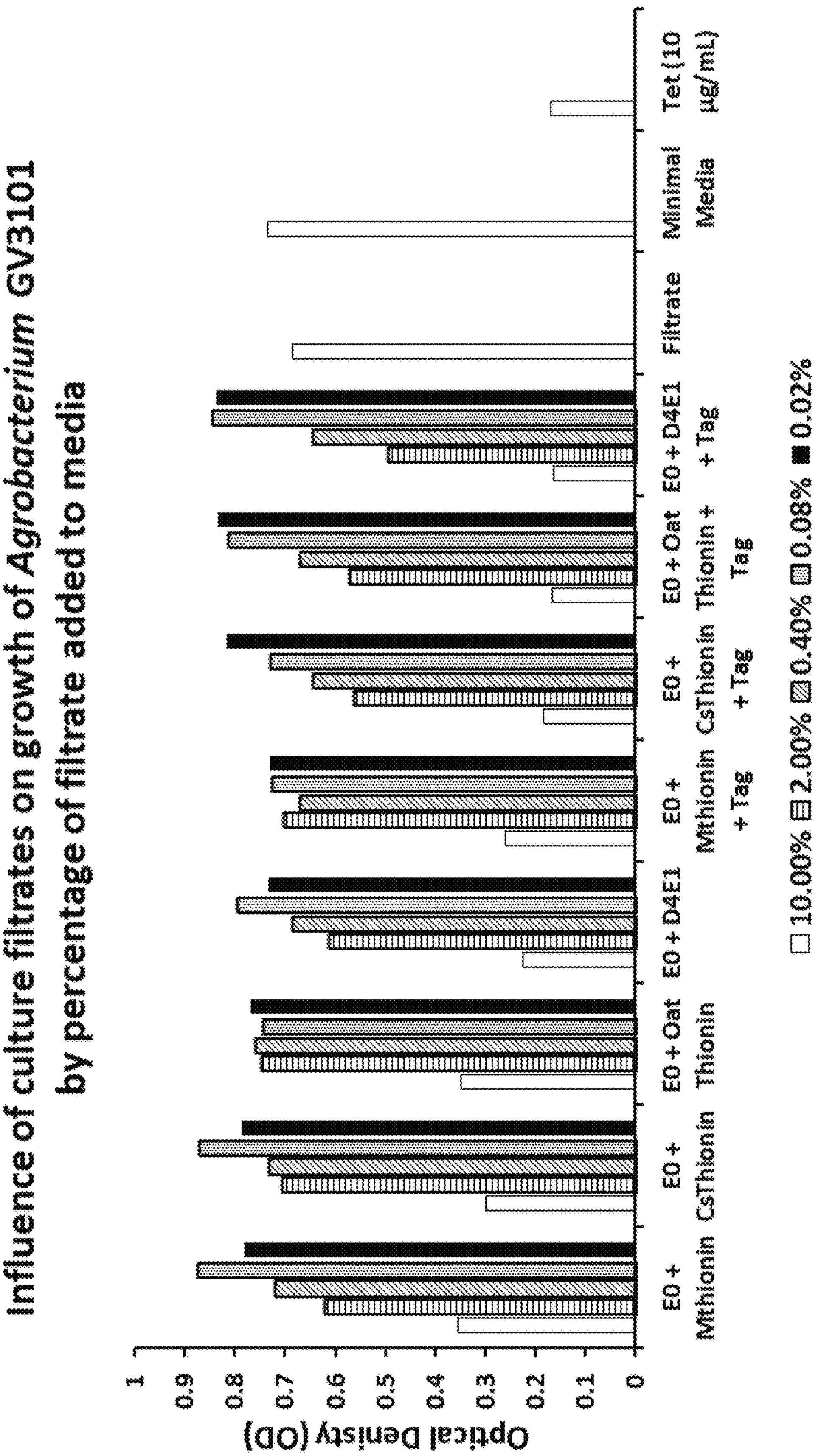
FIG. 8 is directed to the application delivery using thionins to influence (decrease) the growth of *Agrobacterium* strain GV3101 in a rate dependent manner.

As is shown in FIG. 8, the Cs.thionin, As.thionin and Mt.thionin treatments all showed a dose dependent response and decreased growth of the *Agrobacterium* cultures compared to the filtrate, minimal media (LB) or antibiotic (Tet) controls.

Example 30: Treatment of *Candidatus Liberibacter Asiaticus* Infection with Thionins Use of thionins to treat *Candidatus Liberibacter asiaticus* infection will be tested in citrus trees from an orchard located in central Florida (Okeechobee county). Treatment of a total of 26 trees will use formulation mixtures of thionin (SEQ ID NO: 620; 621 and 622) either with or without a phloem localization sequence (SEQ ID NO: 611) to target the thionins specifically to the phloem where *Candidatus Liberibacter asiaticus* reside. Inoculation of Valencia orange (*Citrus sinensis*) trees with these formulations of thionins and mixtures thereof will be conducted using a low-pressure injection device, BRANDT ENTREE. Four total thionin treatments including water as a negative control and oxytetracycline as a positive control will be applied to 5 year-old trees. The citrus trees will be randomized into treatment blocks for control (non-treated), thionin treated and positive control antibiotic (oxytetracycline) treated tree plots. Thionins fused to a phloem targeting sequence will be expressed in a pBC vector, and thionin containing filtrate will be collected from the expressed cells. A total volume of 20 mL containing a mixture of thionins: Cs.thionin (SEQ ID NO: 651), As.thionin (SEQ ID NO: 652) and Ms.thionin (SEQ ID NO: 653) will be provided as 20 mL total volume of filtrate. The thionin treated citrus trees will be compared to the non-treated (control) trees and trees that received a separate positive control of an antibiotic, oxytetracyline, applied with a concentration of 2 grams/tree. Levels of infection of trees with *Candidatus Liberibacter asiaticus* will be confirmed by qPCR detection or amplification using 16S rRNA gene specific primers and nested primers to detect the HLB disease [Sequence 5'» 3':(forward) HLB as TCGAGCGCGTATGCAATACG; (reverse) HLBr GCGTTATCCCGTAGAAAAAGGTAG; HLBpc (probe) AGACGGFTGAGTAACGCG labeled with fluorescein reporter dye].

Plants will be treated in March and leaf samples will be collected one month later in April. Average bacterial counts for *Candidatus Liberibacter asiaticus* will be assessed along with visual symptomology ranking scores for leaf blotch mottling or signs of yellowing of leaves and stems.

Fruit size, shape and level of fruit development or maturity will be collected for 20 representative fruits per tree. Longitudinal length (major diameter, cm) and width (minor diameter, cm, the average of the largest and smallest widths if the fruit is not symmetrical). Fruit shape will be measured by the ratio of width to length. Total fruit weight will be obtained and divided by the total number of fruits (20) to provide an average fruit weight (grams). Total fruit weight will be collected and represented in kg/tree.

Acid-corrected °Brix (°$Brix_c$) values of juice obtained from the juiced (squeezed) grapefruit and orange fruit will be obtained per tree following the USDA minimum standards for °$Brix_c$ laboratory analytical methods. Percent acid (%, w/v) will also be measured. The °Brix reading on a refractometer for a juice to be reconstituted equals the value of the desired acid-corrected °Brix subtracted of the acid contribution and temperature effect. The total titratable acidity (% acid) of the reconstituted juice will also be calculated based on the reconstituted °Brix and Brix/Acid ratio and adjusted using an acid correction and temperature correction factors (JBT FoodTech Laboratory Manual, "Procedures for Analysis of Citrus Products, Sixth Edition).

Bacterial cell counts will be calculated using real time fluorescent PCR, quantitative polymerase chain reaction (qPCR) techniques to detect only live bacterial and subtract out background DNA including naked DNA or DNA from dead cells (Davis and Brlansky, "Quantification of live *Candidatus Liberibacter asiasticus*" populations using real-time PCR and propidium monoazide", Plant Disease 97: 1158-1167, 2013). Colony counts specific for *Candidatus Liberibacter asiasticus* (CLas) cells will be measured in the leaves collected from the thionin treated, non-treated (control) and positive control (antibiotic) treated trees. Calculations for live bacterial titers will be obtained from the DNA yield obtained by qPCR, fit into a regression equation to correlate target copy number to total bacterial counts and represented on a log scale of live cells per gram tissue. Comparisons of titers from treated and non-treated trees will be matched with the degree of disease severity or disease symptoms, such as the classic blotchy mottling on the leaves, deformed or lopsided fruit and greening fruit, etc. for both the red grapefruit and Valencia orange trees.

Example 31: Use of Retro-Inverso Flg Bioactive Priming Polypeptides to Treat and Reduce Citrus Greening Combinations of flagellin-associated polypeptides paired with their retro-inverso counterparts can be used to treat and reduce the greening effect on citrus that results in Asian citrus greening or Huanglongbing disease (HLB).

An early symptom of HLB in citrus is the yellowing of leaves on an individual limb or in one sector of a tree's canopy. Leaves that turn yellow from HLB will show an asymmetrical pattern of blotchy yellowing or mottling of the leaf, with patches of green on one side of the leaf and yellow on the other side. As the HLB disease progresses, the fruit size becomes smaller, and the juice turns bitter. The fruit can remain partially green and tends to drop prematurely.

The retro-inverso forms of Flg22 can compete with native forms of Flg22 for binding to the FLS-associated receptor(s) at the plant surface and thus inhibit/delay the symptom formation of greening associated with HLB disease. Using native Flg22 and RI combinations will assist with a fine tuned immune response to reduce and even eliminate the disease-causing bacteria, *Candidatus Liberibacter asiaticus* and thus prevent acute symptom development, such as leaf yellowing and citrus fruit greening.

Treatment combinations of Flg polypeptides with their retro-inverso (RI) forms will be used to minimize the effect of HLB infection on citrus fruit greening. Thirty-four commercial grapefruit, *Citrus paradise* Macfad., and six sweet orange, *Citrus sinensis* (L.) trees, with or without symptoms of HLB disease, will be treated using flagellin bioactive priming polypeptide combinations described in Table 46, below, using a low pressure injection device called BRANDT enTREE to distribute the Flg polypeptides into the interior of the tree.

TABLE 46

Combinations of Flg22 native and retro-inverso Flg22 bioactive priming polypeptides

| Treatments | SEQ ID NO: | Concentration nM |
|---|---|---|
| Bt.4Q7Flg22 | 226 | 50 nM |
| Bt.4Q7Flg22 | 226 | 100 mM |
| RI Bt.4Q7Flg22 | 376 | 50 nM |
| RI Bt.4Q7Flg22 | 376 | 100 mM |
| Bt.4Q7Flg22 + RI Bt.4Q7Flg22 | 226 & 376 | 50 nM |
| Bt.4Q7Flg22 + RI Bt.4Q7Flg22 | 226 & 376 | 100 mM |
| Ec.Flg22 | 526 | 50 nM |
| Ec.Flg22 | 526 | 100 mM |
| RI Ec.Flg22 | 527 | 50 nM |
| RI Ec.Flg22 | 527 | 100 mM |
| Ec.Flg22 + RI Ec.Flg22 | 526 & 527 | 50 nM |
| Ec.Flg22 + RI Ec.Flg22 | 526 & 527 | 100 mM |

Leaf tissue samples from these treated grapefruit and sweet orange trees will be analyzed using the ROS assay as described in Example 15. Sampling will be conducted in orchard groves from March to August in central Florida. The sample of citrus orchards will be assumed to be representative of the state. The orchard sampled will have a minimum acreage of 2 hectares (range of 2-24 Ha and an average of 5.2 Ha). Selected orchard citrus trees will be randomly selected with the non-treated control trees nested in each randomized plot. Leaf tissues from the grapefruit and orange trees will be collected from trees of approximately the same age. Leaves will be sampled at similar locations on the trees and only from trees that had a new flush of growth at the time of sampling. In the orchards selected for sampling, similar cultural practices will be maintained and include flood irrigation and weed management with herbicides. However, the selected orchards will not receive any pesticide application for a minimum of 30 days before leaf sampling for the ROS assays. Two replicate trials of 10 grapefruit trees exhibiting symptomology of HLB disease will be randomly sampled per orchard and compared to 14 grapefruit trees (non-infected control) sampled that do not exhibit any symptoms. Similar leaf sampling will be performed in sweet orange (four infected samples compared to 2 uninfected controls). Trees will be selected to be representative of the whole orchard. A nested analysis of variance (ANOVA) will be performed to determine the statistical significance of any differences in ROS activities observed from treatment of the control and infected HLB citrus leaf samples.

Example 32: Foliar Application of the Flg22 Polypeptide Reduces *Cercospora* Leaf Blight Disease of Soybean Foliar application of the Bt.4Q7Flg22 bioactive priming polypeptide (SEQ ID NO: 226) derived from *Bacillus thuringiensis* and *Bacillus pseudomycoides* expressing Bt.4Q7Flg22 (H1) were applied to soybean plants (commercial hybrid Beck's 294 NR) at the V3 stage of development that were grown at 3 separate US Midwestern locations that were known to previously have *Cercospora* infection in the fields.

A *Cercospora* leaf blight rating scale (percentage of leaf area affected) was used to rate disease severity in all field experiments. The percentage of leaf area affected was calculated using a visual key based on the ASSESS image analysis for plant disease quantification (Chagas Ferreira da Silva, LSU Master's Theses, 2014). Symptom ranking as a percentage was done for the uppermost trifoliate leaves The results are described in Table 47. Visually, soybean plants that received the foliar treatments of the Bt.4Q7Flg22 bioactive priming polypeptide and *Bacillus pseudomycoides* expressing Bt.4Q7Flg22 (H1) had increased vigor as compared to the non-treated control plants. The control plants showed an increase in early symptom development at the 4 week observation time point, 30% as compared to 20% with the Bt.4Q7Flg22 treatment (0.33 Fl. oz/Ac or 24.1 mL/Ha) and approximately 5% with the Bt.4Q7Flg22 treatment (4.0 Fl. oz/Ac or 292.3 mL/Ha). Soybean plants receiving the *Bacillus pseudomycoides* expressing the Bt.4Q7Flg22 (H1) treatment also showed less early symptom development as a result of *Cercospora* infection than the non-treated control plants, 20% at 4 weeks (0.33 Fl. oz/Ac or 24.1 mL/Ha) and 10% (4.0 Fl. oz/Ac or 292.3 mL/Ha). At 8 weeks post application, the non-treated control plants showed 50% visual symptom damage on the upper foliage of the plant (top 3-4 trifoliate leaves). The symptom ranking for plants that received the foliar treatments of the Bt.4Q7Flg22 polypeptide (0.33 Fl. oz/Ac or 24.1 mL/Ha) was comparable to the non-treated control plants at 8 weeks post foliar treatment. However, the soybean plants that received the foliar treatments of Bt.4Q7Flg22 polypeptide (4.0 Fl. oz/Ac) and *Bacillus pseudomycoides* expressing Bt.4Q7Flg22 (H1) (0.33 Fl. oz/Ac or 24.1 mL/Ha) and 4.0 Fl. oz/Ac or 292.3 mL/Ha) showed considerably less apparent symptoms and damage. Overall the treatment of the Bt.4Q7Flg22 polypeptide (4.0 Fl. oz/Ac or 292.3 mL/Ha) was effective at the prevention of early symptom development from *Cercospora* infection as compared to the non-treated plants that showed blight and purple coloration symptoms as well as defoliation. Therefore, foliar application of Bt.4Q7Flg22 polypeptide applied at a higher application use rate (eg. 4.0 Fl. oz/Ac or 292.3 mL/Ha)) can provide a means of managing early symptom development and provide healthier more vigorous soybean plants grown in field locations that have been impacted by *Cercospora*.

TABLE 47

Foliar treatment of soybean plant with Bt.4Q7Flg22 and Bp. expressing Bt.4Q7Flg22 resulted in disease reduction and symptom development of Cercospora on soybean

| Treatment-Soybean | Application Use Rate Fl. oz/Ac | Percent of Disease Area covering plant, 4 weeks Post Application | Disease Area, 8 weeks Post Application |
|---|---|---|---|
| Control | — | 30% | 50% |
| Bt.4Q7Flg22 | 0.33 Fl. oz/Ac | 20% | 50% |
| Bt.4Q7Flg22 | 4.0 Fl. oz/Ac | 5% | 35% |
| H1 Bt.4Q7Flg22 | 0.33 Fl. oz/Ac | 20% | 40% |
| H1 Bt.4Q7Flg22 | 4.0 Fl. oz/Ac | 10% | 30% |

Example 33: Application to Corn—Enhanced Normalized Difference Vegetation Index (ENDVI) Analysis Enhanced Normalized Difference Vegetation Index (ENDVI) is an indicator of live, photosynthetically-active green vegetation and was used to compare the effectiveness of treatments in field trials using remote sensing technology. In the ENDVI index, values ranging from −1.0 to 0.1, are indicative of unhealthy plants with decreased photosynthesis, whereas values approaching 1 are indicative of lush greenness, high photosynthetic capacity, and increased biomass. Healthy plants strongly absorb visible light from the 400-700 nm spectral wavelength range and reflect the wavelengths in the near-infrared light from 700-1100 nm. ENDVI measurements can correspond to certain vegetative properties, such as plant biomass or greenness, absorption of light by plant canopies, photosynthetic capacity (e.g., leaf area index, biomass, and chlorophyll concentration). ENDVI images were collected using a BGNIR camera (Zenmuse X3) attached to a drone (DJI MATRICE 100) specifically created to capture images and filter different wavelengths of light during the capture. The camera uses sensors to capture visible and near-infrared bands of the electromagnetic spectrum. Healthy plants with large amounts of vegetation or biomass reflect green (G) and near-infrared (NIR) light, while absorbing both blue (B) and red light. Plants that are less healthy or that have less above-ground biomass reflect more visible and less NIR light. ENDVI uses both NIR and G as the reflective channels while using B as the absorption channel. The ENDVI formula below adds the NIR and green channels together for the reflective channel. The blue channel is multiplied by two to compensate for the NIR and G channels being added together. The ENDVI equation uses the following calculation for the NIR, G, and B channels to provide a ratio value as a single output.

$$ENDVI = \frac{(NIR + \text{Green}) - (2 * \text{Blue})}{(NIR + \text{Green}) + (2 * \text{Blue})}$$

Corn seed (DEKALB hybrid DKC 58-89) treated with a seed treatment comprising EVERGOL fungicide (7.18% propiconazole, 3.59% penflufen and combined with 5.74% metalaxyl) and PONCHO/VOTiVO 500 (a mixture of 40.3% clothianidin insecticide and 51.6% *Bacillus firmus* 1-1582, a microbial agent) was planted in the US Midwest (IL). Various foliar treatments containing Bt.4Q7Flg22 and a synthetic version of Bt.4Q7Flg22 (Syn01Flg22 as described in Table 48) were applied to corn plants at the V5-V7 stage of development. BGNIR images were collected by drone flight, 50 m above the trial plot, three weeks after each foliar treatment and after the corn canopy had fully closed. Individual BGNIR images were processed using drone display image analysis software to create a single orthomosaic image of the trial plot that was further analyzed with Fiji imaging software. Within the orthomosaic image, plot regions to identify individual foliar treatments in a field and the replicates per each treatment were clearly established using GPS coordinates in each field trial. The treatment replicates identified for imaging were consistent in size. For each foliar treatment, three replicates were collected with two rows imaged per each replicated plot. Within each replicate, the average intensity of light was measured for each of the image channels [blue, green, and near infrared, (visualized as red)] on a scale of 0-255, with Intensity 0=0% reflection (black pixel) and Intensity 255=100% reflection (white pixel). These average B, G and NIR light intensities were used to calculate an ENDVI value using the ENDVI algorithm for plant health (greenness) for each replicated plot. The ENDVI values were then averaged for the three plot replicates as reported in Tables 49 and 50. ENDVI values for the treatment applications were compared to the control treatments in each plot. Control treatments consisted of corn plants grown from seed that was treated with a base seed treatment only and received no foliar treatments. Foliar treatment compositions were as described using the application use rates as specified in Table 48.

TABLE 48

Compositions of foliar Flg22 treatments for testing on corn and soybean

| Composition | Foliar Formulation | Application Use Rate Fluid ounce/acre (Fl. oz/Ac) Milliliters/hectare (mL/Ha) |
|---|---|---|
| Composition 1 | Bt.4Q7Flg22 (SEQ ID NO: 226) 16.7 μM<br>PROXEL BC preservative: 330.7 μM (BIT); 53.5 μM (CMIT); 26.1 μM (MIT) | 4 Fl. oz/Ac or 292.3 mL/Ha |
| Composition 2 | Bt.4Q7Flg22 (SEQ ID NO: 226) 16.7 μM<br>11.6 mM Sodium Phosphate Dibasic combined with 4.2 mM Citric Acid Monohydrate pH 5.6<br>PROXEL BC preservative: 330.7 μM; 50.1 μM (CMIT); 21.71 μM (MIT) | 4 Fl. oz/Ac or 292.3 mL/Ha |
| Composition 3 | Bt.4Q7Flg22 (SEQ ID NO: 226) 16.7 μM<br>1.67 mM Sodium Phosphate Buffer, pH 5.7<br>PROXEL BC preservative: 330.7 μM; 50.1 μM (CMIT); 21.71 μM (MIT) | 4 Fl. oz/Ac or 292.3 mL/Ha |
| Composition 4 | Bt.4Q7Flg22 (SEQ ID NO: 226) 16.7 μM + Cellobiose: 320 mM<br>1.67 mM Sodium Phosphate Buffer, pH 5.7<br>PROXEL BC preservative: 330.7 μM; 50.1 μM (CMIT); 21.71 μM (MIT) | 4 Fl. oz/Ac (Flg22) 292.3 mL/Ha<br>8 Fl. oz/Ac (Cellobiose) 584.6 mL/Ha |
| Composition 5 | Bt.4Q7Flg22 (SEQ ID NO: 226) 16.7 μM<br>1.67 mM Sodium Phosphate Buffer, pH 5.7<br>PROXEL BC preservative: 330.7 μM; 50.1 μM (CMIT); 21.71 μM (MIT) | 48 Fl. oz/Ac or 3,507.6 mL/Ha |
| Composition 6 | Syn01Flg22 (SEQ ID NO: 571) 16.7 μM<br>1.67 mM Sodium Phosphate Buffer, pH 5.7<br>PROXEL BC preservative: 330.7 μM; 50.1 μM (CMIT); 21.71 μM (MIT) | 4 Fl. oz/Ac or 292.3 mL/Ha |
| Composition 7 | Syn01Flg22 (SEQ ID NO: 571) 16.7 μM<br>1.67 mM Sodium Phosphate Buffer, pH 5.7<br>PROXEL BC preservative: 330.7 μM; 50.1 μM (CMIT); 21.71 μM (MIT) | 0.4 Fl. oz/Ac or 29.23 mL/Ha |
| Composition 8 | Syn01Flg22 (SEQ ID NO: 571) 16.7 μM + Cellobiose: 320 mM<br>1.67 mM Sodium Phosphate Buffer, pH 5.7<br>PROXEL BC preservative: 330.7 μM; 50.1 μM (CMIT); 21.71 μM (MIT) | 0.4 Fl. oz/Ac (Flg22) 29.23 mL/Ha<br>8 Fl. oz/Ac (Cellobiose) 584.6 mL/Ha |
| Composition 9 | At.Flg22-B4 (SEQ ID NO: 300)<br>1.67 mM Sodium Phosphate Buffer, pH 5.7<br>PROXEL BC preservative: 330.7 μM; 50.1 μM (CMIT); 21.71 μM (MIT) | 4 Fl. oz/Ac or 292.3 mL/Ha |

Foliar compositions contained 0.1% (v/v) PROXEL BC preservative, an aqueous dispersion of a blend of 330.7 mM 1,2-benzisothiazolin (BIT), 53.5 mM 5-chloro-2-methyl-4-isolthiazolin-3-one (CMIT), and 26.1 mM 2-methyl-4-iso-thiazolin-3-one (MIT). Foliar compositions were applied at the indicated rates (Fl. oz/Ac or mL/Ha) in a carrier volume of 20 gallons/acre water with 0.1% (v/v) Alligare Surface™ non-ionic surfactant As shown in Table 49, foliar applications with compositions containing Bt.4Q7Flg22 and Syn01Flg 22 applied to corn at the V5-V7 stage of development resulted in increased ENDVI measurement ratio values as compared or normalized to plants that received no foliar treatment (seed treatment control). The Bt.4Q7Flg22 compositions provided as a foliar treatment in buffered formulations (compositions 2, 3, 4 and 5; sodium phosphate pH 5.6-5.7) resulted in plants with higher ENDVI ratio values compared to the plants that received the Bt.4Q7Flg22 provided as a non-buffered composition (composition 1) applied at 4 Fl. oz/Ac or 292.3 mL/Ha. However, ENDVI ration values of Bt.4Q7Flg22 treated plants (compositions 1-5) were all increased relative to the non-treated control plants. Corn plants that received the foliar treatment application of composition 4 consisting of the Bt4Q7Flg22 polypeptide combined with cellobiose in a phosphate buffered formulation provided at 8 Fl. oz/Ac or 584.6 mL/Ha use rate resulted in a +9% increase in the average ENDVI ratio value over the control (seed treatment only) plants. Plants that received foliar applications of composition 1 and 5 which differed in composition only in the respective application use rates (4 and 48 Fl. oz/Ac or 292.3 mL/Ha and 3,507.6 mL/Ha) resulted in plants with similar ENDVI ratio values (+3% and +4%) as compared to the control plants. Importantly, the higher rate of 48 Fl. oz/Ac or 3,507.6 mL/Ha resulted in no detectable phytotoxicity, which would have been observed as a reduced ENDVI value compared to the control (seed treatment only). A synthetic derived variant version of Bt.4Q7Flg22 (Syn01Flg22) compositions 6, 7, and 8 were also provided as a foliar spray to V5-V7 corn plants. The Syn01Flg22 polypeptide provided in a phosphate buffered formulation (composition 6 and composition 7) were compared according to the application use rates. The Syn01Flg22 polypeptide (composition 6) that was provided to corn plants using a higher application use rate (4 Fl. oz/Ac or 292.3 mL/Ha) resulted in a decreased ENDVI ratio value or had a lesser percentage increase in ENDVI as compared to the Syn01Flg22 polypeptide (composition 7) applied to plants using a 0.4 Fl. oz/Ac or 29.23 mL/Ha application use rate, a change of 8% between the composition 6 and 7 treatments. The Syn01Flg22 (composition 8) had the addition of cellobiose and similar to composition 7 was provided at an application use rate of 0.4 Fl. oz/Ac or 29.23 mL/Ha. Foliar application of Syn01Flg22 (composition 7) was compared to Syn01Flg22 combined with cellobiose (320 mM) (composition 8). The Syn01Flg22 composition 7 and composition 8 had similar increases in ENDVI measurement ratios resulting in a +10% increase as compared to control plants or a +8% increase compared to plants that received the Syn01Flg22 (composition 6) provided at the higher 4 Fl.oz/Ac or 292.3 mL per hectare (Ha) use rate.

TABLE 49

ENDVI outputs provided for foliar Flg22 treatments on corn hybrid DKC 52-61

| Treatment | ENDVI (STDEV) | Percentage AVG Change in ENDVI Normalized to Control Plants* |
|---|---|---|
| Seed Treatment Control | 0.253 (0.027) | — |
| Bt.4Q7Flg22 Composition 1 | 0.259 (0.019) | +3% |
| Bt.4Q7Flg22 Composition 2 | 0.269 (0.021) | +6% |
| Bt.4Q7Flg22 Composition 3 | 0.272 (0.003) | +7% |
| Bt.4Q7Flg22 + Cellobiose Composition 4 | 0.276 (0.009) | +9% |
| Bt.4Q7Flg22 Composition 5 | 0.263 (0.010) | +4% |
| Syn01Flg22 Composition 6 | 0.258 (0.016) | +2% |
| Syn01Flg22 Composition 7 | 0.277 (0.018) | +10% |
| Syn01Flg22 + Cellobiose Composition 8 | 0.279 (0.015) | +10% |

*Normalized to seed treatment control: EVERGOL and PONCHO/VOTiVO 500

Corn seed (DEKALB hybrid DKC 52-61) was also treated with Roundup POWERMAX(active ingredient glyphosate, 48.7% in the form of potassium salt) in combination with the Bt.4Q7Flg22 composition 3. Roundup POWERMAX was applied using the recommended use rate on the specimen label of 24 Fl oz/Ac. The Bt.4Q7Flg22 (composition 3) was applied at a rate of 4.0 Fl. oz/Ac or 292.3 mL/Ha. Results are shown in Table 50.

TABLE 50

ENDVI with foliar applications of Flg22 polypeptides combined with an herbicide on corn (hybrid DKC 52-61)

| Treatment Formulation Code Application Use Rate | ENDVI (STDEV) | Percentage AVG Change in ENDVI Normalized to Roundup POWERMAX Treatment |
|---|---|---|
| Roundup POWERMAX | 0.271 (0.006) | — |
| Roundup POWERMAX + Bt.4Q7Flg22 (Composition 3) | 0.293 (0.005) | +8% |

*Normalized to RoundUp POWERMAX foliar treatment

As shown in Table 50, Roundup POWERMAX applied to corn at the V5-V7 stage of development as a foliar herbicide combined with the Bt.4Q7Flg22 (composition 3) resulted in an increased ENDVI measurement ratio, an increase of +8% compared to the treatment with the Roundup POWERMAX applied without the Bt.4Q7Flg22 polypeptide.

Example 34: Application of Bioactive Priming Polypeptides to V4-V7 Corn—Increased Yield Large acre corn trials were planted from corn seed (DEKALB hybrids: DKC 52-61, DKC 58-89, and DKC 65-81) coated with a seed treatment comprising EVERGOL fungicide (7.18% propiconazole, 3.59% penflufen, and 5.74% metalaxyl) with PONCHO/VOTiVO 500 (a mixture of clothianidin insecticide and a microbial agent, *Bacillus firmus* I-1582). Corn field trials were planted in 8 locations throughout the US Midwest (IN, IL, & IA). Field seed beds at each location were prepared using conventional or conservation tillage methods for corn plantings. Fertilizer was applied as recommended by conventional farming practices which remained consistent between the US Midwest locations. Herbicides were applied for weed control and supplemented with cultivation when necessary. Four-row plots, 5.3 meters were planted at all locations. Corn seed was planted 3.8 to 5.1 cm deep to ensure normal root development. Corn was planted at approximately on average of 42,000 plants per acre or 103,782 plants per hectare with an average row width of 0.8 meters with seed spacing of 1.6 to 1.8 seeds per every 30 cm.

Corn plants at approximately the V5 stage of development received foliar applications using a foliar composition comprising a Bt.4Q7Flg22 (SEQ ID NO: 226) polypeptide and a synthetic version of Bt.4Q7Flg22 which is described as Syn01Fflg22 (SEQ ID NO: 571) polypeptide. The foliar compositions comprising the Bt.4Q7Flg22 polypeptide and a synthetic version of Bt.4Q7Flg22 polypeptide were applied to 3 corn hybrids (DEKALB hybrids: hybrid 1: DKC 52-61; hybrid 2: DKC 58-89; hybrid 3: DKC 65-81) planted in 8 locations throughout the US Midwest (IN, IL, & IA). Corn plants received foliar treatments using the concentrations and application use rates as described in Table 51. Corn yield (Bu/Ac) was collected and reported as the average yield (Bu/Ac) across the locations (8 locations for hybrid 1, 7 locations for hybrid 2 and 6 locations for hybrid 3) and as the average change in Bu/Ac compared to the base seed treatment (ST) control treated with surfactant alone in Table 51.

TABLE 51

Foliar treatment using Bt.4Q7Flg22 and a Syn01Flg22 synthetic mutant-increase yield in corn

| Foliar Treatment (Concentration) | Application Use Rate Fl. oz/Ac (mL/hectare) | Average Yield Bu/Ac | Average Change in Yield Bu/Ac compared to Surfactant Control |
|---|---|---|---|
| Bt.4Q7Flg22 (16.7 μM) (Composition 1) | 4.0 Fl. oz/Ac (292.3 m L/hectare) | 201.43 | +1.14 |
| Bt.4Q7Flg22 (16.7 μM) + Cellobiose (320 mM) (Composition 4) | 4.0 Fl. oz/Ac (292.3 mL/hectare) 8.0 Fl. oz/Ac (584.6 mL/hectare) | 205.43 | +2.55 |
| Syn01Flg22 (16.7 μM) (Composition 6) | 4.0 Fl. oz/Ac (292.3 mL/hectare) | 203.79 | +0.90 |
| Syn01Flg22 (16.7 μM) (Composition 7) | 0.4 Fl. oz/Ac (29.2 mL/hectare) | 204.36 | +1.48 |
| (16.7 μM) + Cellobiose (320 mM) (Composition 8) | 0.4 Fl. oz/Ac (29.2 mL/hectare) 8.0 Fl. oz/Ac (584.6 mL/hectare) | 204.47 | +1.59 |

Corn plants at approximately the V5 stage of development received foliar applications using a foliar composition comprising a Bt.4Q7Flg22 and a synthetic version Syn01Flg22 of Bt.4Q7Flg22 polypeptides. The Bt.4Q7Flg22 and a synthetic version of Bt.4Q7Flg22 polypeptides were also combined with cellobiose (320 mM), a reducing sugar, consists of two β-glucose molecules linked by a β-(1→4) bond and provided as an elicitor treatment to enhance the effect of the Flg22 polypeptide. Both the Bt.4Q7Flg22 and the Syn01Flg22 provided in combination with cellobiose to corn plants resulted in an enhanced yield boost over the Bt.4Q7Flg22 and the Syn01Flg22 foliar applied polypeptides. A positive increase in yield of +2.55 Bu/Ac or 160 kg/Ha resulted in the corn plants that received the Bt.4Q7Flg22 foliar treatment with cellobiose as compared to the +1.14 BuAc or 71.6 kg/Ha increase in yield for the Bt. 4Q7Flg22 foliar treatment provided alone. There was also a positive increase in yield of +1.59 Bu/Ac or 99.8 kg/Ha resulted in the corn plants that received the Syn01Flg22 (0.2 Fl. oz/Ac or 14.6 mL/Ha) foliar treatment provided in combination with cellobiose as compared to the +1.48 BuAc or 92.9 kg/Ha increase in yield for the Syn01Flg22 foliar treatment provided at the same application use rate. Whereas, the Bt.4Q7Flg22 and the Syn01Flg22 provided as foliar treatments to corn plants at the V5 stage of development using a 4.0 Fl. oz use rate or 292.3 mL/Ha provided a slightly lower increase in yield +1.14 Bu/Ac (71.6 kg/Ha) and +0.90 Bu/Ac (56.5 kg/Ha) as compared to the combinations of the two Flg22 polypeptides with cellobiose.

Example 35: Combination of a Synthetic-Derived Flg22 (Syn01Flg22) and a Fungicide In a further study, large acre yield trials were conducted using a foliar application comprising a compositions of the Bt.4Q7Flg22 polypeptide and a synthetic derived polypeptide from Bt.4Q7Flg22 (Syn01Flg22) provided with a broad-spectrum fungicide, STRATEGO YLD (10.8% prothioconazole and 32.3% thiofloxystrobin). STRATEGO YLD is a commercially available fungicide suitable for use as an early season foliar application for corn was applied as a foliar spray following the recommendations on the specimen label at a use rate of 4.0 fluid ounces per acre (Fl. oz/Ac) (292.3 mL/hectare). Corn plants at approximately the V5 stage of development received foliar applications using a foliar composition comprising the Bt.4Q7Flg22 polypeptide and Syn0Flg22, the synthetic version of Syn01Flg22 polypeptide combined with the STRATEGO YLD fungicide. Foliar treatments were applied to 2 corn hybrids (DEKALB hybrids: hybrid 1: DKC 52-61; hybrid 2: DKC 58-89) planted in 2 locations Iowa. Corn yield (Bu/Ac) was collected and reported as the average yield (Bu/Ac) across the 2 locations for both hybrids and as the average change in Bu/Ac compared to the corn plants grown from seed that received the base seed treatment (ST) and only the foliar application with the STRATEGOYLD fungicide (Table 52).

TABLE 52

Corn yield foliar applications of a synthetic mutant of Bt.4Q7Flg22 combined with a fungicide

| Foliar Treatment (Concentration) | Application Use Rate Fl. oz/Ac (mL/hectare) | Average Yield Bu/Ac | Average Change in Yield Bu/Ac Compared to Fungicide Control |
|---|---|---|---|
| STRATEGO YLD Fungicide | 4.0 Fl. oz/Ac (292.3 mL/hectare) | 223.13 | — |
| STRATEGO YLD Fungicide + Bt.4Q7Flg22 (SEQ ID NO: 226) (16.7 μM) (Composition 3) | 4.0 Fl. oz/Ac (292.3 mL/hectare) 4.0 Fl. oz/Ac (292.3 mL/hectare) | 228.62 | +5.49 |
| STRATEGO YLD Fungicide + Syn01Flg22 (SEQ ID NO: 571) (16.7 μM) (Composition 6) | 4.0 Fl. oz/Ac (292.3 mL/hectare) 4.0 Fl. oz/Ac (292.3 mL/hectare) | 228.96 | +5.83 |

The base seed treatment (ST) consisted of EVERGOL fungicide + PONCHO/VOTIVO 500.

The STRATEGO YLD fungicide was applied at the concentration and application use rate as recommended on the specimen label.

Foliar application to V5 corn plants with the Bt.4Q7Flg22 and the Syn01Flg22 polypeptides that were provided in combination with a fungicide, STRATEGO YLD at the concentrations and application use rates as specified in Table 5 above resulted in a more than a +5 Bu/Ac. The Syn01Flg22 polypeptide foliar treatment resulted in slightly higher corn yields of +5.84 Bu/Ac (366.6 kg/Ha) than the corn plants that received the Bt.4Q7Flg22 polypeptide treatment which resulted in average yields of +5.50 Bu/Ac (345.2 kg/Ha) as compared to the plants that received the foliar treatment with only the STRATEGO YLD fungicide.

Example 36: Seed Treatment with Flg22 Polypeptides to Increase Yield in Corn

In other studies, large acre yield trials were conducted using a base seed treatment consisting of®EVERGOL fungicide (7.18% propiconazole, 3.59% penflufen and combined with 5.74% metalaxyl) and PONCHO/VOTiVO 500 (a mixture of 40.3% clothianidin insecticide and 51.6% *Bacillus firmus* 1-1582, a microbial agent) provided in combination with various Flg22 polypeptides. Seed treatments were applied to 3 corn hybrids (BECK's 4919V2, 5140HR and 5828YX) planted in 8 locations throughout the US Midwest (IN, IL, & IA). Seed treatment compositions of the Flg22 polypeptides were applied as described in Table 53 as Fl. oz per unit of corn or soy seeds in a total slurry volume containing the base seed treatment Bt.4Q7Flg22 from *Bacillus thuringinesis* (Composition 10) and Pa. Flg22 from *Paenibacillus alvei* (Composition 11). Final concentration of polypeptide in the slurry for Compositions 10 and 11 was 1 uM.

TABLE 53

Compositions of Flg22 seed treatments for testing on corn and soybean

| Composition | Seed Treatment Formulation | Application Use Rate Fluid ounce/ unit corn or soy (Fl. oz/unit) Milliliters/unit (mL/unit) |
|---|---|---|
| Composition 10 | Bt.4Q7Flg22 (SEQ ID NO: 226) 40.0 μM 11.6 mM Sodium Phosphate Dibasic combined with 4.2 mM Citric Acid Monohydrate pH 5.6 | 0.14 Fl. oz/unit or 4.14 mL/unit |
| Composition 11 | Pa.Flg22 (SEQ ID NO: 293) 40.0 μM 11.6 mM Sodium Phosphate Dibasic combined with 4.2 mM Citric Acid Monohydrate pH 5.6 | 0.14 Fl. oz/unit or 4.14 mL/unit |

Corn yield (Bu/Ac) was collected and reported as the yield (Bu/Ac) across the 8 locations averaged for all 3 hybrids. The average change in Bu/Ac was as compared to the corn plants grown from seed that received the only the base seed treatment (ST) and is reported in Table 54.

TABLE 54

Corn seed treatment with Flg22 Polypeptide increases yield

| Foliar Treatment | Application Use Rate | Average Yield (Bu/Ac) | Average Change in Yield (Bu/Ac) compared to ST control |
|---|---|---|---|
| Bt.4Q7Flg22 *Bacillus thuringinesis* (SEQ ID NO: 226) (Composition 10) | 0.14 Fl. oz/unit or 4.14 mL/unit | 179.72 | +4.73 |
| Pa.Flg22 *Paenibacillus alvei* (SEQ ID NO: 293) (Composition 11) | 0.14 Fl. oz/unit or 4.14 mL/unit | 182.24 | +3.57 |

Treatment of corn seed with Bt.4Q7Flg22 (SEQ ID NO: 226) and Pa.Flg22 (SEQ ID NO: 293) polypeptides increased yield as represented as an average over the 3 corn hybrids and the 8 US Midwest locations. The Bt.4Q7Flg22 polypeptide provided as a seed treatment resulted in an even greater yield advantage or a +4.73 Bu/Ac (296.9 kg/Ha) compared to the control plants. The Pa.Flg22 applied as a seed treatment also resulted in a yield gain with a +3.57 Bu/Ac (224 kg/Ha) over corn plants grown from seed that received only the base seed treatment. Thus, Flg22 polypeptides obtained from different species of bacteria (*Bacillus* and *Paenibacillus*) both resulted in substantial yield increases when applied as a seed treatment on corn seed.

Example 37: Application of Flg22 Polypeptides with Cellobiose to Increase Yield in Corn Large acre corn trials were planted from corn seed (DEKALB hybrids: DKC 52-61, DKC 58-89, and DKC 65-81) containing a seed treatment comprising EVERGOL fungicide (7.18% propiconazole, 3.59% penflufen and combined with 5.74% metalaxyl) combined with PONCHO/VOTiVO 500 (a mixture of clothianidin insecticide and a microbial agent, *Bacillus firmus* 1582). Corn plants at approximately the V5 stage of development received foliar applications using an agricultural composition comprising a Bt.4Q7Flg22 and the synthetic Syn01Flg22 polypeptides were provided with and without cellobiose (320 mM). The foliar treatments were applied to 2 corn hybrids (DEKALB hybrids: hybrid 1: DKC 58-89; hybrid 2: DKC 65-81) planted in 2 locations in the US Midwest (IL) that experienced drought-like conditions after foliar application, during the pollination stage of corn development. Corn plants received the Bt.4Q7Flg22 and Syn01Flg22 foliar treatments using the concentrations and application use rates as described in Table 48 with a non-ionic surfactant (Alligare Surface™ applied at a final concentration of 0.1% v/v of spray tank volume). Corn yield (Bu/Ac) was collected and reported as the average yield (Bu/Ac) across the 2 locations for the 2 hybrids and as the average change in Bu/Ac compared to yield from corn plants that received only base seed treatment (ST) and a non-ionic surfactant (Alligare Surface™ applied at a final concentration of 0.1% v/v of spray tank volume) (Table 55).

TABLE 55

| Combinations of Flg22 polypeptides with cellobiose-corn | | | |
|---|---|---|---|
| Foliar Treatment (Concentration) | Application Use Rate Fl. oz/Ac (mL/hectare (Ha) | Average Yield (Bu/Ac) | Average Change in Yield (Bu/Ac) compared to Surfactant control |
| Bt.4Q7Flg22 (SEQ ID NO: 226) (16.7 μM) | 4.0 (292.3 mL/Ha) | 96.46 | +3.70 |
| Bt.4Q7Flg22 (SEQ ID NO: 226) (16.7 μM) + Cellobiose (320 mM) | 4.0 (292.3 mL/Ha) 8.0 (584.6 mL/Ha) | 100.98 | +8.22 |
| Bt.4Q7Flg22 (SEQ ID NO: 226) (16.7 μM) | 48.0 (3507.6 mL/Ha) | 119.37 | +26.61 |
| Syn01Flg22 (SEQ ID NO: 571) (16.7 μM) | 4.0 (292.3 mL/Ha) | 98.48 | +5.72 |
| Syn01Flg22 (SEQ ID NO: 571) (16.7 μM) | 0.4 (29.2 mL/Ha) | 102.36 | +9.60 |
| Syn01Flg22 (SEQ ID NO: 571) (16.7 μM) + Cellobiose (320 mM) | 0.4 (29.2 mL/Ha) 8.0 (584.6 mL/Ha) | 108.24 | +15.48 |

Foliar treatment applications of Bt.4Q7Flg22 (SEQ ID NO: 226) and a synthetic version of Syn01Flg22 (SEQ ID NO: 571) resulted in substantial yield gains in corn plants when combined in a foliar treatment application with cellobiose, a disaccharide that is used as a secondary stabilization agent for the Flg polypeptide and vehicle for delivery to the plant membrane surface. The Bt.4Q7Flg22 polypeptide (16.7 μM) provided with cellobiose (320 mM) as a combination foliar spray applied using 4.0 Fl. oz/Ac application use rate (Flg22) resulted in a more than doubled yield gain, a +8.22 Bu/Ac increase or approximately 516 kg/ha over the control plants in comparison to 4.0 Fl. oz/Ac Bt.4Q7Flg22 polypeptide alone. The Bt.4Q7Flg22 polypeptide applied without cellobiose resulted in a +3.70 Bu/Ac or 232 kg/Ha increase over the control plants grown from the surfactant control. Similar increased yield resulted in corn plants treated with the Syn01Flg22 and the combination of Syn01Flg22 (16.7 μM) provided in combination with cellobiose (320 nM) using a 0.2 Fl. oz/Ac application use rate, a respective increase of +9.60 (602.6 kg/Ha) and +15.48 (971.6 kg/Ha) compared to the yield obtained from the surfactant control plants. Additionally, the Bt.4Q7Flg22 (16.7 μM) polypeptide was provided as a foliar spray application using three different application use rates of 0.2, 2.0 and 24.0 Fl. oz/Ac (14.6 mL/Ha, 146.2 mL/Ha and 1753.8 mL/Ha) to corn plants at the V5-V7 stage of development. The Bt.4Q7Flg22 polypeptide delivered using the highest use rate resulted in a substantially higher yield advantage, an almost +27 Bu/Ac (1694.6 kg/Ha) yield increase over the yield obtained from the control plants. Overall, Bt.4Q7Flg22 and a synthetic version of Syn01Flg22 provided protection from drought-like growth conditions during a critical stage of plant development (i.e. pollination), resulting in increased yield for all combinations of Bt.4Q7Flg22, Syn01Flg22 and cellobiose used as foliar applications.

In another study, seed treatments using Flg22 polypeptides and combinations of Flg22 polypeptides with cellobiose resulted in overall yield increases in field trials reported as an average for four replicated trials (Table 56). Seed treatments were applied to corn hybrid (BECK's 5828YX) planted in 1 locations in the US Midwest (Columbia). Seed treatment compositions of Flg22 were applied as described in Table 56 as 0.14 Fl. oz per unit of corn seeds in a total slurry volume containing the base seed treatment. Final concentration of the Flg22 polypeptides in the slurry for were standardized to 1 uM per seed. The same final concentration of cellobiose that was applied in combination treatments with the Flg22 polypeptides was at 1.0 mM per seed. The average yield in Bu/Ac and the average increase in Bu/Ac as compared to the untreated control (column 1) and to the Bt.4Q7Flg22 (SEQ ID NO:226) (column 2) is reported for corn grown from seed that received the Flg22 polypeptide combination treatments as described below in Table 56.

TABLE 56

| Seed treatment combinations of Flg22 polypeptides and variants of Flg22 polypeptides with cellobiose-corn | | | |
|---|---|---|---|
| Foliar Treatment (Concentration) | Average Yield Bu/Ac (Average Change in Bu/Ac compared to Untreated Control) | Average Change in Bu/Ac compared to Untreated Control | Average Change in Bu/Ac compared to Bt.4Q7Flg22; SEQ ID NO: 226 |
| Base Seed Treatment Control | 28.00 | — | −1.60 |
| Bt.4Q7Flg22 at 1.0 μM (SEQ ID NO: 226) | 29.60 | +1.60 | — |
| Syn01Flg22 at 1.0 μM (SEQ ID NO: 571) | 39.58 | +11.58 | +9.98 |
| Syn03Flg22 at 1.0 μM (SEQ ID NO: 300) | 35.17 | +7.17 | +5.57 |
| Pa.Flg22 *Paenibacillus alvei* at 1.0 μM (SEQ ID NO: 293) | 39.04 | +11.04 | +9.44 |
| La.Flg22 Lysinibacillus at 1.0 μM (SEQ ID NO: 574) | 37.13 | +9.13 | +7.53 |
| Flg22-B2 *Bacillus* at 1.0 μM (SEQ ID NO: 295) | 36.79 | +8.79 | +7.19 |
| Flg22 Combination Syn01Flg22 (SEQ ID NO: 571) + Flg22-B2 (SEQ ID NO: 295) + At.Flg22-B4 (SEQ ID NO: 300) at 0.33 μM each | 45.39 | +17.39 | +15.79 |
| Cellobiose 1 mM | 39.66 | +11.67 | +10.07 |
| Bt.4Q7Flg22 (SEQ ID NO: 226) at 1.0 μM + Cellobiose 1 mM | 36.22 | +8.22 | +6.62 |
| Bt.4Q7Flg22 (SEQ ID NO: 226) at 0.25 μM | 47.06 | +19.07 | +17.47 |
| Bt.4Q7Flg22 (SEQ ID NO: 226) at 0.25 μM + Cellobiose 1 mM | 40.62 | +12.63 | +11.02 |
| Syn01Flg22 (SEQ ID NO: 571) at 0.25 μM | 32.65 | +4.66 | +3.06 |

TABLE 56-continued

Seed treatment combinations of Flg22 polypeptides and variants of Flg22 polypeptides with cellobiose-corn

| Foliar Treatment (Concentration) | Average Yield Bu/Ac (Average Change in Bu/Ac compared to Untreated Control) | Average Change in Bu/Ac compared to Untreated Control | Average Change in Bu/Ac compared to Bt.4Q7Flg22; SEQ ID NO: 226 |
|---|---|---|---|
| Bt.4Q7Flg22 (SEQ ID NO: 571) at 0.25 μM + Cellobiose 1 mM | 31.03 | +3.03 | +1.43 |

Example 38: Application of Flg22 with Cellobiose Additive to V4-V6 Soybean Increased Yield—Large Acre Yield Trials Large acre soybean trials were planted from uncoated soybean seed. Soybean seed was planted 1.5 to 2 inches deep (approximately 5 cm) to ensure normal root development. Soybean was planted in 12.5' (3.8 meter) plots with an average of 150,500 plants per acre, row widths of 30 inch rows (0.8 meter) and seed spacing of 7 to 8 seeds per foot (30 cm).

Agricultural compositions comprising agriculturally effective amounts of compositions of Bt.4Q7Flg22 (SEQ ID NO: 226), Syn01Flg22 (SEQ ID NO: 571) and a Flg22 from *Aneurinbacillus thermoaerophilus*, At.Flg22-B4 (SEQ ID NO: 300) were applied to soybean. The Flg22 polypeptide treatments were applied as a foliar spray at application use rates (Fl. oz/Ac or mL/Ha) as specified in Table 57 to soybean grown at five US Midwest locations (participating sites: IA and IL). The soybean plants received foliar treatments containing Bt.4Q7Flg22 (SEQ ID NO: 226); Syn01Flg22 (SEQ ID NO: 571) and At.Flg22-B4 (SEQ ID NO: 300) at approximately the V4-V6 stage of development with a non-ionic surfactant to facilitate spreading and uptake of treatments (Alligare Surface™ applied at a final concentration of 0.1% v/v of spray tank volume). Soybean yield was collected for the 3 soybean varieties (Asgrow: AG2733, AG3536 and AG4034) for plants receiving the Flg22 compositions. Soybean yield was also reported as the change in yield Bu/Ac compared to the control soybean plants that received a non-ionic surfactant (Alligare Surface™ applied at a final concentration of 0.1% (v/v) only treatment (Table 57).

Foliar application of the Bt.4Q7Flg22 and Syn01Flg22 polypeptides were also combined with cellobiose as an additive and examined for the effect of Flg22 polypeptides combined with the cellobiose additive on yield increase. Cellobiose is a glucose disaccharide and a building block for cellulose polymer. Chemically, it is glucose-beta-1-4-glucose, a reducing sugar that consists of two β-glucose molecules linked by a β (1-4) bond. Cellobiose is obtained by the breakdown of cellulose or lichenin and yields glucose upon hydrolysis. The cellobiose additive combined with Bt.4Q7Flg22 resulted in an increase in reactive oxygen species (ROS) activity in soybean. Soybean yield was collected for the 3 soybean varieties (Asgrow: AG2733, AG3536 and AG4034) for plants receiving the Flg22 compositions with and without the cellobiose additive and reported as the average yield (Bu/Ac) for all 3 varieties across locations. Soybean yield was also reported as the change in yield Bu/Ac compared to the control soybean plants that received a non-ionic surfactant (Alligare Surface™ applied at a final concentration of 0.1% v/v only treatment) (Table 57).

TABLE 57

Soybean yield with foliar treatments using varying Flg22 polypeptides

| Treatment Concentration | Application Use Rate Fl. oz/Ac (mL/hectare (Ha) | Average Bu/Ac (5 locations) | Change in Bu/Ac Over Surfactant Control |
|---|---|---|---|
| Non-ionic Surfactant alone | 0.1% v/v spray | 61.36 | — |
| Bt.4Q7Flg22 (SEQ ID NO: 226) 16.7 μM Composition 1 | 4.0 Fl. oz/Ac (292.3 mL/Ha) | 62.85 | +1.49 |
| Bt.4Q7Flg22 (SEQ ID NO: 226) 16.7 μM Composition 2 | 4.0 Fl. oz/Ac (292.3 mL/Ha) | 64.72 | +1.56 |
| Bt.4Q7Flg22 (SEQ ID NO: 226) 16.7 μM Composition 3 | 4.0 Fl. oz/Ac (292.3 mL/Ha) | 63.87 | +2.51 |
| Bt.4Q7Flg22 (SEQ ID NO: 226): 16.7 μM + Cellobiose: 320 mM Composition 4 | 4.0 Fl. oz/Ac (292.3 mL/Ha) 8.0 Fl. oz/Ac (584.6 mL/Ha) | 63.15 | +1.79 |
| Bt.4Q7Flg22 (SEQ ID NO: 226) 16.7 μM Composition 5 | 48.0 Fl. oz/Ac (3507.6 mL/Ha) | 62.64 | +1.28 |
| Syn01Flg22 (SEQ ID NO: 571) 16.7 μM Composition 6 | 4.0 Fl. oz/Ac (292.3 mL/Ha) | 63.12 | +1.76 |
| Syn01Flg22 (SEQ ID NO: 571) 16.7 μM Composition 7 | 0.4 Fl. oz/Ac (29.2 mL/Ha) | 62.88 | +1.52 |
| Syn01Flg22 (SEQ ID NO: 571) 16.7 μM + Cellobiose (320 mM) Composition 8 | 0.4 Fl. oz/Ac (29.2 mL/Ha) 8.0 (584.6 mL/Ha) | 63.92 | +2.56 |
| At.Flg22-B4 (SEQ ID NO: 300) 16.7 μM Composition 9 | 4.0 Fl. oz/Ac (292.3 mL/Ha) | 63.66 | +2.30 |

Foliar treatment of the various Flg22 polypeptides, Bt.4Q7Flg22; Syn01Flg22 and At.Flg22-B4 (Compositions 1-9) all resulted in yield benefits when applied on soybean at the V4-V6 stage of development compared to the control soybean plants that were treated with a foliar application of surfactant alone. Foliar treatment with Bt.4Q7Flg22 (Composition 3) applied at 4.0 Fl. oz/Ac resulted in a +2.51 Bu/Ac (168.8 kg/Ha) increase over control plants (surfactant only). The Syn01Flg22 (Composition 6) polypeptide applied as a foliar treatment using 4.0 Fl. oz/Ac to soybean plants resulted in a yield gain of +1.76 Bu/Ac (118.4 kg/Ha) compared to the surfactant only control plants. Syn01Flg22 (Composition 7) and Syn01Flg22 with the cellobiose (320 nM) (Composition 8) applied to soybean plants using a lower application use rate of 0.2 Fl. oz/Ac resulted in an increase of +1 Bu/Ac with the addition of the cellobiose additive or an overall +2.56 Bu/Ac (172.2 kg/Ha) increase in yield over the control plants. The At.Flg22-B4 (Composition 9) polypeptide applied to soybean (V4-V6) also resulted in a yield benefit of +2.3 Bu/Ac (154.7 kg/Ha) compared to the control plants or over 3.5 Bu/Ac (235.4 kg/Ha) as compared to plants that received treatment with the non-ionic surfactant only.

In still another study, seed treatments using Flg22 polypeptides and combinations of Flg22 polypeptides with cellobiose were used as seed treatments on soybean and resulted in overall yield increases in field trials reported as an average for four replicated trials (Table 58). Seed treatments were applied to 1 soybean hybrid (variety) planted in 1 locations in the US Midwest (Columbia, Mo.). Seed treatment compositions of Flg22 were applied as described in Table 58 as 0.14 Fl. oz per unit of soybean seeds in a total slurry and provided to soybean seed that had a base seed treatment consisting of Poncho VOTiVO 600 FS and Evergol Energy. The application use rates per each seed treatment were held constant at 0.14 Fl. oz/Ac or 4.14 mL/unit. Final concentration of the Flg22 polypeptides in the slurry for were standardized to 1 uM per seed. The same final concentration of cellobiose that was applied in combination treatments with the Flg22 polypeptides was at 1.0 mM per seed. Four replicate plots per each seed treatment were randomized over the location. The average yield in Bu/Ac and the average change in Bu/Ac as compared to the control plants that received only the base seed treatment are reported in Table 58. The most substantial yield increases were seen with Bt.4Q7Flg22 (SEQ ID NO: 226) and Syn01Flg22 (SEQ ID NO: 571) when applied as a seed treatment on soybean delivered at a final concentration of 1.0 µM of the Flg22 polypeptides and resulting in respective average yield increases of +5.11 (343.7 kg/Ha) and +9.92 (667.1 kg/Ha) over yield from soybean that received the base seed treatment.

TABLE 58

Seed treatment combinations of Flg22 polypeptides and variants of Flg22 polypeptides with cellobiose-soybean

| Foliar Treatment (Concentration) | Average Yield Bu/Ac (Average Change in Bu/Ac compared to Untreated Control) | Average Change in Bu/Ac compared to Untreated Control |
|---|---|---|
| Base Seed Treatment Control | 41.11 | — |
| Bt.4Q7Flg22 at 1.0 µM (SEQ ID NO: 226) | 46.22 | +5.11 |
| Syn01Flg22 at 1.0 µM (SEQ ID NO: 571) | 51.09 | +9.92 |
| Syn03Flg22 at 1.0 µM (SEQ ID NO: 573) | 43.61 | +2.50 |
| Pa.Flg22 *Paenibacillus alvei* at 1.0 µM (SEQ ID NO: 293) | 41.39 | +0.28 |
| An,.Flg22 Aneurillusbacillus at 1.0 µM (SEQ ID NO: 300) | 46.01 | +4.90 |
| Flg22 *Bacillus* species (Combination of Flg22 sequences) Syn01Flg22 (SEQ ID NO: 571, Flg22-B2 (SEQ ID NO: 295) & Flg22-B4 (SEQ ID NO: 300) at 0.33 µM each | 44.43 | +3.32 |

TABLE 58-continued

Seed treatment combinations of Flg22 polypeptides and variants of Flg22 polypeptides with cellobiose-soybean

| Foliar Treatment (Concentration) | Average Yield Bu/Ac (Average Change in Bu/Ac compared to Untreated Control) | Average Change in Bu/Ac compared to Untreated Control |
|---|---|---|
| Cellobiose 1 mM | 43.98 | +2.87 |
| Bt.4Q7Flg22 (SEQ ID NO: 226) at 1.0 µM + Cellobiose 1 mM | 43.40 | +2.29 |
| Bt.4Q7Flg22 (SEQ ID NO: 226) at 0.25 µM | 43.80 | +2.69 |
| Bt.4Q7Flg22 (SEQ ID NO: 226) at 0.25 µM + Cellobiose 1 mM | 43.52 | +2.41 |

Example 39: Application of RHPP to V5 Corn Increased Yield

Large acre corn trials were planted from corn seed (DEKALB hybrids: DKC 52-61, DKC 58-89, and DKC 65-81) containing a seed treatment comprising EVERGOL fungicide (7.18% propiconazole, 3.59% penflufen and combined with 5.74% metalaxyl) combined with PONCHO/VOTiVO 500 (a mixture of clothianidin insecticide and a microbial agent, *Bacillus firmus* 1582). Corn plants at approximately the V5 stage of development received a foliar application using an agricultural composition comprising an Gm.RHPP polypeptide (SEQ ID NO: 600). The formulated Gm.RHPP polypeptide (Table 59) was applied to the corn hybrids using an application use rate of 8.0 Fl. oz/Ac (584.6 mL/Ha) with 0.1% v/v (of spray tank) non-ionic surfactant (Alligare Surface™). In total, the trial was conducted at 6 locations in the US Midwest (IL, IN, IA), with 1-2 hybrids per location and 3 replicated plots per hybrid. Corn yield (Bu/Ac) was collected and reported as the average yield (Bu/Ac). The average change in Bu/Ac was compared to the yield of plants grown from the surfactant control and reported as the combined average yield (Bu/Ac) for the 6 locations (11 replicated plots in total) and as overall change in Bu/Ac as compared to control plants. Results are shown in Table 59.

TABLE 59

Foliar treatment using RHPP-increase yield in corn

| Foliar Treatment Concentration | Application Rate | Average Yield Bu/Ac (Average Change in Bu/Ac compared to surfactant only control) |
|---|---|---|
| Surfactant control (Control) | — | 206.15 |
| Gm.RHPP (SEQ ID: 600) 100 µM PROXEL BC preservative: | 8.0 Fl. oz/Ac (584.6 mL/Ha) | 209.67 (+3.52; 64% |

TABLE 59-continued

| Foliar treatment using RHPP-increase yield in corn | | |
|---|---|---|
| Foliar Treatment Concentration | Application Rate | Average Yield Bu/Ac (Average Change in Bu/Ac compared to surfactant only control) |
| 330.7 μM; 50.1 μM (CMIT); 21.71 μM (MIT) | | win rate) |

Foliar treatment of plants with the Gm.RHPP polypeptide resulted in increased yields in corn compared to plants that received surfactant alone. The average yield per the 6 locations combined for corn plants that received the Gm.RHPP polypeptide foliar treatment was slightly more than 209 Bu/Ac as compared to 206 Bu/Ac or for the control plants. The yield for the Gm.RHPP treated plants was increased by 3.52 Bu/Ac or 220.9 kg/Ha as compared to the yield from the corn control plants (Table 59).

Example 40: RHPP Polypeptide Increases Pod Number in Soybean

Soybean (variety MorSoy) plants were grown from seed with 2 seeds planted per pot in a controlled environmental growth room under conditions of approximately 300 $\mu mol^{-2}$ (light photons) for a 13/11 light/day cycle and a 21° C. day/15° C. night temperature range until the V4 stage of development. Plants were then placed under a long day conditions consisting of 16/8 light/day cycle and temperature 21-26° C. to promote early flowering and speed up progression to the reproductive (R) growth stage. When the soybean plants had reached the R1 stage of development a foliar application containing the Gm.RHPP (SEQ ID NO: 600) polypeptide at a final concentration of 300 nM and a non-ionic surfactant of 0.10% (NIS90:10; Precision Laboratories, LLC) was applied to soybean. Soybean plants were provided with the Gm.RHPP formulation and a non-ionic surfactant only control. Both the Gm.RHPP and the non-ionic surfactant control treatment were applied to 18 plants per treatment. Six equidistant sprays were provided approximately 15 cm above per each plant for complete coverage of foliage. After treatment application, the R1 soybean plants were returned to the control environmental growth room. After seventeen days, the plants received another foliar treatment application with the formulation containing the Gm.RHPP polypeptide and the non-ionic surfactant as well as the non-ionic surfactant only treatment. Soybean pods of more than 1 mm in length were counted on the plants after 31 days from the first foliar spray treatment applications. The average number of pods per plant and the standard deviation from the overall average are reported (Table 60). A p value ($p<0.05$ for significance) was calculated from a paired T-test comparison between pod number from plants that received the Gm.RHPP and the non-ionic surfactant control treatment applications.

TABLE 60

| Number of pods in greenhouse grown soybean at 31 days after foliar treatment with RHPP | | |
|---|---|---|
| Treatment Concentration | Pod Count (STDEV) | p-value |
| Non-Ionic Surfactant (NIS90: 10 Control) 0.01% (v/v) | 1.07 (+0.44) | 0.0116 |
| Gm.RHPP (SEQ ID: 591) + Surfactant 300 nM | 2.00 (+1.22) | |

*p value <0.05 is statistically significant

Foliar application of the Gm.RHPP polypeptide at early reproductive stage (R1) of soybean plants resulted in an approximately doubled pod count as compared to plants that received the non-ionic surfactant control treatment.

Example 41: Flg22 and RHPP Polypeptides Increase Yield in Tomato and Pepper

Foliar application treatments of Bt.4Q7Flg22 (SEQ ID NO: 226) and Gm.RHPP (SEQ ID NO: 600) were applied as an exogenous spray at the pre-bloom stage and used to increase yield in tomatoes and jalapeno peppers.

Small scale plots were designed to simulate commercial growing conditions for tomatoes. Tomato plants, variety Roma were started from transplants that were grown in a greenhouse for 45 days prior to planting into 2 raised field row beds with 2 feet (0.6 meters) between each transplant with an average of 30 plants per row bed. Tomatoes were transplanted three inches beneath the soil surface once the soil temperature reached 15.6° C. Tomatoes were grown on raised beds covered with black plastic mulch. Plants were grown using drip irrigation and fertilizer (80 lbs. or 36.3 kg) nitrogen; 100 lbs. (45.4 kg) phosphate, and 100 lbs. (45.4 kg) potash or potassium) applied following grower guidelines throughout the growing season to provide for optimum plant growth and yields. Small raised bed plots were designed to simulate the planting densities used by commercial growers that generally plant 2,600 to 5,800 plants per acre in single rows with 45.7 to 76.2 cm between plants in the row on 1.5- to 2-meter centers. [Orzolek et al., "Agricultural Alternatives: Tomato Production." University Park: Penn State Extension, 2016].

Foliar treatments using Bt.4Q7Flg22 and Gm.RHPP were applied on the tomato plants directly at early bloom (first flower) stage. The Bt.4Q7Flg22 polypeptide foliar composition was applied using an application use rate of 4.0 Fl. oz/Ac (292.3 mL/hectare) and the Gm.RHPP polypeptide foliar composition was applied using an application use rate of 3.2 Fl. oz/Ac (234 mL/hectare) on tomato plants in 10 gallons of water per acre with 0.1% v/v non-ionic surfactant (Alligare™ Surface). The Bt.4Q7Flg22 and Gm.RHPP treated plants were compared to the control plants that received no foliar treatment application. Plants were treated in replicates of 6 plants, with three replicates per treatment. Effect of the foliar treatments on the yield obtained from tomatoes was determined and reported as normalized to no spray control treatment. The average fruit weight per tomato plant is reported as the combined average for 2 separate harvests and the average percentage change in fruit weight as compared to the no-spray control in Table 61.

TABLE 61

| Foliar treatment on Spring-planted tomato | | |
|---|---|---|
| Foliar Treatment Concentration | Average Fruit Weight (grams) per Plant | Percentage Change in Fruit Weight Compared to No-Spray Control |
| No Spray Control | 1369.9 | — |
| Bt.4Q7Flg22 (SEQ ID NO: 226) 16.7 μM 1.67 mM Sodium Phosphate Buffer, pH 5.7 PROXEL BC preservative: 330.7 μM; 50.1 μM (CMIT); 21.71 μM (MIT) (Composition 3) | 1487.8 | +8.61% |
| Gm.RHPP (SEQ ID NO: 591) 100 μM PROXEL BC preservative: 330.7 μM; 50.1 μM (CMIT); 21.71 μM (MIT) | 1397.1 | +1.99% |

Foliar treatment application with the Bt.4Q7Flg22 polypeptide provided at a concentration of 16.7 μM and an application use rate of 4.0 Fl. oz/Ac (292.3 mL/hectare) resulted in an overall increase in the average fruit weight per plant as reported in total grams and an +8.61% change in fruit weight as compared to the no spray control. The Gm.RHPP polypeptide provided at a concentration of 100 μM and a 3.2 Fl. oz/Ac (234 mL/hectare) application use rate also resulted in yield overall increase in average fruit weight (grams) per plants and an almost +2% change in fruit weight as compared to the no spray control.

In another study, foliar treatments with the Bt.4Q7Flg22 (SEQ ID NO: 226) and Gm.RHPP (SEQ ID NO: 600) polypeptides were applied on jalapeno peppers (*Capsicum*) plants at early bloom (first flower) stage. Small-scale plots were designed to simulate commercial growing conditions for jalapeno peppers. Peppers were grown for 12-weeks in a controlled growth room and then transplanted outside in 2 raised beds covered with black plastic mulch that had good water-holding characteristics and in soil having a pH of 5.8-6.6. Jalapeno pepper plants were spaced 14-16 inches (38 cm) apart with 16-24 inches (50 cm) between plants containing approximately 25 plants per row bed. Plants were grown using drip irrigation and fertilizer applied following grower guidelines throughout the growing season to provide optimum conditions for plant growth. The raised bed plots were designed to simulate the planting densities used by commercial growers that generally plant approximately plants per acre (5,000-6,500 plants per acre or 12,355-16,062 plants per hectare) in double rows 35.6-45.7 cm apart with the beds spaced 5.0-6.5 feet (1.52-1.98 meters) apart from their centers (Orzolek et al., "Agricultural Alternatives: Pepper Production." University Park: Penn State Extension, 2010).

Foliar treatments using the Bt.4Q7Flg22 and Gm.RHPP polypeptides were applied on jalapeno pepper using application use rates of 2.0 Fl. oz/Ac (146.2 mL/hectare) and 4.0 Fl. oz/Ac (292.3 mL/hectare) for Bt.Flg22 and 3.2 Fl. oz/Ac (234 mL/hectare) for the Gm.RHPP polypeptide in a spray volume of 10 gallons of water per acre with 0.1% v/v non-ionic surfactant (Alligare™ Surface). Plants were treated in replicates of 6 plants, with three replicates per treatment. Replicates with average yield per plant 50% above or 50% below the median yield for the trial were excluded as outliers. The Bt.4Q7Flg22 and Gm.RHPP polypeptide foliar treatments applied on jalapeno pepper plants were compared to plants sprayed with 10 gallons of water per acre with 0.1% v/v non-ionic surfactant (Alligare™ Surface) alone.

Effects of the Bt.4Q7Flg22 and Gm.RHPP polypeptides used as foliar spray applications on pepper yield were determined for two separate harvests using a once over harvest approach. The number of peppers and the above ground biomass per plant were normalized to the yield and to the biomass of the pepper control plants that were treated with surfactant alone (Table 62).

TABLE 62

| Foliar treatment on Spring-planted Jalapeno pepper | | |
|---|---|---|
| Foliar Treatment and Rate | Average Fruit Weight (grams) per Plant | Percentage Change in Fruit Weight Compared to Surfactant Control |
| Surfactant control (Alligare™ Surface; 0.1% v/v of spray volume) | 123.7 | — |
| Bt.4Q7Flg22 (SEQ ID NO: 226) 16.7 μM 1.67 mM Sodium Phosphate Buffer, pH 5.7 PROXEL BC preservative: 330.7 μM; 50.1 μM (CMIT); 21.71 μM (MIT) (Composition 3) 2 fl oz/Ac | 184.1 | +49% |
| Bt.4Q7Flg22 (SEQ ID NO: 226) 16.7 μM 1.67 mM Sodium Phosphate Buffer, pH 5.7 PROXEL BC preservative: 330.7 μM; 50.1 μM (CMIT); 21.71 μM (MIT) (Composition 3) 4 fl oz/Ac | 173.7 | +40% |
| Gm. RHPP (SEQ ID NO: 591) 100 μM PROXEL BC preservative: 330.7 μM; 50.1 μM (CMIT); 21.71 μM (MIT) 3.2 fl oz/Ac. | 156.6 | +27% |

The Bt.4Q7Flg22 polypeptide applied as a foliar spray application to Jalapeno pepper at the pre-bloom stage resulted in substantial increases in average fruit weight per plant, a +49% increase for 2 Fl. oz/Ac (146.2 mL/hectare) and +40% increase for 4 Fl. oz/Ac (292.3 mL/Ha) as compared to the surfactant only control plants. The Gm.RHPP polypeptide treatment also applied as a foliar spray at the pre-bloom stage also resulted in an increased average fruit weight in Jalapeno peppers per plant with a +27% increase in the weight of peppers as measured on a per plant basis as compared to the peppers harvested from the surfactant only control plants.

Example 42: Application to Squash—Increased Yield

Foliar treatments containing the Bt.4Q7Flg22 or the Gm.RHPP polypeptide was applied exogenously as a foliar treatment to Crookneck squash at the first bloom stage. Foliar treatments with the Bt.4Q7Flg22 and the Gm.RHPP polypeptide were applied to squash plants using an application use rate of 2.0 Fl. oz/Ac (146.2 mL/hectare) or 3.2 Fl. oz/Ac (234 mL/hectare), respectively, in a spray volume of 10 gallons of water per acre with 0.1% v/v non-ionic surfactant (Alligare™ 90). Yield comparisons were made between the plants treated with the polypeptides compared to surfactant only control plants, with three replicates per treatment. Yield for the foliar treated plants that received the Bt.4Q7Flg22 or Gm.RHPP polypeptide treatment are reported in Table 63 as the average weight (grams) of squash per plant over two harvests per replicate and represented as a percentage change as compared to control plants. Replicates with average yield per plant 50% above or 50% below the median yield for the trial were excluded as outliers.

Squash plants were cultivated in sandy loam soil as follows. 2.5 cm holes were cut in 0.76 meters wide plastic covered mounds, two rows per mound, holes spaced 0.46 meters apart within each row. Rows were staggered within the mound. Mounds were spaced 1.2 meters apart. Three squash seeds were planted per hole and thinned to a single plant per hole 14 days after planting. Drip irrigation tubing was laid in the center of each mound, and plants were watered as necessary.

TABLE 63

Foliar treatment with a composition of Gm.RHPP polypeptide to increase yield in squash

| Foliar Treatment and Rate | Average squash fruit weight (grams) per plant | Percentage Change in Fruit Weight Compared to Surfactant only control |
|---|---|---|
| Surfactant control (Alligare™ 90; 0.1% v/v of spray volume) | 716.7 | — |
| Bt.4Q7Flg22 (SEQ ID NO: 226) 16.7 μM 1.67 mM Sodium Phosphate Buffer, pH 5.7 PROXEL BC preservative: 330.7 μM; 50.1 μM (CMIT); 21.71 μM (MIT) (Composition 3) 2 fl oz/Ac | 748.4 | +4.4% |
| Gm.RHPP (SEQ ID NO: 591) 100 μM PROXEL BC preservative: 330.7 μM; 50.1 μM (CMIT); 21.71 μM (MIT) 3.2 fl oz/Ac. | 748.4 | +4.4% |

Foliar treatment with either Bt.4Q7Flg22 or Gm.RHPP polypeptide on squash plants at the pre-bloom stage both resulted in an increased weight of harvested squash fruit by an average by 31.7 grams per plant or +4.4% change in fruit weight as compared to the surfactant only control plants (Table 63).

Example 43. Flg22 Polypeptide Reduces Severity of White Leaf Spot on Kale

In a replicated Fall season kale trial in the Midwest (Columbia, Mo.), very wet and warm growing conditions led to the development of white leaf spot on the kale leaves, which is typically caused by *Cercospora brassicicola*. The infected kale plants had received no previous foliar treatments for fungal disease prevention. To assess the severity of disease, a scoring rubric (1-5 scale) was established where 1=a healthy plant with three or fewer white fungal spots, 2=a plant with more four or more spots and a portion of the foliage is affected by disease, 3=majority of the foliage shows symptoms and up to one leaf has fallen off due to disease, 4=majority of the foliage shows symptoms and 2-3 leaves have fallen off due to disease, and 5=majority of the foliage shows symptoms and four or more leaves have fallen off due to disease. A single person scored all the plants within the trial area, and then evenly distributed the plants by disease score between the treatments in Table 64, with 6 replicated blocks of 6 plants per treatment (total=36 plants per treatment). To test Bt.4Q7Flg22 (SEQ ID NO: 226) for improvement of disease symptoms on kale, treatments were applied as a foliar spray at the indicated rates in Table 64 in a carrier volume of 10 gallons of water per acre with 0.1% v/v non-ionic surfactant (Alligare™ Surface). Three weeks after foliar treatments, the plants were scored used the same disease severity rubric. The change in disease score was calculated for each plant, and the average change in disease score was determined per treatment. Plants were harvested four days after assessing disease severity, and yield was measured as plant weight (grams). Outlying values with weights that were either 50% below or 50% above the median weight for the trial were excluded from the dataset.

TABLE 64

Foliar kale treatments for amelioration of white leaf spot.

| Foliar Treatment (Concentration) | Application Use Rate Fl. oz/Ac (mL/hectare) | Yield (Average plant weight in grams) Relative to control (%) | Average Change in Disease Score |
|---|---|---|---|
| Surfactant only control | n/a | 14.6 (100%) | 0.6 point improvement |
| Bt.4Q7Flg22 (SEQ ID NO: 226) (100 μM) 1.67 mM Sodium Phosphate Buffer, pH 5.7 PROXEL BC preservative: 330.7 μM; 50.1 μM (CMIT); 21.71 μM (MIT) | 12.0 Fl. oz/Ac (876.9 mL/hectare) | 15.1 (103%) | 1.1 point improvment |
| Liquid Copper Fungicide | Label rate (54.45 Fl oz/Ac) | 11.5 (79%) | 1.1 point improvment |
| Liquid Copper Fungicide + Bt.4Q7Flg22 (SEQ ID NO: 226) (100 μM) 1.67 mM Sodium Phosphate Buffer, pH 5.7 PROXEL BC preservative: 330.7 μM; 50.1 μM (CMIT); 21.71 μM (MIT) | Label Rate (54.45 Fl oz/Ac) + 12.0 Fl. oz/Ac (876.9 mL/hectare) | 12.4 (85%) | 0.8 point improvment |

Foliar treatment of infected kale plants with formulated Bt.4Q7Flg22 (SEQ ID NO: 226) led to an improvement in yield and disease symptoms over the control (Table 64). While untreated controls had an average plant weight of 14.6 g, plants receiving foliar Bt.4Q7Flg22 had an average plant weight of 15.1 g and an average improvement in disease scoring of 0.5 points over control. The application of copper fungicide improved plant disease scores to the same extent as Bt.4Q7Flg22, yet decreased yield by 21% (11.5 g) compared to the control. The combination treatment of copper fungicide with Bt.4Q7Flg22 increased yield to 12.4 g per plant, but overall Bt.4Q7Flg22 alone gave the greatest yield and plant health benefit in the trial. In conclusion, Flg22 polypeptides can used to slow the progression of fungal infections in vegetables and increase yield under stressful growing conditions.

Example 44: ROS Screening Assays to Determine Compatibility of Flg22 Polypeptide with Seed Treatments Seed treatments were examined for compatibility with the production of apoplastic reactive oxygen species (ROS) in corn petiole tissues. Various commercially available seed treatments were examined for compatibility with the Flg22 polypeptide (Bt.4Q7Flg22; SEQ ID NO: 226) shown to increase yield when applied alone as a seed treatment on corn. ROS activity assays were conducted using corn petiole samples from corn hybrid 5828 YX as described in Example 15 with the exception that Relative light units (RLUs) were recorded with a SpectraMax L luminometer (0.5 s integration; 2.0 min intervals) over a time course of 40 minutes. Varying concentrations of Bt.4Q7Flg22 (0 and 1000 μM) were combined with three commercial seed treatments consisting of PPST 2030 (a combination of bacteria, *Bacillus subtilis* 5×108 cfu/mL and *Bacillus pumilis* 5×108 cfu/mL), ILEVO (48.4% fluopyram) and PONCHO/VOTiVO (a mixture of 40.3% clothianidin and a microbial agent, *Bacillus firmus* 1-1582) and tested for the presence of a ROS response in corn petioles. All three seed treatments as described were applied using the application use rates per seed as recommended on the individual specimen label for each seed treatment. A standard curve was generated using varying concentrations of the Bt.4Q7Flg22 polypeptide and resulted in a logarithmic correlation between the RLU and concentration of Flg22 with an R2 of 0.90. The RLU values are the average of 4 separate measurements (4 treatment wells on each plate) and the increase in overall ROS (RLU) (times increase over the background) are shown in parentheses (Table 65).

TABLE 65

Seed treatment compatibility with Flg22 polypeptide using ROS assay

| Seed Treatment | Background | 1 μM Bt.4Q7Flg22 (SEQ ID NO: 226) (Full-strength ST) (Fold increase (X) over background) | 1 μM Bt.4Q7Flg22 (SEQ ID NO: 226) (1:10 dilution of ST) (Fold increase (X) over background) |
|---|---|---|---|
| PPST 2030 | 15952.2 | 109313.7 (6.9X) | 96129.9 (6.0X) |
| ILeVO | 84716.9 | 548686.2 (6.5X) | 382365.1 (4.5X) |
| PONCHO/ VOTiVO | 17379.7 | 120788.9 (6.9X) | 267720.2 (15.4X) |

ROS production as measured by RLUs were increased with the addition of 1 μM Bt.4Q7Flg22 when combined with each of the seed treatments as described in Table 65. The ROS production (RLU values) with the 1:10 dilution of the seed treatments with the addition of 1 μM Bt.4Q7Flg22 was also increased as compared to the back ground RLU level for the seed treatment only or no Bt.4Q7Flg22 polypeptide. The diluted PONCHO/VOTiVO seed treatment combined with 1 μM Bt.4Q7Flg22 was increased more than 15× compared to the background or 2.2× compared to the non-diluted PONCHO/VOTiVO treatment applied per seed following the recommendation on the specimen label. Therefore, the Flg22 polypeptide is detectable by ROS assay when combined with standard seed treatment base at label rates. When combining such Flg22 polypeptides with a particular seed treatment, adjustment of either the polypeptide concentration or the seed treatment concentration can be taken into consideration to ensure an optimal ROS response in the plant. These demonstrate the activity of the Flg22 polypeptides on plants in the presence of other seed treatment packages on the market today.

Example 45: Combinations of Flg22 and FlgII-28 Peptides to Increase ROS Activity in Tomato In a separate study, the Flg22 and FlgII-28 polypeptides derived from distinct regions of flagellin protein were tested separately and in combination for compatibility of response in tomato leaves. While Flg22 and FlgII-28 are both microbe-associated molecular patterns (MAMPs) they may be recognized distinctly by the Flagellin-sensing 2 (FLS2) and Flagellin-sensing 3 (FLS3) receptors, respectively (Hind et al., 2016; Nature Plants 2:16128), and the interactions may differ across plant species. Several Flg22 polypeptides (Bt.4Q7Flg22, SEQ ID NO: 226; Bt.4Q7Flg22-Syn01, SEQ ID NO: 571 and Ec.Flg22, SEQ ID NO: 526) were compared using ROS activity assays in tomato to several FlgII-28 polypeptides (Ps.tomatoFlgII-28, SEQ ID NO: 751; A.sp.FlgII-28, SEQ ID NO: 375).

Tomato leaves were excised from 4-week-old plants using a cork borer to generate 4 mm disks. Each disc was cut in half using the edge of a razor blade, and then each disc half was floated on 150 μL of water in a 96-well plate to rest overnight. The next day, the water was removed from each well just prior to polypeptide treatment. The Flg polypeptides as described in Table 66 were added to water to bring them to a final concentration of 5 nM (Table 67) and 100 nM (Table 68) in solution with luminol and HRP before adding to each treatment well. To maintain activity, the polypeptides were stored in small aliquots to avoid multiple freezing and thawing. All dilutions to obtain working concentrations were done in ultrapure water. Polypeptide solutions were stored at −20° C. for short term usage or −80° C. for long term storage. RLU values and relative ROS activity (Tables 67, 68) is reported as the average of 4 measurements. ROS activity assays were conducted using the methods as previously reported in Example 15 with the exception that Relative light units (RLUs) were recorded with a SpectraMax L luminometer (0.5 s integration; 2.0 min intervals) over a time course of 40 minutes.

TABLE 66

Flg22 and FlgII-28 Polypeptides from various sources

| Flg Polypeptide Description | Amino Acid Length | Sequence |
|---|---|---|
| Bt.4Q7Flg22 *Bacillus thuringiensis* (SEQ ID NO: 226) | 22 | DRLSSGKRINSASDDAAGLAIA |
| Syn01Flg22 Synthetic (SEQ ID NO: 571) | 22 | DRLSSGKRINSAKDDAAGLAIA |
| Ps.tomato FlgII-28 *Pseudomonas syringae* pv. Tomato DC3000 (SEQ ID NO: 751) | 28 | ESTNILQRMRELAVQSRNDSNS ATDREA |

TABLE 66-continued

Flg22 and FlgII-28 Polypeptides from various sources

| Flg Polypeptide Description | Amino Acid Length | Sequence |
|---|---|---|
| Ec.Flg22<br>*Escherichia coli*<br>(J26)<br>(SEQ ID NO: 526) | 22 | ERLSSGLRINSAKDDAAGQAIA |
| A.sp.FlgII-28<br>*Aneurinibacillus*<br>sp. XH2<br>(SEQ ID NO: 300) | 28 | EIHEMLQRMRELAVQAANGTYS<br>DKDKKA |

TABLE 67

Comparison of ROS activity of Flg22 and FlgII-28 polypeptides in tomato leaf tissue

| Polypeptide Treatment | Average RLU value (5 nM Flg polypeptide) (Fold increase (X) over Bt.4Q7Flg22 treatment) |
|---|---|
| Negative control (water) | 24423<br>(0.7 X) |
| Bt.4Q7Flg22<br>*Bacillus thuringiensis*<br>(SEQ ID NO: 226) | 33118<br>(–) |
| Bt.4Q7Flg22-Syn01<br>Synthetic<br>(SEQ ID NO: 571) | 116751<br>(3.5 X) |
| Ps.tomatoFlgII-28<br>*Pseudomonas syringae* pv.<br>Tomato<br>(SEQ ID NO: 751) | 1019995<br>(30.8 X) |
| Ec.Flg22<br>*Escherichia coli*<br>(SEQ ID NO: 526) | 426307<br>(12.9 X) |
| *Aneurinibacillus.* sp. FlgII-28<br>(SEQ ID NO: 375) | 32980<br>(1.0 X) |

TABLE 68

FlgII-28 polypeptides from gram-negative *Pseudomonas syringae* pv. Tomato DC3000 and gram-positive *Aneurinibacillus* sp. XH2 trigger ROS production in tomato leaf tissue

| Polypeptide Treatment Concentration | Average RLU value with 100 nM Flg polypeptide (Fold increase (X) over Bt.4Q7Flg22 treatment) |
|---|---|
| Negative control (water) | 15,824 (0.007X) |
| Bt.4Q7Flg22<br>*Bacillus thuringiensis*<br>(SEQ ID NO: 226)<br>100 nM | 2,118,932 (–) |
| Ps.tomatoFlgII-28<br>*Pseudomonas syringae* pv.<br>Tomato DC3000<br>(SEQ ID NO: 751)<br>100 nM | 3,657,810 (1.7X) |
| Bt.4Q7Flg22<br>(SEQ ID NO: 226; 100 nM) + Ps.tomatoFlgII-28<br>(SEQ ID NO: 751; 100 nM) | 4,222,426 (2.0X) |
| *Aneurinibacillus.* sp.<br>FlgII-28<br>(SEQ ID NO: 375)<br>100 nM | 2,844,947 (1.3X) |

It was determined from the results in Table 67 and Table 68 that a second epitope of flagellin, termed FlgII-28 derived from either Gram-negative *Pseudomonas syringae* pv. tomato DC3000 or Gram-positive *Aneurinibacillus* sp. XH2 (SEQ ID NO: 375) are sufficient to trigger an immune response (e.g. ROS production) in tomato (SEQ ID NO: 751) at both 5 nM and 100 nM concentrations. At the 5 nM concentration, Ps.tomato FlgII-28 had the highest activity as compared to the other Flg22 and FlgII-28 polypeptides and resulted in an almost 31 times increase in RLUs as compared to Bt.4Q7Flg22 at the same concentration, whereas 5 nM A.spp.FlgII28 gave an equally low ROS response to 5 nM Bt.4Q7Flg22. The Flg22 polypeptide (Ec.Flg22; SEQ ID NO: 526) from Gram-negative *Escherichia coli* also resulted in increased ROS activity when applied to tomato leaves, with RLU values 12.9× over the Bt.4Q7Flg22 treatment alone. The Bt.4Q7Flg22 (SEQ ID NO: 226) polypeptide triggered a very low ROS response in tomato leaves at the 5 nM concentration, but provided a high response at the 100 nM concentration. Ps.tomato FlgII-28, on the other hand, provided a strong ROS response in comparison to the negative control (water) at both tested concentrations. Thus, tomato leaves display increased sensitivity to Flg polypeptides derived from gram-negative bacteria Flagellin such as Ps.tomato FlgII-28 and Ec.Flg22. In addition, a synthetic variant of Bt.4Q7Flg22 termed Syn01Flg22 (SEQ ID NO: 571) had substantially increased activity (3.5×) as compared to Bt.4Q7Flg22 treatment when tested at the 5 nM concentration.

As indicated in Table 68, combinations of Gram-positive (Bt.4Q7Flg22; SEQ ID NO: 226) and Gram-negative Ps.tomato FlgII-28 (*Pseudomonas syringae* pv. tomato DC3000; SEQ ID NO: 751) can be used as a combined foliar application to increase ROS production over either treatment alone, and enhance plant immunity against certain pathogenic organisms.

Example 46: Synthetic Flg22Syn01 and Flg-15Syn01 Polypeptides to Increase ROS Activity in Corn and Soybean A truncated version of Syn01Flg22 derived from Bt.4Q&Flg22 lacking seven N-terminal amino acids was generated, resulting in the 15 amino acid polypeptide with the sequence nh2-RINSAKDDAAGLAIA-cooh. This polypeptide, termed Bt.4Q7Syn01Flg15 (SEQ ID NO: 752) is a naturally occurring polypeptide among the Gram-negative proteobacteria but is absent from Gram-positive protein sequences. The core sequence required for receptor interaction, RINSAKDD, is retained in the shortened polypeptide, and thus the 15-amino acid variant was predicted to be active for triggering ROS production in plants. To test this, Syn01Flg15 was compared to Bt.4Q7Flg22 and Syn01Flg22 in ROS assays with both corn (Table 69) and soybean (Table 70). ROS activity assays were conducted using the methods as previously reported in Example 15 with the exception that Relative light units (RLUs) were recorded with a SpectraMax L luminometer (0.5 s integration; 2.0 min intervals) over a time course of 40 minutes.

TABLE 69

Flg22Syn01 and Flg15Syn01 variants have greater activity than Bt.4Q7Flg22 in a ROS activity assay with corn stalk tissue.

| Flg Polypeptide Concentration (nM) | Bt.4Q7Flg22 (SEQ ID NO: 226) | Syn01Flg22 (SEQ ID NO: 571) | Syn01Flg15 (SEQ ID NO: 752) |
|---|---|---|---|
| 100 | 33037 (1X*) | 54888 (1.6X) | n.d. |
| 10 | 6032 (0.2X) | 17660 (0.5X) | 14079 (0.4X) |

*Relative ROS activity was normalized to the average RLU values of Bt.4Q7Flg22 (SEQ ID NO: 226).
n.d. indicates that a value was not tested and therefore a relative value was not determined.

In the ROS activity assay with corn (Table 69), the Flg22□Syn01 (SEQ ID NO: 571) had the greatest ROS response in corn stalk tissue at both the 100 nM and 10 nM concentrations as indicated by the relative respective activities of 1.6× (100 nM) and 0.5× (10 nM) as compared to treatment using Bt.4Q7Flg22 (SEQ ID NO: 226) that has an attenuated ROS response of 0.2× at 10 nM. The shortened version of Syn01Flg22 (SEQ ID NO: 571) or Syn01Flg15 (SEQ ID NO: 752) also exhibited a greater ROS response of 0.4× at 10 nM, which was twice the relative ROS activity of Bt.4Q7Flg22 (SEQ ID NO: 226) at the same concentration.

TABLE 70

Flg22Syn01 and Flg15Syn01 variants have greater activity than Bt.4Q7Flg22 in a ROS assay with soybean leaf tissue

| Flg Polypeptide Concentration (nM) | Relative ROS Activity BL4Q7Flg22 (SEQ ID NO: 226) | Relative ROS Activity Flg22Syn01 (SEQ ID NO: 571) | Relative ROS Activity Syn01Flg15 (SEQ ID NO: 752) |
|---|---|---|---|
| 100 | 250,432 (1X)* | 315,961 (1.25X) | n.d. |
| 10 | 10,754 (0.04X) | 62,020 (0.25X) | 42,983 (0.17X) |

*Relative ROS activity was normalized to the average RLU values of Bt.4Q7Flg22 (SEQ ID NO: 226).
n.d. indicates that a value was not tested and therefore a relative value was not determined.

Likewise, in the ROS activity assay with soybean (Table 70), the synthetic derived mutant of Bt.4Q7Flg22 described as Bt.4Q7Flg22□Syn01 (SEQ ID NO: 571) also had the greatest ROS response in soy leaf tissue at both the 100 nM and 10 nM concentrations as indicated by the relative respective activities of 1.25× (100 nM) and 0.25× (10 nM) as compared to treatment using Bt.4Q7Flg22 (SEQ ID NO: 226) that has a highly attenuated ROS response of 0.04× at 10 nM. The shortened version of Syn01Flg22 or Syn01Flg15 also exhibited a greater ROS response of 0.17× at 10 nM, which was four times the relative ROS activity of Bt.4Q7Flg22 at the same concentration.

Overall, the Syn01Flg22 had higher ROS activity at both concentrations tested in both corn and soy tissues in comparison to Bt.4Q7Flg22 (SEQ ID NO: 226). The shortened 15-amino acid polypeptide Syn01Flg15 was 2-4× more active than Bt.4Q7Flg22 and only slightly less active than the 22-amino acid Syn01Flg22 at 10 nM, indicating that key amino acids for eliciting a plant immune response are retained within the sequence.

Example 47: Chemical Modification to Increase ROS Activity for Flg22 Polypeptides Chemical modifications can be made to Flg22 polypeptides to increase protein stability against proteolysis and/or promote a longer duration of activity that can result in greater availability to the FLS2 receptor. In general, polypeptide modifications can be utilized to 1) stabilize a polypeptide under adverse conditions or in the presence of proteases, or 2) provide additional function or molecular characteristics to the peptide. Modifications for improved stability include polypeptide cyclization and alternations at the N- and C-termini. Head-to-tail cyclization (i.e. amide bond formation between N-terminal amino and C-terminal carboxyl ends) results in a rigid polypeptide backbone that resists conformational changes, often stabilizing peptide-receptor binding and protecting the polypeptide termini from exoproteases. Alternatively, modification of the polypeptide termini can stabilize polypeptides through neutralization (C-terminal amidation) and prevention of N-terminal degradation (N-terminal acetylation). Increased polypeptide solubility and stability can also be conferred through the conjugation of a hydrophilic molecule such as polyethylene glycol (PEG).

Such modifications used to stabilize Flg22 polypeptides include PEGylation, cyclization and amidation/acetylation, all of which are described in Table 71. Stabilization of polypeptides using PEGylation is carried out by linking the polypeptide to polyethylene glycol (PEG). Once linked to the polypeptide, each PEG subunit becomes tightly associated with 2 to 3 water molecules, which then function in increasing the solubility of the polypeptide as well as increasing its overall structure to make it less susceptible to proteolytic degradation and more accessible to the membrane FLS2 receptor at the plant surface. Cyclization can also be used to increase the stability of the Flg polypeptide. Stabilization of a polypeptide can also be obtained using N-terminal acetylation and C-terminus through amidation where these modifications generate a closer mimic of the native protein and therefore may increase the biological activity of the polypeptide.

TABLE 71

Modified Flg22 polypeptides

| Peptide Description (Reference Code) | Modification | MW | Sequence |
|---|---|---|---|
| Bt.4Q7Flg22 (modified SEQ ID NO: 226) | Native derived sequence from *Bacillus thuringiensis* | 2229.42 | nh2 DRLSSGKRINSASDDAAGLAIA conh2 |
| Bt.4Q7Flg22 Mod-1 (modified SEQ ID NO: 226) | N-terminal acetylation C-terminal amidation | 229.3 | Ac DRLSSGKRINSASDDAAGLAIA nh2 |

TABLE 71-continued

| Modified Flg22 polypeptides | | | |
|---|---|---|---|
| Peptide Description (Reference Code) | Modification | MW | Sequence |
| Syn05Flg22 (modified SEQ ID NO: 578) | Amino acid substitution (A16P) N-terminal acetylation C-terminal amidation | 2255.46 | Ac DRLSSGKRINSASDDPAGLAIA nh2 |
| Syn05Flg22-PEG4 (modified SEQ ID NO: 578) | PEGylation before amide bond conjugated to Flg22 | 2461 | peg4 (where x = 4) DRLSSGKRINSASDDPAGLAIA conh2 |
| Syn05Flg22-Cyc (modified SEQ ID NO: 578) | Cyclization Head-to-Tail | 2196 | Cyc(DRLSSGKRINSASDDPAGLAIA) |

The specialized, modified polypeptides as described in Table 71 including Syn05Flg22-Syn05 (J36), Syn05Flg22-PEG (J37) and Syn05Flg22-Cyc were synthesized by the University of Missouri Molecular Interactions Core (Columbia, Mo. USA), lyophilized to a dry powder, and determined to be of the correct MW and desired purity (>70%) by liquid chromatography-mass spectrometry (LC-MS) and high-performance liquid chromatography (HPLC), respectively. Standard synthesis polypeptides including Bt.4Q7Flg22 (SEQ ID NO: 226) and Bt.4Q7Flg22 Mod-1 (SEQ ID NO: 226; J41) were obtained from Genscript (Piscataway, N.J. USA). All lyophilized polypeptides were resuspended in ultrapure water to a 10 mM concentration and serially diluted in ultrapure water to the desired concentration for testing in soybean and corn ROS assays as described previously in Example 15.

For soybean samples, fully expanded trifoliate leaves were removed from V1 to V3 stage plants (variety Morsoy). Leaf discs (4 mm) were removed using a cork borer and then floated on 150 μL of water, abaxial side down, overnight before performing the ROS assay previously described.

For corn samples, aerial tissue from V1 to V4 stage corn plants (Beck's hybrid 5828 YX) were prepared as previously described. The 1-mm excised leaf slices were then floated on 150 uL of water overnight.

ROS activity assays were conducted using the methods as previously reported in Example 15 with the exception that Relative light units (RLUs) were recorded with a SpectraMax L luminometer (0.5 s integration; 2.0 min intervals) over a time course of 40 minutes. Relative light units (RLUs) were first plotted over time using a kinetic time course for each concentration tested, followed by integration under the curve to calculate total RLU values produced. Average total RLUs (n=4 samples per treatment) were then graphed versus polypeptide concentration for each polypeptide for soybean (Tables 72-73) and corn (Table 74).

A best fit logarithmic or linear regression (R>0.80) was fit to the data for each treatment. Using the best-fit regression, the polypeptide concentration required to reach a total RLU production of 15,000 total RLU (corn) or a 50,000 total RLU (soybean) was calculated for each polypeptide and % activity was compared within each data set to the control treatment (Tables 72-74).

TABLE 72

Flg22-Bt modified at the N- and C-termini polypeptides trigger reactive oxygen species production in soybean

| Treatment (Code) | Polypeptide Concentration (nM) for $5 \times 10^4$ total RLU production | % Activity (compared to unmodified Bt.4Q7Flg22 (SEQ ID NO: 226) |
|---|---|---|
| Bt.4Q7Flg22 (SEQ ID NO: 226) | 31.4 | 100.0% |
| Bt.4Q7Flg22 Mod-1 (SEQ ID NO: 226) | 29.6 | 106.14% |

The Flg22 polypeptide concentration required to result in an RLU output of 50,000 RLU for the Bt.4Q7Flg22S Mod-1 (SEQ ID NO: 226) was less than the current Bt.4Q7Flg22 (SEQ ID NO: 226) that has been shown to produce yield gains and impart plant protective qualities to soybean plants. This indicates that the modification of Flg22 by N-terminal acetylation and/or C-terminal amidation does not interfere with polypeptide binding to the FLS2 receptor, and modifications may be used to produce a more active and/or stable version of Flg22 as indicated by the +6% increase in activity of Bt.4Q7Flg22S Mod-1 over Bt.4Q7Flg22 (Table 72).

Novel polypeptides were generated at the University of Missouri Molecular Interactions Core (Columbia, Mo.) with a single amino acid substitution (A16P) in comparison to the Bt.4Q7Flg22 (SEQ ID NO: 226) unmodified polypeptide, resulting in the Syn05Flg22 (SEQ ID NO: 578) polypeptide which was amenable to further modification by N-terminal PEGylation Syn05Flg22-PEG (SEQ ID NO: 578) and Head-to-Tail cyclization Syn05Flg22-Cyc (SEQ ID NO: 578). A soy ROS assay was performed to assess the effect of these two additional modifications, namely N-terminal PEGylation and Head-to-Tail cyclization to a Flg22 polypeptide, with results shown in Table 73.

TABLE 73

Modified, synthetic Flg22-Bt polypeptides trigger reactive oxygen species production in soybean

| Treatment | Polypeptide Concentration (nM) for 5 × $10^4$ total RLU production | % Activity (compared to Syn0Flg22; SEQ ID NO: 578) |
|---|---|---|
| Syn05Flg22 (SEQ ID NO: 578) | 89.8 | 100.0% |
| Syn05Flg22-PEG (SEQ ID NO: 578) | 64.8 | 138.6% |
| Syn05Flg22-Cyc (SEQ ID NO: 578) | 146.9 | 61.1% |

In a soy ROS assay to compare the relative activities of Syn05Flg22 (SEQ ID NO: 578) to two modified versions of the polypeptide, the PEGylated polypeptide Syn05Flg22-PEG (SEQ ID NO: 578) required substantially less amount of the polypeptide to achieve a total of 50,000 RLU, which resulted in an increased activity of +38% as compared to the non-PEGylated version or Syn05Flg22 (SEQ ID NO: 578). PEGylation of the N-terminus of the peptide increases the hydrophilicity of the polypeptide and may increase affinity for the peptide-binding pocket of the FLS2 receptor. The cyclized version of Syn05Flg22-Cyc (SEQ ID NO: 578), however, required more polypeptide provided in the ROS activity assay (+57.1 nM more) compared to the non-cyclized version of Syn05Flg22 to reach a total RLU production of 50,000 RLU in the soybean ROS assay. This suggests that the cyclization of the Flg22 polypeptide (Syn05Bt.4Q7Flg22-Cyc) may result in a more rigid polypeptide backbone with altered binding to the FLS2 receptor, such that more cyclized peptide is required to reach an equivalent ROS response. However, increased stability of a cyclized polypeptide in the environment may compensate for the slight loss in activity.

TABLE 74

Modified, synthetic Flg22-Bt polypeptides trigger reactive oxygen species production in corn

| Treatment | Polypeptide Concentration (nM) for 5 × $10^4$ total RLU production | % Activity (compared to unmodified Syn05Flg22 (SEQ ID NO: 578) |
|---|---|---|
| Syn05Flg22 (SEQ ID NO: 578) | 19.5 | 100.0% |
| Syn05Flg22-PEG (SEQ ID NO: 578) | 15.0 | 130.3% |

In a corn ROS assay, the PEGylated version of Syn05Flg22-PEG required substantially less amount (almost 5 nM less) of the polypeptide to achieve a total of 15,000 RLU, which resulted in an increased activity of +30% as compared to the non-PEGylated version or Syn05Flg22 (Table 74).

Modification of Flg22 (Bt) or Syn05Flg22 (Bt) polypeptides by N-terminal acetylation, N-terminal PEGylation, C-terminal amidation, and/or head-to-tail cyclization produces a peptide that retains activity, as measured through ROS assays with corn and soy tissues. These polypeptides could be used to deliver a further stabilized Syn05Flg22 (SEQ ID NO: 578) derived polypeptide variant for agricultural uses (either by foliar application, seed treatment, in furrow application, application at transplant, or trunk injection). Cyclization of Syn05Flg22-Cyc may be used to increase the stability of the polypeptide yet compromised the ROS activity, likely by affecting the affinity of the synthetic polypeptide to the membrane FLS2 receptor.

Example 48. Adjuvant Compatibility with Flg22 Polypeptides

Product formulations using Flg22 polypeptides can generally include antimicrobial biostatic preservatives such as Proxel and surfactants. Therefore, the compatibility of these types of adjuvants were tested using ROS activity assays to determine the effect in solution on Flg22 responsiveness when used in combination with such adjuvants. Proxels in general are broad spectrum biocides for the preservation of many agricultural based products that protect them against spoilage from bacteria, yeast and fungi. Surfactants in general are also commonly used in agricultural formulations to improve the penetration of many agrochemical products into the plant for improved performance. In this study, five different Proxels and two different non-ionic surfactants were tested in formulations combined with Bt.4Q7Flg22 (SEQ ID NO: 226) for effectiveness in producing a ROS response using a ROS activity assay in soybean leaves. The different Proxel formulations (Lonza) are described below in Table 75. Theses Proxel formulations were mixed with 40 μM Flg22 polypeptide at a range of recommended label rates by the manufacturer (Lonza), and then diluted into the ROS assay to a final polypeptide concentration of 100 nM and Proxel concentrations indicated in Table 75. The tested non-ionic surfactants were provided in the ROS assay at a range of recommended label rates by the individual distributer or manufacturer. The average four sample measurements RLU values obtained after performing a ROS assay were collected using soybean leaf disks as previously described in Example 15 with the exception that Relative light units (RLUs) were recorded with a SpectraMax L luminometer (0.5 s integration; 2.0 min intervals) over a time course of 40 minutes. The average of these 4 RLU values is reported in Table 76.

TABLE 75

Different PROXEL additives used as adjuvants in formulations with polypeptides

| PROXEL Formulations | Chemical Description |
|---|---|
| PROXEL BD20 | A 20% aqueous dispersion of 1,2-benzisothiazoline-3-one |
| PROXELBC | An aqueous dispersion of a blend of 1,2-benzisothiazoline-3-one (BIT), 5-chloro-2-methyl-4-isothhiazoline-3-one (CIMT) and 2-methyl-4-isothiazoline-3-one (MIT) |
| PROXELGXL | A 20% aqueous dipropylene glycol solution of 1,2-benzisothiazoline-3-one |
| PROXELBN | An aqueous dispersion of 1,2-benzisothiazoline-3-one and 2-bromo-2-nitropropen-1,3-diol |
| PROXEL AQ | A solution of 1,2-benzisothiazoline-3-one in water |

TABLE 76

RLU output values from ROS activity assays in soybean leaves using Flg22 polypeptide formulated using different Proxel preservatives

| Treatment Comparison with and without PROXEL preservative Concentration | Average RLU values (Fold increase over negative control) |
|---|---|
| Mock (water) Negative Control | 4823 |
| Bt.4Q7Flg22 | 81887 |

TABLE 76-continued

RLU output values from ROS activity assays in soybean leaves using Flg22 polypeptide formulated using different Proxel preservatives

| Treatment Comparison with and without PROXEL preservative Concentration | Average RLU values (Fold increase over negative control) |
|---|---|
| (SEQ ID NO: 226 at 100 nM) (No PROXEL Preservative Added) | (17.0X) |
| Bt.4Q7Flg22 (SEQ ID NO: 226 at 100 nM) + PROXEL BD20 (0.0005988%) | 89188 (18.5X) |
| Bt.4Q7Flg22 (SEQ ID NO: 226 at 100 nM) + PROXELBD20 (0.00011976%) | 105527 (21.9X) |
| Bt.4Q7Flg22 (SEQ ID NO: 226 at 100 nM) + PROXELBC (0.0005988%) | 136575 (28.3X) |
| Bt.4Q7Flg22 (SEQ ID NO: 226 at 100 nM) + PROXELBC (0.00011976%) | 92808 (19.2X) |
| Bt.4Q7Flg22 (SEQ ID NO: 226 at 100 nM) + PROXELGXL (0.0002994%) | 128410 (26.6X) |
| Bt.4Q7Flg22 (SEQ ID NO: 226 at 100 nM) + PROXELGXL (0.0008982%) | 101847 (21.1X) |
| Bt.4Q7Flg22 (SEQ ID NO: 226 at 100 nM) + PROXELBN (0.0002994%) | 91554 (19.0X) |
| Bt.4Q7Flg22 (SEQ ID NO: 226 at 100 nM) + PROXELBN (0.00017964%) | 105164 (21.8X) |
| Bt.4Q7Flg22 (SEQ ID NO: 226 at 100 nM) + PROXELAQ (0.0005988%) | 116634 (24.2X) |
| Bt.4Q7Flg22 (SEQ ID NO: 226 at 100 nM) + PROXELAQ (0.0035928%) | 98394 (20.4X) |

All Proxel preservative treatments as described in Table 76 were compatible when used in formulations with the Flg22 polypeptide (Bt.4Q7Flg22; SEQ ID NO: 226) as indicated by the high RLU values (19.0-28.3× fold increase over mock treatment) as comparable to the Bt.4Q7Flg2 polypeptide control without a Proxel preservative (17.0× fold increase over mock treatment).

TABLE 77

RLU output values from ROS activity assays in soybean leaf tissues using Flg22 polypeptide formulated using different non-ionic surfactants

| Treatment Comparison with and without Surfactant Concentration | Average RLU values (Fold increase over negative control) |
|---|---|
| Mock (water) Negative Control | 51288 |
| Bt.4Q7Flg22 (SEQ ID NO: 226) 52.2 nM Equivalent: 4.0 Fl. oz/Ac in 10 gallons water/Ac | 350503 (6.8X) |
| Bt.4Q7Flg22 (SEQ ID NO: 226) 52.2 nM + Silwet-L77 (0.025%) | 142478 (2.8X) |
| Bt.4Q7Flg22 (SEQ ID NO: 226) 52.2 nM + Silwet-L77 (0.10%) | 163517 (3.2X) |
| Bt.4Q7Flg22 (SEQ ID NO: 226) 52.2 nM + NIS90:10 (0.25%) | 329295 (6.4X) |
| Bt.4Q7Flg22 (SEQ ID NO: 226) 52.2 nM + NIS90:10 (0.5%) | 295726 (5.8X) |

All surfactant (non-ionic) treatments as described in Table 77 were compatible when mixed at the indicated concentrations with 52.2 nM Flg22 polypeptide (Bt.4Q7Flg22; SEQ ID NO: 226), a polypeptide concentration equivalent to 4.0 Fl oz/Ac usage rate of Composition 1 (Bt.4Q7Flg22; SEQ ID NO: 226; 16.7 μM) applied in water at a spray rate of 10 gallons per acre. Fold-increase in ROS production over the mock-treated control were comparable between the Bt.4Q7Flg2 polypeptide control without a surfactant (6.8× over control) versus Bt.4Q7Flg2 polypeptide with non-ionic surfactant NIS90:10 applied at 0.25% v/v or 0.5% v/v of treatment solution (5.8-6.4×), or slightly lower for Bt.4Q7Flg2 polypeptide with Silwet-L77 applied at 0.025% v/v or 0.1% v/v of treatment solution (2.8-3.2×). Silwet-L77 (Helena), a non-ionic organosilicone surfactant is formulated as a co-polymer that has enhanced wetting and spreading characteristics when used in aqueous sprays. NIS90:10 (Precision Laboratories) is a low-foaming, non-ionic surfactant that enhances crop protection and performance by improving spray solution coverage and penetration of target leaf surfaces. Both the non-ionic surfactants combined with Bt.4Q7Flg22 permitted ROS production in response to the Flg22 polypeptide in target leaf tissues (Table 77), and as such, are compatible with Flg22 polypeptide foliar application in the field.

Example 49: Production of Bt.4Q7Flg22 Using Fermentation Methods and Activation by Enterokinase Cleavage for Disease Prevention Trials in Potato, Lentils and Citrus Trees The Bt.4Q7Flg22 (SEQ ID NO: 226) was provided in a confirmation to stabilize the polypeptide and enhance activity for an alternative production method, namely bacterial fermentation. The Bt.4Q7Flg22 polypeptide was combined with an amyQ secretion signal from *Bacillus amyloliquefaciens* alpha-amylase) fused to glutathione S-transferase (GST) and an enterokinase cleavage tag sequence as described: amyQ secretion signal (*Bacillus amyloliquefaciens* alpha-amylase) GST (*Schistosoma japonicum*)_ linker_ Enterokinase cleavage site_Bt.4Q7Flg22_stop codon (Table 78).

TABLE 78

Cloning of Bt.4Q7Flg22 with sequences to increase polypeptide stability and activity

| Description | Amino Acid Sequences |
|---|---|
| amyQ secretion signal (*Bacillus amyloliquefaciens*) SEQ ID NO: 769 | MIQKRKRTVSFRLVLMCTLLFVSLPITKTSA |
| GST (*Schistosoma japonicum*) | MSPILGYWKIKGLVQPTRLLLEYLEEKYEEH LYERDEGDKWRNKKFELGLEFPNLPYYIDGD VKLTQSMAIIRYIADKHNMLGGCPKERAEIS |

TABLE 78-continued

Cloning of Bt.4Q7Flg22 with sequences to increase polypeptide stability and activity

| Description | Amino Acid Sequences |
|---|---|
| SEQ ID NO: 770 | MLEGAVLDIRYGVSRIAYSKDFETLKVDFLS KLPEMLKFEDRLCHKTYLNGDHVTHPDFMLM YDALDVVLYMDPMCLDAFPKLVCFKKRIEAI PQIDKYLKSSKYIAWPLQGWQATFGGGDHP PK |
| linker SEQ ID NO: 771 | GGGGGGS |
| Enterokinase cleavage tag (Consensus cleavage target for bovine Enterokinase, light chain protease) SEQ ID NO: 772 | DDDDK |
| Bt.4Q7Flg22 (SEQ ID NO: 226) (*Bacillus thuringiensis* strain 4Q7) | DRLSSGKRINSASDDAAGLAIA |

*DNA used for cloning from the amy E secretion signal, GST and Bt.4Q7Flg22 (SEQ ID NO: 226) sequences came from internal proprietary libraries; production stain code = H101 (Chloramphenicol resistant)

TABLE 79

Cloning of Syn01Flg22 (SEQ ID NO: 571) with sequences to increase polypeptide stability and activity

| Description | Amino Acid Sequence |
|---|---|
| amyQ secretion signal (*Bacillus amyloliquefaciens*) SEQ ID NO: 769 | MIQKRKRTVSFRLVLMCTLLFVSLPITKTSA |
| GST (*Schistosoma japonicum*) SEQ ID NO: 770 | MSPILGYWKIKGLVQPTRLLLEYLEEKYEEH LYERDEGDKWRNKKFELGLEFPNLPYYIDGD VKLTQSMAIIRYIADKHNMLGGCPKERAEIS MLEGAVLDIRYGVSRIAYSKDFETLKVDFLS KLPEMLKMFEDRLCHKTYLNGDHVTHPDFML YDALDVVLYMDPMCLDAFPKLVCFKKRIEAI PQIDKYLKSSKYIAWPLQGWQATFGGGDHP PK |
| linker SEQ ID NO: 771 | GGGGGGS |
| Enterokinase cleavage tag (Consensus cleavage target for bovine Enterokinase, light chain protease) SEQ ID NO: 772 | DDDDK |
| Bt.4Q7Flg22-Syn01 (SEQ ID NO: 226) (*Bacillus thuringiensis* strain 4Q7) | DRLSSGKRINSAKDDAAGLAIA |

*DNA used for cloning from the amy E secretion signal, GST and SynFlg22 (SEQ ID NO: 571) sequences came from internal proprietary libraries. Production strain code = H114 (Tetracycline resistant)

TABLE 80

Cloning of thionin-like protein with sequence for secretion into fermentation growth media

| Description | Amino Acid Sequence |
|---|---|
| amyQ secretion signal SEQ ID NO: 769 (*Bacillus amyloliquefaciens*) | MIQKRKRTVSFRLVLMCTLLFVSLPITKTSA |
| Thionin-like protein (SEQ ID NO: 650) (Synthetic) | RTCESQSHRFKGPCSRDSNCATVCLTEGFSG GDCRGFRRRCRCTRPCVFDEK |

The sequences in Tables 78, 79 and 80 were cloned into a standard cloning vector containing an ampicillin selection marker and either a chloramphenicol (Cm) or Tetracycline (Tet) selection marker that can replicate in *E. coli* and then be transferred to *Bacillus subtilis* strain K08 for production purposes (Production strain codes: H101=amyQ-GST-EK-BtFlg22, H114=amyQ-GST-EK-BtFlg22-Syn01, and H117=amyQ-Thionin-like). The fermentation production was carried out by starting an overnight culture in sterile 2XYT media (16 g Bacto tryptone, 10 g yeast extract, and 5 g NaCl per liter; pH adjusted to 7.0) with 10 μg/mL Cm or Tet, and then diluted into fresh 2XYT media with 10 μg/mL Cm or Tet the following day. Productions were performed using 50 mL (shake flask) or 3 L (glass bioreactor vessel) media volumes with a constant temperature of 30° C. Larger scale up volumes can include 5L to 1000L+, including up to 30,000 L volumes). Bacterial growth was monitored until the culture reached an optical density of 0.6-1.0, after which Isopropyl β-D-1-thiogalactopyranoside (IPTG) was added to a final concentration of 0.1-1.0 mM to induce production of the GST-Bt.4Q7Flg22 fusion protein. The induced production continued in culture conditions for an additional 12-24 hours to produce the fusion protein which is secreted into the growth media. Upon secretion, the amyQ secretion tag is cleaved from the fusion protein. The cultures were then centrifuged at 5000×g for 20 min and filtered through a 0.22 μm bottle-top vacuum filter to remove the bacterial cells. The sterile filtrate was then collected and used as a foliar treatment on lentil and potato plants in *Sclerotinia* disease prevention trials (Example 50) or as a trunk injection of citrus trees for eradication and prevention of HLB disease symptoms (Example 51).

After fermentation, two versions of the Bt.4Q7Flg22 (SEQ ID NO: 226) polypeptide product were used in potato and lentil disease prevention trials, one without enterokinase treatment (H101 filtrate, non-activated) and another with activation using a enterokinase to cleave off the GST tag fused to the Flg22 polypeptide (H101 filtrate EK-activated). To activate Bt.4Q7Flg22, the addition of 32 U (units) of enterokinase (EK: Enterokinase light chain; New England BioLabs, Inc, Product No. P8070) was added per 1 mL of H101 filtrate with an incubation period for 2-3 hours at 30° C. for the enzymatic release of Bt.4Q7Flg22 from the GST-EK cleavage site resulting in an activated and released product comprising the 22 amino acid Bt.4Q7Flg22 polypeptides. For the citrus tree injection trial, H101 filtrate and H114 filtrate were EK-activated with the addition of 0.8 U Enterokinse, light chain (New England Biolabs, Inc, Product No. P8070) per mL of filtrate with an incubation of 3 hours at 30° C. for the enzymatic release of Flg22 polypeptide. No activation treatment was required for release of the thionin-like peptide which was produced without a GST tag.

Example 50: Foliar Pre-Treatment with Bt.4Q7Flg22 Polypeptides Protect Lentil and Potato Plants from *Sclerotinia* Stem Rot (White Mold) Disease Treatment applications of Bt.4Q7Flg22 (SEQ ID NO: 226) were examined for protection of lentil and potato plants against disease infection and progression with *Sclerotinia sclerotorium* strain MT07 (white mold). Three different versions of the Bt.4Q7Flg22 polypeptides were examined in the disease assessment studies. A formulated Bt.4Q7Flg22 (100 μM) in sodium phosphate buffer, pH 5.7 and two different versions of Bt.4Q7Flg22 produced using fermentation methods as described (Example 49) and provided with and without activation of Flg22 with an enterokinase (EK) and referred to as H101 filtrate.

Prior to using the three versions of the polypeptides in disease protection assays with lentil and potato plants, a ROS activity assay was performed using corn petiole tissues using methods as described previously in Example 15 to ensure that the Bt.4Q7Flg22 H101 filtrate, particularly with the EK was active. The H101 Bt.4Q7Flg22 filtrates without and with enterokinase (EK=8 U/mL filtrate) activation were compared to the synthetic Bt.4Q7Flg22 (SEQ ID NO: 226) which was used to generate a series of concentration comparisons to predict the Flg22 concentrations in the H101 filtrates generated using fermentation procedures.

TABLE 81

ROS activity assay using Flg22 produced by fermentation with and without enterokinase activation in corn

| Flg22 Polypeptide Concentration | Average RLU of Flg22 Polypeptide Treatment | Change (X) in RLU of Flg22 Polypeptide Compared to Negative Control |
|---|---|---|
| Bt.4Q7Flg22 (SEQ ID NO: 226) (1.0 nM) | 6851 | 0.8X |
| Bt.4Q7Flg22 (SEQ ID NO: 226) (5 nM) | 9389 | 1.1X |
| Bt.4Q7Flg22 (SEQ ID NO: 226) (25 nM) | 12157 | 1.4X |
| Bt.4Q7Flg22 (fermentation H101 filtrate) With (+) Enterokinase 8 U/mL (0.1% v/v) | 25212 | 3.0X |
| Bt.4Q7Flg22 (fermentation H101 filtrate) Without (−) Enterokinase (0.1% v/v) | 16891 | 2.0X |

*RLU values are reported as an average of 4 separate measurements after the background RLU levels were subtracted.

The fermentation produced H101 filtrates of Bt.4Q7Flg22 provided with and without EK activation both resulted in ROS activities (RLU values) that were higher than the control (0 nM Bt.4Q7Flg22). The H101 Bt.4Q7Flg22 filtrates (0.1% v/v) with EK treatment provided to corn stem in the ROS assay resulted in a 3.0× increase in RLU values as compared to the control treatment without any Flg22 polypeptide and the ROS response was greater than Bt.4Q7Flg22 (SEQ ID NO: 226) provided at a concentration of 25 nM; therefore, the estimated Bt.4Q7Flg22 activity in the undiluted EK-activated filtrate was ≥25 μM The fermentation produced H101 filtrates of Bt.4Q7Flg22 treatments that were provided without EK still had ROS activity (2.0×RLU) over the negative control treatment but with a lower increase seen in RLU values as compared to the H101 filtrates of Bt.4Q7Flg22 with EK. Once it was confirmed that the H101 filtrates had activity in ROS assays (Table 81) they were assessed in disease protection studies with potato and lentil.

Various formulations of Bt.4Q7Flg22 polypeptides were provided to lentil and potato plants as a foliar pre-treatment to plants 48 hours prior to inoculation with the *Sclerotinia* sclerotorium fungus and provided in combination with and without a fungicide (Endura, active ingredient 70% boscalid), which is effective in the treatment and protection of plants from infection with the *Sclerotinia* fungus (white mold). The Bt.4Q7Flg22 formulations were tested using a crop-disease model (Montana State University, Extension Services Crop Protection) to examine the effects of each of the foliar pre-treatments on the prevention and protection against disease and the development of symptoms. All treatments including the water control were applied to the lentil and potato plants using an air brush connected to a regulated air compressor set with an output pressure to the brush at 50 psi. After the pre-treatment, plants were inoculated with *Sclerotinia* sclerotorium using mycelial plug (agar plug covered with mycelium) placed with the mycelia side touching the plant stem and placed in humidity (100%) chambers for a set amount of time.

Lentils

Lentil (variety Pennel) plants were grown in soilless media consisting of a mixture of 1:1 peat moss to perlite in 4'4' pots with one plant per pot for 24 days in a controlled growth chamber under growth conditions: 300-400 μmol $m^{-2}$ $s^{-1}$ (light photons) for a 13/11 light/day cycle and a 21° C. day/15° C. night temperature range. The disease studies included five lentil plants per each of six different foliar treatments with 6 replicate plants per treatment, a total of 30 plants per foliar treatment as described in Table 35. All of the foliar treatments used for pre-treatments were applied with the addition of a non-ionic surfactant (ALLIGARE SURFACE; Alligare, LLC) to a final concentration of 0.1% (v/v) or a concentration of alkylpolyoxethylene, glycol derivatives. Each of the Bt.4Q7Flg22 treatments from the formulated and fermentation-derived productions were provided at an application use rate of 0.1% (v/v) or 300 μL of product to 300 mL water and provided to each plant in an equivalent number of sprays completely covering the foliage, using 8 mL of each treatment application for all 30 plants per treatment. The Endura fungicide pre-treatment was applied at an equivalent application use rate of 11 Fl. oz/Ac (803.8 mL/Ha) following the application instructions on the specimen label. The treatments were randomized using a complete random block design. Approximately 48 hours after the pre-treatment, plants were inoculated with a *Sclerotinia* sclerotorium strain isolated locally in Montana using mycelial plug (agar plug covered with mycelium) placed with the mycelia side touching the plant stem. The lentil plants were then placed in humidity (100%) chamber for a period of 72 hours. At 11 days after inoculation disease symptoms were assessed and scored and average fresh weight (total weight of each replicate—grams) were collected (Table 82). Plants were allowed to dry for approximately 3 weeks, and then dry weight was collected (total weight per replicate—grams) (Table 82)

Disease scoring (disease scoring scale 0-7) and fresh weight and dry weight (grams) were collected for each replicate of five plants and then averaged for the total number of plants (n=30). The disease scoring was ranked on a scale of 0-7, with a score of 0 equivalent to no disease and a score of 10 ranked as all plants did not survive (Table 82).

TABLE 82

Disease assessment in lentils 10-days post infection with *Sclerotinia sclerotiorum*

| Treatment | Disease Scoring Scale 0-7 (STDEV) | Average Total Fresh Weight per Plant (grams) (STDEV) | Average Total Dry Weight per Plant (grams) (STDEV) |
|---|---|---|---|
| Water control | 2.83 (±1.84) | 4.52 (±1.18) | 0.95 (±0.21) |
| Endura Fungicide | 0.50 (±0.84) | 2.89 (±0.30) | 0.68 (±0.05) |
| Formulated Bt.4Q7Flg22 | 1.33 (±0.82) | 5.44 (±0.48) | 0.99 (±0.07) |
| Endura Fungicide + Formulated Bt.4Q7Flg22 | 1.0 (±0.89) | 4.95 (±0.59) | 0.96 (±0.05) |
| H101 filtrate non-activated | 2.17 (±1.47) | 4.51 (±0.93) | 0.85 (±0.06) |
| H101 filtrate EK activated | 2.17 (±1.33) | 6.11 (±0.69) | 1.09 (±0.11) |

*p value of ≤0.1 means there is a statistically significant difference between treatments and the water control.

Foliar application of formulated Bt.4Q7Flg22 was compared to the Endura fungicide, the Endura fungicide combined with formulated Bt.4Q7Flg22 and the two Bt.4Q7Flg22 treatments provided with the Flg22 polypeptides produced from the fermentation reactions with and without EK activation as previously described in Table 82. All of the foliar treatments in the crop-disease model were compared to the each other and to water control treated plants and assessed 11 days post inoculation for the appearance of disease symptoms. Each plant was assigned a disease score from 0-7. The total fresh and dry weights (grams) were also determined per plant.

The Endura fungicide, a commercially available treatment for *Sclerotinia sclerotium* resulted in the least disease symptom development on lentil compared across all of the foliar treatments with a disease score of 0.50 whereas, the water treatment (control) resulted in a disease ranking score of 2.83. Foliar application of the formulated Bt.4Q7Flg22 treatment to lentil plants resulted in an increased resistance to *Sclerotinia* with a disease score of 1.33 (p value=0.0972) compared to plants that received the water control treatment. Unlike the Endura fungicide treatment which resulted in slowed growth compared to the plants treated with the water control, the formulated Bt.4Q7Flg22 treatment resulted in continued vigorous growth during early symptom development. The lentil plants that received the pre-treatment with the formulated Bt.4Q7Flg22 had an average fresh weight of 5.44 grams per plant compared to plants treated with the Endura fungicide alone (2.89 g) or the water control (4.52 g). The combination treatment of the Endura fungicide with the formulated Bt.4Q7Flg22 polypeptide further increased protection of the lentil plants from symptom development with a disease score of 1.0 (p value=0.0524) compared to the plants treated with the water control. Plant weight (fresh and dry) for plants that received the pre-treatment with the formulated Bt.4Q7Flg22 polypeptide was greater than the fresh or dry weights from plants that received the water control or the Endura fungicide alone. The Bt.4Q7Flg22 polypeptides provided from the fermentation derived products (non-EK activated and EK activated) were equivalent in the disease symptom ranking with a disease score of 2.17, which was less than the disease score of plants treated with the water only control application. However, the fresh weight per plant treated with the EK-activated version of the Bt.4Q7Flg22 polypeptide had a significantly increased fresh weight of 6.11 grams (p value=0.0266) as compared to the water treated plants. The EK-activated version of the Bt.4Q7Flg22 polypeptide also had the overall highest fresh and dry weights compared to all of the other treatments in Table 82. Other significant findings of this study were that the formulated Bt.4Q7Flg22 polypeptide pre-treatment of lentil plants protected the lentils from fungicide-induced damage. The average fresh weight of the plants that received the Endura fungicide was 2.89 g while the formulated Bt.4Q7Flg22 treatment was 5.44 g (p value=2.645×10-05). The fermentation produced Bt.4Q7Flg22 containing the enterokinase (EK) enzyme was used to cleave the Bt.4Q7Flg22 polypeptide from the GST-EK-Bt.4Q7Flg22 as previously described. This Bt.4Q7Flg22 filtrate treatment provided to lentil increased activity of the Flg22 polypeptide thus resulting in significantly enhanced plant growth during the infection period compared to the water treated control plants (p value=1.180×10-05). The non-activated EK or GST-EK-Bt.4Q7Flg22 or non-cleaved Bt.4Q7Flg22 filtrate did not increase plant growth compared to the plants that received the water control only treatment (p value=0.9852).

Potatoes

Seed potatoes (variety: Russet Burbank) were planted from 2 cm potato sections from which eye buds protrude (1 section per pot) with the cut side down and planted approximately 7-8 cm deep in soilless media consisting of a mixture of 1:1 peat moss to perlite in 10×10 cm pots. Potatoes were grown with one plant per pot for 19 days in a controlled growth chamber under standard conditions of receiving approximately 300-400 μmol $m^{-2}$ $s^{-1}$ (light photons) for a 13/11 light/day cycle and a 21° C. day/15° C. night temperature range. 19 days after planting, the potato plants were pre-treated with the foliar applications as described in Table 36. The disease studies included five potato plants per each of six different foliar treatments with 6 replicate plants per treatment, a total of 30 plants per foliar treatment as described in Table 83. All of the foliar treatments used for pre-treatments were foliar applied with the addition of a non-ionic surfactant (ALLIGARE SURFACE; Alligare LLC) to a final concentration of 0.1% (v/v) or a concentration of alkylpolyoxethylene, glycol derivatives. Each of the Bt.4Q7Flg22 treatments from the formulated and fermentation derived productions were provided at an application use rate of 0.1% (v/v) or 300 μL of product to 300 mL water and provided to each plant in an equivalent number of sprays completely covering the foliage using 15 mL of each treatment application for all 30 plants per treatment. The Endura fungicide pre-treatment was applied at an equivalent application use rate of 11 Fl. oz/Ac (803.8 mL/Ha) following the application instructions on the specimen label. The treatments were randomized using a complete random block design. Approximately 48 hours after the pre-treatment, plants were inoculated with *Sclerotinia* sclerotorium using mycelial plug (agar plug covered with mycelium) placed with the mycelia side touching the plant stem and placed in a humid chamber (100%) for 192 hours. At 16 days after inoculation disease symptoms were assessed and scored and average stem fresh weight (total stem weight—grams) were collected (Table 83). Plants were allowed to dry for 12 days, and then dry weights were recorded (total stem weight—grams) (Table 83).

After 48 hours, the potato plants were inoculated with mycelia plugs placed on the soil near each plant and placed in a humid misting chamber. The treatments were randomized using a random block design. Disease scoring (scoring scale 0-6). Stem fresh and dry weight (grams) were also collected from each plant and then averaged for the total number of plants (n=30). Stem dry weight was taken after the plants were fully desiccated at approximately 12 days after harvest. Disease scores were assessed 16 days after the initial inoculation. The disease scoring was ranked on a scale of 0-6, with a score of 0 equivalent to no disease and a score of 6 ranked as all plants did not survive.

TABLE 83

Disease assessment in potatoes 15-days post infection with *Sclerotinia sclerotiorum*

| Treatment | Disease Scoring Scale 0-6 (STDEV) | Average Fresh Stem Weight per Plant (grams; "g") (STDEV) | Average Dry Stem Weight per Plant (grams; "g") (STDEV) |
|---|---|---|---|
| Water control | 2.83 (±1.33) | 96.01 (±17.05) | 12.08 (±2.75) |
| Endura Fungicide | 0.50 (±0.84) | 110.98 (±18.32) | 16.86 (±8.69) |
| Formulated Bt.4Q7Flg22 (SEQ ID NO: 226) | 1.83 (±0.98) | 113.37 (±14.58) | 15.01 (±3.72) |
| H101 filtrate non-activated | 2.33 (±1.03) | 98.08 (±15.34) | 12.96 (±2.77) |
| H101 filtrate EK activated | 1.83 (±0.75) | 117.76 (±15.83) | 17.66 (±8.70) |

*p value of ≤0.1 means there is a statistically significant difference between treatments and the water control.

Foliar pre-treatment applications using the formulated Bt.4Q7Flg22 and Bt.4Q7Flg22 polypeptides derived from the fermentation products (H101 filtrates) were compared for disease symptom development on potato plants that received the Endura fungicide and the water control treatment. Foliar application of formulated Bt.4Q7Flg22 (SEQ ID NO: 226) provided as a pre-treatment to potato plants resulted in a disease score of 1.83 as compared to plants that received the water control (disease score=2.83). Plants that received pre-treatment with the Endura fungicide had the least disease symptoms with a disease score of 0.50 (p value=0.0045) compared to plants treated with the water control. The formulated Bt.4Q7Flg22 polypeptide pre-treatment resulted in plants with an average disease score similar to the enterokinase activated Bt.4Q7Flg22 (H101 EK-activated) provided in a filtrate (fermentation product)—both had disease scores of 1.83. The non-activated EK or GST-EK-Bt.4Q7Flg22 or non-cleaved Flg22 filtrate (H101 non-activated) provided to plants had a score of 2.33 and was not significantly different from the disease score of plants that were treated with the water control (p value=0.4835). However, potato plants that received the pre-treatment with the EK-activated Bt.4Q7Flg22 filtrate resulted in an increased average stem fresh and dry weight per plant compared across all treatments with approximately a 20 g increase in stem fresh weight and an almost 6 g increase in stem dry weight per plant compared to plants that received the water control pre-treatment. Plants that received the formulated Bt.4Q7Flg22 polypeptide all had increased stem fresh and dry weight as measured on a per plant basis compared to plants that received the water only control application.

Example 51: Treatment of *Candidatus Liberibacter Asiaticus* Infection with Flg22 and Anti-Microbial Polypeptides Bt.4Q7Flg22 formulations were applied by trunk injection treatments to both Valencia orange (*Citrus sinensis*) and Ruby Red grapefruit (*Citrus×paradisi*) trees. The study was conducted at a commercial grove orchard located in central Florida (Okeechobee county). Injection treatment using the Bt.4Q7Flg22 polypeptide (SEQ ID NO: 226) provided using a 1× Low Rate (0.55 micromoles peptide; 0.138 µM estimated concentration in phloem) and a 10× High Rate (5.5 micromoles peptide; 1.38 µM estimated concentration in phloem) was compared to the non-treated control trees. The injection treatments were set up using a randomized complete block design with 10 grapefruit trees (4 years old) per treatment. The injections were provided in April (2017) at first flush, a stage in growth from the emergence of leaves until they expand to full size. Injection of grapefruit trees were conducted using a low-pressure injection device, BRANDTENTREE (BRANDT). Leaves from each of the grapefruit trees were sampled at the time of injection (Day 0), 21 and 56 days post injection. A total of six leaf samples per tree were selected to represent the population of leaves on the tree in terms of leaf age, location, and presence of visual symptoms. Each midrib was separated from the leaf blade and immediately chopped into very small pieces with a new sterile razor blade. Leaf samples from each tree were then placed in an individual tube that was subsequently stored in a freezer at −80° C. until further processing. DNA extraction and real-time polymerase chain reaction or quantitative PCR (qPCR) analysis on these leaves was performed at Southern Gardens Citrus (Clewiston, Florida).

The presences of the CLas bacterial titers in the HLB infected citrus trees can be determined with quantitative real-time polymerase chain reaction (qPCR) methods using specific primers to confirm the presence of the disease (Li, W. B., Hartung, J. S. and Levy, L. 2008 "Optimized quantification of unculturable '*Candidatus Liberibacter* spp.' In host plants using real-time PCR", Plant Disease 92: 854-861). DNA extraction and quantitative PCR (qPCR) analysis on these leaves was performed at Southern Gardens Citrus (Clewiston, Fla.) using HLB primer set targeting the 16S DNA of *C. liberibacter* bacteria 5'»3' (forward): HLB as TCGAGCGCGTATGCAATACG (SEQ ID NO: 773); (reverse) HLBr: GCGTTATCCCGTAGAAAAAGGTAG (SEQ ID NO: 774); HLBpc (probe): AGACGGFT-GAGTAACGCG (SEQ ID NO: 775) labeled with an intercalating fluorescent reporter dye]. Forty cycles of qPCR were conducted and the fluorescent signal which is proportional to the amount of dsDNA in solution was measured. The qPCR analysis allows for the detection of the CLas bacteria in citrus tissue. The cycle threshold (Ct) values from the qPCR analysis were obtained per each treatment. The Ct measurement is equivalent to the number of PCR cycles required to produce a relative threshold level. As in common practice within the field of molecular biology, the change in Ct value is reported to indicate the relative quantity of CLas DNA either in treated vs untreated samples or in treated samples at one time point vs another time. The higher the Ct value, the greater or more effective the treatment effect, which is indicated by the reduction/elimination of CLas bacteria from the tree. A percentage reduction in bacterial load can be computed as:

$$\% \text{ reduction in sample over time} = 1 - 2^{[Ct(initial\ time) - Ct(later\ time)]} * 100\%$$

or $$\%\ \text{reduction in treated vs. control sample}=(1-2^{[Ct(control\ sample)-Ct(treated\ sample)]})*100\%$$

Figure 9:
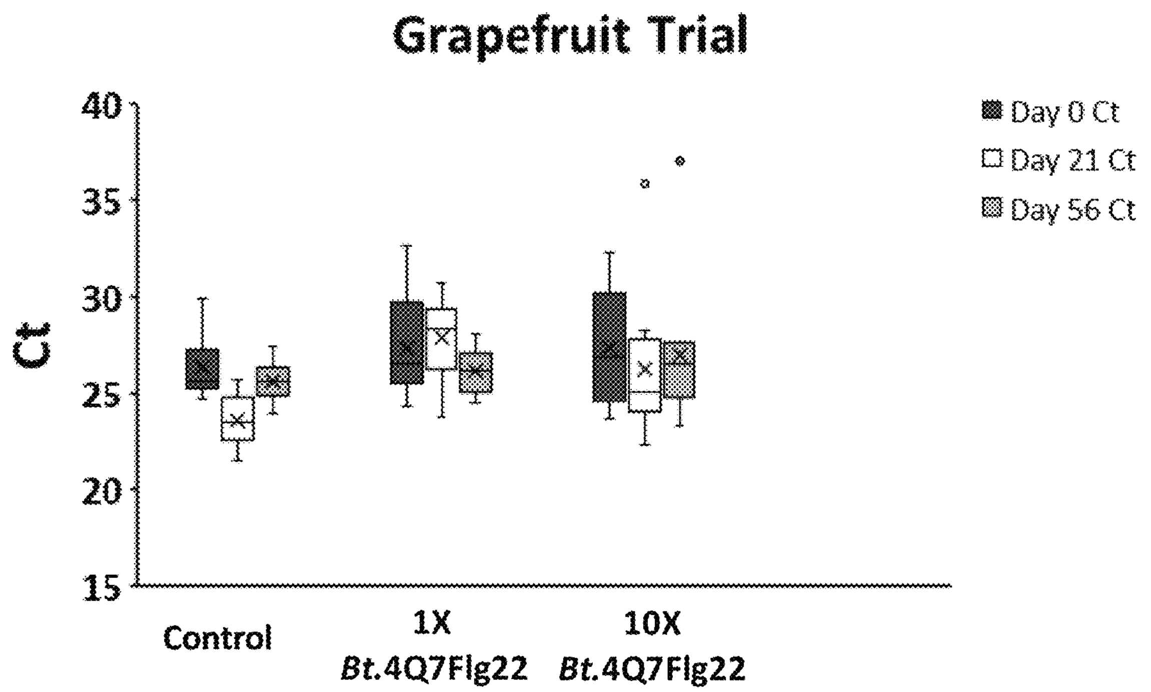
FIG. 9 is directed to the application delivery of Bt4Q7 Flg22 polypeptides tagged or untagged with thionins to decrease the growth of *Candidatus Liberibacter* spp in HLB infected citrus trees. Data represent quantitative PCR results (Ct values) of *C. Liberibacter* in leaf samples taken from treated infected trees.

The results from the grapefruit trial are shown in FIG. 9. The average values from the Ct comparisons (n=10 trees per treatment) obtained from the qPCR analysis from the T0 timepoint (day of injection), the T21 and the T56 timepoints (21 and 56 days post injection) are reported with the standard error from the mean Ct values in FIG. 9 (T0=dark grey bars; T21=white bars; T56=light gray bars; average Ct values marked with an "x"). Any outlier values are indicated by the small circles located outside the standard error bars for each treatment. The control or grapefruit trees that were not injected had the lowest Ct values in a range of Ct near 25 for all treatment timepoints. Leaves sampled from grapefruit trees that received injection treatments with the 1× and 10× Bt.4Q7Flg22 polypeptide formulations resulted in slightly higher Ct counts as compared to leaves from the control trees (FIG. 9). The higher the Ct. value, the greater the treatment effect for controlling or reducing the infection of the CLas bacteria from spreading. The average Ct value in leaves taken from the T21 sampling was greater than the Ct value from the T56 sampling but both were significantly increased over the non-injected control leaves or leaves from trees that received injections with the Bt.4Q7Flg22 polypeptide formulations (FIG. 9, average Ct values marked with "x").

In another study using Valencia orange (*Citrus sinensis*) also conducted at the commercial grove orchard located in central Florida (Okeechobee county). Injection treatments using formulations of Bt.4QFlg22 (SEQ ID NO: 226) were compared to antimicrobial polypeptides known as thionins. Thionin injection was provided as a mixture of thionin polypeptides (SEQ ID NOs: 651, 652 and 653) which are characterized as "un-tagged" or without a phloem localization sequence. In addition to the un-tagged thionin mixture, a "tagged" thionin polypeptide that comprised a phloem localization sequence (SEQ ID NO: 650) was used as a comparative injection treatment. The phloem targeted or "tagged" version was used to target the thionin specifically to the phloem where CLas bacteria reside and multiply. The injection treatments were applied to orange trees using a randomized complete block design with a total of 8 orange trees (8 years old) per treatment for the untreated control and Bt.4QFlg22 treatments, and a total of 5 orange trees per treatment for the thionin treatments. The injections were provided in April (2017) at first flush, a stage in growth from the emergence of leaves until they expand to full size. Injection of the orange trees were conducted using a low-pressure injection device, BRANDTENTREE (BRANDT). The Bt.4Q7Flg22 polypeptide 1× (0.138 μM) and a 10× (1.37 μM) concentrations, the "untagged" and the "tagged" thionin polypeptides were all compared to trees that received no injection treatment (control). Leaves from the orange trees were sampled per each treatment at the time of injection (Day 0) and at T56, or 56 days post injection.

A total of six leaf samples per tree, were selected to represent the population of leaves on the tree in terms of leaf age, location, and presence of visual symptoms. Each midrib was separated from the leaf blade and immediately chopped into very small pieces with a new sterile razor blade. Leaf samples from each tree were then placed in an individual tube that was subsequently stored in a freezer at −80° C. until further processing. DNA extraction and real-time polymerase chain reaction or quantitative PCR (qPCR) analysis on these leaves was performed at Southern Gardens Citrus (Clewiston, Fla.) using the methods as described above for performing Ct analysis.

Figure 10:
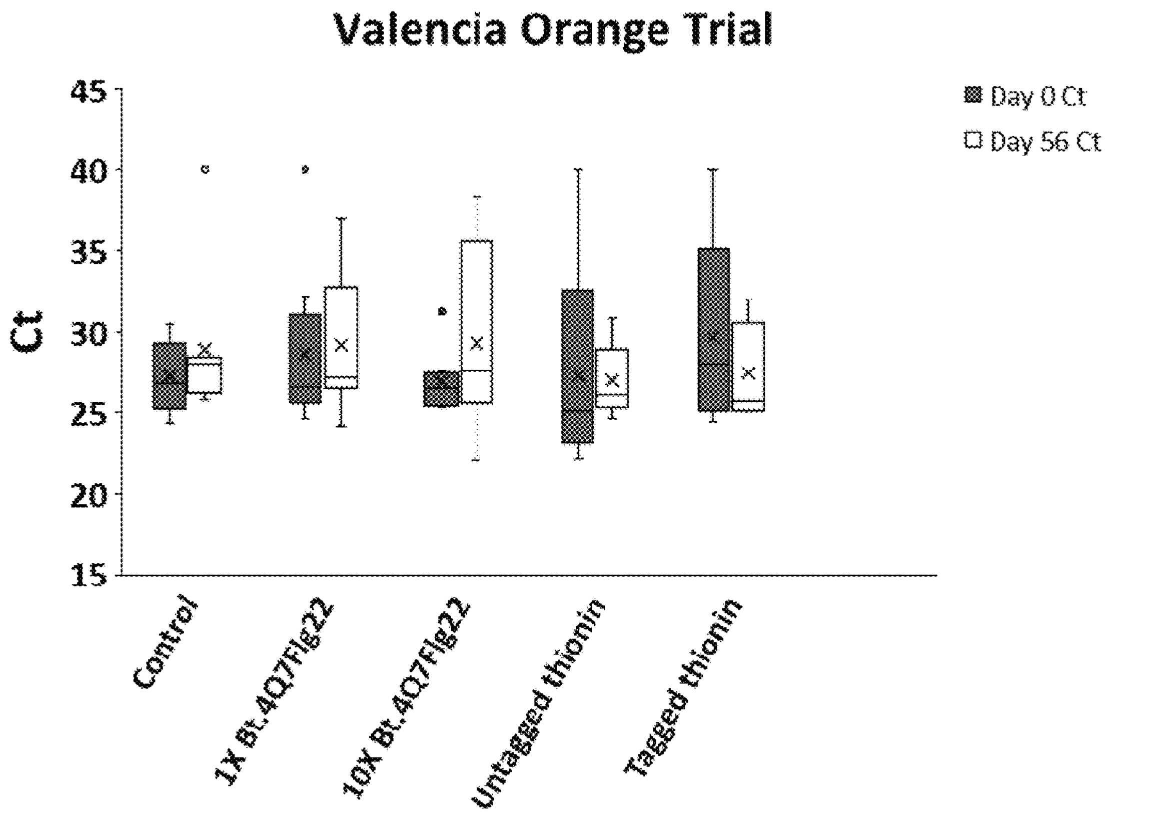
FIG. 10 is directed to the application delivery to citrus in trees injected with 1× or 10× Bt.4Q7Flg22 (SEQ ID NO: 226) to decrease the growth of *Candidatus Liberibacter* spp in HLB infected citrus trees. Data represent quantitative PCR results (Ct values) of *C. Liberibacter* in leaf samples taken from treated infected trees.

Results from the Valencia orange trial are shown in FIG. 10 (T0=dark grey bars; T56=white bars). Leaf tissues from the control orange trees had the lowest Ct values in a range of Ct near 25-30 for treatment timepoints T0 and T56 indicating that titer levels of the CLas bacteria did not change in these trees. Both of the thionin treatments "untagged" and "tagged" had higher average Ct values in leaves taken from the T56 sampling as compared to the average Ct values from T56 leaves sampled from the water-injected controls (FIG. 10; average Ct values marked with "x"). Any outlier values are indicated by the small circles located outside the standard error bars for each treatment. Leaves sampled from trees that received the phloem targeted thionin "tagged" treatment had a higher average Ct value at T56 compared to leaves from trees that received non-targeted or "un-tagged" thionin treatment. Leaves sampled from orange trees that received injection treatments with the 1× and 10× Bt.4Q7Flg22 polypeptide formulations resulted in significantly higher Ct counts from the T0 to T56 timepoints shown by the average increase in Ct at T56 compared to T0 (FIG. 10; average Ct values marked with "x"). Leaves from trees injected with both Bt.4Q7Flg22 polypeptide formulations (1× and 10×) also had significantly higher Ct values compared to leaves samples from the control trees. The Bt.4Q7Flg22 are effective treatments for controlling or reducing the titer levels of the CLas bacteria in the infected orange trees (FIG. 9).

The Bt.4Q7Flg22 polypeptides provided as injection treatments using final concentrations at the 1× (0.138 μM) and 10× (1.38 μM) were both effective in reducing CLas titer levels in the leaf tissue sampled 8 weeks post injection. The higher concentration of the Bt.4Q7Flg22 polypeptide 10× (1.38 μM) however was even more effective resulting in a 37% reduction (Trial 1) and a 43% reduction (Trial 2) in CLas titer levels.

TABLE 84

Treatment effectiveness of Bt.4Q7Flg22 on reducing CLas bacterial titer levels 8 weeks post injection treatment on citrus (Valencia orange and Ruby Red Grapefruit)

| | Percentage Reduction in CLas titer Normalized to the Control | |
|---|---|---|
| Injection Treatment Concentration | Trial 1 | Trial 2 |
| 1X Bt.4Q7Flg22 (SEQ ID NO: 226) 0.138 μM estimated concentration in tree vasculature | 33% | 21% |
| 10X Bt.4Q7Flg22 (SEQ ID NO: 226) 1.38 μM estimated concentration in tree vasculature | 37% | 43% |

Previous results indicate that Bt.4Q7Flg22 (SEQ ID NO: 226) promotes plant growth throughout periods of disease (Example 50). To assess for a potential plant growth benefit to injecting H LB-infected 'Valencia' Orange and 'Ruby Red' Grapefruit trees with Bt.4Q7Flg22 (SEQ ID NO: 226), current year growth was measured in May 2018 for the same trees that were injected with Bt.4Q7Flg22 in April 2017 and assessed for CLas bacterial titer at the commercial grove orchard located in central Florida (Okeechobee county). Each tree was visually assessed for regions of current season growth with green color to the branches, as compared to old growth branches that are more woody in appearance with a dark greenish-brown to brown hue. Three representative branches with new growth were selected per tree, and the distance in inches from the start of green growth (oldest node) to the tip of the youngest node was measured with a flexible measuring tape. Data was collected for trees injected with 1× and 10× Bt.4Q7Flg22 (SEQ ID NO: 226) as well as the untreated control, with 8 trees per treatment for the 'Valencia' orange trial and 9-10 trees per treatment for the 'Ruby Red' Grapefruit trial (n=24-30 measurements per treatment). Only one tree in the 'Ruby Red' Grapefruit trial was lost from the original trial (1× Bt.4Q7Flg22 treatment group), presumably due to hurricane-strength wind damage in September 2017. For each trial, the average new growth length (inches) was calculated and normalized to the untreated control (Table 85).

TABLE 85

Bt.4Q7Flg22 trunk injection increases new branch growth in 'Valencia' orange and 'Ruby Red' grapefruit

| Trial | Treatment | Average Flush Length (inches) | Flush length (% of control) |
|---|---|---|---|
| Valencia Orange-Injected April 2017, Measured May 2018 | Control | 7.23 | 100% |
| | 1X Bt.4Q7Flg22 (SEQ ID NO: 226) 0.138 μM estimated concentration in tree vasculature | 13.33 | 184% |
| | 10X Bt.4Q7Flg22 (SEQ ID NO: 226) 1.38 μM estimated concentration in tree vasculature | 12.29 | 170% |
| Red Grapefruit-Injected April 2017, Measured May 2018 | Control | 8.05 | 100% |
| | 1X Bt.4Q7Flg22 (SEQ ID NO: 226) 0.138 μM estimated concentration in tree vasculature | 10.83 | 135% |
| | 10X Bt.4Q7Flg22 (SEQ ID NO: 226) 1.38 μM estimated concentration in tree vasculature | 9.13 | 113% |

These results demonstrate the ability of Flg22 compositions, which displayed reduced CLas bacterial titer compared to untreated plants (FIG. 9 and FIG. 10), to also enhance the growth of sweet orange and grapefruit trees (Table 85). Enhanced branch growth serves as an indicator of enhanced fruit yield as more leaves are produced to sustain fruit growth throughout the season. In comparison to the untreated control, orange and grapefruit trees receiving the 1× Bt.4Q7Flg22 injection in April 2017 had on average 6.1 more inches (+85%) or 2.8 more inches (+35%) of new branch growth, respectively. The 10× injection dose of Bt.4Q7Flg22 was also effective at increasing growth, with 5.1 more inches (70%) and +1.1 more inches (+13%) of new branch growth in orange and grapefruit trees, respectively. As the 10× Bt.4Q7Flg22 injection did not perform better than the 1× injection for enhancing growth in 2018, and bacterial titer reductions were similar in 2017. The 1× Bt.4Q7Flg22 injection provides a sufficient response in the plant. Importantly, growth measurement indicated that no phytotoxicity occurred after Flg22 trunk injection at either the 1× or 10× rate.

As these plants were not 100% cleared of disease-causing bacteria, these results also demonstrate the ability of the plants injected with Bt.4Q7Flg22 to continue to grow despite the presence of HLB-causing bacteria. Provided that CLas strains with antibiotic resistance are predicted to emerge and become an additional hurdle for HLB-control, Flg22 injection represents a desirable alternative to antibiotic treatments for ameliorating plant growth and reducing bacterial titer. The trees receiving the Flg22 injections in this example were maintained with a standard commercial citrus treatment program, which further demonstrates the ability to add Flg22 citrus injections to standard grower practices.

Example 52: Foliar and Trunk Injection of Flg22 Applied Alone or in Combination with Antimicrobial or Plant-Health Promoting Compounds Increase New Shoot Growth in Orange Trees In subsequent trials in April (2018), Flg22 formulations were applied by trunk injection treatments or foliar spray at two independent trial sites. Trials were designed to 1) test Flg22 polypeptide variants produced synthetically and by fermentation, 2) compare the efficacy of the Flg22 variant previously used for citrus injection trials in 2017, Bt.4Q7Flg22 (SEQ ID NO: 226), versus Syn01Bt.4Q7Flg22 (SEQ ID NO: 571) which was effective as both a foliar and seed treatment for increasing yield in row crops, 3) compare Flg22 application methods, namely trunk injection versus foliar spray to the canopy, and 4) test combinatorial treatments between Flg22 peptides and oxytetracycline injection, L-cysteine, and Benzo (1,2,3) thiadiazole-7-carbothioic acid-S-methyl ester (also known as BTH) as the commercially available formulation ACTIGARD WG. L-cysteine is an essential, proteinogenic amino acid; and BTH is a salicylic acid analog with increased stability that is used agriculturally as an activator of plant immune responses and is approved for application to citrus trees as root drench or irrigation treatment to prevent citrus canker caused by *Xanthomonas axonopodis* pv *citri.*

In March 2018, trees were treated at two separate sites. Three-year old Hamlin orange trees (*Citrus sinensis*) were treated at a commerical grove orchard located in central Florida (Okeechobee County). A similar trial was conducted in a commercial grove of 6-year old Vernia orange trees on Swingle rootstock at Lake Wales, Fla. (Polk County). Treatments were applied as listed in Table 85 below using a low-pressure injection device, BRANDT ENTREE (BRANDT) for trunk injection or a CO2-pressurized backpack sprayer that produced a fine mist for foliar spray. Trunk injections were as described in Example 51. Foliar compositions of Bt.4Q7Flg22 were diluted in water with a non-ionic surfactant (Precision Labs NIS90:10; 0.1% v/v of spray tank volume) and evenly applied to the canopy of the tree at a spray rate of 3 Liters per tree. Blocks of trees receiving a foliar treatment were spaced in the trial area with a gap (skipped tree) in between treatment blocks to avoid drift of treatment into neighboring treatment blocks. Treatments were applied during the early morning or late evening during a period of low wind (<5 mph), and conditions were such all spray treatments dried on leaves within a period of 4 hours. Combination treatments described in Table 86 were either co-injected in the same BRANDT ENTREE bottle (Citrus Composition 7, Citrus Composition 8) or applied separately as an oxytetracycline injection followed by a Bt.4Q7Flg22-Syn01 foliar treatment on the same day (Citrus Composition 11, Citrus Composition 12). For all treatments, 10 trees were used per treatment, separated into two replicated blocks of five trees each. Citrus compositions 1-8 were applied at both the Okeechobee and Polk County groves, while Citrus Compositions 9-12 were applied at Okeechobee grove alone.

TABLE 86

Treatment compositions tested for ameliorating the effects of HLB in orange trees

| Composition | Formulation | Treatment Method | Application Use Rate |
|---|---|---|---|
| Citrus Composition 1 | Bt.4Q7Flg22 (SEQ ID NO: 226) 100 μM 10 mM Sodium Phosphate Buffer, pH 5.7 | Trunk Injection | 2.75 mL/tree (estimated 0.138 μM in plant vasculature) |
| Citrus Composition 2 | Bt.4Q7Flg22-Syn01 (SEQ ID NO: 571) 100 μM 10 mM Sodium Phosphate Buffer, pH 5.7 | Trunk Injection | 2.75 mL/tree (estimated 0.138 μM in plant vasculature) |
| Citrus Composition 3 | Bt.4Q7Flg22 (SEQ ID NO: 226) (fermentation brothfiltrate) With (+) Enterokinase 0.8 U/mL | Trunk Injection | 80 mL/tree |
| Citrus Composition 4 | Bt.4Q7Flg22-Syn01 (SEQ ID NO: 571) (fermentation broth filtrate) With (+) Enterokinase 0.8 U/mL | Trunk Injection | 80 mL/tree |
| Citrus Composition 5 | Bt.4Q7Flg22-Syn01 (SEQ ID NO: 571) 100 μM 10 mM Sodium Phosphate Buffer, pH 5.7 | Foliar Spray | 3.0 mL/tree in a spray carrier volume of 3 L water + 0.1% v/v Precision Labs NI590:10 |
| Citrus Composition 6 | Bt.4Q7Flg22-Syn01 (SEQ ID NO: 571) 100 μM 10 mM Sodium Phosphate Buffer, pH 5.7 | Foliar Spray | 12.0 mL/tree in a spray carrier volume of 3 L water + 0.1% v/v Precision Labs NI590:10 |
| Citrus Composition 7 | Part A Bt.4Q7Flg22-Syn01 (SEQ ID NO: 571) 100 μM 10 mM Sodium Phosphate Buffer, pH 5.7 | Trunk Injection | 2.75 mL/tree (estimated 0.138 μM in plant vasculature) |
| | Part B ACTIGARDWG (Active Ingredient: 50% Acibenzolar-S-methyl: Benzo(1,2,3)thiadiazole-7-carbothioic acid-S-methyl ester; BTH) (50 mg/mL solution in water) | Trunk Injection | 20 mL/tree (1 g per tree) |
| Citrus Composition 8 | Part A Bt.4Q7Flg22-Syn01 (SEQ ID NO: 571) 100 μM 10 mM Sodium Phosphate Buffer, pH 5.7 | Trunk Injection | 2.75 mL/tree (estimated 0.138 μM in plant vasculature) |
| | Part B L-Cysteine (3 mg/mL solution in water) | Trunk Injection | 20 mL/tree (60 mg per tree) |
| Citrus Composition 10 | Part A Bt.4Q7Flg22-Syn01 (SEQ ID NO: 571) 100 μM 10 mM Sodium Phosphate Buffer, pH 5.7 | Foliar Spray | 3.0 mL/tree in a spray carrier volume of 3 L water + 0.1% v/v Precision Labs NIS90:10 |
| | Part B Oxytetracycline-HCl (22.5 mg/mL solution in water) | Trunk Injection | 20 mL/tree (0.45 g per tree) |
| Citrus Composition 11 | Part A Bt.4Q7Flg22-Syn01 (SEQ ID NO: 571) 100 μM 10 mM Sodium Phosphate Buffer, pH 5.7 | Foliar Spray | 12.0 mL/tree in a spray carrier volume of 3 L water + 0.1% v/v Precision Labs NIS90:10 |
| | Part B Oxytetracycline-HCl (22.5 mg/mL solution in water) | Trunk Injection | 20 mL/tree (0.45 g per tree) |

To assess for a potential plant growth benefit to injecting or spraying HLB-infected orange trees with different formulations of Flg22 polypeptides alone or in combination with antimicrobial or plant-health promoting compounds, new flush length was measured in May 2018 for trees that were treated in March 2018 at commercial groves in Okeechobee county, FL and Polk county, FL. At the time of treating plants at both locations (March 2018), trees exhibited darker green leaves with 2018 season fruit beginning to develop. In the two-month interval between treatment (March 2018) and the time of tree measurement (May 2018), trees entered a period of spring flush with new growth visible as very light green, flexible branches with similarly light green leaves. Each tree was assessed for new flush, and three representative branches with new growth were selected per tree. The distance in inches from the start of light green growth (oldest node) to the tip of the youngest node was measured with a flexible measuring tape. Data was collected for 10 trees per treatment including the untreated control, for a total of 30 measurements per treatment. Represented in Table 86 is the average flush length (inches) for each treatment across the two grove sites in Okeechobee and Polk counties, with growth normalized to the untreated control.

TABLE 87

Flg22 variants applied as either a trunk injection or foliar spray increase new branch growth in 'Hamlin' and 'Vernia' orange trees

| Treatment | Average Flush Length (inches) | Flush length (% of control) |
|---|---|---|
| Untreated Control | 3.08 | 100% |
| Citrus Composition 1<br>Bt.4Q7Flg22 (SEQ ID NO: 226)<br>2.75 mL/tree injection | 3.84 | 125% |
| Citrus Composition 2<br>Bt.4Q7Flg22-Syn01 (SEQ ID NO: 571)<br>2.75 mL/tree injection | 4.48 | 146% |
| Citrus Composition 3<br>Bt.4Q7Flg22 (SEQ ID NO: 226)<br>Enterokinase (EK)-activated filtrate<br>80 mL/tree injection | 5.18 | 169% |
| Citrus Composition 4<br>Bt.4Q7Flg22-Syn01 (SEQ ID NO: 571)<br>Enterokinase (EK)-activated filtrate<br>80 mL/tree injection | 3.28 | 107% |
| Citrus Composition 5<br>Bt.4Q7Flg22-Syn01 (SEQ ID NO: 571)<br>1X foliar spray | 3.66 | 119% |
| Citrus Composition 6<br>Bt.4Q7Flg22-Syn01 (SEQ ID NO: 571)<br>4X foliar spray | 3.76 | 122% |

Growth measurements of 'Hamlin' and 'Vernia' new shoots, taken two months after either trunk injection or foliar spray application of Flg22 variants, indicated that Bt.4Q7Flg22 (SEQ ID NO: 226) and Syn01Flg22 (SEQ ID NO: 571) are both effective at promoting greater growth than the untreated control. On average, untreated control shoots were 3.08 inches in length, while Bt.4Q7Flg22-injected trees had 25% longer shoots (3.84 inches) and Syn01Flg22 injected trees 146% longer shoots (4.48 inches). Bt.4Q7Flg22 and Syn01Flg22 produced through fermentation methods described in Example 49 were also effective at increasing shoot growth when injected into the trunk at a rate of 80 mL/tree. Citrus composition 3 containing Bt.4Q7Flg22 produced by fermentation of strain H101 and treated with 0.8 U/mL Enterokinase (New England Biolabs; Product Code P8070) was the most effective, with shoots measuring on average 169% (5.18 inches) longer than the untreated control.

Foliar application of Flg22 variants, which is effective for promoting growth of kiwi, soy, lentils, and potatoes under disease pressure were also tested for the ability to promote growth of HLB-infected orange trees. Table 88 shows that Citrus Compositions 5 and 6 comprised of a 1× or 4× dose of Syn01Bt.4Q7Flg22 (SEQ ID NO: 571), respectively, are also effective at promoting new shoot growth in orange trees. The 1× and 4× doses were similarly effective, with the 1× foliar rate measuring 119% longer shoots than the control, and the 4× rate measuring 122% longer shoots than the control. These results show that a foliar application of Flg22 polypeptide can be used as part of a standard program of care of citrus grove trees.

TABLE 88

Injection of Bt.4Q7Flg22-Syn01 in combination with plant-health promoting compounds increases new branch growth in 'Hamlin' and 'Vernia' orange trees

| Treatment | Average Flush Length (inches) | Flush length (% of control) |
|---|---|---|
| Untreated Control | 3.08 | 100% |
| Citrus Composition 2<br>Bt.4Q7Flg22-Syn01 (SEQ ID NO: 571)<br>2.75 mL/tree injection | 4.48 | 146% |
| Citrus Composition 7<br>Bt.4Q7Flg22-Syn01 (SEQ ID NO: 571)<br>2.75 mL/tree injection +<br>BTH (ACTIGARD WG; 1 g/tree injection) | 3.44 | 112% |
| Citrus Composition 8<br>Bt.4Q7Flg22-Syn01 (SEQ ID NO: 571)<br>2.75 mL/tree injection + L-Cysteine<br>(60 mg/tree injection) | 5.87 | 191% |

Next, the combination of Syn01Bt.4Q7Flg22 (SEQ ID NO: 571) with BTH (ACTIGARD WG) or L-cysteine was investigated at both the Melvin locations and Lake Wales groves. Both combination treatments in Table 88 showed greater new flush length in comparison to the untreated control, showing that Flg22 polypeptides can be used in combination with amino acids, plant hormones, or plant hormone-mimics to improve citrus tree health.

TABLE 89

Foliar spray application of Bt.4Q7Flg22-Syn01 in combination with oxytetracycline injection increases new branch growth in 3-year old 'Hamlin' orange trees

| Treatment (see table 85) | Average Flush Length (inches) | Flush Length (% of control) |
|---|---|---|
| Untreated Control | 1.67 | 100% |
| Citrus Composition 9<br>Oxytetracycline-HCl<br>(0.45 g/tree) +<br>Syn01Bt.4Q7Flg22 (SEQ ID NO: 571)<br>1X foliar spray | 3.80 | 228% |
| Citrus Composition 10<br>Oxytetracycline-HCl<br>(0.45 g/tree) +<br>Syn01Bt.4Q7Flg22 (SEQ ID NO: 571)<br>4X foliar spray | 3.32 | 199% |

In a separate trial, the combination of Syn01Flg22 (SEQ ID NO: 571) and oxytetracycline treatments were observed. On the same day that trees were injected with oxytetracycline, groups of 10 trees were also sprayed with a foliar application of Syn01Flg22 at a 1× rate or 10× rate. These results show that the antibiotic and polypeptide treatments are compatible and that no phytoxicity was observed due to the dual treatment. A standard program could be envisioned where grower alternated tree injections with foliar treatments for enhanced control of HLB symptoms and for reducing CLas titer.

Example 53: Disease Protection Using Bt.4Q7Flg22 and Gm.RHPP Foliar Applications on Soybean Plants to Protect from Diseases Caused by *Phakopsora pachyrhizi* and *Cercospora kikuchii*

Table 90 describes the compositions and corresponding use rates tested in the following example.

TABLE 90

Bt.4Q7Flg22 and Gm.RHPP foliar applications on soy protect plants from *Phakopsora pachyrhizi* and *Cercospora kikuchii*

| Composition | Foliar Formulation | Application Use Rate Fluid ounce/acre (Fl. oz/Ac) Milliliters/hectare (mL/Ha) |
|---|---|---|
| Composition 12 | FOX Fungicide | 5.48 Fl. oz/Ac or 400 mL/Ha |
| Composition 13 | Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) | 2.05 Fl. oz/Ac or 150 mL/Ha |
| Composition 14 | Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) | 4.11 Fl. oz/Ac or 300 mL/Ha |
| Composition 15 | Gm.RHPP (SEQ ID NO: 600) 100 μM PROXEL BC preservative: 330.7 μM; 50.1 μM (CMIT); 21.71 μM (MIT) | 2.05 Fl. oz/Ac or 150 mL/Ha |
| Composition 16 | Gm.RHPP (SEQ ID NO: 600) 100 μM PROXEL BC preservative: 330.7 μM; 50.1 μM (CMIT); 21.71 μM (MIT) | 4.11 Fl. oz/Ac or 300 mL/Ha |
| Composition 17 | FOX Fungicide + Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) | 5.48 Fl. oz/Ac or 400 mL/Ha + 2.05 Fl. oz/Ac or 150 mL/Ha |
| Composition 18 | FOX Fungicide + Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) | 5.48 Fl. oz/Ac or 400 mL/Ha + 4.11 Fl. oz/Ac or 300 mL/Ha |
| Composition 19 | FOX Fungicide + Gm.RHPP (SEQ ID NO: 600) 100 μM PROXEL BC preservative: 330.7 μM; 50.1 μM (CMIT); 21.71 μM (MIT) | 5.48 Fl. oz/Ac or 400 mL/Ha + 2.05 Fl. oz/Ac or 150 mL/Ha |
| Composition 20 | FOX Fungicide + Gm.RHPP (SEQ ID NO: 600) 100 μM PROXEL BC preservative: 330.7 μM; 50.1 μM (CMIT); 21.71 μM (MIT) | 5.48 Fl. oz/Ac or 400 mL/Ha + 300 mL/Ha |

* Foliar compositions contained 0.1% (v/v) PROXEL BC preservative, an aqueous dispersion of a blend of 330.7 mM 1,2-benzisothiazolin (BIT), 53.5 mM 5-chloro-2-methyl-4-isolthiazolin-3-one (CMIT), and 26.1 mM 2-methyl-4-isothiazolin-3-one (MIT). Foliar compositions were applied at the indicated rates (Fl. oz/Ac or mL/Ha) in a carrier volume of 150 L/Ha or 16 gallons/acre water with 0.5% (v/v) AUREO methylated bean oil surfactant (Composition 13) or with 0.33% (v/v) Agris Parrafinic mineral oil (stock concentration of 795 g/L or 79.5% (p/v) (Compositions 13-20).

Replicated field trials were conducted across three locations in Paraguay (Yatytay, Obligado, and Capitan Miranda) using a foliar application comprising a compositions of the Bt.4Q7Flg22 polypeptide and RHPP polypeptide provided with a broad-spectrum fungicide, Fox (16.0% prothioconazole and 13.7% thiofloxystrobin). FOX is a commercially available foliar fungicide in South America with limited efficacy for preventative and curative treatment of Asian soybean rust caused by *Phakopsora pachyrhizi* and *Cercospora* leaf blight of soybean caused by *Cercospora kikuchii* applied as a foliar spray following the recommendations on the specimen label at a use rate of 5.48 fluid ounces per acre (Fl. oz/Ac) (400 mL/hectare). Beginning at the R1 stage of development, soybean plants received two foliar applications of the compositions described in Table 90 with an interval of 13-14 days between spray applications. Foliar treatments were applied to a single soy variety (which one? Same at all 3 sites) at the three sites, with 4 replicated plots (3×10 meters, 30 m2; with minimum of 6 rows per treatment). Disease assessments for trials that were naturally infected were scored for the severity of infection (0-100% of foliage affected) were scored for 10 plants within each plot for both Asian soybean rust caused by *Phakopsora pachyrhizi* and *Cercospora* leaf blight of soybean caused by *Cercospora kikuchii* at the R4-R5 stage of soy development (4-15 days after second foliar application) with guidance from Godoy et al (1997; Journal of plant diseases and protection 104:336-345). Percent phytotoxicity (0-100% of foliage affected) was also scored at the R4-R5 stage of soy development. Severity of infection and phytotoxicity were averaged across all four replicates per site (Total=12 replicates, 3 sites with 4 replicates each). Standard deviation for each treatment between the three sites was calculated. Untreated control plants at the Yatytay site displayed 99% defoliation at 11 days post-application of the second foliar treatment and were scored for defoliation (0-100% defoliated) at this time. Disease severity, phytotoxicity, and defoliation results are provided in Table 91 as percentages, with standard deviation in parentheses.

TABLE 91

Incidence of Asian Soybean Rust disease symptoms after foliar application of fungicide and polypeptide compositions in Paraguay

| Foliar Formulation | Application Use Rate Fluid ounce/acre (Fl. oz/Ac) Milliliters/hectare (mL/Ha) | Incidence of Asian Soybean Rust symptoms after 2 foliar applications (% of foliage affected); N = 12 reps per treatment | Change in Asian Soybean Rust symptoms, relative to control (%); N = 12 reps per treatment | Defoliation (% of foliage) after 2 foliar applications (Yatytay only; N = 4 reps per treatment) |
|---|---|---|---|---|
| Untreated Control | n/a | 35.1% (±13.8%) | — | 99% |
| FOX Fungicide (Composition 12) | 5.48 Fl. oz/Ac or 400 mL/Ha | 19.4% (±10.3%) (−15.7%) | −15.7% | 45% |
| Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 13) | 2.05 Fl. oz/Ac or 150 mL/Ha | 22.7% (±14.4%) | −12.4% | 70% |
| Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 14) | 4.11 Fl. oz/Ac or 300 mL/Ha | 22.1% (±14.6%) | −13.0% | 60% |
| Gm.RHPP (SEQ ID NO: 600) 100 μM PROXEL BC preservative: 330.7 μM; 50.1 μM (CMIT); 21.71 μM (MIT) (Composition 15) | 2.05 Fl. oz/Ac or 150 mL/Ha | 24.6% (±13.4%) | −10.5% | 96% |
| Gm.RHPP (SEQ ID NO: 600) 100 μM PROXEL BC preservative: 330.7 μM; 50.1 μM (CMIT); 21.71 μM (MIT) (Composition 16) | 4.11 Fl. oz/Ac or 300 mL/Ha | 23.8% (±11.5%) | −11.3% | 70% |

TABLE 91-continued

Incidence of Asian Soybean Rust disease symptoms after foliar application of fungicide and polypeptide compositions in Paraguay

| Foliar Formulation | Application Use Rate Fluid ounce/acre (Fl. oz/Ac) Milliliters/hectare (mL/Ha) | Incidence of Asian Soybean Rust symptoms after 2 foliar applications (% of foliage affected); N = 12 reps per treatment | Change in Asian Soybean Rust symptoms, relative to control (%); N = 12 reps per treatment | Defoliation (% of foliage) after 2 foliar applications (Yatytay only; N = 4 reps per treatment) |
|---|---|---|---|---|
| FOX Fungicide + Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 17) | 5.48 Fl. oz/Ac or 400 mL/Ha + 2.05 Fl. oz/Ac or 150 mL/Ha | 9.3% (±3.9%) | −25.8% | 25% |
| FOX Fungicide + Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 18) | 5.48 Fl. oz/Ac or 400 mL/Ha + 4.11 Fl. oz/Ac or 300 mL/Ha | 8.0% (±5.1%) | −27.1% | 25% |
| FOX Fungicide + Gm.RHPP (SEQ ID NO: 600) 100 μM PROXEL BC preservative: 330.7 μM; 50.1 μM (CMIT); 21.71 μM (MIT) (Composition 19) | 5.48 Fl. oz/Ac or 400 mL/Ha 2.05 Fl. oz/Ac or 150 mL/Ha | 8.3% (±5.8%) | −26.8% | 25% |
| FOX Fungicide + Gm.RHPP (SEQ ID NO: 600) 100 μM PROXEL BC preservative: 330.7 μM; 50.1 μM (CMIT); 21.71 μM (MIT) (Composition 20) | 5.48 Fl. oz/Ac or 400 mL/Ha 300 mL/Ha | 11.0% (±3.3%) | −24.1% | 25% |

TABLE 92

Incidence of *Cercospora* leaf blight symptoms after foliar application of fungicide and polypeptide compositions in Paraguay

| Foliar Formulation | Application Use Rate Fluid ounce/acre (Fl. oz/Ac) Milliliters/hectare (mL/Ha) | Incidence of *Cercospora* symptoms after 2 foliar applications, (% of foliar affected). N = 12 reps per treatment | Change in *Cercospora* symptoms, relative to control (%); N = 12 reps per treatment |
|---|---|---|---|
| Untreated Control | n/a | 19.3% (±5.1%) | — |
| FOX Fungicide (Composition 12) | 5.48 Fl. oz/Ac or 400 mL/Ha | 15.0% (±9.6%) | −4.3% |
| Bt.4Q7Flg22 (SEQ ID NO: 226) 16.7 μM 1.67 mM Sodium Phosphate Buffer, pH 5.7 PROXELBC preservative: 330.7 μM (BIT); 53.5 μM (CMIT); 26.1 μM (MIT) (Composition 13) | 2.05 Fl. oz/Ac or 150 mL/Ha | 16.4% (±7.7%) | −2.8% |
| Bt.4Q7Flg22 (SEQ ID NO: 226) 16.7 μM 1.67 mM Sodium Phosphate Buffer, pH 5.7 PROXELBC preservative: 330.7 μM (BIT); 53.5 μM (CMIT); 26.1 μM (MIT) (Composition 14) | 4.11 Fl. oz/Ac or 300 mL/Ha | 15.8% (±6.3%) | −3.5% |
| Gm.RHPP (SEQ ID NO: 600) 100 μM PROXELBC preservative: 330.7 μM; 50.1 μM (CMIT); 21.71 μM (MIT) (Composition 15) | 2.05 Fl. oz/Ac or 150 mL/Ha | 15.9% (±6.9%) | −3.3% |
| Gm.RHPP (SEQ ID NO: 600) 100 μM PROXELBC preservative: 330.7 μM; 50.1 μM (CMIT); 21.71 μM (MIT) (Composition 16) | 4.11 Fl. oz/Ac or 300 mL/Ha | 14.8% (±5.3%) | −4.5% |
| FOX Fungicide + Bt.4Q7Flg22 (SEQ ID NO: 226) 16.7 μM 1.67 mM Sodium Phosphate Buffer, pH 5.7 PROXELBC preservative: 330.7 μM (BIT); 53.5 μM (CMIT); 26.1 μM (MIT) (Composition 17) | 5.48 Fl. oz/Ac or 400 mL/Ha + 2.05 Fl. oz/Ac or 150 mL/Ha | 10.6% (±3.9%) | −8.7% |
| FOX Fungicide + Bt.4Q7Flg22 (SEQ ID NO: 226) 16.7 μM 1.67 mM Sodium Phosphate Buffer, pH 5.7 PROXELBC preservative: 330.7 μM (BIT); 53.5 μM (CMIT); 26.1 μM (MIT) (Composition 18) | 5.48 Fl. oz/Ac or 400 mL/Ha + 4.11 Fl. oz/Ac or 300 mL/Ha | 10.6% (±4.4%) | −9.2% |
| FOX Fungicide + Gm.RHPP (SEQ ID NO: 600) 100 μM PROXEL BC preservative: 330.7 μM; 50.1 μM (CMIT); 21.71 μM (MIT) (Composition 19) | 5.48 Fl. oz/Ac or 400 mL/Ha + 2.05 Fl. oz/Ac or 150 mL/Ha | 11.3% (±4.2%) | −8.0% |
| FOX Fungicide + Gm.RHPP (SEQ ID NO: 600) 100 μM PROXEL BC preservative: 330.7 μM; 50.1 μM (CMIT); 21.71 μM (MIT) (Composition 20) | 5.48 Fl. oz/Ac or 400 mL/Ha + 300 mL/Ha | 11.3% (±4.2%) | −8.0% |

TABLE 93

Phytotoxicity after foliar application of fungicide and polypeptide compositions in Paraguay

| Foliar Formulation | Application Use Rate Fluid ounce/acre (Fl. oz/Ac) Milliliters/hectare (mL/Ha) | Phytotoxicity (% of foliage affected) after 2 foliar applications; N = 12 reps per treatment |
|---|---|---|
| Untreated Control | n/a | 0.00% (±0.00%) |
| FOX Fungicide (Composition 12) | 5.48 Fl. oz/Ac or 400 mL/Ha | 2.25% (±32.9%) |
| Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 13) | 2.05 Fl. oz/Ac or 150 mL/Ha | 0.00% (±0.00%) |
| Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 14) | 4.11 Fl. oz/Ac or 300 mL/Ha | 0.00% (±0.00%) |
| Gm.RHPP (SEQ ID NO: 600) 100 μM PROXEL BC preservative: 330.7 μM; 50.1 μM (CMIT); 21.71 μM (MIT) (Composition 15) | 2.05 Fl. oz/Ac or 150 mL/Ha | 0.00% (±0.00%) |
| Gm.RHPP (SEQ ID NO: 600) 100 μM PROXEL BC preservative: 330.7 μM; 50.1 μM (CMIT); 21.71 μM (MIT) (Composition 16) | 4.11 Fl. oz/Ac or 300 mL/Ha | 0.00% (±0.00%) |
| FOX Fungicide + Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 17) | 5.48 Fl. oz/Ac or 400 mL/Ha + 2.05 Fl. oz/Ac or 150 mL/Ha | 2.33% (±0.14%) |
| FOX Fungicide + Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 18) | 5.48 Fl. oz/Ac or 400 mL/Ha + 4.11 Fl. oz/Ac or 300 mL/Ha | 2.25% (±0.25%) |
| FOX Fungicide + Gm.RHPP (SEQ ID NO: 600) 100 μM PROXEL BC preservative: 330.7 μM; 50.1 μM (CMIT); 21.71 μM (MIT) (Composition 19) | 5.48 Fl. oz/Ac or 400 mL/Ha + 2.05 Fl. oz/Ac or 150 mL/Ha | 2.42% (±0.29%) |
| FOX Fungicide + Gm.RHPP (SEQ ID NO: 600) 100 μM PROXEL BC preservative: 330.7 μM; 50.1 μM (CMIT); 21.71 μM (MIT) (Composition 20) | 5.48 Fl. oz/Ac or 400 mL/Ha + 300 mL/Ha | 2.17% (±0.29%) |

Foliar application of Bt.4Q7Flg22 and Gm.RHPP during reproductive phases of soy development provided increased protection against Asian soybean rust and *Cercospora* leaf blight as compared to the untreated control. Foliar applications of Bt.4Q7Flg22-treated plants at 150 and 300 mL/Ha displayed 12.4-13.0% less Asian soybean rust leaf area damage and 2.8-3.5% less *Cercospora* leaf area damage compared to the untreated control; and foliar applications of Gm.RHPP-treated plants at 150 and 300 mL/Ha displayed 10.5-11.3% less Asian soybean rust leaf area damage and 3.3-4.5% less *Cercospora* leaf area damage compared to the untreated control. Combination treatments including either Bt.4Q7Flg22 or RHPP with FOX fungicide increased protection against Asian Soybean Rust and *Cercospora* relative to the Fox Fungicide treatment alone. At the Yatytay site, less defoliation was observed at the R7 stage of development due to severe disease symptoms upon Bt.4Q7Flg22 or Gm.RHPP treatments+/−FOX fungicide. While the untreated control was 99% defoliated at this stage, Bt.4Q7Flg22 treatment at 150 or 300 mL/Ha decreased defoliation to 70 or 60% with green leaves still visible, respectively. The Gm.RHPP treatment at 150 or 300 mL/Ha decreased defoliation to 96% or 70%, respectively. Combination treatment with Bt.4Q7Flg22 or Gm.RHPP treatments with FOX fungicide decreased defoliation to 25% with green leaves visible, while Fox fungicide alone decreased defoliation to only 45% without green leaves visible. Overall, polypeptide treatments provided increased protection over FOX Fungicide alone for control of Asian soybean rust and *Cercospora* leaf blight. No phytotoxicity was observed for any polypeptide application alone, and combination of either polypeptide with FOX fungicide neither significantly increased or decreased phytotoxicity relative to the FOX Fungicide alone (Table 93).

Example 54. Flg22-PSA Foliar Application on Kiwi Protects Plants from *Pseudomonas syringae* pv. *actinidiae* (PSA-V)

*Pseudomonas syringae* pv. *actinidiae* (PSA) is a devastating plant pathogen causing bacterial canker of both green- (*Actinidiae deliciosa*) and yellow-flesh (*Actinidiae chinesis*) kiwi plants throughout zones of kiwi production, causing severe harvest loss in New Zealand, China, and Italy. In New Zealand alone, cumulative revenue losses to the most devastating biovar PSA-V are predicted to approach $740 million New Zealand leaves Dollars (NZD) by 2025 (Agribusiness and Economics Research Institute of Lincoln University "The Costs of Psa-V to the New Zealand Kiwifruit Industry and the Wider Community"; May 2012). PSA-V colonizes the outer and inner surfaces of the kiwi plant and can spread through the xylem and phloem tissues. Disease symptoms of PSA-V on kiwi include bacterial leaf spot, bacterial canker of the trunk, red exudates, blossom rot, discoloration of twigs, and ultimately dieback of kiwi vines. The standard method of control for PSA-V currently employs frequent foliar applications of metallic copper to kiwi vines which is predicted to lead to the selection of copper-resistant form of the pathogen and loss of disease control. Novel methods of control are urgently needed.

To test the sensitivity of kiwi leaves to 22-amino acid fragments of flagellin, 1 mm slices were cut through *Actinidiae deliciosa* Kiwi 'Hayward' leaf petioles and floated in 150 μL of water in a 96-well plate, with one slice per well. Flg22 polypeptides in Table 94 were prepared for the assay by re-suspending lyophilized polypeptide in deionized water to a concentration of 10 mM; peptides were then serially diluted to 10 μM in 100 mM sodium phosphate (pH 7.8-8.0) buffer with 0.1% Tween-20. Water was removed from kiwi leaf petiole samples after 20 hours and replaced with 100 μL of an elicitation solution containing 100 nM peptide (diluted from 10 μM stock), 34 μg/mL luminol, and 20 μg/mL horseradish peroxidase in deionized water. Recognition of the Flg22 polypeptide by the plant tissue resulted in activation of immune signaling and the production of apoplastic reactive oxygen species (ROS). In the presence of ROS (H2O2), horseradish peroxidase catalyzed the oxidation of luminol and production of visible light. Relative light units (RLUs) were recorded with a SpectraMax L luminometer (0.5 s integration; 2.0 min intervals) over a time course of 40 minutes. In two independent experiments, a total of 6 kiwi leaf petiole samples were treated with each Flg22 polypeptide in Table 94. The average total RLU and standard error of the means (SEM) was calculated for each treatment. A two-tailed T-test was used to determine significance at the 90% confidence level (P<0.1) between treatments. Relative ROS production was determined for each polypeptide in comparison to total RLUs for the 100 nM Bt.4Q7Flg22 control.

TABLE 94

Kiwi leaf petioles are most sensitive to Flg22-PSA

| Treatment | Average Total Relative Light Units (RLUs); SEM in parentheses | P-value compared to 100 nM Bt.4Q7Flg22 | ROS production relative to Bt4Q7Flg22 (%) |
|---|---|---|---|
| 100 nM Bt.4Q7Flg22- (SEQ ID NO: 226) | 47,457 (±12,900) | n/a | 100% |
| 100 nM Syn01Flg22 (SEQ ID: 571) | 81,848 (±27,631) | p = 0.286 | 172% |
| 100 nM Flg22-PSA (SEQ ID: 540) | 124,550 (±33,555) | p = 0.058* | 262% |

*Significant difference at the 90% confidence level

Across two independent experiments Kiwi 'Hayward' leaf petioles were significantly more sensitive to Flg22 derived from *Pseudomonas syringae* pv. *actinidiae* (Flg22-PSA; SEQ ID NO:540) in comparison to Flg22 derived from *Bacillus thuringiensis* strain 4Q7 (Bt.4Q7Flg22; SEQ ID NO: 226). While ROS production was increased in kiwi leaf petioles in response to the synthetic Syn01Flg22 (SEQ ID NO: 571) in comparison to Bt.4Q7 Flg22 (SEQ ID NO: 226) the difference was not significant. Based on these results, Flg22-PSA (SEQ ID NO: 540) was formulated as indicated at 100 nM final concentration (Table 94) for disease prevention trials in potted Kiwi 'Hayward' plants in New Zealand.

TABLE 95

Treatments applied to potted kiwi trial

| Composition | Foliar Formulation | Product dilution for spray application Milliliters product/Liter water (mL/L) or Grams product/Liter water (g/L) |
|---|---|---|
| Composition 21 | ChampION++ ™ (46.1% Copper Hydroxide; 30% metallic copper equivalent) | 0.9 g ChampION++ ™/ L water |
| Composition 22 | Flg22-PSA (SEQ ID NO: 540) 100 μM<br>10 mM Sodium Phosphate Buffer, pH 5.7<br>PROXEL BC preservative: 330.7 μM (BIT); 53.5 μM (CMIT); 26.1 μM (MIT) | 4 mL/L water |

Foliar compositions contained 0.1% (v/v) PROXEL BC preservative, an aqueous dispersion of a blend of 330.7 mM 1,2-benzisothiazolin (BIT), 53.5 mM 5-chloro-2-methyl-4-isolthiazolin-3-one (CMIT), and 26.1 mM 2-methyl-4-isothiazolin-3-one (MIT). Foliar compositions were diluted to the indicated concentrations in water (g/L water or mL/L water) with 0.05% (v/v) Contact Xcel™ non-ionic surfactant. The diluted products were applied in fine droplets with a pressurized backpack sprayer to the entire canopy of each plant, until thoroughly covered.

To assess the efficacy of Flg22-PSA (SEQ ID NO: 540) for control of *Pseudomonas syringae* pv. *actinidiae* (PSA-V), a potted kiwi disease trial was conducted in the Bay of Plenty area of New Zealand by HortEvaluation Ltd in collaboration with NuFarm Limited. PSA-V symptom-free potted kiwi *Actinidiae deliciosa* 'Hayward' plants were evenly distributed between the 6 treatment groups, with 12 potted plants per group. One day prior to inoculation with PSA-V, potted plants were treated with ChampION++TM, the industry standard for PSA-V control, or formulated Flg22-PSA according to the application rates in Table 96 (Treatment groups 3,4) at a plant nursery in Te Puka, New Zealand. After 24 hours, all plants except for the uninfected controls were sprayed with 1×108 cfu/mL PSA-V inoculum using a 5L hand-held pressurized sprayer aimed at the underside of leaves until thoroughly covered. The uninfected control was sprayed with water alone. Potted plants were then transported to Pukehina and placed in an area with overhead misting for 48 hours to mimic environmental conditions for PSA-V infection, with uninfected control plants separated from infected plants. After 48 hours, a subset of plants was then removed from the misting area and allowed to briefly dry. After the final treatments, all plants were moved to their final outdoor trial site, randomized positions in Pukehina. Average daily temperature at the trial site was 20.75° C. with a total rainfall of 277 mm over 34 days. Additionally, each plant was watered twice a day for two hours at a time by drip irrigation. Environmental conditions were favorable for progression of PSA-V disease symptoms. Plants were visually monitored throughout the trial period for PSA-V disease assessments, with the same assessor recording the % of leaf area covered in spots at 6 days after inoculation (6 DAI), 16 DAI, 23 DAI and 29 DAI. Additionally, each plant was assessed for treatment phytotoxicity effects at 29 DAI on a scale of 0-10, with 0=no leaf phytotoxicity and 10=very severe leaf phytotoxicity symptoms. The average disease scores at 6, 16, 23, and 29 DAI and phytotoxicity score at 29 DAI are reported in Table 96 for each treatment (n=12 plants per treatment). P-values were calculated for each treatment vs. the untreated control.

TABLE 96

Flg22-PSA foliar application reduces PSA-V disease symptoms in kiwi plants

| Treatment group #/ Foliar Formulation | Application Rate and Timing | Foliage Affected (% leaf surface area); p-values vs. untreated control 6 DAI | 16 DAI | 23 DAI | 29 DAI |
|---|---|---|---|---|---|
| Treatment group 1 Uninfected plants | n/a | 0.00% | 1.66% | 7.89% | 18.14% |
| Treatment group 2 Untreated Control | n/a | 15.12% | 40.36% | 54.64% | 67.82% |
| Treatment group 3 ChampION++ ™ (Composition 21) | 0.9 g/L; One day pre-inoculation | 3.23% ($p < 0.001$) | 12.48% ($p < 0.001$) | 16.57% ($p < 0.001$) | 25.20% ($p < 0.001$) |
| Treatment group 4 Flg22-PSA (Composition 22) | 4 mL/L; One day pre-inoculation | 7.31% ($p < 0.001$) | 29.41% ($p = 0.013$) | 45.97% ($p = 0.085$) | 61.91% ($p = 0.190$) |

Application of Flg22-PSA significantly reduced PSA-V leaf spot symptoms (P<0.1; 90% confidence interval) at 6, 16 and 23 DAI in comparison to the untreated control. Combination of Flg22-PSA pre-treatment further decreased the severity of leaf spot compared to Flg22-PSA treatment alone at all assessment timepoints and prolongs the period of significant protection to 29 DAI (14.3% less leaf spot compared to untreated control; P=0.002). In conclusion, Flg22-PSA can be used both as a stand-alone treatment and in combination with other treatments aimed at restricting pathogen growth. While the industry standard ChampION++TM which is the currently used copper containing treatment to treat PSA causes mild leaf phytotoxicity (AVE score=1.6), no significant phytotoxicity was observed for Treatments 3-4 (Table 97). Flg22-PSA can be used as an alternative to other phytotoxic treatments.

TABLE 97

FLG22-PSA foliar application does not cause leaf phytotoxicity of kiwi plants

| Treatment group #/Foliar Formulation | Application Rate and Timing | Average Phytotoxicity Score (0-10); 29 DAI |
|---|---|---|
| Treatment group 1 Uninfected plants | n/a | 0.0 (±0.0) |
| Treatment group 2 Untreated Control | n/a | 0.0 (±0.0) |
| Treatment group 3 ChampION++ ™ (Composition 21) | 0.9 g/L; One day pre-inoculation | 1.6 (±0.9) |
| Treatment group 4 Flg22-PSA (Composition 22) | 4 mL/L; One day pre-inoculation | 0.1 (±0.3) |

Example 55: Polypeptides Derived from Elongation Factor Tu

Elf18 and Elf26 polypeptides derived from the consensus *Bacillus cereus* Elongation Factor-TU (EF-Tu) protein were tested for ability to produce a ROS response in corn (hybrid 5828 YX), soy (variety Morsoy), and *Arabidopsis thaliana*. Polypeptides were synthesized by Genscript USA (Piscataway, N.J.) using standard solid-phase synthesis methods and provided as a lyophilized powder with greater than or equal to 70% purity. Dry powder was re-suspended to a concentration of 10 mM in ultrapure water, and then serially diluted in ultrapure water to the concentrations tested in the ROS assay in Table 98.

For the ROS assay, *Arabidopsis* leaves were excised from 4-week-old plants, and using a cork borer 4 mm disks were removed from the leaves. Each disc was cut in half using the edge of a razor blade, and then each disc half was floated on 150 μL of water abaxial side touching the water in a 96-well plate to rest overnight. The next day, the water was removed from each well just prior to polypeptide treatment. RLU values and relative ROS activity was reported as the average of 4 measurements. ROS activity assays were conducted using the methods as previously reported in Example 15). ROS activity results are reported in Table 97 below.

TABLE 98

Elf18 and Elf26 Polypeptides from *Bacillus cereus*

| EF-Tu Polypeptide Description | Amino Acid Length | Sequence |
|---|---|---|
| N terminus of EF Tu (modified) *Bacillus cereus* (SEQ ID NO: 616) | 18 | Ac-AKAKFERSKPHVNIGTIG-conh2 |
| N terminus of EF Tu (modified) *Bacillus cereus* (SEQ ID NO: 617) | 26 | Ac-AKAKFERSKPHVNIGTIGH VDHGKTT-conh2 |

TABLE 99

Comparison of ROS activity of elf18 and elf26 polypeptides in *Arabidopsis* leaf tissue

| Polypeptide Treatment | Average RLU value (Fold increase (X) over mock treatment) |
|---|---|
| Negative control (water) | 82896 (1 X) |
| N terminus of EF Tu (100 nM) (SEQ ID NO: 616) | 264194 (3.2 X) |
| N terminus of EF Tu (100 nM) (SEQ ID NO: 617) | 211383 (2.5 X) |
| Bt.4Q7Flg22 (100 nM) (SEQ ID NO: 226) | 258073 (3.1 X) |
| N terminus of EF Tu (100 nM) (SEQ ID NO: 616) + Bt.4Q7Flg22 (100 nM) (SEQ ID NO: 226) | 254344 (3.1 X) |
| N terminus of EF Tu (100 nM) (SEQ ID NO: 617) + Bt.4Q7Flg22 (100 nM)(SEQ ID NO: 226) | 181504 (2.2 X) |

The receptor for EF-Tu polypeptides, EF-Tu Receptor (EFR) was previously identified in the *Brassica* clade, of which *Arabidsopis thaliana* is a model plant. Results in Table 99 indicate that newly identified polypeptides from *Bacillus cereus* EF-Tu (SEQ ID NO: 616 and SEQ ID NO: 617) can be used to elicit a ROS response similar in magnitude to Bt.4Q7Flg22 (SEQ ID NO: 226) when each was tested at a 100 nM concentration. In comparison to the mock-treated control, EF-Tu N-terminal polypeptides gave a response that was 3.2- to 2.5-fold increased, while Bt.4Q7Flg22 was 3.1-fold increased over mock control. These results suggest that 18- and 26-amino acid fragments from the N-terminus of *Bacillus cereus* can be used similarly to Bt.4Q7Flg22 in the *Brassica* crops, including but not limited to kale, cabbage, collard greens, cauliflower, Brussel sprouts, savoy, kohlrabi and gai Ian, to increase plant biomass, yield and disease prevention.

Combination treatments of EF-Tu N-terminal peptides (SEQ ID NO: 616 and SEQ ID NO: 617) and Bt.4Q7Flg22 (SEQ ID NO: 226) resulted in similar ROS responses to the EF-Tu peptides alone, indicating that the combination of peptides treatments in the field would provide no interference of activity; however, due to the shared mechanisms between downstream signaling events for EF-Tu and Flg22 peptides, recognized by the EFR and FLS2 receptors respectively, a staggered application of peptide treatments may provide the greatest growth benefit to the plant.

Example 56: Disease Protection Using Bt.4Q7Flg22 and Gm.RHPP Foliar Applications on Soybean Plants to Protect from Diseases Caused by *Phakopsora pachyrhizi* and *Cercospora kikuchii*

Foliar application of Bt.4Q7Flg22 (SEQ ID NO: 226) and Gm.RHPP (SEQ ID NO: 600) during reproductive phases of soy development was previously found to decrease disease symptoms caused by *Phakopsora pachyrhizi* and *Cercospora kikuchii* infections (Example 53). These plants were taken to yield, and Bt.4Q7Flg22 (SEQ ID NO: 226) and Gm.RHPP (SEQ ID NO: 600) foliar applications were found to increase yield in comparison to the untreated control plants in replicated trials in Paraguay where plants were infected with Asian soybean rust and *Cercospora* leaf blight. Foliar applications of Bt.4Q7Flg22 at 150 and 300 mL/Ha increased yield by +342.2 kg/Ha and +427.2 kg/Ha, respectively, in trials where the average yield for untreated plants was 1266.3 Kg/Ha. The increase in yield for 300 mL/Ha foliar application of Bt.4Q7Flg22 (36.1%) was comparable to FOX Fungicide alone (36.6%), demonstrating that Bt.4Q7Flg22 is effective as an anti-fungal foliar treatment for both reducing disease symptoms and boosting yield. The relative yield across all three trial sites was for plants treated with a combined application of FOX Fungicide and Bt.4Q7Flg22 was slightly increased over FOX fungicide or Bt.4Q7Flg22 foliar application alone, demonstrating that the treatments are compatible. Foliar applications of Gm.RHPP at 150 and 300 mL/Ha further increased yield by +294.2 kg/Ha and 506.8 kg/Ha, respectively, in comparison to the untreated control. When applied in combination with FOX Fungicide, Gm.RHPP provided the greatest protection against disease in the trials as evidenced by increased yield of +517.6 kg/Ha and +539.9 kg/Ha for the 150 mL/Ha and 300 mL/Ha application rates of Gm.RHPP, respectively. Foliar application of Gm.RHPP consistently improved plant health and increased yield, thus Gm.RHPP is an effective treatment for growth promotion and fungal disease resistance.

TABLE 100

Soybean yield for replicated field trials infected with *Phakopsora pachyrhizi* and *Cercospora kikuchii* where plants were treated with Bt.4Q7Flg22 or RHPP

| Foliar Formulation | Application Use Rate Fluid ounce/ acre (Fl. oz/Ac) Milliliters/ hectare (mL/Ha) | Average change in yield in comparison to Untreated Control [1266.3 Kilograms/ Hectare (Kg/Ha)]; N = 12 reps per treatment | Yield relative to Untreated Control (%); N = 12 reps per treatment |
|---|---|---|---|
| Untreated Control | n/a | — | 100% |
| FOX Fungicide (Composition 12) | 5.48 Fl. oz/Ac or 400 mL/Ha | +445.6 kg/Ha | 136.6% |
| Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 13) | 2.05 Fl. oz/Ac or 150 mL/Ha | +342.2 kg/Ha | 130.7% |
| Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 14) | 4.11 Fl. oz/Ac or 300 mL/Ha | +427.2 kg/Ha | 136.1% |
| Gm.RHPP (SEQ ID NO: 600) 100 μM PROXEL BC preservative: 330.7 μM; 50.1 μM (CMIT); 21.71 μM (MIT) (Composition 15) | 2.05 Fl. oz/Ac or 150 mL/Ha | +294.2 kg/Ha | 125.5% |
| Gm.RHPP (SEQ ID NO: 600) 100 μM PROXEL BC preservative: 330.7 μM; 50.1 μM (CMIT); 21.71 μM (MIT) (Composition 16) | 4.11 Fl. oz/Ac or 300 mL/Ha | +506.8 kg/Ha | 143.5% |
| FOX Fungicide + Bt.4Q7Flg22 (SEQ ID NO: 226) 16.7 μM | 5.48 Fl. oz/Ac or 400 mL/Ha + | +426.5 kg/Ha | 138.4% |

TABLE 100-continued

Soybean yield for replicated field trials infected with *Phakopsora pachyrhizi* and *Cercospora kikuchii* where plants were treated with Bt.4Q7Flg22 or RHPP

| Foliar Formulation | Application Use Rate Fluid ounce/ acre (Fl. oz/Ac) Milliliters/ hectare (mL/Ha) | Average change in yield in comparison to Untreated Control [1266.3 Kilograms/ Hectare (Kg/Ha)]; N = 12 reps per treatment | Yield relative to Untreated Control (%); N = 12 reps per treatment |
|---|---|---|---|
| 1.67 mM Sodium Phosphate Buffer, pH 5.7 PROXEL BC preservative: 330.7 μM (BIT); 53.5 μM (CMIT); 26.1 μM (MIT) (Composition 17) | 2.05 Fl. oz/Ac or 150 mL/Ha | | |
| FOX Fungicide + Bt.4Q7Flg22 (SEQ ID NO: 226) 16.7 μM 1.67 mM Sodium Phosphate Buffer, pH 5.7 PROXEL BC preservative: 330.7 μM (BIT); 53.5 μM (CMIT); 26.1 μM (MIT) (Composition 18) | 5.48 Fl. oz/Ac or 400 mL/Ha + 4.11 Fl. oz/Ac or 300 mL/Ha | +418.5 kg/Ha | 137.2% |
| FOX Fungicide + Gm.RHPP (SEQ ID NO: 600) 100 μM PROXEL BC preservative: 330.7 μM; 50.1 μM (CMIT); 21.71 μM (MIT) (Composition 19) | 5.48 Fl. oz/Ac or 400 mL/Ha + 2.05 Fl. oz/Ac or 150 mL/Ha | +517.6 kg/Ha | 145.5% |
| FOX Fungicide + Gm.RHPP (SEQ ID NO: 600) 100 μM PROXEL BC preservative: 330.7 μM; 50.1 μM (CMIT); 21.71 μM (MIT) (Composition 20) | 5.48 Fl. oz/Ac or 400 mL/Ha + 300 mL/Ha | +539.9 kg/Ha | 146.9% |

Example 57. Treatment of Citrus Trees Infected with *Candidatus Liberibacter asiaticus* with Flg22 Increases Fruit Set Previous results summarized in Example 51 indicate that Bt.4Q7Flg22 (SEQ ID NO: 226) trunk injection reduces pathogen titer and promotes new growth in citrus trees infected with *Candidatus Liberibacter asiaticus*, the causative agent of Huanglongbing (HLB). To assess for a potential increase in fruiting and obtain early estimates of yield, fruit set was measured in June 2018 for the same HLB-infected 'Valencia' Orange (to be harvested spring 2019) and 'Ruby Red' Grapefruit trees (to be harvested fall 2018) that were trunk-injected with Bt.4Q7Flg22 in April 2017 at the commercial grove orchard located in central Florida (Okeechobee county). As described in Example 51, trees were injected in April 2017 with either a 1× Bt.4Q7Flg22-Low Rate (0.55 micromoles peptide; 0.138 μM estimated phloem concentration) or a 10× Bt.4Q7Flg22-High Rate (5.5 micromoles peptide; 1.38 μM estimated phloem concentration). In June 2018, the Bt.4Q7Flg22-injected trees were compared to untreated control trees within the same area of the grove using established methods for projecting citrus tree yield ("Forecasting Florida Citrus Production: Methodology & Development; 1971; by S. R. Williams for Florida Crop and Livestock Reporting Service). To quantify fruit set, three quaternary limbs at eye level were randomly chosen on each tree (n=8 trees per treatment 'Valencia' orange, n=10 trees per treatment 'Ruby Red' grapefruit). The circumference of each quaternary limb was measured at the junction where the limb began and used to calculate the cross-sectional area (CSA) of the limb using the following equations (where C=circumference, CSA=cross-sectional area, and r=radius):

$$r = \frac{C}{2\pi} \text{ and } CSA = \pi r^2$$

Then, the total number of fruit on the quaternary limb distal to that junction were counted. To normalize for limb size, fruit set for each quaternary limb was quantified as the number of fruit on the limb divided by the CSA of the quaternary limb:

$$\text{Fruit set} = \frac{\text{Total fruit per limb}}{\text{Limb } CSA}$$

Figure 11:
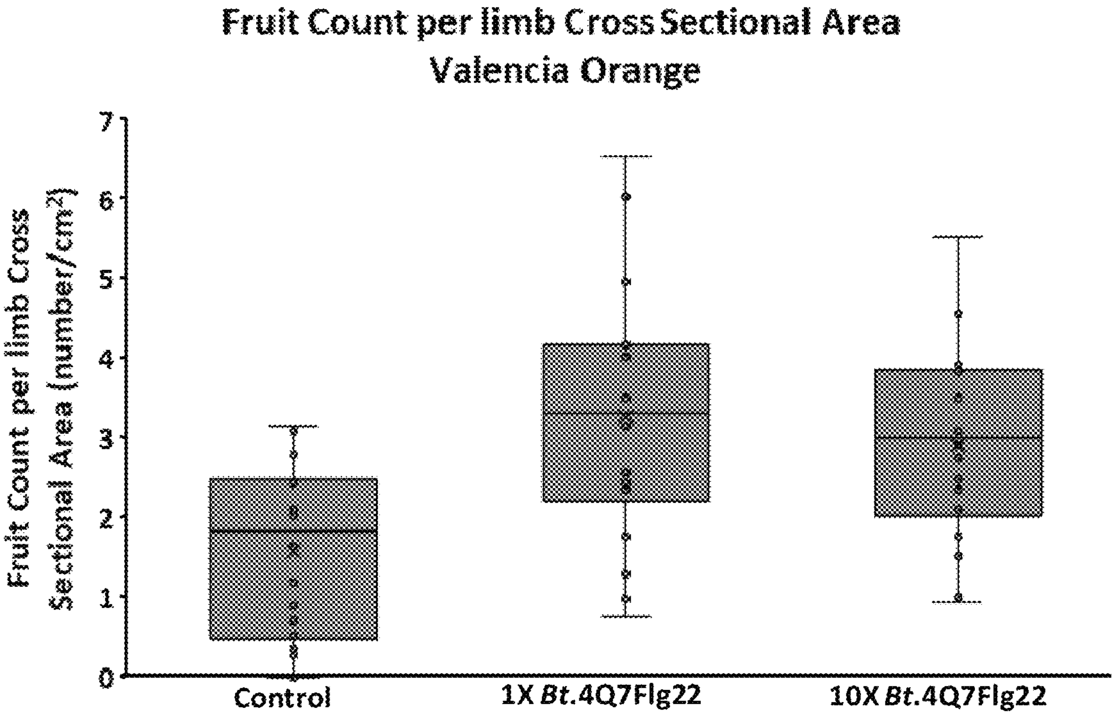
FIG. 11 is directed to 'Valencia' orange trees injected with 1× or 10× Bt.4Q7Flg22 (SEQ ID NO: 226) to increase fruit set per limb.
Figure 12:
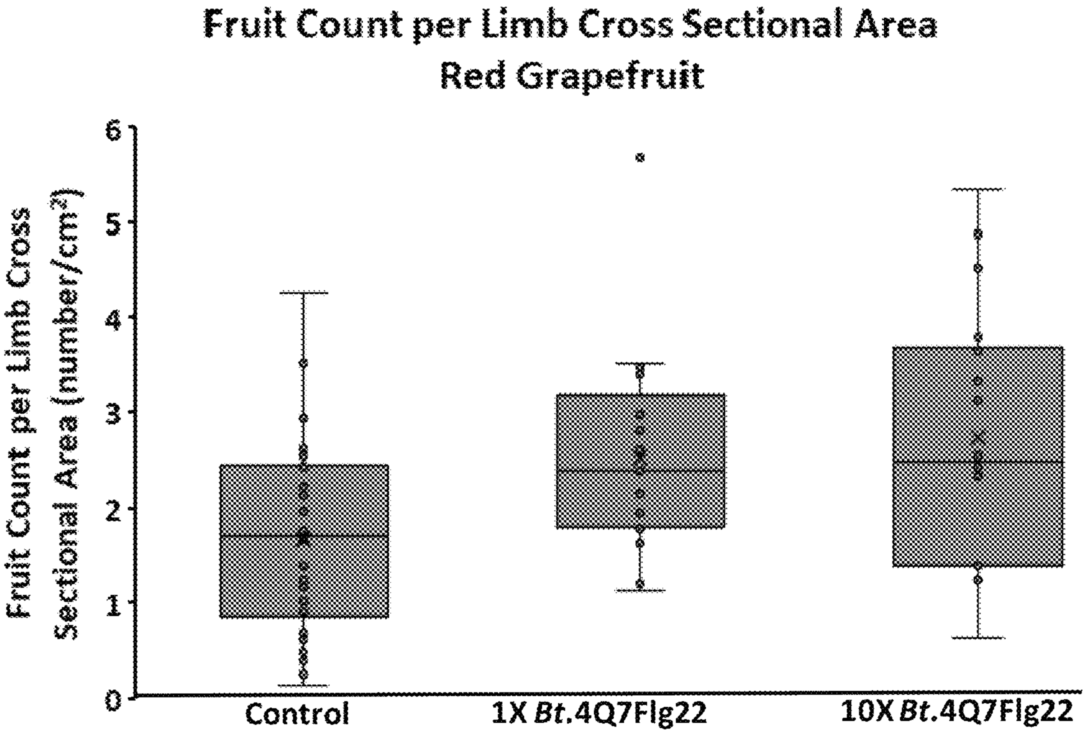
FIG. 12 is directed to 'Valencia' orange trees injected with 1× or 10× Bt.4Q7Flg22 (SEQ ID NO: 226) to increase fruit growth as measured in centimeters.

The fruit count per quaternary limb CSA is reported in FIG. 11 ('Valencia' orange) and FIG. 12 (Red Grapefruit) in box and whisker plots, where the median value for each treatment is marked as the vertical line within the box, the mean or average value is marked by the "x", the upper and lower quartiles are marked by the ends of the box, and the whiskers extend to the highest and lowest observed fruit counts per limb CSA. Any outlier values are indicated by the small circles located outside the standard error bars for each treatment.

Figure 13:
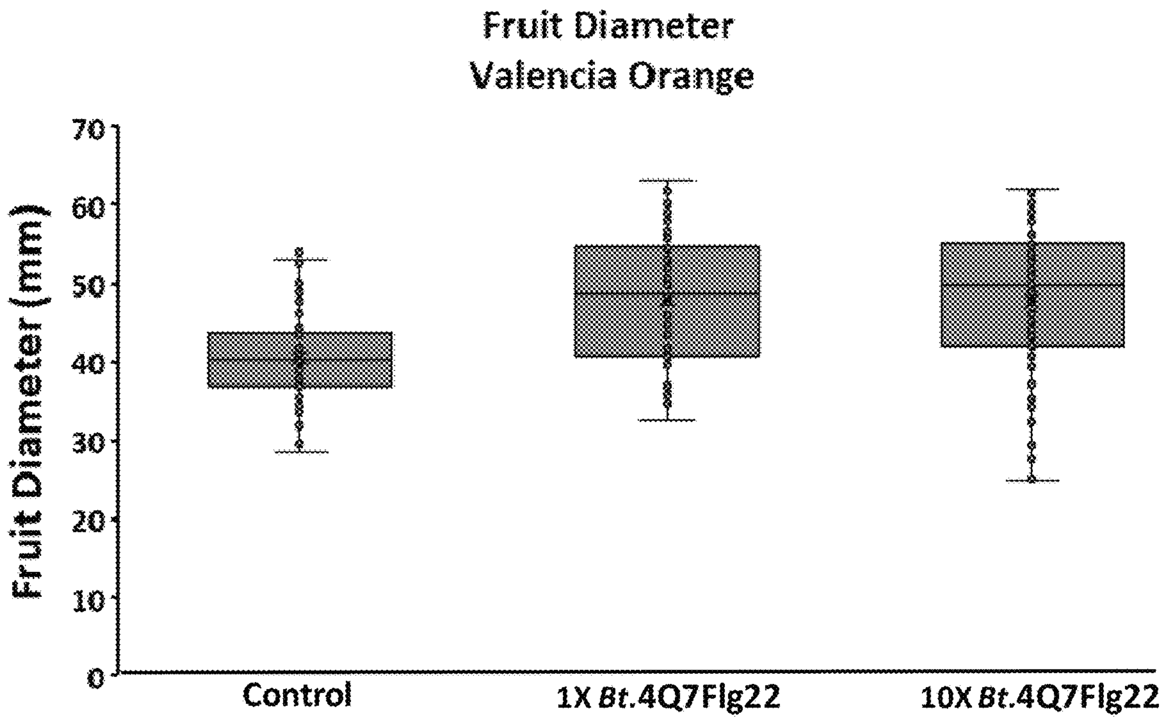
FIG. 13 is directed to 'Valencia' orange trees injected with 1× or 10× Bt.4Q7Flg22 (SEQ ID NO: 226) to increase fruit set as indicated by estimated fruit volume per limb.
Figure 14:
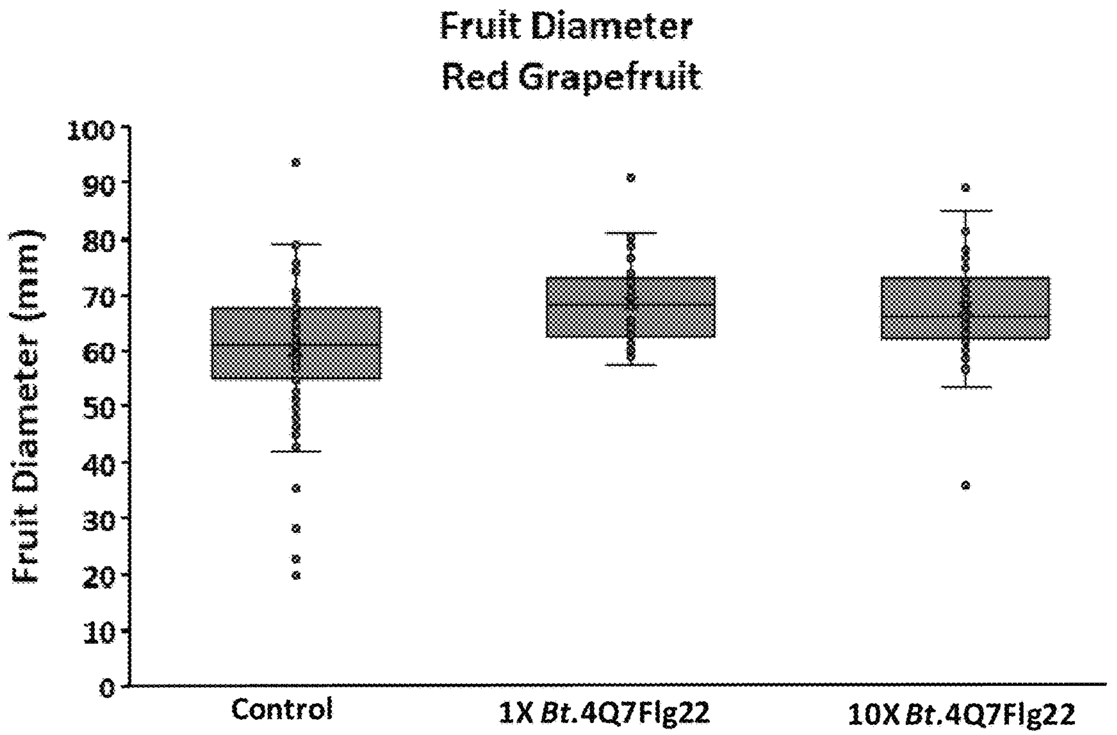
FIG. 14 is directed to 'Ruby Red' grapefruit trees injected with 1× or 10× Bt.4Q7Flg22 (SEQ ID NO: 226) to increase fruit set per limb.

To further assess the size and volume of fruit setting per tree, the fruit diameter (mm) of at least 10 randomly chosen fruit per tree was measured using calipers placed at the widest point on each fruit. The average fruit diameter (mm) per tree for each treatment is reported in FIG. 13 ('Valencia' orange) and FIG. 14 (Red Grapefruit) in box and whisker plots. The average fruit diameter was used to estimate the total fruit volume per limb for each treatment. For these estimates, the volume in milliliters (mL) of a theoretically spherical orange was calculated using the following equation, where the radius (r) of the fruit is the average diameter (measured in mm) per limb divided by 2:

$$\text{Total Fruit Volume per limb (mL)} = \text{Total fruit per limb} * \frac{4}{3}\pi r^3 * \frac{1 \text{ mL}}{1000 \text{ cubic millimeters}}$$

Figure 15:
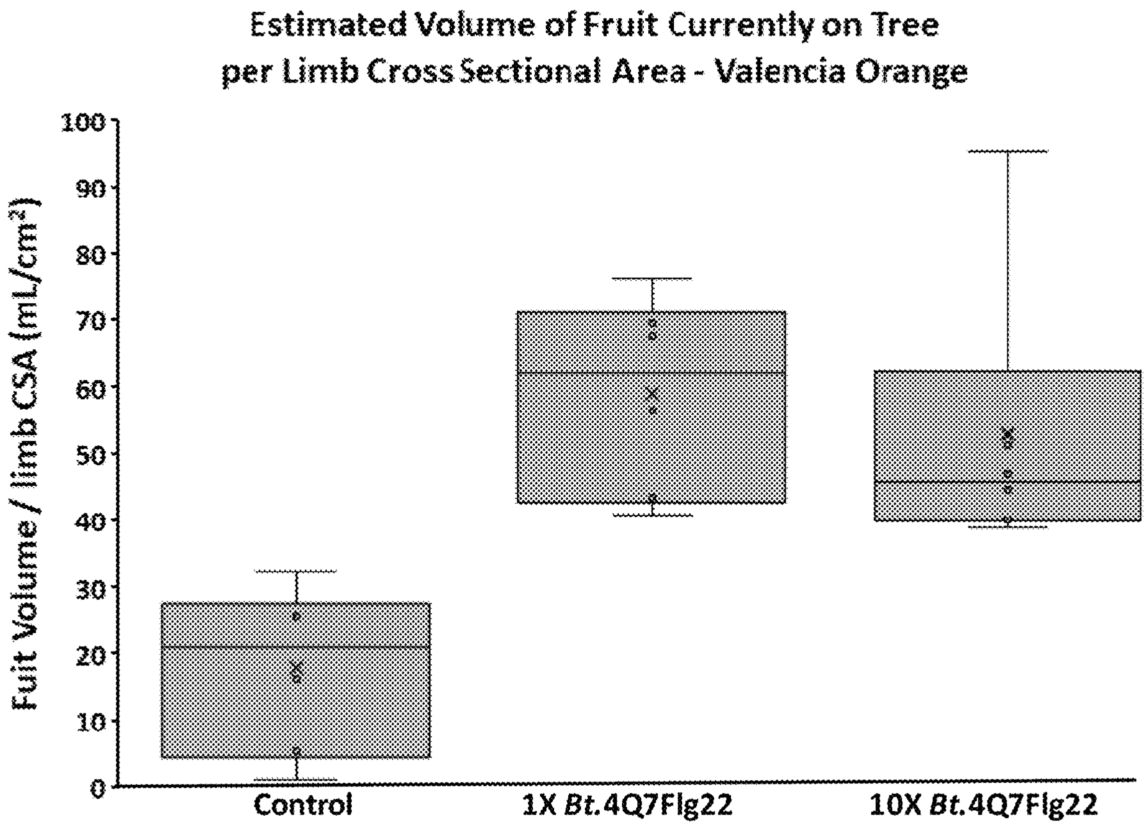
FIG. 15 is directed to 'Ruby Red' grapefruit trees injected with 1× or 10× Bt.4Q7Flg22 (SEQ ID NO: 226) to increase fruit growth as measured in centimeters.
Figure 16:
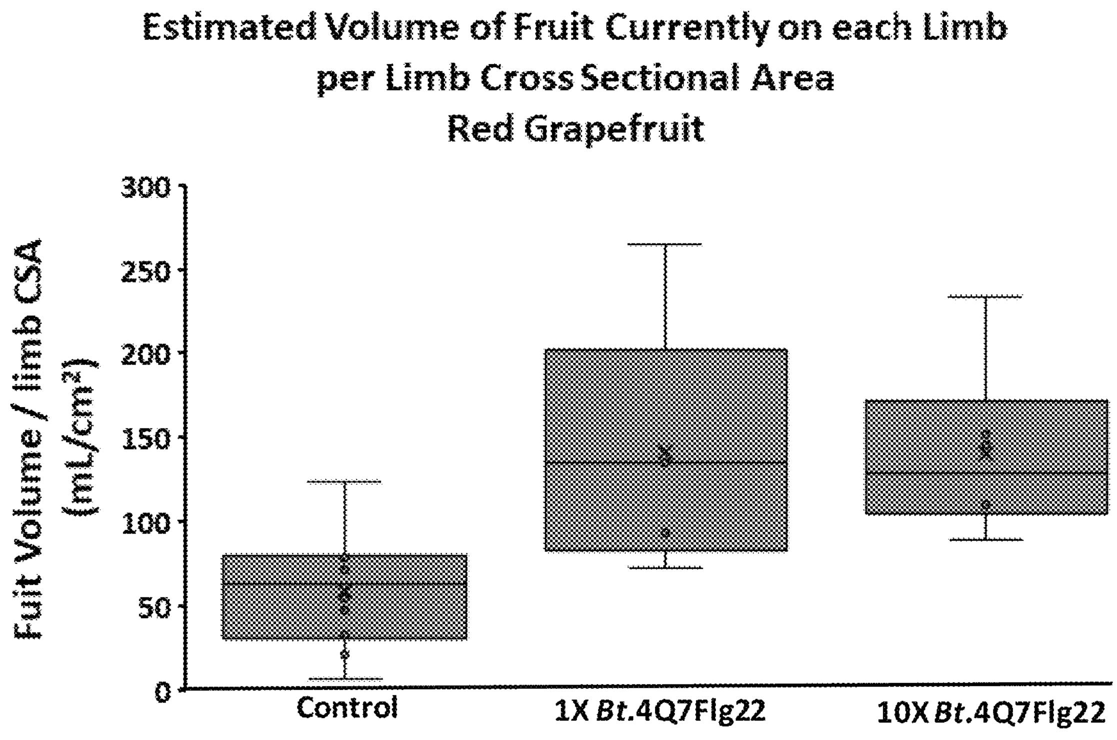
FIG. 16 is directed to 'Ruby Red' grapefruit trees injected with 1× or 10× Bt.4Q7Flg22 (SEQ ID NO: 226) to increase fruit set as indicated by estimated fruit volume per limb.

The estimated volume of fruit normalized by limb CSA for each treatment is reported in FIG. 15 ('Valencia' orange) and FIG. 16 (Red Grapefruit) in box and whisker plots.

The measurements collected in June 2018 to assess fruit set in 'Valencia' orange and 'Ruby Red' grapefruit trees in Okeechobee, Fla. show increased fruit per limb and increased fruit size for trees of both varieties receiving trunk injections of 1× Low and 10× High rates of Bt.4Q7Flg22

(SEQ ID NO: 226) in April 2017, when comparing the mean and median values for all parameters measured versus the untreated control. The increased fruit set and size are predicative of increased yield. These results provide further evidence that trunk injection of citrus trees with Bt.4Q7Flg22 can be utilized to reduce *C. liberibacter* bacterial titers in orange (FIG. 9) and grapefruit (FIG. 10; Table 84) and stimulate new shoot and fruit growth (Table 85, FIGS. 11-16) in citrus trees.

In view of the above, it will be seen that the several objects of the invention are achieved and other advantageous results attained.

As various changes could be made in the above polypeptides, recombinant organisms, methods, and seeds, without departing from the scope of the invention, it is intended that all matter contained in the above description shall be interpreted as illustrative and not in a limiting sense.

What is claimed is:

1. An isolated flagellin or flagellin-associated peptide for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture, wherein:

the peptide consists of the amino acid sequence SEQ ID NO: 752; and a) arginine at amino acid position 1 of SEQ ID NO: 752 is optionally substituted with glutamine or lysine; or
b) serine at amino acid position 4 of SEQ ID NO: 752 is optionally substituted with glycine, threonine, asparagine, or arginine; or
c) lysine at amino acid position 6 of SEQ ID NO: 752 is optionally substituted with serine, alanine or glycine; or
d) aspartic acid at amino acid position 8 of SEQ ID NO: 752 is optionally substituted with proline; or
e) alanine at amino acid position 9 of SEQ ID NO: 752 is optionally substituted with proline; or
f) the flagellin or flagellin-associated peptide optionally has a chemical modification selected from the group consisting of acetylation, amidation, cyclization, and PEGylation, is part of a fusion protein wherein the fusion protein contains a protease recognition sequence, or a combination thereof; or
g) the peptide is optionally part of a fusion protein and the fusion protein has a signature peptide, wherein the amino acid sequence of the signature peptide has any one of SEQ ID NOs: 542-548, or any combination thereof; or a signal anchor sorting peptide, wherein the amino acid sequence of the signal anchor sorting peptide has any one of SEQ ID NOs: 549-562, or a combination thereof; or a secretion peptide, wherein the amino acid sequence of the secretion peptide has any one of SEQ ID NOs: 563-570 or 769.

2. The isolated peptide of claim 1, wherein the flagellin or flagellin-associated peptide has a substitution selected from the group consisting of:

a) arginine at amino acid position 1 of SEQ ID NO: 752 is substituted with glutamine or lysine;
b) serine at amino acid position 4 of SEQ ID NO: 752 is substituted with glycine, threonine, asparagine, or arginine;
c) lysine at amino acid position 6 of SEQ ID NO: 752 is substituted with serine, alanine or glycine;
d) aspartic acid at amino acid position 8 of SEQ ID NO: 752 is substituted with proline; and
e) alanine at amino acid position 9 of SEQ ID NO: 752 is substituted with proline.

3. The peptide of claim 2, wherein the flagellin or flagellin-associated peptide: has the chemical modification, is part of the fusion protein wherein the fusion protein-contains the protease recognition sequence, or the combination thereof.

4. The peptide of claim 3, wherein the flagellin or flagellin-associated peptide has the chemical modification.

5. The peptide of claim 2, wherein the peptide is part of the fusion protein and the fusion protein the secretion peptide, wherein the amino acid sequence of the secretion peptide has any one of SEQ ID NOS: 563-570 or 769.

6. The peptide of claim 2, wherein the peptide is chemically synthesized, concentrated from a fermentation product, and/or purified, by filtration, chromatography, or from a recombinant microorganism.

7. A composition for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture, the composition comprising the peptide of claim 2 and an agrochemical or a carrier.

8. A seed coated with the peptide of claim 2, a composition comprising the peptide and a carrier or agrochemical, or a recombinant microorganism expressing or overexpressing at least the peptide.

9. The peptide of claim 1, wherein the flagellin or flagellin-associated peptide: has the chemical modification, is part of the fusion protein wherein the fusion protein-contains the protease recognition sequence, or the combination thereof.

10. The peptide of claim 9, wherein the flagellin or flagellin-associated peptide has the chemical modification.

11. The peptide of claim 1, wherein the peptide is part of the fusion protein and the fusion protein the secretion peptide, wherein the amino acid sequence of the secretion peptide has any one of SEQ ID NOS: 563-570 or 769.

12. The peptide of claim 11, wherein the peptide is part of the fusion protein and the fusion protein has the signature peptide, wherein the amino acid sequence of the signature peptide has any one of SEQ ID NOs: 542-548, or any combination thereof; or the peptide is part of the fusion protein and the fusion protein has the signal anchor sorting peptide, wherein the amino acid sequence of the signal anchor sorting peptide has any one of SEQ ID NOs: 549-562, or combination thereof.

13. The peptide of claim 1, wherein the peptide is chemically synthesized, concentrated from a fermentation product, and/or purified, by filtration, chromatography, or from a recombinant microorganism.

14. A composition for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture, the composition comprising the peptide of claim 1 and an agrochemical or a carrier.

15. A seed coated with the peptide of claim 1, a composition comprising the peptide and a carrier or agrochemical, or a recombinant microorganism expressing or overexpressing at least the peptide.

16. An isolated flagellin or flagellin-associated peptide for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture, wherein:

the peptide consists of the amino acid sequence SEQ ID NO: 753 ; and a) aspartic acid at amino acid position 1 of the 22 amino acid peptide is optionally substituted with aspartic acid, asparagine, glutamic acid, glycine, glutamine, leucine or threonine; or b) arginine at amino acid position 2 of the 22 amino acid peptide is optionally substituted with lysine; or c) leucine at amino acid position 3 of the 22 amino acid peptide is optionally substituted with isoleucine; or d) lysine at amino acid position 7 of the 22 amino acid peptide is optionally substituted with leucine, glutamine, tyrosine or serine; or e) arginine at amino acid position 8 of the 22 amino acid peptide is optionally substituted with glutamine or lysine; or f) serine at amino acid position 11 of the 22 amino acid peptide is optionally substituted with glycine, threonine, asparagine, or arginine; or g) serine at amino acid position 13 of the 22 amino acid peptide is optionally substituted with lysine, alanine or glycine; or h) alanine at amino acid position 16 of the 22 amino acid peptide is optionally substituted with proline; or i) leucine at amino acid position 19 of the 22 amino acid peptide is optionally substituted with glutamine; or j) alanine at amino acid position 20 of the 22 amino acid peptide is optionally substituted with glutamine; or k) alanine at amino acid position 22 of the 22 amino acid peptide is optionally substituted with serine; or l) the flagellin or flagellin-associated peptide optionally has a chemical modification selected from the group consisting of acetylation, amidation, cyclization, and PEGylation, is part of a fusion protein wherein the fusion protein-contains a protease recognition sequence, or a combination thereof; or m) the peptide is optionally part of a fusion protein and the fusion protein has a signature peptide, wherein the amino acid sequence of the signature peptide has any one of SEQ ID NOs: 542-548, or any combination thereof; or a signal anchor sorting peptide, wherein the amino acid sequence of the signal anchor sorting peptide has any one of SEQ ID NOs: 549-562, or a combination thereof; or a secretion peptide, wherein the amino acid sequence of the secretion peptide has any one of SEQ ID NOs: 563-570 or 769.

17. The peptide of claim 16, wherein the peptide is part of the fusion protein and the fusion protein has the signature peptide, wherein the amino acid sequence of the signature peptide has any one of SEQ ID NOs: 542-548, or any combination thereof; or the peptide is part of the fusion protein and the fusion protein has the signal anchor sorting peptide, wherein the amino acid sequence of the signal anchor sorting peptide has any one of SEQ ID NOs: 549-562, or a combination thereof.

18. The peptide of claim 16, wherein the peptide is chemically synthesized, concentrated from a fermentation product, and/or purified, by filtration, chromatography, or from a recombinant microorganism.

19. A composition for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture, the composition comprising the peptide of claim 16 and an agrochemical or a carrier.

20. A seed coated with the peptide of claim 16, a composition comprising the peptide and a carrier or agrochemical, or a recombinant microorganism expressing or overexpressing at least the peptide.

21. An isolated flagellin or flagellin-associated peptide for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture, wherein:

the peptide consists of the amino acid sequence of any one of SEQ ID NOs: 754, 756, 758, 761, and 763-765; and a) the flagellin or flagellin-associated peptide optionally has a chemical modification selected from the group consisting of acetylation, amidation, cyclization, and PEGylation, is part of a fusion protein wherein the fusion protein-contains a protease recognition sequence, or a combination thereof; or b) the peptide is optionally part of a fusion protein and the fusion protein has a signature peptide, wherein the amino acid sequence of the signature peptide has any one of SEQ ID NOs: 542-548, or any combination thereof; or a signal anchor sorting peptide, wherein the amino acid sequence of the signal anchor sorting peptide has any one of SEQ ID NOs: 549-562, or a combination thereof; or a secretion peptide, wherein the amino acid sequence of the secretion peptide has any one of SEQ ID NOs: 563-570 or 769.

22. The peptide of claim 21, wherein the peptide is part of the fusion protein and the fusion protein has the signature peptide, wherein the amino acid sequence of the signature peptide has any one of SEQ ID NOs: 542-548, or any combination thereof; or the peptide is part of the fusion protein and the fusion protein has the signal anchor sorting peptide, wherein the amino acid sequence of the signal anchor sorting peptide has any one of SEQ ID NOs: 549-562, or a combination thereof.

23. The peptide of claim 21, wherein the peptide is chemically synthesized, concentrated from a fermentation product, and/or purified, by filtration, chromatography, or from a recombinant microorganism.

24. A composition for bioactive priming of a plant or a plant part to increase growth, yield, health, longevity, productivity, and/or vigor of a plant or a plant part and/or decrease abiotic stress in the plant or the plant part and/or protect the plant or the plant part from disease, insects and/or nematodes, and/or increase the innate immune response of the plant or the plant part and/or change plant architecture, the composition comprising the peptide of claim 21 and an agrochemical or a carrier.

25. A seed coated with the peptide of claim 21, a composition comprising the peptide and a carrier or agrochemical, or a recombinant microorganism expressing or overexpressing at least the peptide.

* * * * *

SEQUENCE LISTING

```
<160> NUMBER OF SEQ ID NOS: 775

<210> SEQ ID NO 1
<211> LENGTH: 283
<212> TYPE: PRT
<213> ORGANISM: Bacillus thuringiensis

<400> SEQUENCE: 1

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Ser Ala Ser Asp Asp Ala Ala Gly Leu Ala Ile
        35                  40                  45

Ala Thr Arg Met Lys Ala Arg Glu Gly Gly Leu Asn Val Ala Gly Arg
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Lys Gly Asn Gln Ala Ser Leu Gln Lys
            100                 105                 110

Glu Phe Ala Gln Leu Thr Glu Gln Ile Asp Tyr Ile Ala Lys Asn Thr
        115                 120                 125

Gln Phe Asn Asp Gln Gln Leu Leu Gly Thr Ala Asp Lys Lys Ile Lys
    130                 135                 140

Ile Gln Thr Leu Asp Thr Gly Ser Thr Asn Pro Ala Gln Ile Glu Ile
145                 150                 155                 160

Thr Leu Asn Ser Val Lys Ser Ala Asp Leu Gly Leu Asp Val Gln Ile
                165                 170                 175

Gly Asp Glu Gly Asp Ala Glu Ser Thr Ala Ala Ala Asp Pro Thr Ser
            180                 185                 190

Ala Lys Gln Ala Ile Asp Ala Ile Asp Ala Ala Ile Thr Thr Val Ala
        195                 200                 205

Gly Gln Arg Ala Thr Leu Gly Ala Thr Leu Asn Arg Phe Glu Phe Asn
    210                 215                 220

Ala Asn Asn Leu Lys Ser Gln Glu Thr Ser Met Ala Asp Ala Ala Ser
225                 230                 235                 240

Gln Ile Glu Asp Ala Asp Met Ala Lys Glu Met Ser Glu Met Thr Lys
                245                 250                 255

Phe Lys Ile Leu Asn Glu Ala Gly Ile Ser Met Leu Ser Gln Ala Asn
            260                 265                 270

Gln Thr Pro Gln Met Val Ser Lys Leu Leu Gln
        275                 280


<210> SEQ ID NO 2
<211> LENGTH: 283
```

<212> TYPE: PRT
<213> ORGANISM: Bacillus thuringiensis

<400> SEQUENCE: 2

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Ser Ala Ser Asp Asp Ala Ala Gly Leu Ala Ile
        35                  40                  45

Ala Thr Arg Met Lys Ala Arg Glu Gly Gly Leu Asn Val Ala Gly Arg
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Lys Gly Asn Gln Ala Ser Leu Gln Lys
            100                 105                 110

Glu Phe Ala Gln Leu Thr Glu Gln Ile Asp Tyr Ile Ala Lys Asn Thr
        115                 120                 125

Gln Phe Asn Asp Gln Gln Leu Leu Gly Thr Ala Asp Lys Lys Ile Lys
    130                 135                 140

Ile Gln Thr Leu Asp Thr Gly Ser Thr Asn Pro Ala Gln Ile Glu Ile
145                 150                 155                 160

Thr Leu Asn Ser Val Lys Ser Ala Asp Leu Gly Leu Asp Val Gln Ile
                165                 170                 175

Gly Asp Glu Gly Asp Ala Glu Ser Thr Ala Ala Ala Asp Pro Thr Ser
            180                 185                 190

Ala Lys Gln Ala Ile Asp Ala Ile Asp Ala Ala Ile Thr Thr Val Ala
        195                 200                 205

Gly Gln Arg Ala Thr Leu Gly Ala Thr Leu Asn Arg Phe Glu Phe Asn
    210                 215                 220

Ala Asn Asn Leu Lys Ser Gln Glu Thr Ser Met Ala Asp Ala Ala Ser
225                 230                 235                 240

Gln Ile Glu Asp Ala Asp Met Ala Lys Glu Met Ser Glu Met Thr Lys
                245                 250                 255

Phe Lys Ile Leu Asn Glu Ala Gly Ile Ser Met Leu Ser Gln Ala Asn
            260                 265                 270

Gln Thr Pro Gln Met Val Ser Lys Leu Leu Gln
        275                 280

<210> SEQ ID NO 3
<211> LENGTH: 283
<212> TYPE: PRT
<213> ORGANISM: Bacillus thuringiensis

<400> SEQUENCE: 3

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Ser Ala Ser Asp Asp Ala Ala Gly Leu Ala Ile
        35                  40                  45

Ala Thr Arg Met Lys Ala Arg Glu Gly Gly Leu Asn Val Ala Gly Arg
    50                  55                  60

```
Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Lys Gly Asn Gln Ala Ser Leu Gln Lys
            100                 105                 110

Glu Phe Ala Gln Leu Thr Glu Gln Ile Asp Tyr Ile Ala Lys Asn Thr
        115                 120                 125

Gln Phe Asn Asp Gln Gln Leu Leu Gly Thr Ala Asp Lys Lys Ile Lys
    130                 135                 140

Ile Gln Thr Leu Asp Thr Gly Ser Thr Asn Pro Ala Gln Ile Glu Ile
145                 150                 155                 160

Thr Leu Asn Ser Val Lys Ser Ala Asp Leu Gly Leu Asp Val Gln Ile
                165                 170                 175

Gly Asp Glu Gly Asp Ala Glu Ser Thr Ala Ala Ala Asp Pro Thr Ser
            180                 185                 190

Ala Lys Gln Ala Ile Asp Ala Ile Asp Ala Ala Ile Thr Thr Val Ala
        195                 200                 205

Gly Gln Arg Ala Thr Leu Gly Ala Thr Leu Asn Arg Phe Glu Phe Asn
    210                 215                 220

Ala Asn Asn Leu Lys Ser Gln Glu Thr Ser Met Ala Asp Ala Ala Ser
225                 230                 235                 240

Gln Ile Glu Asp Ala Asp Met Ala Lys Glu Met Ser Glu Met Thr Lys
                245                 250                 255

Phe Lys Ile Leu Asn Glu Ala Gly Ile Ser Met Leu Ser Gln Ala Asn
            260                 265                 270

Gln Thr Pro Gln Met Val Ser Lys Leu Leu Gln
        275                 280


<210> SEQ ID NO 4
<211> LENGTH: 283
<212> TYPE: PRT
<213> ORGANISM: Bacillus cereus

<400> SEQUENCE: 4

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Ser Ala Ser Asp Asp Ala Ala Gly Leu Ala Ile
        35                  40                  45

Ala Thr Arg Met Lys Ala Arg Glu Gly Gly Leu Asn Val Ala Gly Arg
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Lys Gly Asn Gln Ala Ser Leu Gln Lys
            100                 105                 110

Glu Phe Ala Gln Leu Thr Glu Gln Ile Asp Tyr Ile Ala Lys Asn Thr
        115                 120                 125

Gln Phe Asn Asp Gln Gln Leu Leu Gly Thr Ala Asp Lys Lys Ile Lys
    130                 135                 140

Ile Gln Thr Leu Asp Thr Gly Ser Thr Asn Pro Ala Gln Ile Glu Ile
145                 150                 155                 160
```

```
Thr Leu Asn Ser Val Lys Ser Ala Asp Leu Gly Leu Asp Val Gln Ile
                165                 170                 175

Gly Asp Glu Gly Asp Ala Glu Ser Thr Ala Ala Ala Asp Pro Thr Ser
            180                 185                 190

Ala Lys Gln Ala Ile Asp Ala Ile Asp Ala Ala Ile Thr Thr Val Ala
        195                 200                 205

Gly Gln Arg Ala Thr Leu Gly Ala Thr Leu Asn Arg Phe Glu Phe Asn
    210                 215                 220

Ala Asn Asn Leu Lys Ser Gln Glu Thr Ser Met Ala Asp Ala Ala Ser
225                 230                 235                 240

Gln Ile Glu Asp Ala Asp Met Ala Lys Glu Met Ser Glu Met Thr Lys
                245                 250                 255

Phe Lys Ile Leu Asn Glu Ala Gly Ile Ser Met Leu Ser Gln Ala Asn
            260                 265                 270

Gln Thr Pro Gln Met Val Ser Lys Leu Leu Gln
        275                 280


<210> SEQ ID NO 5
<211> LENGTH: 266
<212> TYPE: PRT
<213> ORGANISM: Bacillus thuringiensis

<400> SEQUENCE: 5

Met Arg Ile Gly Thr Asn Val Leu Ser Met Asn Ala Arg Gln Ser Leu
1               5                   10                  15

Tyr Glu Asn Glu Lys His Met Asn Val Ala Met Glu His Leu Ala Thr
            20                  25                  30

Gly Lys Lys Leu Asn Asn Ala Ser Asp Asn Pro Ala Asn Ile Ala Ile
        35                  40                  45

Val Thr Arg Met His Ala Arg Ala Ser Gly Met Arg Val Ala Ile Arg
    50                  55                  60

Asn Asn Glu Asp Ala Ile Ser Met Leu Arg Thr Ala Glu Ala Ala Leu
65                  70                  75                  80

Gln Thr Val Thr Asn Ile Leu Gln Arg Met Arg Asp Leu Ala Val Gln
                85                  90                  95

Ser Ala Asn Gly Thr Asn Ser Asn Lys Asn Arg His Ser Leu Asn Lys
            100                 105                 110

Glu Phe Gln Ser Leu Thr Glu Lys Ile Gly Tyr Ile Gly Glu Thr Thr
        115                 120                 125

Glu Phe Asn Asp Leu Ser Val Phe Glu Gly Gln Asn Arg Pro Ile Thr
    130                 135                 140

Leu Asp Asp Ile Gly His Thr Ile Asn Met Met Lys His Ile Pro Pro
145                 150                 155                 160

Ser Pro Thr Gln His Asp Ile Lys Ile Ser Thr Glu Gln Glu Ala Arg
                165                 170                 175

Ala Ala Ile Leu Lys Ile Glu Asp Ala Leu Gln Ser Val Ser Leu His
            180                 185                 190

Arg Ala Asp Leu Gly Ala Met Ile Asn Arg Leu Gln Phe Asn Ile Glu
        195                 200                 205

Asn Leu Asn Ser Gln Ser Met Ala Leu Thr Asp Ala Ala Ser Leu Ile
    210                 215                 220

Glu Asp Ala Asp Met Ala Gln Glu Met Ser Asp Phe Leu Lys Phe Lys
225                 230                 235                 240

Leu Leu Thr Glu Val Ala Leu Ser Met Val Ser Gln Ala Asn Gln Ile
```

```
            245                 250                 255

Pro Gln Met Val Ser Lys Leu Leu Gln Ser
            260                 265


<210> SEQ ID NO 6
<211> LENGTH: 375
<212> TYPE: PRT
<213> ORGANISM: Bacillus thuringiensis

<400> SEQUENCE: 6

Met Arg Ile Asn Thr Asn Ile Asn Ser Met Arg Thr Gln Glu Tyr Met
1               5                   10                  15

Arg Gln Asn Gln Ala Lys Met Ser Asn Ser Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asp
    50                  55                  60

Asn Thr Gln Asn Gly Met Ser Leu Ile Arg Thr Ala Asp Ser Ala Met
65                  70                  75                  80

Asn Ser Val Ser Asn Ile Leu Leu Arg Met Arg Asp Ile Ala Asn Gln
                85                  90                  95

Ser Ala Asn Gly Thr Asn Thr Asn Glu Asn Lys Ser Ala Leu Gln Lys
            100                 105                 110

Glu Phe Ala Gln Leu Gln Lys Gln Ile Thr Tyr Ile Ala Glu Asn Thr
        115                 120                 125

Gln Phe Asn Asp Lys Asn Leu Leu Asn Glu Asp Ser Glu Val Lys Ile
    130                 135                 140

Gln Thr Leu Asp Ser Ser Lys Gly Glu Gln Gln Ile Thr Ile Asp Leu
145                 150                 155                 160

Lys Ala Val Thr Leu Glu Lys Leu Asn Ile Lys Asp Ile Ala Ile Gly
                165                 170                 175

Lys Ala Asp Ala Ala Asp Lys Pro Val Thr Pro Gly Ala Thr Val Asp
            180                 185                 190

Gln Lys Asp Leu Asp Ser Val Thr Asp Lys Ile Ala Ala Leu Thr Glu
        195                 200                 205

Thr Ser Ser Lys Ala Asp Ile Asp Ala Ile Gln Ser Ser Leu Asp Asn
    210                 215                 220

Phe Lys Ala Ser Met Thr Pro Glu Asp Val Lys Thr Leu Glu Asp Ala
225                 230                 235                 240

Leu Lys Gly Phe Lys Thr Gly Gln Ala Asn Pro Ala Asp Ala Gly Val
                245                 250                 255

Asp Ala Ile Gln Asp Ala Leu Ser Lys Val Lys Leu Pro Thr Ala Thr
            260                 265                 270

Ala Ala Ala Pro Ala Ala Asp Ala Asp Lys Ser Asp Ala Leu Ala Ala
        275                 280                 285

Ile Ala Ala Ile Asp Ala Ala Leu Thr Lys Val Ala Asp Asn Arg Ala
    290                 295                 300

Thr Leu Gly Ala Thr Leu Asn Arg Leu Asp Phe Asn Val Asn Asn Leu
305                 310                 315                 320

Lys Ser Gln Ser Ser Ser Met Ala Ser Ala Ala Ser Gln Ile Glu Asp
                325                 330                 335

Ala Asp Met Ala Lys Glu Met Ser Glu Met Thr Lys Phe Lys Ile Leu
            340                 345                 350
```

```
Asn Glu Ala Gly Ile Ser Met Leu Ser Gln Ala Asn Gln Thr Pro Gln
        355                 360                 365

Met Val Ser Lys Leu Leu Gln
    370                 375


<210> SEQ ID NO 7
<211> LENGTH: 416
<212> TYPE: PRT
<213> ORGANISM: Bacillus thuringiensis

<400> SEQUENCE: 7

Met Thr Gly Ile Thr Ile Asn Leu Glu Ile Asp Phe Phe Ala Tyr Tyr
1               5                   10                  15

Arg Phe Ser Ile Cys Arg Lys Val Asn Ile Lys Lys Trp Gly Phe Leu
            20                  25                  30

Asn Met Arg Ile Asn Thr Asn Ile Asn Ser Met Arg Thr Gln Glu Tyr
        35                  40                  45

Met Arg Gln Asn Gln Ala Lys Met Ser Asn Ala Met Asp Arg Leu Ser
    50                  55                  60

Ser Gly Lys Arg Ile Asn Asn Ala Ser Asp Asp Ala Ala Gly Leu Ala
65                  70                  75                  80

Ile Ala Thr Arg Met Arg Ala Arg Glu Asn Gly Leu Gly Val Ala Ala
                85                  90                  95

Asn Asn Thr Gln Asp Gly Met Ser Leu Ile Arg Thr Ala Asp Ser Ala
            100                 105                 110

Met Asn Ser Val Ser Asn Ile Leu Leu Arg Met Arg Asp Leu Ala Asn
        115                 120                 125

Gln Ser Ala Asn Gly Thr Asn Thr Asp Asp Asn Gln Lys Ala Leu Asp
    130                 135                 140

Lys Glu Phe Ser Ala Leu Lys Glu Gln Ile Asp Tyr Ile Ser Lys Asn
145                 150                 155                 160

Thr Glu Phe Asn Asp Lys Lys Leu Leu Asn Gly Glu Asn Lys Thr Ile
                165                 170                 175

Ala Ile Gln Thr Leu Asp Asn Ala Asp Thr Thr Lys Gln Ile Asn Ile
            180                 185                 190

Asn Leu Ala Asp Ser Ser Thr Ser Ala Leu Gln Ile Asp Lys Leu Thr
        195                 200                 205

Ile Ser Gly Lys Thr Thr Asp Thr Thr Lys Thr Glu Thr Ile Thr Val
    210                 215                 220

Thr Asp Asp Glu Ile Lys Ala Ala Lys Thr Asp Ile Asp Glu Phe Asn
225                 230                 235                 240

Asp Ala Lys Lys Ala Leu Ala Asp Leu Lys Ala Glu Thr Ser Ala Gly
                245                 250                 255

Lys Ala Asp Gly Ser Thr Asp Asp Glu Ile Lys Thr Ala Val Ser Asn
            260                 265                 270

Phe Thr Lys Ser Phe Glu Lys Ile Gln Lys Phe Met Asn Asp Ser Asp
        275                 280                 285

Ile Lys Thr Val Gln Thr Glu Ile Glu Lys Phe Asp Ala Ala Ala Pro
    290                 295                 300

Ala Leu Asp Lys Ala Lys Gly Met Gly Ile Ala Phe Thr Ser Ala Met
305                 310                 315                 320

Asp Pro Lys Ala Gly Thr Ile Thr Lys Ala Ala Thr Arg Gln Asn Ala
                325                 330                 335

Ser Asp Ala Ile Lys Ser Ile Asp Ala Ala Leu Glu Thr Ile Ala Ser
            340                 345                 350
```

Asn Arg Ala Thr Leu Gly Ala Thr Leu Asn Arg Leu Asp Phe Asn Val
355 360 365

Asn Asn Leu Lys Ser Gln Ser Ser Ser Met Ala Ala Ala Ala Ser Gln
370 375 380

Ile Glu Asp Ala Asp Met Ala Lys Glu Met Ser Glu Met Thr Lys Phe
385 390 395 400

Lys Ile Leu Asn Glu Ala Gly Ile Ser Met Leu Ser Gln Ala Asn Val
405 410 415

<210> SEQ ID NO 8
<211> LENGTH: 368
<212> TYPE: PRT
<213> ORGANISM: Bacillus thuringiensis

<400> SEQUENCE: 8

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Asn Gly Leu Gly Val Ala Ala Asn
50 55 60

Asn Thr Gln Asp Gly Met Ser Leu Ile Arg Thr Ala Asp Ser Ala Leu
65 70 75 80

Gln Ser Val Ser Asn Ile Leu Leu Arg Met Arg Asp Leu Ala Asn Gln
85 90 95

Ser Ala Asn Gly Thr Asn Thr Asp Glu Asn Lys Ala Ala Met Glu Lys
100 105 110

Glu Phe Gly Gln Leu Lys Asp Gln Ile Lys Tyr Ile Thr Asp Asn Thr
115 120 125

Gln Phe Asn Asp Lys Asn Leu Leu Asp Ala Ala Ser Gly Thr Thr Lys
130 135 140

Ser Ile Ala Ile Gln Thr Leu Asp Ser Asp Gln Ala Ser Thr Gln Ile
145 150 155 160

Glu Ile Lys Ile Ala Gly Ser Ser Leu Ala Ala Leu Gly Leu Asp Lys
165 170 175

Val Gln Ile Gly Gln Glu Thr Val Ala Gln Lys Asp Leu Asp Val Leu
180 185 190

Thr Lys Ala Met Gly Arg Leu Ala Ala Pro Asp Ala Asp Ala Thr Thr
195 200 205

Arg Asp Leu Asp Val Gln Val Ala Lys Asp Ala Phe Asp Lys Val Lys
210 215 220

Gly Phe Ile Ala Asp Pro Ala Gln Ala Lys Ala Val Glu Arg Ala Phe
225 230 235 240

Glu Asp Tyr Thr Ala Ala Glu Ala Gly Lys Glu Glu Asp Ala Ala Lys
245 250 255

Ala Ile Asp Ala Ala Tyr Lys Lys Val Thr Gly Leu Thr Ala Gly Thr
260 265 270

Thr Gly Thr Val Asp Ala His Asn Ala Val Asn Lys Ile Asp Ala Ala
275 280 285

Leu Lys Thr Val Ala Asp Asn Arg Ala Thr Leu Gly Ala Thr Leu Asn
290 295 300

Arg Leu Asp Phe Asn Val Asn Asn Leu Lys Ser Gln Ser Ala Ser Met

```
305                 310                 315                 320

Ala Ser Ala Ala Ser Gln Ile Glu Asp Ala Asp Met Ala Lys Glu Met
                325                 330                 335

Ser Glu Met Thr Lys Phe Lys Ile Leu Asn Glu Ala Gly Ile Ser Met
            340                 345                 350

Leu Ser Gln Ala Asn Gln Thr Pro Gln Met Val Ser Lys Leu Leu Gln
        355                 360                 365


<210> SEQ ID NO 9
<211> LENGTH: 374
<212> TYPE: PRT
<213> ORGANISM: Bacillus cereus

<400> SEQUENCE: 9

Met Arg Ile Asn Thr Asn Ile Asn Ser Met Arg Thr Gln Glu Tyr Met
1               5                   10                  15

Arg Gln Asn Gln Ala Lys Met Ser Asn Ser Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Ile Ala Asn Gln
                85                  90                  95

Ser Ala Asn Gly Thr Asn Thr Asp Lys Asn Gln Val Ala Leu Gln Lys
            100                 105                 110

Glu Phe Gly Glu Leu Gln Lys Gln Ile Asp Tyr Ile Ala Lys Asn Thr
        115                 120                 125

Gln Phe Asn Asp Lys Asn Leu Leu Ser Gly Lys Ala Gly Ala Pro Asp
    130                 135                 140

Gln Ala Leu Glu Ile Asn Ile Gln Thr Leu Asp Ser Ser Asp Pro Asn
145                 150                 155                 160

Gln Gln Ile Lys Ile Ser Leu Asp Ser Val Ser Thr Ala Gln Leu Gly
                165                 170                 175

Val Lys Asp Leu Gln Ile Gly Ser Ser Ser Ile Thr Gln Gln Gln Leu
            180                 185                 190

Asp Thr Leu Asp Asn Ala Met Lys Arg Leu Glu Thr Ala Ser Thr Thr
        195                 200                 205

Ala Ala Val Arg Asp Gln Asp Val Ala Asp Ala Lys Ala Ala Phe Glu
    210                 215                 220

Asn Val Lys Gly Phe Phe Ser Glu Gly Asn Val Asp Ser Ile Asn Arg
225                 230                 235                 240

Ala Phe Thr Asp Phe Ala Asn Glu Thr Thr Asn Lys Asp Asp Lys Ala
                245                 250                 255

Glu Ala Ile Tyr Ala Leu Tyr Asn Asn Ala Thr Leu Ile Thr Lys Pro
            260                 265                 270

Thr Pro Asp Ala Ser Asn Pro Ala Ser Val Asp Pro Ala Asn Ala Ile
        275                 280                 285

Lys Lys Ile Asp Gln Ala Ile Glu Lys Ile Ala Ser Ser Arg Ala Thr
    290                 295                 300

Leu Gly Ala Thr Leu Asn Arg Leu Asp Phe Asn Val Asn Asn Leu Lys
305                 310                 315                 320
```

```
Ser Gln Gln Ser Ser Met Ala Ser Ala Ala Ser Gln Val Glu Asp Ala
            325                 330                 335

Asp Met Ala Lys Glu Met Ser Glu Met Thr Lys Phe Lys Ile Leu Asn
            340                 345                 350

Glu Ala Gly Ile Ser Met Leu Ser Gln Ala Asn Gln Thr Pro Gln Met
        355                 360                 365

Val Ser Lys Leu Leu Gln
    370
```

<210> SEQ ID NO 10
<211> LENGTH: 266
<212> TYPE: PRT
<213> ORGANISM: Bacillus cereus

<400> SEQUENCE: 10

```
Met Arg Ile Gly Thr Asn Val Leu Ser Met Asn Ala Arg Gln Ser Phe
1               5                   10                  15

Tyr Glu Asn Glu Lys Arg Met Asn Val Ala Ile Glu His Leu Ala Thr
            20                  25                  30

Gly Lys Lys Leu Asn His Ala Ser Asp Asn Pro Ala Asn Val Ala Ile
        35                  40                  45

Val Thr Arg Met His Ala Arg Thr Ser Gly Ile His Val Ala Ile Arg
    50                  55                  60

Asn Asn Glu Asp Ala Ile Ser Met Leu Arg Thr Ala Glu Ala Ala Leu
65                  70                  75                  80

Gln Thr Val Thr Asn Ile Leu Gln Arg Met Arg Asp Val Ala Val Gln
                85                  90                  95

Ser Ala Asn Gly Thr Asn Ser Asn Lys Asn Arg Asp Ser Leu Asn Lys
            100                 105                 110

Glu Phe Gln Ser Leu Thr Glu Gln Ile Gly Tyr Ile Asp Glu Thr Thr
        115                 120                 125

Glu Phe Asn Asp Leu Ser Val Phe Asp Arg Gln Asn Cys Pro Val Thr
    130                 135                 140

Leu Asp Asp Ile Gly His Thr Val Asn Val Thr Lys His Ile Pro Pro
145                 150                 155                 160

Ser Pro Thr Gln His Asp Ile Asn Ile Ser Thr Glu Gln Glu Ala Arg
                165                 170                 175

Ala Ala Ile Arg Lys Ile Glu Glu Thr Leu Gln Asn Val Ser Leu His
            180                 185                 190

Arg Ala Asp Leu Gly Ala Met Ile Asn Gln Leu Gln Phe Asn Ile Glu
        195                 200                 205

Asn Leu Asn Ser Gln Ser Thr Ala Leu Thr Asp Ala Ala Ser Arg Ile
    210                 215                 220

Glu Asp Ala Asp Met Ala Gln Glu Met Ser Asp Phe Leu Lys Phe Lys
225                 230                 235                 240

Leu Leu Thr Glu Val Ala Leu Ser Met Val Ser Gln Ala Asn Gln Ile
                245                 250                 255

Pro Gln Met Val Tyr Lys Leu Leu Gln Ser
            260                 265
```

<210> SEQ ID NO 11
<211> LENGTH: 341
<212> TYPE: PRT
<213> ORGANISM: Bacillus thuringiensis

<400> SEQUENCE: 11

-continued

```
Met Asp Arg Leu Ser Ser Gly Lys Arg Ile Asn Asn Ala Ser Asp Asp
1               5                   10                  15

Ala Ala Gly Leu Ala Ile Ala Thr Arg Met Arg Ala Arg Glu Ser Gly
            20                  25                  30

Leu Gly Val Ala Ala Asn Asn Thr Gln Asp Gly Met Ser Leu Ile Arg
        35                  40                  45

Thr Ala Asp Ser Ala Leu Asn Ser Val Ser Asn Ile Leu Leu Arg Met
    50                  55                  60

Arg Asp Ile Ala Asn Gln Ser Ala Asn Gly Thr Asn Thr Ala Asp Asn
65                  70                  75                  80

Gln Gln Ala Leu Gln Lys Glu Phe Gly Gln Leu Lys Glu Gln Ile Ser
                85                  90                  95

Tyr Ile Ala Asp Asn Thr Glu Phe Asn Asp Lys Thr Leu Leu Lys Ala
            100                 105                 110

Asp Asn Ser Val Lys Ile Gln Thr Leu Asp Ser Ala Asp Thr Asn Lys
        115                 120                 125

Gln Ile Ser Ile Asp Leu Lys Gly Val Thr Leu Asn Gln Leu Gly Leu
    130                 135                 140

Asp Thr Val Asn Ile Gly Ser Glu Lys Leu Ser Ala Glu Ser Leu Asn
145                 150                 155                 160

Val Ala Lys Ala Thr Met Ala Arg Leu Val Lys Ala Asp Gln Asn Ala
                165                 170                 175

Asp Pro Ser Thr Phe Ala Leu Asp Val Asn Thr Ala Lys Glu Ser Phe
            180                 185                 190

Asp Lys Ile Lys Gly Phe Ile Ala Asn Lys Thr Asn Val Gln Asn Val
        195                 200                 205

Glu Asn Ala Phe Asn Asp Tyr Ala Val Ala Asp Pro Ala Asp Lys Ala
    210                 215                 220

Asp Lys Ala Asp Ala Ile Gln Ala Ala Phe Asn Thr Ala Ile Thr Gly
225                 230                 235                 240

Leu Thr Ala Gly Thr Pro Asn Thr Ser Asn Pro Ser Ser Ala Val Asp
                245                 250                 255

Ser Ile Asp Ala Ala Leu Lys Thr Val Ala Ser Asn Arg Ala Thr Leu
            260                 265                 270

Gly Ala Thr Leu Asn Arg Leu Asp Phe Asn Val Asn Asn Leu Lys Ser
        275                 280                 285

Gln Ser Ala Ser Met Ala Ser Ala Ala Ser Gln Ile Glu Asp Ala Asp
    290                 295                 300

Met Ala Lys Glu Met Ser Glu Met Thr Lys Phe Lys Ile Leu Asn Glu
305                 310                 315                 320

Ala Gly Ile Ser Met Leu Ser Gln Ala Asn Gln Thr Pro Gln Met Val
                325                 330                 335

Ser Lys Leu Leu Gln
            340


<210> SEQ ID NO 12
<211> LENGTH: 367
<212> TYPE: PRT
<213> ORGANISM: Bacillus bombysepticus

<400> SEQUENCE: 12

Met Arg Ile Asn Thr Asn Ile Asn Ser Met Arg Thr Gln Glu Tyr Met
1               5                   10                  15

Arg Gln Asn Gln Ala Lys Met Ser Asn Ser Met Asp Arg Leu Ser Ser
            20                  25                  30
```

```
Gly Lys Arg Ile Asn Asn Ala Ser Asp Asp Ala Ala Gly Leu Ala Ile
        35                  40                  45

Ala Thr Arg Met Arg Ser Arg Glu Gly Gly Leu Asn Val Ala Ala Arg
    50                  55                  60

Asn Thr Glu Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Ser Gly Thr Asn Thr Asp Lys Asn Gln Ala Ala Met Gln Lys
            100                 105                 110

Glu Phe Asp Gln Leu Lys Glu Gln Ile Gln Tyr Ile Ala Asp Asn Thr
        115                 120                 125

Glu Phe Asn Asp Lys Lys Leu Leu Asp Gly Ser Asn Ser Thr Ile Asn
    130                 135                 140

Ile Gln Thr Leu Asp Ser His Asp Lys Asn Lys Gln Ile Thr Ile Ser
145                 150                 155                 160

Leu Asp Ser Ala Ser Leu Lys Asn Leu Asp Ile Lys Asp Leu Ala Ile
                165                 170                 175

Gly Ser Ala Thr Ile Asn Gln Thr Asp Leu Asp Thr Ala Thr Asn Ser
            180                 185                 190

Met Lys Arg Leu Ala Thr Pro Ala Thr Asp Gly Lys Val Leu Ala Gln
        195                 200                 205

Asp Ile Ala Asp Ala Lys Ala Ala Phe Asn Lys Val Gln Ser Ala Tyr
    210                 215                 220

Thr Pro Ala Glu Val Asp Lys Ile Gln Asp Ala Phe Lys Ala Tyr Asp
225                 230                 235                 240

Lys Leu Ala Ala Asp Pro Ala Ser Lys Ala Thr Asp Ile Ala Asp Ala
                245                 250                 255

Ala Lys Asn Val Asn Thr Val Phe Gly Thr Leu Ala Thr Pro Thr Ala
            260                 265                 270

Thr Lys Phe Asp Pro Ser Ser Ala Val Glu Lys Ile Asp Lys Ala Ile
        275                 280                 285

Glu Thr Ile Ala Ser Ser Arg Ala Thr Leu Gly Ala Thr Leu Asn Arg
    290                 295                 300

Leu Asp Phe Asn Val Thr Asn Leu Lys Ser Gln Glu Asn Ser Met Ala
305                 310                 315                 320

Ala Ser Ala Ser Gln Ile Glu Asp Ala Asp Met Ala Lys Glu Met Ser
                325                 330                 335

Glu Met Thr Lys Phe Lys Ile Leu Asn Glu Ala Gly Ile Ser Met Leu
            340                 345                 350

Ser Gln Ala Asn Gln Thr Pro Gln Met Val Ser Lys Leu Leu Gln
        355                 360                 365
```

<210> SEQ ID NO 13
<211> LENGTH: 400
<212> TYPE: PRT
<213> ORGANISM: Bacillus thuringiensis

<400> SEQUENCE: 13

```
Met Thr Gly Ile Thr Ile Asn Leu Glu Ile Asp Phe Phe Ala Tyr Tyr
1               5                   10                  15

Arg Phe Ser Ile Cys Arg Lys Val Asn Ile Lys Lys Trp Gly Phe Leu
            20                  25                  30

Asn Met Arg Ile Asn Thr Asn Ile Asn Ser Met Arg Thr Gln Glu Tyr
```

```
        35                  40                  45

Met Arg Gln Asn Gln Ala Lys Met Ser Asn Ser Met Asp Arg Leu Ser
    50                  55                  60

Ser Gly Lys Arg Ile Asn Asn Ala Ser Asp Asp Ala Ala Gly Leu Ala
65                  70                  75                  80

Ile Ala Thr Arg Met Arg Ser Arg Glu Gly Gly Leu Asn Val Ala Ala
                85                  90                  95

Arg Asn Thr Glu Asp Gly Met Ser Leu Ile Arg Thr Ala Asp Ser Ala
            100                 105                 110

Leu Asn Ser Val Ser Asn Ile Leu Leu Arg Met Arg Asp Leu Ala Asn
        115                 120                 125

Gln Ser Ala Ser Gly Thr Asn Thr Asp Lys Asn Gln Ala Ala Met Gln
    130                 135                 140

Lys Glu Phe Asp Gln Leu Lys Glu Gln Ile Gln Tyr Ile Ala Asp Asn
145                 150                 155                 160

Thr Glu Phe Asn Asp Lys Lys Leu Leu Asp Gly Ser Asn Ser Thr Ile
                165                 170                 175

Asn Ile Gln Thr Leu Asp Ser His Asp Lys Asn Lys Gln Ile Thr Ile
            180                 185                 190

Ser Leu Asp Ser Ala Ser Leu Lys Asn Leu Asp Ile Lys Asp Leu Ala
        195                 200                 205

Ile Gly Ser Ala Thr Ile Asn Gln Thr Asp Leu Asp Thr Ala Thr Asn
    210                 215                 220

Ser Met Lys Arg Leu Ala Thr Pro Ala Thr Asp Gly Lys Val Leu Ala
225                 230                 235                 240

Gln Asp Ile Ala Asp Ala Lys Ala Ala Phe Asn Lys Val Gln Ser Ala
                245                 250                 255

Tyr Thr Pro Ala Glu Val Asp Lys Ile Gln Asp Ala Phe Lys Ala Tyr
            260                 265                 270

Asp Lys Leu Ala Ala Asp Pro Ala Ser Lys Asp Thr Asp Ile Ala Asp
        275                 280                 285

Ala Ala Lys Asn Val Asn Thr Val Phe Gly Thr Leu Ala Thr Pro Thr
    290                 295                 300

Ala Thr Lys Phe Asp Pro Ser Ser Ala Val Glu Lys Ile Asp Lys Ala
305                 310                 315                 320

Ile Glu Thr Ile Ala Ser Ser Arg Ala Thr Leu Gly Ala Thr Leu Asn
                325                 330                 335

Arg Leu Asp Phe Asn Val Thr Asn Leu Lys Ser Gln Glu Asn Ser Met
            340                 345                 350

Ala Ala Ser Ala Ser Gln Ile Glu Asp Ala Asp Met Ala Lys Glu Met
        355                 360                 365

Ser Glu Met Thr Lys Phe Lys Ile Leu Asn Glu Ala Gly Ile Ser Met
    370                 375                 380

Leu Ser Gln Ala Asn Gln Thr Pro Gln Met Val Ser Lys Leu Leu Gln
385                 390                 395                 400
```

<210> SEQ ID NO 14
<211> LENGTH: 367
<212> TYPE: PRT
<213> ORGANISM: Bacillus thuringiensis

<400> SEQUENCE: 14

```
Met Arg Ile Asn Thr Asn Ile Asn Ser Met Arg Thr Gln Glu Tyr Met
1               5                   10                  15
```

-continued

```
Arg Gln Asn Gln Ala Lys Met Ser Asn Ser Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ser Arg Glu Gly Gly Leu Asn Val Ala Ala Arg
    50                  55                  60

Asn Thr Glu Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Ser Gly Thr Asn Thr Asp Lys Asn Gln Ala Ala Met Gln Lys
            100                 105                 110

Glu Phe Asp Gln Leu Lys Glu Gln Ile Gln Tyr Ile Ala Asp Asn Thr
        115                 120                 125

Glu Phe Asn Asp Lys Lys Leu Leu Asp Gly Ser Asn Ser Thr Ile Asn
    130                 135                 140

Ile Gln Ala Leu Asp Ser His Asp Lys Asn Lys Gln Ile Thr Ile Ser
145                 150                 155                 160

Leu Asp Ser Ala Ser Leu Lys Asn Leu Asp Ile Lys Asp Leu Ala Ile
                165                 170                 175

Gly Ser Ala Thr Ile Asn Gln Thr Asp Leu Asp Thr Ala Thr Asn Ser
            180                 185                 190

Met Lys Arg Leu Ala Thr Pro Ala Thr Asp Gly Lys Val Leu Ala Gln
        195                 200                 205

Asp Ile Ala Asp Ala Lys Ala Ala Phe Asn Lys Val Gln Ser Ala Tyr
    210                 215                 220

Thr Pro Ala Glu Val Asp Lys Ile Gln Asp Ala Phe Lys Ala Tyr Asp
225                 230                 235                 240

Lys Leu Ala Ala Asp Pro Ala Ser Lys Asp Thr Asp Ile Ala Asp Ala
                245                 250                 255

Ala Lys Asn Val Asn Thr Val Phe Gly Thr Leu Ala Thr Pro Thr Ala
            260                 265                 270

Thr Lys Phe Asp Pro Ser Ser Ala Val Glu Lys Ile Asp Lys Ala Ile
        275                 280                 285

Glu Thr Ile Ala Ser Ser Arg Ala Thr Leu Gly Ala Thr Leu Asn Arg
    290                 295                 300

Leu Asp Phe Asn Val Thr Asn Leu Lys Ser Gln Glu Asn Ser Met Ala
305                 310                 315                 320

Ala Ser Ala Ser Gln Ile Glu Asp Ala Asp Met Ala Lys Glu Met Ser
                325                 330                 335

Glu Met Thr Lys Phe Lys Ile Leu Asn Glu Ala Gly Ile Ser Met Leu
            340                 345                 350

Ser Gln Ala Asn Gln Thr Pro Gln Met Val Ser Lys Leu Leu Gln
        355                 360                 365


<210> SEQ ID NO 15
<211> LENGTH: 397
<212> TYPE: PRT
<213> ORGANISM: Bacillus cereus

<400> SEQUENCE: 15

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30
```

```
Gly Lys Arg Ile Asn Asn Ala Ser Asp Asp Ala Ala Gly Leu Ala Ile
        35                  40                  45

Ala Thr Arg Met Arg Ala Arg Glu Asn Gly Leu Gly Val Ala Ala Asn
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Gly Asp Asn Gln Lys Ala Leu Asp Lys
            100                 105                 110

Glu Phe Ser Ala Leu Lys Glu Gln Ile Asp Tyr Ile Ser Lys Asn Thr
        115                 120                 125

Glu Phe Asn Asp Lys Lys Leu Leu Asn Gly Asp Asn Lys Thr Ile Ala
    130                 135                 140

Ile Gln Thr Leu Asp Asn Ala Asp Thr Ser Lys Gln Ile Asn Ile Asn
145                 150                 155                 160

Leu Ala Asp Ser Ser Thr Ser Ala Leu Lys Ile Glu Lys Leu Thr Ile
                165                 170                 175

Ser Gly Ser Thr Ala Ile Ala Gly Lys Thr Glu Lys Val Thr Ile Thr
            180                 185                 190

Ala Glu Asp Ile Lys Ala Ala Glu Glu Asp Ile Lys Ala Phe Thr Gln
        195                 200                 205

Ala Gln Glu Gly Leu Ala Asn Leu Val Lys Glu Val Lys Asp Thr Asp
    210                 215                 220

Gly Ser Val Lys Thr Pro Gly Ser Thr Pro Asp Asp Ile Lys Lys Ala
225                 230                 235                 240

Val Thr Ala Phe Thr Glu Ser Phe Glu Lys Met Lys Lys Phe Met Asn
                245                 250                 255

Asp Glu Asp Ile Thr Lys Val Glu Glu Lys Ile Lys Ala Phe Asp Ala
            260                 265                 270

Ala Ser Pro Asp Leu Asp Ala Ala Lys Glu Met Gly Thr Ala Phe Thr
        275                 280                 285

Ala Ala Met Lys Pro Ala Ala Gly Glu Ile Thr Lys Ala Ala Met Lys
    290                 295                 300

Pro Asn Ala Ser Asp Ala Ile Lys Ser Ile Asp Glu Ala Leu Glu Thr
305                 310                 315                 320

Ile Ala Ser Asn Arg Ala Thr Leu Gly Ala Thr Leu Asn Arg Leu Asp
                325                 330                 335

Phe Asn Val Asn Asn Leu Lys Ser Gln Ser Ser Ser Met Ala Ser Ala
            340                 345                 350

Ala Ser Gln Ile Glu Asp Ala Asp Met Ala Lys Glu Met Ser Glu Met
        355                 360                 365

Thr Lys Phe Lys Ile Leu Asn Glu Ala Gly Ile Ser Met Leu Ser Gln
    370                 375                 380

Ala Asn Gln Thr Pro Gln Met Val Ser Lys Leu Leu Gln
385                 390                 395


<210> SEQ ID NO 16
<211> LENGTH: 266
<212> TYPE: PRT
<213> ORGANISM: Bacillus cereus

<400> SEQUENCE: 16

Met Arg Ile Gly Thr Asn Val Leu Ser Met Asn Ala Arg Gln Ser Leu
```

```
1               5                   10                  15

Tyr Glu Asn Glu Lys Arg Met Asn Val Ala Met Glu His Leu Ala Thr
            20                  25                  30

Gly Lys Lys Leu Asn Asn Ala Ser Asp Asn Pro Ala Asn Ile Ala Ile
        35                  40                  45

Val Thr Arg Met His Ala Arg Ala Ser Gly Met Arg Leu Ala Ile Arg
    50                  55                  60

Asn Asn Glu Asp Thr Ile Ser Met Leu Arg Thr Ala Glu Ala Ala Leu
65                  70                  75                  80

Gln Thr Leu Thr Asn Ile Leu Gln Arg Met Arg Asp Leu Ala Val Gln
                85                  90                  95

Ser Ala Asn Gly Thr Asn Ser Asn Lys Asn Arg Asp Ser Leu Asn Lys
            100                 105                 110

Glu Phe Gln Ser Leu Thr Glu Gln Ile Gly Tyr Ile Gly Glu Thr Thr
        115                 120                 125

Glu Phe Asn Asp Leu Ser Val Phe Asp Gly Gln Asn Arg Pro Val Thr
    130                 135                 140

Leu Asp Asp Ile Asp His Thr Ile Asn Met Thr Lys His Ile Pro Pro
145                 150                 155                 160

Ser Pro Thr Gln His Asp Ile Lys Ile Ser Thr Glu Gln Glu Ala Arg
                165                 170                 175

Ala Ala Ile Leu Lys Ile Glu Glu Ala Leu Gln Ser Val Ser Ile His
            180                 185                 190

Arg Ala Asp Leu Gly Ser Met Ile Asn Arg Leu Gln Phe Asn Ile Glu
        195                 200                 205

Asn Leu Asn Ser Gln Ser Met Ala Leu Thr Asp Ala Ala Ser Arg Ile
    210                 215                 220

Glu Asp Ala Asp Met Ala Gln Glu Met Ser Asp Phe Leu Lys Phe Lys
225                 230                 235                 240

Leu Leu Thr Glu Val Ala Leu Ser Met Val Ser Gln Ala Asn Gln Ile
                245                 250                 255

Pro Gln Met Val Ser Lys Leu Leu Gln Ser
            260                 265


<210> SEQ ID NO 17
<211> LENGTH: 266
<212> TYPE: PRT
<213> ORGANISM: Bacillus thuringiensis

<400> SEQUENCE: 17

Met Arg Ile Gly Thr Asn Val Leu Ser Met Asn Ala Arg Gln Ser Leu
1               5                   10                  15

Tyr Glu Asn Glu Lys Arg Met Asn Val Ala Met Glu His Leu Ala Thr
            20                  25                  30

Gly Lys Lys Leu Asn His Ala Ser Asp Asn Pro Ala Asn Val Ala Ile
        35                  40                  45

Val Thr Arg Met His Ala Arg Ala Ser Gly Met Arg Val Ala Ile Arg
    50                  55                  60

Asn Asn Glu Asp Ala Ile Ser Met Leu Arg Thr Ala Glu Ala Ala Leu
65                  70                  75                  80

Gln Thr Val Thr Asn Val Leu Gln Arg Met Arg Asp Val Ala Val Gln
                85                  90                  95

Ser Ala Asn Gly Thr Asn Leu Asn Lys Asn Arg Asp Ser Leu Asn Asn
            100                 105                 110
```

Glu Phe Gln Ser Leu Thr Glu Gln Ile Gly Tyr Ile Asp Glu Thr Thr
115 120 125

Ala Phe Asn Asp Leu Ser Val Phe Asp Gly Gln Asn Arg Pro Val Thr
130 135 140

Leu Asp Asp Ile Gly His Thr Val Asn Val Thr Lys His Ile Ser Pro
145 150 155 160

Ser Pro Thr Gln His Asp Ile Asn Ile Ser Thr Glu Gln Glu Ala Arg
165 170 175

Ala Ala Ile Arg Lys Ile Glu Glu Ala Leu Gln Asn Val Ser Leu Tyr
180 185 190

Arg Ala Asp Leu Gly Ala Met Ile Asn Arg Leu Gln Phe Asn Ile Glu
195 200 205

Asn Leu Asn Ser Gln Ser Thr Ala Leu Thr Asp Ala Ala Ser Arg Ile
210 215 220

Glu Asp Ala Asp Met Ala Gln Glu Met Ser Asp Phe Leu Lys Phe Lys
225 230 235 240

Leu Leu Thr Glu Val Ala Leu Ser Met Val Ser Gln Ala Asn Gln Ile
245 250 255

Pro Gln Met Val Tyr Lys Leu Leu Gln Ser
260 265

<210> SEQ ID NO 18
<211> LENGTH: 460
<212> TYPE: PRT
<213> ORGANISM: Bacillus thuringiensis

<400> SEQUENCE: 18

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Ser Gly Leu Asn Val Ala Ala Asp
50 55 60

Asn Thr Gln Asn Gly Met Ser Leu Ile Arg Thr Ala Asp Ser Ala Met
65 70 75 80

Asn Ser Val Ser Asn Ile Leu Leu Arg Met Arg Asp Ile Ala Asn Gln
85 90 95

Ser Ala Asn Gly Thr Asn Thr Asp Ser Asn Lys Ser Ala Leu Gln Lys
100 105 110

Glu Phe Ala Glu Leu Gln Lys Gln Ile Thr Tyr Ile Ala Asp Asn Thr
115 120 125

Gln Phe Asn Asp Lys Asn Leu Leu Lys Glu Asp Ser Glu Val Lys Ile
130 135 140

Gln Thr Leu Asp Ser Ser Lys Gly Glu Gln Gln Ile Gly Ile Asp Leu
145 150 155 160

Lys Ala Val Thr Leu Glu Lys Leu Gly Ile Asn Asn Ile Ser Ile Gly
165 170 175

Lys Ala Asp Gly Thr Thr Glu Gly Thr Lys Ala Asp Leu Thr Ala Leu
180 185 190

Gln Ala Ala Ala Lys Lys Leu Glu Lys Pro Asp Thr Gly Thr Met Glu
195 200 205

Lys Asp Val Lys Asp Ala Lys Glu Glu Phe Asp Lys Val Lys Ala Ser
210 215 220

```
Leu Ser Asp Glu Asp Val Lys Lys Ile Glu Ala Ala Phe Gly Glu Phe
225                 230                 235                 240

Asp Lys Asp Lys Thr Asn Thr Thr Lys Ala Ser Asp Ile Phe Asn Ala
                245                 250                 255

Ile Lys Asp Val Lys Leu Ala Asp Lys Ala Ala Ala Ala Pro Ala Pro
            260                 265                 270

Ala Asp Leu Thr Lys Phe Lys Ala Ala Leu Asp Lys Leu Gln Thr Pro
        275                 280                 285

Asn Ala Gly Thr Met Val Asp Asp Val Lys Asp Ala Lys Asp Glu Phe
    290                 295                 300

Glu Lys Ile Lys Gly Ser Leu Ser Asp Ala Asp Ala Gln Lys Ile Gln
305                 310                 315                 320

Ala Ala Phe Glu Glu Phe Glu Lys Ala Asn Thr Asp Asp Ser Lys Ala
                325                 330                 335

Ser Ala Ile Tyr Asn Leu Ala Lys Asp Val Lys Val Asn Ala Thr Asp
            340                 345                 350

Thr Thr Thr Gly Thr Asp Lys Asp Thr Thr Thr Ser Thr Asp Lys Asp
        355                 360                 365

Ala Ala Leu Ala Ala Ile Ala Ala Ile Asp Ala Ala Leu Thr Lys Val
    370                 375                 380

Ala Asp Asn Arg Ala Thr Leu Gly Ala Thr Leu Asn Arg Leu Asp Phe
385                 390                 395                 400

Asn Val Asn Asn Leu Lys Ser Gln Ser Ser Ser Met Ala Ser Ala Ala
                405                 410                 415

Ser Gln Ile Glu Asp Ala Asp Met Ala Lys Glu Met Ser Glu Met Thr
            420                 425                 430

Lys Phe Lys Ile Leu Asn Glu Ala Gly Ile Ser Met Leu Ser Gln Ala
        435                 440                 445

Asn Gln Thr Pro Gln Met Val Ser Lys Leu Leu Gln
    450                 455                 460


<210> SEQ ID NO 19
<211> LENGTH: 367
<212> TYPE: PRT
<213> ORGANISM: Bacillus cereus

<400> SEQUENCE: 19

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Ala Glu Asn Lys Ala Ala Met Gln Lys
            100                 105                 110

Glu Phe Gly Glu Leu Lys Asp Gln Ile Lys Tyr Ile Ser Glu Asn Thr
        115                 120                 125

Gln Phe Asn Asp Gln His Leu Leu Asn Ala Ala Lys Gly Ser Thr Asn
```

-continued

```
    130                 135                 140

Glu Ile Ala Ile Gln Thr Leu Asp Ser Asp Ser Ser Ser Lys Gln Ile
145                 150                 155                 160

Lys Ile Thr Leu Gln Gly Ala Ser Leu Asp Ser Leu Asp Ile Lys Asp
                165                 170                 175

Leu Gln Ile Gly Ser Gly Ser Thr Val Ser Gln Thr Asp Leu Asp Val
            180                 185                 190

Leu Asp Ala Thr Met Thr Arg Val Lys Thr Ala Thr Gly Ala Thr Arg
        195                 200                 205

Asp Val Asp Val Gln Ala Ala Lys Ser Ala Phe Asp Lys Val Lys Gly
    210                 215                 220

Leu Met Thr Lys Pro Ala Glu Val Lys Ala Ile Glu Arg Ala Phe Glu
225                 230                 235                 240

Asp Tyr Asn Ala Gly Lys Thr Asp Ala Leu Ala Thr Ala Ile Glu Ala
                245                 250                 255

Ala Tyr Thr Ala Asn Lys Thr Gly Leu Pro Ala Pro Ala Ala Ala Ala
            260                 265                 270

Gly Thr Val Asp Ala Leu Gly Ala Ile Thr Lys Ile Asp Ala Ala Leu
        275                 280                 285

Lys Thr Val Ala Asp Asn Arg Ala Thr Leu Gly Ala Thr Leu Asn Arg
    290                 295                 300

Leu Asp Phe Asn Val Asn Asn Leu Lys Ser Gln Ser Ala Ser Met Ala
305                 310                 315                 320

Ser Ala Ala Ser Gln Ile Glu Asp Ala Asp Met Ala Lys Glu Met Ser
                325                 330                 335

Glu Met Thr Lys Phe Lys Ile Leu Asn Glu Ala Gly Ile Ser Met Leu
            340                 345                 350

Ser Gln Ala Asn Gln Thr Pro Gln Met Val Ser Lys Leu Leu Gln
        355                 360                 365


<210> SEQ ID NO 20
<211> LENGTH: 377
<212> TYPE: PRT
<213> ORGANISM: Bacillus thuringiensis

<400> SEQUENCE: 20

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Ile Ala Asn Gln
                85                  90                  95

Ser Ala Asn Gly Thr Asn Thr Ser Asp Asn Gln Lys Ala Leu Asp Lys
            100                 105                 110

Glu Phe Ser Ala Leu Lys Glu Gln Ile Asp Tyr Ile Ser Lys Asn Thr
        115                 120                 125

Glu Phe Asn Asp Lys Lys Leu Leu Asn Gly Asp Asn Lys Ser Ile Ala
    130                 135                 140
```

Ile Gln Thr Leu Asp Asn Ala Asp Thr Thr Lys Gln Ile Asn Ile Asn
145 150 155 160

Leu Ala Asp Ser Ser Thr Thr Ala Leu Asn Ile Asp Lys Leu Ser Ile
165 170 175

Glu Gly Thr Gly Asn Lys Thr Ile Thr Leu Thr Ala Ala Asp Ile Ala
180 185 190

Lys Asp Lys Ala Asn Ile Asp Ala Val Gly Thr Ala Lys Thr Ala Leu
195 200 205

Ala Gly Leu Thr Gly Thr Pro Ala Ala Ala Ala Ile Asn Ser Ala Val
210 215 220

Ala Asp Phe Lys Thr Ala Phe Ala Lys Ala Asp Lys Asn Leu Met Ser
225 230 235 240

Asp Ala Gln Ile Lys Ala Val Thr Asp Ala Ile Thr Ala Phe Glu Ala
245 250 255

Asp Ala Thr Pro Asp Leu Thr Lys Ala Lys Ala Ile Gly Thr Ala Tyr
260 265 270

Thr Ala Pro Ala Ala Gly Asp Ile Thr Lys Ala Ser Pro Asn Ala Ser
275 280 285

Glu Ala Ile Lys Ser Ile Asp Ala Ala Leu Asp Thr Ile Ala Ser Asn
290 295 300

Arg Ala Thr Leu Gly Ala Thr Leu Asn Arg Leu Asp Phe Asn Val Asn
305 310 315 320

Asn Leu Lys Ser Gln Ser Ser Ser Met Ala Ser Ala Ala Ser Gln Ile
325 330 335

Glu Asp Ala Asp Met Ala Lys Glu Met Ser Glu Met Thr Lys Phe Lys
340 345 350

Ile Leu Asn Glu Ala Gly Ile Ser Met Leu Ser Gln Ala Asn Gln Thr
355 360 365

Pro Gln Met Val Ser Lys Leu Leu Gln
370 375

<210> SEQ ID NO 21
<211> LENGTH: 367
<212> TYPE: PRT
<213> ORGANISM: Bacillus thuringiensis

<400> SEQUENCE: 21

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Ser Gly Leu Gly Val Ala Ala Asn
50 55 60

Asn Thr Gln Asp Gly Met Ser Leu Ile Arg Thr Ala Asp Ser Ala Leu
65 70 75 80

Asn Ser Val Ser Asn Ile Leu Leu Arg Met Arg Asp Ile Ala Asn Gln
85 90 95

Ser Ala Asn Gly Thr Asn Thr Ala Asp Asn Gln Gln Ala Leu Gln Lys
100 105 110

Glu Phe Gly Gln Leu Lys Glu Gln Ile Ser Tyr Ile Ala Asp Asn Thr
115 120 125

Glu Phe Asn Asp Lys Thr Leu Leu Lys Ala Asp Asn Ser Val Lys Ile
130 135 140

```
Gln Thr Leu Asp Ser Ala Asp Thr Asn Lys Gln Ile Ser Ile Asp Leu
145                 150                 155                 160

Lys Gly Val Thr Leu Asn Gln Leu Gly Leu Asp Thr Val Asn Ile Gly
                165                 170                 175

Ser Glu Thr Leu Ser Ala Glu Ser Leu Asn Val Ala Lys Ala Thr Met
            180                 185                 190

Ala Arg Leu Val Lys Ala Asp Gln Asn Ala Asp Pro Ser Thr Phe Ala
        195                 200                 205

Leu Asp Val Asn Thr Ala Lys Glu Ser Phe Asp Lys Ile Lys Gly Phe
    210                 215                 220

Ile Thr Asn Lys Thr Asn Val Gln Asn Val Glu Asn Ala Phe Asn Asp
225                 230                 235                 240

Tyr Thr Val Ala Asp Pro Ala Asp Lys Ala Asp Lys Ala Asp Ala Ile
                245                 250                 255

Gln Ala Ala Phe Asn Thr Ala Ile Thr Gly Leu Thr Ala Gly Thr Pro
            260                 265                 270

Asn Thr Ser Asn Pro Ser Ser Ala Val Asp Ala Ile Asp Ala Ala Leu
        275                 280                 285

Lys Thr Val Ala Ser Asn Arg Ala Thr Leu Gly Ala Thr Leu Asn Arg
    290                 295                 300

Leu Asp Phe Asn Val Asn Asn Leu Lys Ser Gln Ser Ala Ser Met Ala
305                 310                 315                 320

Ser Ala Ala Ser Gln Ile Glu Asp Ala Asp Met Ala Lys Glu Met Ser
                325                 330                 335

Glu Met Thr Lys Phe Lys Ile Leu Asn Glu Ala Gly Ile Ser Met Leu
            340                 345                 350

Ser Gln Ala Asn Gln Thr Pro Gln Met Val Ser Lys Leu Leu Gln
        355                 360                 365


<210> SEQ ID NO 22
<211> LENGTH: 266
<212> TYPE: PRT
<213> ORGANISM: Bacillus thuringiensis

<400> SEQUENCE: 22

Met Arg Ile Gly Thr Asn Val Leu Ser Met Asn Ala Arg Gln Ser Leu
1               5                   10                  15

Tyr Glu Asn Glu Lys Arg Met Asn Val Ala Met Glu His Phe Ala Thr
            20                  25                  30

Gly Lys Lys Leu Asn His Ala Ser Asp Asn Pro Ala Asn Val Ala Ile
        35                  40                  45

Val Thr Arg Met His Ala Arg Ala Ser Gly Met Arg Val Ala Ile Arg
    50                  55                  60

Asn Asn Glu Asp Ala Ile Ser Met Leu Arg Thr Ala Glu Ala Ala Leu
65                  70                  75                  80

Gln Thr Val Met Asn Ile Leu Gln Arg Met Arg Asp Leu Ala Val Gln
                85                  90                  95

Ser Ala Asn Gly Thr Asn Ser Asn Lys Asn Arg Asp Ser Leu Asn Lys
            100                 105                 110

Glu Phe Gln Ser Leu Thr Glu Gln Ile Gly Tyr Ile Gly Glu Thr Thr
        115                 120                 125

Glu Phe Asn Asp Leu Ser Val Phe Asp Gly Gln Asn Arg Pro Val Thr
    130                 135                 140

Leu Asp Asp Ile Gly His Thr Val Asn Val Thr Lys His Thr Ser Pro
```

145 150 155 160

Ser Pro Thr Lys His Asp Ile Lys Ile Ser Thr Glu Gln Glu Ala Arg
165 170 175

Ala Ala Ile Arg Lys Ile Glu Glu Ala Leu Gln Asn Val Ser Leu His
180 185 190

Arg Ala Asp Phe Gly Ala Met Ile Asn Arg Leu Gln Phe Asn Ile Glu
195 200 205

Asn Leu Asn Ser Gln Ser Met Ala Leu Thr Asp Ala Ala Ser Arg Ile
210 215 220

Glu Asp Ala Asp Met Ala Gln Glu Met Ser Asp Phe Leu Lys Phe Lys
225 230 235 240

Leu Leu Thr Glu Val Ala Leu Ser Met Val Ser Gln Ala Asn Gln Ile
245 250 255

Pro Gln Met Val Ser Lys Leu Leu Gln Ser
260 265

<210> SEQ ID NO 23
<211> LENGTH: 367
<212> TYPE: PRT
<213> ORGANISM: Bacillus thuringiensis

<400> SEQUENCE: 23

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Ser Gly Leu Gly Val Ala Ala Asn
50 55 60

Asn Thr Gln Asp Gly Met Ser Leu Ile Arg Thr Ala Asp Ser Ala Leu
65 70 75 80

Asn Ser Val Ser Asn Ile Leu Leu Arg Met Arg Asp Ile Ala Asn Gln
85 90 95

Ser Ala Asn Gly Thr Asn Thr Ala Asp Asn Gln Gln Ala Leu Gln Lys
100 105 110

Glu Phe Gly Gln Leu Lys Glu Gln Ile Ser Tyr Ile Ala Asp Asn Thr
115 120 125

Glu Phe Asn Asp Lys Thr Leu Leu Lys Ala Asp Asn Ser Val Lys Ile
130 135 140

Gln Thr Leu Asp Ser Ala Asp Thr Asn Lys Gln Ile Ser Ile Asp Leu
145 150 155 160

Lys Gly Val Thr Leu Asn Gln Leu Gly Leu Asp Thr Val Asn Ile Gly
165 170 175

Ser Glu Thr Leu Ser Ala Glu Ser Leu Asn Val Ala Lys Ala Thr Met
180 185 190

Ala Arg Leu Val Lys Ala Asp Gln Asn Ala Asp Pro Ser Thr Phe Ala
195 200 205

Leu Asp Val Asn Thr Ala Lys Glu Ser Phe Asp Lys Ile Lys Gly Phe
210 215 220

Ile Thr Asn Lys Thr Asn Val Gln Asn Val Glu Asn Ala Phe Asn Asp
225 230 235 240

Tyr Thr Val Ala Asp Pro Ala Asp Lys Ala Asp Lys Ala Asp Ala Ile
245 250 255

-continued

Gln Ala Ala Phe Asn Thr Ala Ile Thr Gly Leu Thr Ala Gly Thr Pro
260 265 270

Asn Thr Ser Asn Pro Ser Ser Ala Val Asp Ala Ile Asp Ala Ala Leu
275 280 285

Lys Thr Val Ala Ser Asn Arg Ala Thr Leu Gly Ala Thr Leu Asn Arg
290 295 300

Leu Asp Phe Asn Val Asn Asn Leu Lys Ser Gln Ser Ala Ser Met Ala
305 310 315 320

Ser Ala Ala Ser Gln Ile Glu Asp Ala Asp Met Ala Lys Glu Met Ser
325 330 335

Glu Met Thr Lys Phe Lys Ile Leu Asn Glu Ala Gly Ile Ser Met Leu
340 345 350

Ser Gln Ala Asn Gln Thr Pro Gln Met Val Ser Lys Leu Leu Gln
355 360 365

<210> SEQ ID NO 24
<211> LENGTH: 266
<212> TYPE: PRT
<213> ORGANISM: Bacillus thuringiensis

<400> SEQUENCE: 24

Met Arg Ile Gly Thr Asn Val Leu Ser Met Asn Ala Arg Gln Ser Leu
1 5 10 15

Tyr Glu Asn Glu Lys Arg Met Asn Val Ala Met Glu His Leu Ala Thr
20 25 30

Gly Lys Lys Leu Asn His Ala Ser Asp Asn Pro Ala Asn Ile Val Ile
35 40 45

Val Thr Arg Met Tyr Ala Arg Ala Ser Gly Met Arg Val Ala Ile Arg
50 55 60

Asn Asn Glu Asp Ala Ile Ser Met Leu Arg Thr Ala Glu Ala Ala Leu
65 70 75 80

Gln Thr Val Thr Asn Ile Leu Gln His Met Arg Asp Phe Ala Ile Gln
85 90 95

Ser Ala Asn Gly Thr Asn Ser Asn Thr Asn Arg Asp Ser Leu Asn Lys
100 105 110

Glu Phe Gln Ser Leu Thr Glu Pro Ile Gly Tyr Ile Gly Glu Thr Thr
115 120 125

Glu Phe Asn Asp Leu Ser Val Phe Asp Gly Gln Asn Arg Pro Ile Thr
130 135 140

Leu Asp Asp Ile Gly His Thr Ile Asn Met Thr Lys His Ile Pro Pro
145 150 155 160

Ser Pro Thr Gln His Asp Ile Lys Ile Ser Thr Glu Gln Glu Ala Arg
165 170 175

Ala Ala Ile Arg Lys Ile Glu Glu Ala Leu Gln Asn Val Ser Leu His
180 185 190

Arg Ala Asp Leu Gly Ser Met Ile Asn Arg Leu Gln Phe Asn Ile Glu
195 200 205

Asn Leu Asn Ser Gln Ser Met Ala Leu Ile Asp Thr Ala Ser Gln Val
210 215 220

Glu Asp Ala Asp Met Ala Gln Glu Ile Ser Asp Phe Leu Lys Phe Lys
225 230 235 240

Leu Leu Thr Ala Val Ala Leu Ser Val Val Ser Gln Ala Asn Gln Ile
245 250 255

Pro Gln Ile Val Ser Lys Leu Leu Gln Ser
260 265

<210> SEQ ID NO 25
<211> LENGTH: 381
<212> TYPE: PRT
<213> ORGANISM: Bacillus thuringiensis

<400> SEQUENCE: 25

```
Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Ile Ser Asn Gln
                85                  90                  95

Ser Ala Asn Gly Thr Asn Thr Asp Lys Asn Gln Ser Ala Leu Asp Lys
            100                 105                 110

Glu Phe Ala Ala Leu Lys Asp Gln Ile Asp Tyr Ile Ser Lys Asn Thr
        115                 120                 125

Glu Phe Asn Asp Gln Lys Leu Leu Asp Gly Ser Lys Lys Ser Ile Ala
    130                 135                 140

Ile Gln Thr Leu Asp Asn Ala Asp Thr Asn Lys Gln Ile Asp Ile Gln
145                 150                 155                 160

Leu Ser Asn Val Ser Thr Lys Glu Leu Lys Leu Asp Thr Leu Ser Ile
                165                 170                 175

Glu Gly Ser Ser Ser Lys Thr Phe Thr Ile Thr Ala Asp Asp Met Leu
            180                 185                 190

Ala Val Gly Thr Ala Asn Ala Thr Ala Lys Ala Lys Ala Gly Thr Leu
        195                 200                 205

Lys Gly Leu Asn Val Thr Thr Gly Asp Leu Thr Ala Ala Lys Thr Asp
    210                 215                 220

Val Gln Asp Phe Arg Ala Ala Phe Asp Lys Val Lys Gly Phe Met Gly
225                 230                 235                 240

Ser Thr Glu Val Thr Asn Ile Glu Lys Ala Leu Thr Lys Phe Asp Gly
                245                 250                 255

Asp Gln Ser Leu Ala Asn Ala Lys Ala Ile Gly Asp Ala Leu Thr Ser
            260                 265                 270

Asp Leu Ala Thr Thr Ile Ala Lys Asp Gln Thr Tyr Ser Lys Asn Val
        275                 280                 285

Ser Asn Ala Ser Ser Ala Ile Ala Ser Ile Asp Ala Ala Leu Glu Ser
    290                 295                 300

Ile Ala Ser Asn Arg Ala Thr Leu Gly Ala Thr Leu Asn Arg Leu Asp
305                 310                 315                 320

Phe Asn Val Asn Asn Leu Lys Ser Gln Ser Ser Ser Met Ala Ser Ala
                325                 330                 335

Ala Ser Gln Ile Glu Asp Ala Asp Met Ala Lys Glu Met Ser Glu Met
            340                 345                 350

Thr Lys Phe Lys Ile Leu Asn Glu Ala Gly Ile Ser Met Leu Ser Gln
        355                 360                 365

Ala Asn Gln Thr Pro Gln Met Val Ser Lys Leu Leu Gln
```

370 375 380

<210> SEQ ID NO 26
<211> LENGTH: 381
<212> TYPE: PRT
<213> ORGANISM: Bacillus thuringiensis

<400> SEQUENCE: 26

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Ser Gly Leu Gly Val Ala Ala Asn
50 55 60

Asn Thr Gln Asp Gly Met Ser Leu Ile Arg Thr Ala Asp Ser Ala Met
65 70 75 80

Asn Ser Val Ser Asn Ile Leu Leu Arg Met Arg Asp Ile Ser Asn Gln
85 90 95

Ser Ala Asn Gly Thr Asn Thr Asp Lys Asn Gln Ser Ala Leu Asp Lys
100 105 110

Glu Phe Ala Ala Leu Lys Asp Gln Ile Asp Tyr Ile Ser Lys Asn Thr
115 120 125

Glu Phe Asn Asp Gln Lys Leu Leu Asp Gly Ser Lys Lys Ser Ile Ala
130 135 140

Ile Gln Thr Leu Asp Asn Ala Asp Thr Asn Lys Gln Ile Asp Ile Gln
145 150 155 160

Leu Ser Asn Val Ser Thr Lys Glu Leu Lys Leu Asp Thr Leu Ser Ile
165 170 175

Glu Gly Ser Ser Ser Lys Thr Phe Thr Ile Thr Ala Asp Asp Met Leu
180 185 190

Ala Val Gly Thr Ala Asn Ala Thr Ala Lys Ala Lys Ala Gly Thr Leu
195 200 205

Lys Gly Leu Asn Val Thr Thr Gly Asp Leu Thr Ala Ala Lys Thr Asp
210 215 220

Val Gln Asp Phe Arg Ala Ala Phe Asp Lys Val Lys Gly Phe Met Gly
225 230 235 240

Ser Thr Glu Val Thr Asn Ile Glu Lys Ala Leu Thr Lys Phe Asp Gly
245 250 255

Asp Gln Ser Leu Ala Asn Ala Lys Ala Ile Gly Asp Ala Leu Thr Ser
260 265 270

Asp Leu Ala Thr Thr Ile Ala Lys Asp Gln Thr Tyr Ser Lys Asn Val
275 280 285

Ser Asn Ala Ser Ser Ala Ile Ala Ser Ile Asp Ala Ala Leu Glu Ser
290 295 300

Ile Ala Ser Asn Arg Ala Thr Leu Gly Ala Thr Leu Asn Arg Leu Asp
305 310 315 320

Phe Asn Val Asn Asn Leu Lys Ser Gln Ser Ser Ser Met Ala Ser Ala
325 330 335

Ala Ser Gln Ile Glu Asp Ala Asp Met Ala Lys Glu Met Ser Glu Met
340 345 350

Thr Lys Phe Lys Ile Leu Asn Glu Ala Gly Ile Ser Met Leu Ser Gln
355 360 365

```
Ala Asn Gln Thr Pro Gln Met Val Ser Lys Leu Leu Gln
    370                 375                 380


<210> SEQ ID NO 27
<211> LENGTH: 381
<212> TYPE: PRT
<213> ORGANISM: Bacillus thuringiensis

<400> SEQUENCE: 27

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Ile Ser Asn Gln
                85                  90                  95

Ser Ala Asn Gly Thr Asn Thr Asp Lys Asn Gln Ser Ala Leu Asp Lys
            100                 105                 110

Glu Phe Ala Ala Leu Lys Asp Gln Ile Asp Tyr Ile Ser Lys Asn Thr
        115                 120                 125

Glu Phe Asn Asp Gln Lys Leu Leu Asp Gly Ser Lys Lys Ser Ile Ala
    130                 135                 140

Ile Gln Thr Leu Asp Asn Ala Asp Thr Asn Lys Gln Ile Asp Ile Gln
145                 150                 155                 160

Leu Ser Asn Val Ser Thr Lys Glu Leu Lys Leu Asp Thr Leu Ser Ile
                165                 170                 175

Glu Gly Ser Ser Ser Lys Thr Phe Thr Ile Thr Ala Asp Asp Met Leu
            180                 185                 190

Ala Val Gly Thr Ala Asn Ala Thr Ala Lys Ala Lys Ala Gly Thr Leu
        195                 200                 205

Lys Gly Leu Asn Val Thr Thr Gly Asp Leu Thr Ala Ala Lys Thr Asp
    210                 215                 220

Val Gln Asp Phe Arg Ala Ala Phe Asp Lys Val Lys Gly Phe Met Gly
225                 230                 235                 240

Ser Thr Glu Val Thr Asn Ile Glu Lys Ala Leu Thr Lys Phe Asp Gly
                245                 250                 255

Asp Gln Ser Leu Ala Asn Ala Lys Ala Ile Gly Asp Ala Leu Thr Ser
            260                 265                 270

Asp Leu Ala Thr Thr Ile Ala Lys Asp Gln Thr Tyr Ser Lys Asn Val
        275                 280                 285

Ser Asn Ala Ser Ser Ala Ile Ala Ser Ile Asp Ala Ala Leu Glu Ser
    290                 295                 300

Ile Ala Ser Asn Arg Ala Thr Leu Gly Ala Thr Leu Asn Arg Leu Asp
305                 310                 315                 320

Phe Asn Val Asn Asn Leu Lys Ser Gln Ser Ser Ser Met Ala Ser Ala
                325                 330                 335

Ala Ser Gln Ile Glu Asp Ala Asp Met Ala Lys Glu Met Ser Glu Met
            340                 345                 350

Thr Lys Phe Lys Ile Leu Asn Glu Ala Gly Ile Ser Met Leu Ser Gln
        355                 360                 365
```

```
Ala Asn Gln Thr Pro Gln Met Val Ser Lys Leu Leu Gln
    370                 375                 380


<210> SEQ ID NO 28
<211> LENGTH: 397
<212> TYPE: PRT
<213> ORGANISM: Bacillus thuringiensis

<400> SEQUENCE: 28

Met Thr Gly Ile Thr Ile Asn Leu Glu Ile Asp Phe Phe Ala Tyr Tyr
1               5                   10                  15

Arg Phe Ser Ile Cys Arg Lys Val Asn Ile Lys Lys Trp Gly Phe Leu
            20                  25                  30

Asn Met Arg Ile Asn Thr Asn Ile Asn Ser Met Arg Thr Gln Glu Tyr
        35                  40                  45

Met Arg Gln Asn Gln Ala Lys Met Ser Asn Ala Met Asp Arg Leu Ser
    50                  55                  60

Ser Gly Lys Arg Ile Asn Asn Ala Ser Asp Asp Ala Ala Gly Leu Ala
65                  70                  75                  80

Ile Ala Thr Arg Met Arg Ala Arg Glu Ser Gly Leu Gly Val Ala Ala
                85                  90                  95

Asn Asn Thr Gln Asp Gly Ile Ser Leu Ile Arg Thr Ala Asp Ser Ala
            100                 105                 110

Met Asn Ser Val Ser Asn Ile Leu Leu Arg Met Arg Asp Leu Ala Asn
        115                 120                 125

Gln Ser Ala Asn Gly Thr Asn Thr Asn Glu Asn Gln Ala Ala Leu Asn
    130                 135                 140

Lys Glu Phe Asp Ala Leu Lys Glu Gln Ile Asp Tyr Ile Ser Thr Asn
145                 150                 155                 160

Thr Glu Phe Asn Asp Lys Lys Leu Leu Asp Gly Ser Asn Lys Thr Ile
                165                 170                 175

Ala Val Gln Thr Leu Asp Asn Ala Asp Thr Ser Lys Gln Ile Asn Ile
            180                 185                 190

Asn Leu Ser Asn Val Ser Thr Lys Glu Leu Gly Leu Asp Thr Leu Ser
        195                 200                 205

Ile Gly Thr Asp Lys Val Glu Lys Thr Val Tyr Asp Ala Thr Thr Lys
    210                 215                 220

Ala Phe Ala Asp Leu Gly Ala Lys Thr Gly Ala Asp Lys Ala Ala Phe
225                 230                 235                 240

Asp Ala Asp Val Thr Ala Ala Met Lys Glu Phe Asp Lys Val Lys Pro
                245                 250                 255

Phe Met Ser Ala Asp Asp Val Lys Lys Ile Glu Thr Lys Leu Glu Asp
            260                 265                 270

Tyr Asn Lys Ala Asn Asp Ala Gly Ala Gln Thr Ala Ala Gln Ala Leu
        275                 280                 285

Gly Lys Glu Phe Ala Thr Leu Thr Lys Leu Glu Thr Thr Asp Leu Lys
    290                 295                 300

Ala Asn Ala Ser Gly Ala Ile Ala Ser Ile Asp Thr Ala Leu Lys Asn
305                 310                 315                 320

Ile Ala Ser Asn Arg Ala Thr Leu Gly Ala Thr Leu Asn Arg Leu Asp
                325                 330                 335

Phe Asn Val Asn Asn Leu Lys Ser Gln Ser Ser Ser Met Ala Ser Ala
            340                 345                 350

Ala Ser Gln Ile Glu Asp Ala Asp Met Ala Lys Glu Met Ser Glu Met
```

355 360 365

Thr Lys Phe Lys Ile Leu Asn Glu Ala Gly Ile Ser Met Leu Ser Gln
370 375 380

Ala Asn Gln Thr Pro Gln Met Val Ser Lys Leu Leu Gln
385 390 395

<210> SEQ ID NO 29
<211> LENGTH: 397
<212> TYPE: PRT
<213> ORGANISM: Bacillus thuringiensis

<400> SEQUENCE: 29

Met Thr Gly Ile Thr Ile Asn Leu Glu Ile Asp Phe Phe Ala Tyr Tyr
1 5 10 15

Arg Phe Ser Ile Cys Arg Lys Val Asn Ile Lys Lys Trp Gly Phe Leu
20 25 30

Asn Met Arg Ile Asn Thr Asn Ile Asn Ser Met Arg Thr Gln Glu Tyr
35 40 45

Met Arg Gln Asn Gln Ala Lys Met Ser Asn Ala Met Asp Arg Leu Ser
50 55 60

Ser Gly Lys Arg Ile Asn Asn Ala Ser Asp Asp Ala Ala Gly Leu Ala
65 70 75 80

Ile Ala Thr Arg Met Arg Ala Arg Glu Ser Gly Leu Gly Val Ala Ala
85 90 95

Asn Asn Thr Gln Asp Gly Ile Ser Leu Ile Arg Thr Ala Asp Ser Ala
100 105 110

Met Asn Ser Val Ser Asn Ile Leu Leu Arg Met Arg Asp Leu Ala Asn
115 120 125

Gln Ser Ala Asn Gly Thr Asn Thr Asn Glu Asn Gln Ala Ala Leu Asn
130 135 140

Lys Glu Phe Asp Ala Leu Lys Glu Gln Ile Asp Tyr Ile Ser Thr Asn
145 150 155 160

Thr Glu Phe Asn Asp Lys Lys Leu Leu Asp Gly Ser Asn Lys Thr Ile
165 170 175

Ala Val Gln Thr Leu Asp Asn Ala Asp Thr Ser Lys Gln Ile Asn Ile
180 185 190

Asn Leu Ser Asn Val Ser Thr Lys Glu Leu Gly Leu Ser Thr Leu Ser
195 200 205

Ile Gly Thr Asp Lys Val Glu Lys Thr Val Tyr Asp Ala Thr Thr Lys
210 215 220

Ala Phe Ala Asp Leu Gly Ala Lys Thr Gly Thr Asp Lys Ala Ala Phe
225 230 235 240

Ala Ala Asp Val Thr Ala Ala Met Lys Glu Phe Asp Lys Val Lys Pro
245 250 255

Phe Met Ser Ala Asp Asp Val Lys Lys Ile Glu Thr Lys Leu Glu Asp
260 265 270

Tyr Asn Lys Ala Asn Asp Ala Gly Ala Glu Ala Ala Ala Gln Ala Leu
275 280 285

Gly Lys Glu Phe Ala Thr Leu Thr Lys Leu Glu Thr Thr Asp Leu Lys
290 295 300

Ala Asn Ala Ser Gly Ala Ile Ala Ser Ile Asp Thr Ala Leu Lys Asn
305 310 315 320

Ile Ala Ser Asn Arg Ala Thr Leu Gly Ala Thr Leu Asn Arg Leu Asp
325 330 335

```
Phe Asn Val Asn Asn Leu Lys Ser Gln Ser Ser Ser Met Ala Ser Ala
            340                 345                 350

Ala Ser Gln Ile Glu Asp Ala Asp Met Ala Lys Glu Met Ser Glu Met
        355                 360                 365

Thr Lys Phe Lys Ile Leu Asn Glu Ala Gly Ile Ser Met Leu Ser Gln
    370                 375                 380

Ala Asn Gln Thr Pro Gln Met Val Ser Lys Leu Leu Gln
385                 390                 395


<210> SEQ ID NO 30
<211> LENGTH: 406
<212> TYPE: PRT
<213> ORGANISM: Bacillus weihenstephanensis

<400> SEQUENCE: 30

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Ser Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Leu Ser Asn Gln
                85                  90                  95

Ser Ala Asn Gly Thr Asn Thr Asp Glu Asn Gln Gln Ala Leu Asn Lys
            100                 105                 110

Glu Phe Ala Ala Leu Lys Asp Gln Ile Asp Tyr Ile Ser Lys Asn Thr
        115                 120                 125

Glu Phe Asn Asp Lys Lys Leu Leu Asp Gly Ser Asn Lys Ser Ile Ala
    130                 135                 140

Ile Gln Thr Leu Asp Asn Ala Asp Thr Thr Lys Gln Ile Asn Ile Asp
145                 150                 155                 160

Leu Ser Asn Val Ser Thr Asp Thr Leu Asn Ile Ser Gly Leu Thr Ile
                165                 170                 175

Asn Gly Lys Lys Asp Ile Thr Val Thr Ile Ser Asp Lys Asp Ile Ala
            180                 185                 190

Asn Ala Ala Thr Asp Ile Gly Lys Ala Thr Ser Ala Gln Gln Gly Leu
        195                 200                 205

Ala Asp Leu Thr Asp Thr Thr Pro Ala Val Pro Asp Thr Pro Ala Val
    210                 215                 220

Ile Gly Thr Gly Thr Ala Gly Asn Pro Gln Phe Pro Ala Val Lys Gly
225                 230                 235                 240

Thr Pro Glu Ile Pro Gly Ser Ser Pro Ala Glu Ile Ala Lys Ala Val
                245                 250                 255

Asp Asp Phe Lys Gln Ala Phe Asn Lys Val Lys Gly Leu Met Ser Asp
            260                 265                 270

Ser Ala Val Ser Ala Met Glu Gln Lys Phe Ala Thr Phe Glu Lys Asp
        275                 280                 285

Lys Ser Leu Ala Asn Ala Lys Asp Ile Gly Thr Ala Phe Ser Ala Pro
    290                 295                 300

Ile Ala Gly Asn Ile Thr Lys Gly Glu Gln Asn Ala Ser Gly Ala Ile
305                 310                 315                 320
```

Lys Ser Ile Asp Ala Ala Leu Glu Lys Ile Ala Ser Asn Arg Ala Thr
325 330 335

Leu Gly Ala Thr Leu Asn Arg Leu Asp Phe Asn Val Asn Asn Leu Lys
340 345 350

Ser Gln Ser Ser Ser Met Ala Ser Ala Ala Ser Gln Ile Glu Asp Ala
355 360 365

Asp Met Ala Lys Glu Met Ser Glu Met Thr Lys Phe Lys Ile Leu Asn
370 375 380

Glu Ala Gly Ile Ser Met Leu Ser Gln Ala Asn Gln Thr Pro Gln Met
385 390 395 400

Val Ser Lys Leu Leu Gln
405

<210> SEQ ID NO 31
<211> LENGTH: 406
<212> TYPE: PRT
<213> ORGANISM: Bacillus thuringiensis

<400> SEQUENCE: 31

Met Thr Gly Ile Thr Ile Asn Leu Glu Ile Asp Phe Phe Ala Tyr Tyr
1 5 10 15

Arg Phe Ser Ile Cys Arg Lys Val Asn Ile Lys Lys Trp Gly Phe Leu
20 25 30

Asn Met Arg Ile Asn Thr Asn Ile Asn Ser Met Arg Thr Gln Glu Tyr
35 40 45

Met Arg Gln Asn Gln Ala Lys Met Ser Asn Ala Met Asp Arg Leu Ser
50 55 60

Ser Gly Lys Arg Ile Asn Asn Ala Ser Asp Asp Ala Ala Gly Leu Ala
65 70 75 80

Ile Ala Thr Arg Met Arg Ala Arg Glu Ser Gly Leu Gly Val Ala Ala
85 90 95

Asn Asn Thr Gln Asp Gly Met Ser Leu Ile Arg Thr Ala Asp Ser Ala
100 105 110

Leu Asn Ser Val Ser Asn Ile Leu Leu Arg Met Arg Asp Ile Ala Asn
115 120 125

Gln Ser Ala Asn Gly Thr Asn Thr Gly Asp Asn Gln Lys Ala Leu Asp
130 135 140

Lys Glu Phe Ser Ala Leu Lys Glu Gln Ile Asp Tyr Ile Ser Lys Asn
145 150 155 160

Thr Glu Phe Asn Asp Lys Lys Leu Leu Asn Gly Asp Asn Lys Ser Ile
165 170 175

Ala Ile Gln Thr Leu Asp Asn Ala Asp Thr Ala Lys Gln Ile Asn Ile
180 185 190

Asn Leu Ala Asp Ser Ser Thr Lys Ala Leu Asn Ile Asp Thr Leu Ser
195 200 205

Ile Ala Gly Thr Thr Asp Lys Thr Ile Thr Ile Thr Ala Lys Asp Leu
210 215 220

Thr Asp Asn Lys Thr Thr Leu Asp Ala Leu Lys Thr Ala Lys Asp Asp
225 230 235 240

Leu Ala Lys Leu Asp Asp Lys Ser Asp Gln Ala Thr Ile Asp Lys Ala
245 250 255

Val Asp Ala Phe Lys Thr Ala Phe Asn Asn Val Asp Lys Asn Leu Leu
260 265 270

Ser Asp Lys Ala Ile Glu Gly Ile Thr Glu Lys Met Thr Ala Phe Asp

```
        275                 280                 285

Gly Thr His Thr Ala Ala Ala Ala Ile Gly Ala Ala Tyr Thr Glu Pro
    290                 295                 300

Thr Ala Ala Asp Ile Lys Lys Ser Ala Pro Asn Ala Ser Gly Ala Ile
305                 310                 315                 320

Lys Ser Ile Asp Ala Ala Leu Glu Thr Ile Ala Ser Asn Arg Ala Thr
                325                 330                 335

Leu Gly Ala Thr Leu Asn Arg Leu Asp Phe Asn Val Asn Asn Leu Lys
            340                 345                 350

Ser Gln Ser Ser Ser Met Ala Ser Ala Ala Ser Gln Ile Glu Asp Ala
        355                 360                 365

Asp Met Ala Lys Glu Met Ser Glu Met Thr Lys Phe Lys Ile Leu Asn
    370                 375                 380

Glu Ala Gly Ile Ser Met Leu Ser Gln Ala Asn Gln Thr Pro Gln Met
385                 390                 395                 400

Val Ser Lys Leu Leu Gln
                405


<210> SEQ ID NO 32
<211> LENGTH: 266
<212> TYPE: PRT
<213> ORGANISM: Bacillus thuringiensis

<400> SEQUENCE: 32

Met Arg Ile Gly Thr Asn Val Leu Ser Met Asn Ala Arg Gln Ser Leu
1               5                   10                  15

Tyr Glu Asn Glu Lys Arg Met Asn Val Ala Met Glu His Leu Ala Thr
            20                  25                  30

Gly Lys Lys Leu Asn His Ala Ser Asp Asn Pro Ala Asn Val Ala Ile
        35                  40                  45

Val Thr Arg Met His Ala Arg Ala Ser Gly Met Arg Val Ala Ile Arg
    50                  55                  60

Asn Asn Glu Asp Ala Leu Ser Met Leu Arg Thr Ala Glu Ala Thr Leu
65                  70                  75                  80

Gln Thr Val Ala Asn Ile Leu Gln Arg Met Arg Asp Leu Ala Val Gln
                85                  90                  95

Ser Ser Asn Asp Thr Asn Ser Asn Lys Asn Arg Asp Ser Leu Asn Lys
            100                 105                 110

Glu Phe Gln Ser Leu Thr Glu Gln Ile Ser Tyr Ile Gly Glu Thr Thr
        115                 120                 125

Glu Phe Asn Asp Leu Ser Val Phe Asp Gly Gln Asn Arg Pro Val Thr
    130                 135                 140

Leu Asp Asp Ile Gly His Thr Val Asn Val Thr Lys His Ile Ser Pro
145                 150                 155                 160

Ser Pro Thr Gln His Asp Ile Lys Ile Ser Thr Glu Gln Glu Ala Arg
                165                 170                 175

Ala Ala Ile Arg Lys Ile Glu Glu Ala Leu Gln Asn Val Leu Leu His
            180                 185                 190

Arg Ala Asp Leu Gly Ala Met Ile Asn Arg Leu Gln Phe Asn Ile Glu
        195                 200                 205

Asn Leu Asn Ser Gln Ser Met Ala Leu Thr Asp Ala Ala Ser Arg Ile
    210                 215                 220

Glu Asp Ala Asp Met Ala Gln Glu Met Ser Asp Phe Leu Lys Phe Lys
225                 230                 235                 240
```

```
Leu Leu Ser Glu Val Ala Leu Ser Met Val Ser Gln Ala Asn Gln Ile
            245                 250                 255

Pro Gln Met Val Ser Glu Leu Leu Gln Ser
        260                 265


<210> SEQ ID NO 33
<211> LENGTH: 393
<212> TYPE: PRT
<213> ORGANISM: Bacillus thuringiensis

<400> SEQUENCE: 33

Met Arg Ile Asn Thr Asn Ile Asn Ser Met Arg Thr Gln Glu Tyr Met
1               5                   10                  15

Arg Gln Asn Gln Thr Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Asn Gly Leu Gly Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Asp Asp Asn Gln Lys Ala Leu Asp Lys
            100                 105                 110

Glu Phe Ser Ala Leu Lys Glu Gln Ile Asp Tyr Ile Ser Lys Asn Thr
        115                 120                 125

Glu Phe Asn Asp Lys Lys Leu Leu Asn Gly Glu Asn Lys Thr Ile Ala
    130                 135                 140

Ile Gln Thr Leu Asp Asn Ala Asp Thr Thr Lys Gln Ile Asn Ile Asn
145                 150                 155                 160

Leu Ala Asp Ser Ser Thr Ser Ala Leu Gln Ile Asp Lys Leu Thr Ile
                165                 170                 175

Ser Gly Lys Thr Thr Asp Thr Thr Lys Thr Gln Thr Ile Thr Val Thr
            180                 185                 190

Asp Asp Glu Ile Lys Ala Ala Lys Thr Asp Ile Asp Glu Phe Asn Asp
        195                 200                 205

Ala Lys Lys Ala Leu Ala Asp Leu Lys Ala Glu Ser Ala Pro Ser Lys
    210                 215                 220

Gly Asp Gly Ser Ser Asp Asp Glu Ile Lys Glu Ala Val Ser Asn Phe
225                 230                 235                 240

Lys Lys Ser Phe Glu Lys Ile Gln Lys Phe Met Asn Asp Ser Asp Ile
                245                 250                 255

Lys Thr Val Gln Thr Glu Ile Glu Lys Phe Asp Ala Ala Ala Pro Ala
            260                 265                 270

Leu Asp Lys Ala Lys Gly Met Gly Ile Ala Phe Thr Ser Ala Met Asp
        275                 280                 285

Pro Lys Ala Gly Thr Ile Thr Lys Ala Ala Thr Arg Gln Asn Ala Ser
    290                 295                 300

Asp Ala Ile Lys Ser Ile Asp Ala Ala Leu Glu Thr Ile Ala Ser Asn
305                 310                 315                 320

Arg Ala Thr Leu Gly Ala Thr Leu Asn Arg Leu Asp Phe Asn Val Asn
                325                 330                 335

Asn Leu Lys Ser Gln Ser Ser Ser Met Ala Ala Ala Ala Ser Gln Ile
            340                 345                 350
```

Glu Asp Ala Asp Met Ala Lys Glu Met Ser Glu Met Thr Lys Phe Lys
        355                 360                 365

Ile Leu Asn Glu Ala Gly Ile Ser Met Leu Ser Gln Ala Asn Gln Thr
    370                 375                 380

Pro Gln Met Val Ser Lys Leu Leu Gln
385                 390

<210> SEQ ID NO 34
<211> LENGTH: 426
<212> TYPE: PRT
<213> ORGANISM: Bacillus thuringiensis

<400> SEQUENCE: 34

Met Thr Gly Ile Thr Ile Asn Leu Glu Ile Asp Phe Phe Ala Tyr Tyr
1               5                   10                  15

Arg Phe Ser Ile Cys Arg Lys Val Asn Ile Lys Lys Trp Gly Phe Leu
            20                  25                  30

Ile Met Arg Ile Asn Thr Asn Ile Asn Ser Met Arg Thr Gln Glu Tyr
        35                  40                  45

Met Arg Gln Asn Gln Thr Lys Met Ser Asn Ala Met Asp Arg Leu Ser
    50                  55                  60

Ser Gly Lys Arg Ile Asn Asn Ala Ser Asp Asp Ala Ala Gly Leu Ala
65                  70                  75                  80

Ile Ala Thr Arg Met Arg Ala Arg Glu Asn Gly Leu Gly Val Ala Ala
                85                  90                  95

Asn Asn Thr Gln Asp Gly Met Ser Leu Ile Arg Thr Ala Asp Ser Ala
            100                 105                 110

Met Asn Ser Val Ser Asn Ile Leu Leu Arg Met Arg Asp Leu Ala Asn
        115                 120                 125

Gln Ser Ala Asn Gly Thr Asn Thr Asp Asp Asn Gln Lys Ala Leu Asp
    130                 135                 140

Lys Glu Phe Ser Ala Leu Lys Glu Gln Ile Asp Tyr Ile Ser Lys Asn
145                 150                 155                 160

Thr Glu Phe Asn Asp Lys Lys Leu Leu Asn Gly Glu Asn Lys Thr Ile
                165                 170                 175

Ala Ile Gln Thr Leu Asp Asn Ala Asp Thr Thr Lys Gln Ile Asn Ile
            180                 185                 190

Asn Leu Ala Asp Ser Ser Thr Ser Ala Leu Gln Ile Asp Lys Leu Thr
        195                 200                 205

Ile Ser Gly Lys Thr Thr Asp Thr Thr Lys Thr Gln Thr Ile Thr Val
    210                 215                 220

Thr Asp Asp Glu Ile Lys Ala Ala Lys Thr Asp Ile Asp Glu Phe Asn
225                 230                 235                 240

Asp Ala Lys Lys Ala Leu Ala Asp Leu Lys Ala Glu Ser Ala Pro Ser
                245                 250                 255

Lys Gly Asp Gly Ser Ser Asp Asp Glu Ile Lys Glu Ala Val Ser Asn
            260                 265                 270

Phe Lys Lys Ser Phe Glu Lys Ile Gln Lys Phe Met Asn Asp Ser Asp
        275                 280                 285

Ile Lys Thr Val Gln Thr Glu Ile Glu Lys Phe Asp Ala Ala Ala Pro
    290                 295                 300

Ala Leu Asp Lys Ala Lys Gly Met Gly Ile Ala Phe Thr Ser Ala Met
305                 310                 315                 320

Asp Pro Lys Ala Gly Thr Ile Thr Lys Ala Ala Thr Arg Gln Asn Ala

```
                325                 330                 335

Ser Asp Ala Ile Lys Ser Ile Asp Ala Ala Leu Glu Thr Ile Ala Ser
            340                 345                 350

Asn Arg Ala Thr Leu Gly Ala Thr Leu Asn Arg Leu Asp Phe Asn Val
        355                 360                 365

Asn Asn Leu Lys Ser Gln Ser Ser Ser Met Ala Ala Ala Ala Ser Gln
    370                 375                 380

Ile Glu Asp Ala Asp Met Ala Lys Glu Met Ser Glu Met Thr Lys Phe
385                 390                 395                 400

Lys Ile Leu Asn Glu Ala Gly Ile Ser Met Leu Ser Gln Ala Asn Gln
                405                 410                 415

Thr Pro Gln Met Val Ser Lys Leu Leu Gln
            420                 425


<210> SEQ ID NO 35
<211> LENGTH: 269
<212> TYPE: PRT
<213> ORGANISM: Bacillus thuringiensis

<400> SEQUENCE: 35

Met Ser Ile Met Arg Ile Gly Thr Asn Val Leu Ser Met Asn Ala Arg
1               5                   10                  15

Gln Ser Leu Tyr Glu Asn Glu Lys Arg Met Asn Val Ala Met Glu His
            20                  25                  30

Leu Ala Thr Gly Lys Lys Leu Asn His Ala Ser Asp Asn Pro Ala Asn
        35                  40                  45

Ile Val Ile Val Thr Arg Met Tyr Ala Arg Ala Ser Gly Met Arg Val
    50                  55                  60

Ala Ile Arg Asn Asn Glu Asp Ala Ile Ser Met Leu Arg Thr Ala Glu
65                  70                  75                  80

Ala Ala Leu Gln Thr Val Thr Asn Ile Leu Gln His Met Arg Asp Phe
                85                  90                  95

Ala Ile Gln Ser Ala Asn Gly Thr Asn Ser Asn Thr Asn Arg Asp Ser
            100                 105                 110

Leu Asn Lys Glu Phe Gln Ser Leu Thr Glu Pro Ile Gly Tyr Ile Gly
        115                 120                 125

Glu Thr Thr Glu Phe Asn Asp Leu Ser Val Phe Asp Gly Gln Asn Arg
    130                 135                 140

Pro Ile Thr Leu Asp Asp Ile Gly His Thr Ile Asn Met Thr Lys His
145                 150                 155                 160

Ile Pro Pro Ser Pro Thr Gln His Asp Ile Lys Ile Ser Thr Glu Gln
                165                 170                 175

Glu Ala Arg Ala Ala Ile Arg Lys Ile Glu Glu Ala Leu Gln Asn Val
            180                 185                 190

Ser Leu His Arg Ala Asp Leu Gly Ser Met Ile Asn Arg Leu Gln Phe
        195                 200                 205

Asn Ile Glu Asn Leu Asn Ser Gln Ser Met Ala Leu Ile Asp Thr Ala
    210                 215                 220

Ser Gln Val Glu Asp Ala Asp Met Ala Gln Glu Ile Ser Asp Phe Leu
225                 230                 235                 240

Lys Phe Lys Leu Leu Thr Ala Val Ala Leu Ser Val Val Ser Gln Ala
                245                 250                 255

Asn Gln Ile Pro Gln Ile Val Ser Lys Leu Leu Gln Ser
            260                 265
```

<210> SEQ ID NO 36
<211> LENGTH: 414
<212> TYPE: PRT
<213> ORGANISM: Bacillus thuringiensis

<400> SEQUENCE: 36

```
Met Ala Arg Ile Thr Ile Asn Leu Glu Ile Asp Phe Phe Ala Tyr Tyr
1               5                   10                  15

Arg Phe Ser Ile Cys Arg Lys Val Asn Ile Lys Lys Trp Gly Phe Leu
            20                  25                  30

Asn Met Arg Ile Asn Thr Asn Ile Asn Ser Met Arg Thr Gln Asp Tyr
        35                  40                  45

Met Arg Gln Asn Gln Ala Lys Met Ser Asn Ala Met Asp Arg Leu Ser
    50                  55                  60

Ser Gly Lys Arg Ile Asn Asn Ala Ser Asp Asp Ala Ala Gly Leu Ala
65                  70                  75                  80

Ile Ala Thr Arg Met Arg Ala Arg Glu Ser Gly Leu Gly Val Ala Ala
                85                  90                  95

Asn Asn Thr Gln Asp Gly Met Ser Leu Ile Arg Thr Ala Asp Ser Ala
            100                 105                 110

Met Asn Ser Val Ser Asn Ile Leu Leu Arg Met Arg Asp Ile Ser Asn
        115                 120                 125

Gln Ser Ala Asn Gly Thr Asn Thr Asp Lys Asn Gln Ser Ala Leu Asp
    130                 135                 140

Lys Glu Phe Ala Ala Leu Lys Asp Gln Ile Asp Tyr Ile Ser Lys Asn
145                 150                 155                 160

Thr Glu Phe Asn Asp Gln Lys Leu Leu Asp Gly Ser Lys Lys Ser Ile
                165                 170                 175

Ala Ile Gln Thr Leu Asp Asn Ala Asp Thr Asn Lys Gln Ile Asp Ile
            180                 185                 190

Gln Leu Ser Asn Val Ser Thr Lys Glu Leu Lys Leu Asp Thr Leu Ser
        195                 200                 205

Ile Glu Gly Ser Ser Ser Lys Thr Phe Thr Ile Thr Ala Asp Asp Met
    210                 215                 220

Leu Ala Val Gly Thr Ala Asn Ala Thr Ala Lys Ala Lys Ala Gly Thr
225                 230                 235                 240

Leu Lys Gly Leu Asn Val Thr Thr Gly Asp Leu Thr Ala Ala Lys Thr
                245                 250                 255

Asp Val Gln Asp Phe Arg Ala Ala Phe Asp Lys Val Lys Gly Phe Met
            260                 265                 270

Gly Ser Thr Glu Val Thr Asn Ile Glu Lys Ala Leu Thr Lys Phe Asp
        275                 280                 285

Gly Asp Gln Ser Leu Ala Asn Ala Lys Ala Ile Gly Asp Ala Leu Thr
    290                 295                 300

Ser Asp Leu Ala Thr Thr Ile Ala Lys Asp Gln Thr Tyr Ser Lys Asn
305                 310                 315                 320

Val Ser Asn Ala Ser Ser Ala Ile Ala Ser Ile Asp Ala Ala Leu Glu
                325                 330                 335

Ser Ile Ala Ser Asn Arg Ala Thr Leu Gly Ala Thr Leu Asn Arg Leu
            340                 345                 350

Asp Phe Asn Val Asn Asn Leu Lys Ser Gln Ser Ser Ser Met Ala Ser
        355                 360                 365

Ala Ala Ser Gln Ile Glu Asp Ala Asp Met Ala Lys Glu Met Ser Glu
    370                 375                 380
```

Met Thr Lys Phe Lys Ile Leu Asn Glu Ala Gly Ile Ser Met Leu Ser
385 390 395 400

Gln Ala Asn Gln Thr Pro Gln Met Val Ser Lys Leu Leu Gln
405 410

<210> SEQ ID NO 37
<211> LENGTH: 266
<212> TYPE: PRT
<213> ORGANISM: Bacillus cereus

<400> SEQUENCE: 37

Met Arg Ile Gly Thr Asn Val Leu Ser Met Asn Ala Arg Gln Ser Leu
1 5 10 15

Tyr Glu Asn Glu Lys Arg Met Asn Val Ala Met Glu His Leu Ala Thr
20 25 30

Gly Lys Lys Leu Asn His Ala Ser Asn Asn Pro Ala Asn Val Ala Ile
35 40 45

Val Thr Arg Met His Ala Arg Ala Ser Gly Met Arg Val Ala Ile Arg
50 55 60

Asn Asn Glu Asp Ala Ile Ser Met Leu Arg Thr Ala Glu Ala Ala Leu
65 70 75 80

Gln Thr Val Thr Asn Val Leu Gln Arg Met Arg Asp Val Ala Val Gln
85 90 95

Ser Ala Asn Gly Thr Asn Ser Ser Lys Asn Arg Asp Ser Leu Asn Lys
100 105 110

Glu Phe Gln Ser Leu Thr Glu Gln Ile Gly Tyr Ile Asp Glu Thr Thr
115 120 125

Glu Phe Asn Asp Leu Ser Val Phe Asp Gly Gln Asn Arg Thr Val Thr
130 135 140

Leu Asp Asp Ile Gly His Thr Val Asn Val Thr Lys His Ile Pro Pro
145 150 155 160

Ser Pro Thr Gln His Asp Ile Asn Ile Ser Thr Glu Gln Glu Ala Arg
165 170 175

Ala Ala Ile Arg Lys Ile Glu Glu Ala Leu Gln Asn Val Ser Leu His
180 185 190

Arg Ala Asp Leu Gly Ala Met Ile Asn Arg Leu Gln Phe Asn Ile Glu
195 200 205

Asn Leu Asn Ser Gln Ser Thr Ala Leu Thr Asp Ala Ala Ser Arg Ile
210 215 220

Glu Asp Ala Asp Met Ala Gln Glu Met Ser Asp Phe Leu Lys Phe Lys
225 230 235 240

Leu Leu Thr Glu Val Ala Leu Ser Met Val Ser Gln Ala Asn Gln Ile
245 250 255

Pro Gln Met Val Ser Lys Leu Leu Gln Ser
260 265

<210> SEQ ID NO 38
<211> LENGTH: 494
<212> TYPE: PRT
<213> ORGANISM: Bacillus cereus

<400> SEQUENCE: 38

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

-continued

```
Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Ser Val Ala Ala Asp
    50                  55                  60

Asn Thr Gln Asn Gly Met Ser Leu Ile Arg Thr Ala Asp Ser Ala Met
65                  70                  75                  80

Asn Ser Val Ser Asn Ile Leu Leu Arg Met Arg Asp Ile Ala Asn Gln
                85                  90                  95

Ser Ala Asn Gly Thr Asn Thr Asp Lys Asn Gln Val Ala Leu Gln Lys
            100                 105                 110

Glu Phe Ala Ala Leu Lys Glu Gln Ile Thr Tyr Ile Ala Asp Asn Thr
        115                 120                 125

Gln Phe Asn Asp Lys Asn Leu Leu Asn Gly Asn Gln Thr Ile Asn Ile
    130                 135                 140

Gln Thr Leu Asp Ser His Asp Ser Thr Lys Gln Ile Gly Ile Asp Leu
145                 150                 155                 160

Lys Ser Ala Thr Leu Glu Ala Leu Gly Ile Lys Asp Leu Thr Val Gly
                165                 170                 175

Ala Val Gly Ser Thr Glu Ala Lys Asn Tyr Val Asp Ala Lys Glu Ala
            180                 185                 190

Leu Ala Lys Asn Val Ala Ala Asn Glu Phe Ile Asp Ala Lys Lys Ala
        195                 200                 205

Leu Asp Gly Asn Ala Ile Ala Lys Gly Tyr Val Glu Ala Lys Thr Ala
    210                 215                 220

Phe Asp Asp Ala Lys Pro Glu Val Lys Ala Leu Val Ser Asn Tyr Thr
225                 230                 235                 240

Asp Ala Leu Ala Ala Leu Ala Lys Asp Asp Thr Asn Asp Asp Leu Lys
                245                 250                 255

Lys Asp Val Ala Asp Thr Lys Ala Leu Met Asp Ala Asn Thr Val Ala
            260                 265                 270

Lys Thr Tyr Phe Glu Ala Lys Thr Ala His Asp Gly Ala Asp Gln Ala
        275                 280                 285

Ile Lys Asp Ile Val Thr Thr Tyr Asp Ser Lys Leu Gly Ala Leu Asp
    290                 295                 300

Asp Ala Ala Asn Lys Ala Ile Ser Asp Phe Asp Lys Ala Lys Ala Ala
305                 310                 315                 320

Phe Asp Glu Ser Pro Ala Ala Lys Glu Leu Val Lys Thr Met Asp Asp
                325                 330                 335

Ala Lys Gln Ala Ala Thr Gln Asn Asn Thr Ala Asn Ala Tyr Leu Val
            340                 345                 350

Ala Lys Ala Ala Ala Glu Leu Ala Pro Asn Asp Ala Asp Lys Lys Ala
        355                 360                 365

Glu Leu Glu Asn Ala Thr Lys Ala Leu Glu Lys Asp Asp Thr Ala Lys
    370                 375                 380

Gly Leu Val Lys Thr Tyr Glu Asn Ala Lys Glu Ala Leu Asn Pro Ala
385                 390                 395                 400

Asn Ala Met Pro Leu Asp Ala Val Lys Gln Ile Asp Ala Ala Leu Lys
                405                 410                 415

Thr Val Ala Asp Asn Arg Ala Thr Leu Gly Ala Thr Leu Asn Arg Leu
            420                 425                 430

Asp Phe Asn Val Asn Asn Leu Lys Ser Gln Ser Ser Ala Met Ala Ala
        435                 440                 445
```

```
Ser Ala Ser Gln Ile Glu Asp Ala Asp Met Ala Lys Glu Met Ser Glu
    450                 455                 460

Met Thr Lys Phe Lys Ile Leu Asn Glu Ala Gly Ile Ser Met Leu Ser
465                 470                 475                 480

Gln Ala Asn Gln Thr Pro Gln Met Val Ser Lys Leu Leu Gln
                485                 490


<210> SEQ ID NO 39
<211> LENGTH: 267
<212> TYPE: PRT
<213> ORGANISM: Bacillus thuringiensis

<400> SEQUENCE: 39

Met Arg Ile Gly Thr Asn Phe Leu Ser Met Asn Ala Arg Gln Ser Leu
1               5                   10                  15

Tyr Glu Asn Glu Lys Arg Met Asn Val Ala Met Glu His Leu Ala Thr
            20                  25                  30

Gly Lys Lys Leu Asn His Ala Ser Asp Asn Pro Ala Asn Ile Ala Ile
        35                  40                  45

Val Thr Arg Met His Ala Arg Ala Asn Gly Met Arg Val Ala Ile Arg
    50                  55                  60

Asn Asn Glu Asp Ala Ile Ser Met Leu Arg Thr Ala Glu Ala Ala Leu
65                  70                  75                  80

Gln Thr Val Met Asn Ile Leu Gln Arg Met Arg Asp Leu Ala Ile Gln
                85                  90                  95

Ser Ala Asn Ser Thr Asn Ser Asn Lys Asn Arg Asp Ser Leu Asn Lys
            100                 105                 110

Glu Phe Gln Ser Leu Thr Glu Gln Ile Ser Tyr Ile Gly Glu Thr Thr
        115                 120                 125

Glu Phe Asn Asp Leu Ser Val Phe Asp Gly Gln Asn Arg Pro Val Thr
    130                 135                 140

Leu Asp Asp Ile Gly His Thr Val His Ile Ser Lys Ser Ile Pro Pro
145                 150                 155                 160

Pro Ser Pro Thr Gln His Asp Ile Lys Ile Ser Thr Glu Gln Glu Ala
                165                 170                 175

Arg Ala Ala Ile Leu Lys Ile Glu Glu Ala Leu Gln Ser Val Ser Leu
            180                 185                 190

His Arg Ala Asp Leu Gly Ala Met Ile Asn Arg Leu His Phe Asn Ile
        195                 200                 205

Glu Asn Leu Asn Ser Gln Ser Met Ala Leu Thr Asp Ala Ala Ser Arg
    210                 215                 220

Ile Glu Asp Ala Asp Met Ala Gln Glu Met Ser Asp Phe Leu Lys Phe
225                 230                 235                 240

Lys Leu Leu Thr Glu Val Ala Leu Ser Met Val Ser Gln Ala Asn Gln
                245                 250                 255

Ile Pro Gln Met Val Ser Lys Leu Leu Gln Ser
            260                 265


<210> SEQ ID NO 40
<211> LENGTH: 377
<212> TYPE: PRT
<213> ORGANISM: Bacillus thuringiensis

<400> SEQUENCE: 40

Met Arg Ile Asn Thr Asn Ile Asn Ser Met Arg Thr Gln Glu Tyr Met
1               5                   10                  15
```

Arg Gln Asn Gln Thr Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Asn Gly Leu Gly Val Ala Ala Asn
50 55 60

Asn Thr Gln Asp Gly Met Ser Leu Ile Arg Thr Ala Asp Ser Ala Leu
65 70 75 80

Asn Ser Val Ser Asn Ile Leu Leu Arg Met Arg Asp Ile Ala Asn Gln
85 90 95

Ser Ala Asn Gly Thr Asn Thr Ser Asp Asn Gln Lys Ala Leu Asp Lys
100 105 110

Glu Phe Ser Ala Leu Lys Glu Gln Ile Asp Tyr Ile Ser Lys Asn Thr
115 120 125

Glu Phe Asn Asp Lys Lys Leu Leu Asn Gly Asp Asn Lys Ser Ile Ala
130 135 140

Ile Gln Thr Leu Asp Asn Ala Asp Thr Thr Lys Gln Ile Asn Ile Asn
145 150 155 160

Leu Ala Asp Ser Ser Thr Ser Ala Leu Asn Ile Asp Lys Leu Ser Ile
165 170 175

Glu Gly Thr Gly Asn Lys Thr Ile Thr Leu Thr Ala Ala Asp Ile Ala
180 185 190

Lys Asp Lys Thr Asn Ile Asp Ala Val Gly Thr Ala Lys Thr Ala Leu
195 200 205

Ala Gly Leu Thr Gly Thr Pro Ala Ala Ala Ala Ile Asn Ser Ala Val
210 215 220

Ala Asp Phe Lys Thr Ala Phe Ala Lys Ala Asp Lys Asn Leu Met Ser
225 230 235 240

Asp Ala Gln Ile Lys Ser Val Thr Asp Ala Ile Thr Ala Phe Glu Ala
245 250 255

Asp Ala Thr Pro Asp Leu Thr Lys Ala Lys Ala Ile Gly Thr Ala Tyr
260 265 270

Thr Ala Pro Ala Ala Gly Asp Ile Thr Lys Ala Ser Pro Asn Ala Ser
275 280 285

Glu Ala Ile Lys Ser Ile Asp Ala Ala Leu Asp Thr Ile Ala Ser Asn
290 295 300

Arg Ala Thr Leu Gly Ala Thr Leu Asn Arg Leu Asp Phe Asn Val Asn
305 310 315 320

Asn Leu Lys Ser Gln Ser Ser Ser Met Ala Ser Ala Ala Ser Gln Ile
325 330 335

Glu Asp Ala Asp Met Ala Lys Glu Met Ser Glu Met Thr Lys Phe Lys
340 345 350

Ile Leu Asn Glu Ala Gly Ile Ser Met Leu Ser Gln Ala Asn Gln Thr
355 360 365

Pro Gln Met Val Ser Lys Leu Leu Gln
370 375

<210> SEQ ID NO 41
<211> LENGTH: 406
<212> TYPE: PRT
<213> ORGANISM: Bacillus thuringiensis

<400> SEQUENCE: 41

Met Thr Gly Ile Thr Ile Asn Leu Glu Ile Asp Phe Phe Ala Tyr Tyr
1 5 10 15

```
Arg Phe Ser Ile Cys Arg Lys Val Asn Ile Lys Lys Trp Gly Phe Leu
            20                  25                  30

Asn Met Arg Ile Asn Thr Asn Ile Asn Ser Met Arg Thr Gln Glu Tyr
        35                  40                  45

Met Arg Gln Asn Gln Ala Lys Met Ser Asn Ala Met Asp Arg Leu Ser
    50                  55                  60

Ser Gly Lys Arg Ile Asn Asn Ala Ser Asp Asp Ala Ala Gly Leu Ala
65                  70                  75                  80

Ile Ala Thr Arg Met Arg Ala Arg Glu Ser Gly Leu Gly Val Ala Ala
                85                  90                  95

Asn Asn Thr Gln Asp Gly Met Ser Leu Ile Arg Thr Ala Asp Ser Ala
            100                 105                 110

Leu Asn Ser Val Ser Asn Ile Leu Leu Arg Met Arg Asp Ile Ala Asn
        115                 120                 125

Gln Ser Ala Asn Gly Thr Asn Thr Gly Asp Asn Gln Lys Ala Leu Asp
    130                 135                 140

Lys Glu Phe Ser Ala Leu Lys Glu Gln Ile Asp Tyr Ile Ser Lys Asn
145                 150                 155                 160

Thr Glu Phe Asn Asp Lys Lys Leu Leu Asn Gly Asp Asn Lys Ser Ile
                165                 170                 175

Ala Ile Gln Thr Leu Asp Asn Ala Asp Thr Ala Lys Gln Ile Asn Ile
            180                 185                 190

Asn Leu Ala Asp Ser Ser Thr Lys Ala Leu Asn Ile Asp Thr Leu Ser
        195                 200                 205

Ile Ala Gly Thr Thr Asp Lys Thr Ile Thr Ile Thr Ala Lys Asp Leu
    210                 215                 220

Thr Asp Asn Lys Ala Thr Leu Asp Ala Leu Lys Thr Ala Lys Ala Asp
225                 230                 235                 240

Leu Ala Lys Leu Asp Asp Lys Ser Asp Gln Ala Thr Ile Asp Lys Ala
                245                 250                 255

Val Asp Ala Phe Lys Thr Ala Phe Asn Asn Val Asp Lys Asn Leu Leu
            260                 265                 270

Ser Asp Lys Ala Ile Glu Gly Ile Thr Asp Lys Met Thr Ala Phe Asp
        275                 280                 285

Gly Thr His Thr Ala Ala Ala Ala Ile Gly Thr Ala Tyr Thr Glu Pro
    290                 295                 300

Thr Ala Gly Asp Ile Thr Lys Ser Ala Pro Asn Ala Ser Gly Ala Ile
305                 310                 315                 320

Lys Ser Ile Asp Ala Ala Leu Glu Thr Ile Ala Ser Asn Arg Ala Thr
                325                 330                 335

Leu Gly Ala Thr Leu Asn Arg Leu Asp Phe Asn Val Asn Asn Leu Lys
            340                 345                 350

Ser Gln Ser Ser Ser Met Ala Ser Ala Ala Ser Gln Ile Glu Asp Ala
        355                 360                 365

Asp Met Ala Lys Glu Met Ser Glu Met Thr Lys Phe Lys Ile Leu Asn
    370                 375                 380

Glu Ala Gly Ile Ser Met Leu Ser Gln Ala Asn Gln Thr Pro Gln Met
385                 390                 395                 400

Val Ser Lys Leu Leu Gln
                405
```

<210> SEQ ID NO 42
<211> LENGTH: 373

<212> TYPE: PRT
<213> ORGANISM: Bacillus thuringiensis

<400> SEQUENCE: 42

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Ser Gly Leu Gly Val Ala Ala Asn
50 55 60

Asn Thr Gln Asp Gly Met Ser Leu Ile Arg Thr Ala Asp Ser Ala Leu
65 70 75 80

Asn Ser Val Ser Asn Ile Leu Leu Arg Met Arg Asp Ile Ala Asn Gln
85 90 95

Ser Ala Asn Gly Thr Asn Thr Gly Asp Asn Gln Lys Ala Leu Asp Lys
100 105 110

Glu Phe Ser Ala Leu Lys Glu Gln Ile Asp Tyr Ile Ser Lys Asn Thr
115 120 125

Glu Phe Asn Asp Lys Lys Leu Leu Asn Gly Asp Asn Lys Ser Ile Ala
130 135 140

Ile Gln Thr Leu Asp Asn Ala Asp Thr Ala Lys Gln Ile Asn Ile Asn
145 150 155 160

Leu Ala Asp Ser Ser Thr Lys Ala Leu Asn Ile Asp Thr Leu Ser Ile
165 170 175

Ala Gly Thr Thr Asp Lys Thr Ile Thr Ile Thr Ala Lys Asp Leu Thr
180 185 190

Asp Asn Lys Ala Thr Leu Asp Ala Leu Lys Thr Ala Lys Ala Asp Leu
195 200 205

Ala Lys Leu Asp Asp Lys Ser Asp Gln Ala Thr Ile Asp Lys Ala Val
210 215 220

Asp Ala Phe Lys Thr Ala Phe Asn Asn Val Asp Lys Asn Leu Leu Ser
225 230 235 240

Asp Lys Ala Ile Glu Gly Ile Thr Asp Lys Met Thr Ala Phe Asp Gly
245 250 255

Thr His Thr Ala Ala Ala Ala Ile Gly Thr Ala Tyr Thr Glu Pro Thr
260 265 270

Ala Gly Asp Ile Thr Lys Ser Ala Pro Asn Ala Ser Gly Ala Ile Lys
275 280 285

Ser Ile Asp Ala Ala Leu Glu Thr Ile Ala Ser Asn Arg Ala Thr Leu
290 295 300

Gly Ala Thr Leu Asn Arg Leu Asp Phe Asn Val Asn Asn Leu Lys Ser
305 310 315 320

Gln Ser Ser Ser Met Ala Ser Ala Ala Ser Gln Ile Glu Asp Ala Asp
325 330 335

Met Ala Lys Glu Met Ser Glu Met Thr Lys Phe Lys Ile Leu Asn Glu
340 345 350

Ala Gly Ile Ser Met Leu Ser Gln Ala Asn Gln Thr Pro Gln Met Val
355 360 365

Ser Lys Leu Leu Gln
370

<210> SEQ ID NO 43

```
<211> LENGTH: 361
<212> TYPE: PRT
<213> ORGANISM: Bacillus thuringiensis

<400> SEQUENCE: 43

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Ile Ala Asn Gln
                85                  90                  95

Ser Ala Asn Gly Thr Asn Thr Asn Gly Asn Gln Ala Ala Leu Asn Lys
            100                 105                 110

Glu Phe Asp Ala Leu Lys Gln Gln Ile Asn Tyr Ile Ser Thr Asn Thr
        115                 120                 125

Glu Phe Asn Asp Lys Lys Leu Leu Asp Gly Ser Asn Lys Thr Ile Ala
    130                 135                 140

Ile Gln Thr Leu Asp Asn Ala Asp Thr Ser Lys Lys Ile Asp Ile Gln
145                 150                 155                 160

Leu Ala Asp Val Ser Thr Lys Ser Leu Asn Ile Asp Lys Leu Lys Ile
                165                 170                 175

Gly Gly Val Ser Lys Glu Thr Thr Asp Ala Val Gly Asp Thr Phe Thr
            180                 185                 190

Lys Leu Ser Thr Thr Ala Thr Thr Asp Met Gly Ala Leu Lys Ile Glu
        195                 200                 205

Val Glu Ala Ala Met Lys Glu Phe Asp Lys Val Lys Gly Ala Met Ser
    210                 215                 220

Ala Glu Asp Ala Lys Ala Val Thr Asp Lys Leu Asp Ala Phe Asn Thr
225                 230                 235                 240

Ala Ala Ala Ala Thr Asn Asp Ala Ala Thr Ile Ala Ala Ala Lys Ala
                245                 250                 255

Leu Gly Ala Ala Phe Asp Lys Thr Lys Val Glu Met Ala Asp Pro Asn
            260                 265                 270

Ala Ser Val Ala Ala Ile Asp Ser Ala Leu Glu Asn Ile Ala Ser Asn
        275                 280                 285

Arg Ala Thr Leu Gly Ala Thr Leu Asn Arg Leu Asp Phe Asn Val Asn
    290                 295                 300

Asn Leu Lys Ser Gln Gln Ser Ser Met Ala Ser Ala Ala Ser Gln Ile
305                 310                 315                 320

Glu Asp Ala Asp Met Ala Lys Glu Met Ser Glu Met Thr Lys Phe Lys
                325                 330                 335

Ile Leu Asn Glu Ala Gly Ile Ser Met Leu Ser Gln Ala Asn Gln Thr
            340                 345                 350

Pro Gln Met Val Ser Lys Leu Leu Gln
        355                 360


<210> SEQ ID NO 44
<211> LENGTH: 465
<212> TYPE: PRT
```

<213> ORGANISM: Bacillus cereus

<400> SEQUENCE: 44

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Ser Gly Leu Gly Val Ala Ala Asn
50 55 60

Asn Thr Gln Asp Gly Met Ala Leu Ile Arg Thr Ala Asp Ser Ala Met
65 70 75 80

Asn Ser Val Ser Asn Ile Leu Leu Arg Met Arg Asp Ile Ala Asn Gln
85 90 95

Ser Ala Asn Gly Thr Asn Thr Asp Lys Asn Gln Ala Ala Leu Gln Lys
100 105 110

Glu Phe Gly Glu Leu Gln Lys Gln Ile Asp Tyr Ile Ala Gly Asn Thr
115 120 125

Gln Phe Asn Asp Lys Asn Leu Leu Asp Gly Ser Asn Pro Ser Ile Ser
130 135 140

Ile Gln Thr Leu Asp Ser Ala Asp Gln Ser Lys Gln Ile Ser Ile Asp
145 150 155 160

Leu Lys Ser Ala Thr Leu Glu Ala Leu Gly Ile Lys Asp Leu Thr Val
165 170 175

Gly Ala Thr Glu Asn Thr Leu Ala Lys Ala Thr Ile Thr Ala Lys Asp
180 185 190

Ala Phe Asp Ala Ala Lys Asp Ala Ser Asp Ala Ala Lys Lys Glu Ile
195 200 205

Asp Ala Ala Ala Lys Asp Thr Pro Ser Lys Asn Asp Ala Gln Leu Ala
210 215 220

Lys Glu Tyr Ile Glu Ala Lys Ala Thr Leu Ala Thr Leu Lys Pro Thr
225 230 235 240

Asp Ala Thr Tyr Ala Ala Lys Ala Ala Glu Leu Asp Ala Ala Thr Thr
245 250 255

Ala Leu Asn Asp Asn Ala Lys Val Leu Val Asp Gly Tyr Glu Lys Lys
260 265 270

Leu Thr Thr Thr Lys Thr Lys Glu Ala Glu Tyr Thr Ala Ala Lys Glu
275 280 285

Gln Ser Thr Lys Ser Thr Ala Ala Ala Asp Leu Val Thr Lys Tyr Glu
290 295 300

Thr Ala Lys Ser Asn Ala Leu Gly Asn Asp Ile Ala Lys Glu Tyr Leu
305 310 315 320

Glu Ala Lys Thr Ala Tyr Glu Ala Asn Lys Asn Asp Ile Ser Ser Lys
325 330 335

Ser Arg Phe Glu Ala Ala Glu Thr Glu Leu Asn Lys Asp Ile Thr Ala
340 345 350

Asn Lys Ala Ala Lys Val Leu Val Glu Thr Tyr Glu Lys Ala Lys Thr
355 360 365

Ala Gly Thr Thr Glu Lys Ser Leu Val Ala Val Asp Lys Ile Asp Glu
370 375 380

Ala Leu Lys Thr Ile Ala Asp Asn Arg Ala Thr Leu Gly Ala Thr Leu
385 390 395 400

-continued

```
Asn Arg Leu Asp Phe Asn Val Asn Asn Leu Lys Ser Gln Ser Ala Ser
                405                 410                 415

Met Ala Ser Ala Ala Ser Gln Ile Glu Asp Ala Asp Met Ala Lys Glu
            420                 425                 430

Met Ser Glu Met Thr Lys Phe Lys Ile Leu Asn Glu Ala Gly Ile Ser
        435                 440                 445

Met Leu Ser Gln Ala Asn Gln Thr Pro Gln Met Val Ser Lys Leu Leu
    450                 455                 460

Gln
465


<210> SEQ ID NO 45
<211> LENGTH: 394
<212> TYPE: PRT
<213> ORGANISM: Bacillus thuringiensis

<400> SEQUENCE: 45

Met Thr Gly Ile Thr Ile Asn Leu Glu Ile Asp Phe Phe Ala Tyr Tyr
1               5                   10                  15

Arg Phe Ser Ile Cys Arg Lys Val Asn Ile Lys Lys Trp Gly Phe Leu
            20                  25                  30

Ile Met Arg Ile Asn Thr Asn Ile Asn Ser Met Arg Thr Gln Glu Tyr
        35                  40                  45

Met Arg Gln Asn Gln Ala Lys Met Ser Asn Ala Met Asp Arg Leu Ser
    50                  55                  60

Ser Gly Lys Arg Ile Asn Asn Ala Ser Asp Asp Ala Ala Gly Leu Ala
65                  70                  75                  80

Ile Ala Thr Arg Met Arg Ala Arg Glu Ser Gly Leu Gly Val Ala Ala
                85                  90                  95

Asn Asn Thr Gln Asp Gly Met Ser Leu Ile Arg Thr Ala Asp Ser Ala
            100                 105                 110

Met Asn Ser Val Ser Asn Ile Leu Leu Arg Met Arg Asp Leu Ala Asn
        115                 120                 125

Gln Ser Ala Asn Gly Thr Asn Thr Asn Glu Asn Gln Ala Ala Leu Asn
    130                 135                 140

Lys Glu Phe Asp Ala Leu Lys Glu Gln Ile Asn Tyr Ile Ser Thr Asn
145                 150                 155                 160

Thr Glu Phe Asn Asp Lys Lys Leu Leu Asp Gly Ser Asn Lys Thr Ile
                165                 170                 175

Ala Ile Gln Thr Leu Asp Asn Ala Asp Thr Ser Lys Lys Ile Asp Ile
            180                 185                 190

Lys Leu Ala Asp Val Ser Thr Glu Ser Leu Lys Ile Asp Lys Leu Lys
        195                 200                 205

Ile Gly Gly Val Ser Lys Glu Thr Thr Asp Ala Val Ser Glu Thr Phe
    210                 215                 220

Thr Lys Leu Ser Thr Thr Lys Thr Thr Asp Lys Asp Ala Leu Lys Ala
225                 230                 235                 240

Glu Val Glu Ala Ala Met Lys Glu Phe Asp Lys Val Lys Gly Ala Met
                245                 250                 255

Ser Thr Glu Asp Ala Lys Ala Val Thr Asp Lys Leu Gly Leu Phe Asn
            260                 265                 270

Thr Ala Ala Ala Gly Thr Asp Asp Thr Ala Ile Ala Thr Ala Ala Lys
        275                 280                 285

Asn Leu Gly Ala Ala Phe Asp Lys Thr Lys Val Asn Met Ala Asp Pro
    290                 295                 300
```

```
Asn Ala Ser Val Ala Ala Ile Asp Ser Ala Leu Glu Asn Ile Ala Ser
305                 310                 315                 320

Asn Arg Ala Thr Leu Gly Ala Thr Leu Asn Arg Leu Asp Phe Asn Val
                325                 330                 335

Asn Asn Leu Lys Ser Gln Gln Ser Ser Met Ala Ser Ala Ala Ser Gln
            340                 345                 350

Ile Glu Asp Ala Asp Met Ala Lys Glu Met Ser Glu Met Thr Lys Phe
        355                 360                 365

Lys Ile Leu Asn Glu Ala Gly Ile Ser Met Leu Ser Gln Ala Asn Gln
    370                 375                 380

Thr Pro Gln Met Val Ser Lys Leu Leu Gln
385                 390


<210> SEQ ID NO 46
<211> LENGTH: 266
<212> TYPE: PRT
<213> ORGANISM: Bacillus cereus

<400> SEQUENCE: 46

Met Arg Ile Gly Thr Asn Val Leu Ser Leu Asn Ala Arg Gln Ser Leu
1               5                   10                  15

Tyr Glu Asn Glu Lys Arg Met Asn Val Ala Met Glu His Leu Ala Thr
            20                  25                  30

Gly Lys Lys Leu Asn Asn Ala Ser Asp Asn Pro Ala Asn Ile Ala Ile
        35                  40                  45

Val Thr Arg Met His Ala Arg Ala Ser Ser Met Arg Val Ala Ile Arg
    50                  55                  60

Asn Asn Glu Asp Ala Ile Ser Met Leu Arg Thr Ala Glu Ala Ala Leu
65                  70                  75                  80

Gln Thr Val Thr Asn Val Leu Gln Arg Met Arg Asp Leu Ala Val Gln
                85                  90                  95

Ser Ala Asn Asp Thr Asn Ser Asn Lys Asn Arg Asp Ser Leu Asn Lys
            100                 105                 110

Glu Phe Gln Ser Leu Thr Glu Gln Ile Gly Tyr Ile Asp Glu Thr Thr
        115                 120                 125

Asp Phe Asn Asp Leu Ser Val Phe Asp Gly Gln Asn Arg Thr Val Thr
    130                 135                 140

Leu Asp Asp Ile Gly His Thr Val Asn Val Thr Lys His Ile Pro Pro
145                 150                 155                 160

Ser Pro Thr Gln His Asp Ile Asn Ile Ser Thr Glu Gln Glu Ala Arg
                165                 170                 175

Ala Ala Ile Arg Lys Ile Glu Glu Ala Leu Gln Asn Val Ser Leu His
            180                 185                 190

Arg Ala Asp Leu Gly Ala Met Ile Asn Arg Leu Gln Phe Asn Ile Glu
        195                 200                 205

Asn Leu Asn Ser Gln Ser Thr Ala Leu Thr Asp Ala Ala Ser Arg Ile
    210                 215                 220

Glu Asp Ala Asp Met Ala Gln Glu Met Ser Asp Phe Leu Lys Phe Lys
225                 230                 235                 240

Leu Leu Thr Glu Val Ala Leu Ser Met Val Ser Gln Ala Asn Gln Ile
                245                 250                 255

Pro Gln Met Val Ser Lys Leu Leu Gln Ser
            260                 265
```

<210> SEQ ID NO 47
<211> LENGTH: 373
<212> TYPE: PRT
<213> ORGANISM: Bacillus cereus

<400> SEQUENCE: 47

```
Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ser Asn
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Asn Glu Asn Lys Ala Ala Met Gln Lys
            100                 105                 110

Glu Phe Gly Glu Leu Lys Glu Gln Ile Lys Tyr Ile Ala Glu Asn Thr
        115                 120                 125

Gln Phe Asn Asp Gln His Leu Leu Asn Ala Asp Lys Gly Ile Thr Lys
    130                 135                 140

Glu Ile Ala Ile Gln Thr Leu Asp Ser Asp Ser Asp Ser Lys Gln Ile
145                 150                 155                 160

Lys Ile Lys Leu Gln Gly Ser Ser Leu Glu Ala Leu Asp Ile Lys Asp
                165                 170                 175

Leu Gln Ile Gly Asn Thr Glu Leu Ala Gln Lys Asp Leu Asp Leu Leu
            180                 185                 190

Asn Ala Thr Met Asp Arg Leu Asp Ala Thr Val Pro Gly Thr Arg Asp
        195                 200                 205

Val Asp Val Gln Ala Ala Lys Asp Ala Phe Asp Lys Val Lys Gly Phe
    210                 215                 220

Tyr Thr Asn Ser Asp Ser Val Lys Ala Ile Glu Arg Ala Phe Glu Asp
225                 230                 235                 240

Tyr Ala Thr Ala Ser Thr Ala Gly Thr Ala Lys Ala Asp Ala Ala Thr
                245                 250                 255

Ala Ile Lys Ala Ala Phe Asp Leu Ala Ala Asn Lys Val Gly Lys Pro
            260                 265                 270

Ala Thr Gly Gly Ala Gln Gly Ser Ala Asn Ser Leu Gly Ala Ile Thr
        275                 280                 285

Lys Ile Asp Ala Ala Leu Lys Thr Val Ala Asp Asn Arg Ala Thr Leu
    290                 295                 300

Gly Ala Thr Leu Asn Arg Leu Asp Phe Asn Val Asn Asn Leu Lys Ser
305                 310                 315                 320

Gln Ala Ser Ser Met Ala Ala Ala Ala Ser Gln Val Glu Asp Ala Asp
                325                 330                 335

Met Ala Lys Glu Met Ser Glu Met Thr Lys Phe Lys Ile Leu Asn Glu
            340                 345                 350

Ala Gly Ile Ser Met Leu Ser Gln Ala Asn Gln Thr Pro Gln Met Val
        355                 360                 365

Ser Lys Leu Leu Gln
    370
```

-continued

<210> SEQ ID NO 48
<211> LENGTH: 447
<212> TYPE: PRT
<213> ORGANISM: Bacillus cereus

<400> SEQUENCE: 48

```
Met Arg Ile Asn Thr Asn Ile Asn Ser Leu Arg Thr Gln Glu Tyr Met
1               5                   10                  15

Arg Gln Asn Gln Ala Lys Met Ser Asn Ser Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Asn Val Ala Ala Asn
    50                  55                  60

Asn Thr Gln Asp Gly Met Ser Leu Ile Arg Thr Ala Asp Ser Ala Leu
65                  70                  75                  80

Gly Ser Val Ser Asn Ile Leu Leu Arg Met Arg Asp Leu Ala Asn Gln
                85                  90                  95

Ser Ala Asn Gly Thr Asn Thr Ser Asp Asn Gln Ala Ala Met Gln Lys
            100                 105                 110

Glu Phe Ala Glu Leu Gln Lys Gln Ile Thr Tyr Ile Ala Asp Asn Thr
        115                 120                 125

Gln Phe Asn Asp Lys Asn Leu Leu Gln Ser Asn Ser Ser Ile Asn Ile
    130                 135                 140

Gln Thr Leu Asp Ser Ser Asp Gly Asn Gln Gln Ile Gly Ile Glu Leu
145                 150                 155                 160

Lys Ser Ala Ser Leu Lys Ser Leu Gly Ile Glu Asp Leu Ala Ile Gly
                165                 170                 175

Ala Ser Val Asn Pro Leu Ala Lys Ala Thr Val Glu Ala Ser Glu Ala
            180                 185                 190

Tyr Asp Lys Ala Lys Ala Asp Thr Ala Ala Phe Ala Lys Ser Ile Ala
        195                 200                 205

Asp Thr Ala Ala Thr Gly Thr Gly Ala Ala Lys Ala Asp Ala Ala Ala
    210                 215                 220

Val Asp Ala Tyr Ile Lys Glu Ala Asp Pro Thr Ala Lys Gly Asn Leu
225                 230                 235                 240

Tyr Thr Gly Leu Thr Ala Asp Gln Lys Lys Leu Ala Asp Glu His Asn
                245                 250                 255

Thr Leu Lys Ala Ala Glu Asp Gly Lys Lys Ala Glu Leu Thr Met Ala
            260                 265                 270

Thr Thr Lys Ser Thr Ala Asp Gly Thr Ala Lys Gly Leu Val Asp Ala
        275                 280                 285

Tyr Asp Asn Ala Lys Ser Asp Ala Met Asn Asp Pro Lys Ala Lys Ala
    290                 295                 300

Tyr Leu Glu Ala Lys Met Ala Tyr Glu Lys Asp Thr Ser Asn Val Ala
305                 310                 315                 320

Asn Lys Gln Lys Leu Asp Ser Thr Lys Glu Ala Met Glu Lys Asp Pro
                325                 330                 335

Ala Ser Lys Asp Leu Val Val Lys Leu Asp Ala Ala Lys Ala Ala Ala
            340                 345                 350

Thr Asn Gly Thr Pro Leu Asp Ala Val Ser Lys Ile Asp Ala Ala Leu
        355                 360                 365

Lys Thr Val Ala Asp Asn Arg Ala Thr Leu Gly Ala Thr Leu Asn Arg
    370                 375                 380
```

Leu Asp Phe Asn Val Asn Asn Leu Lys Ser Gln Ser Ser Ser Met Ala
385 390 395 400

Ser Ala Ala Ser Gln Ile Glu Asp Ala Asp Met Ala Lys Glu Met Ser
405 410 415

Glu Met Thr Lys Phe Lys Ile Leu Asn Glu Ala Gly Ile Ser Met Leu
420 425 430

Ser Gln Ala Asn Gln Thr Pro Gln Met Val Ser Lys Leu Leu Gln
435 440 445

<210> SEQ ID NO 49
<211> LENGTH: 373
<212> TYPE: PRT
<213> ORGANISM: Bacillus cereus

<400> SEQUENCE: 49

Met Arg Ile Asn Thr Asn Ile Asn Ser Met Arg Thr Gln Glu Tyr Met
1 5 10 15

Arg Gln Asn Gln Ala Lys Met Ser Asn Ala Met Asp Arg Leu Ser Ser
20 25 30

Gly Lys Arg Ile Asn Asn Ala Ser Asp Asp Ala Ala Gly Leu Ala Ile
35 40 45

Ala Thr Arg Met Arg Ala Arg Glu Ser Gly Leu Gly Val Ala Ser Asn
50 55 60

Asn Thr Gln Asp Gly Met Ser Leu Ile Arg Thr Ala Asp Ser Ala Leu
65 70 75 80

Asn Ser Val Ser Asn Ile Leu Leu Arg Met Arg Asp Leu Ala Asn Gln
85 90 95

Ser Ala Asn Gly Thr Asn Thr Asn Glu Asn Lys Ala Ala Met Gln Lys
100 105 110

Glu Phe Gly Glu Leu Lys Glu Gln Ile Lys Tyr Ile Ala Glu Asn Thr
115 120 125

Gln Phe Asn Asp Gln His Leu Leu Asn Ala Asp Lys Gly Ile Thr Lys
130 135 140

Glu Ile Ala Ile Gln Thr Leu Asp Ser Asp Ser Asp Ser Lys Gln Ile
145 150 155 160

Lys Ile Lys Leu Gln Gly Ser Ser Leu Glu Ala Leu Asp Ile Lys Asp
165 170 175

Leu Gln Ile Gly Asn Thr Glu Leu Ala Gln Lys Asp Leu Asp Leu Leu
180 185 190

Asn Ala Thr Met Asp Arg Leu Asp Ala Thr Val Pro Gly Thr Arg Asp
195 200 205

Val Asp Val Gln Ala Ala Lys Asp Ala Phe Asp Lys Val Lys Gly Phe
210 215 220

Tyr Thr Asn Ser Asp Ser Val Lys Ala Ile Glu Arg Ala Phe Glu Asp
225 230 235 240

Tyr Ala Thr Ala Ser Thr Ala Gly Thr Ala Lys Ala Asp Ala Ala Thr
245 250 255

Ala Ile Lys Ala Ala Phe Asp Leu Ala Ala Asn Lys Val Gly Lys Pro
260 265 270

Ala Thr Gly Gly Ala Gln Gly Ser Ala Asn Ser Leu Gly Ala Ile Thr
275 280 285

Lys Ile Asp Ala Ala Leu Lys Thr Val Ala Asp Asn Arg Ala Thr Leu
290 295 300

Gly Ala Thr Leu Asn Arg Leu Asp Phe Asn Val Asn Asn Leu Lys Ser

-continued

```
305                 310                 315                 320

Gln Ala Ser Ser Met Ala Ala Ala Ala Ser Gln Val Glu Asp Ala Asp
                325                 330                 335

Met Ala Lys Glu Met Ser Glu Met Thr Lys Phe Lys Ile Leu Asn Glu
            340                 345                 350

Ala Gly Ile Ser Met Leu Ser Gln Ala Asn Gln Thr Pro Gln Met Val
        355                 360                 365

Ser Lys Leu Leu Gln
    370


<210> SEQ ID NO 50
<211> LENGTH: 397
<212> TYPE: PRT
<213> ORGANISM: Bacillus cereus

<400> SEQUENCE: 50

Met Asp Phe Phe Ala Tyr Tyr Arg Phe Ser Ile Cys Arg Lys Val Asn
1               5                   10                  15

Ile Lys Lys Trp Gly Phe Phe Tyr Met Arg Ile Asn Thr Asn Ile Asn
            20                  25                  30

Ser Met Arg Thr Gln Glu Tyr Met Arg Gln Asn Gln Ala Lys Met Ser
        35                  40                  45

Asn Ala Met Asp Arg Leu Ser Ser Gly Lys Arg Ile Asn Asn Ala Ser
    50                  55                  60

Asp Asp Ala Ala Gly Leu Ala Ile Ala Thr Arg Met Arg Ala Arg Glu
65                  70                  75                  80

Ser Gly Leu Gly Val Ala Ser Asn Asn Thr Gln Asp Gly Met Ser Leu
                85                  90                  95

Ile Arg Thr Ala Asp Ser Ala Leu Asn Ser Val Ser Asn Ile Leu Leu
            100                 105                 110

Arg Met Arg Asp Leu Ala Asn Gln Ser Ala Asn Gly Thr Asn Thr Asn
        115                 120                 125

Glu Asn Lys Ala Ala Met Gln Lys Glu Phe Gly Glu Leu Lys Glu Gln
    130                 135                 140

Ile Lys Tyr Ile Ala Glu Asn Thr Gln Phe Asn Asp Gln His Leu Leu
145                 150                 155                 160

Asn Ala Asp Lys Gly Ile Thr Lys Glu Ile Ala Ile Gln Thr Leu Asp
                165                 170                 175

Ser Asp Ser Asp Ser Lys Gln Ile Lys Ile Lys Leu Gln Gly Ser Ser
            180                 185                 190

Leu Glu Ala Leu Asp Ile Lys Asp Leu Gln Ile Gly Asn Thr Glu Leu
        195                 200                 205

Ala Gln Lys Asp Leu Asp Leu Leu Asn Ala Thr Met Asp Arg Leu Asp
    210                 215                 220

Ala Thr Val Pro Gly Thr Arg Asp Val Asp Val Gln Ala Ala Lys Asp
225                 230                 235                 240

Ala Phe Asp Lys Val Lys Gly Phe Tyr Thr Asn Ser Asp Ser Val Lys
                245                 250                 255

Ala Ile Glu Arg Ala Phe Glu Asp Tyr Ala Thr Ala Ser Thr Ala Gly
            260                 265                 270

Thr Ala Lys Ala Asp Ala Ala Thr Ala Ile Lys Ala Ala Phe Asp Leu
        275                 280                 285

Ala Ala Asn Lys Val Gly Lys Pro Ala Thr Gly Gly Ala Gln Gly Ser
    290                 295                 300
```

```
Ala Asn Ser Leu Gly Ala Ile Thr Lys Ile Asp Ala Ala Leu Lys Thr
305                 310                 315                 320

Val Ala Asp Asn Arg Ala Thr Leu Gly Ala Thr Leu Asn Arg Leu Asp
                325                 330                 335

Phe Asn Val Asn Asn Leu Lys Ser Gln Ala Ser Ser Met Ala Ala Ala
            340                 345                 350

Ala Ser Gln Val Glu Asp Ala Asp Met Ala Lys Glu Met Ser Glu Met
        355                 360                 365

Thr Lys Phe Lys Ile Leu Asn Glu Ala Gly Ile Ser Met Leu Ser Gln
    370                 375                 380

Ala Asn Gln Thr Pro Gln Met Val Ser Lys Leu Leu Gln
385                 390                 395


<210> SEQ ID NO 51
<211> LENGTH: 455
<212> TYPE: PRT
<213> ORGANISM: Bacillus cereus

<400> SEQUENCE: 51

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Ile Ala Asn Gln
                85                  90                  95

Ser Ala Asn Gly Thr Asn Thr Gly Asp Asn Gln Lys Ala Leu Asp Lys
            100                 105                 110

Glu Phe Ser Ala Leu Lys Glu Gln Ile Asp Tyr Ile Ser Lys Asn Thr
        115                 120                 125

Glu Phe Asn Asp Lys Lys Leu Leu Asn Gly Glu Asn Thr Ser Ile Ala
    130                 135                 140

Ile Gln Thr Leu Asp Ser Ala Asp Thr Ala Lys Gln Ile Asn Ile Asn
145                 150                 155                 160

Leu Ala Asp Ser Ser Thr Ser Ala Leu Leu Ile Asp Lys Leu Ser Ile
                165                 170                 175

Ser Gly Ala Gly Ala Gly Thr Ala Leu Ala Gly Val Ala Thr Ala Asp
            180                 185                 190

Ile Asn Ala Ala Gly Thr Lys Gln Ala Ala Leu Ser Gly Leu Thr Gly
        195                 200                 205

Ser Lys Thr Thr Asp Glu Leu Asp Asp Ala Val Lys Glu Phe Lys Thr
    210                 215                 220

Glu Phe Asp Lys Val Lys Ser Gly Leu Ser Ala Glu Asn Ala Asp Lys
225                 230                 235                 240

Ile Thr Ala Ala Met Asp Lys Tyr Thr Asn Asn Lys Thr Leu Asp Asn
                245                 250                 255

Ala Lys Ala Ile Gly Asp Leu Tyr Lys Thr Met Ala Pro Ala Asp Ser
            260                 265                 270

Thr Val Val Gly Thr Ala Gly Thr Lys Gly Gln Ala Leu Ile Asp Leu
        275                 280                 285
```

```
Asn Ala Thr Ala Thr Gly Asp Thr Ala Gln Lys Arg Gln Val Ala Val
    290                 295                 300

Asp Ala Phe Lys Asp Asp Phe Asp Lys Ile Lys Gly Gly Leu Asn Ala
305                 310                 315                 320

Gln Asp Ala Ala Lys Val Thr Ala Ala Leu Asp Lys Phe Asn Lys Ala
                325                 330                 335

Asp Gly Ser Gly Asn Thr Leu Glu Asn Ala Gln Glu Ile Gly Lys Val
            340                 345                 350

Phe Ala Glu Val Ala Ala Gly Ser Thr Lys Ser Asn Ala Ser Asp Ala
        355                 360                 365

Ile Lys Ser Ile Asp Lys Ala Leu Glu Thr Ile Ala Ser Asn Arg Ala
    370                 375                 380

Thr Leu Gly Ala Thr Leu Asn Arg Leu Asp Phe Asn Val Asn Asn Leu
385                 390                 395                 400

Lys Ser Gln Ser Ser Ser Met Ala Ser Ala Ala Ser Gln Ile Glu Asp
                405                 410                 415

Ala Asp Met Ala Lys Glu Met Ser Glu Met Thr Lys Phe Lys Ile Leu
            420                 425                 430

Asn Glu Ala Gly Ile Ser Met Leu Ser Gln Ala Asn Gln Thr Pro Gln
        435                 440                 445

Met Val Ser Lys Leu Leu Gln
    450                 455
```

<210> SEQ ID NO 52
<211> LENGTH: 367
<212> TYPE: PRT
<213> ORGANISM: Bacillus thuringiensis

<400> SEQUENCE: 52

```
Met Arg Ile Asn Thr Asn Ile Asn Ser Met Arg Thr Gln Glu Tyr Met
1               5                   10                  15

Arg Gln Asn Gln Thr Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ser Arg Glu Gly Gly Leu Asn Val Ala Ala Arg
    50                  55                  60

Asn Thr Glu Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Ser Glu Thr Asn Thr Ser Lys Asn Gln Ala Ala Met Gln Lys
            100                 105                 110

Glu Phe Asp Gln Leu Lys Glu Gln Ile Gln Tyr Ile Ala Asp Asn Thr
        115                 120                 125

Glu Phe Asn Asp Lys Lys Leu Leu Asp Gly Ser Asn Ser Thr Ile Asn
    130                 135                 140

Ile Gln Thr Leu Asp Ser His Asp Lys Asn Lys Gln Ile Thr Ile Ser
145                 150                 155                 160

Leu Asp Ser Ala Ser Leu Lys Asn Leu Asp Ile Thr Asp Leu Ala Ile
                165                 170                 175

Gly Ser Asn Thr Val Asn Lys Asn Asp Leu Asp Thr Leu Asn Asn Ser
            180                 185                 190

Met Lys Arg Leu Glu Thr Ala Ala Ala Asp Ala Ala Val Gln Ala Gln
```

```
        195                 200                 205

Asp Val Thr Asp Ala Lys Asn Ala Phe Asn Lys Val Lys Ser Gly Tyr
    210                 215                 220

Thr Pro Ala Glu Val Glu Lys Met Glu Asp Ala Phe Lys Ala Tyr Asp
225                 230                 235                 240

Lys Val Val Ala Asp Pro Ala Lys Thr Asp Ala Leu Leu Lys Ala Ala
                245                 250                 255

Ala Glu Lys Ile Asn Thr Glu Phe Lys Thr Leu Thr Ala Pro Thr Ala
            260                 265                 270

Thr Ala Phe Asp Pro Ser Ser Ser Val Glu Lys Ile Asp Lys Ala Ile
        275                 280                 285

Glu Thr Ile Ala Ser Ser Arg Ala Thr Leu Gly Ala Thr Leu Asn Arg
    290                 295                 300

Leu Asp Phe Asn Val Thr Asn Leu Lys Ser Gln Glu Asn Ser Met Ala
305                 310                 315                 320

Ala Ser Ala Ser Gln Ile Glu Asp Ala Asp Met Ala Lys Glu Met Ser
                325                 330                 335

Glu Met Thr Lys Phe Lys Ile Leu Asn Glu Ala Gly Ile Ser Met Leu
            340                 345                 350

Ser Gln Ala Asn Gln Thr Pro Gln Met Val Ser Lys Leu Leu Gln
        355                 360                 365


<210> SEQ ID NO 53
<211> LENGTH: 367
<212> TYPE: PRT
<213> ORGANISM: Bacillus thuringiensis

<400> SEQUENCE: 53

Met Arg Ile Asn Thr Asn Ile Asn Ser Met Arg Thr Gln Glu Tyr Met
1               5                   10                  15

Arg Gln Asn Gln Thr Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ser Arg Glu Gly Gly Leu Asn Val Ala Ala Arg
    50                  55                  60

Asn Thr Glu Asp Gly Met Ser Leu Ile Arg Thr Ala Asp Ser Ala Leu
65                  70                  75                  80

Asn Ser Val Ser Asn Ile Leu Leu Arg Met Arg Asp Leu Ala Asn Gln
                85                  90                  95

Ser Ala Ser Glu Thr Asn Thr Ser Lys Asn Gln Ala Ala Met Gln Lys
            100                 105                 110

Glu Phe Asp Gln Leu Lys Glu Gln Ile Gln Tyr Ile Ala Asp Asn Thr
        115                 120                 125

Glu Phe Asn Asp Lys Lys Leu Leu Asp Gly Ser Asn Ser Thr Ile Asn
    130                 135                 140

Ile Gln Thr Leu Asp Ser His Asp Lys Asn Lys Gln Ile Thr Ile Ser
145                 150                 155                 160

Leu Asp Ser Ala Ser Leu Lys Asn Leu Asp Ile Thr Asp Leu Ala Ile
                165                 170                 175

Gly Ser Asn Thr Val Asn Lys Asn Asp Leu Asp Thr Leu Asn Asn Ser
            180                 185                 190

Met Lys Arg Leu Glu Thr Ala Ala Ala Asp Ala Ala Val Gln Ala Gln
        195                 200                 205
```

```
Asp Val Thr Asp Ala Lys Asn Ala Phe Asn Lys Val Lys Ser Gly Tyr
    210                 215                 220

Thr Pro Ala Glu Val Glu Lys Met Glu Asp Ala Phe Lys Ala Tyr Asp
225                 230                 235                 240

Lys Val Val Ala Asp Pro Ala Lys Thr Asp Ala Leu Leu Lys Ala Ala
                245                 250                 255

Ala Glu Lys Ile Asn Thr Glu Phe Lys Thr Leu Thr Ala Pro Thr Ala
            260                 265                 270

Thr Ala Phe Asp Pro Ser Ser Ser Val Glu Lys Ile Asp Lys Ala Ile
        275                 280                 285

Glu Thr Ile Ala Ser Ser Arg Ala Thr Leu Gly Ala Thr Leu Asn Arg
    290                 295                 300

Leu Asp Phe Asn Val Thr Asn Leu Lys Ser Gln Glu Asn Ser Met Ala
305                 310                 315                 320

Ala Ser Ala Ser Gln Ile Glu Asp Ala Asp Met Ala Lys Glu Met Ser
                325                 330                 335

Glu Met Thr Lys Phe Lys Ile Leu Asn Glu Ala Gly Ile Ser Met Leu
            340                 345                 350

Ser Gln Ala Asn Gln Thr Pro Gln Met Val Ser Lys Leu Leu Gln
        355                 360                 365


<210> SEQ ID NO 54
<211> LENGTH: 381
<212> TYPE: PRT
<213> ORGANISM: Bacillus thuringiensis

<400> SEQUENCE: 54

Met Gly Val Leu Asn Met Arg Ile Asn Thr Asn Ile Asn Ser Met Arg
1               5                   10                  15

Thr Gln Glu Tyr Met Arg Gln Asn Gln Ala Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Asn Gly Leu
    50                  55                  60

Gly Val Ala Ala Asn Asn Thr Gln Asp Gly Met Ser Leu Ile Arg Thr
65                  70                  75                  80

Ala Asp Ser Ala Leu Asn Ser Val Ser Asn Ile Leu Leu Arg Met Arg
                85                  90                  95

Asp Ile Ala Asn Gln Ser Ala Asn Gly Thr Asn Thr Gly Asp Asn Gln
            100                 105                 110

Lys Ala Leu Asp Lys Glu Phe Ser Ala Leu Lys Glu Gln Ile Asp Tyr
        115                 120                 125

Ile Ser Lys Asn Thr Glu Phe Asn Asp Lys Lys Leu Leu Asn Gly Asp
    130                 135                 140

Asn Lys Ser Ile Ala Ile Gln Thr Leu Asp Asn Ala Asp Thr Ser Lys
145                 150                 155                 160

Gln Ile Asn Ile Asp Leu Ala Asn Thr Ser Thr Ser Ser Leu Lys Ile
                165                 170                 175

Asp Lys Leu Ser Ile Glu Gly Lys Gly Asn Gln Thr Ile Ala Ile Thr
            180                 185                 190

Ala Ala Asp Ile Ala Lys Asp Thr Asn Ile Ala Ala Leu Thr Ser Ala
        195                 200                 205

Gln Gly Lys Leu Ala Ala Leu Thr Gly Thr Pro Ala Pro Ala Ala Leu
    210                 215                 220
```

Thr Thr Ala Val Asp Glu Phe Lys Ala Ala Phe Glu Lys Val Asp Lys
225 230 235 240

Asn Leu Met Ser Asp Thr Gln Ile Thr Gly Ile Glu Asn Ala Ile Lys
245 250 255

Ala Tyr Asp Gly Ala Thr Thr Lys Thr Leu Ala Leu Ala Gln Ala Val
260 265 270

Gly Thr Ala Tyr Thr Ala Pro Thr Pro Gly Asp Ile Thr Lys Glu Leu
275 280 285

Pro Asn Ala Ser Ser Ser Ile Lys Ser Ile Asp Ala Ala Leu Glu Thr
290 295 300

Ile Ala Ser Asn Arg Ala Thr Leu Gly Ala Thr Leu Asn Arg Leu Asp
305 310 315 320

Phe Asn Val Asn Asn Leu Lys Ser Gln Ala Ser Ser Met Ala Ser Ala
325 330 335

Ala Ser Gln Ile Glu Asp Ala Asp Met Ala Lys Glu Met Ser Glu Met
340 345 350

Thr Lys Phe Lys Ile Leu Asn Glu Ala Gly Ile Ser Met Leu Ser Gln
355 360 365

Ala Asn Gln Thr Pro Gln Met Val Ser Lys Leu Leu Gln
370 375 380

<210> SEQ ID NO 55
<211> LENGTH: 364
<212> TYPE: PRT
<213> ORGANISM: Bacillus thuringiensis

<400> SEQUENCE: 55

Met Gly Val Leu Asn Met Arg Ile Asn Thr Asn Ile Asn Ser Met Arg
1 5 10 15

Thr Gln Glu Tyr Met Arg Gln Asn Gln Ala Lys Met Ser Asn Ala Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ala Asn Asn Thr Gln Asp Gly Ile Ser Leu Ile Arg Thr
65 70 75 80

Ala Asp Ser Ala Met Asn Ser Val Ser Asn Ile Leu Leu Arg Met Arg
85 90 95

Asp Leu Ala Asn Gln Ser Ala Asn Gly Thr Asn Thr Ser Glu Asn Gln
100 105 110

Ala Ala Leu Asp Lys Glu Phe Gly Ala Leu Lys Glu Gln Ile Asn Tyr
115 120 125

Ile Ser Thr Asn Thr Glu Phe Asn Asp Lys Lys Leu Leu Asp Gly Ser
130 135 140

Asn Glu Thr Ile Ala Ile Gln Thr Leu Asp Asn Ala Asp Glu Gly Lys
145 150 155 160

Lys Ile Asp Ile Lys Leu Ala Asn Val Ser Thr Asp Ser Leu Lys Ile
165 170 175

Asp Lys Leu Thr Ile Gly Gly Ala Ala Gln Lys Thr Val Asp Ala Val
180 185 190

Ala Asp Lys Phe Asn Ala Leu Lys Thr Thr Thr Thr Thr Asp Lys Ala
195 200 205

Ala Ile Gln Thr Glu Val Asp Ala Val Met Lys Glu Phe Asp Lys Val

```
    210                 215                 220

Lys Gly Ser Met Ser Ala Glu Asp Ala Lys Val Ile Thr Asp Lys Leu
225                 230                 235                 240

Lys Asp Tyr Asn Asp Ala Ala Asp Thr Asp Thr Ala Lys Ala Thr Ala
                245                 250                 255

Ala Lys Asp Leu Gly Ala Ala Phe Asp Lys Thr Lys Val Asn Ile Ala
            260                 265                 270

Asn Pro Asn Ala Ala Val Ala Ala Ile Asp Ser Ala Leu Glu Asn Ile
        275                 280                 285

Ala Ser Asn Arg Ala Thr Leu Gly Ala Thr Leu Asn Arg Leu Asp Phe
    290                 295                 300

Asn Val Asn Asn Leu Lys Ser Gln Ser Ser Ser Met Ala Ser Ala Ala
305                 310                 315                 320

Ser Gln Ile Glu Asp Ala Asp Met Ala Lys Glu Met Ser Glu Met Thr
                325                 330                 335

Lys Phe Lys Ile Leu Asn Glu Ala Gly Ile Ser Met Leu Ser Gln Ala
            340                 345                 350

Asn Gln Thr Pro Gln Met Val Ser Lys Leu Leu Gln
        355                 360


<210> SEQ ID NO 56
<211> LENGTH: 266
<212> TYPE: PRT
<213> ORGANISM: Bacillus cereus

<400> SEQUENCE: 56

Met Arg Ile Gly Thr Asn Val Leu Ser Met Asn Ala Arg Gln Ser Leu
1               5                   10                  15

Tyr Glu Asn Glu Lys Arg Met Asn Val Ala Met Glu His Leu Ala Thr
            20                  25                  30

Gly Lys Lys Leu Asn His Ala Ser Asn Asn Pro Ala Asn Ile Ala Ile
        35                  40                  45

Val Thr Arg Met His Ala Arg Ala Ser Gly Met Arg Val Ala Ile Arg
    50                  55                  60

Asn Asn Glu Asp Ala Leu Ser Met Leu Arg Thr Ala Glu Ala Ala Leu
65                  70                  75                  80

Gln Thr Val Thr Asn Ile Leu Gln Arg Met Arg Asp Leu Ala Val Gln
                85                  90                  95

Ser Ala Asn Val Thr Asn Ser Asn Lys Asn Arg Asn Ser Leu Asn Lys
            100                 105                 110

Glu Phe Gln Ser Leu Thr Glu Gln Ile Ser Tyr Ile Gly Glu Thr Thr
        115                 120                 125

Glu Phe Asn Asp Leu Ser Val Phe Asp Gly Gln Asn Arg Pro Val Thr
    130                 135                 140

Leu Asp Asp Ile Gly Tyr Thr Val Asn Val Thr Lys His Thr Pro Pro
145                 150                 155                 160

Ser Pro Thr Gln His Asp Ile Lys Ile Ser Thr Glu Gln Glu Ala Arg
                165                 170                 175

Ala Ala Ile Arg Lys Ile Glu Glu Ala Leu Gln Asn Val Ser Leu His
            180                 185                 190

Arg Ala Asp Leu Gly Ser Met Met Asn Arg Leu Gln Phe Asn Ile Glu
        195                 200                 205

Asn Leu Asn Ser Gln Ser Met Ala Leu Thr Asp Ala Ala Ser Arg Ile
    210                 215                 220
```

```
Glu Asp Ala Asp Met Ala Gln Glu Met Ser Asp Phe Leu Lys Phe Lys
225                 230                 235                 240

Leu Leu Thr Glu Val Ala Leu Ser Met Val Ser Gln Ala Asn Gln Ile
                245                 250                 255

Pro Gln Met Val Ser Lys Leu Leu Gln Ser
            260                 265


<210> SEQ ID NO 57
<211> LENGTH: 460
<212> TYPE: PRT
<213> ORGANISM: Bacillus cereus

<400> SEQUENCE: 57

Met Arg Ile Asn Thr Asn Ile Asn Ser Met Arg Thr Gln Glu Tyr Met
1               5                   10                  15

Arg Gln Asn Gln Ala Lys Met Ser Thr Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Ile Ser Leu Ile Arg Thr Ala Asp Ser Ala Met
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Asp Lys Asn Gln Gly Ala Leu Asp Lys
            100                 105                 110

Glu Phe Ala Ala Leu Lys Glu Gln Ile Asp Tyr Ile Ser Lys Asn Thr
        115                 120                 125

Glu Phe Asn Asp Lys Lys Leu Leu Asp Gly Ser Asn Lys Ala Ile Ala
    130                 135                 140

Ile Gln Thr Leu Asp Ser Asp Asp Lys Gly Lys Gln Ile Asp Ile Ser
145                 150                 155                 160

Leu Ser Asp Thr Ser Thr Thr Ala Leu Lys Ile Asn Asn Leu Ser Ile
                165                 170                 175

Ala Ala Asn Gly Leu Gly Ile Gly Ser Gly Lys Glu Leu Val Gly Val
            180                 185                 190

Ala Asp Asn Thr Ile Ala Asn Ala Ser Ala Glu Ala Leu Lys Lys Leu
        195                 200                 205

Asp Gly Thr Thr Gly Asp Thr Asp Val Lys Arg Ser Asn Ala Val Lys
    210                 215                 220

Ala Phe Thr Asp Gln Tyr Lys Asp Leu Lys Val Ala Met Asn Ala Lys
225                 230                 235                 240

Asp Val Glu Thr Ile Asp Ala Ala Ile Lys Lys Phe Glu Gly Ala Asn
                245                 250                 255

Thr Leu Glu Asn Ala Gln Ala Ile Gly Ala Ala Phe Glu Gly Ala Ala
            260                 265                 270

Lys Ala Thr Leu Thr Thr Asp Ile Asn Asn Ala Thr Leu Thr Ser Lys
        275                 280                 285

Ala Leu Ser Asp Leu Asp Thr Asp Ser Thr Thr Glu Thr Arg Lys Ala
    290                 295                 300

Ala Met Lys Asp Phe Val Ala Ala Phe Asp Lys Val Lys Gly Ser Met
305                 310                 315                 320

Asn Ser Ser Asp Val Thr Lys Ile Ser Asp Ala Ile Asp Arg Phe Ser
                325                 330                 335
```

```
Lys Thr Asp Asp Ser Gly Asn Thr Leu Glu Ala Ala Arg Ala Ile Gly
            340                 345                 350

Asp Ala Phe Lys Ala Ala Thr Thr Asn Gly Lys Thr Ser Thr Ala Thr
        355                 360                 365

Asp Ala Asn Ser Ala Ile Lys Ala Ile Asp Glu Ala Leu Glu Thr Ile
    370                 375                 380

Ala Ser Asn Arg Ala Thr Leu Gly Ala Thr Leu Asn Arg Leu Asp Phe
385                 390                 395                 400

Asn Val Asn Asn Leu Lys Asn Gln Ala Ser Ser Met Ala Ser Ala Ala
                405                 410                 415

Ser Gln Val Glu Asp Ala Asp Met Ala Lys Glu Met Ser Glu Met Thr
            420                 425                 430

Lys Phe Lys Ile Leu Asn Glu Ala Gly Ile Ser Met Leu Ser Gln Ala
        435                 440                 445

Asn Gln Thr Pro Gln Met Val Ser Lys Leu Leu Gln
    450                 455                 460


<210> SEQ ID NO 58
<211> LENGTH: 399
<212> TYPE: PRT
<213> ORGANISM: Bacillus cereus

<400> SEQUENCE: 58

Met Arg Ile Asn Thr Asn Ile Asn Ser Met Arg Thr Gln Glu Tyr Met
1               5                   10                  15

Arg Gln Asn Gln Ala Lys Met Ser Thr Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Ile Ser Leu Ile Arg Thr Ala Asp Ser Ala Met
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Asp Lys Asn Gln Ala Ala Leu Asp Lys
            100                 105                 110

Glu Phe Asn Ala Leu Lys Glu Gln Ile Asp Tyr Ile Ser Lys Asn Thr
        115                 120                 125

Glu Phe Asn Asp Lys Lys Leu Leu Asp Gly Ser Asn Lys Ser Ile Ala
    130                 135                 140

Val Gln Thr Leu Asp Asn Ala Asp Thr Ser Lys Gln Ile Asn Ile Asn
145                 150                 155                 160

Leu Ser Asn Thr Ser Thr Lys Ala Leu Glu Ile Asn Ser Leu Thr Ile
                165                 170                 175

Ser Gly Thr Thr Pro Ile Ala Gly Lys Asn Glu Thr Ser Lys Ile Thr
            180                 185                 190

Ala Glu Gln Met Thr Ala Ala Ser Asp Ala Leu Glu Lys Phe Lys Thr
        195                 200                 205

Ala Gln Glu Gly Leu Ala Asn Leu Thr Glu Pro Thr Lys Gly Ser Asp
    210                 215                 220

Gly Lys Pro Glu Ala Gly Thr Gly Ser Ser Asn Glu Asp Ile Val Lys
225                 230                 235                 240

Ala Val Lys Ala Phe Lys Glu Ala Phe Lys Asn Ile Gln Pro Leu Met
```

245 250 255

Ser Asp Thr Asp Ile Thr Thr Val Gln Asn Lys Ile Asp Leu Phe Asp
260 265 270

Glu Asp Ala Pro Asp Leu Ser Ala Ala Lys Leu Ile Gly Thr Thr Phe
275 280 285

Glu Glu Ser Met Lys Pro Val Ala Asp Lys Glu Ile Thr Lys Ala Ala
290 295 300

Val Lys Pro Asn Ala Ser Asp Ala Ile Ala Ala Ile Asp Ala Ala Leu
305 310 315 320

Thr Lys Val Ala Asp Asn Arg Ala Thr Leu Gly Ala Thr Leu Asn Arg
325 330 335

Leu Asp Phe Asn Val Asn Asn Leu Lys Ser Gln Ala Ser Ser Met Ala
340 345 350

Ser Ala Ala Ser Gln Val Glu Asp Ala Asp Met Ala Lys Glu Met Ser
355 360 365

Glu Met Thr Lys Phe Lys Ile Leu Asn Glu Ala Gly Ile Ser Met Leu
370 375 380

Ser Gln Ala Asn Gln Thr Pro Gln Met Val Ser Lys Leu Leu Gln
385 390 395

<210> SEQ ID NO 59
<211> LENGTH: 266
<212> TYPE: PRT
<213> ORGANISM: Bacillus cereus

<400> SEQUENCE: 59

Met Arg Ile Gly Thr Asn Val Leu Ser Leu Asn Ala Arg Gln Ser Leu
1 5 10 15

Tyr Glu Asn Glu Lys Arg Met Asn Val Ala Met Glu His Leu Ala Thr
20 25 30

Gly Lys Lys Leu Asn Asn Ala Ser Asp Asn Pro Ala Asn Ile Ala Ile
35 40 45

Val Thr Arg Met His Ala Arg Ala Ser Gly Met Arg Val Ala Ile Arg
50 55 60

Asn Asn Glu Asp Ala Ile Ser Met Leu Arg Thr Ala Glu Ala Ala Leu
65 70 75 80

Gln Thr Val Thr Asn Val Leu Gln Arg Met Arg Asp Leu Ala Val Gln
85 90 95

Ser Ala Asn Gly Thr Asn Ser Asn Lys Asn Arg Asp Ser Leu Asn Lys
100 105 110

Glu Phe Gln Ser Leu Thr Glu Gln Ile Gly Tyr Ile Asp Glu Thr Thr
115 120 125

Glu Phe Asn Asn Leu Ser Val Phe Asp Gly Gln Asn Arg Pro Val Thr
130 135 140

Leu Asp Asp Ile Gly His Thr Val Asn Val Thr Lys His Ile Pro Pro
145 150 155 160

Phe Pro Thr Gln His Asp Ile Asn Ile Ser Thr Glu Gln Glu Ala Arg
165 170 175

Ala Ala Ile Arg Lys Ile Glu Glu Ala Leu Gln Asn Val Ser Leu His
180 185 190

Arg Ala Asp Leu Gly Ala Met Ile Asn Arg Leu Gln Phe Asn Ile Glu
195 200 205

Asn Leu Asn Ser Gln Ser Thr Ala Leu Thr Asp Ala Ala Ser Arg Ile
210 215 220

```
Glu Asp Ala Asp Met Ala Gln Glu Met Ser Asp Phe Leu Lys Phe Lys
225                 230                 235                 240

Leu Leu Thr Glu Val Ala Leu Ser Met Val Ser Gln Ala Asn Gln Val
                245                 250                 255

Pro Gln Met Val Ser Lys Leu Leu Gln Ser
            260                 265


<210> SEQ ID NO 60
<211> LENGTH: 269
<212> TYPE: PRT
<213> ORGANISM: Bacillus thuringiensis

<400> SEQUENCE: 60

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala His Glu Ser Gly Leu Ser Val Ala Ala Arg
    50                  55                  60

Asn Thr Ser Asp Gly Ile Ser Leu Ile Arg Thr Ala Asp Ser Ala Leu
65                  70                  75                  80

Gln Ser Val Ser Asn Ile Leu Leu Arg Met Arg Asp Ile Ala Asn Gln
                85                  90                  95

Thr Ala Asn Gly Thr Asn Lys Asp Thr Asp Ile Glu Ala Leu Gly Lys
            100                 105                 110

Glu Phe Ala Ala Leu Lys Glu Gln Ile Thr Tyr Val Ser Asp Asn Thr
        115                 120                 125

Lys Phe Asn Gly Arg Glu Leu Leu Lys Gly Gly Asp Asp Ile Asn Ile
    130                 135                 140

Gln Thr Tyr Asp Gly Ser Asp Glu Ser Gln Gln Ile Lys Ile Lys Ile
145                 150                 155                 160

Ser Glu Leu Asp Leu Ser Ser Leu Asp Thr Gly Glu Val Thr Asp Ser
                165                 170                 175

Asp Thr Ala Arg Gly Thr Val Ser Thr Leu Asp Asp Ala Ile Thr Asn
            180                 185                 190

Ile Ala Ser Lys Arg Ala Glu Leu Gly Ala Thr Leu Asn Arg Leu Asp
        195                 200                 205

Tyr Asn Thr Gln Asn Val Asn Ser Glu Ala Ala Ser Met Ala Ala Ser
    210                 215                 220

Ala Ser Gln Ile Glu Asp Ala Asp Met Ala Lys Glu Met Ser Glu Met
225                 230                 235                 240

Thr Lys Phe Lys Ile Leu Ser Glu Ala Gly Ile Ser Met Leu Ser Gln
                245                 250                 255

Ala Asn Gln Thr Pro Gln Met Val Ser Lys Leu Leu Gln
            260                 265


<210> SEQ ID NO 61
<211> LENGTH: 269
<212> TYPE: PRT
<213> ORGANISM: Bacillus cereus

<400> SEQUENCE: 61

Met Arg Ile Asn Thr Asn Ile Asn Ser Met Arg Thr Gln Glu Tyr Met
1               5                   10                  15
```

```
Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala His Glu Ser Gly Leu Ser Val Ala Ala Arg
    50                  55                  60

Asn Thr Ser Asp Gly Ile Ser Leu Ile Arg Thr Ala Asp Ser Ala Leu
65                  70                  75                  80

Gln Ser Val Ser Asn Ile Leu Leu Arg Met Arg Asp Ile Ala Asn Gln
                85                  90                  95

Thr Ala Asn Gly Thr Asn Lys Asp Thr Asp Ile Glu Ala Leu Gly Lys
            100                 105                 110

Glu Phe Ala Ala Leu Lys Glu Gln Ile Thr Tyr Val Ser Asp Asn Thr
        115                 120                 125

Lys Phe Asn Gly Arg Glu Leu Leu Lys Gly Gly Asp Asp Ile Asn Ile
    130                 135                 140

Gln Thr Tyr Asp Gly Ser Asp Glu Ser Gln Gln Ile Lys Ile Lys Ile
145                 150                 155                 160

Ser Glu Leu Asp Leu Ser Ser Leu Asp Thr Gly Glu Val Thr Asp Ser
                165                 170                 175

Asp Thr Ala Arg Gly Thr Val Ser Thr Leu Asp Asp Ala Ile Thr Asn
            180                 185                 190

Ile Ala Ser Lys Arg Ala Glu Leu Gly Ala Thr Leu Asn Arg Leu Asp
        195                 200                 205

Tyr Asn Thr Gln Asn Val Asn Ser Glu Ala Ala Ser Met Ala Ala Ser
    210                 215                 220

Ala Ser Gln Ile Glu Asp Ala Asp Met Ala Lys Glu Met Ser Glu Met
225                 230                 235                 240

Thr Lys Phe Lys Ile Leu Ser Glu Ala Gly Ile Ser Met Leu Ser Gln
                245                 250                 255

Ala Asn Gln Thr Pro Gln Met Val Ser Lys Leu Leu Gln
            260                 265


<210> SEQ ID NO 62
<211> LENGTH: 267
<212> TYPE: PRT
<213> ORGANISM: Bacillus thuringiensis

<400> SEQUENCE: 62

Met Arg Ile Gly Thr Asn Phe Leu Ser Met Asn Ala Arg Gln Ser Leu
1               5                   10                  15

Tyr Glu Asn Glu Lys Arg Met Asn Val Ala Met Glu His Leu Ala Thr
            20                  25                  30

Gly Lys Lys Leu Asn His Ala Ser Asp Asn Pro Ala Asn Ile Ala Ile
        35                  40                  45

Val Thr Arg Met His Ala Arg Ala Asn Gly Met Arg Val Ala Ile Arg
    50                  55                  60

Asn Asn Glu Asp Ala Ile Ser Met Leu Arg Thr Ala Glu Ala Ala Leu
65                  70                  75                  80

Gln Thr Val Met Asn Ile Leu Gln Arg Met Arg Asp Leu Ala Ile Gln
                85                  90                  95

Ser Ala Asn Ser Thr Asn Ser Asn Lys Asn Arg Asp Ser Leu Asn Lys
            100                 105                 110

Glu Phe Gln Ser Leu Thr Glu Gln Ile Ser Tyr Ile Gly Glu Thr Thr
        115                 120                 125
```

```
Glu Phe Asn Asp Leu Ser Val Phe Asp Gly Gln Asn Arg Pro Val Thr
    130                 135                 140

Leu Asp Asp Ile Gly His Thr Val His Ile Ser Lys Ser Ile Pro Pro
145                 150                 155                 160

Pro Ser Pro Thr Gln His Asp Ile Lys Ile Ser Thr Glu Gln Glu Ala
                165                 170                 175

Arg Ala Ala Ile Leu Lys Ile Glu Glu Ala Leu Gln Ser Val Ser Leu
            180                 185                 190

His Arg Ala Asp Leu Gly Ala Met Ile Asn Arg Leu His Phe Asn Ile
        195                 200                 205

Glu Asn Leu Asn Ser Gln Ser Met Ala Leu Thr Asp Ala Ala Ser Arg
    210                 215                 220

Ile Glu Asp Ala Asp Met Ala Gln Glu Met Ser Asp Phe Leu Lys Phe
225                 230                 235                 240

Lys Leu Leu Thr Glu Val Ala Leu Ser Met Val Ser Gln Ala Asn Gln
                245                 250                 255

Ile Pro Gln Met Val Ser Lys Leu Leu Gln Ser
            260                 265


<210> SEQ ID NO 63
<211> LENGTH: 373
<212> TYPE: PRT
<213> ORGANISM: Bacillus thuringiensis

<400> SEQUENCE: 63

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Leu
65                  70                  75                  80

Asn Ser Val Ser Asn Ile Leu Leu Arg Met Arg Asp Ile Ala Asn Gln
                85                  90                  95

Ser Ala Asn Gly Thr Asn Thr Gly Asp Asn Gln Lys Ala Leu Asp Lys
            100                 105                 110

Glu Phe Ser Ala Leu Lys Glu Gln Ile Asp Tyr Ile Ser Lys Asn Thr
        115                 120                 125

Glu Phe Asn Asp Lys Lys Leu Leu Asn Gly Asp Asn Lys Ser Ile Ala
    130                 135                 140

Ile Gln Thr Leu Asp Asn Ala Asp Thr Ala Lys Gln Ile Asn Ile Asn
145                 150                 155                 160

Leu Ala Asp Ser Ser Thr Lys Ala Leu Asn Ile Asp Thr Leu Ser Ile
                165                 170                 175

Ala Gly Thr Thr Asp Lys Thr Ile Thr Ile Thr Ala Lys Asp Leu Thr
            180                 185                 190

Asp Asn Lys Ala Thr Leu Asp Ala Leu Lys Thr Ala Lys Ala Asp Leu
        195                 200                 205

Ala Lys Leu Asp Asp Lys Ser Asp Gln Ala Thr Ile Asp Lys Ala Val
    210                 215                 220

Asp Ala Phe Lys Thr Ala Phe Asn Asn Val Asp Lys Asn Leu Leu Ser
```

225 230 235 240

Asp Lys Ala Ile Glu Gly Ile Thr Asp Lys Met Thr Ala Phe Asp Gly
245 250 255

Thr His Thr Ala Ala Ala Ala Ile Gly Thr Ala Tyr Thr Glu Pro Thr
260 265 270

Ala Gly Asp Ile Thr Lys Ser Ala Pro Asn Ala Ser Gly Ala Ile Lys
275 280 285

Ser Ile Asp Ala Ala Leu Glu Thr Ile Ala Ser Asn Arg Ala Thr Leu
290 295 300

Gly Ala Thr Leu Asn Arg Leu Asp Phe Asn Val Asn Asn Leu Lys Ser
305 310 315 320

Gln Ser Ser Ser Met Ala Ser Ala Ala Ser Gln Ile Glu Asp Ala Asp
325 330 335

Met Ala Lys Glu Met Ser Glu Met Thr Lys Phe Lys Ile Leu Asn Glu
340 345 350

Ala Gly Ile Ser Met Leu Ser Gln Ala Asn Gln Thr Pro Gln Met Val
355 360 365

Ser Lys Leu Leu Gln
370

<210> SEQ ID NO 64
<211> LENGTH: 257
<212> TYPE: PRT
<213> ORGANISM: Bacillus aryabhattai

<400> SEQUENCE: 64

Met Arg Ile Asn His Asn Ile Thr Ala Leu Asn Thr Tyr Arg Gln Phe
1 5 10 15

Asn Asn Ala Asn Asn Ala Gln Ala Lys Ser Met Glu Lys Leu Ser Ser
20 25 30

Gly Gln Arg Ile Asn Ser Ala Ser Asp Asp Ala Ala Gly Leu Ala Ile
35 40 45

Ser Glu Lys Met Arg Gly Gln Ile Arg Gly Leu Asp Gln Ala Ser Arg
50 55 60

Asn Ala Gln Asp Gly Val Ser Leu Ile Gln Thr Ala Glu Gly Ala Leu
65 70 75 80

Asn Glu Thr His Asp Ile Leu Gln Arg Met Arg Glu Leu Val Val Gln
85 90 95

Ala Gly Asn Gly Thr Asn Lys Thr Glu Asp Leu Asp Ala Ile Gln Asp
100 105 110

Glu Ile Gly Ser Leu Ile Glu Glu Ile Gly Gly Glu Thr Asp Ser Lys
115 120 125

Gly Ile Ser Asp Arg Ala Gln Phe Asn Gly Arg Asn Leu Leu Asp Gly
130 135 140

Ser Leu Asp Ile Thr Leu Gln Val Gly Ala Asn Ala Gly Gln Gln Val
145 150 155 160

Asn Leu Lys Ile Gly Asp Met Ser Ala Gly Ala Leu Gly Ala Asp Thr
165 170 175

Asp Ser Asp Gly Ala Ala Asp Ala Phe Val Asn Ser Ile Asn Val Lys
180 185 190

Asp Phe Ala Thr Thr Ser Phe Asp Asp Gln Leu Ala Ile Ile Asp Gly
195 200 205

Ala Ile Asn Gln Val Ser Glu Gln Arg Ser Gly Leu Gly Ala Thr Gln
210 215 220

```
Asn Arg Leu Asp His Thr Ile Asn Asn Leu Ser Thr Ser Ser Glu Asn
225                 230                 235                 240

Leu Thr Ala Ser Glu Ser Arg Ile Arg Asp Val Asp Tyr Ala Leu Ala
                245                 250                 255

Ala


<210> SEQ ID NO 65
<211> LENGTH: 270
<212> TYPE: PRT
<213> ORGANISM: Bacillus manliponensis

<400> SEQUENCE: 65

Met Arg Ile Asn Thr Asn Ile Asn Ser Met Arg Thr Gln Glu Tyr Met
1               5                   10                  15

Arg Gln Asn Gln Asp Lys Met Asn Thr Ser Met Asn Arg Leu Ser Ser
            20                  25                  30

Gly Lys Gln Ile Asn Ser Ala Ser Asp Asp Ala Ala Gly Leu Ala Ile
        35                  40                  45

Ala Thr Arg Met Arg Ala Lys Glu Gly Gly Leu Asn Val Gly Ala Lys
    50                  55                  60

Asn Thr Gln Asp Gly Met Ser Ala Leu Arg Thr Met Asp Ser Ala Leu
65                  70                  75                  80

Asn Ser Val Ser Asn Ile Leu Leu Arg Met Arg Asp Leu Ala Thr Gln
                85                  90                  95

Ser Ala Thr Gly Thr Asn Gln Gly Asn Asp Arg Glu Ser Leu Asp Leu
            100                 105                 110

Glu Phe Gln Gln Leu Thr Glu Glu Ile Thr His Ile Ala Glu Lys Thr
        115                 120                 125

Asn Phe Asn Gly Asn Ala Leu Leu Ser Gly Ser Gly Ser Ala Ile Asn
    130                 135                 140

Val Gln Leu Ser Asp Ala Ala Glu Asp Lys Leu Thr Ile Ala Ala Ile
145                 150                 155                 160

Asp Ala Thr Ala Ser Thr Leu Leu Lys Gly Ala Val Asp Val Lys Thr
                165                 170                 175

Glu Asp Lys Ala Asp Ala Ala Ile Thr Lys Ile Asp Gln Ala Ile Gln
            180                 185                 190

Asp Ile Ala Asp Asn Arg Ala Thr Tyr Gly Ser Gln Leu Asn Arg Leu
        195                 200                 205

Asp His Asn Leu Asn Asn Val Asn Ser Gln Ala Thr Asn Met Ala Ala
    210                 215                 220

Ala Ala Ser Gln Ile Glu Asp Ala Asp Met Ala Lys Glu Met Ser Glu
225                 230                 235                 240

Met Thr Lys Phe Lys Ile Leu Ser Glu Ala Gly Val Ser Met Leu Ser
                245                 250                 255

Gln Ala Asn Gln Thr Pro Gln Met Val Ser Lys Leu Leu Gln
            260                 265                 270


<210> SEQ ID NO 66
<211> LENGTH: 273
<212> TYPE: PRT
<213> ORGANISM: Lysinibacillus sp.

<400> SEQUENCE: 66

Met Arg Ile Gly Ser Trp Thr Ala Thr Gly Met Ser Ile Val Asn His
1               5                   10                  15

Met Asn Arg Asn Trp Asn Ala Ala Ser Lys Ser Met Leu Arg Leu Ser
```

```
            20                  25                  30

Ser Gly Tyr Arg Ile Asn Ser Ala Ala Asp Asp Ala Ala Gly Leu Ala
        35                  40                  45

Ile Ser Glu Lys Met Arg Gly Gln Ile Arg Gly Leu Thr Met Ala Ser
    50                  55                  60

Lys Asn Ile Met Asp Gly Val Ser Leu Ile Gln Thr Ala Glu Gly Ala
65                  70                  75                  80

Leu Asn Glu Thr His Ala Ile Val Gln Arg Met Arg Glu Leu Ala Val
                85                  90                  95

Gln Ala Ala Thr Asp Thr Asn Thr Asp Asp Asp Arg Ala Lys Leu Asp
            100                 105                 110

Leu Glu Phe Gln Glu Leu Lys Lys Glu Ile Asp Arg Ile Ser Thr Asp
        115                 120                 125

Thr Glu Phe Asn Thr Arg Thr Leu Leu Asn Gly Asp Tyr Lys Asp Asn
    130                 135                 140

Gly Leu Lys Ile Gln Val Gly Ala Asn Ser Gly Gln Ala Ile Glu Val
145                 150                 155                 160

Lys Ile Gly Asp Ala Gly Leu Ala Gly Ile Gly Leu Ser Thr Glu Ser
                165                 170                 175

Ile Ala Thr Arg Glu Gly Ala Asn Ala Ala Leu Gly Lys Leu Asp Glu
            180                 185                 190

Ala Thr Lys Asn Val Ser Met Glu Arg Ser Arg Leu Gly Ala Tyr Gln
        195                 200                 205

Asn Arg Leu Glu His Ala Tyr Asn Val Ala Glu Asn Thr Ala Ile Asn
    210                 215                 220

Leu Gln Asp Ala Glu Ser Arg Ile Arg Asp Val Asp Ile Ala Lys Glu
225                 230                 235                 240

Met Met Asn Met Val Lys Ser Gln Ile Leu Ala Gln Val Gly Gln Gln
                245                 250                 255

Val Leu Ala Met His Met Gln Gln Ala Gln Gly Ile Leu Arg Leu Leu
            260                 265                 270

Gly


<210> SEQ ID NO 67
<211> LENGTH: 273
<212> TYPE: PRT
<213> ORGANISM: Lysinibacillus sp.

<400> SEQUENCE: 67

Met Lys Ile Gly Ser Trp Thr Ala Thr Gly Met Ser Ile Val Asn His
1               5                   10                  15

Met Asn Arg Asn Trp Asn Ala Ala Ser Lys Ser Met Leu Arg Leu Ser
            20                  25                  30

Ser Gly Tyr Arg Ile Asn Ser Ala Ala Asp Asp Ala Ala Gly Leu Ala
        35                  40                  45

Ile Ser Glu Lys Met Arg Gly Gln Ile Arg Gly Leu Thr Met Ala Ser
    50                  55                  60

Lys Asn Ile Met Asp Gly Val Ser Leu Ile Gln Thr Ala Glu Gly Ala
65                  70                  75                  80

Leu Asn Glu Thr His Ala Ile Val Gln Arg Met Arg Glu Leu Ala Val
                85                  90                  95

Gln Ala Ala Thr Asp Thr Asn Thr Asp Asp Asp Arg Ala Lys Leu Asp
            100                 105                 110

Leu Glu Phe Gln Glu Leu Lys Lys Glu Ile Asp Arg Ile Ser Thr Asp
```

```
        115                 120                 125

Thr Ala Phe Asn Thr Arg Thr Leu Leu Asn Gly Asp Tyr Lys Asp Asn
    130                 135                 140

Gly Leu Lys Ile Gln Val Gly Ala Asn Ser Gly Gln Ala Ile Glu Val
145                 150                 155                 160

Lys Ile Gly Asp Ala Gly Leu Ala Gly Ile Gly Leu Ser Thr Glu Ser
                165                 170                 175

Ile Ala Thr Arg Glu Gly Ala Asn Ala Ala Leu Gly Lys Leu Asp Glu
            180                 185                 190

Ala Thr Lys Asn Val Ser Met Glu Arg Ser Arg Leu Gly Ala Tyr Gln
        195                 200                 205

Asn Arg Leu Glu His Ala Tyr Asn Val Ala Glu Asn Thr Ala Ile Asn
    210                 215                 220

Leu Gln Asp Ala Glu Ser Arg Ile Arg Asp Val Asp Ile Ala Lys Glu
225                 230                 235                 240

Met Met His Met Val Lys Ser Gln Ile Leu Ala Gln Val Gly Gln Gln
                245                 250                 255

Val Leu Ala Met His Ile Gln Gln Ala Gln Gly Ile Leu Arg Leu Leu
            260                 265                 270

Gly


<210> SEQ ID NO 68
<211> LENGTH: 418
<212> TYPE: PRT
<213> ORGANISM: Paenibacillus sp.

<400> SEQUENCE: 68

Met Ile Ile Ser His Asn Leu Thr Ala Leu Asn Thr Met Asn Lys Leu
1               5                   10                  15

Lys Gln Lys Asp Leu Ala Val Ser Lys Ser Leu Gly Lys Leu Ser Ser
            20                  25                  30

Gly Leu Arg Ile Asn Gly Ala Ser Asp Asp Ala Ala Gly Leu Ala Ile
        35                  40                  45

Ser Glu Lys Met Arg Gly Gln Ile Arg Gly Leu Asn Gln Ala Ser Arg
    50                  55                  60

Asn Ile Gln Asp Gly Ile Ser Leu Ile Gln Val Ala Asp Gly Ala Met
65                  70                  75                  80

Gln Glu Ile His Ser Met Leu Gln Arg Met Asn Glu Leu Ala Val Gln
                85                  90                  95

Ala Ser Asn Gly Thr Tyr Ser Gly Ser Asp Arg Leu Asn Ile Gln Ser
            100                 105                 110

Glu Val Glu Gln Leu Ile Glu Glu Ile Asp Glu Ile Ala Gly Asn Thr
        115                 120                 125

Gly Phe Asn Gly Ile Lys Leu Leu Asn Gly Asn Asn Glu Lys Thr Glu
    130                 135                 140

Lys Thr Glu Lys Thr Gly Ser Val Val Ser Val Asn Asn Pro Pro Asn
145                 150                 155                 160

Asn Lys Leu Ile Thr Ile Ser Ser Pro Val Gly Thr Ser Val Ser Glu
                165                 170                 175

Ile Leu Asn Asn Leu Leu Thr Val Phe Asn Glu Ala Lys Asn Gly Gln
            180                 185                 190

Val Gly Asp Ser Asp Ser Lys Arg Val Ser Ser Lys Phe Thr Leu Ser
        195                 200                 205

Ile Asn Asn Asp Glu Leu Ser Ile Val Cys Asp Thr Gly Asp Gly Phe
```

```
    210                 215                 220

Leu Leu Ser Gly Gly Ser Pro Asn Leu Phe Tyr Gln Gly Tyr Ile Gly
225                 230                 235                 240

Gly Ser Tyr Lys Tyr Lys Phe Thr Glu Phe Ile Asn Glu Asn Asp Phe
                245                 250                 255

Ile Asn Ile Met Asp Ile Gly Gly Ala Asn Gly Gly Asp Thr Leu Lys
            260                 265                 270

Phe Asn Phe Ser Ser Ile Ser Lys Glu Pro Glu Glu Gln Lys Glu Gln
        275                 280                 285

Lys Gly Leu Thr Leu Gln Ile Gly Ala Asn Ser Gly Glu Thr Leu Asn
    290                 295                 300

Ile Lys Leu Pro Asn Val Thr Thr Ser Ala Ile Gly Ile Ser Ser Ile
305                 310                 315                 320

Asp Val Ser Thr Ile Pro Asn Ala Glu Ser Ser Leu Ser Ser Ile Ser
                325                 330                 335

Ala Ala Ile Asp Lys Val Ser Ala Glu Arg Ala Arg Met Gly Ala Tyr
            340                 345                 350

Gln Asn Arg Leu Glu His Ser Arg Asn Asn Val Val Thr Tyr Ala Glu
        355                 360                 365

Asn Leu Thr Ala Ala Glu Ser Arg Ile Arg Asp Val Asp Met Ala Lys
    370                 375                 380

Glu Met Met Glu Leu Met Lys Asn Gln Ile Phe Thr Gln Ala Gly Gln
385                 390                 395                 400

Ala Met Leu Leu Gln Thr Asn Thr Gln Pro Gln Ala Ile Leu Gln Leu
                405                 410                 415

Leu Lys


<210> SEQ ID NO 69
<211> LENGTH: 387
<212> TYPE: PRT
<213> ORGANISM: Bacillus anthracis

<400> SEQUENCE: 69

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Lys Glu Asn Gln Asp Ala Leu Asp Lys
            100                 105                 110

Glu Phe Gly Ala Leu Lys Glu Gln Ile Asp Tyr Ile Ser Lys Asn Thr
        115                 120                 125

Glu Phe Asn Asp Lys Lys Leu Leu Asn Gly Asp Asn Lys Ser Ile Ala
    130                 135                 140

Ile Gln Thr Leu Asp Asn Ala Asp Thr Ala Lys Gln Ile Asn Ile Asn
145                 150                 155                 160

Leu Ala Asp Ser Ser Thr Lys Ala Leu Asn Ile Asp Ser Leu Thr Ile
```

```
                165                 170                 175

Ser Gly Ser Lys Asp Ala Thr Ile Thr Ile Thr Ala Glu Asp Ile Thr
            180                 185                 190

Ala Ala Ser Ala Glu Ile Thr Ala Ala Lys Gly Ala Arg Thr Ala Leu
        195                 200                 205

Ala Asn Leu Lys Asp Thr Pro Ala Asp Pro Thr Lys Asp Pro Ala Ala
    210                 215                 220

Ser Thr Pro Ala Glu Ile Lys Ala Ala Val Asp Asp Phe Lys Gly Lys
225                 230                 235                 240

Phe Glu Lys Ile Lys Gly Leu Met Asn Asp Thr Asp Val Lys Ala Val
                245                 250                 255

Glu Glu Lys Ile Lys Glu Phe Glu Thr Thr Ser Thr Leu Ala Lys Ala
            260                 265                 270

Gln Ala Ile Gly Thr Ala Phe Thr Thr Gly Met Glu Pro Lys Ala Gly
        275                 280                 285

Asn Ile Thr Lys Asn Val Pro Ala Ala Ser Ser Ser Ile Lys Ala Ile
    290                 295                 300

Asp Ser Ala Leu Glu Thr Ile Ala Ser Asn Arg Ala Thr Leu Gly Ala
305                 310                 315                 320

Thr Leu Asn Arg Leu Asp Phe Asn Val Asn Asn Leu Lys Ser Gln Ser
                325                 330                 335

Ser Ala Met Ala Ser Ala Ala Ser Gln Ile Glu Asp Ala Asp Met Ala
            340                 345                 350

Lys Glu Met Ser Glu Met Thr Lys Phe Lys Ile Leu Asn Glu Ala Gly
        355                 360                 365

Ile Ser Met Leu Ser Gln Ala Asn Gln Thr Pro Gln Met Val Ser Lys
    370                 375                 380

Leu Leu Gln
385


<210> SEQ ID NO 70
<211> LENGTH: 300
<212> TYPE: PRT
<213> ORGANISM: Bacillus anthracis

<400> SEQUENCE: 70

Met Gln Lys Ser Gln Tyr Lys Lys Met Gly Val Leu Lys Met Arg Ile
1               5                   10                  15

Asn Thr Asn Ile Asn Ser Met Arg Thr Gln Glu Tyr Met Arg Gln Asn
            20                  25                  30

Gln Asp Lys Met Asn Val Ser Met Asn Arg Leu Ser Ser Gly Lys Arg
        35                  40                  45

Ile Asn Ser Ala Ala Asp Asp Ala Ala Gly Leu Ala Ile Ala Thr Arg
    50                  55                  60

Met Arg Ala Arg Gln Ser Gly Leu Glu Lys Ala Ser Gln Asn Thr Gln
65                  70                  75                  80

Asp Gly Met Ser Leu Ile Arg Thr Ala Glu Ser Ala Met Asn Ser Val
                85                  90                  95

Ser Asn Ile Leu Thr Arg Met Arg Asp Ile Ala Val Gln Ser Ser Asn
            100                 105                 110

Gly Thr Asn Thr Ala Glu Asn Gln Ser Ala Leu Gln Lys Glu Phe Ala
        115                 120                 125

Glu Leu Gln Glu Gln Ile Asp Tyr Ile Ala Lys Asn Thr Glu Phe Asn
    130                 135                 140
```

```
Asp Lys Asn Leu Leu Ala Gly Thr Gly Ala Val Thr Ile Gly Ser Thr
145                 150                 155                 160

Ser Ile Ser Gly Ala Glu Ile Ser Ile Glu Thr Leu Asp Ser Ser Ala
                165                 170                 175

Thr Asn Gln Gln Ile Thr Ile Lys Leu Ala Asn Thr Thr Ala Glu Lys
            180                 185                 190

Leu Gly Ile Asp Ala Thr Thr Ser Asn Ile Ser Ile Ser Gly Ala Ala
        195                 200                 205

Ser Ala Leu Ala Ala Ile Ser Ala Leu Asn Thr Ala Leu Asn Thr Val
    210                 215                 220

Ala Gly Asn Arg Ala Thr Leu Gly Ala Thr Leu Asn Arg Leu Asp Arg
225                 230                 235                 240

Asn Val Glu Asn Leu Asn Asn Gln Ala Thr Asn Met Ala Ser Ala Ala
                245                 250                 255

Ser Gln Ile Glu Asp Ala Asp Met Ala Lys Glu Met Ser Glu Met Thr
            260                 265                 270

Lys Phe Lys Ile Leu Asn Glu Ala Gly Ile Ser Met Leu Ser Gln Ala
        275                 280                 285

Asn Gln Thr Pro Gln Met Val Ser Lys Leu Leu Gln
    290                 295                 300


<210> SEQ ID NO 71
<211> LENGTH: 287
<212> TYPE: PRT
<213> ORGANISM: Bacillus anthracis

<400> SEQUENCE: 71

Met Arg Ile Asn Thr Asn Ile Asn Ser Met Arg Thr Gln Glu Tyr Met
1               5                   10                  15

Arg Gln Asn Gln Asp Lys Met Asn Val Ser Met Asn Arg Leu Ser Ser
            20                  25                  30

Gly Lys Arg Ile Asn Ser Ala Ala Asp Asp Ala Ala Gly Leu Ala Ile
        35                  40                  45

Ala Thr Arg Met Arg Ala Arg Gln Ser Gly Leu Glu Lys Ala Ser Gln
    50                  55                  60

Asn Thr Gln Asp Gly Met Ser Leu Ile Arg Thr Ala Glu Ser Ala Met
65                  70                  75                  80

Asn Ser Val Ser Asn Ile Leu Thr Arg Met Arg Asp Ile Ala Val Gln
                85                  90                  95

Ser Ser Asn Gly Thr Asn Thr Ala Glu Asn Gln Ser Ala Leu Gln Lys
            100                 105                 110

Glu Phe Ala Glu Leu Gln Glu Gln Ile Asp Tyr Ile Ala Lys Asn Thr
        115                 120                 125

Glu Phe Asn Asp Lys Asn Leu Leu Ala Gly Thr Gly Ala Val Thr Ile
    130                 135                 140

Gly Ser Thr Ser Ile Ser Gly Ala Glu Ile Ser Ile Glu Thr Leu Asp
145                 150                 155                 160

Ser Ser Ala Thr Asn Gln Gln Ile Thr Ile Lys Leu Ala Asn Thr Thr
                165                 170                 175

Ala Glu Lys Leu Gly Ile Asp Ala Thr Thr Ser Asn Ile Ser Ile Ser
            180                 185                 190

Gly Ala Ala Ser Ala Leu Ala Ala Ile Ser Ala Leu Asn Thr Ala Leu
        195                 200                 205

Asn Thr Val Ala Gly Asn Arg Ala Thr Leu Gly Ala Thr Leu Asn Arg
    210                 215                 220
```

```
Leu Asp Arg Asn Val Glu Asn Leu Asn Asn Gln Ala Thr Asn Met Ala
225                 230                 235                 240

Ser Ala Ala Ser Gln Ile Lys Asp Ala Asp Lys Ala Lys Glu Met Ser
                245                 250                 255

Glu Met Thr Lys Phe Lys Ile Leu Asn Glu Ala Gly Ile Ser Met Leu
            260                 265                 270

Ser Gln Ala Asn Gln Thr Pro Gln Met Val Ser Lys Leu Leu Gln
        275                 280                 285


<210> SEQ ID NO 72
<211> LENGTH: 282
<212> TYPE: PRT
<213> ORGANISM: Bacillus anthracis

<400> SEQUENCE: 72

Met Arg Ile Asn Thr Asn Ile Asn Ser Met Arg Thr Gln Glu Tyr Met
1               5                   10                  15

Arg Gln Asn Gln Asp Lys Met Asn Val Ser Met Asn Arg Leu Ser Ser
            20                  25                  30

Gly Lys Arg Ile Asn Ser Ala Ala Asp Asp Ala Ala Gly Leu Ala Ile
        35                  40                  45

Ala Thr Arg Met Arg Ala Arg Gln Ser Gly Leu Glu Lys Ala Ser Gln
    50                  55                  60

Asn Thr Gln Asp Gly Met Ser Leu Ile Arg Thr Ala Glu Ser Ala Met
65                  70                  75                  80

Asn Ser Val Ser Asn Ile Leu Thr Arg Met Arg Asp Ile Ala Val Gln
                85                  90                  95

Ser Ser Asn Gly Thr Asn Thr Ala Glu Asn Gln Ser Ala Leu Gln Lys
            100                 105                 110

Glu Phe Ala Glu Leu Gln Glu Gln Ile Asp Tyr Ile Ala Lys Asn Thr
        115                 120                 125

Glu Phe Asn Asp Lys Asn Leu Leu Ala Gly Thr Gly Ala Val Thr Ile
    130                 135                 140

Gly Ser Thr Ser Ile Ser Gly Ala Glu Ile Ser Ile Glu Thr Leu Asp
145                 150                 155                 160

Ser Ser Ala Thr Asn Gln Gln Ile Thr Ile Lys Leu Ala Asn Thr Thr
                165                 170                 175

Ala Glu Lys Leu Gly Ile Asp Ala Thr Thr Ser Asn Ile Ser Ile Ser
            180                 185                 190

Gly Ala Ala Ser Ala Leu Ala Ala Ile Ser Ala Leu Asn Thr Ala Leu
        195                 200                 205

Asn Thr Val Ala Gly Asn Arg Ala Thr Leu Gly Ala Thr Leu Asn Arg
    210                 215                 220

Leu Asp Arg Asn Val Glu Asn Leu Asn Asn Gln Ala Thr Asn Met Ala
225                 230                 235                 240

Ser Ala Ala Ser Gln Ile Glu Asp Ala Asp Met Ala Lys Glu Met Ser
                245                 250                 255

Glu Met Thr Lys Phe Lys Ile Leu Asn Glu Ala Gly Ile Ser Met Leu
            260                 265                 270

Ser Gln Ala Asn Gln Thr Pro Gln Met Val
        275                 280


<210> SEQ ID NO 73
<211> LENGTH: 265
<212> TYPE: PRT
```

<213> ORGANISM: Bacillus anthracis

<400> SEQUENCE: 73

Met Asn Val Ser Met Asn Arg Leu Ser Ser Gly Lys Arg Ile Asn Ser
1 5 10 15

Ala Ala Asp Asp Ala Ala Gly Leu Ala Ile Ala Thr Arg Met Arg Ala
20 25 30

Arg Gln Ser Gly Leu Glu Lys Ala Ser Gln Asn Thr Gln Asp Gly Met
35 40 45

Ser Leu Ile Arg Thr Ala Glu Ser Ala Met Asn Ser Val Ser Asn Ile
50 55 60

Leu Thr Arg Met Arg Asp Ile Ala Val Gln Ser Ser Asn Gly Thr Asn
65 70 75 80

Thr Ala Glu Asn Gln Ser Ala Leu Gln Lys Glu Phe Ala Glu Leu Gln
85 90 95

Glu Gln Ile Asp Tyr Ile Ala Lys Asn Thr Glu Phe Asn Asp Lys Asn
100 105 110

Leu Leu Ala Gly Thr Gly Ala Val Thr Ile Gly Ser Thr Ser Ile Ser
115 120 125

Gly Ala Glu Ile Ser Ile Glu Thr Leu Asp Ser Ser Ala Thr Asn Gln
130 135 140

Gln Ile Thr Ile Lys Leu Ala Asn Thr Thr Ala Glu Lys Leu Gly Ile
145 150 155 160

Asp Ala Thr Thr Ser Asn Ile Ser Ile Ser Gly Ala Ala Ser Ala Leu
165 170 175

Ala Ala Ile Ser Ala Leu Asn Thr Ala Leu Asn Thr Val Ala Gly Asn
180 185 190

Arg Ala Thr Leu Gly Ala Thr Leu Asn Arg Leu Asp Arg Asn Val Glu
195 200 205

Asn Leu Asn Asn Gln Ala Thr Asn Met Ala Ser Ala Ala Ser Gln Ile
210 215 220

Glu Asp Ala Asp Met Ala Lys Glu Met Ser Glu Met Thr Lys Phe Lys
225 230 235 240

Ile Leu Asn Glu Ala Gly Ile Ser Met Leu Ser Gln Ala Asn Gln Thr
245 250 255

Pro Gln Met Val Ser Lys Leu Leu Gln
260 265

<210> SEQ ID NO 74
<211> LENGTH: 257
<212> TYPE: PRT
<213> ORGANISM: Bacillus megaterium

<400> SEQUENCE: 74

Met Arg Ile Asn His Asn Ile Thr Ala Leu Asn Thr Tyr Arg Gln Phe
1 5 10 15

Asn Asn Ala Asn Asn Ala Gln Ala Lys Ser Met Glu Lys Leu Ser Ser
20 25 30

Gly Gln Arg Ile Asn Ser Ala Ser Asp Asp Ala Ala Gly Leu Ala Ile
35 40 45

Ser Glu Lys Met Arg Gly Gln Ile Arg Gly Leu Asp Gln Ala Ser Arg
50 55 60

Asn Ala Gln Asp Gly Val Ser Leu Ile Gln Thr Ala Glu Gly Ala Leu
65 70 75 80

Asn Glu Thr His Asp Ile Leu Gln Arg Met Arg Glu Leu Val Val Gln

```
                85                  90                  95

Ala Gly Asn Gly Thr Asn Lys Thr Glu Asp Leu Asp Ala Ile Gln Asp
            100                 105                 110

Glu Ile Gly Ser Leu Ile Glu Glu Ile Gly Gly Glu Ala Asp Ser Lys
        115                 120                 125

Gly Ile Ser Asp Arg Ala Gln Phe Asn Gly Arg Asn Leu Leu Asp Gly
    130                 135                 140

Ser Leu Asp Ile Thr Leu Gln Val Gly Ala Asn Ala Gly Gln Gln Val
145                 150                 155                 160

Asn Leu Lys Ile Gly Asp Met Ser Ala Gly Ala Leu Gly Ala Asp Thr
                165                 170                 175

Asn Ser Asp Gly Ala Ala Asp Ala Phe Val Asn Ser Ile Asn Val Lys
            180                 185                 190

Asp Phe Thr Ala Thr Ser Phe Asp Asp Gln Leu Ala Ile Ile Asp Gly
        195                 200                 205

Ala Ile Asn Gln Val Ser Glu Gln Arg Ser Gly Leu Gly Ala Thr Gln
    210                 215                 220

Asn Arg Leu Asp His Thr Ile Asn Asn Leu Ser Thr Ser Ser Glu Asn
225                 230                 235                 240

Leu Thr Ala Ser Glu Ser Arg Ile Arg Asp Val Asp Tyr Ala Leu Ala
                245                 250                 255

Ala
```

<210> SEQ ID NO 75
<211> LENGTH: 286
<212> TYPE: PRT
<213> ORGANISM: Aneurinibacillus sp.

<400> SEQUENCE: 75

```
Met Arg Ile Asn His Asn Leu Pro Ala Leu Asn Ala Tyr Arg Asn Leu
1               5                   10                  15

Ala Gln Asn Gln Ile Gly Thr Ser Lys Ile Leu Glu Arg Leu Ser Ser
            20                  25                  30

Gly Tyr Arg Ile Asn Arg Ala Ser Asp Asp Ala Ala Gly Leu Ala Ile
        35                  40                  45

Ser Glu Lys Met Arg Gly Gln Ile Arg Gly Leu Glu Gln Gly Gln Arg
    50                  55                  60

Asn Thr Met Asp Gly Val Ser Leu Ile Gln Thr Ala Glu Gly Ala Leu
65                  70                  75                  80

Gln Glu Ile His Glu Met Leu Gln Arg Met Arg Glu Leu Ala Val Gln
                85                  90                  95

Ala Ala Asn Gly Thr Tyr Ser Asp Lys Asp Lys Lys Ala Ile Glu Asp
            100                 105                 110

Glu Ile Asn Gln Leu Thr Ala Gln Ile Asp Gln Ile Ala Lys Thr Thr
        115                 120                 125

Glu Phe Asn Gly Ile Gln Leu Ile Gly Asp Ser Asp Ser Thr Ser Leu
    130                 135                 140

Gln Asp Val Lys Ile Gln Tyr Gly Pro Lys Lys Glu Asp Ser Leu Thr
145                 150                 155                 160

Leu Glu Leu Thr Thr Gln Pro Glu Ala Asp Pro Pro Phe Ala Ala Gly
                165                 170                 175

Cys Lys Ala Asp Lys Ala Ser Leu Lys Ile Asp Asn Val Asp Val Ile
            180                 185                 190

Ser Asp Pro Glu Gly Ala Ile Glu Thr Phe Lys Ala Ala Ile Asp Gln
```

-continued

```
        195                 200                 205

Val Ser Arg Ile Arg Ser Tyr Phe Gly Ala Ile Gln Asn Arg Leu Glu
    210                 215                 220

His Val Val Asn Asn Leu Ser Asn Tyr Thr Glu Asn Leu Thr Gly Ala
225                 230                 235                 240

Glu Ser Arg Ile Arg Asp Ala Asp Met Ala Lys Glu Met Thr Glu Phe
                245                 250                 255

Thr Arg Phe Asn Ile Ile Asn Gln Ser Ala Thr Ala Met Leu Ala Gln
            260                 265                 270

Ala Asn Gln Leu Pro Gln Gly Val Leu Gln Leu Leu Lys Gly
        275                 280                 285


<210> SEQ ID NO 76
<211> LENGTH: 152
<212> TYPE: PRT
<213> ORGANISM: Bacillus thuringiensis

<400> SEQUENCE: 76

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Ser Ala Ser Asp Asp Ala Ala
        35                  40                  45

Gly Leu Ala Ile Ala Thr Arg Met Lys Ala Arg Glu Gly Gly Leu Asn
    50                  55                  60

Val Ala Gly Arg Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Asn Gly Thr Asn Thr Lys Gly Asn Gln Ala
            100                 105                 110

Ser Leu Gln Lys Glu Phe Ala Gln Leu Thr Glu Gln Ile Asp Tyr Ile
        115                 120                 125

Ala Lys Asn Thr Gln Phe Asn Asp Gln Gln Leu Leu Gly Thr Ala Asp
    130                 135                 140

Lys Lys Ile Lys Ile Gln Thr Leu
145                 150


<210> SEQ ID NO 77
<211> LENGTH: 84
<212> TYPE: PRT
<213> ORGANISM: Bacillus thuringiensis

<400> SEQUENCE: 77

Ile Asp Ala Ala Ile Thr Thr Val Ala Gly Gln Arg Ala Thr Leu Gly
1               5                   10                  15

Ala Thr Leu Asn Arg Phe Glu Phe Asn Ala Asn Asn Leu Lys Ser Gln
            20                  25                  30

Glu Thr Ser Met Ala Asp Ala Ala Ser Gln Ile Glu Asp Ala Asp Met
        35                  40                  45

Ala Lys Glu Met Ser Glu Met Thr Lys Phe Lys Ile Leu Asn Glu Ala
    50                  55                  60

Gly Ile Ser Met Leu Ser Gln Ala Asn Gln Thr Pro Gln Met Val Ser
65                  70                  75                  80

Lys Leu Leu Gln
```

<210> SEQ ID NO 78
<211> LENGTH: 151
<212> TYPE: PRT
<213> ORGANISM: Bacillus thuringiensis

<400> SEQUENCE: 78

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Ser Ala Ser Asp Asp Ala Ala
        35                  40                  45

Gly Leu Ala Ile Ala Thr Arg Met Lys Ala Arg Glu Gly Gly Leu Asn
    50                  55                  60

Val Ala Gly Arg Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Asn Gly Thr Asn Thr Lys Gly Asn Gln Ala
            100                 105                 110

Ser Leu Gln Lys Glu Phe Ala Gln Leu Thr Glu Gln Ile Asp Tyr Ile
        115                 120                 125

Ala Lys Asn Thr Gln Phe Asn Asp Gln Gln Leu Leu Gly Thr Ala Asp
    130                 135                 140

Lys Lys Ile Lys Ile Gln Thr
145                 150

<210> SEQ ID NO 79
<211> LENGTH: 84
<212> TYPE: PRT
<213> ORGANISM: Bacillus thuringiensis

<400> SEQUENCE: 79

Ile Asp Ala Ala Ile Thr Thr Val Ala Gly Gln Arg Ala Thr Leu Gly
1               5                   10                  15

Ala Thr Leu Asn Arg Phe Glu Phe Asn Ala Asn Asn Leu Lys Ser Gln
            20                  25                  30

Glu Thr Ser Met Ala Asp Ala Ala Ser Gln Ile Glu Asp Ala Asp Met
        35                  40                  45

Ala Lys Glu Met Ser Glu Met Thr Lys Phe Lys Ile Leu Asn Glu Ala
    50                  55                  60

Gly Ile Ser Met Leu Ser Gln Ala Asn Gln Thr Pro Gln Met Val Ser
65                  70                  75                  80

Lys Leu Leu Gln

<210> SEQ ID NO 80
<211> LENGTH: 152
<212> TYPE: PRT
<213> ORGANISM: Bacillus thuringiensis

<400> SEQUENCE: 80

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Ser Ala Ser Asp Asp Ala Ala

```
        35                  40                  45

Gly Leu Ala Ile Ala Thr Arg Met Lys Ala Arg Glu Gly Gly Leu Asn
    50                  55                  60

Val Ala Gly Arg Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Asn Gly Thr Asn Thr Lys Gly Asn Gln Ala
            100                 105                 110

Ser Leu Gln Lys Glu Phe Ala Gln Leu Thr Glu Gln Ile Asp Tyr Ile
        115                 120                 125

Ala Lys Asn Thr Gln Phe Asn Asp Gln Gln Leu Leu Gly Thr Ala Asp
    130                 135                 140

Lys Lys Ile Lys Ile Gln Thr Leu
145                 150


<210> SEQ ID NO 81
<211> LENGTH: 84
<212> TYPE: PRT
<213> ORGANISM: Bacillus thuringiensis

<400> SEQUENCE: 81

Ile Asp Ala Ala Ile Thr Thr Val Ala Gly Gln Arg Ala Thr Leu Gly
1               5                   10                  15

Ala Thr Leu Asn Arg Phe Glu Phe Asn Ala Asn Asn Leu Lys Ser Gln
            20                  25                  30

Glu Thr Ser Met Ala Asp Ala Ala Ser Gln Ile Glu Asp Ala Asp Met
        35                  40                  45

Ala Lys Glu Met Ser Glu Met Thr Lys Phe Lys Ile Leu Asn Glu Ala
    50                  55                  60

Gly Ile Ser Met Leu Ser Gln Ala Asn Gln Thr Pro Gln Met Val Ser
65                  70                  75                  80

Lys Leu Leu Gln


<210> SEQ ID NO 82
<211> LENGTH: 152
<212> TYPE: PRT
<213> ORGANISM: Bacillus cereus

<400> SEQUENCE: 82

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Ser Ala Ser Asp Asp Ala Ala
        35                  40                  45

Gly Leu Ala Ile Ala Thr Arg Met Lys Ala Arg Glu Gly Gly Leu Asn
    50                  55                  60

Val Ala Gly Arg Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Asn Gly Thr Asn Thr Lys Gly Asn Gln Ala
            100                 105                 110

Ser Leu Gln Lys Glu Phe Ala Gln Leu Thr Glu Gln Ile Asp Tyr Ile
        115                 120                 125
```

Ala Lys Asn Thr Gln Phe Asn Asp Gln Gln Leu Leu Gly Thr Ala Asp
    130                 135                 140

Lys Lys Ile Lys Ile Gln Thr Leu
145                 150

<210> SEQ ID NO 83
<211> LENGTH: 84
<212> TYPE: PRT
<213> ORGANISM: Bacillus cereus

<400> SEQUENCE: 83

Ile Asp Ala Ala Ile Thr Thr Val Ala Gly Gln Arg Ala Thr Leu Gly
1               5                   10                  15

Ala Thr Leu Asn Arg Phe Glu Phe Asn Ala Asn Asn Leu Lys Ser Gln
            20                  25                  30

Glu Thr Ser Met Ala Asp Ala Ala Ser Gln Ile Glu Asp Ala Asp Met
        35                  40                  45

Ala Lys Glu Met Ser Glu Met Thr Lys Phe Lys Ile Leu Asn Glu Ala
    50                  55                  60

Gly Ile Ser Met Leu Ser Gln Ala Asn Gln Thr Pro Gln Met Val Ser
65                  70                  75                  80

Lys Leu Leu Gln

<210> SEQ ID NO 84
<211> LENGTH: 151
<212> TYPE: PRT
<213> ORGANISM: Bacillus thuringiensis

<400> SEQUENCE: 84

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ser Met Asp
            20                  25                  30

Arg Leu Ser Ser Gly Lys Arg Ile Asn Ser Ala Ala Asp Asp Ala Ala
        35                  40                  45

Gly Leu Ala Ile Ala Thr Arg Met Lys Ala Arg Glu Gly Gly Leu Asn
    50                  55                  60

Val Ala Ala Arg Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Thr Gly Thr Asn Thr Thr Lys Asn Gln Val
            100                 105                 110

Ala Leu Asn Lys Glu Phe Ala Ala Leu Lys Glu Gln Ile Thr Tyr Ile
        115                 120                 125

Ala Asp Asn Thr Gln Phe Asn Asp Lys Asn Leu Leu Lys Ser Thr Gln
    130                 135                 140

Glu Ile Lys Ile Gln Thr Leu
145                 150

<210> SEQ ID NO 85
<211> LENGTH: 85
<212> TYPE: PRT
<213> ORGANISM: Bacillus thuringiensis

<400> SEQUENCE: 85

Gln Leu Asp Ala Ala Leu Thr Lys Val Ala Asp Asn Arg Ala Thr Leu

```
1               5                   10                  15

Gly Ala Thr Leu Asn Arg Leu Asp Phe Asn Val Asn Asn Leu Lys Ser
            20                  25                  30

Gln Glu Asn Ser Met Ala Ala Ser Ala Ser Gln Ile Glu Asp Ala Asp
        35                  40                  45

Met Ala Lys Glu Met Ser Glu Met Thr Lys Phe Lys Ile Leu Asn Glu
    50                  55                  60

Ala Gly Ile Ser Met Leu Ser Gln Ala Asn Gln Thr Pro Gln Met Val
65                  70                  75                  80

Ser Lys Leu Leu Gln
                85


<210> SEQ ID NO 86
<211> LENGTH: 154
<212> TYPE: PRT
<213> ORGANISM: Bacillus thuringiensis

<400> SEQUENCE: 86

Trp Gly Phe Leu Ile Met Arg Ile Asn Thr Asn Ile Asn Ser Met Arg
1               5                   10                  15

Thr Gln Glu Tyr Met Arg Gln Asn Gln Ala Lys Met Ser Asn Ser Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
    50                  55                  60

Gly Val Ala Ala Asp Asn Thr Gln Asn Gly Met Ser Leu Ile Arg Thr
65                  70                  75                  80

Ala Asp Ser Ala Met Asn Ser Val Ser Asn Ile Leu Leu Arg Met Arg
                85                  90                  95

Asp Ile Ala Asn Gln Ser Ala Asn Gly Thr Asn Thr Asn Glu Asn Lys
            100                 105                 110

Ser Ala Leu Gln Lys Glu Phe Ala Gln Leu Gln Lys Gln Ile Thr Tyr
        115                 120                 125

Ile Ala Glu Asn Thr Gln Phe Asn Asp Lys Asn Leu Leu Asn Glu Asp
    130                 135                 140

Ser Glu Val Lys Ile Gln Thr Leu Asp Ser
145                 150


<210> SEQ ID NO 87
<211> LENGTH: 88
<212> TYPE: PRT
<213> ORGANISM: Bacillus thuringiensis

<400> SEQUENCE: 87

Ala Ile Ala Ala Ile Asp Ala Ala Leu Thr Lys Val Ala Asp Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ser Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
```

85

<210> SEQ ID NO 88
<211> LENGTH: 140
<212> TYPE: PRT
<213> ORGANISM: Bacillus thuringiensis

<400> SEQUENCE: 88

Gly Phe Leu Asn Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Asn Gly Leu Gly
50 55 60

Val Ala Ala Asn Asn Thr Gln Asp Gly Met Ser Leu Ile Arg Thr Ala
65 70 75 80

Asp Ser Ala Met Asn Ser Val Ser Asn Ile Leu Leu Arg Met Arg Asp
85 90 95

Leu Ala Asn Gln Ser Ala Asn Gly Thr Asn Thr Asp Asp Asn Gln Lys
100 105 110

Ala Leu Asp Lys Glu Phe Ser Ala Leu Lys Glu Gln Ile Asp Tyr Ile
115 120 125

Ser Lys Asn Thr Glu Phe Asn Asp Lys Lys Leu Leu
130 135 140

<210> SEQ ID NO 89
<211> LENGTH: 62
<212> TYPE: PRT
<213> ORGANISM: Bacillus thuringiensis

<400> SEQUENCE: 89

Arg Ala Thr Leu Gly Ala Thr Leu Asn Arg Leu Asp Phe Asn Val Asn
1 5 10 15

Asn Leu Lys Ser Gln Ser Ser Ser Met Ala Ala Ala Ala Ser Gln Ile
20 25 30

Glu Asp Ala Asp Met Ala Lys Glu Met Ser Glu Met Thr Lys Phe Lys
35 40 45

Ile Leu Asn Glu Ala Gly Ile Ser Met Leu Ser Gln Ala Asn
50 55 60

<210> SEQ ID NO 90
<211> LENGTH: 142
<212> TYPE: PRT
<213> ORGANISM: Bacillus thuringiensis

<400> SEQUENCE: 90

Gly Phe Leu Asn Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Asn Gly Leu Gly
50 55 60

Val Ala Ala Asn Asn Thr Gln Asp Gly Met Ser Leu Ile Arg Thr Ala
65 70 75 80

Asp Ser Ala Leu Gln Ser Val Ser Asn Ile Leu Leu Arg Met Arg Asp
85 90 95

Leu Ala Asn Gln Ser Ala Asn Gly Thr Asn Thr Asp Glu Asn Lys Ala
100 105 110

Ala Met Glu Lys Glu Phe Gly Gln Leu Lys Asp Gln Ile Lys Tyr Ile
115 120 125

Thr Asp Asn Thr Gln Phe Asn Asp Lys Asn Leu Leu Asp Ala
130 135 140

<210> SEQ ID NO 91
<211> LENGTH: 84
<212> TYPE: PRT
<213> ORGANISM: Bacillus thuringiensis

<400> SEQUENCE: 91

Ile Asp Ala Ala Leu Lys Thr Val Ala Asp Asn Arg Ala Thr Leu Gly
1 5 10 15

Ala Thr Leu Asn Arg Leu Asp Phe Asn Val Asn Asn Leu Lys Ser Gln
20 25 30

Ser Ala Ser Met Ala Ser Ala Ala Ser Gln Ile Glu Asp Ala Asp Met
35 40 45

Ala Lys Glu Met Ser Glu Met Thr Lys Phe Lys Ile Leu Asn Glu Ala
50 55 60

Gly Ile Ser Met Leu Ser Gln Ala Asn Gln Thr Pro Gln Met Val Ser
65 70 75 80

Lys Leu Leu Gln

<210> SEQ ID NO 92
<211> LENGTH: 137
<212> TYPE: PRT
<213> ORGANISM: Bacillus cereus

<400> SEQUENCE: 92

Met Gly Val Leu Asn Met Arg Ile Asn Thr Asn Ile Asn Ser Met Arg
1 5 10 15

Thr Gln Glu Tyr Met Arg Gln Asn Gln Ala Lys Met Ser Asn Ser Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ala Asn Asn Thr Gln Asp Gly Met Ser Leu Ile Arg Thr
65 70 75 80

Ala Asp Ser Ala Met Asn Ser Val Ser Asn Ile Leu Leu Arg Met Arg
85 90 95

Asp Ile Ala Asn Gln Ser Ala Asn Gly Thr Asn Thr Asp Lys Asn Gln
100 105 110

Val Ala Leu Gln Lys Glu Phe Gly Glu Leu Gln Lys Gln Ile Asp Tyr
115 120 125

Ile Ala Lys Asn Thr Gln Phe Asn Asp
130 135

<210> SEQ ID NO 93
<211> LENGTH: 73
<212> TYPE: PRT
<213> ORGANISM: Bacillus cereus

<400> SEQUENCE: 93

Arg Ala Thr Leu Gly Ala Thr Leu Asn Arg Leu Asp Phe Asn Val Asn
1 5 10 15

Asn Leu Lys Ser Gln Gln Ser Ser Met Ala Ser Ala Ala Ser Gln Val
20 25 30

Glu Asp Ala Asp Met Ala Lys Glu Met Ser Glu Met Thr Lys Phe Lys
35 40 45

Ile Leu Asn Glu Ala Gly Ile Ser Met Leu Ser Gln Ala Asn Gln Thr
50 55 60

Pro Gln Met Val Ser Lys Leu Leu Gln
65 70

<210> SEQ ID NO 94
<211> LENGTH: 137
<212> TYPE: PRT
<213> ORGANISM: Bacillus cereus

<400> SEQUENCE: 94

Met Gly Val Leu Asn Met Arg Ile Gly Thr Asn Val Leu Ser Met Asn
1 5 10 15

Ala Arg Gln Ser Phe Tyr Glu Asn Glu Lys Arg Met Asn Val Ala Ile
20 25 30

Glu His Leu Ala Thr Gly Lys Lys Leu Asn His Ala Ser Asp Asn Pro
35 40 45

Ala Asn Val Ala Ile Val Thr Arg Met His Ala Arg Thr Ser Gly Ile
50 55 60

His Val Ala Ile Arg Asn Asn Glu Asp Ala Ile Ser Met Leu Arg Thr
65 70 75 80

Ala Glu Ala Ala Leu Gln Thr Val Thr Asn Ile Leu Gln Arg Met Arg
85 90 95

Asp Val Ala Val Gln Ser Ala Asn Gly Thr Asn Ser Asn Lys Asn Arg
100 105 110

Asp Ser Leu Asn Lys Glu Phe Gln Ser Leu Thr Glu Gln Ile Gly Tyr
115 120 125

Ile Asp Glu Thr Thr Glu Phe Asn Asp
130 135

<210> SEQ ID NO 95
<211> LENGTH: 73
<212> TYPE: PRT
<213> ORGANISM: Bacillus cereus

<400> SEQUENCE: 95

Arg Ala Asp Leu Gly Ala Met Ile Asn Gln Leu Gln Phe Asn Ile Glu
1 5 10 15

Asn Leu Asn Ser Gln Ser Thr Ala Leu Thr Asp Ala Ala Ser Arg Ile
20 25 30

Glu Asp Ala Asp Met Ala Gln Glu Met Ser Asp Phe Leu Lys Phe Lys
35 40 45

Leu Leu Thr Glu Val Ala Leu Ser Met Val Ser Gln Ala Asn Gln Ile
50 55 60

Pro Gln Met Val Tyr Lys Leu Leu Gln
65 70

<210> SEQ ID NO 96
<211> LENGTH: 140
<212> TYPE: PRT

<213> ORGANISM: Bacillus thuringiensis

<400> SEQUENCE: 96

```
Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Ile Ala Asn Gln Ser Ala Asn Gly Thr Asn Thr Ala Asp Asn Gln Gln
            100                 105                 110

Ala Leu Gln Lys Glu Phe Gly Gln Leu Lys Glu Gln Ile Ser Tyr Ile
        115                 120                 125

Ala Asp Asn Thr Glu Phe Asn Asp Lys Thr Leu Leu
    130                 135                 140
```

<210> SEQ ID NO 97
<211> LENGTH: 88
<212> TYPE: PRT
<213> ORGANISM: Bacillus thuringiensis

<400> SEQUENCE: 97

```
Ala Val Asp Ser Ile Asp Ala Ala Leu Lys Thr Val Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ala Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85
```

<210> SEQ ID NO 98
<211> LENGTH: 128
<212> TYPE: PRT
<213> ORGANISM: Bacillus bombysepticus

<400> SEQUENCE: 98

```
Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ser Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ser Arg Glu Gly Gly Leu Asn
    50                  55                  60

Val Ala Ala Arg Asn Thr Glu Asp Gly Met Ser Leu Ile Arg Thr Ala
65                  70                  75                  80
```

```
Asp Ser Ala Leu Asn Ser Val Ser Asn Ile Leu Leu Arg Met Arg Asp
                85                  90                  95

Leu Ala Asn Gln Ser Ala Ser Gly Thr Asn Thr Asp Lys Asn Gln Ala
            100                 105                 110

Ala Met Gln Lys Glu Phe Asp Gln Leu Lys Glu Gln Ile Gln Tyr Ile
        115                 120                 125


<210> SEQ ID NO 99
<211> LENGTH: 70
<212> TYPE: PRT
<213> ORGANISM: Bacillus bombysepticus

<400> SEQUENCE: 99

Leu Gly Ala Thr Leu Asn Arg Leu Asp Phe Asn Val Thr Asn Leu Lys
1               5                   10                  15

Ser Gln Glu Asn Ser Met Ala Ala Ser Ala Ser Gln Ile Glu Asp Ala
            20                  25                  30

Asp Met Ala Lys Glu Met Ser Glu Met Thr Lys Phe Lys Ile Leu Asn
        35                  40                  45

Glu Ala Gly Ile Ser Met Leu Ser Gln Ala Asn Gln Thr Pro Gln Met
    50                  55                  60

Val Ser Lys Leu Leu Gln
65                  70


<210> SEQ ID NO 100
<211> LENGTH: 128
<212> TYPE: PRT
<213> ORGANISM: Bacillus thuringiensis

<400> SEQUENCE: 100

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ser Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ser Arg Glu Gly Gly Leu Asn
    50                  55                  60

Val Ala Ala Arg Asn Thr Glu Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Ser Gly Thr Asn Thr Asp Lys Asn Gln Ala
            100                 105                 110

Ala Met Gln Lys Glu Phe Asp Gln Leu Lys Glu Gln Ile Gln Tyr Ile
        115                 120                 125


<210> SEQ ID NO 101
<211> LENGTH: 73
<212> TYPE: PRT
<213> ORGANISM: Bacillus thuringiensis

<400> SEQUENCE: 101

Arg Ala Thr Leu Gly Ala Thr Leu Asn Arg Leu Asp Phe Asn Val Thr
1               5                   10                  15

Asn Leu Lys Ser Gln Glu Asn Ser Met Ala Ala Ser Ala Ser Gln Ile
            20                  25                  30
```

```
Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70


<210> SEQ ID NO 102
<211> LENGTH: 128
<212> TYPE: PRT
<213> ORGANISM: Bacillus thuringiensis

<400> SEQUENCE: 102

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ser Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ser Arg Glu Gly Gly Leu Asn
    50                  55                  60

Val Ala Ala Arg Asn Thr Glu Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Ser Gly Thr Asn Thr Asp Lys Asn Gln Ala
            100                 105                 110

Ala Met Gln Lys Glu Phe Asp Gln Leu Lys Glu Gln Ile Gln Tyr Ile
        115                 120                 125


<210> SEQ ID NO 103
<211> LENGTH: 73
<212> TYPE: PRT
<213> ORGANISM: Bacillus thuringiensis

<400> SEQUENCE: 103

Arg Ala Thr Leu Gly Ala Thr Leu Asn Arg Leu Asp Phe Asn Val Thr
1               5                   10                  15

Asn Leu Lys Ser Gln Glu Asn Ser Met Ala Ala Ser Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70


<210> SEQ ID NO 104
<211> LENGTH: 140
<212> TYPE: PRT
<213> ORGANISM: Bacillus cereus

<400> SEQUENCE: 104

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
```

```
        35                  40                  45

Gly Leu Ala Ile Ala Thr Arg Met Arg Ala Arg Glu Asn Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Asn Gly Thr Asn Thr Gly Asp Asn Gln Lys
            100                 105                 110

Ala Leu Asp Lys Glu Phe Ser Ala Leu Lys Glu Gln Ile Asp Tyr Ile
        115                 120                 125

Ser Lys Asn Thr Glu Phe Asn Asp Lys Lys Leu Leu
    130                 135                 140


<210> SEQ ID NO 105
<211> LENGTH: 73
<212> TYPE: PRT
<213> ORGANISM: Bacillus cereus

<400> SEQUENCE: 105

Arg Ala Thr Leu Gly Ala Thr Leu Asn Arg Leu Asp Phe Asn Val Asn
1               5                   10                  15

Asn Leu Lys Ser Gln Ser Ser Ser Met Ala Ser Ala Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70


<210> SEQ ID NO 106
<211> LENGTH: 136
<212> TYPE: PRT
<213> ORGANISM: Bacillus cereus

<400> SEQUENCE: 106

Gly Phe Leu Asn Met Arg Ile Gly Thr Asn Val Leu Ser Met Asn Ala
1               5                   10                  15

Arg Gln Ser Leu Tyr Glu Asn Glu Lys Arg Met Asn Val Ala Met Glu
            20                  25                  30

His Leu Ala Thr Gly Lys Lys Leu Asn Asn Ala Ser Asp Asn Pro Ala
        35                  40                  45

Asn Ile Ala Ile Val Thr Arg Met His Ala Arg Ala Ser Gly Met Arg
    50                  55                  60

Leu Ala Ile Arg Asn Asn Glu Asp Thr Ile Ser Met Leu Arg Thr Ala
65                  70                  75                  80

Glu Ala Ala Leu Gln Thr Leu Thr Asn Ile Leu Gln Arg Met Arg Asp
                85                  90                  95

Leu Ala Val Gln Ser Ala Asn Gly Thr Asn Ser Asn Lys Asn Arg Asp
            100                 105                 110

Ser Leu Asn Lys Glu Phe Gln Ser Leu Thr Glu Gln Ile Gly Tyr Ile
        115                 120                 125

Gly Glu Thr Thr Glu Phe Asn Asp
    130                 135
```

<210> SEQ ID NO 107
<211> LENGTH: 73
<212> TYPE: PRT
<213> ORGANISM: Bacillus cereus

<400> SEQUENCE: 107

```
Arg Ala Asp Leu Gly Ser Met Ile Asn Arg Leu Gln Phe Asn Ile Glu
1               5                   10                  15

Asn Leu Asn Ser Gln Ser Met Ala Leu Thr Asp Ala Ala Ser Arg Ile
            20                  25                  30

Glu Asp Ala Asp Met Ala Gln Glu Met Ser Asp Phe Leu Lys Phe Lys
        35                  40                  45

Leu Leu Thr Glu Val Ala Leu Ser Met Val Ser Gln Ala Asn Gln Ile
    50                  55                  60

Pro Gln Met Val Ser Lys Leu Leu Gln
65                  70
```

<210> SEQ ID NO 108
<211> LENGTH: 153
<212> TYPE: PRT
<213> ORGANISM: Bacillus thuringiensis

<400> SEQUENCE: 108

```
Gly Val Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Asn
    50                  55                  60

Val Ala Ala Asp Asn Thr Gln Asn Gly Met Ser Leu Ile Arg Thr Ala
65                  70                  75                  80

Asp Ser Ala Met Asn Ser Val Ser Asn Ile Leu Leu Arg Met Arg Asp
                85                  90                  95

Ile Ala Asn Gln Ser Ala Asn Gly Thr Asn Thr Asp Ser Asn Lys Ser
            100                 105                 110

Ala Leu Gln Lys Glu Phe Ala Glu Leu Gln Lys Gln Ile Thr Tyr Ile
        115                 120                 125

Ala Asp Asn Thr Gln Phe Asn Asp Lys Asn Leu Leu Lys Glu Asp Ser
    130                 135                 140

Glu Val Lys Ile Gln Thr Leu Asp Ser
145                 150
```

<210> SEQ ID NO 109
<211> LENGTH: 85
<212> TYPE: PRT
<213> ORGANISM: Bacillus thuringiensis

<400> SEQUENCE: 109

```
Ala Ile Asp Ala Ala Leu Thr Lys Val Ala Asp Asn Arg Ala Thr Leu
1               5                   10                  15

Gly Ala Thr Leu Asn Arg Leu Asp Phe Asn Val Asn Asn Leu Lys Ser
            20                  25                  30

Gln Ser Ser Ser Met Ala Ser Ala Ala Ser Gln Ile Glu Asp Ala Asp
        35                  40                  45

Met Ala Lys Glu Met Ser Glu Met Thr Lys Phe Lys Ile Leu Asn Glu
    50                  55                  60
```

Ala Gly Ile Ser Met Leu Ser Gln Ala Asn Gln Thr Pro Gln Met Val
65 70 75 80

Ser Lys Leu Leu Gln
85

<210> SEQ ID NO 110
<211> LENGTH: 153
<212> TYPE: PRT
<213> ORGANISM: Bacillus thuringiensis

<400> SEQUENCE: 110

Gly Val Leu Asn Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Ser Gly Leu Asn
50 55 60

Val Ala Ala Asp Asn Thr Gln Asn Gly Met Ser Leu Ile Arg Thr Ala
65 70 75 80

Asp Ser Ala Met Asn Ser Val Ser Asn Ile Leu Leu Arg Met Arg Asp
85 90 95

Ile Ala Asn Gln Ser Ala Asn Gly Thr Asn Thr Asp Ser Asn Lys Ser
100 105 110

Ala Leu Gln Lys Glu Phe Ala Glu Leu Gln Lys Gln Ile Thr Tyr Ile
115 120 125

Ala Asp Asn Thr Gln Phe Asn Asp Lys Asn Leu Leu Lys Glu Asp Ser
130 135 140

Glu Val Lys Ile Gln Thr Leu Asp Ser
145 150

<210> SEQ ID NO 111
<211> LENGTH: 86
<212> TYPE: PRT
<213> ORGANISM: Bacillus thuringiensis

<400> SEQUENCE: 111

Ala Ala Ile Asp Ala Ala Leu Thr Lys Val Ala Asp Asn Arg Ala Thr
1 5 10 15

Leu Gly Ala Thr Leu Asn Arg Leu Asp Phe Asn Val Asn Asn Leu Lys
20 25 30

Ser Gln Ser Ser Ser Met Ala Ser Ala Ala Ser Gln Ile Glu Asp Ala
35 40 45

Asp Met Ala Lys Glu Met Ser Glu Met Thr Lys Phe Lys Ile Leu Asn
50 55 60

Glu Ala Gly Ile Ser Met Leu Ser Gln Ala Asn Gln Thr Pro Gln Met
65 70 75 80

Val Ser Lys Leu Leu Gln
85

<210> SEQ ID NO 112
<211> LENGTH: 140
<212> TYPE: PRT
<213> ORGANISM: Bacillus cereus

<400> SEQUENCE: 112

```
Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Asn Gly Thr Asn Thr Ala Glu Asn Lys Ala
            100                 105                 110

Ala Met Gln Lys Glu Phe Gly Glu Leu Lys Asp Gln Ile Lys Tyr Ile
        115                 120                 125

Ser Glu Asn Thr Gln Phe Asn Asp Gln His Leu Leu
    130                 135                 140


<210> SEQ ID NO 113
<211> LENGTH: 78
<212> TYPE: PRT
<213> ORGANISM: Bacillus cereus

<400> SEQUENCE: 113

Thr Val Ala Asp Asn Arg Ala Thr Leu Gly Ala Thr Leu Asn Arg Leu
1               5                   10                  15

Asp Phe Asn Val Asn Asn Leu Lys Ser Gln Ser Ala Ser Met Ala Ser
            20                  25                  30

Ala Ala Ser Gln Ile Glu Asp Ala Asp Met Ala Lys Glu Met Ser Glu
        35                  40                  45

Met Thr Lys Phe Lys Ile Leu Asn Glu Ala Gly Ile Ser Met Leu Ser
    50                  55                  60

Gln Ala Asn Gln Thr Pro Gln Met Val Ser Lys Leu Leu Gln
65                  70                  75


<210> SEQ ID NO 114
<211> LENGTH: 140
<212> TYPE: PRT
<213> ORGANISM: Bacillus thuringiensis

<400> SEQUENCE: 114

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Ile Ala Asn Gln Ser Ala Asn Gly Thr Asn Thr Ser Asp Asn Gln Lys
            100                 105                 110
```

```
Ala Leu Asp Lys Glu Phe Ser Ala Leu Lys Glu Gln Ile Asp Tyr Ile
        115                 120                 125

Ser Lys Asn Thr Glu Phe Asn Asp Lys Lys Leu Leu
    130                 135                 140


<210> SEQ ID NO 115
<211> LENGTH: 88
<212> TYPE: PRT
<213> ORGANISM: Bacillus thuringiensis

<400> SEQUENCE: 115

Ala Ile Lys Ser Ile Asp Ala Ala Leu Asp Thr Ile Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ser Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85


<210> SEQ ID NO 116
<211> LENGTH: 137
<212> TYPE: PRT
<213> ORGANISM: Bacillus thuringiensis

<400> SEQUENCE: 116

Trp Gly Phe Leu Ile Met Arg Ile Asn Thr Asn Ile Asn Ser Met Arg
1               5                   10                  15

Thr Gln Glu Tyr Met Arg Gln Asn Gln Ala Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
    50                  55                  60

Gly Val Ala Ala Asn Asn Thr Gln Asp Gly Met Ser Leu Ile Arg Thr
65                  70                  75                  80

Ala Asp Ser Ala Leu Asn Ser Val Ser Asn Ile Leu Leu Arg Met Arg
                85                  90                  95

Asp Ile Ala Asn Gln Ser Ala Asn Gly Thr Asn Thr Ala Asp Asn Gln
            100                 105                 110

Gln Ala Leu Gln Lys Glu Phe Gly Gln Leu Lys Glu Gln Ile Ser Tyr
        115                 120                 125

Ile Ala Asp Asn Thr Glu Phe Asn Asp
    130                 135


<210> SEQ ID NO 117
<211> LENGTH: 88
<212> TYPE: PRT
<213> ORGANISM: Bacillus thuringiensis

<400> SEQUENCE: 117

Ala Val Asp Ala Ile Asp Ala Ala Leu Lys Thr Val Ala Ser Asn Arg
1               5                   10                  15

Ala Thr Leu Gly Ala Thr Leu Asn Arg Leu Asp Phe Asn Val Asn Asn
```

```
            20                  25                  30

Leu Lys Ser Gln Ser Ala Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85


<210> SEQ ID NO 118
<211> LENGTH: 141
<212> TYPE: PRT
<213> ORGANISM: Bacillus thuringiensis

<400> SEQUENCE: 118

Trp Gly Phe Leu Ile Met Arg Ile Asn Thr Asn Ile Asn Ser Met Arg
1               5                   10                  15

Thr Gln Glu Tyr Met Arg Gln Asn Gln Ala Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
    50                  55                  60

Gly Val Ala Ala Asn Asn Thr Gln Asp Gly Met Ser Leu Ile Arg Thr
65                  70                  75                  80

Ala Asp Ser Ala Leu Asn Ser Val Ser Asn Ile Leu Leu Arg Met Arg
                85                  90                  95

Asp Ile Ala Asn Gln Ser Ala Asn Gly Thr Asn Thr Ala Asp Asn Gln
            100                 105                 110

Gln Ala Leu Gln Lys Glu Phe Gly Gln Leu Lys Glu Gln Ile Ser Tyr
        115                 120                 125

Ile Ala Asp Asn Thr Glu Phe Asn Asp Lys Thr Leu Leu
    130                 135                 140


<210> SEQ ID NO 119
<211> LENGTH: 88
<212> TYPE: PRT
<213> ORGANISM: Bacillus thuringiensis

<400> SEQUENCE: 119

Ala Val Asp Ala Ile Asp Ala Ala Leu Lys Thr Val Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ala Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85


<210> SEQ ID NO 120
<211> LENGTH: 141
<212> TYPE: PRT
```

<213> ORGANISM: Bacillus thuringiensis

<400> SEQUENCE: 120

Trp Gly Phe Leu Ile Met Arg Ile Asn Thr Asn Ile Asn Ser Met Arg
1 5 10 15

Thr Gln Glu Tyr Met Arg Gln Asn Gln Ala Lys Met Ser Asn Ala Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ala Asn Asn Thr Gln Asp Gly Met Ser Leu Ile Arg Thr
65 70 75 80

Ala Asp Ser Ala Met Asn Ser Val Ser Asn Ile Leu Leu Arg Met Arg
85 90 95

Asp Ile Ser Asn Gln Ser Ala Asn Gly Thr Asn Thr Asp Lys Asn Gln
100 105 110

Ser Ala Leu Asp Lys Glu Phe Ala Ala Leu Lys Asp Gln Ile Asp Tyr
115 120 125

Ile Ser Lys Asn Thr Glu Phe Asn Asp Gln Lys Leu Leu
130 135 140

<210> SEQ ID NO 121
<211> LENGTH: 88
<212> TYPE: PRT
<213> ORGANISM: Bacillus thuringiensis

<400> SEQUENCE: 121

Ala Ile Ala Ser Ile Asp Ala Ala Leu Glu Ser Ile Ala Ser Asn Arg
1 5 10 15

Ala Thr Leu Gly Ala Thr Leu Asn Arg Leu Asp Phe Asn Val Asn Asn
20 25 30

Leu Lys Ser Gln Ser Ser Ser Met Ala Ser Ala Ala Ser Gln Ile Glu
35 40 45

Asp Ala Asp Met Ala Lys Glu Met Ser Glu Met Thr Lys Phe Lys Ile
50 55 60

Leu Asn Glu Ala Gly Ile Ser Met Leu Ser Gln Ala Asn Gln Thr Pro
65 70 75 80

Gln Met Val Ser Lys Leu Leu Gln
85

<210> SEQ ID NO 122
<211> LENGTH: 140
<212> TYPE: PRT
<213> ORGANISM: Bacillus thuringiensis

<400> SEQUENCE: 122

Gly Phe Leu Asn Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Ser Gly Leu Gly
50 55 60

Val Ala Ala Asn Asn Thr Gln Asp Gly Met Ser Leu Ile Arg Thr Ala
65 70 75 80

```
Asp Ser Ala Met Asn Ser Val Ser Asn Ile Leu Leu Arg Met Arg Asp
                85                  90                  95

Ile Ser Asn Gln Ser Ala Asn Gly Thr Asn Thr Asp Lys Asn Gln Ser
            100                 105                 110

Ala Leu Asp Lys Glu Phe Ala Ala Leu Lys Asp Gln Ile Asp Tyr Ile
        115                 120                 125

Ser Lys Asn Thr Glu Phe Asn Asp Gln Lys Leu Leu
    130                 135                 140


<210> SEQ ID NO 123
<211> LENGTH: 88
<212> TYPE: PRT
<213> ORGANISM: Bacillus thuringiensis

<400> SEQUENCE: 123

Ala Ile Ala Ser Ile Asp Ala Ala Leu Glu Ser Ile Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ser Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85


<210> SEQ ID NO 124
<211> LENGTH: 140
<212> TYPE: PRT
<213> ORGANISM: Bacillus thuringiensis

<400> SEQUENCE: 124

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Met Asn Ser Val Ser Asn Ile Leu Leu Arg Met Arg Asp
                85                  90                  95

Ile Ser Asn Gln Ser Ala Asn Gly Thr Asn Thr Asp Lys Asn Gln Ser
            100                 105                 110

Ala Leu Asp Lys Glu Phe Ala Ala Leu Lys Asp Gln Ile Asp Tyr Ile
        115                 120                 125

Ser Lys Asn Thr Glu Phe Asn Asp Gln Lys Leu Leu
    130                 135                 140


<210> SEQ ID NO 125
<211> LENGTH: 88
<212> TYPE: PRT
<213> ORGANISM: Bacillus thuringiensis
```

<400> SEQUENCE: 125

Ala Ile Ala Ser Ile Asp Ala Ala Leu Glu Ser Ile Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ser Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85

<210> SEQ ID NO 126
<211> LENGTH: 140
<212> TYPE: PRT
<213> ORGANISM: Bacillus thuringiensis

<400> SEQUENCE: 126

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Met Asn Ser Val Ser Asn Ile Leu Leu Arg Met Arg Asp
                85                  90                  95

Ile Ser Asn Gln Ser Ala Asn Gly Thr Asn Thr Asp Lys Asn Gln Ser
            100                 105                 110

Ala Leu Asp Lys Glu Phe Ala Ala Leu Lys Asp Gln Ile Asp Tyr Ile
        115                 120                 125

Ser Lys Asn Thr Glu Phe Asn Asp Gln Lys Leu Leu
    130                 135                 140

<210> SEQ ID NO 127
<211> LENGTH: 88
<212> TYPE: PRT
<213> ORGANISM: Bacillus thuringiensis

<400> SEQUENCE: 127

Ala Ile Ala Ser Ile Asp Ala Ala Leu Glu Ser Ile Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ser Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
85

<210> SEQ ID NO 128
<211> LENGTH: 140
<212> TYPE: PRT
<213> ORGANISM: Bacillus thuringiensis

<400> SEQUENCE: 128

Gly Phe Leu Asn Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Ser Gly Leu Gly
50 55 60

Val Ala Ala Asn Asn Thr Gln Asp Gly Met Ser Leu Ile Arg Thr Ala
65 70 75 80

Asp Ser Ala Met Asn Ser Val Ser Asn Ile Leu Leu Arg Met Arg Asp
85 90 95

Ile Ser Asn Gln Ser Ala Asn Gly Thr Asn Thr Asp Lys Asn Gln Ser
100 105 110

Ala Leu Asp Lys Glu Phe Ala Ala Leu Lys Asp Gln Ile Asp Tyr Ile
115 120 125

Ser Lys Asn Thr Glu Phe Asn Asp Gln Lys Leu Leu
130 135 140

<210> SEQ ID NO 129
<211> LENGTH: 88
<212> TYPE: PRT
<213> ORGANISM: Bacillus thuringiensis

<400> SEQUENCE: 129

Ala Ile Ala Ser Ile Asp Ala Ala Leu Glu Ser Ile Ala Ser Asn Arg
1 5 10 15

Ala Thr Leu Gly Ala Thr Leu Asn Arg Leu Asp Phe Asn Val Asn Asn
20 25 30

Leu Lys Ser Gln Ser Ser Ser Met Ala Ser Ala Ala Ser Gln Ile Glu
35 40 45

Asp Ala Asp Met Ala Lys Glu Met Ser Glu Met Thr Lys Phe Lys Ile
50 55 60

Leu Asn Glu Ala Gly Ile Ser Met Leu Ser Gln Ala Asn Gln Thr Pro
65 70 75 80

Gln Met Val Ser Lys Leu Leu Gln
85

<210> SEQ ID NO 130
<211> LENGTH: 140
<212> TYPE: PRT
<213> ORGANISM: Bacillus thuringiensis

<400> SEQUENCE: 130

Gly Phe Leu Asn Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala

```
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Ile Ser Leu Ile Arg Thr Ala
65                  70                  75                  80

Asp Ser Ala Met Asn Ser Val Ser Asn Ile Leu Leu Arg Met Arg Asp
                85                  90                  95

Leu Ala Asn Gln Ser Ala Asn Gly Thr Asn Thr Asn Glu Asn Gln Ala
            100                 105                 110

Ala Leu Asn Lys Glu Phe Asp Ala Leu Lys Glu Gln Ile Asp Tyr Ile
        115                 120                 125

Ser Thr Asn Thr Glu Phe Asn Asp Lys Lys Leu Leu
    130                 135                 140


<210> SEQ ID NO 131
<211> LENGTH: 73
<212> TYPE: PRT
<213> ORGANISM: Bacillus thuringiensis

<400> SEQUENCE: 131

Arg Ala Thr Leu Gly Ala Thr Leu Asn Arg Leu Asp Phe Asn Val Asn
1               5                   10                  15

Asn Leu Lys Ser Gln Ser Ser Ser Met Ala Ser Ala Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70


<210> SEQ ID NO 132
<211> LENGTH: 140
<212> TYPE: PRT
<213> ORGANISM: Bacillus thuringiensis

<400> SEQUENCE: 132

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Ile Ser Leu Ile Arg Thr Ala
65                  70                  75                  80

Asp Ser Ala Met Asn Ser Val Ser Asn Ile Leu Leu Arg Met Arg Asp
                85                  90                  95

Leu Ala Asn Gln Ser Ala Asn Gly Thr Asn Thr Asn Glu Asn Gln Ala
            100                 105                 110

Ala Leu Asn Lys Glu Phe Asp Ala Leu Lys Glu Gln Ile Asp Tyr Ile
        115                 120                 125

Ser Thr Asn Thr Glu Phe Asn Asp Lys Lys Leu Leu
    130                 135                 140
```

<210> SEQ ID NO 133
<211> LENGTH: 73
<212> TYPE: PRT
<213> ORGANISM: Bacillus thuringiensis

<400> SEQUENCE: 133

```
Arg Ala Thr Leu Gly Ala Thr Leu Asn Arg Leu Asp Phe Asn Val Asn
1               5                   10                  15

Asn Leu Lys Ser Gln Ser Ser Ser Met Ala Ser Ala Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70
```

<210> SEQ ID NO 134
<211> LENGTH: 140
<212> TYPE: PRT
<213> ORGANISM: Bacillus weihenstephanensis

<400> SEQUENCE: 134

```
Gly Val Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Ser
    50                  55                  60

Val Ala Ala Asn Asn Thr Gln Asp Gly Met Ser Leu Ile Arg Thr Ala
65                  70                  75                  80

Asp Ser Ala Met Asn Ser Val Ser Asn Ile Leu Leu Arg Met Arg Asp
                85                  90                  95

Leu Ser Asn Gln Ser Ala Asn Gly Thr Asn Thr Asp Glu Asn Gln Gln
            100                 105                 110

Ala Leu Asn Lys Glu Phe Ala Ala Leu Lys Asp Gln Ile Asp Tyr Ile
        115                 120                 125

Ser Lys Asn Thr Glu Phe Asn Asp Lys Lys Leu Leu
    130                 135                 140
```

<210> SEQ ID NO 135
<211> LENGTH: 73
<212> TYPE: PRT
<213> ORGANISM: Bacillus weihenstephanensis

<400> SEQUENCE: 135

```
Arg Ala Thr Leu Gly Ala Thr Leu Asn Arg Leu Asp Phe Asn Val Asn
1               5                   10                  15

Asn Leu Lys Ser Gln Ser Ser Ser Met Ala Ser Ala Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70
```

<210> SEQ ID NO 136
<211> LENGTH: 140
<212> TYPE: PRT
<213> ORGANISM: Bacillus thuringiensis

<400> SEQUENCE: 136

```
Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Ile Ala Asn Gln Ser Ala Asn Gly Thr Asn Thr Gly Asp Asn Gln Lys
            100                 105                 110

Ala Leu Asp Lys Glu Phe Ser Ala Leu Lys Glu Gln Ile Asp Tyr Ile
        115                 120                 125

Ser Lys Asn Thr Glu Phe Asn Asp Lys Lys Leu Leu
    130                 135                 140
```

<210> SEQ ID NO 137
<211> LENGTH: 85
<212> TYPE: PRT
<213> ORGANISM: Bacillus thuringiensis

<400> SEQUENCE: 137

```
Ile Asp Ala Ala Leu Glu Thr Ile Ala Ser Asn Arg Ala Thr Leu Gly
1               5                   10                  15

Ala Thr Leu Asn Arg Leu Asp Phe Asn Val Asn Asn Leu Lys Ser Gln
            20                  25                  30

Ser Ser Ser Met Ala Ser Ala Ala Ser Gln Ile Glu Asp Ala Asp Met
        35                  40                  45

Ala Lys Glu Met Ser Glu Met Thr Lys Phe Lys Ile Leu Asn Glu Ala
    50                  55                  60

Gly Ile Ser Met Leu Ser Gln Ala Asn Gln Thr Pro Gln Met Val Ser
65                  70                  75                  80

Lys Leu Leu Gln Ser
                85
```

<210> SEQ ID NO 138
<211> LENGTH: 141
<212> TYPE: PRT
<213> ORGANISM: Bacillus thuringiensis

<400> SEQUENCE: 138

```
Trp Gly Phe Leu Ile Met Arg Ile Asn Thr Asn Ile Asn Ser Met Arg
1               5                   10                  15

Thr Gln Glu Tyr Met Arg Gln Asn Gln Thr Lys Met Ser Asn Ala Met
            20                  25                  30

Asp Arg Leu Ser Ser Gly Lys Arg Ile Asn Asn Ala Ser Asp Asp Ala
        35                  40                  45
```

```
Ala Gly Leu Ala Ile Ala Thr Arg Met Arg Ala Arg Glu Asn Gly Leu
    50                  55                  60

Gly Val Ala Ala Asn Asn Thr Gln Asp Gly Met Ser Leu Ile Arg Thr
65                  70                  75                  80

Ala Asp Ser Ala Met Asn Ser Val Ser Asn Ile Leu Leu Arg Met Arg
                85                  90                  95

Asp Leu Ala Asn Gln Ser Ala Asn Gly Thr Asn Thr Asp Asp Asn Gln
            100                 105                 110

Lys Ala Leu Asp Lys Glu Phe Ser Ala Leu Lys Glu Gln Ile Asp Tyr
        115                 120                 125

Ile Ser Lys Asn Thr Glu Phe Asn Asp Lys Lys Leu Leu
    130                 135                 140


<210> SEQ ID NO 139
<211> LENGTH: 70
<212> TYPE: PRT
<213> ORGANISM: Bacillus thuringiensis

<400> SEQUENCE: 139

Leu Gly Ala Thr Leu Asn Arg Leu Asp Phe Asn Val Asn Asn Leu Lys
1               5                   10                  15

Ser Gln Ser Ser Ser Met Ala Ala Ala Ala Ser Gln Ile Glu Asp Ala
            20                  25                  30

Asp Met Ala Lys Glu Met Ser Glu Met Thr Lys Phe Lys Ile Leu Asn
        35                  40                  45

Glu Ala Gly Ile Ser Met Leu Ser Gln Ala Asn Gln Thr Pro Gln Met
    50                  55                  60

Val Ser Lys Leu Leu Gln
65                  70


<210> SEQ ID NO 140
<211> LENGTH: 141
<212> TYPE: PRT
<213> ORGANISM: Bacillus thuringiensis

<400> SEQUENCE: 140

Trp Gly Phe Leu Ile Met Arg Ile Asn Thr Asn Ile Asn Ser Met Arg
1               5                   10                  15

Thr Gln Glu Tyr Met Arg Gln Asn Gln Thr Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Asn Gly Leu
    50                  55                  60

Gly Val Ala Ala Asn Asn Thr Gln Asp Gly Met Ser Leu Ile Arg Thr
65                  70                  75                  80

Ala Asp Ser Ala Met Asn Ser Val Ser Asn Ile Leu Leu Arg Met Arg
                85                  90                  95

Asp Leu Ala Asn Gln Ser Ala Asn Gly Thr Asn Thr Asp Asp Asn Gln
            100                 105                 110

Lys Ala Leu Asp Lys Glu Phe Ser Ala Leu Lys Glu Gln Ile Asp Tyr
        115                 120                 125

Ile Ser Lys Asn Thr Glu Phe Asn Asp Lys Lys Leu Leu
    130                 135                 140


<210> SEQ ID NO 141
<211> LENGTH: 70
```

<212> TYPE: PRT
<213> ORGANISM: Bacillus thuringiensis

<400> SEQUENCE: 141

Leu Gly Ala Thr Leu Asn Arg Leu Asp Phe Asn Val Asn Asn Leu Lys
1               5                   10                  15

Ser Gln Ser Ser Ser Met Ala Ala Ala Ala Ser Gln Ile Glu Asp Ala
            20                  25                  30

Asp Met Ala Lys Glu Met Ser Glu Met Thr Lys Phe Lys Ile Leu Asn
        35                  40                  45

Glu Ala Gly Ile Ser Met Leu Ser Gln Ala Asn Gln Thr Pro Gln Met
    50                  55                  60

Val Ser Lys Leu Leu Gln
65                  70

<210> SEQ ID NO 142
<211> LENGTH: 141
<212> TYPE: PRT
<213> ORGANISM: Bacillus thuringiensis

<400> SEQUENCE: 142

Trp Gly Phe Leu Ile Met Arg Ile Asn Thr Asn Ile Asn Ser Met Arg
1               5                   10                  15

Thr Gln Glu Tyr Met Arg Gln Asn Gln Thr Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Asn Gly Leu
    50                  55                  60

Gly Val Ala Ala Asn Asn Thr Gln Asp Gly Met Ser Leu Ile Arg Thr
65                  70                  75                  80

Ala Asp Ser Ala Met Asn Ser Val Ser Asn Ile Leu Leu Arg Met Arg
                85                  90                  95

Asp Leu Ala Asn Gln Ser Ala Asn Gly Thr Asn Thr Asp Asp Asn Gln
            100                 105                 110

Lys Ala Leu Asp Lys Glu Phe Ser Ala Leu Lys Glu Gln Ile Asp Tyr
        115                 120                 125

Ile Ser Lys Asn Thr Glu Phe Asn Asp Lys Lys Leu Leu
    130                 135                 140

<210> SEQ ID NO 143
<211> LENGTH: 73
<212> TYPE: PRT
<213> ORGANISM: Bacillus thuringiensis

<400> SEQUENCE: 143

Arg Ala Thr Leu Gly Ala Thr Leu Asn Arg Leu Asp Phe Asn Val Asn
1               5                   10                  15

Asn Leu Lys Ser Gln Ser Ser Ser Met Ala Ala Ala Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70

<210> SEQ ID NO 144
<211> LENGTH: 140
<212> TYPE: PRT
<213> ORGANISM: Bacillus thuringiensis

<400> SEQUENCE: 144

```
Gly Phe Leu Asn Met Arg Ile Asn Thr Asn Ile Asn Ser Met Arg Thr
1               5                   10                  15

Gln Asp Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Met Asn Ser Val Ser Asn Ile Leu Leu Arg Met Arg Asp
                85                  90                  95

Ile Ser Asn Gln Ser Ala Asn Gly Thr Asn Thr Asp Lys Asn Gln Ser
            100                 105                 110

Ala Leu Asp Lys Glu Phe Ala Ala Leu Lys Asp Gln Ile Asp Tyr Ile
        115                 120                 125

Ser Lys Asn Thr Glu Phe Asn Asp Gln Lys Leu Leu
    130                 135                 140
```

<210> SEQ ID NO 145
<211> LENGTH: 88
<212> TYPE: PRT
<213> ORGANISM: Bacillus thuringiensis

<400> SEQUENCE: 145

```
Ala Ile Ala Ser Ile Asp Ala Ala Leu Glu Ser Ile Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ser Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85
```

<210> SEQ ID NO 146
<211> LENGTH: 173
<212> TYPE: PRT
<213> ORGANISM: Bacillus thuringiensis

<400> SEQUENCE: 146

```
Gly Phe Leu Asn Met Ala Arg Ile Thr Ile Asn Leu Glu Ile Asp Phe
1               5                   10                  15

Phe Ala Tyr Tyr Arg Phe Ser Ile Cys Arg Lys Val Asn Ile Lys Lys
            20                  25                  30

Trp Gly Phe Leu Asn Met Arg Ile Asn Thr Asn Ile Asn Ser Met Arg
        35                  40                  45

Thr Gln Asp Tyr Met Arg Gln Asn Gln Ala Lys Met Ser Asn Ala Met
    50                  55                  60
```

Asp Arg Leu Ser Ser Gly Lys Arg Ile Asn Asn Ala Ser Asp Asp Ala
65 70 75 80

Ala Gly Leu Ala Ile Ala Thr Arg Met Arg Ala Arg Glu Ser Gly Leu
85 90 95

Gly Val Ala Ala Asn Asn Thr Gln Asp Gly Met Ser Leu Ile Arg Thr
100 105 110

Ala Asp Ser Ala Met Asn Ser Val Ser Asn Ile Leu Leu Arg Met Arg
115 120 125

Asp Ile Ser Asn Gln Ser Ala Asn Gly Thr Asn Thr Asp Lys Asn Gln
130 135 140

Ser Ala Leu Asp Lys Glu Phe Ala Ala Leu Lys Asp Gln Ile Asp Tyr
145 150 155 160

Ile Ser Lys Asn Thr Glu Phe Asn Asp Gln Lys Leu Leu
165 170

<210> SEQ ID NO 147
<211> LENGTH: 88
<212> TYPE: PRT
<213> ORGANISM: Bacillus thuringiensis

<400> SEQUENCE: 147

Ala Ile Ala Ser Ile Asp Ala Ala Leu Glu Ser Ile Ala Ser Asn Arg
1 5 10 15

Ala Thr Leu Gly Ala Thr Leu Asn Arg Leu Asp Phe Asn Val Asn Asn
20 25 30

Leu Lys Ser Gln Ser Ser Ser Met Ala Ser Ala Ala Ser Gln Ile Glu
35 40 45

Asp Ala Asp Met Ala Lys Glu Met Ser Glu Met Thr Lys Phe Lys Ile
50 55 60

Leu Asn Glu Ala Gly Ile Ser Met Leu Ser Gln Ala Asn Gln Thr Pro
65 70 75 80

Gln Met Val Ser Lys Leu Leu Gln
85

<210> SEQ ID NO 148
<211> LENGTH: 157
<212> TYPE: PRT
<213> ORGANISM: Bacillus cereus

<400> SEQUENCE: 148

Gly Val Leu Tyr Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Ser Gly Leu Ser
50 55 60

Val Ala Ala Asp Asn Thr Gln Asn Gly Met Ser Leu Ile Arg Thr Ala
65 70 75 80

Asp Ser Ala Met Asn Ser Val Ser Asn Ile Leu Leu Arg Met Arg Asp
85 90 95

Ile Ala Asn Gln Ser Ala Asn Gly Thr Asn Thr Asp Lys Asn Gln Val
100 105 110

Ala Leu Gln Lys Glu Phe Ala Ala Leu Lys Glu Gln Ile Thr Tyr Ile
115 120 125

Ala Asp Asn Thr Gln Phe Asn Asp Lys Asn Leu Leu Asn Gly Asn Gln
130 135 140

Thr Ile Asn Ile Gln Thr Leu Asp Ser His Asp Ser Thr
145 150 155

<210> SEQ ID NO 149
<211> LENGTH: 78
<212> TYPE: PRT
<213> ORGANISM: Bacillus cereus

<400> SEQUENCE: 149

Thr Val Ala Asp Asn Arg Ala Thr Leu Gly Ala Thr Leu Asn Arg Leu
1 5 10 15

Asp Phe Asn Val Asn Asn Leu Lys Ser Gln Ser Ser Ala Met Ala Ala
20 25 30

Ser Ala Ser Gln Ile Glu Asp Ala Asp Met Ala Lys Glu Met Ser Glu
35 40 45

Met Thr Lys Phe Lys Ile Leu Asn Glu Ala Gly Ile Ser Met Leu Ser
50 55 60

Gln Ala Asn Gln Thr Pro Gln Met Val Ser Lys Leu Leu Gln
65 70 75

<210> SEQ ID NO 150
<211> LENGTH: 157
<212> TYPE: PRT
<213> ORGANISM: Bacillus cereus

<400> SEQUENCE: 150

Gly Val Leu Tyr Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Ser Gly Leu Ser
50 55 60

Val Ala Ala Asp Asn Thr Gln Asn Gly Met Ser Leu Ile Arg Thr Ala
65 70 75 80

Asp Ser Ala Met Asn Ser Val Ser Asn Ile Leu Leu Arg Met Arg Asp
85 90 95

Ile Ala Asn Gln Ser Ala Asn Gly Thr Asn Thr Asp Lys Asn Gln Val
100 105 110

Ala Leu Gln Lys Glu Phe Ala Ala Leu Lys Glu Gln Ile Thr Tyr Ile
115 120 125

Ala Asp Asn Thr Gln Phe Asn Asp Lys Asn Leu Leu Asn Gly Asn Gln
130 135 140

Thr Ile Asn Ile Gln Thr Leu Asp Ser His Asp Ser Thr
145 150 155

<210> SEQ ID NO 151
<211> LENGTH: 78
<212> TYPE: PRT
<213> ORGANISM: Bacillus cereus

<400> SEQUENCE: 151

Thr Val Ala Asp Asn Arg Ala Thr Leu Gly Ala Thr Leu Asn Arg Leu
1 5 10 15

Asp Phe Asn Val Asn Asn Leu Lys Ser Gln Ser Ser Ala Met Ala Ala
20 25 30

Ser Ala Ser Gln Ile Glu Asp Ala Asp Met Ala Lys Glu Met Ser Glu
35 40 45

Met Thr Lys Phe Lys Ile Leu Asn Glu Ala Gly Ile Ser Met Leu Ser
50 55 60

Gln Ala Asn Gln Thr Pro Gln Met Val Ser Lys Leu Leu Gln
65 70 75

<210> SEQ ID NO 152
<211> LENGTH: 140
<212> TYPE: PRT
<213> ORGANISM: Bacillus thuringiensis

<400> SEQUENCE: 152

Gly Phe Leu Asn Met Arg Ile Asn Thr Asn Ile Asn Ser Met Arg Thr
1 5 10 15

Gln Glu Tyr Met Arg Gln Asn Gln Ala Lys Met Ser Asn Ala Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Ser Gly Leu Gly
50 55 60

Val Ala Ala Asn Asn Thr Gln Asp Gly Met Ser Leu Ile Arg Thr Ala
65 70 75 80

Asp Ser Ala Leu Asn Ser Val Ser Asn Ile Leu Leu Arg Met Arg Asp
85 90 95

Ile Ala Asn Gln Ser Ala Asn Gly Thr Asn Thr Gly Asp Asn Gln Lys
100 105 110

Ala Leu Asp Lys Glu Phe Ser Ala Leu Lys Glu Gln Ile Asp Tyr Ile
115 120 125

Ser Lys Asn Thr Glu Phe Asn Asp Lys Lys Leu Leu
130 135 140

<210> SEQ ID NO 153
<211> LENGTH: 70
<212> TYPE: PRT
<213> ORGANISM: Bacillus thuringiensis

<400> SEQUENCE: 153

Leu Gly Ala Thr Leu Asn Arg Leu Asp Phe Asn Val Asn Asn Leu Lys
1 5 10 15

Ser Gln Ser Ser Ser Met Ala Ser Ala Ala Ser Gln Ile Glu Asp Ala
20 25 30

Asp Met Ala Lys Glu Met Ser Glu Met Thr Lys Phe Lys Ile Leu Asn
35 40 45

Glu Ala Gly Ile Ser Met Leu Ser Gln Ala Asn Gln Thr Pro Gln Met
50 55 60

Val Ser Lys Leu Leu Gln
65 70

<210> SEQ ID NO 154
<211> LENGTH: 140
<212> TYPE: PRT
<213> ORGANISM: Bacillus thuringiensis

<400> SEQUENCE: 154

Gly Phe Leu Asn Met Arg Ile Asn Thr Asn Ile Asn Ser Met Arg Thr

```
1               5                   10                  15

Gln Glu Tyr Met Arg Gln Asn Gln Thr Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Asn Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Ile Ala Asn Gln Ser Ala Asn Gly Thr Asn Thr Ser Asp Asn Gln Lys
            100                 105                 110

Ala Leu Asp Lys Glu Phe Ser Ala Leu Lys Glu Gln Ile Asp Tyr Ile
        115                 120                 125

Ser Lys Asn Thr Glu Phe Asn Asp Lys Lys Leu Leu
    130                 135                 140


<210> SEQ ID NO 155
<211> LENGTH: 88
<212> TYPE: PRT
<213> ORGANISM: Bacillus thuringiensis

<400> SEQUENCE: 155

Ala Ile Lys Ser Ile Asp Ala Ala Leu Asp Thr Ile Ala Ser Asn Arg
1               5                   10                  15

Ala Thr Leu Gly Ala Thr Leu Asn Arg Leu Asp Phe Asn Val Asn Asn
            20                  25                  30

Leu Lys Ser Gln Ser Ser Ser Met Ala Ser Ala Ala Ser Gln Ile Glu
        35                  40                  45

Asp Ala Asp Met Ala Lys Glu Met Ser Glu Met Thr Lys Phe Lys Ile
    50                  55                  60

Leu Asn Glu Ala Gly Ile Ser Met Leu Ser Gln Ala Asn Gln Thr Pro
65                  70                  75                  80

Gln Met Val Ser Lys Leu Leu Gln
                85


<210> SEQ ID NO 156
<211> LENGTH: 140
<212> TYPE: PRT
<213> ORGANISM: Bacillus thuringiensis

<400> SEQUENCE: 156

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Ile Ala Asn Gln Ser Ala Asn Gly Thr Asn Thr Gly Asp Asn Gln Lys
```

100                 105                 110

Ala Leu Asp Lys Glu Phe Ser Ala Leu Lys Glu Gln Ile Asp Tyr Ile
        115                 120                 125

Ser Lys Asn Thr Glu Phe Asn Asp Lys Lys Leu Leu
    130                 135                 140

<210> SEQ ID NO 157
<211> LENGTH: 73
<212> TYPE: PRT
<213> ORGANISM: Bacillus thuringiensis

<400> SEQUENCE: 157

Arg Ala Thr Leu Gly Ala Thr Leu Asn Arg Leu Asp Phe Asn Val Asn
1               5                   10                  15

Asn Leu Lys Ser Gln Ser Ser Ser Met Ala Ser Ala Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70

<210> SEQ ID NO 158
<211> LENGTH: 140
<212> TYPE: PRT
<213> ORGANISM: Bacillus thuringiensis

<400> SEQUENCE: 158

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Ile Ala Asn Gln Ser Ala Asn Gly Thr Asn Thr Gly Asp Asn Gln Lys
            100                 105                 110

Ala Leu Asp Lys Glu Phe Ser Ala Leu Lys Glu Gln Ile Asp Tyr Ile
        115                 120                 125

Ser Lys Asn Thr Glu Phe Asn Asp Lys Lys Leu Leu
    130                 135                 140

<210> SEQ ID NO 159
<211> LENGTH: 73
<212> TYPE: PRT
<213> ORGANISM: Bacillus thuringiensis

<400> SEQUENCE: 159

Arg Ala Thr Leu Gly Ala Thr Leu Asn Arg Leu Asp Phe Asn Val Asn
1               5                   10                  15

Asn Leu Lys Ser Gln Ser Ser Ser Met Ala Ser Ala Ala Ser Gln Ile
            20                  25                  30

```
Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70


<210> SEQ ID NO 160
<211> LENGTH: 153
<212> TYPE: PRT
<213> ORGANISM: Bacillus thuringiensis

<400> SEQUENCE: 160

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Met Asn Ser Val Ser Asn Ile Leu Leu Arg Met Arg Asp
                85                  90                  95

Ile Ala Asn Gln Ser Ala Asn Gly Thr Asn Thr Asn Gly Asn Gln Ala
            100                 105                 110

Ala Leu Asn Lys Glu Phe Asp Ala Leu Lys Gln Gln Ile Asn Tyr Ile
        115                 120                 125

Ser Thr Asn Thr Glu Phe Asn Asp Lys Lys Leu Leu Asp Gly Ser Asn
    130                 135                 140

Lys Thr Ile Ala Ile Gln Thr Leu Asp
145                 150


<210> SEQ ID NO 161
<211> LENGTH: 70
<212> TYPE: PRT
<213> ORGANISM: Bacillus thuringiensis

<400> SEQUENCE: 161

Leu Gly Ala Thr Leu Asn Arg Leu Asp Phe Asn Val Asn Asn Leu Lys
1               5                   10                  15

Ser Gln Gln Ser Ser Met Ala Ser Ala Ala Ser Gln Ile Glu Asp Ala
            20                  25                  30

Asp Met Ala Lys Glu Met Ser Glu Met Thr Lys Phe Lys Ile Leu Asn
        35                  40                  45

Glu Ala Gly Ile Ser Met Leu Ser Gln Ala Asn Gln Thr Pro Gln Met
    50                  55                  60

Val Ser Lys Leu Leu Gln
65                  70


<210> SEQ ID NO 162
<211> LENGTH: 136
<212> TYPE: PRT
<213> ORGANISM: Bacillus cereus

<400> SEQUENCE: 162
```

```
Gly Val Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ala Leu Ile Arg Thr Ala
65                  70                  75                  80

Asp Ser Ala Met Asn Ser Val Ser Asn Ile Leu Leu Arg Arg Asp Ile
                85                  90                  95

Ala Asn Gln Ser Ala Asn Gly Thr Asn Thr Asp Lys Asn Gln Ala Ala
            100                 105                 110

Leu Gln Lys Glu Phe Gly Glu Leu Gln Lys Gln Ile Asp Tyr Ile Ala
        115                 120                 125

Gly Asn Thr Gln Phe Asn Asp Lys
    130                 135


<210> SEQ ID NO 163
<211> LENGTH: 86
<212> TYPE: PRT
<213> ORGANISM: Bacillus cereus

<400> SEQUENCE: 163

Asp Lys Ile Asp Glu Ala Leu Lys Thr Ile Ala Asp Asn Arg Ala Thr
1               5                   10                  15

Leu Gly Ala Thr Leu Asn Arg Leu Asp Phe Asn Val Asn Asn Leu Lys
            20                  25                  30

Ser Gln Ser Ala Ser Met Ala Ser Ala Ala Ser Gln Ile Glu Asp Ala
        35                  40                  45

Asp Met Ala Lys Glu Met Ser Glu Met Thr Lys Phe Lys Ile Leu Asn
    50                  55                  60

Glu Ala Gly Ile Ser Met Leu Ser Gln Ala Asn Gln Thr Pro Gln Met
65                  70                  75                  80

Val Ser Lys Leu Leu Gln
                85


<210> SEQ ID NO 164
<211> LENGTH: 141
<212> TYPE: PRT
<213> ORGANISM: Bacillus thuringiensis

<400> SEQUENCE: 164

Trp Gly Phe Leu Ile Met Arg Ile Asn Thr Asn Ile Asn Ser Met Arg
1               5                   10                  15

Thr Gln Glu Tyr Met Arg Gln Asn Gln Ala Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
    50                  55                  60

Gly Val Ala Ala Asn Asn Thr Gln Asp Gly Met Ser Leu Ile Arg Thr
65                  70                  75                  80

Ala Asp Ser Ala Met Asn Ser Val Ser Asn Ile Leu Leu Arg Met Arg
                85                  90                  95
```

```
Asp Leu Ala Asn Gln Ser Ala Asn Gly Thr Asn Thr Asn Glu Asn Gln
            100                 105                 110

Ala Ala Leu Asn Lys Glu Phe Asp Ala Leu Lys Glu Gln Ile Asn Tyr
        115                 120                 125

Ile Ser Thr Asn Thr Glu Phe Asn Asp Lys Lys Leu Leu
    130                 135                 140


<210> SEQ ID NO 165
<211> LENGTH: 73
<212> TYPE: PRT
<213> ORGANISM: Bacillus thuringiensis

<400> SEQUENCE: 165

Arg Ala Thr Leu Gly Ala Thr Leu Asn Arg Leu Asp Phe Asn Val Asn
1               5                   10                  15

Asn Leu Lys Ser Gln Gln Ser Ser Met Ala Ser Ala Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70


<210> SEQ ID NO 166
<211> LENGTH: 141
<212> TYPE: PRT
<213> ORGANISM: Bacillus cereus

<400> SEQUENCE: 166

Trp Gly Phe Phe Tyr Met Arg Ile Asn Thr Asn Ile Asn Ser Met Arg
1               5                   10                  15

Thr Gln Glu Tyr Met Arg Gln Asn Gln Ala Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
    50                  55                  60

Gly Val Ala Ser Asn Asn Thr Gln Asp Gly Met Ser Leu Ile Arg Thr
65                  70                  75                  80

Ala Asp Ser Ala Leu Asn Ser Val Ser Asn Ile Leu Leu Arg Met Arg
                85                  90                  95

Asp Leu Ala Asn Gln Ser Ala Asn Gly Thr Asn Thr Asn Glu Asn Lys
            100                 105                 110

Ala Ala Met Gln Lys Glu Phe Gly Glu Leu Lys Glu Gln Ile Lys Tyr
        115                 120                 125

Ile Ala Glu Asn Thr Gln Phe Asn Asp Gln His Leu Leu
    130                 135                 140


<210> SEQ ID NO 167
<211> LENGTH: 78
<212> TYPE: PRT
<213> ORGANISM: Bacillus cereus

<400> SEQUENCE: 167

Thr Val Ala Asp Asn Arg Ala Thr Leu Gly Ala Thr Leu Asn Arg Leu
1               5                   10                  15

Asp Phe Asn Val Asn Asn Leu Lys Ser Gln Ala Ser Ser Met Ala Ala
```

```
            20                  25                  30

Ala Ala Ser Gln Val Glu Asp Ala Asp Met Ala Lys Glu Met Ser Glu
        35                  40                  45

Met Thr Lys Phe Lys Ile Leu Asn Glu Ala Gly Ile Ser Met Leu Ser
    50                  55                  60

Gln Ala Asn Gln Thr Pro Gln Met Val Ser Lys Leu Leu Gln
65                  70                  75


<210> SEQ ID NO 168
<211> LENGTH: 141
<212> TYPE: PRT
<213> ORGANISM: Bacillus cereus

<400> SEQUENCE: 168

Trp Gly Phe Phe Tyr Met Arg Ile Asn Thr Asn Ile Asn Ser Met Arg
1               5                   10                  15

Thr Gln Glu Tyr Met Arg Gln Asn Gln Ala Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
    50                  55                  60

Gly Val Ala Ser Asn Asn Thr Gln Asp Gly Met Ser Leu Ile Arg Thr
65                  70                  75                  80

Ala Asp Ser Ala Leu Asn Ser Val Ser Asn Ile Leu Leu Arg Met Arg
                85                  90                  95

Asp Leu Ala Asn Gln Ser Ala Asn Gly Thr Asn Thr Asn Glu Asn Lys
            100                 105                 110

Ala Ala Met Gln Lys Glu Phe Gly Glu Leu Lys Glu Gln Ile Lys Tyr
        115                 120                 125

Ile Ala Glu Asn Thr Gln Phe Asn Asp Gln His Leu Leu
    130                 135                 140


<210> SEQ ID NO 169
<211> LENGTH: 78
<212> TYPE: PRT
<213> ORGANISM: Bacillus cereus

<400> SEQUENCE: 169

Thr Val Ala Asp Asn Arg Ala Thr Leu Gly Ala Thr Leu Asn Arg Leu
1               5                   10                  15

Asp Phe Asn Val Asn Asn Leu Lys Ser Gln Ala Ser Ser Met Ala Ala
            20                  25                  30

Ala Ala Ser Gln Val Glu Asp Ala Asp Met Ala Lys Glu Met Ser Glu
        35                  40                  45

Met Thr Lys Phe Lys Ile Leu Asn Glu Ala Gly Ile Ser Met Leu Ser
    50                  55                  60

Gln Ala Asn Gln Thr Pro Gln Met Val Ser Lys Leu Leu Gln
65                  70                  75


<210> SEQ ID NO 170
<211> LENGTH: 140
<212> TYPE: PRT
<213> ORGANISM: Bacillus cereus

<400> SEQUENCE: 170

Gly Val Leu Asn Met Arg Ile Asn Thr Asn Ile Asn Ser Leu Arg Thr
1               5                   10                  15
```

Gln Glu Tyr Met Arg Gln Asn Gln Ala Lys Met Ser Asn Ser Met Asp
20 25 30

Arg Leu Ser Ser Gly Lys Arg Ile Asn Asn Ala Ser Asp Asp Ala Ala
35 40 45

Gly Leu Ala Ile Ala Thr Arg Met Arg Ala Arg Glu Ser Gly Leu Asn
50 55 60

Val Ala Ala Asn Asn Thr Gln Asp Gly Met Ser Leu Ile Arg Thr Ala
65 70 75 80

Asp Ser Ala Leu Gly Ser Val Ser Asn Ile Leu Leu Arg Met Arg Asp
85 90 95

Leu Ala Asn Gln Ser Ala Asn Gly Thr Asn Thr Ser Asp Asn Gln Ala
100 105 110

Ala Met Gln Lys Glu Phe Ala Glu Leu Gln Lys Gln Ile Thr Tyr Ile
115 120 125

Ala Asp Asn Thr Gln Phe Asn Asp Lys Asn Leu Leu
130 135 140

<210> SEQ ID NO 171
<211> LENGTH: 84
<212> TYPE: PRT
<213> ORGANISM: Bacillus cereus

<400> SEQUENCE: 171

Ile Asp Ala Ala Leu Lys Thr Val Ala Asp Asn Arg Ala Thr Leu Gly
1 5 10 15

Ala Thr Leu Asn Arg Leu Asp Phe Asn Val Asn Asn Leu Lys Ser Gln
20 25 30

Ser Ser Ser Met Ala Ser Ala Ala Ser Gln Ile Glu Asp Ala Asp Met
35 40 45

Ala Lys Glu Met Ser Glu Met Thr Lys Phe Lys Ile Leu Asn Glu Ala
50 55 60

Gly Ile Ser Met Leu Ser Gln Ala Asn Gln Thr Pro Gln Met Val Ser
65 70 75 80

Lys Leu Leu Gln

<210> SEQ ID NO 172
<211> LENGTH: 141
<212> TYPE: PRT
<213> ORGANISM: Bacillus cereus

<400> SEQUENCE: 172

Trp Gly Phe Phe Tyr Met Arg Ile Asn Thr Asn Ile Asn Ser Met Arg
1 5 10 15

Thr Gln Glu Tyr Met Arg Gln Asn Gln Ala Lys Met Ser Asn Ala Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ser Asn Asn Thr Gln Asp Gly Met Ser Leu Ile Arg Thr
65 70 75 80

Ala Asp Ser Ala Leu Asn Ser Val Ser Asn Ile Leu Leu Arg Met Arg
85 90 95

Asp Leu Ala Asn Gln Ser Ala Asn Gly Thr Asn Thr Asn Glu Asn Lys
100 105 110

Ala Ala Met Gln Lys Glu Phe Gly Glu Leu Lys Glu Gln Ile Lys Tyr
115 120 125

Ile Ala Glu Asn Thr Gln Phe Asn Asp Gln His Leu Leu
130 135 140

<210> SEQ ID NO 173
<211> LENGTH: 78
<212> TYPE: PRT
<213> ORGANISM: Bacillus cereus

<400> SEQUENCE: 173

Thr Val Ala Asp Asn Arg Ala Thr Leu Gly Ala Thr Leu Asn Arg Leu
1 5 10 15

Asp Phe Asn Val Asn Asn Leu Lys Ser Gln Ala Ser Ser Met Ala Ala
20 25 30

Ala Ala Ser Gln Val Glu Asp Ala Asp Met Ala Lys Glu Met Ser Glu
35 40 45

Met Thr Lys Phe Lys Ile Leu Asn Glu Ala Gly Ile Ser Met Leu Ser
50 55 60

Gln Ala Asn Gln Thr Pro Gln Met Val Ser Lys Leu Leu Gln
65 70 75

<210> SEQ ID NO 174
<211> LENGTH: 141
<212> TYPE: PRT
<213> ORGANISM: Bacillus cereus

<400> SEQUENCE: 174

Trp Gly Phe Phe Tyr Met Arg Ile Asn Thr Asn Ile Asn Ser Met Arg
1 5 10 15

Thr Gln Glu Tyr Met Arg Gln Asn Gln Ala Lys Met Ser Asn Ala Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ser Asn Asn Thr Gln Asp Gly Met Ser Leu Ile Arg Thr
65 70 75 80

Ala Asp Ser Ala Leu Asn Ser Val Ser Asn Ile Leu Leu Arg Met Arg
85 90 95

Asp Leu Ala Asn Gln Ser Ala Asn Gly Thr Asn Thr Asn Glu Asn Lys
100 105 110

Ala Ala Met Gln Lys Glu Phe Gly Glu Leu Lys Glu Gln Ile Lys Tyr
115 120 125

Ile Ala Glu Asn Thr Gln Phe Asn Asp Gln His Leu Leu
130 135 140

<210> SEQ ID NO 175
<211> LENGTH: 77
<212> TYPE: PRT
<213> ORGANISM: Bacillus cereus

<400> SEQUENCE: 175

Thr Val Ala Asp Asn Arg Ala Thr Leu Gly Ala Thr Leu Asn Arg Leu
1 5 10 15

Asp Phe Asn Val Asn Asn Leu Lys Ser Gln Ala Ser Ser Ala Ala Ala
20 25 30

Ala Ser Gln Val Glu Asp Ala Asp Met Ala Lys Glu Met Ser Glu Met

```
        35                  40                  45

Thr Lys Phe Lys Ile Leu Asn Glu Ala Gly Ile Ser Met Leu Ser Gln
    50                  55                  60

Ala Asn Gln Thr Pro Gln Met Val Ser Lys Leu Leu Gln
65                  70                  75


<210> SEQ ID NO 176
<211> LENGTH: 140
<212> TYPE: PRT
<213> ORGANISM: Bacillus cereus

<400> SEQUENCE: 176

Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Ile Ala Asn Gln Ser Ala Asn Gly Thr Asn Thr Gly Asp Asn Gln Lys
            100                 105                 110

Ala Leu Asp Lys Glu Phe Ser Ala Leu Lys Glu Gln Ile Asp Tyr Ile
        115                 120                 125

Ser Lys Asn Thr Glu Phe Asn Asp Lys Lys Leu Leu
    130                 135                 140


<210> SEQ ID NO 177
<211> LENGTH: 70
<212> TYPE: PRT
<213> ORGANISM: Bacillus cereus

<400> SEQUENCE: 177

Leu Gly Ala Thr Leu Asn Arg Leu Asp Phe Asn Val Asn Asn Leu Lys
1               5                   10                  15

Ser Gln Ser Ser Ser Met Ala Ser Ala Ala Ser Gln Ile Glu Asp Ala
            20                  25                  30

Asp Met Ala Lys Glu Met Ser Glu Met Thr Lys Phe Lys Ile Leu Asn
        35                  40                  45

Glu Ala Gly Ile Ser Met Leu Ser Gln Ala Asn Gln Thr Pro Gln Met
    50                  55                  60

Val Ser Lys Leu Leu Gln
65                  70


<210> SEQ ID NO 178
<211> LENGTH: 128
<212> TYPE: PRT
<213> ORGANISM: Bacillus thuringiensis

<400> SEQUENCE: 178

Gly Phe Leu Asn Met Arg Ile Asn Thr Asn Ile Asn Ser Met Arg Thr
1               5                   10                  15

Gln Glu Tyr Met Arg Gln Asn Gln Thr Lys Met Ser Asn Ala Met Asp
            20                  25                  30
```

```
Arg Leu Ser Ser Gly Lys Arg Ile Asn Asn Ala Ser Asp Asp Ala Ala
        35                  40                  45

Gly Leu Ala Ile Ala Thr Arg Met Arg Ser Arg Glu Gly Gly Leu Asn
    50                  55                  60

Val Ala Ala Arg Asn Thr Glu Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Ser Glu Thr Asn Thr Ser Lys Asn Gln Ala
            100                 105                 110

Ala Met Gln Lys Glu Phe Asp Gln Leu Lys Glu Gln Ile Gln Tyr Ile
        115                 120                 125


<210> SEQ ID NO 179
<211> LENGTH: 73
<212> TYPE: PRT
<213> ORGANISM: Bacillus thuringiensis

<400> SEQUENCE: 179

Arg Ala Thr Leu Gly Ala Thr Leu Asn Arg Leu Asp Phe Asn Val Thr
1               5                   10                  15

Asn Leu Lys Ser Gln Glu Asn Ser Met Ala Ala Ser Ala Ser Gln Ile
            20                  25                  30

Glu Asp Ala Asp Met Ala Lys Glu Met Ser Glu Met Thr Lys Phe Lys
        35                  40                  45

Ile Leu Asn Glu Ala Gly Ile Ser Met Leu Ser Gln Ala Asn Gln Thr
    50                  55                  60

Pro Gln Met Val Ser Lys Leu Leu Gln
65                  70


<210> SEQ ID NO 180
<211> LENGTH: 128
<212> TYPE: PRT
<213> ORGANISM: Bacillus thuringiensis

<400> SEQUENCE: 180

Gly Phe Leu Asn Met Arg Ile Asn Thr Asn Ile Asn Ser Met Arg Thr
1               5                   10                  15

Gln Glu Tyr Met Arg Gln Asn Gln Thr Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ser Arg Glu Gly Gly Leu Asn
    50                  55                  60

Val Ala Ala Arg Asn Thr Glu Asp Gly Met Ser Leu Ile Arg Thr Ala
65                  70                  75                  80

Asp Ser Ala Leu Asn Ser Val Ser Asn Ile Leu Leu Arg Met Arg Asp
                85                  90                  95

Leu Ala Asn Gln Ser Ala Ser Glu Thr Asn Thr Ser Lys Asn Gln Ala
            100                 105                 110

Ala Met Gln Lys Glu Phe Asp Gln Leu Lys Glu Gln Ile Gln Tyr Ile
        115                 120                 125


<210> SEQ ID NO 181
<211> LENGTH: 73
<212> TYPE: PRT
<213> ORGANISM: Bacillus thuringiensis
```

<400> SEQUENCE: 181

Arg Ala Thr Leu Gly Ala Thr Leu Asn Arg Leu Asp Phe Asn Val Thr
1 5 10 15

Asn Leu Lys Ser Gln Glu Asn Ser Met Ala Ala Ser Ala Ser Gln Ile
20 25 30

Glu Asp Ala Asp Met Ala Lys Glu Met Ser Glu Met Thr Lys Phe Lys
35 40 45

Ile Leu Asn Glu Ala Gly Ile Ser Met Leu Ser Gln Ala Asn Gln Thr
50 55 60

Pro Gln Met Val Ser Lys Leu Leu Gln
65 70

<210> SEQ ID NO 182
<211> LENGTH: 141
<212> TYPE: PRT
<213> ORGANISM: Bacillus thuringiensis

<400> SEQUENCE: 182

Met Gly Val Leu Asn Met Arg Ile Asn Thr Asn Ile Asn Ser Met Arg
1 5 10 15

Thr Gln Glu Tyr Met Arg Gln Asn Gln Ala Lys Met Ser Thr Ala Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ala Asn Asn Thr Gln Asp Gly Ile Ser Leu Ile Arg Thr
65 70 75 80

Ala Asp Ser Ala Met Asn Ser Val Ser Asn Ile Leu Leu Arg Met Arg
85 90 95

Asp Leu Ala Asn Gln Ser Ala Asn Gly Thr Asn Thr Asp Lys Asn Gln
100 105 110

Gly Ala Leu Asp Lys Glu Phe Ala Ala Leu Lys Glu Gln Ile Asp Tyr
115 120 125

Ile Ser Lys Asn Thr Glu Phe Asn Asp Lys Lys Leu Leu
130 135 140

<210> SEQ ID NO 183
<211> LENGTH: 88
<212> TYPE: PRT
<213> ORGANISM: Bacillus thuringiensis

<400> SEQUENCE: 183

Ala Ile Lys Ala Ile Asp Glu Ala Leu Glu Thr Ile Ala Ser Asn Arg
1 5 10 15

Ala Thr Leu Gly Ala Thr Leu Asn Arg Leu Asp Phe Asn Val Asn Asn
20 25 30

Leu Lys Asn Gln Ala Ser Ser Met Ala Ser Ala Ala Ser Gln Val Glu
35 40 45

Asp Ala Asp Met Ala Lys Glu Met Ser Glu Met Thr Lys Phe Lys Ile
50 55 60

Leu Asn Glu Ala Gly Ile Ser Met Leu Ser Gln Ala Asn Gln Thr Pro
65 70 75 80

Gln Met Val Ser Lys Leu Leu Gln
85

<210> SEQ ID NO 184
<211> LENGTH: 141
<212> TYPE: PRT
<213> ORGANISM: Bacillus thuringiensis

<400> SEQUENCE: 184

```
Met Gly Val Leu Asn Met Arg Ile Asn Thr Asn Ile Asn Ser Met Arg
1               5                   10                  15

Thr Gln Glu Tyr Met Arg Gln Asn Gln Ala Lys Met Ser Asn Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
    50                  55                  60

Gly Val Ala Ala Asn Asn Thr Gln Asp Gly Ile Ser Leu Ile Arg Thr
65                  70                  75                  80

Ala Asp Ser Ala Met Asn Ser Val Ser Asn Ile Leu Leu Arg Met Arg
                85                  90                  95

Asp Leu Ala Asn Gln Ser Ala Asn Gly Thr Asn Thr Ser Glu Asn Gln
            100                 105                 110

Ala Ala Leu Asp Lys Glu Phe Gly Ala Leu Lys Glu Gln Ile Asn Tyr
        115                 120                 125

Ile Ser Thr Asn Thr Glu Phe Asn Asp Lys Lys Leu Leu
    130                 135                 140
```

<210> SEQ ID NO 185
<211> LENGTH: 85
<212> TYPE: PRT
<213> ORGANISM: Bacillus thuringiensis

<400> SEQUENCE: 185

```
Ala Ile Asp Ser Ala Leu Glu Asn Ile Ala Ser Asn Arg Ala Thr Leu
1               5                   10                  15

Gly Ala Thr Leu Asn Arg Leu Asp Phe Asn Val Asn Asn Leu Lys Ser
            20                  25                  30

Gln Ser Ser Ser Met Ala Ser Ala Ala Ser Gln Ile Glu Asp Ala Asp
        35                  40                  45

Met Ala Lys Glu Met Ser Glu Met Thr Lys Phe Lys Ile Leu Asn Glu
    50                  55                  60

Ala Gly Ile Ser Met Leu Ser Gln Ala Asn Gln Thr Pro Gln Met Val
65                  70                  75                  80

Ser Lys Leu Leu Gln
                85
```

<210> SEQ ID NO 186
<211> LENGTH: 141
<212> TYPE: PRT
<213> ORGANISM: Bacillus cereus

<400> SEQUENCE: 186

```
Met Gly Val Leu Asn Met Arg Ile Asn Thr Asn Ile Asn Ser Met Arg
1               5                   10                  15

Thr Gln Glu Tyr Met Arg Gln Asn Gln Ala Lys Met Ser Thr Ala Met
            20                  25                  30

Asp Arg Leu Ser Ser Gly Lys Arg Ile Asn Asn Ala Ser Asp Asp Ala
        35                  40                  45

Ala Gly Leu Ala Ile Ala Thr Arg Met Arg Ala Arg Glu Ser Gly Leu
```

50 55 60

Gly Val Ala Ala Asn Asn Thr Gln Asp Gly Ile Ser Leu Ile Arg Thr
65 70 75 80

Ala Asp Ser Ala Met Asn Ser Val Ser Asn Ile Leu Leu Arg Met Arg
85 90 95

Asp Leu Ala Asn Gln Ser Ala Asn Gly Thr Asn Thr Asp Lys Asn Gln
100 105 110

Gly Ala Leu Asp Lys Glu Phe Ala Ala Leu Lys Glu Gln Ile Asp Tyr
115 120 125

Ile Ser Lys Asn Thr Glu Phe Asn Asp Lys Lys Leu Leu
130 135 140

<210> SEQ ID NO 187
<211> LENGTH: 70
<212> TYPE: PRT
<213> ORGANISM: Bacillus cereus

<400> SEQUENCE: 187

Leu Gly Ala Thr Leu Asn Arg Leu Asp Phe Asn Val Asn Asn Leu Lys
1 5 10 15

Asn Gln Ala Ser Ser Met Ala Ser Ala Ala Ser Gln Val Glu Asp Ala
20 25 30

Asp Met Ala Lys Glu Met Ser Glu Met Thr Lys Phe Lys Ile Leu Asn
35 40 45

Glu Ala Gly Ile Ser Met Leu Ser Gln Ala Asn Gln Thr Pro Gln Met
50 55 60

Val Ser Lys Leu Leu Gln
65 70

<210> SEQ ID NO 188
<211> LENGTH: 141
<212> TYPE: PRT
<213> ORGANISM: Bacillus cereus

<400> SEQUENCE: 188

Met Gly Val Leu Asn Met Arg Ile Asn Thr Asn Ile Asn Ser Met Arg
1 5 10 15

Thr Gln Glu Tyr Met Arg Gln Asn Gln Ala Lys Met Ser Thr Ala Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ala Asn Asn Thr Gln Asp Gly Ile Ser Leu Ile Arg Thr
65 70 75 80

Ala Asp Ser Ala Met Asn Ser Val Ser Asn Ile Leu Leu Arg Met Arg
85 90 95

Asp Leu Ala Asn Gln Ser Ala Asn Gly Thr Asn Thr Asp Lys Asn Gln
100 105 110

Gly Ala Leu Asp Lys Glu Phe Ala Ala Leu Lys Glu Gln Ile Asp Tyr
115 120 125

Ile Ser Lys Asn Thr Glu Phe Asn Asp Lys Lys Leu Leu
130 135 140

<210> SEQ ID NO 189
<211> LENGTH: 68
<212> TYPE: PRT

<213> ORGANISM: Bacillus cereus

<400> SEQUENCE: 189

Ala Thr Leu Asn Arg Leu Asp Phe Asn Val Asn Asn Leu Lys Asn Gln
1 5 10 15

Ala Ser Ser Met Ala Ser Ala Ala Ser Gln Val Glu Asp Ala Asp Met
20 25 30

Ala Lys Glu Met Ser Glu Met Thr Lys Phe Lys Ile Leu Asn Glu Ala
35 40 45

Gly Ile Ser Met Leu Ser Gln Ala Asn Gln Thr Pro Gln Met Val Ser
50 55 60

Lys Leu Leu Gln
65

<210> SEQ ID NO 190
<211> LENGTH: 140
<212> TYPE: PRT
<213> ORGANISM: Bacillus cereus

<400> SEQUENCE: 190

Trp Gly Phe Phe Tyr Met Arg Ile Asn Thr Asn Ile Asn Ser Met Arg
1 5 10 15

Thr Gln Glu Tyr Met Arg Gln Asn Gln Ala Lys Met Ser Thr Ala Met
20 25 30

Asp Arg Leu Ser Ser Gly Lys Arg Ile Asn Asn Ala Ser Asp Asp Ala
35 40 45

Ala Gly Leu Ala Ile Ala Thr Arg Met Arg Ala Arg Glu Ser Gly Leu
50 55 60

Gly Val Ala Ala Asn Asn Thr Gln Asp Gly Ile Ser Leu Ile Arg Thr
65 70 75 80

Ala Asp Ser Ala Met Asn Ser Val Ser Asn Ile Leu Leu Arg Met Arg
85 90 95

Asp Leu Ala Asn Gln Ser Ala Asn Gly Thr Asn Thr Asp Lys Asn Gln
100 105 110

Ala Ala Leu Asp Lys Glu Phe Asn Ala Leu Lys Glu Gln Ile Asp Tyr
115 120 125

Ile Ser Lys Asn Thr Glu Phe Asn Asp Lys Lys Leu
130 135 140

<210> SEQ ID NO 191
<211> LENGTH: 88
<212> TYPE: PRT
<213> ORGANISM: Bacillus cereus

<400> SEQUENCE: 191

Ala Ile Ala Ala Ile Asp Ala Ala Leu Thr Lys Val Ala Asp Asn Arg
1 5 10 15

Ala Thr Leu Gly Ala Thr Leu Asn Arg Leu Asp Phe Asn Val Asn Asn
20 25 30

Leu Lys Ser Gln Ala Ser Ser Met Ala Ser Ala Ala Ser Gln Val Glu
35 40 45

Asp Ala Asp Met Ala Lys Glu Met Ser Glu Met Thr Lys Phe Lys Ile
50 55 60

Leu Asn Glu Ala Gly Ile Ser Met Leu Ser Gln Ala Asn Gln Thr Pro
65 70 75 80

Gln Met Val Ser Lys Leu Leu Gln
85

<210> SEQ ID NO 192
<211> LENGTH: 137
<212> TYPE: PRT
<213> ORGANISM: Bacillus cereus

<400> SEQUENCE: 192

Trp Gly Phe Phe Tyr Met Arg Ile Gly Thr Asn Val Leu Ser Leu Asn
1               5                   10                  15

Ala Arg Gln Ser Leu Tyr Glu Asn Glu Lys Arg Met Asn Val Ala Met
            20                  25                  30

Glu His Leu Ala Thr Gly Lys Lys Leu Asn Asn Ala Ser Asp Asn Pro
        35                  40                  45

Ala Asn Ile Ala Ile Val Thr Arg Met His Ala Arg Ala Ser Gly Met
    50                  55                  60

Arg Val Ala Ile Arg Asn Asn Glu Asp Ala Ile Ser Met Leu Arg Thr
65                  70                  75                  80

Ala Glu Ala Ala Leu Gln Thr Val Thr Asn Val Leu Gln Arg Met Arg
                85                  90                  95

Asp Leu Ala Val Gln Ser Ala Asn Gly Thr Asn Ser Asn Lys Asn Arg
            100                 105                 110

Asp Ser Leu Asn Lys Glu Phe Gln Ser Leu Thr Glu Gln Ile Gly Tyr
        115                 120                 125

Ile Asp Glu Thr Thr Glu Phe Asn Asn
    130                 135

<210> SEQ ID NO 193
<211> LENGTH: 88
<212> TYPE: PRT
<213> ORGANISM: Bacillus cereus

<400> SEQUENCE: 193

Ala Ile Arg Lys Ile Glu Glu Ala Leu Gln Asn Val Ser Leu His Arg
1               5                   10                  15

Ala Asp Leu Gly Ala Met Ile Asn Arg Leu Gln Phe Asn Ile Glu Asn
            20                  25                  30

Leu Asn Ser Gln Ser Thr Ala Leu Thr Asp Ala Ala Ser Arg Ile Glu
        35                  40                  45

Asp Ala Asp Met Ala Gln Glu Met Ser Asp Phe Leu Lys Phe Lys Leu
    50                  55                  60

Leu Thr Glu Val Ala Leu Ser Met Val Ser Gln Ala Asn Gln Val Pro
65                  70                  75                  80

Gln Met Val Ser Lys Leu Leu Gln
                85

<210> SEQ ID NO 194
<211> LENGTH: 106
<212> TYPE: PRT
<213> ORGANISM: Bacillus thuringiensis

<400> SEQUENCE: 194

Leu Val Pro Phe Ala Val Trp Leu Ala Met Ser Arg Ile Arg Arg Arg
1               5                   10                  15

Ile Leu Asp Thr Asp Cys Lys Ala Glu Ser Ala Val Arg Ile Lys Glu
            20                  25                  30

Ile Pro Ser Asp Val Leu Arg Ala Ala Thr Glu Arg Pro Leu Ser Cys
        35                  40                  45

Ala Arg Ile Arg Val Ala Ile Ala Arg Pro Ala Ala Ser Ser Glu Ala
    50                  55                  60

Leu Leu Ile Arg Leu Pro Leu Asp Lys Arg Ser Ile Ala Leu Leu Ile
65                  70                  75                  80

Leu Ala Trp Phe Trp Arg Met Tyr Ser Cys Val Arg Met Leu Leu Met
                85                  90                  95

Phe Val Leu Ile Leu Met Leu Arg Thr Pro
            100                 105

<210> SEQ ID NO 195
<211> LENGTH: 49
<212> TYPE: PRT
<213> ORGANISM: Bacillus thuringiensis

<400> SEQUENCE: 195

Met Ala Ala Ser Ala Ser Gln Ile Glu Asp Ala Asp Met Ala Lys Glu
1               5                   10                  15

Met Ser Glu Met Thr Lys Phe Lys Ile Leu Ser Glu Ala Gly Ile Ser
            20                  25                  30

Met Leu Ser Gln Ala Asn Gln Thr Pro Gln Met Val Ser Lys Leu Leu
        35                  40                  45

Gln

<210> SEQ ID NO 196
<211> LENGTH: 102
<212> TYPE: PRT
<213> ORGANISM: Bacillus cereus

<400> SEQUENCE: 196

Ala Val Trp Leu Ala Met Ser Arg Ile Arg Arg Arg Ile Leu Asp Thr
1               5                   10                  15

Asp Cys Lys Ala Glu Ser Ala Val Arg Ile Lys Glu Ile Pro Ser Asp
            20                  25                  30

Val Leu Arg Ala Ala Thr Glu Arg Pro Leu Ser Cys Ala Arg Ile Arg
        35                  40                  45

Val Ala Ile Ala Arg Pro Ala Ala Ser Ser Glu Ala Leu Leu Ile Arg
    50                  55                  60

Leu Pro Leu Asp Lys Arg Ser Ile Ala Leu Leu Ile Leu Ala Trp Phe
65                  70                  75                  80

Trp Arg Met Tyr Ser Cys Val Arg Met Leu Leu Met Phe Val Leu Ile
                85                  90                  95

Leu Met Leu Arg Thr Pro
            100

<210> SEQ ID NO 197
<211> LENGTH: 50
<212> TYPE: PRT
<213> ORGANISM: Bacillus cereus

<400> SEQUENCE: 197

Ser Met Ala Ala Ser Ala Ser Gln Ile Glu Asp Ala Asp Met Ala Lys
1               5                   10                  15

Glu Met Ser Glu Met Thr Lys Phe Lys Ile Leu Ser Glu Ala Gly Ile
            20                  25                  30

Ser Met Leu Ser Gln Ala Asn Gln Thr Pro Gln Met Val Ser Lys Leu
        35                  40                  45

Leu Gln
    50

<210> SEQ ID NO 198
<211> LENGTH: 128
<212> TYPE: PRT
<213> ORGANISM: Bacillus thuringiensis

<400> SEQUENCE: 198

```
Gly Phe Leu Asn Met Arg Ile Gly Thr Asn Phe Leu Ser Met Asn Ala
1               5                   10                  15

Arg Gln Ser Leu Tyr Glu Asn Glu Lys Arg Met Asn Val Ala Met Glu
            20                  25                  30

His Leu Ala Thr Gly Lys Lys Leu Asn His Ala Ser Asp Asn Pro Ala
        35                  40                  45

Asn Ile Ala Ile Val Thr Arg Met His Ala Arg Ala Asn Gly Met Arg
    50                  55                  60

Val Ala Ile Arg Asn Asn Glu Asp Ala Ile Ser Met Leu Arg Thr Ala
65                  70                  75                  80

Glu Ala Ala Leu Gln Thr Val Met Asn Ile Leu Gln Arg Met Arg Asp
                85                  90                  95

Leu Ala Ile Gln Ser Ala Asn Ser Thr Asn Ser Asn Lys Asn Arg Asp
            100                 105                 110

Ser Leu Asn Lys Glu Phe Gln Ser Leu Thr Glu Gln Ile Ser Tyr Ile
        115                 120                 125
```

<210> SEQ ID NO 199
<211> LENGTH: 70
<212> TYPE: PRT
<213> ORGANISM: Bacillus thuringiensis

<400> SEQUENCE: 199

```
Leu Gly Ala Met Ile Asn Arg Leu His Phe Asn Ile Glu Asn Leu Asn
1               5                   10                  15

Ser Gln Ser Met Ala Leu Thr Asp Ala Ala Ser Arg Ile Glu Asp Ala
            20                  25                  30

Asp Met Ala Gln Glu Met Ser Asp Phe Leu Lys Phe Lys Leu Leu Thr
        35                  40                  45

Glu Val Ala Leu Ser Met Val Ser Gln Ala Asn Gln Ile Pro Gln Met
    50                  55                  60

Val Ser Lys Leu Leu Gln
65                  70
```

<210> SEQ ID NO 200
<211> LENGTH: 128
<212> TYPE: PRT
<213> ORGANISM: Bacillus thuringiensis

<400> SEQUENCE: 200

```
Gly Phe Leu Asn Met Arg Ile Asn Thr Asn Ile Asn Ser Met Arg Thr
1               5                   10                  15

Gln Glu Tyr Met Arg Gln Asn Gln Ala Lys Met Ser Asn Ala Met Asp
            20                  25                  30

Arg Leu Ser Ser Gly Lys Arg Ile Asn Asn Ala Ser Asp Asp Ala Ala
        35                  40                  45

Gly Leu Ala Ile Ala Thr Arg Met Arg Ala Arg Glu Ser Gly Leu Gly
    50                  55                  60

Val Ala Ala Asn Asn Thr Gln Asp Gly Met Ser Leu Ile Arg Thr Ala
65                  70                  75                  80
```

Asp Ser Ala Leu Asn Ser Val Ser Asn Ile Leu Leu Arg Met Arg Asp
85 90 95

Ile Ala Asn Gln Ser Ala Asn Gly Thr Asn Thr Gly Asp Asn Gln Lys
100 105 110

Ala Leu Asp Lys Glu Phe Ser Ala Leu Lys Glu Gln Ile Asp Tyr Ile
115 120 125

<210> SEQ ID NO 201
<211> LENGTH: 70
<212> TYPE: PRT
<213> ORGANISM: Bacillus thuringiensis

<400> SEQUENCE: 201

Leu Gly Ala Thr Leu Asn Arg Leu Asp Phe Asn Val Asn Asn Leu Lys
1 5 10 15

Ser Gln Ser Ser Ser Met Ala Ser Ala Ala Ser Gln Ile Glu Asp Ala
20 25 30

Asp Met Ala Lys Glu Met Ser Glu Met Thr Lys Phe Lys Ile Leu Asn
35 40 45

Glu Ala Gly Ile Ser Met Leu Ser Gln Ala Asn Gln Thr Pro Gln Met
50 55 60

Val Ser Lys Leu Leu Gln
65 70

<210> SEQ ID NO 202
<211> LENGTH: 154
<212> TYPE: PRT
<213> ORGANISM: Bacillus aryabhattai

<400> SEQUENCE: 202

Met Arg Ile Asn His Asn Ile Thr Ala Leu Asn Thr Tyr Arg Gln Phe
1 5 10 15

Asn Asn Ala Asn Asn Ala Gln Ala Lys Ser Met Glu Lys Leu Ser Ser
20 25 30

Gly Gln Arg Ile Asn Ser Ala Ser Asp Asp Ala Ala Gly Leu Ala Ile
35 40 45

Ser Glu Lys Met Arg Gly Gln Ile Arg Gly Leu Asp Gln Ala Ser Arg
50 55 60

Asn Ala Gln Asp Gly Val Ser Leu Ile Gln Thr Ala Glu Gly Ala Leu
65 70 75 80

Asn Glu Thr His Asp Ile Leu Gln Arg Met Arg Glu Leu Val Val Gln
85 90 95

Ala Gly Asn Gly Thr Asn Lys Thr Glu Asp Leu Asp Ala Ile Gln Asp
100 105 110

Glu Ile Gly Ser Leu Ile Glu Glu Ile Gly Gly Glu Thr Asp Ser Lys
115 120 125

Gly Ile Ser Asp Arg Ala Gln Phe Asn Gly Arg Asn Leu Leu Asp Gly
130 135 140

Ser Leu Asp Ile Thr Leu Gln Val Gly Ala
145 150

<210> SEQ ID NO 203
<211> LENGTH: 52
<212> TYPE: PRT
<213> ORGANISM: Bacillus aryabhattai

<400> SEQUENCE: 203

Ile Asp Gly Ala Ile Asn Gln Val Ser Glu Gln Arg Ser Gly Leu Gly

-continued

```
1               5                   10                  15

Ala Thr Gln Asn Arg Leu Asp His Thr Ile Asn Asn Leu Ser Thr Ser
            20                  25                  30

Ser Glu Asn Leu Thr Ala Ser Glu Ser Arg Ile Arg Asp Val Asp Tyr
        35                  40                  45

Ala Leu Ala Ala
    50


<210> SEQ ID NO 204
<211> LENGTH: 148
<212> TYPE: PRT
<213> ORGANISM: Bacillus manliponensis

<400> SEQUENCE: 204

Met Arg Ile Asn Thr Asn Ile Asn Ser Met Arg Thr Gln Glu Tyr Met
1               5                   10                  15

Arg Gln Asn Gln Asp Lys Met Asn Thr Ser Met Asn Arg Leu Ser Ser
            20                  25                  30

Gly Lys Gln Ile Asn Ser Ala Ser Asp Asp Ala Ala Gly Leu Ala Ile
        35                  40                  45

Ala Thr Arg Met Arg Ala Lys Glu Gly Gly Leu Asn Val Gly Ala Lys
    50                  55                  60

Asn Thr Gln Asp Gly Met Ser Ala Leu Arg Thr Met Asp Ser Ala Leu
65                  70                  75                  80

Asn Ser Val Ser Asn Ile Leu Leu Arg Met Arg Asp Leu Ala Thr Gln
                85                  90                  95

Ser Ala Thr Gly Thr Asn Gln Gly Asn Asp Arg Glu Ser Leu Asp Leu
            100                 105                 110

Glu Phe Gln Gln Leu Thr Glu Glu Ile Thr His Ile Ala Glu Lys Thr
        115                 120                 125

Asn Phe Asn Gly Asn Ala Leu Leu Ser Gly Ser Gly Ser Ala Ile Asn
    130                 135                 140

Val Gln Leu Ser
145


<210> SEQ ID NO 205
<211> LENGTH: 84
<212> TYPE: PRT
<213> ORGANISM: Bacillus manliponensis

<400> SEQUENCE: 205

Ile Asp Gln Ala Ile Gln Asp Ile Ala Asp Asn Arg Ala Thr Tyr Gly
1               5                   10                  15

Ser Gln Leu Asn Arg Leu Asp His Asn Leu Asn Asn Val Asn Ser Gln
            20                  25                  30

Ala Thr Asn Met Ala Ala Ala Ala Ser Gln Ile Glu Asp Ala Asp Met
        35                  40                  45

Ala Lys Glu Met Ser Glu Met Thr Lys Phe Lys Ile Leu Ser Glu Ala
    50                  55                  60

Gly Val Ser Met Leu Ser Gln Ala Asn Gln Thr Pro Gln Met Val Ser
65                  70                  75                  80

Lys Leu Leu Gln


<210> SEQ ID NO 206
<211> LENGTH: 151
<212> TYPE: PRT
<213> ORGANISM: Lysinibacillus sp.
```

<400> SEQUENCE: 206

Met Arg Ile Gly Ser Trp Thr Ala Thr Gly Met Ser Ile Val Asn His
1               5                   10                  15

Met Asn Arg Asn Trp Asn Ala Ala Ser Lys Ser Met Leu Arg Leu Ser
            20                  25                  30

Ser Gly Tyr Arg Ile Asn Ser Ala Ala Asp Asp Ala Ala Gly Leu Ala
        35                  40                  45

Ile Ser Glu Lys Met Arg Gly Gln Ile Arg Gly Leu Thr Met Ala Ser
    50                  55                  60

Lys Asn Ile Met Asp Gly Val Ser Leu Ile Gln Thr Ala Glu Gly Ala
65                  70                  75                  80

Leu Asn Glu Thr His Ala Ile Val Gln Arg Met Arg Glu Leu Ala Val
                85                  90                  95

Gln Ala Ala Thr Asp Thr Asn Thr Asp Asp Asp Arg Ala Lys Leu Asp
            100                 105                 110

Leu Glu Phe Gln Glu Leu Lys Lys Glu Ile Asp Arg Ile Ser Thr Asp
        115                 120                 125

Thr Glu Phe Asn Thr Arg Thr Leu Leu Asn Gly Asp Tyr Lys Asp Asn
    130                 135                 140

Gly Leu Lys Ile Gln Val Gly
145                 150

<210> SEQ ID NO 207
<211> LENGTH: 84
<212> TYPE: PRT
<213> ORGANISM: Lysinibacillus sp.

<400> SEQUENCE: 207

Leu Asp Glu Ala Thr Lys Asn Val Ser Met Glu Arg Ser Arg Leu Gly
1               5                   10                  15

Ala Tyr Gln Asn Arg Leu Glu His Ala Tyr Asn Val Ala Glu Asn Thr
            20                  25                  30

Ala Ile Asn Leu Gln Asp Ala Glu Ser Arg Ile Arg Asp Val Asp Ile
        35                  40                  45

Ala Lys Glu Met Met Asn Met Val Lys Ser Gln Ile Leu Ala Gln Val
    50                  55                  60

Gly Gln Gln Val Leu Ala Met His Met Gln Gln Ala Gln Gly Ile Leu
65                  70                  75                  80

Arg Leu Leu Gly

<210> SEQ ID NO 208
<211> LENGTH: 151
<212> TYPE: PRT
<213> ORGANISM: Lysinibacillus sp.

<400> SEQUENCE: 208

Met Lys Ile Gly Ser Trp Thr Ala Thr Gly Met Ser Ile Val Asn His
1               5                   10                  15

Met Asn Arg Asn Trp Asn Ala Ala Ser Lys Ser Met Leu Arg Leu Ser
            20                  25                  30

Ser Gly Tyr Arg Ile Asn Ser Ala Ala Asp Asp Ala Ala Gly Leu Ala
        35                  40                  45

Ile Ser Glu Lys Met Arg Gly Gln Ile Arg Gly Leu Thr Met Ala Ser
    50                  55                  60

Lys Asn Ile Met Asp Gly Val Ser Leu Ile Gln Thr Ala Glu Gly Ala 65 70 75 80

Leu Asn Glu Thr His Ala Ile Val Gln Arg Met Arg Glu Leu Ala Val
85 90 95

Gln Ala Ala Thr Asp Thr Asn Thr Asp Asp Asp Arg Ala Lys Leu Asp
100 105 110

Leu Glu Phe Gln Glu Leu Lys Lys Glu Ile Asp Arg Ile Ser Thr Asp
115 120 125

Thr Ala Phe Asn Thr Arg Thr Leu Leu Asn Gly Asp Tyr Lys Asp Asn
130 135 140

Gly Leu Lys Ile Gln Val Gly
145 150

<210> SEQ ID NO 209
<211> LENGTH: 84
<212> TYPE: PRT
<213> ORGANISM: Lysinibacillus sp.

<400> SEQUENCE: 209

Leu Asp Glu Ala Thr Lys Asn Val Ser Met Glu Arg Ser Arg Leu Gly
1 5 10 15

Ala Tyr Gln Asn Arg Leu Glu His Ala Tyr Asn Val Ala Glu Asn Thr
20 25 30

Ala Ile Asn Leu Gln Asp Ala Glu Ser Arg Ile Arg Asp Val Asp Ile
35 40 45

Ala Lys Glu Met Met His Met Val Lys Ser Gln Ile Leu Ala Gln Val
50 55 60

Gly Gln Gln Val Leu Ala Met His Ile Gln Gln Ala Gln Gly Ile Leu
65 70 75 80

Arg Leu Leu Gly

<210> SEQ ID NO 210
<211> LENGTH: 148
<212> TYPE: PRT
<213> ORGANISM: Paenibacillus sp.

<400> SEQUENCE: 210

Met Ile Ile Ser His Asn Leu Thr Ala Leu Asn Thr Met Asn Lys Leu
1 5 10 15

Lys Gln Lys Asp Leu Ala Val Ser Lys Ser Leu Gly Lys Leu Ser Ser
20 25 30

Gly Leu Arg Ile Asn Gly Ala Ser Asp Asp Ala Ala Gly Leu Ala Ile
35 40 45

Ser Glu Lys Met Arg Gly Gln Ile Arg Gly Leu Asn Gln Ala Ser Arg
50 55 60

Asn Ile Gln Asp Gly Ile Ser Leu Ile Gln Val Ala Asp Gly Ala Met
65 70 75 80

Gln Glu Ile His Ser Met Leu Gln Arg Met Asn Glu Leu Ala Val Gln
85 90 95

Ala Ser Asn Gly Thr Tyr Ser Gly Ser Asp Arg Leu Asn Ile Gln Ser
100 105 110

Glu Val Glu Gln Leu Ile Glu Glu Ile Asp Glu Ile Ala Gly Asn Thr
115 120 125

Gly Phe Asn Gly Ile Lys Leu Leu Asn Gly Asn Asn Glu Lys Thr Glu
130 135 140

Lys Thr Glu Lys
145

<210> SEQ ID NO 211
<211> LENGTH: 84
<212> TYPE: PRT
<213> ORGANISM: Paenibacillus sp.

<400> SEQUENCE: 211

Ile Ser Ala Ala Ile Asp Lys Val Ser Ala Glu Arg Ala Arg Met Gly
1               5                   10                  15

Ala Tyr Gln Asn Arg Leu Glu His Ser Arg Asn Asn Val Val Thr Tyr
            20                  25                  30

Ala Glu Asn Leu Thr Ala Ala Glu Ser Arg Ile Arg Asp Val Asp Met
        35                  40                  45

Ala Lys Glu Met Met Glu Leu Met Lys Asn Gln Ile Phe Thr Gln Ala
    50                  55                  60

Gly Gln Ala Met Leu Leu Gln Thr Asn Thr Gln Pro Gln Ala Ile Leu
65                  70                  75                  80

Gln Leu Leu Lys

<210> SEQ ID NO 212
<211> LENGTH: 148
<212> TYPE: PRT
<213> ORGANISM: Bacillus anthracis

<400> SEQUENCE: 212

Met Arg Ile Asn Thr Asn Ile Asn Ser Met Arg Thr Gln Glu Tyr Met
1               5                   10                  15

Arg Gln Asn Gln Ala Lys Met Ser Asn Ala Met Asp Arg Leu Ser Ser
            20                  25                  30

Gly Lys Arg Ile Asn Asn Ala Ser Asp Asp Ala Ala Gly Leu Ala Ile
        35                  40                  45

Ala Thr Arg Met Arg Ala Arg Glu Ser Gly Leu Gly Val Ala Ala Asn
    50                  55                  60

Asn Thr Gln Asp Gly Met Ser Leu Ile Arg Thr Ala Asp Ser Ala Met
65                  70                  75                  80

Asn Ser Val Ser Asn Ile Leu Leu Arg Met Arg Asp Leu Ala Asn Gln
                85                  90                  95

Ser Ala Asn Gly Thr Asn Thr Lys Glu Asn Gln Asp Ala Leu Asp Lys
            100                 105                 110

Glu Phe Gly Ala Leu Lys Glu Gln Ile Asp Tyr Ile Ser Lys Asn Thr
        115                 120                 125

Glu Phe Asn Asp Lys Lys Leu Leu Asn Gly Asp Asn Lys Ser Ile Ala
    130                 135                 140

Ile Gln Thr Leu
145

<210> SEQ ID NO 213
<211> LENGTH: 84
<212> TYPE: PRT
<213> ORGANISM: Bacillus anthracis

<400> SEQUENCE: 213

Ile Asp Ser Ala Leu Glu Thr Ile Ala Ser Asn Arg Ala Thr Leu Gly
1               5                   10                  15

Ala Thr Leu Asn Arg Leu Asp Phe Asn Val Asn Asn Leu Lys Ser Gln
            20                  25                  30

Ser Ser Ala Met Ala Ser Ala Ala Ser Gln Ile Glu Asp Ala Asp Met 35 40 45

Ala Lys Glu Met Ser Glu Met Thr Lys Phe Lys Ile Leu Asn Glu Ala
50 55 60

Gly Ile Ser Met Leu Ser Gln Ala Asn Gln Thr Pro Gln Met Val Ser
65 70 75 80

Lys Leu Leu Gln

<210> SEQ ID NO 214
<211> LENGTH: 172
<212> TYPE: PRT
<213> ORGANISM: Bacillus anthracis

<400> SEQUENCE: 214

Met Gln Lys Ser Gln Tyr Lys Lys Met Gly Val Leu Lys Met Arg Ile
1 5 10 15

Asn Thr Asn Ile Asn Ser Met Arg Thr Gln Glu Tyr Met Arg Gln Asn
20 25 30

Gln Asp Lys Met Asn Val Ser Met Asn Arg Leu Ser Ser Gly Lys Arg
35 40 45

Ile Asn Ser Ala Ala Asp Asp Ala Ala Gly Leu Ala Ile Ala Thr Arg
50 55 60

Met Arg Ala Arg Gln Ser Gly Leu Glu Lys Ala Ser Gln Asn Thr Gln
65 70 75 80

Asp Gly Met Ser Leu Ile Arg Thr Ala Glu Ser Ala Met Asn Ser Val
85 90 95

Ser Asn Ile Leu Thr Arg Met Arg Asp Ile Ala Val Gln Ser Ser Asn
100 105 110

Gly Thr Asn Thr Ala Glu Asn Gln Ser Ala Leu Gln Lys Glu Phe Ala
115 120 125

Glu Leu Gln Glu Gln Ile Asp Tyr Ile Ala Lys Asn Thr Glu Phe Asn
130 135 140

Asp Lys Asn Leu Leu Ala Gly Thr Gly Ala Val Thr Ile Gly Ser Thr
145 150 155 160

Ser Ile Ser Gly Ala Glu Ile Ser Ile Glu Thr Leu
165 170

<210> SEQ ID NO 215
<211> LENGTH: 81
<212> TYPE: PRT
<213> ORGANISM: Bacillus anthracis

<400> SEQUENCE: 215

Ala Leu Asn Thr Val Ala Gly Asn Arg Ala Thr Leu Gly Ala Thr Leu
1 5 10 15

Asn Arg Leu Asp Arg Asn Val Glu Asn Leu Asn Asn Gln Ala Thr Asn
20 25 30

Met Ala Ser Ala Ala Ser Gln Ile Glu Asp Ala Asp Met Ala Lys Glu
35 40 45

Met Ser Glu Met Thr Lys Phe Lys Ile Leu Asn Glu Ala Gly Ile Ser
50 55 60

Met Leu Ser Gln Ala Asn Gln Thr Pro Gln Met Val Ser Lys Leu Leu
65 70 75 80

Gln

<210> SEQ ID NO 216
<211> LENGTH: 159

<212> TYPE: PRT
<213> ORGANISM: Bacillus anthracis

<400> SEQUENCE: 216

Met Arg Ile Asn Thr Asn Ile Asn Ser Met Arg Thr Gln Glu Tyr Met
1               5                   10                  15

Arg Gln Asn Gln Asp Lys Met Asn Val Ser Met Asn Arg Leu Ser Ser
            20                  25                  30

Gly Lys Arg Ile Asn Ser Ala Ala Asp Asp Ala Ala Gly Leu Ala Ile
        35                  40                  45

Ala Thr Arg Met Arg Ala Arg Gln Ser Gly Leu Glu Lys Ala Ser Gln
    50                  55                  60

Asn Thr Gln Asp Gly Met Ser Leu Ile Arg Thr Ala Glu Ser Ala Met
65                  70                  75                  80

Asn Ser Val Ser Asn Ile Leu Thr Arg Met Arg Asp Ile Ala Val Gln
                85                  90                  95

Ser Ser Asn Gly Thr Asn Thr Ala Glu Asn Gln Ser Ala Leu Gln Lys
            100                 105                 110

Glu Phe Ala Glu Leu Gln Glu Gln Ile Asp Tyr Ile Ala Lys Asn Thr
        115                 120                 125

Glu Phe Asn Asp Lys Asn Leu Leu Ala Gly Thr Gly Ala Val Thr Ile
    130                 135                 140

Gly Ser Thr Ser Ile Ser Gly Ala Glu Ile Ser Ile Glu Thr Leu
145                 150                 155

<210> SEQ ID NO 217
<211> LENGTH: 81
<212> TYPE: PRT
<213> ORGANISM: Bacillus anthracis

<400> SEQUENCE: 217

Ala Leu Asn Thr Val Ala Gly Asn Arg Ala Thr Leu Gly Ala Thr Leu
1               5                   10                  15

Asn Arg Leu Asp Arg Asn Val Glu Asn Leu Asn Asn Gln Ala Thr Asn
            20                  25                  30

Met Ala Ser Ala Ala Ser Gln Ile Lys Asp Ala Asp Lys Ala Lys Glu
        35                  40                  45

Met Ser Glu Met Thr Lys Phe Lys Ile Leu Asn Glu Ala Gly Ile Ser
    50                  55                  60

Met Leu Ser Gln Ala Asn Gln Thr Pro Gln Met Val Ser Lys Leu Leu
65                  70                  75                  80

Gln

<210> SEQ ID NO 218
<211> LENGTH: 159
<212> TYPE: PRT
<213> ORGANISM: Bacillus anthracis

<400> SEQUENCE: 218

Met Arg Ile Asn Thr Asn Ile Asn Ser Met Arg Thr Gln Glu Tyr Met
1               5                   10                  15

Arg Gln Asn Gln Asp Lys Met Asn Val Ser Met Asn Arg Leu Ser Ser
            20                  25                  30

Gly Lys Arg Ile Asn Ser Ala Ala Asp Asp Ala Ala Gly Leu Ala Ile
        35                  40                  45

Ala Thr Arg Met Arg Ala Arg Gln Ser Gly Leu Glu Lys Ala Ser Gln
    50                  55                  60

Asn Thr Gln Asp Gly Met Ser Leu Ile Arg Thr Ala Glu Ser Ala Met
65 70 75 80

Asn Ser Val Ser Asn Ile Leu Thr Arg Met Arg Asp Ile Ala Val Gln
85 90 95

Ser Ser Asn Gly Thr Asn Thr Ala Glu Asn Gln Ser Ala Leu Gln Lys
100 105 110

Glu Phe Ala Glu Leu Gln Glu Gln Ile Asp Tyr Ile Ala Lys Asn Thr
115 120 125

Glu Phe Asn Asp Lys Asn Leu Leu Ala Gly Thr Gly Ala Val Thr Ile
130 135 140

Gly Ser Thr Ser Ile Ser Gly Ala Glu Ile Ser Ile Glu Thr Leu
145 150 155

<210> SEQ ID NO 219
<211> LENGTH: 76
<212> TYPE: PRT
<213> ORGANISM: Bacillus anthracis

<400> SEQUENCE: 219

Ala Leu Asn Thr Val Ala Gly Asn Arg Ala Thr Leu Gly Ala Thr Leu
1 5 10 15

Asn Arg Leu Asp Arg Asn Val Glu Asn Leu Asn Asn Gln Ala Thr Asn
20 25 30

Met Ala Ser Ala Ala Ser Gln Ile Glu Asp Ala Asp Met Ala Lys Glu
35 40 45

Met Ser Glu Met Thr Lys Phe Lys Ile Leu Asn Glu Ala Gly Ile Ser
50 55 60

Met Leu Ser Gln Ala Asn Gln Thr Pro Gln Met Val
65 70 75

<210> SEQ ID NO 220
<211> LENGTH: 137
<212> TYPE: PRT
<213> ORGANISM: Bacillus anthracis

<400> SEQUENCE: 220

Met Asn Val Ser Met Asn Arg Leu Ser Ser Gly Lys Arg Ile Asn Ser
1 5 10 15

Ala Ala Asp Asp Ala Ala Gly Leu Ala Ile Ala Thr Arg Met Arg Ala
20 25 30

Arg Gln Ser Gly Leu Glu Lys Ala Ser Gln Asn Thr Gln Asp Gly Met
35 40 45

Ser Leu Ile Arg Thr Ala Glu Ser Ala Met Asn Ser Val Ser Asn Ile
50 55 60

Leu Thr Arg Met Arg Asp Ile Ala Val Gln Ser Ser Asn Gly Thr Asn
65 70 75 80

Thr Ala Glu Asn Gln Ser Ala Leu Gln Lys Glu Phe Ala Glu Leu Gln
85 90 95

Glu Gln Ile Asp Tyr Ile Ala Lys Asn Thr Glu Phe Asn Asp Lys Asn
100 105 110

Leu Leu Ala Gly Thr Gly Ala Val Thr Ile Gly Ser Thr Ser Ile Ser
115 120 125

Gly Ala Glu Ile Ser Ile Glu Thr Leu
130 135

<210> SEQ ID NO 221

<211> LENGTH: 84
<212> TYPE: PRT
<213> ORGANISM: Bacillus anthracis

<400> SEQUENCE: 221

Leu Asn Thr Ala Leu Asn Thr Val Ala Gly Asn Arg Ala Thr Leu Gly
1 5 10 15

Ala Thr Leu Asn Arg Leu Asp Arg Asn Val Glu Asn Leu Asn Asn Gln
20 25 30

Ala Thr Asn Met Ala Ser Ala Ala Ser Gln Ile Glu Asp Ala Asp Met
35 40 45

Ala Lys Glu Met Ser Glu Met Thr Lys Phe Lys Ile Leu Asn Glu Ala
50 55 60

Gly Ile Ser Met Leu Ser Gln Ala Asn Gln Thr Pro Gln Met Val Ser
65 70 75 80

Lys Leu Leu Gln

<210> SEQ ID NO 222
<211> LENGTH: 154
<212> TYPE: PRT
<213> ORGANISM: Bacillus megaterium

<400> SEQUENCE: 222

Met Arg Ile Asn His Asn Ile Thr Ala Leu Asn Thr Tyr Arg Gln Phe
1 5 10 15

Asn Asn Ala Asn Asn Ala Gln Ala Lys Ser Met Glu Lys Leu Ser Ser
20 25 30

Gly Gln Arg Ile Asn Ser Ala Ser Asp Asp Ala Ala Gly Leu Ala Ile
35 40 45

Ser Glu Lys Met Arg Gly Gln Ile Arg Gly Leu Asp Gln Ala Ser Arg
50 55 60

Asn Ala Gln Asp Gly Val Ser Leu Ile Gln Thr Ala Glu Gly Ala Leu
65 70 75 80

Asn Glu Thr His Asp Ile Leu Gln Arg Met Arg Glu Leu Val Val Gln
85 90 95

Ala Gly Asn Gly Thr Asn Lys Thr Glu Asp Leu Asp Ala Ile Gln Asp
100 105 110

Glu Ile Gly Ser Leu Ile Glu Glu Ile Gly Gly Glu Ala Asp Ser Lys
115 120 125

Gly Ile Ser Asp Arg Ala Gln Phe Asn Gly Arg Asn Leu Leu Asp Gly
130 135 140

Ser Leu Asp Ile Thr Leu Gln Val Gly Ala
145 150

<210> SEQ ID NO 223
<211> LENGTH: 53
<212> TYPE: PRT
<213> ORGANISM: Bacillus megaterium

<400> SEQUENCE: 223

Ile Ile Asp Gly Ala Ile Asn Gln Val Ser Glu Gln Arg Ser Gly Leu
1 5 10 15

Gly Ala Thr Gln Asn Arg Leu Asp His Thr Ile Asn Asn Leu Ser Thr
20 25 30

Ser Ser Glu Asn Leu Thr Ala Ser Glu Ser Arg Ile Arg Asp Val Asp
35 40 45

Tyr Ala Leu Ala Ala

50

<210> SEQ ID NO 224
<211> LENGTH: 148
<212> TYPE: PRT
<213> ORGANISM: Aneurinibacillus sp.

<400> SEQUENCE: 224

```
Met Arg Ile Asn His Asn Leu Pro Ala Leu Asn Ala Tyr Arg Asn Leu
1               5                   10                  15

Ala Gln Asn Gln Ile Gly Thr Ser Lys Ile Leu Glu Arg Leu Ser Ser
            20                  25                  30

Gly Tyr Arg Ile Asn Arg Ala Ser Asp Asp Ala Ala Gly Leu Ala Ile
        35                  40                  45

Ser Glu Lys Met Arg Gly Gln Ile Arg Gly Leu Glu Gln Gly Gln Arg
    50                  55                  60

Asn Thr Met Asp Gly Val Ser Leu Ile Gln Thr Ala Glu Gly Ala Leu
65                  70                  75                  80

Gln Glu Ile His Glu Met Leu Gln Arg Met Arg Glu Leu Ala Val Gln
                85                  90                  95

Ala Ala Asn Gly Thr Tyr Ser Asp Lys Asp Lys Lys Ala Ile Glu Asp
            100                 105                 110

Glu Ile Asn Gln Leu Thr Ala Gln Ile Asp Gln Ile Ala Lys Thr Thr
        115                 120                 125

Glu Phe Asn Gly Ile Gln Leu Ile Gly Asp Ser Asp Ser Thr Ser Leu
    130                 135                 140

Gln Asp Val Lys
145
```

<210> SEQ ID NO 225
<211> LENGTH: 85
<212> TYPE: PRT
<213> ORGANISM: Aneurinibacillus sp.

<400> SEQUENCE: 225

```
Phe Lys Ala Ala Ile Asp Gln Val Ser Arg Ile Arg Ser Tyr Phe Gly
1               5                   10                  15

Ala Ile Gln Asn Arg Leu Glu His Val Val Asn Asn Leu Ser Asn Tyr
            20                  25                  30

Thr Glu Asn Leu Thr Gly Ala Glu Ser Arg Ile Arg Asp Ala Asp Met
        35                  40                  45

Ala Lys Glu Met Thr Glu Phe Thr Arg Phe Asn Ile Ile Asn Gln Ser
    50                  55                  60

Ala Thr Ala Met Leu Ala Gln Ala Asn Gln Leu Pro Gln Gly Val Leu
65                  70                  75                  80

Gln Leu Leu Lys Gly
                85
```

<210> SEQ ID NO 226
<211> LENGTH: 22
<212> TYPE: PRT
<213> ORGANISM: Bacillus thuringiensis

<400> SEQUENCE: 226

```
Asp Arg Leu Ser Ser Gly Lys Arg Ile Asn Ser Ala Ser Asp Asp Ala
1               5                   10                  15

Ala Gly Leu Ala Ile Ala
            20
```

<210> SEQ ID NO 227
<211> LENGTH: 22
<212> TYPE: PRT
<213> ORGANISM: Bacillus thuringiensis

<400> SEQUENCE: 227

```
Asp Arg Leu Ser Ser Gly Lys Arg Ile Asn Ser Ala Ser Asp Asp Ala
1               5                   10                  15

Ala Gly Leu Ala Ile Ala
            20
```

<210> SEQ ID NO 228
<211> LENGTH: 22
<212> TYPE: PRT
<213> ORGANISM: Bacillus thuringiensis

<400> SEQUENCE: 228

```
Asp Arg Leu Ser Ser Gly Lys Arg Ile Asn Ser Ala Ser Asp Asp Ala
1               5                   10                  15

Ala Gly Leu Ala Ile Ala
            20
```

<210> SEQ ID NO 229
<211> LENGTH: 22
<212> TYPE: PRT
<213> ORGANISM: Bacillus cereus

<400> SEQUENCE: 229

```
Asp Arg Leu Ser Ser Gly Lys Arg Ile Asn Ser Ala Ser Asp Asp Ala
1               5                   10                  15

Ala Gly Leu Ala Ile Ala
            20
```

<210> SEQ ID NO 230
<211> LENGTH: 22
<212> TYPE: PRT
<213> ORGANISM: Bacillus thuringiensis

<400> SEQUENCE: 230

```
Glu His Leu Ala Thr Gly Lys Lys Leu Asn Asn Ala Ser Asp Asn Pro
1               5                   10                  15

Ala Asn Ile Ala Ile Val
            20
```

<210> SEQ ID NO 231
<211> LENGTH: 23
<212> TYPE: PRT
<213> ORGANISM: Bacillus thuringiensis

<400> SEQUENCE: 231

```
Asp Arg Leu Ser Ser Gly Lys Arg Ile Asn Asn Ala Ser Asp Asp Ala
1               5                   10                  15

Ala Gly Leu Ala Ile Ala Thr
            20
```

<210> SEQ ID NO 232
<211> LENGTH: 22
<212> TYPE: PRT
<213> ORGANISM: Bacillus thuringiensis

<400> SEQUENCE: 232

Asp Arg Leu Ser Ser Gly Lys Arg Ile Asn Asn Ala Ser Asp Asp Ala
1               5                   10                  15

Ala Gly Leu Ala Ile Ala
            20

<210> SEQ ID NO 233
<211> LENGTH: 22
<212> TYPE: PRT
<213> ORGANISM: Bacillus thuringiensis

<400> SEQUENCE: 233

Asp Arg Leu Ser Ser Gly Lys Arg Ile Asn Asn Ala Ser Asp Asp Ala
1               5                   10                  15

Ala Gly Leu Ala Ile Ala
            20

<210> SEQ ID NO 234
<211> LENGTH: 22
<212> TYPE: PRT
<213> ORGANISM: Bacillus cereus

<400> SEQUENCE: 234

Asp Arg Leu Ser Ser Gly Lys Arg Ile Asn Asn Ala Ser Asp Asp Ala
1               5                   10                  15

Ala Gly Leu Ala Ile Ala
            20

<210> SEQ ID NO 235
<211> LENGTH: 22
<212> TYPE: PRT
<213> ORGANISM: Bacillus cereus

<400> SEQUENCE: 235

Glu His Leu Ala Thr Gly Lys Lys Leu Asn His Ala Ser Asp Asn Pro
1               5                   10                  15

Ala Asn Val Ala Ile Val
            20

<210> SEQ ID NO 236
<211> LENGTH: 22
<212> TYPE: PRT
<213> ORGANISM: Bacillus thuringiensis

<400> SEQUENCE: 236

Asp Arg Leu Ser Ser Gly Lys Arg Ile Asn Asn Ala Ser Asp Asp Ala
1               5                   10                  15

Ala Gly Leu Ala Ile Ala
            20

<210> SEQ ID NO 237
<211> LENGTH: 22
<212> TYPE: PRT
<213> ORGANISM: Bacillus bombysepticus

<400> SEQUENCE: 237

Asp Arg Leu Ser Ser Gly Lys Arg Ile Asn Asn Ala Ser Asp Asp Ala
1               5                   10                  15

Ala Gly Leu Ala Ile Ala
            20

<210> SEQ ID NO 238
<211> LENGTH: 22

<212> TYPE: PRT
<213> ORGANISM: Bacillus thuringiensis

<400> SEQUENCE: 238

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 239
<211> LENGTH: 22
<212> TYPE: PRT
<213> ORGANISM: Bacillus thuringiensis

<400> SEQUENCE: 239

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 240
<211> LENGTH: 22
<212> TYPE: PRT
<213> ORGANISM: Bacillus cereus

<400> SEQUENCE: 240

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 241
<211> LENGTH: 22
<212> TYPE: PRT
<213> ORGANISM: Bacillus cereus

<400> SEQUENCE: 241

```
Glu His Leu Ala Thr Gly Lys Lys Leu Asn Asn Ala Ser Asp Asn Pro
1               5                   10                  15

Ala Asn Ile Ala Ile Val
            20
```

<210> SEQ ID NO 242
<211> LENGTH: 22
<212> TYPE: PRT
<213> ORGANISM: Bacillus thuringiensis

<400> SEQUENCE: 242

```
Glu His Leu Ala Thr Gly Lys Lys Leu Asn His Ala Ser Asp Asn Pro
1               5                   10                  15

Ala Asn Val Ala Ile Val
            20
```

<210> SEQ ID NO 243
<211> LENGTH: 22
<212> TYPE: PRT
<213> ORGANISM: Bacillus thuringiensis

<400> SEQUENCE: 243

```
Asp Arg Leu Ser Ser Gly Lys Arg Ile Asn Asn Ala Ser Asp Asp Ala
1               5                   10                  15

Ala Gly Leu Ala Ile Ala
```

20

<210> SEQ ID NO 244
<211> LENGTH: 22
<212> TYPE: PRT
<213> ORGANISM: Bacillus cereus

<400> SEQUENCE: 244

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 245
<211> LENGTH: 22
<212> TYPE: PRT
<213> ORGANISM: Bacillus thuringiensis

<400> SEQUENCE: 245

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 246
<211> LENGTH: 22
<212> TYPE: PRT
<213> ORGANISM: Bacillus thuringiensis

<400> SEQUENCE: 246

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 247
<211> LENGTH: 22
<212> TYPE: PRT
<213> ORGANISM: Bacillus thuringiensis

<400> SEQUENCE: 247

Glu His Phe Ala Thr Gly Lys Lys Leu Asn His Ala Ser Asp Asn Pro
1 5 10 15

Ala Asn Val Ala Ile Val
20

<210> SEQ ID NO 248
<211> LENGTH: 22
<212> TYPE: PRT
<213> ORGANISM: Bacillus thuringiensis

<400> SEQUENCE: 248

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 249
<211> LENGTH: 22
<212> TYPE: PRT
<213> ORGANISM: Bacillus thuringiensis

<400> SEQUENCE: 249

```
Glu His Leu Ala Thr Gly Lys Lys Leu Asn His Ala Ser Asp Asn Pro
1               5                   10                  15

Ala Asn Ile Val Ile Val
            20


<210> SEQ ID NO 250
<211> LENGTH: 22
<212> TYPE: PRT
<213> ORGANISM: Bacillus thuringiensis

<400> SEQUENCE: 250

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 251
<211> LENGTH: 22
<212> TYPE: PRT
<213> ORGANISM: Bacillus thuringiensis

<400> SEQUENCE: 251

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 252
<211> LENGTH: 22
<212> TYPE: PRT
<213> ORGANISM: Bacillus thuringiensis

<400> SEQUENCE: 252

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 253
<211> LENGTH: 22
<212> TYPE: PRT
<213> ORGANISM: Bacillus thuringiensis

<400> SEQUENCE: 253

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 254
<211> LENGTH: 22
<212> TYPE: PRT
<213> ORGANISM: Bacillus thuringiensis

<400> SEQUENCE: 254

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 255
```

<211> LENGTH: 22
<212> TYPE: PRT
<213> ORGANISM: Bacillus weihenstephanensis

<400> SEQUENCE: 255

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 256
<211> LENGTH: 22
<212> TYPE: PRT
<213> ORGANISM: Bacillus thuringiensis

<400> SEQUENCE: 256

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 257
<211> LENGTH: 22
<212> TYPE: PRT
<213> ORGANISM: Bacillus thuringiensis

<400> SEQUENCE: 257

Glu His Leu Ala Thr Gly Lys Lys Leu Asn His Ala Ser Asp Asn Pro
1 5 10 15

Ala Asn Val Ala Ile Val
20

<210> SEQ ID NO 258
<211> LENGTH: 22
<212> TYPE: PRT
<213> ORGANISM: Bacillus thuringiensis

<400> SEQUENCE: 258

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 259
<211> LENGTH: 22
<212> TYPE: PRT
<213> ORGANISM: Bacillus thuringiensis

<400> SEQUENCE: 259

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 260
<211> LENGTH: 22
<212> TYPE: PRT
<213> ORGANISM: Bacillus thuringiensis

<400> SEQUENCE: 260

Glu His Leu Ala Thr Gly Lys Lys Leu Asn His Ala Ser Asp Asn Pro
1 5 10 15

Ala Asn Ile Val Ile Val
20

<210> SEQ ID NO 261
<211> LENGTH: 22
<212> TYPE: PRT
<213> ORGANISM: Bacillus thuringiensis

<400> SEQUENCE: 261

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 262
<211> LENGTH: 22
<212> TYPE: PRT
<213> ORGANISM: Bacillus cereus

<400> SEQUENCE: 262

Glu His Leu Ala Thr Gly Lys Lys Leu Asn His Ala Ser Asn Asn Pro
1 5 10 15

Ala Asn Val Ala Ile Val
20

<210> SEQ ID NO 263
<211> LENGTH: 22
<212> TYPE: PRT
<213> ORGANISM: Bacillus cereus

<400> SEQUENCE: 263

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 264
<211> LENGTH: 22
<212> TYPE: PRT
<213> ORGANISM: Bacillus thuringiensis

<400> SEQUENCE: 264

Glu His Leu Ala Thr Gly Lys Lys Leu Asn His Ala Ser Asp Asn Pro
1 5 10 15

Ala Asn Ile Ala Ile Val
20

<210> SEQ ID NO 265
<211> LENGTH: 22
<212> TYPE: PRT
<213> ORGANISM: Bacillus thuringiensis

<400> SEQUENCE: 265

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 266
<211> LENGTH: 22
<212> TYPE: PRT
<213> ORGANISM: Bacillus thuringiensis

<400> SEQUENCE: 266

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 267
<211> LENGTH: 22
<212> TYPE: PRT
<213> ORGANISM: Bacillus thuringiensis

<400> SEQUENCE: 267

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 268
<211> LENGTH: 22
<212> TYPE: PRT
<213> ORGANISM: Bacillus thuringiensis

<400> SEQUENCE: 268

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 269
<211> LENGTH: 22
<212> TYPE: PRT
<213> ORGANISM: Bacillus cereus

<400> SEQUENCE: 269

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 270
<211> LENGTH: 22
<212> TYPE: PRT
<213> ORGANISM: Bacillus thuringiensis

<400> SEQUENCE: 270

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 271
<211> LENGTH: 22
<212> TYPE: PRT
<213> ORGANISM: Bacillus cereus

<400> SEQUENCE: 271

Glu His Leu Ala Thr Gly Lys Lys Leu Asn Asn Ala Ser Asp Asn Pro
1 5 10 15

Ala Asn Ile Ala Ile Val
20

<210> SEQ ID NO 272
<211> LENGTH: 22
<212> TYPE: PRT
<213> ORGANISM: Bacillus cereus

<400> SEQUENCE: 272

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 273
<211> LENGTH: 22
<212> TYPE: PRT
<213> ORGANISM: Bacillus cereus

<400> SEQUENCE: 273

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 274
<211> LENGTH: 22
<212> TYPE: PRT
<213> ORGANISM: Bacillus cereus

<400> SEQUENCE: 274

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 275
<211> LENGTH: 22
<212> TYPE: PRT
<213> ORGANISM: Bacillus cereus

<400> SEQUENCE: 275

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 276
<211> LENGTH: 22
<212> TYPE: PRT
<213> ORGANISM: Bacillus cereus

<400> SEQUENCE: 276

```
Asp Arg Leu Ser Ser Gly Lys Arg Ile Asn Asn Ala Ser Asp Asp Ala
1               5                   10                  15

Ala Gly Leu Ala Ile Ala
            20
```

<210> SEQ ID NO 277
<211> LENGTH: 22
<212> TYPE: PRT
<213> ORGANISM: Bacillus thuringiensis

<400> SEQUENCE: 277

```
Asp Arg Leu Ser Ser Gly Lys Arg Ile Asn Asn Ala Ser Asp Asp Ala
1               5                   10                  15
```

```
Ala Gly Leu Ala Ile Ala
            20


<210> SEQ ID NO 278
<211> LENGTH: 22
<212> TYPE: PRT
<213> ORGANISM: Bacillus thuringiensis

<400> SEQUENCE: 278

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 279
<211> LENGTH: 22
<212> TYPE: PRT
<213> ORGANISM: Bacillus thuringiensis

<400> SEQUENCE: 279

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 280
<211> LENGTH: 22
<212> TYPE: PRT
<213> ORGANISM: Bacillus thuringiensis

<400> SEQUENCE: 280

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 281
<211> LENGTH: 22
<212> TYPE: PRT
<213> ORGANISM: Bacillus cereus

<400> SEQUENCE: 281

Glu His Leu Ala Thr Gly Lys Lys Leu Asn His Ala Ser Asn Asn Pro
1               5                   10                  15

Ala Asn Ile Ala Ile Val
            20


<210> SEQ ID NO 282
<211> LENGTH: 22
<212> TYPE: PRT
<213> ORGANISM: Bacillus cereus

<400> SEQUENCE: 282

Asp Arg Leu Ser Ser Gly Lys Arg Ile Asn Asn Ala Ser Asp Asp Ala
1               5                   10                  15

Ala Gly Leu Ala Ile Ala
            20


<210> SEQ ID NO 283
<211> LENGTH: 22
<212> TYPE: PRT
<213> ORGANISM: Bacillus cereus
```

<400> SEQUENCE: 283

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 284
<211> LENGTH: 22
<212> TYPE: PRT
<213> ORGANISM: Bacillus cereus

<400> SEQUENCE: 284

Glu His Leu Ala Thr Gly Lys Lys Leu Asn Asn Ala Ser Asp Asn Pro
1 5 10 15

Ala Asn Ile Ala Ile Val
20

<210> SEQ ID NO 285
<211> LENGTH: 22
<212> TYPE: PRT
<213> ORGANISM: Bacillus thuringiensis

<400> SEQUENCE: 285

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 286
<211> LENGTH: 22
<212> TYPE: PRT
<213> ORGANISM: Bacillus cereus

<400> SEQUENCE: 286

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 287
<211> LENGTH: 22
<212> TYPE: PRT
<213> ORGANISM: Bacillus thuringiensis

<400> SEQUENCE: 287

Glu His Leu Ala Thr Gly Lys Lys Leu Asn His Ala Ser Asp Asn Pro
1 5 10 15

Ala Asn Ile Ala Ile Val
20

<210> SEQ ID NO 288
<211> LENGTH: 22
<212> TYPE: PRT
<213> ORGANISM: Bacillus thuringiensis

<400> SEQUENCE: 288

Asp Arg Leu Ser Ser Gly Lys Arg Ile Asn Asn Ala Ser Asp Asp Ala
1 5 10 15

Ala Gly Leu Ala Ile Ala
20

<210> SEQ ID NO 289
<211> LENGTH: 22
<212> TYPE: PRT
<213> ORGANISM: Bacillus aryabhattai

<400> SEQUENCE: 289

```
Glu Lys Leu Ser Ser Gly Gln Arg Ile Asn Ser Ala Ser Asp Asp Ala
1               5                   10                  15

Ala Gly Leu Ala Ile Ser
            20
```

<210> SEQ ID NO 290
<211> LENGTH: 22
<212> TYPE: PRT
<213> ORGANISM: Bacillus manliponensis

<400> SEQUENCE: 290

```
Asn Arg Leu Ser Ser Gly Lys Gln Ile Asn Ser Ala Ser Asp Asp Ala
1               5                   10                  15

Ala Gly Leu Ala Ile Ala
            20
```

<210> SEQ ID NO 291
<211> LENGTH: 22
<212> TYPE: PRT
<213> ORGANISM: Lysinibacillus sp.

<400> SEQUENCE: 291

```
Leu Arg Leu Ser Ser Gly Tyr Arg Ile Asn Ser Ala Ala Asp Asp Ala
1               5                   10                  15

Ala Gly Leu Ala Ile Ser
            20
```

<210> SEQ ID NO 292
<211> LENGTH: 22
<212> TYPE: PRT
<213> ORGANISM: Lysinibacillus sp.

<400> SEQUENCE: 292

```
Leu Arg Leu Ser Ser Gly Tyr Arg Ile Asn Ser Ala Ala Asp Asp Ala
1               5                   10                  15

Ala Gly Leu Ala Ile Ser
            20
```

<210> SEQ ID NO 293
<211> LENGTH: 22
<212> TYPE: PRT
<213> ORGANISM: Paenibacillus sp.

<400> SEQUENCE: 293

```
Gly Lys Leu Ser Ser Gly Leu Arg Ile Asn Gly Ala Ser Asp Asp Ala
1               5                   10                  15

Ala Gly Leu Ala Ile Ser
            20
```

<210> SEQ ID NO 294
<211> LENGTH: 22
<212> TYPE: PRT
<213> ORGANISM: Bacillus anthracis

<400> SEQUENCE: 294

```
Asp Arg Leu Ser Ser Gly Lys Arg Ile Asn Asn Ala Ser Asp Asp Ala
```

```
1               5                   10                  15

Ala Gly Leu Ala Ile Ala
            20


<210> SEQ ID NO 295
<211> LENGTH: 22
<212> TYPE: PRT
<213> ORGANISM: Bacillus anthracis

<400> SEQUENCE: 295

Asn Arg Leu Ser Ser Gly Lys Arg Ile Asn Ser Ala Ala Asp Asp Ala
1               5                   10                  15

Ala Gly Leu Ala Ile Ala
            20


<210> SEQ ID NO 296
<211> LENGTH: 22
<212> TYPE: PRT
<213> ORGANISM: Bacillus anthracis

<400> SEQUENCE: 296

Asn Arg Leu Ser Ser Gly Lys Arg Ile Asn Ser Ala Ala Asp Asp Ala
1               5                   10                  15

Ala Gly Leu Ala Ile Ala
            20


<210> SEQ ID NO 297
<211> LENGTH: 22
<212> TYPE: PRT
<213> ORGANISM: Bacillus anthracis

<400> SEQUENCE: 297

Asn Arg Leu Ser Ser Gly Lys Arg Ile Asn Ser Ala Ala Asp Asp Ala
1               5                   10                  15

Ala Gly Leu Ala Ile Ala
            20


<210> SEQ ID NO 298
<211> LENGTH: 22
<212> TYPE: PRT
<213> ORGANISM: Bacillus anthracis

<400> SEQUENCE: 298

Asn Arg Leu Ser Ser Gly Lys Arg Ile Asn Ser Ala Ala Asp Asp Ala
1               5                   10                  15

Ala Gly Leu Ala Ile Ala
            20


<210> SEQ ID NO 299
<211> LENGTH: 22
<212> TYPE: PRT
<213> ORGANISM: Bacillus megaterium

<400> SEQUENCE: 299

Glu Lys Leu Ser Ser Gly Gln Arg Ile Asn Ser Ala Ser Asp Asp Ala
1               5                   10                  15

Ala Gly Leu Ala Ile Ser
            20


<210> SEQ ID NO 300
<211> LENGTH: 22
<212> TYPE: PRT
```

<213> ORGANISM: Aneurinibacillus sp.

<400> SEQUENCE: 300

Glu Arg Leu Ser Ser Gly Tyr Arg Ile Asn Arg Ala Ser Asp Asp Ala
1               5                   10                  15

Ala Gly Leu Ala Ile Ser
            20

<210> SEQ ID NO 301
<211> LENGTH: 28
<212> TYPE: PRT
<213> ORGANISM: Bacillus thuringiensis

<400> SEQUENCE: 301

Ser Val Ser Asn Ile Leu Leu Arg Met Arg Asp Leu Ala Asn Gln Ser
1               5                   10                  15

Ala Asn Gly Thr Asn Thr Lys Gly Asn Gln Ala Ser
            20                  25

<210> SEQ ID NO 302
<211> LENGTH: 28
<212> TYPE: PRT
<213> ORGANISM: Bacillus thuringiensis

<400> SEQUENCE: 302

Ser Val Ser Asn Ile Leu Leu Arg Met Arg Asp Leu Ala Asn Gln Ser
1               5                   10                  15

Ala Asn Gly Thr Asn Thr Lys Gly Asn Gln Ala Ser
            20                  25

<210> SEQ ID NO 303
<211> LENGTH: 28
<212> TYPE: PRT
<213> ORGANISM: Bacillus thuringiensis

<400> SEQUENCE: 303

Ser Val Ser Asn Ile Leu Leu Arg Met Arg Asp Leu Ala Asn Gln Ser
1               5                   10                  15

Ala Asn Gly Thr Asn Thr Lys Gly Asn Gln Ala Ser
            20                  25

<210> SEQ ID NO 304
<211> LENGTH: 28
<212> TYPE: PRT
<213> ORGANISM: Bacillus cereus

<400> SEQUENCE: 304

Ser Val Ser Asn Ile Leu Leu Arg Met Arg Asp Leu Ala Asn Gln Ser
1               5                   10                  15

Ala Asn Gly Thr Asn Thr Lys Gly Asn Gln Ala Ser
            20                  25

<210> SEQ ID NO 305
<211> LENGTH: 28
<212> TYPE: PRT
<213> ORGANISM: Bacillus thuringiensis

<400> SEQUENCE: 305

Thr Val Thr Asn Ile Leu Gln Arg Met Arg Asp Leu Ala Val Gln Ser
1               5                   10                  15

Ala Asn Gly Thr Asn Ser Asn Lys Asn Arg His Ser
            20                  25

<210> SEQ ID NO 306
<211> LENGTH: 28
<212> TYPE: PRT
<213> ORGANISM: Bacillus thuringiensis

<400> SEQUENCE: 306

```
Ser Val Ser Asn Ile Leu Leu Arg Met Arg Asp Ile Ala Asn Gln Ser
1               5                   10                  15

Ala Asn Ile Thr Asn Thr Asn Glu Asn Lys Ser Ala
            20                  25
```

<210> SEQ ID NO 307
<211> LENGTH: 28
<212> TYPE: PRT
<213> ORGANISM: Bacillus thuringiensis

<400> SEQUENCE: 307

```
Ser Val Ser Asn Ile Leu Leu Arg Met Arg Asp Leu Ala Asn Gln Ser
1               5                   10                  15

Ala Asn Gly Thr Asn Thr Asp Asp Asn Gln Lys Ala
            20                  25
```

<210> SEQ ID NO 308
<211> LENGTH: 28
<212> TYPE: PRT
<213> ORGANISM: Bacillus thuringiensis

<400> SEQUENCE: 308

```
Ser Val Ser Asn Ile Leu Leu Arg Met Arg Asp Leu Ala Asn Gln Ser
1               5                   10                  15

Ala Asn Gly Thr Asn Thr Asp Glu Asn Lys Ala Ala
            20                  25
```

<210> SEQ ID NO 309
<211> LENGTH: 28
<212> TYPE: PRT
<213> ORGANISM: Bacillus cereus

<400> SEQUENCE: 309

```
Ser Val Ser Asn Ile Leu Leu Arg Met Arg Asp Ile Ala Asn Gln Ser
1               5                   10                  15

Ala Asn Gly Thr Asn Thr Asp Lys Asn Gln Val Ala
            20                  25
```

<210> SEQ ID NO 310
<211> LENGTH: 28
<212> TYPE: PRT
<213> ORGANISM: Bacillus cereus

<400> SEQUENCE: 310

```
Thr Val Thr Asn Ile Leu Gln Arg Met Arg Asp Val Ala Val Gln Ser
1               5                   10                  15

Ala Asn Gly Thr Asn Ser Asn Lys Asn Arg Asp Ser
            20                  25
```

<210> SEQ ID NO 311
<211> LENGTH: 28
<212> TYPE: PRT
<213> ORGANISM: Bacillus thuringiensis

<400> SEQUENCE: 311

Ser Val Ser Asn Ile Leu Leu Arg Met Arg Asp Ile Ala Asn Gln Ser
1               5                   10                  15

Ala Asn Gly Thr Asn Thr Ala Asp Asn Gln Gln Ala
            20                  25

<210> SEQ ID NO 312
<211> LENGTH: 28
<212> TYPE: PRT
<213> ORGANISM: Bacillus bombysepticus

<400> SEQUENCE: 312

Ser Val Ser Asn Ile Leu Leu Arg Met Arg Asp Leu Ala Asn Gln Ser
1               5                   10                  15

Ala Ser Gly Thr Asn Thr Asp Lys Asn Gln Ala Ala
            20                  25

<210> SEQ ID NO 313
<211> LENGTH: 28
<212> TYPE: PRT
<213> ORGANISM: Bacillus thuringiensis

<400> SEQUENCE: 313

Ser Val Ser Asn Ile Leu Leu Arg Met Arg Asp Leu Ala Asn Gln Ser
1               5                   10                  15

Ala Ser Gly Thr Asn Thr Asp Lys Asn Gln Ala Ala
            20                  25

<210> SEQ ID NO 314
<211> LENGTH: 28
<212> TYPE: PRT
<213> ORGANISM: Bacillus thuringiensis

<400> SEQUENCE: 314

Ser Val Ser Asn Ile Leu Leu Arg Met Arg Asp Leu Ala Asn Gln Ser
1               5                   10                  15

Ala Ser Gly Thr Asn Thr Asp Lys Asn Gln Ala Ala
            20                  25

<210> SEQ ID NO 315
<211> LENGTH: 28
<212> TYPE: PRT
<213> ORGANISM: Bacillus cereus

<400> SEQUENCE: 315

Ser Val Ser Asn Ile Leu Leu Arg Met Arg Asp Leu Ala Asn Gln Ser
1               5                   10                  15

Ala Asn Gly Thr Asn Thr Gly Asp Asn Gln Lys Ala
            20                  25

<210> SEQ ID NO 316
<211> LENGTH: 28
<212> TYPE: PRT
<213> ORGANISM: Bacillus cereus

<400> SEQUENCE: 316

Thr Asn Ile Leu Gln Arg Met Arg Asp Leu Ala Val Gln Ser Ala Asn
1               5                   10                  15

Gly Thr Asn Ser Asn Lys Asn Arg Asp Ser Leu Asn
            20                  25

<210> SEQ ID NO 317
<211> LENGTH: 28

<212> TYPE: PRT
<213> ORGANISM: Bacillus thuringiensis

<400> SEQUENCE: 317

Thr Asn Val Leu Gln Arg Met Arg Asp Val Ala Val Gln Ser Ala Asn
1 5 10 15

Gly Thr Asn Leu Asn Lys Asn Arg Asp Ser Leu Asn
20 25

<210> SEQ ID NO 318
<211> LENGTH: 28
<212> TYPE: PRT
<213> ORGANISM: Bacillus thuringiensis

<400> SEQUENCE: 318

Ser Val Ser Asn Ile Leu Leu Arg Met Arg Asp Ile Ala Asn Gln Ser
1 5 10 15

Ala Asn Gly Thr Asn Thr Asp Ser Asn Lys Ser Ala
20 25

<210> SEQ ID NO 319
<211> LENGTH: 28
<212> TYPE: PRT
<213> ORGANISM: Bacillus cereus

<400> SEQUENCE: 319

Ser Val Ser Asn Ile Leu Leu Arg Met Arg Asp Leu Ala Asn Gln Ser
1 5 10 15

Ala Asn Gly Thr Asn Thr Ala Glu Asn Lys Ala Ala
20 25

<210> SEQ ID NO 320
<211> LENGTH: 28
<212> TYPE: PRT
<213> ORGANISM: Bacillus thuringiensis

<400> SEQUENCE: 320

Ser Val Ser Asn Ile Leu Leu Arg Met Arg Asp Ile Ala Asn Gln Ser
1 5 10 15

Ala Asn Gly Thr Asn Thr Ser Asp Asn Gln Lys Ala
20 25

<210> SEQ ID NO 321
<211> LENGTH: 28
<212> TYPE: PRT
<213> ORGANISM: Bacillus thuringiensis

<400> SEQUENCE: 321

Ser Val Ser Asn Ile Leu Leu Arg Met Arg Asp Ile Ala Asn Gln Ser
1 5 10 15

Ala Asn Gly Thr Asn Thr Ala Asp Asn Gln Gln Ala
20 25

<210> SEQ ID NO 322
<211> LENGTH: 28
<212> TYPE: PRT
<213> ORGANISM: Bacillus thuringiensis

<400> SEQUENCE: 322

Thr Val Met Asn Ile Leu Gln Arg Met Arg Asp Leu Ala Val Gln Ser
1 5 10 15

Ala Asn Gly Thr Asn Ser Asn Lys Asn Arg Asp Ser 20 25

<210> SEQ ID NO 323
<211> LENGTH: 28
<212> TYPE: PRT
<213> ORGANISM: Bacillus thuringiensis

<400> SEQUENCE: 323

Ser Val Ser Asn Ile Leu Leu Arg Met Arg Asp Ile Ala Asn Gln Ser
1 5 10 15

Ala Asn Gly Thr Asn Thr Ala Asp Asn Gln Gln Ala
20 25

<210> SEQ ID NO 324
<211> LENGTH: 28
<212> TYPE: PRT
<213> ORGANISM: Bacillus thuringiensis

<400> SEQUENCE: 324

Thr Val Thr Asn Ile Leu Gln His Met Arg Asp Phe Ala Ile Gln Ser
1 5 10 15

Ala Asn Gly Thr Asn Ser Asn Thr Asn Arg Asp Ser
20 25

<210> SEQ ID NO 325
<211> LENGTH: 28
<212> TYPE: PRT
<213> ORGANISM: Bacillus thuringiensis

<400> SEQUENCE: 325

Ser Val Ser Asn Ile Leu Leu Arg Met Arg Asp Ile Ser Asn Gln Ser
1 5 10 15

Ala Asn Gly Thr Asn Thr Asp Lys Asn Gln Ser Ala
20 25

<210> SEQ ID NO 326
<211> LENGTH: 28
<212> TYPE: PRT
<213> ORGANISM: Bacillus thuringiensis

<400> SEQUENCE: 326

Ser Val Ser Asn Ile Leu Leu Arg Met Arg Asp Ile Ser Asn Gln Ser
1 5 10 15

Ala Asn Gly Thr Asn Thr Asp Lys Asn Gln Ser Ala
20 25

<210> SEQ ID NO 327
<211> LENGTH: 28
<212> TYPE: PRT
<213> ORGANISM: Bacillus thuringiensis

<400> SEQUENCE: 327

Ser Val Ser Asn Ile Leu Leu Arg Met Arg Asp Ile Ser Asn Gln Ser
1 5 10 15

Ala Asn Gly Thr Asn Thr Asp Lys Asn Gln Ser Ala
20 25

<210> SEQ ID NO 328
<211> LENGTH: 28
<212> TYPE: PRT
<213> ORGANISM: Bacillus thuringiensis

<400> SEQUENCE: 328

```
Ser Val Ser Asn Ile Leu Leu Arg Met Arg Asp Leu Ala Asn Gln Ser
1               5                   10                  15

Ala Asn Gly Thr Asn Thr Asn Glu Asn Gln Ala Ala
            20                  25


<210> SEQ ID NO 329
<211> LENGTH: 28
<212> TYPE: PRT
<213> ORGANISM: Bacillus thuringiensis

<400> SEQUENCE: 329

Ser Val Ser Asn Ile Leu Leu Arg Met Arg Asp Leu Ala Asn Gln Ser
1               5                   10                  15

Ala Asn Gly Thr Asn Thr Asn Glu Asn Gln Ala Ala
            20                  25


<210> SEQ ID NO 330
<211> LENGTH: 28
<212> TYPE: PRT
<213> ORGANISM: Bacillus weihenstephanensis

<400> SEQUENCE: 330

Ser Val Ser Asn Ile Leu Leu Arg Met Arg Asp Leu Ser Asn Gln Ser
1               5                   10                  15

Ala Asn Gly Thr Asn Thr Asp Glu Asn Gln Gln Ala
            20                  25


<210> SEQ ID NO 331
<211> LENGTH: 28
<212> TYPE: PRT
<213> ORGANISM: Bacillus thuringiensis

<400> SEQUENCE: 331

Ser Val Ser Asn Ile Leu Leu Arg Met Arg Asp Ile Ala Asn Gln Ser
1               5                   10                  15

Ala Asn Gly Thr Asn Thr Gly Asp Asn Gln Lys Ala
            20                  25


<210> SEQ ID NO 332
<211> LENGTH: 28
<212> TYPE: PRT
<213> ORGANISM: Bacillus thuringiensis

<400> SEQUENCE: 332

Thr Val Ala Asn Ile Leu Gln Arg Met Arg Asp Leu Ala Val Gln Ser
1               5                   10                  15

Ser Asn Asp Thr Asn Ser Asn Lys Asn Arg Asp Ser
            20                  25


<210> SEQ ID NO 333
<211> LENGTH: 28
<212> TYPE: PRT
<213> ORGANISM: Bacillus thuringiensis

<400> SEQUENCE: 333

Ser Val Ser Asn Ile Leu Leu Arg Met Arg Asp Leu Ala Asn Gln Ser
1               5                   10                  15

Ala Asn Gly Thr Asn Thr Asp Asp Asn Gln Lys Ala
            20                  25


<210> SEQ ID NO 334
```

<211> LENGTH: 28
<212> TYPE: PRT
<213> ORGANISM: Bacillus thuringiensis

<400> SEQUENCE: 334

Ser Val Ser Asn Ile Leu Leu Arg Met Arg Asp Leu Ala Asn Gln Ser
1 5 10 15

Ala Asn Gly Thr Asn Thr Asp Asp Asn Gln Lys Ala
20 25

<210> SEQ ID NO 335
<211> LENGTH: 28
<212> TYPE: PRT
<213> ORGANISM: Bacillus thuringiensis

<400> SEQUENCE: 335

Thr Val Thr Asn Ile Leu Gln His Met Arg Asp Phe Ala Ile Gln Ser
1 5 10 15

Ala Asn Gly Thr Asn Ser Asn Thr Asn Arg Asp Ser
20 25

<210> SEQ ID NO 336
<211> LENGTH: 28
<212> TYPE: PRT
<213> ORGANISM: Bacillus thuringiensis

<400> SEQUENCE: 336

Ser Val Ser Asn Ile Leu Leu Arg Met Arg Asp Ile Ser Asn Gln Ser
1 5 10 15

Ala Asn Gly Thr Asn Thr Asp Lys Asn Gln Ser Ala
20 25

<210> SEQ ID NO 337
<211> LENGTH: 28
<212> TYPE: PRT
<213> ORGANISM: Bacillus cereus

<400> SEQUENCE: 337

Thr Val Thr Asn Val Leu Gln Arg Met Arg Asp Val Ala Val Gln Ser
1 5 10 15

Ala Asn Gly Thr Asn Ser Ser Lys Asn Arg Asp Ser
20 25

<210> SEQ ID NO 338
<211> LENGTH: 28
<212> TYPE: PRT
<213> ORGANISM: Bacillus cereus

<400> SEQUENCE: 338

Ser Val Ser Asn Ile Leu Leu Arg Met Arg Asp Ile Ala Asn Gln Ser
1 5 10 15

Ala Asn Gly Thr Asn Thr Asp Lys Asn Gln Val Ala
20 25

<210> SEQ ID NO 339
<211> LENGTH: 28
<212> TYPE: PRT
<213> ORGANISM: Bacillus thuringiensis

<400> SEQUENCE: 339

Thr Val Met Asn Ile Leu Gln Arg Met Arg Asp Leu Ala Ile Gln Ser
1 5 10 15

```
Ala Asn Ser Thr Asn Ser Asn Lys Asn Arg Asp Ser
            20                  25


<210> SEQ ID NO 340
<211> LENGTH: 28
<212> TYPE: PRT
<213> ORGANISM: Bacillus thuringiensis

<400> SEQUENCE: 340

Ser Val Ser Asn Ile Leu Leu Arg Met Arg Asp Ile Ala Asn Gln Ser
1               5                   10                  15

Ala Asn Gly Thr Asn Thr Ser Asp Asn Gln Lys Ala
            20                  25


<210> SEQ ID NO 341
<211> LENGTH: 28
<212> TYPE: PRT
<213> ORGANISM: Bacillus thuringiensis

<400> SEQUENCE: 341

Ser Val Ser Asn Ile Leu Leu Arg Met Arg Asp Ile Ala Asn Gln Ser
1               5                   10                  15

Ala Asn Gly Thr Asn Thr Gly Asp Asn Gln Lys Ala
            20                  25


<210> SEQ ID NO 342
<211> LENGTH: 28
<212> TYPE: PRT
<213> ORGANISM: Bacillus thuringiensis

<400> SEQUENCE: 342

Ser Val Ser Asn Ile Leu Leu Arg Met Arg Asp Ile Ala Asn Gln Ser
1               5                   10                  15

Ala Asn Gly Thr Asn Thr Gly Asp Asn Gln Lys Ala
            20                  25


<210> SEQ ID NO 343
<211> LENGTH: 28
<212> TYPE: PRT
<213> ORGANISM: Bacillus thuringiensis

<400> SEQUENCE: 343

Ser Val Ser Asn Ile Leu Leu Arg Met Arg Asp Ile Ala Asn Gln Ser
1               5                   10                  15

Ala Asn Gly Thr Asn Thr Asn Gly Asn Gln Ala Ala
            20                  25


<210> SEQ ID NO 344
<211> LENGTH: 28
<212> TYPE: PRT
<213> ORGANISM: Bacillus cereus

<400> SEQUENCE: 344

Ser Val Ser Asn Ile Leu Leu Arg Met Arg Asp Ile Ala Asn Gln Ser
1               5                   10                  15

Ala Asn Gly Thr Asn Thr Asp Lys Asn Gln Ala Ala
            20                  25


<210> SEQ ID NO 345
<211> LENGTH: 28
<212> TYPE: PRT
<213> ORGANISM: Bacillus thuringiensis
```

<400> SEQUENCE: 345

Ser Val Ser Asn Ile Leu Leu Arg Met Arg Asp Leu Ala Asn Gln Ser
1               5                   10                  15

Ala Asn Gly Thr Asn Thr Asn Glu Asn Gln Ala Ala
            20                  25

<210> SEQ ID NO 346
<211> LENGTH: 28
<212> TYPE: PRT
<213> ORGANISM: Bacillus cereus

<400> SEQUENCE: 346

Thr Val Thr Asn Val Leu Gln Arg Met Arg Asp Leu Ala Val Gln Ser
1               5                   10                  15

Ala Asn Asp Thr Asn Ser Asn Lys Asn Arg Asp Ser
            20                  25

<210> SEQ ID NO 347
<211> LENGTH: 28
<212> TYPE: PRT
<213> ORGANISM: Bacillus cereus

<400> SEQUENCE: 347

Ser Val Ser Asn Ile Leu Leu Arg Met Arg Asp Leu Ala Asn Gln Ser
1               5                   10                  15

Ala Asn Gly Thr Asn Thr Asn Glu Asn Lys Ala Ala
            20                  25

<210> SEQ ID NO 348
<211> LENGTH: 28
<212> TYPE: PRT
<213> ORGANISM: Bacillus cereus

<400> SEQUENCE: 348

Ser Val Ser Asn Ile Leu Leu Arg Met Arg Asp Leu Ala Asn Gln Ser
1               5                   10                  15

Ala Asn Gly Thr Asn Thr Ser Asp Asn Gln Ala Ala
            20                  25

<210> SEQ ID NO 349
<211> LENGTH: 28
<212> TYPE: PRT
<213> ORGANISM: Bacillus cereus

<400> SEQUENCE: 349

Ser Val Ser Asn Ile Leu Leu Arg Met Arg Asp Leu Ala Asn Gln Ser
1               5                   10                  15

Ala Asn Gly Thr Asn Thr Asn Glu Asn Lys Ala Ala
            20                  25

<210> SEQ ID NO 350
<211> LENGTH: 28
<212> TYPE: PRT
<213> ORGANISM: Bacillus cereus

<400> SEQUENCE: 350

Ser Val Ser Asn Ile Leu Leu Arg Met Arg Asp Leu Ala Asn Gln Ser
1               5                   10                  15

Ala Asn Gly Thr Asn Thr Asn Glu Asn Lys Ala Ala
            20                  25

<210> SEQ ID NO 351
<211> LENGTH: 28
<212> TYPE: PRT
<213> ORGANISM: Bacillus cereus

<400> SEQUENCE: 351

Ser Val Ser Asn Ile Leu Leu Arg Met Arg Asp Ile Ala Asn Gln Ser
1 5 10 15

Ala Asn Gly Thr Asn Thr Gly Asp Asn Gln Lys Ala
20 25

<210> SEQ ID NO 352
<211> LENGTH: 28
<212> TYPE: PRT
<213> ORGANISM: Bacillus thuringiensis

<400> SEQUENCE: 352

Ser Val Ser Asn Ile Leu Leu Arg Met Arg Asp Leu Ala Asn Gln Ser
1 5 10 15

Ala Ser Glu Thr Asn Thr Ser Lys Asn Gln Ala Ala
20 25

<210> SEQ ID NO 353
<211> LENGTH: 28
<212> TYPE: PRT
<213> ORGANISM: Bacillus thuringiensis

<400> SEQUENCE: 353

Ser Val Ser Asn Ile Leu Leu Arg Met Arg Asp Leu Ala Asn Gln Ser
1 5 10 15

Ala Ser Glu Thr Asn Thr Ser Lys Asn Gln Ala Ala
20 25

<210> SEQ ID NO 354
<211> LENGTH: 28
<212> TYPE: PRT
<213> ORGANISM: Bacillus thuringiensis

<400> SEQUENCE: 354

Ser Val Ser Asn Ile Leu Leu Arg Met Arg Asp Ile Ala Asn Gln Ser
1 5 10 15

Ala Asn Gly Thr Asn Thr Gly Asp Asn Gln Lys Ala
20 25

<210> SEQ ID NO 355
<211> LENGTH: 28
<212> TYPE: PRT
<213> ORGANISM: Bacillus thuringiensis

<400> SEQUENCE: 355

Ser Val Ser Asn Ile Leu Leu Arg Met Arg Asp Leu Ala Asn Gln Ser
1 5 10 15

Ala Asn Gly Thr Asn Thr Ser Glu Asn Gln Ala Ala
20 25

<210> SEQ ID NO 356
<211> LENGTH: 28
<212> TYPE: PRT
<213> ORGANISM: Bacillus cereus

<400> SEQUENCE: 356

Thr Val Thr Asn Ile Leu Gln Arg Met Arg Asp Leu Ala Val Gln Ser
1 5 10 15

Ala Asn Val Thr Asn Ser Asn Lys Asn Arg Asn Ser
20 25

<210> SEQ ID NO 357
<211> LENGTH: 28
<212> TYPE: PRT
<213> ORGANISM: Bacillus cereus

<400> SEQUENCE: 357

Ser Val Ser Asn Ile Leu Leu Arg Met Arg Asp Leu Ala Asn Gln Ser
1 5 10 15

Ala Asn Gly Thr Asn Thr Asp Lys Asn Gln Gly Ala
20 25

<210> SEQ ID NO 358
<211> LENGTH: 28
<212> TYPE: PRT
<213> ORGANISM: Bacillus cereus

<400> SEQUENCE: 358

Ser Val Ser Asn Ile Leu Leu Arg Met Arg Asp Leu Ala Asn Gln Ser
1 5 10 15

Ala Asn Gly Thr Asn Thr Asp Lys Asn Gln Ala Ala
20 25

<210> SEQ ID NO 359
<211> LENGTH: 28
<212> TYPE: PRT
<213> ORGANISM: Bacillus cereus

<400> SEQUENCE: 359

Thr Val Thr Asn Val Leu Gln Arg Met Arg Asp Leu Ala Val Gln Ser
1 5 10 15

Ala Asn Gly Thr Asn Ser Asn Lys Asn Arg Asp Ser
20 25

<210> SEQ ID NO 360
<211> LENGTH: 28
<212> TYPE: PRT
<213> ORGANISM: Bacillus thuringiensis

<400> SEQUENCE: 360

Ser Val Ser Asn Ile Leu Leu Arg Met Arg Asp Ile Ala Asn Gln Thr
1 5 10 15

Ala Asn Gly Thr Asn Lys Asp Thr Asp Ile Glu Ala
20 25

<210> SEQ ID NO 361
<211> LENGTH: 28
<212> TYPE: PRT
<213> ORGANISM: Bacillus cereus

<400> SEQUENCE: 361

Ser Val Ser Asn Ile Leu Leu Arg Met Arg Asp Ile Ala Asn Gln Thr
1 5 10 15

Ala Asn Gly Thr Asn Lys Asp Thr Asp Ile Glu Ala
20 25

<210> SEQ ID NO 362
<211> LENGTH: 28
<212> TYPE: PRT
<213> ORGANISM: Bacillus thuringiensis

<400> SEQUENCE: 362

Thr Val Met Asn Ile Leu Gln Arg Met Arg Asp Leu Ala Ile Gln Ser
1 5 10 15

Ala Asn Ser Thr Asn Ser Asn Lys Asn Arg Asp Ser
20 25

<210> SEQ ID NO 363
<211> LENGTH: 28
<212> TYPE: PRT
<213> ORGANISM: Bacillus thuringiensis

<400> SEQUENCE: 363

Ser Val Ser Asn Ile Leu Leu Arg Met Arg Asp Ile Ala Asn Gln Ser
1 5 10 15

Ala Asn Gly Thr Asn Thr Gly Asp Asn Gln Lys Ala
20 25

<210> SEQ ID NO 364
<211> LENGTH: 28
<212> TYPE: PRT
<213> ORGANISM: Bacillus aryabhattai

<400> SEQUENCE: 364

Glu Thr His Asp Ile Leu Gln Arg Met Arg Glu Leu Val Val Gln Ala
1 5 10 15

Gly Asn Gly Thr Asn Lys Thr Glu Asp Leu Asp Ala
20 25

<210> SEQ ID NO 365
<211> LENGTH: 28
<212> TYPE: PRT
<213> ORGANISM: Bacillus manliponensis

<400> SEQUENCE: 365

Ser Val Ser Asn Ile Leu Leu Arg Met Arg Asp Leu Ala Thr Gln Ser
1 5 10 15

Ala Thr Gly Thr Asn Gln Gly Asn Asp Arg Glu Ser
20 25

<210> SEQ ID NO 366
<211> LENGTH: 28
<212> TYPE: PRT
<213> ORGANISM: Lysinibacillus sp.

<400> SEQUENCE: 366

Glu Thr His Ala Ile Val Gln Arg Met Arg Glu Leu Ala Val Gln Ala
1 5 10 15

Ala Thr Asp Thr Asn Thr Asp Asp Asp Arg Ala Lys
20 25

<210> SEQ ID NO 367
<211> LENGTH: 28
<212> TYPE: PRT
<213> ORGANISM: Lysinibacillus sp.

<400> SEQUENCE: 367

Glu Thr His Ala Ile Val Gln Arg Met Arg Glu Leu Ala Val Gln Ala
1 5 10 15

Ala Thr Asp Thr Asn Thr Asp Asp Asp Arg Ala Lys
20 25

<210> SEQ ID NO 368
<211> LENGTH: 28
<212> TYPE: PRT
<213> ORGANISM: Paenibacillus sp.

<400> SEQUENCE: 368

Glu Ile His Ser Met Leu Gln Arg Met Asn Glu Leu Ala Val Gln Ala
1 5 10 15

Ser Asn Gly Thr Tyr Ser Gly Ser Asp Arg Leu Asn
20 25

<210> SEQ ID NO 369
<211> LENGTH: 28
<212> TYPE: PRT
<213> ORGANISM: Bacillus anthracis

<400> SEQUENCE: 369

Ser Val Ser Asn Ile Leu Leu Arg Met Arg Asp Leu Ala Asn Gln Ser
1 5 10 15

Ala Asn Gly Thr Asn Thr Lys Glu Asn Gln Asp Ala
20 25

<210> SEQ ID NO 370
<211> LENGTH: 28
<212> TYPE: PRT
<213> ORGANISM: Bacillus anthracis

<400> SEQUENCE: 370

Ser Val Ser Asn Ile Leu Thr Arg Met Arg Asp Ile Ala Val Gln Ser
1 5 10 15

Ser Asn Gly Thr Asn Thr Ala Glu Asn Gln Ser Ala
20 25

<210> SEQ ID NO 371
<211> LENGTH: 28
<212> TYPE: PRT
<213> ORGANISM: Bacillus anthracis

<400> SEQUENCE: 371

Ser Val Ser Asn Ile Leu Thr Arg Met Arg Asp Ile Ala Val Gln Ser
1 5 10 15

Ser Asn Gly Thr Asn Thr Ala Glu Asn Gln Ser Ala
20 25

<210> SEQ ID NO 372
<211> LENGTH: 28
<212> TYPE: PRT
<213> ORGANISM: Bacillus anthracis

<400> SEQUENCE: 372

Ser Val Ser Asn Ile Leu Thr Arg Met Arg Asp Ile Ala Val Gln Ser
1 5 10 15

Ser Asn Gly Thr Asn Thr Ala Glu Asn Gln Ser Ala
20 25

<210> SEQ ID NO 373
<211> LENGTH: 28
<212> TYPE: PRT
<213> ORGANISM: Bacillus anthracis

<400> SEQUENCE: 373

Ser Val Ser Asn Ile Leu Thr Arg Met Arg Asp Ile Ala Val Gln Ser

-continued

```
1               5                   10                  15

Ser Asn Gly Thr Asn Thr Ala Glu Asn Gln Ser Ala
            20                  25


<210> SEQ ID NO 374
<211> LENGTH: 28
<212> TYPE: PRT
<213> ORGANISM: Bacillus megaterium

<400> SEQUENCE: 374

Glu Thr His Asp Ile Leu Gln Arg Met Arg Glu Leu Val Val Gln Ala
1               5                   10                  15

Gly Asn Gly Thr Asn Lys Thr Glu Asp Leu Asp Ala
            20                  25


<210> SEQ ID NO 375
<211> LENGTH: 28
<212> TYPE: PRT
<213> ORGANISM: Aneurinibacillus sp.

<400> SEQUENCE: 375

Glu Ile His Glu Met Leu Gln Arg Met Arg Glu Leu Ala Val Gln Ala
1               5                   10                  15

Ala Asn Gly Thr Tyr Ser Asp Lys Asp Lys Lys Ala
            20                  25


<210> SEQ ID NO 376
<211> LENGTH: 22
<212> TYPE: PRT
<213> ORGANISM: Bacillus thuringiensis

<400> SEQUENCE: 376

Ala Ile Ala Leu Gly Ala Ala Asp Asp Ser Ala Ser Asn Ile Arg Lys
1               5                   10                  15

Gly Ser Ser Leu Arg Asp
            20


<210> SEQ ID NO 377
<211> LENGTH: 22
<212> TYPE: PRT
<213> ORGANISM: Bacillus thuringiensis

<400> SEQUENCE: 377

Ala Ile Ala Leu Gly Ala Ala Asp Asp Ser Ala Ser Asn Ile Arg Lys
1               5                   10                  15

Gly Ser Ser Leu Arg Asp
            20


<210> SEQ ID NO 378
<211> LENGTH: 21
<212> TYPE: PRT
<213> ORGANISM: Bacillus thuringiensis

<400> SEQUENCE: 378

Ala Ile Ala Leu Gly Ala Ala Asp Asp Ala Ser Asn Ile Arg Lys Gly
1               5                   10                  15

Ser Ser Leu Arg Asp
            20


<210> SEQ ID NO 379
<211> LENGTH: 22
<212> TYPE: PRT
```

<213> ORGANISM: Bacillus cereus

<400> SEQUENCE: 379

Ala Ile Ala Leu Gly Ala Ala Asp Asp Ser Ala Ser Asn Ile Arg Lys
1 5 10 15

Gly Ser Ser Leu Arg Asp
20

<210> SEQ ID NO 380
<211> LENGTH: 21
<212> TYPE: PRT
<213> ORGANISM: Bacillus thuringiensis

<400> SEQUENCE: 380

Val Ile Ala Asn Ala Pro Asn Asp Ser Ala Asn Asn Leu Lys Lys Gly
1 5 10 15

Thr Ala Leu His Glu
20

<210> SEQ ID NO 381
<211> LENGTH: 22
<212> TYPE: PRT
<213> ORGANISM: Bacillus thuringiensis

<400> SEQUENCE: 381

Thr Ala Ile Ala Gly Ala Ala Asp Asp Ser Ala Asn Asn Ile Arg Lys
1 5 10 15

Gly Ser Ser Leu Arg Asp
20

<210> SEQ ID NO 382
<211> LENGTH: 22
<212> TYPE: PRT
<213> ORGANISM: Bacillus thuringiensis

<400> SEQUENCE: 382

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 383
<211> LENGTH: 22
<212> TYPE: PRT
<213> ORGANISM: Bacillus thuringiensis

<400> SEQUENCE: 383

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 384
<211> LENGTH: 22
<212> TYPE: PRT
<213> ORGANISM: Bacillus cereus

<400> SEQUENCE: 384

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 385
<211> LENGTH: 22
<212> TYPE: PRT
<213> ORGANISM: Bacillus cereus

<400> SEQUENCE: 385

Val Ile Ala Val Asn Ala Pro Asn Asp Ser Ala His Asn Leu Lys Lys
1 5 10 15

Gly Thr Ala Leu His Glu
20

<210> SEQ ID NO 386
<211> LENGTH: 22
<212> TYPE: PRT
<213> ORGANISM: Bacillus thuringiensis

<400> SEQUENCE: 386

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 387
<211> LENGTH: 22
<212> TYPE: PRT
<213> ORGANISM: Bacillus bombysepticus

<400> SEQUENCE: 387

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 388
<211> LENGTH: 22
<212> TYPE: PRT
<213> ORGANISM: Bacillus thuringiensis

<400> SEQUENCE: 388

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 389
<211> LENGTH: 22
<212> TYPE: PRT
<213> ORGANISM: Bacillus thuringiensis

<400> SEQUENCE: 389

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 390
<211> LENGTH: 22
<212> TYPE: PRT
<213> ORGANISM: Bacillus cereus

<400> SEQUENCE: 390

-continued

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 391
<211> LENGTH: 22
<212> TYPE: PRT
<213> ORGANISM: Bacillus cereus

<400> SEQUENCE: 391

Val Ile Ala Ile Asn Ala Pro Asn Asp Ala Ser Asn Asn Leu Lys Lys
1 5 10 15

Gly Thr Ala Leu His Glu
20

<210> SEQ ID NO 392
<211> LENGTH: 21
<212> TYPE: PRT
<213> ORGANISM: Bacillus thuringiensis

<400> SEQUENCE: 392

Val Ile Ala Asn Ala Pro Asn Asp Ser Ala His Asn Leu Lys Lys Gly
1 5 10 15

Thr Ala Leu His Glu
20

<210> SEQ ID NO 393
<211> LENGTH: 22
<212> TYPE: PRT
<213> ORGANISM: Bacillus thuringiensis

<400> SEQUENCE: 393

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 394
<211> LENGTH: 22
<212> TYPE: PRT
<213> ORGANISM: Bacillus cereus

<400> SEQUENCE: 394

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 395
<211> LENGTH: 22
<212> TYPE: PRT
<213> ORGANISM: Bacillus thuringiensis

<400> SEQUENCE: 395

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 396
<211> LENGTH: 22

<212> TYPE: PRT
<213> ORGANISM: Bacillus thuringiensis

<400> SEQUENCE: 396

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 397
<211> LENGTH: 21
<212> TYPE: PRT
<213> ORGANISM: Bacillus thuringiensis

<400> SEQUENCE: 397

Val Ile Ala Asn Ala Pro Asn Asp Ser Ala His Asn Leu Lys Lys Gly
1 5 10 15

Thr Ala Phe His Glu
20

<210> SEQ ID NO 398
<211> LENGTH: 21
<212> TYPE: PRT
<213> ORGANISM: Bacillus thuringiensis

<400> SEQUENCE: 398

Ala Ile Ala Leu Gly Ala Ala Asp Asp Ser Ala Asn Asn Arg Lys Gly
1 5 10 15

Ser Ser Leu Arg Asp
20

<210> SEQ ID NO 399
<211> LENGTH: 22
<212> TYPE: PRT
<213> ORGANISM: Bacillus thuringiensis

<400> SEQUENCE: 399

Val Ile Val Ile Asn Ala Pro Asn Asp Ser Ala His Asn Leu Lys Lys
1 5 10 15

Gly Thr Ala Leu His Glu
20

<210> SEQ ID NO 400
<211> LENGTH: 22
<212> TYPE: PRT
<213> ORGANISM: Bacillus thuringiensis

<400> SEQUENCE: 400

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 401
<211> LENGTH: 22
<212> TYPE: PRT
<213> ORGANISM: Bacillus thuringiensis

<400> SEQUENCE: 401

Ala Ile Ala Leu Gly Ala Ala Asp Asp Ser Ala Asn Asn Ile Arg Lys
1 5 10 15

Gly Ser Ser Leu Arg Asp

20

<210> SEQ ID NO 402
<211> LENGTH: 22
<212> TYPE: PRT
<213> ORGANISM: Bacillus thuringiensis

<400> SEQUENCE: 402

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 403
<211> LENGTH: 22
<212> TYPE: PRT
<213> ORGANISM: Bacillus thuringiensis

<400> SEQUENCE: 403

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 404
<211> LENGTH: 22
<212> TYPE: PRT
<213> ORGANISM: Bacillus thuringiensis

<400> SEQUENCE: 404

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 405
<211> LENGTH: 22
<212> TYPE: PRT
<213> ORGANISM: Bacillus weihenstephanensis

<400> SEQUENCE: 405

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 406
<211> LENGTH: 22
<212> TYPE: PRT
<213> ORGANISM: Bacillus thuringiensis

<400> SEQUENCE: 406

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 407
<211> LENGTH: 21
<212> TYPE: PRT
<213> ORGANISM: Bacillus thuringiensis

<400> SEQUENCE: 407

-continued

```
Val Ile Ala Asn Ala Pro Asn Asp Ser Ala His Asn Leu Lys Lys Gly
1               5                   10                  15

Thr Ala Leu His Glu
            20


<210> SEQ ID NO 408
<211> LENGTH: 22
<212> TYPE: PRT
<213> ORGANISM: Bacillus thuringiensis

<400> SEQUENCE: 408

Ala Ile Ala Leu Gly Ala Ala Asp Asp Ser Ala Asn Asn Ile Arg Lys
1               5                   10                  15

Gly Ser Ser Leu Arg Asp
            20


<210> SEQ ID NO 409
<211> LENGTH: 22
<212> TYPE: PRT
<213> ORGANISM: Bacillus thuringiensis

<400> SEQUENCE: 409

Ala Ile Ala Leu Gly Ala Ala Asp Asp Ser Ala Asn Asn Ile Arg Lys
1               5                   10                  15

Gly Ser Ser Leu Arg Asp
            20


<210> SEQ ID NO 410
<211> LENGTH: 22
<212> TYPE: PRT
<213> ORGANISM: Bacillus thuringiensis

<400> SEQUENCE: 410

Val Ile Val Ile Asn Ala Pro Asn Asp Ala Ser His Asn Leu Lys Lys
1               5                   10                  15

Gly Thr Ala Leu His Glu
            20


<210> SEQ ID NO 411
<211> LENGTH: 22
<212> TYPE: PRT
<213> ORGANISM: Bacillus thuringiensis

<400> SEQUENCE: 411

Ala Ile Ala Leu Gly Ala Ala Asp Asp Ser Ala Asn Asn Ile Arg Lys
1               5                   10                  15

Gly Ser Ser Leu Arg Asp
            20


<210> SEQ ID NO 412
<211> LENGTH: 22
<212> TYPE: PRT
<213> ORGANISM: Bacillus cereus

<400> SEQUENCE: 412

Val Ile Ala Val Ala Asn Pro Asn Asn Ser Ala His Asn Leu Lys Lys
1               5                   10                  15

Gly Thr Ala Leu His Glu
            20


<210> SEQ ID NO 413
```

<211> LENGTH: 22
<212> TYPE: PRT
<213> ORGANISM: Bacillus cereus

<400> SEQUENCE: 413

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 414
<211> LENGTH: 21
<212> TYPE: PRT
<213> ORGANISM: Bacillus thuringiensis

<400> SEQUENCE: 414

Val Ile Ala Asn Ala Pro Asn Asp Ser Ala His Asn Leu Lys Lys Gly
1 5 10 15

Thr Ala Leu His Glu
20

<210> SEQ ID NO 415
<211> LENGTH: 22
<212> TYPE: PRT
<213> ORGANISM: Bacillus thuringiensis

<400> SEQUENCE: 415

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 416
<211> LENGTH: 22
<212> TYPE: PRT
<213> ORGANISM: Bacillus thuringiensis

<400> SEQUENCE: 416

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 417
<211> LENGTH: 22
<212> TYPE: PRT
<213> ORGANISM: Bacillus thuringiensis

<400> SEQUENCE: 417

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 418
<211> LENGTH: 22
<212> TYPE: PRT
<213> ORGANISM: Bacillus thuringiensis

<400> SEQUENCE: 418

Ala Ile Ala Leu Gly Ala Ala Asp Asp Ser Ala Asn Asn Ile Arg Lys
1 5 10 15

-continued

Gly Ser Ser Leu Arg Asp
20

<210> SEQ ID NO 419
<211> LENGTH: 22
<212> TYPE: PRT
<213> ORGANISM: Bacillus cereus

<400> SEQUENCE: 419

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 420
<211> LENGTH: 22
<212> TYPE: PRT
<213> ORGANISM: Bacillus thuringiensis

<400> SEQUENCE: 420

Ala Ile Ala Leu Gly Ala Ala Asp Asp Ala Ser Asn Asn Ile Arg Lys
1 5 10 15

Gly Ser Ser Leu Arg Asp
20

<210> SEQ ID NO 421
<211> LENGTH: 21
<212> TYPE: PRT
<213> ORGANISM: Bacillus cereus

<400> SEQUENCE: 421

Val Ile Ala Asn Ala Pro Asn Asp Ser Ala Asn Asn Leu Lys Lys Gly
1 5 10 15

Thr Ala Leu His Glu
20

<210> SEQ ID NO 422
<211> LENGTH: 22
<212> TYPE: PRT
<213> ORGANISM: Bacillus cereus

<400> SEQUENCE: 422

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 423
<211> LENGTH: 22
<212> TYPE: PRT
<213> ORGANISM: Bacillus cereus

<400> SEQUENCE: 423

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 424
<211> LENGTH: 22
<212> TYPE: PRT
<213> ORGANISM: Bacillus cereus

<400> SEQUENCE: 424

Ala Ile Ala Leu Gly Ala Ala Asp Asp Ser Ala Asn Asn Ile Arg Lys
1               5                   10                  15

Gly Ser Ser Leu Arg Asp
            20

<210> SEQ ID NO 425
<211> LENGTH: 22
<212> TYPE: PRT
<213> ORGANISM: Bacillus cereus

<400> SEQUENCE: 425

Ala Ile Ala Leu Gly Ala Ala Asp Asp Ser Ala Asn Asn Ile Arg Lys
1               5                   10                  15

Gly Ser Ser Leu Arg Asp
            20

<210> SEQ ID NO 426
<211> LENGTH: 22
<212> TYPE: PRT
<213> ORGANISM: Bacillus cereus

<400> SEQUENCE: 426

Ala Ile Ala Leu Gly Ala Ala Asp Asp Ser Ala Asn Asn Ile Arg Lys
1               5                   10                  15

Gly Ser Ser Leu Arg Asp
            20

<210> SEQ ID NO 427
<211> LENGTH: 22
<212> TYPE: PRT
<213> ORGANISM: Bacillus thuringiensis

<400> SEQUENCE: 427

Ala Ile Ala Leu Gly Ala Ala Asp Asp Ser Ala Asn Asn Ile Arg Lys
1               5                   10                  15

Gly Ser Ser Leu Arg Asp
            20

<210> SEQ ID NO 428
<211> LENGTH: 21
<212> TYPE: PRT
<213> ORGANISM: Bacillus thuringiensis

<400> SEQUENCE: 428

Ala Ile Ala Leu Gly Ala Ala Asp Asp Ala Asn Asn Ile Arg Lys Gly
1               5                   10                  15

Ser Ser Leu Arg Asp
            20

<210> SEQ ID NO 429
<211> LENGTH: 22
<212> TYPE: PRT
<213> ORGANISM: Bacillus thuringiensis

<400> SEQUENCE: 429

Ala Ile Ala Leu Gly Ala Ala Asp Asp Ser Ala Asn Asn Ile Arg Lys
1               5                   10                  15

Gly Ser Ser Leu Arg Asp
            20

<210> SEQ ID NO 430
<211> LENGTH: 22
<212> TYPE: PRT
<213> ORGANISM: Bacillus thuringiensis

<400> SEQUENCE: 430

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 431
<211> LENGTH: 22
<212> TYPE: PRT
<213> ORGANISM: Bacillus cereus

<400> SEQUENCE: 431

Val Ile Ala Ile Asn Ala Pro Asn Asn Ser Ala His Asn Leu Lys Lys
1 5 10 15

Gly Thr Ala Leu His Glu
20

<210> SEQ ID NO 432
<211> LENGTH: 22
<212> TYPE: PRT
<213> ORGANISM: Bacillus cereus

<400> SEQUENCE: 432

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 433
<211> LENGTH: 22
<212> TYPE: PRT
<213> ORGANISM: Bacillus cereus

<400> SEQUENCE: 433

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 434
<211> LENGTH: 22
<212> TYPE: PRT
<213> ORGANISM: Bacillus cereus

<400> SEQUENCE: 434

Val Ile Ala Ile Asn Ala Pro Asn Asp Ser Ala Asn Asn Leu Lys Lys
1 5 10 15

Gly Thr Ala Leu His Glu
20

<210> SEQ ID NO 435
<211> LENGTH: 22
<212> TYPE: PRT
<213> ORGANISM: Bacillus thuringiensis

<400> SEQUENCE: 435

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 436
<211> LENGTH: 21
<212> TYPE: PRT
<213> ORGANISM: Bacillus cereus

<400> SEQUENCE: 436

Ala Ile Ala Leu Gly Ala Ala Asp Asp Ala Asn Asn Ile Arg Lys Gly
1 5 10 15

Ser Ser Leu Arg Asp
20

<210> SEQ ID NO 437
<211> LENGTH: 21
<212> TYPE: PRT
<213> ORGANISM: Bacillus thuringiensis

<400> SEQUENCE: 437

Val Ile Ala Asn Ala Pro Asn Asp Ser Ala His Asn Leu Lys Lys Gly
1 5 10 15

Thr Ala Leu His Glu
20

<210> SEQ ID NO 438
<211> LENGTH: 22
<212> TYPE: PRT
<213> ORGANISM: Bacillus thuringiensis

<400> SEQUENCE: 438

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 439
<211> LENGTH: 22
<212> TYPE: PRT
<213> ORGANISM: Bacillus aryabhattai

<400> SEQUENCE: 439

Ser Ile Ala Leu Gly Ala Ala Asp Asp Ser Ala Ser Asn Ile Arg Gln
1 5 10 15

Gly Ser Ser Leu Lys Glu
20

<210> SEQ ID NO 440
<211> LENGTH: 22
<212> TYPE: PRT
<213> ORGANISM: Bacillus manliponensis

<400> SEQUENCE: 440

Ala Ile Ala Leu Gly Ala Ala Asp Asp Ser Ala Ser Asn Ile Gln Lys
1 5 10 15

Gly Ser Ser Leu Arg Asn
20

<210> SEQ ID NO 441
<211> LENGTH: 22
<212> TYPE: PRT
<213> ORGANISM: Lysinibacillus sp.

<400> SEQUENCE: 441

Ser Ile Ala Leu Gly Ala Ala Asp Asp Ala Ala Ser Asn Ile Arg Tyr
1 5 10 15

Gly Ser Ser Leu Arg Leu
20

<210> SEQ ID NO 442
<211> LENGTH: 22
<212> TYPE: PRT
<213> ORGANISM: Lysinibacillus sp.

<400> SEQUENCE: 442

Ser Ile Ala Leu Gly Ala Ala Asp Asp Ala Ala Ser Asn Ile Arg Tyr
1 5 10 15

Gly Ser Ser Leu Arg Leu
20

<210> SEQ ID NO 443
<211> LENGTH: 22
<212> TYPE: PRT
<213> ORGANISM: Paenibacillus sp.

<400> SEQUENCE: 443

Ser Ile Ala Gly Leu Ala Ala Asp Asp Ser Ala Gly Asn Ile Arg Leu
1 5 10 15

Gly Ser Ser Leu Lys Gly
20

<210> SEQ ID NO 444
<211> LENGTH: 22
<212> TYPE: PRT
<213> ORGANISM: Bacillus anthracis

<400> SEQUENCE: 444

Ala Ile Ala Leu Gly Ala Ala Asp Asp Ser Ala Asn Asn Ile Arg Lys
1 5 10 15

Gly Ser Ser Leu Arg Asp
20

<210> SEQ ID NO 445
<211> LENGTH: 22
<212> TYPE: PRT
<213> ORGANISM: Bacillus anthracis

<400> SEQUENCE: 445

Ala Ile Ala Leu Gly Ala Ala Asp Asp Ala Ala Ser Asn Ile Arg Lys
1 5 10 15

Gly Ser Ser Leu Arg Asn
20

<210> SEQ ID NO 446
<211> LENGTH: 22
<212> TYPE: PRT
<213> ORGANISM: Bacillus anthracis

<400> SEQUENCE: 446

Ala Ile Ala Leu Gly Ala Ala Asp Asp Ala Ala Ser Asn Ile Arg Lys
1 5 10 15

Gly Ser Ser Leu Arg Asn
20

-continued

<210> SEQ ID NO 447
<211> LENGTH: 22
<212> TYPE: PRT
<213> ORGANISM: Bacillus anthracis

<400> SEQUENCE: 447

Ala Ile Ala Leu Gly Ala Ala Asp Asp Ala Ala Ser Asn Ile Arg Lys
1               5                   10                  15

Gly Ser Ser Leu Arg Asn
            20

<210> SEQ ID NO 448
<211> LENGTH: 22
<212> TYPE: PRT
<213> ORGANISM: Bacillus anthracis

<400> SEQUENCE: 448

Ala Ile Ala Leu Gly Ala Ala Asp Asp Ala Ala Ser Asn Ile Arg Lys
1               5                   10                  15

Gly Ser Ser Leu Arg Asn
            20

<210> SEQ ID NO 449
<211> LENGTH: 22
<212> TYPE: PRT
<213> ORGANISM: Bacillus megaterium

<400> SEQUENCE: 449

Ser Ile Ala Leu Gly Ala Ala Asp Asp Ser Ala Ser Asn Ile Arg Gln
1               5                   10                  15

Gly Ser Ser Leu Lys Glu
            20

<210> SEQ ID NO 450
<211> LENGTH: 22
<212> TYPE: PRT
<213> ORGANISM: Aneurinibacillus sp.

<400> SEQUENCE: 450

Ser Ile Ala Leu Gly Ala Ala Asp Asp Ser Ala Arg Asn Ile Arg Tyr
1               5                   10                  15

Gly Ser Ser Leu Arg Glu
            20

<210> SEQ ID NO 451
<211> LENGTH: 28
<212> TYPE: PRT
<213> ORGANISM: Bacillus thuringiensis

<400> SEQUENCE: 451

Ser Ala Gln Asn Gly Lys Thr Asn Thr Gly Asn Ala Ser Gln Asn Ala
1               5                   10                  15

Leu Asp Arg Met Arg Leu Leu Ile Asn Ser Val Ser
            20                  25

<210> SEQ ID NO 452
<211> LENGTH: 28
<212> TYPE: PRT
<213> ORGANISM: Bacillus thuringiensis

<400> SEQUENCE: 452

Ser Ala Gln Asn Gly Lys Thr Asn Thr Gly Asn Ala Ser Gln Asn Ala 1 5 10 15

Leu Asp Arg Met Arg Leu Leu Ile Asn Ser Val Ser
20 25

<210> SEQ ID NO 453
<211> LENGTH: 28
<212> TYPE: PRT
<213> ORGANISM: Bacillus thuringiensis

<400> SEQUENCE: 453

Ser Ala Gln Asn Gly Lys Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 454
<211> LENGTH: 28
<212> TYPE: PRT
<213> ORGANISM: Bacillus cereus

<400> SEQUENCE: 454

Ser Ala Gln Asn Gly Lys Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 455
<211> LENGTH: 28
<212> TYPE: PRT
<213> ORGANISM: Bacillus thuringiensis

<400> SEQUENCE: 455

Ser His Arg Asn Lys Asn Ser Asn Thr Gly Asn Ala Ser Gln Val Ala
1 5 10 15

Leu Asp Arg Met Arg Gln Leu Ile Asn Thr Val Thr
20 25

<210> SEQ ID NO 456
<211> LENGTH: 28
<212> TYPE: PRT
<213> ORGANISM: Bacillus thuringiensis

<400> SEQUENCE: 456

Ala Ser Lys Asn Glu Asn Thr Asn Thr Gly Asn Ala Ser Gln Asn Ala
1 5 10 15

Ile Asp Arg Met Arg Leu Leu Ile Asn Ser Val Ser
20 25

<210> SEQ ID NO 457
<211> LENGTH: 28
<212> TYPE: PRT
<213> ORGANISM: Bacillus thuringiensis

<400> SEQUENCE: 457

Ala Lys Gln Asn Asp Asp Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 458
<211> LENGTH: 28
<212> TYPE: PRT

<213> ORGANISM: Bacillus thuringiensis

<400> SEQUENCE: 458

Ala Ala Lys Asn Glu Asp Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 459
<211> LENGTH: 29
<212> TYPE: PRT
<213> ORGANISM: Bacillus cereus

<400> SEQUENCE: 459

Leu Ala Val Gln Asn Lys Asp Thr Asn Thr Gly Asn Ala Ser Gln Asn
1 5 10 15

Ala Ile Asp Arg Met Arg Leu Leu Ile Asn Ser Val Ser
20 25

<210> SEQ ID NO 460
<211> LENGTH: 28
<212> TYPE: PRT
<213> ORGANISM: Bacillus cereus

<400> SEQUENCE: 460

Ser Asp Arg Asn Lys Asn Ser Asn Thr Gly Asn Ala Ser Gln Val Ala
1 5 10 15

Val Asp Arg Met Arg Gln Leu Ile Asn Thr Val Thr
20 25

<210> SEQ ID NO 461
<211> LENGTH: 28
<212> TYPE: PRT
<213> ORGANISM: Bacillus thuringiensis

<400> SEQUENCE: 461

Ala Gln Gln Asn Asp Ala Thr Asn Thr Gly Asn Ala Ser Gln Asn Ala
1 5 10 15

Ile Asp Arg Met Arg Leu Leu Ile Asn Ser Val Ser
20 25

<210> SEQ ID NO 462
<211> LENGTH: 28
<212> TYPE: PRT
<213> ORGANISM: Bacillus bombysepticus

<400> SEQUENCE: 462

Ala Ala Gln Asn Lys Asp Thr Asn Thr Gly Ser Ala Ser Gln Asn Ala
1 5 10 15

Leu Asp Arg Met Arg Leu Leu Ile Asn Ser Val Ser
20 25

<210> SEQ ID NO 463
<211> LENGTH: 28
<212> TYPE: PRT
<213> ORGANISM: Bacillus thuringiensis

<400> SEQUENCE: 463

Ala Ala Gln Asn Lys Asp Thr Asn Thr Gly Ser Ala Ser Gln Asn Ala
1 5 10 15

Leu Asp Arg Met Arg Leu Leu Ile Asn Ser Val Ser
20 25

<210> SEQ ID NO 464
<211> LENGTH: 28
<212> TYPE: PRT
<213> ORGANISM: Bacillus thuringiensis

<400> SEQUENCE: 464

```
Ala Ala Gln Asn Lys Asp Thr Asn Thr Gly Ser Ala Ser Gln Asn Ala
1               5                   10                  15

Leu Asp Arg Met Arg Leu Leu Ile Asn Ser Val Ser
            20                  25
```

<210> SEQ ID NO 465
<211> LENGTH: 28
<212> TYPE: PRT
<213> ORGANISM: Bacillus cereus

<400> SEQUENCE: 465

```
Ala Lys Gln Asn Asp Gly Thr Asn Thr Gly Asn Ala Ser Gln Asn Ala
1               5                   10                  15

Leu Asp Arg Met Arg Leu Leu Ile Asn Ser Val Ser
            20                  25
```

<210> SEQ ID NO 466
<211> LENGTH: 28
<212> TYPE: PRT
<213> ORGANISM: Bacillus cereus

<400> SEQUENCE: 466

```
Asn Leu Ser Asp Arg Asn Lys Asn Ser Asn Thr Gly Asn Ala Ser Gln
1               5                   10                  15

Val Ala Leu Asp Arg Met Arg Gln Leu Ile Asn Thr
            20                  25
```

<210> SEQ ID NO 467
<211> LENGTH: 28
<212> TYPE: PRT
<213> ORGANISM: Bacillus thuringiensis

<400> SEQUENCE: 467

```
Asn Leu Ser Asp Arg Asn Lys Asn Leu Asn Thr Gly Asn Ala Ser Gln
1               5                   10                  15

Val Ala Val Asp Arg Met Arg Gln Leu Val Asn Thr
            20                  25
```

<210> SEQ ID NO 468
<211> LENGTH: 28
<212> TYPE: PRT
<213> ORGANISM: Bacillus thuringiensis

<400> SEQUENCE: 468

```
Ala Ser Lys Asn Ser Asp Thr Asn Thr Gly Asn Ala Ser Gln Asn Ala
1               5                   10                  15

Ile Asp Arg Met Arg Leu Leu Ile Asn Ser Val Ser
            20                  25
```

<210> SEQ ID NO 469
<211> LENGTH: 28
<212> TYPE: PRT
<213> ORGANISM: Bacillus cereus

<400> SEQUENCE: 469

```
Ala Ala Lys Asn Glu Ala Thr Asn Thr Gly Asn Ala Ser Gln Asn Ala
1               5                   10                  15

Leu Asp Arg Met Arg Leu Leu Ile Asn Ser Val Ser
            20                  25


<210> SEQ ID NO 470
<211> LENGTH: 28
<212> TYPE: PRT
<213> ORGANISM: Bacillus thuringiensis

<400> SEQUENCE: 470

Ala Lys Gln Asn Asp Ser Thr Asn Thr Gly Asn Ala Ser Gln Asn Ala
1               5                   10                  15

Ile Asp Arg Met Arg Leu Leu Ile Asn Ser Val Ser
            20                  25


<210> SEQ ID NO 471
<211> LENGTH: 28
<212> TYPE: PRT
<213> ORGANISM: Bacillus thuringiensis

<400> SEQUENCE: 471

Ala Gln Gln Asn Asp Ala Thr Asn Thr Gly Asn Ala Ser Gln Asn Ala
1               5                   10                  15

Ile Asp Arg Met Arg Leu Leu Ile Asn Ser Val Ser
            20                  25


<210> SEQ ID NO 472
<211> LENGTH: 28
<212> TYPE: PRT
<213> ORGANISM: Bacillus thuringiensis

<400> SEQUENCE: 472

Ser Asp Arg Asn Lys Asn Ser Asn Thr Gly Asn Ala Ser Gln Val Ala
1               5                   10                  15

Leu Asp Arg Met Arg Gln Leu Ile Asn Met Val Thr
            20                  25


<210> SEQ ID NO 473
<211> LENGTH: 28
<212> TYPE: PRT
<213> ORGANISM: Bacillus thuringiensis

<400> SEQUENCE: 473

Ala Gln Gln Asn Asp Ala Thr Asn Thr Gly Asn Ala Ser Gln Asn Ala
1               5                   10                  15

Ile Asp Arg Met Arg Leu Leu Ile Asn Ser Val Ser
            20                  25


<210> SEQ ID NO 474
<211> LENGTH: 28
<212> TYPE: PRT
<213> ORGANISM: Bacillus thuringiensis

<400> SEQUENCE: 474

Ser Asp Arg Asn Thr Asn Ser Asn Thr Gly Asn Ala Ser Gln Ile Ala
1               5                   10                  15

Phe Asp Arg Met His Gln Leu Ile Asn Thr Val Thr
            20                  25


<210> SEQ ID NO 475
<211> LENGTH: 28
```

<212> TYPE: PRT
<213> ORGANISM: Bacillus thuringiensis

<400> SEQUENCE: 475

Ala Ser Gln Asn Lys Asp Thr Asn Thr Gly Asn Ala Ser Gln Asn Ser
1 5 10 15

Ile Asp Arg Met Arg Leu Leu Ile Asn Ser Val Ser
20 25

<210> SEQ ID NO 476
<211> LENGTH: 28
<212> TYPE: PRT
<213> ORGANISM: Bacillus thuringiensis

<400> SEQUENCE: 476

Ala Ser Gln Asn Lys Asp Thr Asn Thr Gly Asn Ala Ser Gln Asn Ser
1 5 10 15

Ile Asp Arg Met Arg Leu Leu Ile Asn Ser Val Ser
20 25

<210> SEQ ID NO 477
<211> LENGTH: 28
<212> TYPE: PRT
<213> ORGANISM: Bacillus thuringiensis

<400> SEQUENCE: 477

Ala Ser Gln Asn Lys Asp Thr Asn Thr Gly Asn Ala Ser Gln Asn Ser
1 5 10 15

Ile Ser Arg Met Arg Leu Leu Ile Asn Ser Val Ser
20 25

<210> SEQ ID NO 478
<211> LENGTH: 28
<212> TYPE: PRT
<213> ORGANISM: Bacillus thuringiensis

<400> SEQUENCE: 478

Ala Ala Gln Asn Glu Asn Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 479
<211> LENGTH: 28
<212> TYPE: PRT
<213> ORGANISM: Bacillus thuringiensis

<400> SEQUENCE: 479

Ala Gln Gln Asn Glu Asp Thr Asn Thr Gly Asn Ala Ser Gln Asn Ser
1 5 10 15

Leu Asp Arg Met Arg Leu Leu Ile Asn Ser Val Ser
20 25

<210> SEQ ID NO 480
<211> LENGTH: 28
<212> TYPE: PRT
<213> ORGANISM: Bacillus weihenstephanensis

<400> SEQUENCE: 480

Ala Gln Gln Asn Glu Asp Thr Asn Thr Gly Asn Ala Ser Gln Asn Ser
1 5 10 15

Leu Asp Arg Met Arg Leu Leu Ile Asn Ser Val Ser 20 25

<210> SEQ ID NO 481
<211> LENGTH: 28
<212> TYPE: PRT
<213> ORGANISM: Bacillus thuringiensis

<400> SEQUENCE: 481

Ala Lys Gln Asn Asp Gly Thr Asn Thr Gly Asn Ala Ser Gln Asn Ala
1 5 10 15

Ile Asp Arg Met Arg Leu Leu Ile Asn Ser Val Ser
20 25

<210> SEQ ID NO 482
<211> LENGTH: 28
<212> TYPE: PRT
<213> ORGANISM: Bacillus thuringiensis

<400> SEQUENCE: 482

Ser Asp Arg Asn Lys Asn Ser Asn Thr Asp Asn Ser Ser Gln Val Ala
1 5 10 15

Leu Asp Arg Met Arg Gln Leu Ile Asn Ala Val Thr
20 25

<210> SEQ ID NO 483
<211> LENGTH: 28
<212> TYPE: PRT
<213> ORGANISM: Bacillus thuringiensis

<400> SEQUENCE: 483

Ala Lys Gln Asn Asp Asp Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 484
<211> LENGTH: 28
<212> TYPE: PRT
<213> ORGANISM: Bacillus thuringiensis

<400> SEQUENCE: 484

Ala Lys Gln Asn Asp Asp Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 485
<211> LENGTH: 28
<212> TYPE: PRT
<213> ORGANISM: Bacillus thuringiensis

<400> SEQUENCE: 485

Ser Asp Arg Asn Thr Asn Ser Asn Thr Gly Asn Ala Ser Gln Ile Ala
1 5 10 15

Phe Asp Arg Met His Gln Leu Ile Asn Thr Val Thr
20 25

<210> SEQ ID NO 486
<211> LENGTH: 28
<212> TYPE: PRT
<213> ORGANISM: Bacillus thuringiensis

<400> SEQUENCE: 486

```
Ala Ser Gln Asn Lys Asp Thr Asn Thr Gly Asn Ala Ser Gln Asn Ser
1               5                   10                  15

Ile Asp Arg Met Arg Leu Leu Ile Asn Ser Val Ser
            20                  25


<210> SEQ ID NO 487
<211> LENGTH: 28
<212> TYPE: PRT
<213> ORGANISM: Bacillus cereus

<400> SEQUENCE: 487

Ser Asp Arg Asn Lys Ser Ser Asn Thr Gly Asn Ala Ser Gln Val Ala
1               5                   10                  15

Val Asp Arg Met Arg Gln Leu Val Asn Thr Val Thr
            20                  25


<210> SEQ ID NO 488
<211> LENGTH: 27
<212> TYPE: PRT
<213> ORGANISM: Bacillus cereus

<400> SEQUENCE: 488

Ala Val Gln Lys Asp Thr Asn Thr Gly Asn Ala Ser Gln Asn Ala Ile
1               5                   10                  15

Asp Arg Met Arg Leu Leu Ile Asn Ser Val Ser
            20                  25


<210> SEQ ID NO 489
<211> LENGTH: 28
<212> TYPE: PRT
<213> ORGANISM: Bacillus thuringiensis

<400> SEQUENCE: 489

Ser Asp Arg Asn Lys Asn Ser Asn Thr Ser Asn Ala Ser Gln Ile Ala
1               5                   10                  15

Leu Asp Arg Met Arg Gln Leu Ile Asn Met Val Thr
            20                  25


<210> SEQ ID NO 490
<211> LENGTH: 28
<212> TYPE: PRT
<213> ORGANISM: Bacillus thuringiensis

<400> SEQUENCE: 490

Ala Lys Gln Asn Asp Ser Thr Asn Ile Gly Asn Ala Ser Gln Asn Ala
1               5                   10                  15

Ile Asp Arg Met Arg Leu Leu Ile Asn Ser Val Ser
            20                  25


<210> SEQ ID NO 491
<211> LENGTH: 28
<212> TYPE: PRT
<213> ORGANISM: Bacillus thuringiensis

<400> SEQUENCE: 491

Ala Lys Gln Asn Asp Gly Thr Asn Thr Phe Asn Ala Ser Gln Asn Ala
1               5                   10                  15

Ile Asp Arg Met Arg Leu Leu Ile Asn Ser Val Ser
            20                  25


<210> SEQ ID NO 492
```

<211> LENGTH: 28
<212> TYPE: PRT
<213> ORGANISM: Bacillus thuringiensis

<400> SEQUENCE: 492

Ala Lys Gln Asn Asp Gly Thr Asn Thr Phe Asn Ala Ser Gln Asn Ala
1 5 10 15

Ile Asp Arg Met Arg Leu Leu Ile Asn Ser Val Ser
20 25

<210> SEQ ID NO 493
<211> LENGTH: 28
<212> TYPE: PRT
<213> ORGANISM: Bacillus thuringiensis

<400> SEQUENCE: 493

Ala Ala Gln Asn Gly Asn Thr Asn Thr Phe Asn Ala Ser Gln Asn Ala
1 5 10 15

Ile Asp Arg Met Arg Leu Leu Ile Asn Ser Val Ser
20 25

<210> SEQ ID NO 494
<211> LENGTH: 28
<212> TYPE: PRT
<213> ORGANISM: Bacillus cereus

<400> SEQUENCE: 494

Ala Ala Gln Asn Lys Asp Thr Asn Thr Gly Asn Ala Ser Gln Asn Ala
1 5 10 15

Ile Asp Arg Met Arg Leu Leu Ile Asn Ser Val Ser
20 25

<210> SEQ ID NO 495
<211> LENGTH: 28
<212> TYPE: PRT
<213> ORGANISM: Bacillus thuringiensis

<400> SEQUENCE: 495

Ala Ala Gln Asn Glu Asn Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 496
<211> LENGTH: 28
<212> TYPE: PRT
<213> ORGANISM: Bacillus cereus

<400> SEQUENCE: 496

Ser Asp Arg Asn Lys Asn Ser Asn Thr Asp Asn Ala Ser Gln Val Ala
1 5 10 15

Leu Asp Arg Met Arg Gln Leu Val Asn Thr Val Thr
20 25

<210> SEQ ID NO 497
<211> LENGTH: 28
<212> TYPE: PRT
<213> ORGANISM: Bacillus cereus

<400> SEQUENCE: 497

Ala Ala Lys Asn Glu Asn Thr Asn Thr Gly Asn Ala Ser Gln Asn Ala
1 5 10 15

-continued

Leu Asp Arg Met Arg Leu Leu Ile Asn Ser Val Ser
20 25

<210> SEQ ID NO 498
<211> LENGTH: 28
<212> TYPE: PRT
<213> ORGANISM: Bacillus cereus

<400> SEQUENCE: 498

Ala Ala Gln Asn Asp Ser Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 499
<211> LENGTH: 28
<212> TYPE: PRT
<213> ORGANISM: Bacillus cereus

<400> SEQUENCE: 499

Ala Ala Lys Asn Glu Asn Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 500
<211> LENGTH: 28
<212> TYPE: PRT
<213> ORGANISM: Bacillus cereus

<400> SEQUENCE: 500

Ala Ala Lys Asn Glu Asn Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 501
<211> LENGTH: 28
<212> TYPE: PRT
<213> ORGANISM: Bacillus cereus

<400> SEQUENCE: 501

Ala Lys Gln Asn Asp Gly Thr Asn Thr Gly Asn Ala Ser Gln Asn Ala
1 5 10 15

Ile Asp Arg Met Arg Leu Leu Ile Asn Ser Val Ser
20 25

<210> SEQ ID NO 502
<211> LENGTH: 28
<212> TYPE: PRT
<213> ORGANISM: Bacillus thuringiensis

<400> SEQUENCE: 502

Ala Ala Gln Asn Lys Ser Thr Asn Thr Glu Ser Ala Ser Gln Asn Ala
1 5 10 15

Leu Asp Arg Met Arg Leu Leu Ile Asn Ser Val Ser
20 25

<210> SEQ ID NO 503
<211> LENGTH: 28
<212> TYPE: PRT
<213> ORGANISM: Bacillus thuringiensis

<400> SEQUENCE: 503

Ala Ala Gln Asn Lys Ser Thr Asn Thr Glu Ser Ala Ser Gln Asn Ala
1 5 10 15

Leu Asp Arg Met Arg Leu Leu Ile Asn Ser Val Ser
20 25

<210> SEQ ID NO 504
<211> LENGTH: 28
<212> TYPE: PRT
<213> ORGANISM: Bacillus thuringiensis

<400> SEQUENCE: 504

Ala Lys Gln Asn Asp Gly Thr Asn Thr Gly Asn Ala Ser Gln Asn Ala
1 5 10 15

Ile Asp Arg Met Arg Leu Leu Ile Asn Ser Val Ser
20 25

<210> SEQ ID NO 505
<211> LENGTH: 27
<212> TYPE: PRT
<213> ORGANISM: Bacillus thuringiensis

<400> SEQUENCE: 505

Ala Ala Gln Asn Glu Ser Thr Asn Thr Gly Asn Ala Gln Asn Ala Leu
1 5 10 15

Asp Arg Met Arg Leu Leu Ile Asn Ser Val Ser
20 25

<210> SEQ ID NO 506
<211> LENGTH: 28
<212> TYPE: PRT
<213> ORGANISM: Bacillus cereus

<400> SEQUENCE: 506

Ser Asn Arg Asn Lys Asn Ser Asn Thr Val Asn Ala Ser Gln Val Ala
1 5 10 15

Leu Asp Arg Met Arg Gln Leu Ile Asn Thr Val Thr
20 25

<210> SEQ ID NO 507
<211> LENGTH: 27
<212> TYPE: PRT
<213> ORGANISM: Bacillus cereus

<400> SEQUENCE: 507

Ala Gly Gln Asn Lys Asp Thr Asn Thr Asn Ala Ser Gln Asn Ala Leu
1 5 10 15

Asp Arg Met Arg Leu Leu Ile Asn Ser Val Ser
20 25

<210> SEQ ID NO 508
<211> LENGTH: 28
<212> TYPE: PRT
<213> ORGANISM: Bacillus cereus

<400> SEQUENCE: 508

Ala Ala Gln Asn Lys Asp Thr Asn Thr Gly Asn Ala Ser Gln Asn Ala
1 5 10 15

Leu Asp Arg Met Arg Leu Leu Ile Asn Ser Val Ser
20 25

<210> SEQ ID NO 509
<211> LENGTH: 28
<212> TYPE: PRT
<213> ORGANISM: Bacillus cereus

<400> SEQUENCE: 509

Ser Asp Arg Asn Lys Asn Ser Asn Thr Gly Asn Ala Ser Gln Val Ala
1 5 10 15

Leu Asp Arg Met Arg Gln Leu Val Asn Thr Val Thr
20 25

<210> SEQ ID NO 510
<211> LENGTH: 28
<212> TYPE: PRT
<213> ORGANISM: Bacillus thuringiensis

<400> SEQUENCE: 510

Ala Glu Ile Asp Thr Asp Lys Asn Thr Gly Asn Ala Thr Gln Asn Ala
1 5 10 15

Ile Asp Arg Met Arg Leu Leu Ile Asn Ser Val Ser
20 25

<210> SEQ ID NO 511
<211> LENGTH: 28
<212> TYPE: PRT
<213> ORGANISM: Bacillus cereus

<400> SEQUENCE: 511

Ala Glu Ile Asp Thr Asp Lys Asn Thr Gly Asn Ala Thr Gln Asn Ala
1 5 10 15

Ile Asp Arg Met Arg Leu Leu Ile Asn Ser Val Ser
20 25

<210> SEQ ID NO 512
<211> LENGTH: 27
<212> TYPE: PRT
<213> ORGANISM: Bacillus thuringiensis

<400> SEQUENCE: 512

Ser Asp Arg Asn Lys Asn Ser Asn Thr Ser Asn Ala Ser Gln Ile Ala
1 5 10 15

Leu Asp Arg Met Arg Gln Leu Ile Asn Met Thr
20 25

<210> SEQ ID NO 513
<211> LENGTH: 28
<212> TYPE: PRT
<213> ORGANISM: Bacillus thuringiensis

<400> SEQUENCE: 513

Ala Lys Gln Asn Asp Gly Thr Asn Thr Gly Asn Ala Ser Gln Asn Ala
1 5 10 15

Ile Asp Arg Met Arg Leu Leu Ile Asn Ser Val Ser
20 25

<210> SEQ ID NO 514
<211> LENGTH: 28
<212> TYPE: PRT
<213> ORGANISM: Bacillus aryabhattai

<400> SEQUENCE: 514

Ala Asp Leu Asp Glu Thr Lys Asn Thr Gly Asn Gly Ala Gln Val Val
1 5 10 15

```
Leu Glu Arg Met Arg Gln Leu Ile Asp His Thr Glu
            20                  25


<210> SEQ ID NO 515
<211> LENGTH: 27
<212> TYPE: PRT
<213> ORGANISM: Bacillus manliponensis

<400> SEQUENCE: 515

Ser Glu Arg Asp Asn Gly Gln Asn Thr Gly Thr Ala Gln Thr Ala Leu
1               5                   10                  15

Asp Arg Met Arg Leu Leu Ile Asn Ser Val Ser
            20                  25


<210> SEQ ID NO 516
<211> LENGTH: 28
<212> TYPE: PRT
<213> ORGANISM: Lysinibacillus sp.

<400> SEQUENCE: 516

Lys Ala Arg Asp Asp Asp Thr Asn Thr Asp Thr Ala Ala Gln Val Ala
1               5                   10                  15

Leu Glu Arg Met Arg Gln Val Ile Ala His Thr Glu
            20                  25


<210> SEQ ID NO 517
<211> LENGTH: 28
<212> TYPE: PRT
<213> ORGANISM: Lysinibacillus sp.

<400> SEQUENCE: 517

Lys Ala Arg Asp Asp Asp Thr Asn Thr Asp Thr Ala Ala Gln Val Ala
1               5                   10                  15

Leu Glu Arg Met Arg Gln Val Ile Ala His Thr Glu
            20                  25


<210> SEQ ID NO 518
<211> LENGTH: 28
<212> TYPE: PRT
<213> ORGANISM: Paenibacillus sp.

<400> SEQUENCE: 518

Asn Leu Arg Asp Ser Gly Ser Tyr Thr Gly Asn Ser Ala Gln Val Ala
1               5                   10                  15

Leu Glu Asn Met Arg Gln Leu Met Ser His Ile Glu
            20                  25


<210> SEQ ID NO 519
<211> LENGTH: 28
<212> TYPE: PRT
<213> ORGANISM: Bacillus anthracis

<400> SEQUENCE: 519

Ala Asp Gln Asn Glu Lys Thr Asn Thr Gly Asn Ala Ser Gln Asn Ala
1               5                   10                  15

Leu Asp Arg Met Arg Leu Leu Ile Asn Ser Val Ser
            20                  25


<210> SEQ ID NO 520
<211> LENGTH: 28
<212> TYPE: PRT
<213> ORGANISM: Bacillus anthracis
```

<400> SEQUENCE: 520

Ala Ser Gln Asn Glu Ala Thr Asn Thr Gly Asn Ser Ser Gln Val Ala
1               5                   10                  15

Ile Asp Arg Met Arg Thr Leu Ile Asn Ser Val Ser
            20                  25

<210> SEQ ID NO 521
<211> LENGTH: 28
<212> TYPE: PRT
<213> ORGANISM: Bacillus anthracis

<400> SEQUENCE: 521

Ala Ser Gln Asn Glu Ala Thr Asn Thr Gly Asn Ser Ser Gln Val Ala
1               5                   10                  15

Ile Asp Arg Met Arg Thr Leu Ile Asn Ser Val Ser
            20                  25

<210> SEQ ID NO 522
<211> LENGTH: 28
<212> TYPE: PRT
<213> ORGANISM: Bacillus anthracis

<400> SEQUENCE: 522

Ala Ser Gln Asn Glu Ala Thr Asn Thr Gly Asn Ser Ser Gln Val Ala
1               5                   10                  15

Ile Asp Arg Met Arg Thr Leu Ile Asn Ser Val Ser
            20                  25

<210> SEQ ID NO 523
<211> LENGTH: 28
<212> TYPE: PRT
<213> ORGANISM: Bacillus anthracis

<400> SEQUENCE: 523

Ala Ser Gln Asn Glu Ala Thr Asn Thr Gly Asn Ser Ser Gln Val Ile
1               5                   10                  15

Ala Asp Arg Met Arg Thr Leu Ile Asn Ser Val Ser
            20                  25

<210> SEQ ID NO 524
<211> LENGTH: 28
<212> TYPE: PRT
<213> ORGANISM: Bacillus megaterium

<400> SEQUENCE: 524

Ala Asp Leu Asp Glu Thr Lys Asn Thr Gly Asn Gly Ala Gln Val Val
1               5                   10                  15

Leu Glu Arg Met Arg Gln Leu Ile Asp His Thr Glu
            20                  25

<210> SEQ ID NO 525
<211> LENGTH: 27
<212> TYPE: PRT
<213> ORGANISM: Aneurinibacillus sp.

<400> SEQUENCE: 525

Ala Lys Lys Asp Lys Ser Tyr Thr Gly Asn Ala Ala Gln Val Ala Leu
1               5                   10                  15

Glu Arg Met Arg Gln Leu Met Glu His Ile Glu
            20                  25

<210> SEQ ID NO 526
<211> LENGTH: 22
<212> TYPE: PRT
<213> ORGANISM: Escherichia coli

<400> SEQUENCE: 526

Glu Arg Leu Ser Ser Gly Leu Arg Ile Asn Ser Ala Lys Asp Asp Ala
1 5 10 15

Ala Gly Gln Ala Ile Ala
20

<210> SEQ ID NO 527
<211> LENGTH: 22
<212> TYPE: PRT
<213> ORGANISM: Escherichia coli

<400> SEQUENCE: 527

Ala Ile Ala Gln Gly Ala Ala Asp Asp Lys Ala Ser Asn Ile Arg Leu
1 5 10 15

Gly Ser Ser Leu Arg Glu
20

<210> SEQ ID NO 528
<211> LENGTH: 15
<212> TYPE: PRT
<213> ORGANISM: Escherichia coli

<400> SEQUENCE: 528

Arg Ile Asn Ser Ala Lys Asp Asp Ala Ala Gly Gln Ala Ile Ala
1 5 10 15

<210> SEQ ID NO 529
<211> LENGTH: 15
<212> TYPE: PRT
<213> ORGANISM: Escherichia coli

<400> SEQUENCE: 529

Ala Ile Ala Gln Gly Ala Ala Asp Asp Lys Ala Ser Asn Ile Arg
1 5 10 15

<210> SEQ ID NO 530
<211> LENGTH: 22
<212> TYPE: PRT
<213> ORGANISM: Pseudomonas aeruginosa

<400> SEQUENCE: 530

Gln Arg Leu Ser Thr Gly Ser Arg Ile Asn Ser Ala Lys Asp Asp Ala
1 5 10 15

Ala Gly Leu Gln Ile Ala
20

<210> SEQ ID NO 531
<211> LENGTH: 22
<212> TYPE: PRT
<213> ORGANISM: Pseudomonas aeruginosa

<400> SEQUENCE: 531

Ala Ile Gln Leu Gly Ala Ala Asp Asp Lys Ala Ser Asn Ile Arg Ser
1 5 10 15

Gly Thr Ser Leu Arg Gln
20

<210> SEQ ID NO 532
<211> LENGTH: 22
<212> TYPE: PRT
<213> ORGANISM: Xanthomonas spp.

<400> SEQUENCE: 532

Gln Arg Leu Ser Ser Gly Leu Arg Ile Asn Ser Ala Lys Asp Asp Ala
1 5 10 15

Ala Gly Leu Ala Ile Ser
20

<210> SEQ ID NO 533
<211> LENGTH: 22
<212> TYPE: PRT
<213> ORGANISM: Xanthomonas spp.

<400> SEQUENCE: 533

Ser Ile Ala Leu Gly Ala Ala Asp Asp Lys Ala Ser Asn Ile Arg Leu
1 5 10 15

Gly Ser Ser Leu Arg Gln
20

<210> SEQ ID NO 534
<211> LENGTH: 22
<212> TYPE: PRT
<213> ORGANISM: Erwinia amylovora

<400> SEQUENCE: 534

Gln Arg Leu Ser Ser Gly Leu Arg Ile Asn Ser Ala Lys Asp Asp Ala
1 5 10 15

Ala Gly Gln Ala Ile Ser
20

<210> SEQ ID NO 535
<211> LENGTH: 22
<212> TYPE: PRT
<213> ORGANISM: Erwinia amylovora

<400> SEQUENCE: 535

Ser Ile Ala Gln Gly Ala Ala Asp Asp Lys Ala Ser Asn Ile Arg Leu
1 5 10 15

Gly Ser Ser Leu Arg Gln
20

<210> SEQ ID NO 536
<211> LENGTH: 22
<212> TYPE: PRT
<213> ORGANISM: Burkholderia phytofirmans

<400> SEQUENCE: 536

Thr Arg Leu Ser Ser Gly Lys Arg Ile Asn Ser Ala Ala Asp Asp Ala
1 5 10 15

Ala Gly Leu Ala Ile Ser
20

<210> SEQ ID NO 537
<211> LENGTH: 22
<212> TYPE: PRT
<213> ORGANISM: Burkholderia phytofirmans

<400> SEQUENCE: 537

Ser Ile Ala Leu Gly Ala Ala Asp Asp Ala Ala Ser Asn Ile Arg Lys
1 5 10 15

Gly Ser Ser Leu Arg Thr
20

<210> SEQ ID NO 538
<211> LENGTH: 22
<212> TYPE: PRT
<213> ORGANISM: Burkholderia ubonensis

<400> SEQUENCE: 538

Asn Arg Leu Ser Ser Gly Lys Arg Ile Asn Thr Ala Ala Asp Asp Ala
1 5 10 15

Ala Gly Leu Ala Ile Ser
20

<210> SEQ ID NO 539
<211> LENGTH: 22
<212> TYPE: PRT
<213> ORGANISM: Burkholderia ubonensis

<400> SEQUENCE: 539

Ser Ile Ala Leu Gly Ala Ala Asp Asp Ala Ala Thr Asn Ile Arg Lys
1 5 10 15

Gly Ser Ser Leu Arg Asn
20

<210> SEQ ID NO 540
<211> LENGTH: 22
<212> TYPE: PRT
<213> ORGANISM: Pseudomonas syringae

<400> SEQUENCE: 540

Thr Arg Leu Ser Ser Gly Leu Lys Ile Asn Ser Ala Lys Asp Asp Ala
1 5 10 15

Ala Gly Leu Gln Ile Ala
20

<210> SEQ ID NO 541
<211> LENGTH: 22
<212> TYPE: PRT
<213> ORGANISM: Pseudomonas syringae

<400> SEQUENCE: 541

Ala Ile Gln Leu Gly Ala Ala Asp Asp Lys Ala Ser Asn Ile Lys Leu
1 5 10 15

Gly Ser Ser Leu Arg Thr
20

<210> SEQ ID NO 542
<211> LENGTH: 4
<212> TYPE: PRT
<213> ORGANISM: Artificial Sequence
<220> FEATURE:
<223> OTHER INFORMATION: Synthetic construct

<400> SEQUENCE: 542

Gly Phe Leu Asn
1

<210> SEQ ID NO 543
<211> LENGTH: 5
<212> TYPE: PRT
<213> ORGANISM: Artificial Sequence
<220> FEATURE:

<223> OTHER INFORMATION: Synthetic construct

<400> SEQUENCE: 543

Trp Gly Phe Leu Ile
1 5

<210> SEQ ID NO 544
<211> LENGTH: 5
<212> TYPE: PRT
<213> ORGANISM: Artificial Sequence
<220> FEATURE:
<223> OTHER INFORMATION: Synthetic construct

<400> SEQUENCE: 544

Met Gly Val Leu Asn
1 5

<210> SEQ ID NO 545
<211> LENGTH: 4
<212> TYPE: PRT
<213> ORGANISM: Artificial Sequence
<220> FEATURE:
<223> OTHER INFORMATION: Synthetic construct

<400> SEQUENCE: 545

Gly Val Leu Asn
1

<210> SEQ ID NO 546
<211> LENGTH: 5
<212> TYPE: PRT
<213> ORGANISM: Artificial Sequence
<220> FEATURE:
<223> OTHER INFORMATION: Synthetic construct

<400> SEQUENCE: 546

Trp Gly Phe Phe Tyr
1 5

<210> SEQ ID NO 547
<211> LENGTH: 9
<212> TYPE: PRT
<213> ORGANISM: Artificial Sequence
<220> FEATURE:
<223> OTHER INFORMATION: Synthetic construct

<400> SEQUENCE: 547

Leu Val Pro Phe Ala Val Trp Leu Ala
1 5

<210> SEQ ID NO 548
<211> LENGTH: 5
<212> TYPE: PRT
<213> ORGANISM: Artificial Sequence
<220> FEATURE:
<223> OTHER INFORMATION: Synthetic construct

<400> SEQUENCE: 548

Ala Val Trp Leu Ala
1 5

<210> SEQ ID NO 549
<211> LENGTH: 12
<212> TYPE: PRT
<213> ORGANISM: Artificial Sequence
<220> FEATURE:
<223> OTHER INFORMATION: Synthetic construct

<400> SEQUENCE: 549

Leu Leu Gly Thr Ala Asp Lys Lys Ile Lys Ile Gln
1 5 10

<210> SEQ ID NO 550
<211> LENGTH: 11
<212> TYPE: PRT
<213> ORGANISM: Artificial Sequence
<220> FEATURE:
<223> OTHER INFORMATION: Synthetic construct

<400> SEQUENCE: 550

Leu Leu Lys Ser Thr Gln Glu Ile Lys Ile Gln
1 5 10

<210> SEQ ID NO 551
<211> LENGTH: 11
<212> TYPE: PRT
<213> ORGANISM: Artificial Sequence
<220> FEATURE:
<223> OTHER INFORMATION: Synthetic construct

<400> SEQUENCE: 551

Leu Leu Asn Glu Asp Ser Glu Val Lys Ile Gln
1 5 10

<210> SEQ ID NO 552
<211> LENGTH: 9
<212> TYPE: PRT
<213> ORGANISM: Artificial Sequence
<220> FEATURE:
<223> OTHER INFORMATION: Synthetic construct

<400> SEQUENCE: 552

Leu Gly Val Ala Ala Asn Asn Thr Gln
1 5

<210> SEQ ID NO 553
<211> LENGTH: 10
<212> TYPE: PRT
<213> ORGANISM: Artificial Sequence
<220> FEATURE:
<223> OTHER INFORMATION: Synthetic construct

<400> SEQUENCE: 553

Leu Leu Arg Met Arg Asp Leu Ala Asn Gln
1 5 10

<210> SEQ ID NO 554
<211> LENGTH: 10
<212> TYPE: PRT
<213> ORGANISM: Artificial Sequence
<220> FEATURE:
<223> OTHER INFORMATION: Synthetic construct

<400> SEQUENCE: 554

Leu Gln Arg Met Arg Asp Val Ala Val Gln
1 5 10

<210> SEQ ID NO 555
<211> LENGTH: 10
<212> TYPE: PRT
<213> ORGANISM: Artificial Sequence
<220> FEATURE:
<223> OTHER INFORMATION: Synthetic construct

<400> SEQUENCE: 555

Leu Leu Arg Met Arg Asp Ile Ser Asn Gln
1 5 10

<210> SEQ ID NO 556
<211> LENGTH: 10
<212> TYPE: PRT
<213> ORGANISM: Artificial Sequence
<220> FEATURE:
<223> OTHER INFORMATION: Synthetic contstruct

<400> SEQUENCE: 556

Leu Leu Arg Met Arg Asp Ile Ala Asn Gln
1 5 10

<210> SEQ ID NO 557
<211> LENGTH: 13
<212> TYPE: PRT
<213> ORGANISM: Artificial Sequence
<220> FEATURE:
<223> OTHER INFORMATION: Synthetic construct

<400> SEQUENCE: 557

Leu Gln Lys Gln Ile Asp Tyr Ile Ala Gly Asn Thr Gln
1 5 10

<210> SEQ ID NO 558
<211> LENGTH: 8
<212> TYPE: PRT
<213> ORGANISM: Artificial Sequence
<220> FEATURE:
<223> OTHER INFORMATION: Synthetic construct

<400> SEQUENCE: 558

Leu Leu Ile Arg Leu Pro Leu Asp
1 5

<210> SEQ ID NO 559
<211> LENGTH: 9
<212> TYPE: PRT
<213> ORGANISM: Artificial Sequence
<220> FEATURE:
<223> OTHER INFORMATION: Synthetic construct

<400> SEQUENCE: 559

Gln Arg Met Arg Glu Leu Ala Val Gln
1 5

<210> SEQ ID NO 560
<211> LENGTH: 9
<212> TYPE: PRT
<213> ORGANISM: Artificial Sequence
<220> FEATURE:
<223> OTHER INFORMATION: Synthetic construct

<400> SEQUENCE: 560

Thr Arg Met Arg Asp Ile Ala Val Gln
1 5

<210> SEQ ID NO 561
<211> LENGTH: 9
<212> TYPE: PRT
<213> ORGANISM: Artificial Sequence
<220> FEATURE:
<223> OTHER INFORMATION: Synthetic construct

<400> SEQUENCE: 561

Thr Arg Met Arg Asp Ile Ala Val Gln
1 5

<210> SEQ ID NO 562
<211> LENGTH: 9
<212> TYPE: PRT
<213> ORGANISM: Artificial Sequence
<220> FEATURE:
<223> OTHER INFORMATION: Synthetic construct

<400> SEQUENCE: 562

Gln Arg Met Arg Glu Leu Val Val Gln
1 5

<210> SEQ ID NO 563
<211> LENGTH: 6
<212> TYPE: PRT
<213> ORGANISM: Artificial Sequence
<220> FEATURE:
<223> OTHER INFORMATION: Synthetic construct

<400> SEQUENCE: 563

Leu Gly Ala Thr Leu Asn
1 5

<210> SEQ ID NO 564
<211> LENGTH: 6
<212> TYPE: PRT
<213> ORGANISM: Artificial Sequence
<220> FEATURE:
<223> OTHER INFORMATION: Synthetic construct

<400> SEQUENCE: 564

Leu Gly Ala Thr Gln Asn
1 5

<210> SEQ ID NO 565
<211> LENGTH: 6
<212> TYPE: PRT
<213> ORGANISM: Artificial Sequence
<220> FEATURE:
<223> OTHER INFORMATION: Synthetic construct

<400> SEQUENCE: 565

Leu Ala Gln Ala Asn Gln
1 5

<210> SEQ ID NO 566
<211> LENGTH: 6
<212> TYPE: PRT
<213> ORGANISM: Artificial Sequence
<220> FEATURE:
<223> OTHER INFORMATION: Synthetic construct

<400> SEQUENCE: 566

Leu Gly Ala Met Ile Asn
1 5

<210> SEQ ID NO 567
<211> LENGTH: 6
<212> TYPE: PRT
<213> ORGANISM: Artificial Sequence
<220> FEATURE:
<223> OTHER INFORMATION: Synthetic construct

<400> SEQUENCE: 567

Leu Gly Ser Met Ile Asn
1 5

<210> SEQ ID NO 568
<211> LENGTH: 6
<212> TYPE: PRT
<213> ORGANISM: Artificial Sequence
<220> FEATURE:
<223> OTHER INFORMATION: Synthetic construct

<400> SEQUENCE: 568

Met Gly Ala Tyr Gln Asn
1 5

<210> SEQ ID NO 569
<211> LENGTH: 6
<212> TYPE: PRT
<213> ORGANISM: Artificial Sequence
<220> FEATURE:
<223> OTHER INFORMATION: Synthetic construct

<400> SEQUENCE: 569

Leu Gly Ala Tyr Gln Asn
1 5

<210> SEQ ID NO 570
<211> LENGTH: 6
<212> TYPE: PRT
<213> ORGANISM: Artificial Sequence
<220> FEATURE:
<223> OTHER INFORMATION: Synthetic construct

<400> SEQUENCE: 570

Tyr Gly Ser Gln Leu Asn
1 5

<210> SEQ ID NO 571
<211> LENGTH: 22
<212> TYPE: PRT
<213> ORGANISM: Bacillus thuringiensis

<400> SEQUENCE: 571

Asp Arg Leu Ser Ser Gly Lys Arg Ile Asn Ser Ala Lys Asp Asp Ala
1 5 10 15

Ala Gly Leu Ala Ile Ala
20

<210> SEQ ID NO 572
<211> LENGTH: 22
<212> TYPE: PRT
<213> ORGANISM: Bacillus thuringiensis

<400> SEQUENCE: 572

Asp Arg Leu Ser Ser Gly Lys Arg Ile Asn Ser Ala Ser Asp Asp Ala
1 5 10 15

Ala Gly Leu Gln Ile Ala
20

<210> SEQ ID NO 573
<211> LENGTH: 22
<212> TYPE: PRT
<213> ORGANISM: Bacillus thuringiensis

<400> SEQUENCE: 573

Gln Arg Leu Ser Ser Gly Lys Arg Ile Asn Ser Ala Ser Asp Asp Ala 1 5 10 15

Ala Gly Leu Ala Ile Ala
20

<210> SEQ ID NO 574
<211> LENGTH: 22
<212> TYPE: PRT
<213> ORGANISM: Bacillus thuringiensis

<400> SEQUENCE: 574

Asn Arg Leu Ser Ser Gly Lys Arg Ile Asn Ser Ala Ser Asp Asp Ala
1 5 10 15

Ala Gly Leu Ala Ile Ala
20

<210> SEQ ID NO 575
<211> LENGTH: 22
<212> TYPE: PRT
<213> ORGANISM: Caballeronia megalochromosomata

<400> SEQUENCE: 575

Thr Arg Leu Ser Ser Gly Lys Arg Ile Asn Ser Ala Ser Asp Asp Ala
1 5 10 15

Ala Gly Leu Ala Ile Ala
20

<210> SEQ ID NO 576
<211> LENGTH: 22
<212> TYPE: PRT
<213> ORGANISM: Bacillus thuringiensis

<400> SEQUENCE: 576

Asp Arg Leu Ser Ser Gly Tyr Arg Ile Asn Ser Ala Ser Asp Asp Ala
1 5 10 15

Ala Gly Leu Ala Ile Ala
20

<210> SEQ ID NO 577
<211> LENGTH: 22
<212> TYPE: PRT
<213> ORGANISM: Bacillus thuringiensis

<400> SEQUENCE: 577

Asp Arg Leu Ser Ser Gly Phe Arg Ile Asn Ser Ala Ser Asp Asp Ala
1 5 10 15

Ala Gly Leu Ala Ile Ala
20

<210> SEQ ID NO 578
<211> LENGTH: 22
<212> TYPE: PRT
<213> ORGANISM: Bacillus thuringiensis

<400> SEQUENCE: 578

Asp Arg Leu Ser Ser Gly Lys Arg Ile Asn Ser Ala Ser Asp Asp Pro
1 5 10 15

Ala Gly Leu Ala Ile Ala
20

<210> SEQ ID NO 579
<211> LENGTH: 22
<212> TYPE: PRT

<213> ORGANISM: Bacillus thuringiensis

<400> SEQUENCE: 579

Asp Arg Leu Ser Ser Gly Gln Arg Ile Asn Ser Ala Ser Asp Asp Ala
1 5 10 15

Ala Gly Leu Ala Ile Ala
20

<210> SEQ ID NO 580
<211> LENGTH: 22
<212> TYPE: PRT
<213> ORGANISM: Lysinibacillus spp.

<400> SEQUENCE: 580

Glu Lys Leu Ser Ser Gly Leu Arg Ile Asn Arg Ala Gly Asp Asp Ala
1 5 10 15

Ala Gly Leu Ala Ile Ser
20

<210> SEQ ID NO 581
<211> LENGTH: 22
<212> TYPE: PRT
<213> ORGANISM: Lysinibacillus spp.

<400> SEQUENCE: 581

Glu Lys Leu Ser Ser Gly Tyr Lys Ile Asn Arg Ala Ser Asp Asp Ala
1 5 10 15

Ala Gly Leu Ala Ile Ser
20

<210> SEQ ID NO 582
<211> LENGTH: 22
<212> TYPE: PRT
<213> ORGANISM: Lysinibacillus spp.

<400> SEQUENCE: 582

Leu Arg Ile Ser Ser Gly Tyr Arg Ile Asn Ser Ala Ala Asp Asp Pro
1 5 10 15

Ala Gly Leu Ala Ile Ser
20

<210> SEQ ID NO 583
<211> LENGTH: 22
<212> TYPE: PRT
<213> ORGANISM: Lysinibacillus fusiformis

<400> SEQUENCE: 583

Leu Arg Ile Ser Thr Gly Tyr Arg Ile Asn Ser Ala Ala Asp Asp Pro
1 5 10 15

Ala Gly Leu Ala Ile Ser
20

<210> SEQ ID NO 584
<211> LENGTH: 22
<212> TYPE: PRT
<213> ORGANISM: Lysinibacillus macroides

<400> SEQUENCE: 584

Glu Lys Leu Ser Ser Gly Phe Arg Ile Asn Arg Ala Gly Asp Asp Ala
1 5 10 15

Ala Gly Leu Ala Ile Ser
20

<210> SEQ ID NO 585
<211> LENGTH: 22
<212> TYPE: PRT
<213> ORGANISM: Lysinibacillus xylanilyticus

<400> SEQUENCE: 585

Glu Lys Leu Ser Ser Gly Tyr Lys Ile Asn Arg Ala Gly Asp Asp Ala
1 5 10 15

Ala Gly Leu Ala Ile Ser
20

<210> SEQ ID NO 586
<211> LENGTH: 22
<212> TYPE: PRT
<213> ORGANISM: Escherichia coli

<400> SEQUENCE: 586

Glu Arg Leu Ser Ser Gly Leu Arg Ile Asn Ser Ala Lys Asp Asp Ala
1 5 10 15

Ala Gly Gln Ala Ile Ala
20

<210> SEQ ID NO 587
<211> LENGTH: 23
<212> TYPE: PRT
<213> ORGANISM: Xanthomonas species

<400> SEQUENCE: 587

Asn Gln Gly Ile Ser Glu Lys Gln Leu Asp Gln Leu Leu Thr Gln Leu
1 5 10 15

Ile Met Ala Leu Leu Gln Gln
20

<210> SEQ ID NO 588
<211> LENGTH: 23
<212> TYPE: PRT
<213> ORGANISM: Xanthomonas species

<400> SEQUENCE: 588

Gln Gln Leu Leu Ala Met Ile Leu Gln Thr Leu Leu Gln Asp Leu Gln
1 5 10 15

Lys Glu Ser Ile Gly Gln Asn
20

<210> SEQ ID NO 589
<211> LENGTH: 12
<212> TYPE: PRT
<213> ORGANISM: Xanthomonas species

<400> SEQUENCE: 589

Leu Asp Gln Leu Leu Thr Gln Leu Ile Met Ala Leu
1 5 10

<210> SEQ ID NO 590
<211> LENGTH: 12
<212> TYPE: PRT
<213> ORGANISM: Xanthomonas species

<400> SEQUENCE: 590

Leu Ala Met Ile Leu Gln Thr Leu Leu Gln Asp Leu
1 5 10

<210> SEQ ID NO 591
<211> LENGTH: 19
<212> TYPE: PRT
<213> ORGANISM: Xanthomonas species

<400> SEQUENCE: 591

Ser Glu Lys Gln Leu Asp Gln Leu Leu Thr Gln Leu Ile Met Ala Leu
1               5                   10                  15

Leu Gln Gln

<210> SEQ ID NO 592
<211> LENGTH: 19
<212> TYPE: PRT
<213> ORGANISM: Xanthomonas species

<400> SEQUENCE: 592

Gln Gln Leu Leu Ala Met Ile Leu Gln Thr Leu Leu Gln Asp Leu Gln
1               5                   10                  15

Lys Glu Ser

<210> SEQ ID NO 593
<211> LENGTH: 143
<212> TYPE: PRT
<213> ORGANISM: Xanthamonas citri

<400> SEQUENCE: 593

Met Met Asn Ser Leu Asn Thr Gln Leu Gly Ala Asn Ser Ser Phe Phe
1               5                   10                  15

Gln Val Asp Pro Ser Gln Asn Thr Gln Ser Gly Ser Asn Gln Gly Asn
            20                  25                  30

Gln Gly Ile Ser Glu Lys Gln Leu Asp Gln Leu Leu Thr Gln Leu Ile
        35                  40                  45

Met Ala Leu Leu Gln Gln Ser Asn Asn Ala Glu Gln Gly Gln Gly Gln
    50                  55                  60

Gly Gln Gly Gly Asp Ser Gly Gly Gln Gly Gly Asn Arg Gln Gln Ala
65                  70                  75                  80

Gly Gln Ser Asn Gly Ser Pro Ser Gln Tyr Thr Gln Met Leu Met Asn
                85                  90                  95

Ile Val Gly Asp Ile Leu Gln Ala Gln Asn Gly Gly Gly Phe Gly Gly
            100                 105                 110

Gly Phe Gly Gly Gly Phe Gly Gly Gly Gly Leu Gly Thr Ser Leu Gly
        115                 120                 125

Thr Ser Leu Gly Thr Ser Leu Ala Ser Asp Thr Gly Ser Met Gln
    130                 135                 140

<210> SEQ ID NO 594
<211> LENGTH: 19
<212> TYPE: PRT
<213> ORGANISM: Pantoea sesami

<400> SEQUENCE: 594

Gln Leu Glu Gln Leu Met Thr Gln Leu Arg Ala Arg Leu Cys Arg Leu
1               5                   10                  15

Met Ala Met

<210> SEQ ID NO 595
<211> LENGTH: 19
<212> TYPE: PRT
<213> ORGANISM: Erwinia gerudensis

<400> SEQUENCE: 595

Gln Leu Glu Gln Leu Met Thr Gln Leu Arg Ala Arg Leu Lys Arg Leu
1 5 10 15

Met Ala Met

<210> SEQ ID NO 596
<211> LENGTH: 19
<212> TYPE: PRT
<213> ORGANISM: Pantoea sesami

<400> SEQUENCE: 596

Met Ala Met Leu Arg Cys Leu Arg Ala Arg Leu Gln Thr Met Leu Gln
1 5 10 15

Glu Leu Gln

<210> SEQ ID NO 597
<211> LENGTH: 19
<212> TYPE: PRT
<213> ORGANISM: Erwinia gerudensis

<400> SEQUENCE: 597

Met Ala Met Leu Arg Lys Leu Arg Ala Arg Leu Gln Thr Met Leu Gln
1 5 10 15

Glu Leu Gln

<210> SEQ ID NO 598
<211> LENGTH: 5
<212> TYPE: PRT
<213> ORGANISM: Arabidopsis thaliana
<220> FEATURE:
<221> NAME/KEY: MISC_FEATURE
<222> LOCATION: (1)..(1)
<223> OTHER INFORMATION: Xaa = sulfonated tyrosine
<220> FEATURE:
<221> NAME/KEY: MISC_FEATURE
<222> LOCATION: (3)..(3)
<223> OTHER INFORMATION: Xaa = sulfonated tyrosine

<400> SEQUENCE: 598

Xaa Ile Xaa Thr Gln
1 5

<210> SEQ ID NO 599
<211> LENGTH: 5
<212> TYPE: PRT
<213> ORGANISM: Arabidopsis thaliana
<220> FEATURE:
<221> NAME/KEY: MISC_FEATURE
<222> LOCATION: (3)..(3)
<223> OTHER INFORMATION: Xaa = sulfonated tyrosine
<220> FEATURE:
<221> NAME/KEY: MISC_FEATURE
<222> LOCATION: (5)..(5)
<223> OTHER INFORMATION: Xaa = sulfonated tyrosine

<400> SEQUENCE: 599

Gln Thr Xaa Ile Xaa
1 5

<210> SEQ ID NO 600
<211> LENGTH: 12
<212> TYPE: PRT
<213> ORGANISM: Glycine max

<400> SEQUENCE: 600

Gly Gly Ile Arg Ala Ala Pro Thr Gly Asn Glu Arg
1 5 10

<210> SEQ ID NO 601
<211> LENGTH: 12
<212> TYPE: PRT
<213> ORGANISM: Glycine max

<400> SEQUENCE: 601

Arg Glu Asn Gly Thr Pro Ala Ala Arg Ile Gly Gly
1 5 10

<210> SEQ ID NO 602
<211> LENGTH: 217
<212> TYPE: PRT
<213> ORGANISM: Glycine max

<400> SEQUENCE: 602

Met Lys Ser Thr Ile Phe Phe Ala Leu Phe Leu Phe Cys Ala Phe Thr
1 5 10 15

Thr Ser Tyr Leu Pro Ser Ala Ile Ala Asp Phe Val Leu Asp Asn Glu
20 25 30

Gly Asn Pro Leu Glu Asn Gly Gly Thr Tyr Tyr Ile Leu Ser Asp Ile
35 40 45

Thr Ala Phe Gly Gly Ile Arg Ala Ala Pro Thr Gly Asn Glu Arg Cys
50 55 60

Pro Leu Thr Val Val Gln Ser Arg Asn Glu Leu Asp Lys Gly Ile Glu
65 70 75 80

Thr Ile Ile Ser Ser Pro Tyr Arg Ile Arg Phe Ile Ala Glu Gly His
85 90 95

Pro Leu Ser Leu Lys Phe Asp Ser Phe Ala Val Ile Met Leu Cys Val
100 105 110

Gly Ile Pro Thr Glu Trp Ser Val Val Glu Asp Leu Pro Glu Gly Pro
115 120 125

Ala Val Lys Ile Gly Glu Asn Lys Asp Ala Met Asp Gly Trp Phe Arg
130 135 140

Leu Glu Arg Val Ser Asp Asp Glu Phe Asn Asn Tyr Lys Leu Val Phe
145 150 155 160

Cys Pro Gln Gln Ala Glu Asp Asp Lys Cys Gly Asp Ile Gly Ile Ser
165 170 175

Ile Asp His Asp Asp Gly Thr Arg Arg Leu Val Val Ser Lys Asn Lys
180 185 190

Pro Leu Val Val Gln Phe Gln Lys Leu Asp Lys Glu Ser Leu Ala Lys
195 200 205

Lys Asn His Gly Leu Ser Arg Ser Glu
210 215

<210> SEQ ID NO 603
<211> LENGTH: 12
<212> TYPE: PRT
<213> ORGANISM: Glycine max

<400> SEQUENCE: 603

Gly Gly Ile Arg Ala Thr Pro Thr Glu Asn Glu Arg
1 5 10

<210> SEQ ID NO 604
<211> LENGTH: 12

<212> TYPE: PRT
<213> ORGANISM: Glycine max

<400> SEQUENCE: 604

Gly Gly Ile Arg Val Ala Ala Thr Gly Lys Glu Arg
1 5 10

<210> SEQ ID NO 605
<211> LENGTH: 12
<212> TYPE: PRT
<213> ORGANISM: Glycine max

<400> SEQUENCE: 605

Arg Glu Asn Glu Thr Pro Thr Ala Arg Ile Gly Gly
1 5 10

<210> SEQ ID NO 606
<211> LENGTH: 12
<212> TYPE: PRT
<213> ORGANISM: Glycine max

<400> SEQUENCE: 606

Arg Glu Lys Gly Thr Ala Ala Val Arg Ile Gly Gly
1 5 10

<210> SEQ ID NO 607
<211> LENGTH: 18
<212> TYPE: PRT
<213> ORGANISM: Arabidopsis lyrata

<400> SEQUENCE: 607

Ala Arg Gly Lys Phe Glu Arg Lys Lys Pro His Val Asn Ile Gly Thr
1 5 10 15

Ile Gly

<210> SEQ ID NO 608
<211> LENGTH: 26
<212> TYPE: PRT
<213> ORGANISM: Arabidopsis lyrata

<400> SEQUENCE: 608

Ala Arg Gly Lys Phe Glu Arg Lys Lys Pro His Val Asn Ile Gly Thr
1 5 10 15

Ile Gly His Val Asp His Gly Lys Thr Thr
20 25

<210> SEQ ID NO 609
<211> LENGTH: 50
<212> TYPE: PRT
<213> ORGANISM: Arabidopsis lyrata

<400> SEQUENCE: 609

Glu Lys Pro Asn Val Lys Arg Gly Glu Asn Lys Trp Val Asp Lys Ile
1 5 10 15

Tyr Glu Leu Met Asp Ser Val Asp Ser Tyr Ile Pro Ile Pro Thr Arg
20 25 30

Gln Thr Glu Leu Pro Phe Leu Leu Ala Val Glu Asp Val Phe Ser Ile
35 40 45

Thr Gly
50

<210> SEQ ID NO 610

<211> LENGTH: 18
<212> TYPE: PRT
<213> ORGANISM: Euglena gracilis

<400> SEQUENCE: 610

Ala Arg Gln Lys Phe Glu Arg Thr Lys Pro His Ile Asn Ile Gly Thr
1 5 10 15

Ile Gly

<210> SEQ ID NO 611
<211> LENGTH: 26
<212> TYPE: PRT
<213> ORGANISM: Euglena gracilis

<400> SEQUENCE: 611

Ala Arg Gln Lys Phe Glu Arg Thr Lys Pro His Ile Asn Ile Gly Thr
1 5 10 15

Ile Gly His Val Asp His Gly Lys Thr Thr
20 25

<210> SEQ ID NO 612
<211> LENGTH: 50
<212> TYPE: PRT
<213> ORGANISM: Euglena gracilis

<400> SEQUENCE: 612

Lys Asn Pro Lys Ile Thr Lys Gly Glu Asn Lys Trp Val Asp Lys Ile
1 5 10 15

Leu Asn Leu Met Asp Gln Val Asp Ser Tyr Ile Pro Thr Pro Thr Arg
20 25 30

Asp Thr Glu Lys Asp Phe Leu Met Ala Ile Glu Asp Val Leu Ser Ile
35 40 45

Thr Gly
50

<210> SEQ ID NO 613
<211> LENGTH: 18
<212> TYPE: PRT
<213> ORGANISM: Acidovorax avenae

<400> SEQUENCE: 613

Ala Lys Gly Lys Phe Glu Arg Thr Lys Pro His Val Asn Val Gly Thr
1 5 10 15

Ile Gly

<210> SEQ ID NO 614
<211> LENGTH: 26
<212> TYPE: PRT
<213> ORGANISM: Acidovorax avenae

<400> SEQUENCE: 614

Ala Lys Gly Lys Phe Glu Arg Thr Lys Pro His Val Asn Val Gly Thr
1 5 10 15

Ile Gly His Val Asp His Gly Lys Thr Thr
20 25

<210> SEQ ID NO 615
<211> LENGTH: 50
<212> TYPE: PRT
<213> ORGANISM: Acidovorax spp.

<400> SEQUENCE: 615

```
Lys Leu Ala Leu Glu Gly Asp Lys Gly Pro Leu Gly Glu Gln Ala Ile
1               5                   10                  15

Asp Lys Leu Ala Glu Ala Leu Asp Thr Tyr Ile Pro Thr Pro Glu Arg
            20                  25                  30

Ala Val Asp Gly Ala Phe Leu Met Pro Val Glu Asp Val Phe Ser Ile
        35                  40                  45

Ser Gly
    50


<210> SEQ ID NO 616
<211> LENGTH: 18
<212> TYPE: PRT
<213> ORGANISM: Bacillus cereus

<400> SEQUENCE: 616

Ala Lys Ala Lys Phe Glu Arg Ser Lys Pro His Val Asn Ile Gly Thr
1               5                   10                  15

Ile Gly


<210> SEQ ID NO 617
<211> LENGTH: 26
<212> TYPE: PRT
<213> ORGANISM: Bacillus cereus

<400> SEQUENCE: 617

Ala Lys Ala Lys Phe Glu Arg Ser Lys Pro His Val Asn Ile Gly Thr
1               5                   10                  15

Ile Gly His Val Asp His Gly Lys Thr Thr
            20                  25


<210> SEQ ID NO 618
<211> LENGTH: 50
<212> TYPE: PRT
<213> ORGANISM: Bacillus cereus

<400> SEQUENCE: 618

Ser Ala Leu Lys Ala Leu Gln Gly Glu Ala Glu Trp Glu Glu Lys Ile
1               5                   10                  15

Ile Glu Leu Met Ala Glu Val Asp Ala Tyr Ile Pro Thr Pro Glu Arg
            20                  25                  30

Glu Thr Asp Lys Pro Phe Leu Met Pro Ile Glu Asp Val Phe Ser Ile
        35                  40                  45

Thr Gly
    50


<210> SEQ ID NO 619
<211> LENGTH: 26
<212> TYPE: PRT
<213> ORGANISM: Burkholderia spp.

<400> SEQUENCE: 619

Ala Lys Gly Lys Phe Glu Arg Thr Lys Pro His Val Asn Val Gly Thr
1               5                   10                  15

Ile Gly His Val Asp His Gly Lys Thr Thr
            20                  25


<210> SEQ ID NO 620
<211> LENGTH: 50
<212> TYPE: PRT
<213> ORGANISM: Burkholderia spp.
```

<400> SEQUENCE: 620

Lys Leu Ala Leu Glu Gly Asp Thr Gly Glu Leu Gly Glu Val Ala Ile
1 5 10 15

Met Asn Leu Ala Asp Ala Leu Asp Thr Tyr Ile Pro Thr Pro Glu Arg
20 25 30

Ala Val Asp Gly Ala Phe Leu Met Pro Val Glu Asp Val Phe Ser Ile
35 40 45

Ser Gly
50

<210> SEQ ID NO 621
<211> LENGTH: 50
<212> TYPE: PRT
<213> ORGANISM: Xanthomonas campestris

<400> SEQUENCE: 621

Arg Leu Ala Leu Asp Gly Asp Gln Ser Glu Ile Gly Val Pro Ala Ile
1 5 10 15

Leu Lys Leu Val Asp Ala Leu Asp Thr Phe Ile Pro Glu Pro Thr Arg
20 25 30

Asp Val Asp Arg Pro Phe Leu Met Pro Val Glu Asp Val Phe Ser Ile
35 40 45

Ser Gly
50

<210> SEQ ID NO 622
<211> LENGTH: 26
<212> TYPE: PRT
<213> ORGANISM: Pseudomonas spp.

<400> SEQUENCE: 622

Ala Lys Glu Lys Phe Glu Arg Ser Lys Pro His Val Asn Val Gly Thr
1 5 10 15

Ile Gly His Val Asp His Gly Lys Thr Thr
20 25

<210> SEQ ID NO 623
<211> LENGTH: 50
<212> TYPE: PRT
<213> ORGANISM: Pseudomonas spp.

<400> SEQUENCE: 623

Met Ala Leu Glu Gly Lys Asp Asp Asn Glu Met Gly Thr Thr Ala Val
1 5 10 15

Lys Lys Leu Val Glu Thr Leu Asp Ser Tyr Ile Pro Glu Pro Glu Arg
20 25 30

Ala Ile Asp Lys Pro Phe Leu Met Pro Ile Glu Asp Val Phe Ser Ile
35 40 45

Ser Gly
50

<210> SEQ ID NO 624
<211> LENGTH: 18
<212> TYPE: PRT
<213> ORGANISM: Arabidopsis lyrata

<400> SEQUENCE: 624

Gly Ile Thr Gly Ile Asn Val His Pro Lys Lys Arg Glu Phe Lys Gly
1 5 10 15

Arg Ala

<210> SEQ ID NO 625
<211> LENGTH: 26
<212> TYPE: PRT
<213> ORGANISM: Arabidopsis lyrata

<400> SEQUENCE: 625

Thr Thr Lys Gly His Asp Val His Gly Ile Thr Gly Ile Asn Val His
1 5 10 15

Pro Lys Lys Arg Glu Phe Lys Gly Arg Ala
20 25

<210> SEQ ID NO 626
<211> LENGTH: 50
<212> TYPE: PRT
<213> ORGANISM: Arabidopsis lyrata

<400> SEQUENCE: 626

Gly Thr Ile Ser Phe Val Asp Glu Val Ala Leu Leu Phe Pro Leu Glu
1 5 10 15

Thr Gln Arg Thr Pro Ile Pro Ile Tyr Ser Asp Val Ser Asp Met Leu
20 25 30

Glu Tyr Ile Lys Asp Val Trp Lys Asn Glu Gly Arg Lys Val Asn Pro
35 40 45

Lys Glu
50

<210> SEQ ID NO 627
<211> LENGTH: 18
<212> TYPE: PRT
<213> ORGANISM: Euglena gracilis

<400> SEQUENCE: 627

Gly Ile Thr Gly Ile Asn Ile His Pro Lys Thr Arg Glu Phe Lys Gln
1 5 10 15

Arg Ala

<210> SEQ ID NO 628
<211> LENGTH: 26
<212> TYPE: PRT
<213> ORGANISM: Euglena gracilis

<400> SEQUENCE: 628

Thr Thr Lys Gly His Asp Val His Gly Ile Thr Gly Ile Asn Ile His
1 5 10 15

Pro Lys Thr Arg Glu Phe Lys Gln Arg Ala
20 25

<210> SEQ ID NO 629
<211> LENGTH: 50
<212> TYPE: PRT
<213> ORGANISM: Euglena gracilis

<400> SEQUENCE: 629

Gly Thr Ile Ser Leu Val Asp Glu Ile Ala Met Leu Phe Asp Lys Glu
1 5 10 15

Thr Asp Arg Thr Pro Thr Pro Ile Tyr Ser Asp Val Gln Asp Met Leu
20 25 30

Asn Leu Ile Lys Asp Val Trp Lys Asn Glu Gly Lys Thr Ile Lys Pro 35 40 45

Asn Lys
50

<210> SEQ ID NO 630
<211> LENGTH: 18
<212> TYPE: PRT
<213> ORGANISM: Acidovorax avenae

<400> SEQUENCE: 630

Gly Ile Thr Gly Val Asn Val His Pro Lys Thr Arg Glu Phe Lys Gly
1 5 10 15

Lys Ala

<210> SEQ ID NO 631
<211> LENGTH: 26
<212> TYPE: PRT
<213> ORGANISM: Acidovorax avenae

<400> SEQUENCE: 631

Thr Thr Lys Gly His Asp Val His Gly Ile Thr Gly Val Asn Val His
1 5 10 15

Pro Lys Thr Arg Glu Phe Lys Gly Lys Ala
20 25

<210> SEQ ID NO 632
<211> LENGTH: 50
<212> TYPE: PRT
<213> ORGANISM: Acidovorax spp.

<400> SEQUENCE: 632

Gly Ser Ile Ser Phe Val Asp Glu Val Pro Met Leu Phe Ala Gly Asp
1 5 10 15

Val Ala Arg Glu Pro Thr Pro Ile Tyr Thr Asp Leu Ala Glu Ala Leu
20 25 30

Lys Asp Ile Ala Gln Glu Gly Leu Pro Gly Lys Asp Gly Glu Leu Ala
35 40 45

Leu Lys
50

<210> SEQ ID NO 633
<211> LENGTH: 18
<212> TYPE: PRT
<213> ORGANISM: Bacillus cereus

<400> SEQUENCE: 633

Gly Ile Thr Gly Ile Asn Val His Pro Lys Ser Arg Glu Phe Lys Ala
1 5 10 15

Lys Ala

<210> SEQ ID NO 634
<211> LENGTH: 26
<212> TYPE: PRT
<213> ORGANISM: Bacillus cereus

<400> SEQUENCE: 634

Thr Thr Lys Gly His Asp Val His Gly Ile Thr Gly Ile Asn Val His
1 5 10 15

Pro Lys Ser Arg Glu Phe Lys Ala Lys Ala
20 25

<210> SEQ ID NO 635
<211> LENGTH: 50
<212> TYPE: PRT
<213> ORGANISM: Bacillus cereus

<400> SEQUENCE: 635

```
Gly Ile Thr Ser Phe Val Asp Glu Ile Pro Met Leu Phe Pro Lys Asp
1               5                   10                  15

Thr Glu Arg Glu Pro Thr Pro Ile Tyr Ala Asp Val Glu Ala Met Leu
            20                  25                  30

Glu Ile Ile Lys Glu Glu Trp Glu Ala Glu Gly Gln Leu Ala Lys Leu
        35                  40                  45

Ala Ser
    50
```

<210> SEQ ID NO 636
<211> LENGTH: 26
<212> TYPE: PRT
<213> ORGANISM: Burkholderia spp.

<400> SEQUENCE: 636

```
Thr Thr Lys Gly His Asp Val His Gly Ile Thr Gly Val Asn Val His
1               5                   10                  15

Pro Lys Thr Arg Glu Phe Lys Gly Lys Ala
            20                  25
```

<210> SEQ ID NO 637
<211> LENGTH: 50
<212> TYPE: PRT
<213> ORGANISM: Burkholderia spp.

<400> SEQUENCE: 637

```
Gly Ser Ile Ser Phe Val Asp Glu Val Pro Met Leu Phe Ala Gly Asp
1               5                   10                  15

Val Ala Arg Glu Pro Thr Pro Ile Tyr Thr Asp Leu Ala Asp Ala Leu
            20                  25                  30

Asn Met Ile Ala Val Glu Gly Leu Glu Gly Thr Asp Gly Glu Leu Ala
        35                  40                  45

Leu Lys
    50
```

<210> SEQ ID NO 638
<211> LENGTH: 50
<212> TYPE: PRT
<213> ORGANISM: Xanthomonas campestris

<400> SEQUENCE: 638

```
Gly Ser Ile Ser Phe Val Asp Glu Val Pro Met Leu Phe Pro Arg Asp
1               5                   10                  15

Val Asp Arg Thr Pro Glu Pro Ile Phe Thr Asp Leu Ala Asp Val Leu
            20                  25                  30

Lys Leu Ile Ala Pro Val Gly Ile Glu Ser Gln Asp Gly Asp Leu Ala
        35                  40                  45

Leu Arg
    50
```

<210> SEQ ID NO 639
<211> LENGTH: 26
<212> TYPE: PRT
<213> ORGANISM: Pseudomonas spp.

<400> SEQUENCE: 639

Thr Thr Lys Gly His Asp Val His Gly Ile Thr Gly Val Asn Val His
1 5 10 15

Pro Lys Ser Arg Glu Phe Lys Glu Lys Ala
20 25

<210> SEQ ID NO 640
<211> LENGTH: 50
<212> TYPE: PRT
<213> ORGANISM: Pseudomonas spp.

<400> SEQUENCE: 640

Gly Ser Ile Ser Phe Val Asp Glu Ile Pro Met Leu Phe Pro Lys Asp
1 5 10 15

Ile Ala Arg Glu Pro Glu Pro Ile Tyr Ser Asp Leu Thr Glu Val Leu
20 25 30

Lys Lys Val Ala Thr Thr Gly Met Glu Asn Asp Asp Lys Gly Glu Leu
35 40 45

Ala Met
50

<210> SEQ ID NO 641
<211> LENGTH: 54
<212> TYPE: PRT
<213> ORGANISM: Artificial Sequence
<220> FEATURE:
<223> OTHER INFORMATION: Synthetic construct

<400> SEQUENCE: 641

Met Ser Thr Ala Thr Phe Val Asp Ile Ile Ile Ala Ile Leu Leu Pro
1 5 10 15

Pro Leu Gly Val Phe Leu Arg Phe Gly Cys Gly Val Glu Phe Trp Ile
20 25 30

Cys Leu Val Leu Thr Leu Leu Gly Tyr Ile Pro Gly Ile Ile Tyr Ala
35 40 45

Ile Tyr Val Leu Thr Lys
50

<210> SEQ ID NO 642
<211> LENGTH: 54
<212> TYPE: PRT
<213> ORGANISM: Citrus clementina

<400> SEQUENCE: 642

Met Gly Ser Glu Thr Phe Leu Glu Val Ile Leu Ala Ile Leu Leu Pro
1 5 10 15

Pro Val Gly Val Phe Leu Arg Tyr Gly Cys Gly Val Glu Phe Trp Ile
20 25 30

Cys Leu Leu Leu Thr Val Leu Gly Tyr Ile Pro Gly Ile Ile Tyr Ala
35 40 45

Ile Tyr Val Leu Val Gly
50

<210> SEQ ID NO 643
<211> LENGTH: 54
<212> TYPE: PRT
<213> ORGANISM: Citrus trifoliata

<400> SEQUENCE: 643

```
Met Gly Thr Ala Thr Cys Val Asp Ile Ile Leu Ala Val Ile Leu Pro
1               5                   10                  15

Pro Leu Gly Val Phe Leu Lys Phe Gly Cys Lys Ala Glu Phe Trp Ile
            20                  25                  30

Cys Leu Leu Leu Thr Ile Leu Gly Tyr Ile Pro Gly Ile Ile Tyr Ala
        35                  40                  45

Val Tyr Val Ile Thr Lys
    50


<210> SEQ ID NO 644
<211> LENGTH: 58
<212> TYPE: PRT
<213> ORGANISM: Citrus sinensis

<400> SEQUENCE: 644

Met Ala Asp Glu Gly Thr Ala Thr Cys Ile Asp Ile Ile Leu Ala Ile
1               5                   10                  15

Ile Leu Pro Pro Leu Gly Val Phe Leu Lys Phe Gly Cys Lys Val Glu
            20                  25                  30

Phe Trp Ile Cys Leu Leu Leu Thr Ile Phe Gly Tyr Ile Pro Gly Ile
        35                  40                  45

Ile Tyr Ala Val Tyr Ala Ile Thr Lys Asn
    50                  55


<210> SEQ ID NO 645
<211> LENGTH: 58
<212> TYPE: PRT
<213> ORGANISM: Citrus sinensis

<400> SEQUENCE: 645

Met Ala Asp Gly Ser Thr Ala Thr Cys Val Asp Ile Leu Leu Ala Val
1               5                   10                  15

Ile Leu Pro Pro Leu Gly Val Phe Leu Lys Phe Gly Cys Lys Ala Glu
            20                  25                  30

Phe Trp Ile Cys Leu Leu Leu Thr Ile Leu Gly Tyr Ile Pro Gly Ile
        35                  40                  45

Ile Tyr Ala Val Tyr Ala Ile Thr Lys Lys
    50                  55


<210> SEQ ID NO 646
<211> LENGTH: 104
<212> TYPE: PRT
<213> ORGANISM: Citrus clementina

<400> SEQUENCE: 646

Phe Tyr Lys Gln Lys Tyr Gln Val Gln Ile Thr Lys Ala Val Thr Gln
1               5                   10                  15

Asn Pro Lys His Phe Phe Asn Gln Ser Ser Cys Phe Leu Thr Leu Asn
            20                  25                  30

Phe Ile Leu Phe His Phe Thr Leu Phe Lys Asn Gln Ser Lys Met Ala
        35                  40                  45

Asp Gly Ser Thr Ala Thr Cys Val Asp Ile Leu Leu Ala Val Ile Leu
    50                  55                  60

Pro Pro Leu Gly Val Phe Leu Lys Phe Gly Cys Lys Ala Glu Phe Trp
65                  70                  75                  80

Ile Cys Leu Leu Leu Thr Ile Leu Gly Tyr Ile Pro Gly Ile Ile Tyr
                85                  90                  95

Ala Val Tyr Ala Ile Thr Lys Lys
```

100

<210> SEQ ID NO 647
<211> LENGTH: 54
<212> TYPE: PRT
<213> ORGANISM: Arabidopsis thaliana

<400> SEQUENCE: 647

Met Ser Thr Ala Thr Phe Val Asp Ile Ile Ile Ala Ile Leu Leu Pro
1 5 10 15

Pro Leu Gly Val Phe Leu Arg Phe Gly Cys Gly Val Glu Phe Trp Ile
20 25 30

Cys Leu Val Leu Thr Leu Leu Gly Tyr Ile Pro Gly Ile Ile Tyr Ala
35 40 45

Ile Tyr Val Leu Thr Lys
50

<210> SEQ ID NO 648
<211> LENGTH: 54
<212> TYPE: PRT
<213> ORGANISM: Camelina sativa

<400> SEQUENCE: 648

Met Ser Thr Ala Thr Phe Val Asp Ile Ile Ile Ala Val Leu Leu Pro
1 5 10 15

Pro Leu Gly Val Phe Leu Arg Phe Gly Cys Gly Val Glu Phe Trp Ile
20 25 30

Cys Leu Val Leu Thr Leu Leu Gly Tyr Ile Pro Gly Ile Ile Tyr Ala
35 40 45

Ile Tyr Val Leu Thr Lys
50

<210> SEQ ID NO 649
<211> LENGTH: 54
<212> TYPE: PRT
<213> ORGANISM: Arabidopsis lyrata

<400> SEQUENCE: 649

Met Gly Thr Ala Thr Cys Val Asp Ile Ile Ile Ala Ile Leu Leu Pro
1 5 10 15

Pro Leu Gly Val Phe Leu Arg Phe Gly Cys Gly Val Glu Phe Trp Ile
20 25 30

Cys Leu Val Leu Thr Leu Leu Gly Tyr Ile Pro Gly Ile Leu Tyr Ala
35 40 45

Leu Tyr Val Leu Thr Lys
50

<210> SEQ ID NO 650
<211> LENGTH: 52
<212> TYPE: PRT
<213> ORGANISM: Artificial Sequence
<220> FEATURE:
<223> OTHER INFORMATION: Synthetic construct

<400> SEQUENCE: 650

Arg Thr Cys Glu Ser Gln Ser His Arg Phe Lys Gly Pro Cys Ser Arg
1 5 10 15

Asp Ser Asn Cys Ala Thr Val Cys Leu Thr Glu Gly Phe Ser Gly Gly
20 25 30

Asp Cys Arg Gly Phe Arg Arg Arg Cys Arg Cys Thr Arg Pro Cys Val

```
        35                  40                  45

Phe Asp Glu Lys
    50


<210> SEQ ID NO 651
<211> LENGTH: 47
<212> TYPE: PRT
<213> ORGANISM: Citrus sinensis

<400> SEQUENCE: 651

Arg Val Cys Gln Ser Gln Ser His His Phe His Gly Ala Cys Phe Ser
1               5                   10                  15

His His Asn Cys Ala Phe Val Cys Arg Asn Glu Gly Phe Ser Gly Gly
            20                  25                  30

Lys Cys Arg Gly Val Arg Arg Arg Cys Phe Cys Ser Lys Leu Cys
        35                  40                  45


<210> SEQ ID NO 652
<211> LENGTH: 46
<212> TYPE: PRT
<213> ORGANISM: Avena sativa

<400> SEQUENCE: 652

Lys Ser Cys Cys Lys Asp Ile Met Ala Arg Asn Cys Tyr Asn Val Cys
1               5                   10                  15

Arg Ile Pro Gly Thr Pro Arg Pro Val Cys Ala Thr Thr Cys Arg Cys
            20                  25                  30

Lys Ile Ile Ser Gly Asn Lys Cys Pro Lys Asp Tyr Pro Lys
        35                  40                  45


<210> SEQ ID NO 653
<211> LENGTH: 52
<212> TYPE: PRT
<213> ORGANISM: Artificial Sequence
<220> FEATURE:
<223> OTHER INFORMATION: Synthetic construct

<400> SEQUENCE: 653

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Arg Cys Thr Arg Pro Cys Val
        35                  40                  45

Phe Asp Glu Lys
    50


<210> SEQ ID NO 654
<211> LENGTH: 75
<212> TYPE: PRT
<213> ORGANISM: Citrus sinensis

<400> SEQUENCE: 654

Met Asp Ser Arg Ser Phe Gly Leu Leu Pro Leu Leu Leu Leu Ile Leu
1               5                   10                  15

Leu Thr Ser Gln Met Thr Val Leu Gln Thr Glu Ala Arg Leu Cys Glu
            20                  25                  30

Ser Gln Ser His Arg Phe His Gly Thr Cys Val Arg Ser His Asn Cys
        35                  40                  45

Asp Leu Val Cys Arg Thr Glu Gly Phe Thr Gly Gly Arg Cys Arg Gly
```

```
    50                  55                  60

Phe Arg Arg Arg Cys Phe Cys Thr Arg Ile Cys
65                  70                  75


<210> SEQ ID NO 655
<211> LENGTH: 73
<212> TYPE: PRT
<213> ORGANISM: Citrus paradise

<400> SEQUENCE: 655

Met Lys Ser Phe Phe Gly Ile Phe Leu Leu Leu Leu Ile Leu Phe Ala
1               5                   10                  15

Ser Gln Glu Ile Met Val Pro Ala Glu Gly Arg Val Cys Gln Ser Gln
            20                  25                  30

Ser His His Phe His Gly Ala Cys Phe Ser His His Asn Cys Ala Phe
        35                  40                  45

Val Cys Arg Asn Glu Gly Phe Ser Gly Gly Lys Cys Arg Gly Val Arg
    50                  55                  60

Arg Arg Cys Phe Cys Ser Lys Leu Cys
65                  70


<210> SEQ ID NO 656
<211> LENGTH: 72
<212> TYPE: PRT
<213> ORGANISM: Citrus clementina

<400> SEQUENCE: 656

Met Lys Ser Phe Phe Gly Ile Phe Leu Leu Leu Leu Ile Leu Phe Ala
1               5                   10                  15

Ser Gln Met Met Val Pro Ala Glu Gly Arg Val Cys Gln Ser Gln Ser
            20                  25                  30

His His Phe His Gly Ala Cys Phe Ser His His Asn Cys Ala Phe Val
        35                  40                  45

Cys Arg Asn Glu Gly Phe Ser Gly Gly Lys Cys Arg Gly Ala Arg Arg
    50                  55                  60

Arg Cys Phe Cys Ser Lys Leu Cys
65                  70


<210> SEQ ID NO 657
<211> LENGTH: 73
<212> TYPE: PRT
<213> ORGANISM: Citrus clementina

<400> SEQUENCE: 657

Met Lys Ser Phe Phe Gly Ile Phe Leu Leu Leu Leu Ile Leu Phe Ala
1               5                   10                  15

Ser Gln Glu Met Met Val Pro Ala Glu Gly Arg Val Cys Gln Ser Gln
            20                  25                  30

Ser His His Phe His Gly Ala Cys Phe Ser His His Asn Cys Ala Phe
        35                  40                  45

Val Cys Arg Asn Glu Gly Phe Ser Gly Gly Lys Cys Arg Gly Ala Arg
    50                  55                  60

Arg Arg Cys Phe Cys Ser Lys Leu Cys
65                  70


<210> SEQ ID NO 658
<211> LENGTH: 72
<212> TYPE: PRT
<213> ORGANISM: Citrus clementina
```

<400> SEQUENCE: 658

Met Lys Ser Phe Phe Gly Ile Phe Leu Leu Leu Leu Ile Leu Phe Ala
1 5 10 15

Ser Gln Met Met Val Pro Ala Glu Gly Arg Val Cys Gln Ser Gln Ser
20 25 30

His His Phe His Gly Ala Cys Phe Ser His His Asn Cys Ala Phe Val
35 40 45

Cys Arg Asn Glu Gly Phe Ser Gly Gly Lys Cys Arg Gly Ala Arg Arg
50 55 60

Arg Cys Phe Cys Ser Lys Leu Cys
65 70

<210> SEQ ID NO 659
<211> LENGTH: 78
<212> TYPE: PRT
<213> ORGANISM: Nicotiana benthamiana

<400> SEQUENCE: 659

Met Ala Asn Ser Met Arg Phe Phe Ala Thr Val Leu Leu Leu Ala Leu
1 5 10 15

Leu Val Met Ala Thr Glu Met Gly Pro Met Thr Ile Ala Glu Ala Arg
20 25 30

Thr Cys Glu Ser Gln Ser His Arg Phe Lys Gly Pro Cys Ser Arg Asp
35 40 45

Ser Asn Cys Ala Thr Val Cys Leu Thr Glu Gly Phe Ser Gly Gly Asp
50 55 60

Cys Arg Gly Phe Arg Arg Arg Cys Phe Cys Thr Arg Pro Cys
65 70 75

<210> SEQ ID NO 660
<211> LENGTH: 78
<212> TYPE: PRT
<213> ORGANISM: Nicotiana sylvestris

<400> SEQUENCE: 660

Met Ala Lys Ser Met Arg Phe Phe Ala Thr Val Leu Leu Leu Ala Leu
1 5 10 15

Leu Val Met Ala Thr Glu Met Gly Pro Thr Thr Ile Ala Glu Ala Arg
20 25 30

Thr Cys Glu Ser Gln Ser His Arg Phe Lys Gly Pro Cys Ser Arg Asp
35 40 45

Ser Asn Cys Ala Thr Val Cys Leu Thr Glu Gly Phe Ser Gly Gly Asp
50 55 60

Cys Arg Gly Phe Arg Arg Arg Cys Phe Cys Thr Arg Pro Cys
65 70 75

<210> SEQ ID NO 661
<211> LENGTH: 78
<212> TYPE: PRT
<213> ORGANISM: Nicotiana tabacum

<400> SEQUENCE: 661

Met Ala Asn Ser Met Arg Phe Phe Ala Thr Val Leu Leu Leu Thr Leu
1 5 10 15

Leu Val Met Ala Thr Glu Met Gly Pro Met Thr Ile Ala Glu Ala Arg
20 25 30

Thr Cys Glu Ser Gln Ser His Arg Phe Lys Gly Pro Cys Ser Arg Asp

```
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Phe Cys Thr Arg Pro Cys
65                  70                  75


<210> SEQ ID NO 662
<211> LENGTH: 78
<212> TYPE: PRT
<213> ORGANISM: Nicotiana tomentosiformis

<400> SEQUENCE: 662

Met Ala Asn Ser Met Arg Phe Phe Ala Thr Val Leu Leu Ile Ala Leu
1               5                   10                  15

Leu Val Met Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Phe Cys Thr Arg Pro Cys
65                  70                  75


<210> SEQ ID NO 663
<211> LENGTH: 78
<212> TYPE: PRT
<213> ORGANISM: Nicotiana tabacum

<400> SEQUENCE: 663

Met Ala Asn Ser Met Arg Phe Phe Ala Thr Val Leu Leu Ile Ala Leu
1               5                   10                  15

Leu Val Thr Ala Thr Glu Met Gly Pro Met Thr Ile Ala Glu Ala Arg
            20                  25                  30

Thr Cys Glu Ser Gln Ser His Arg Phe Lys Gly Pro Cys Ser Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Phe Cys Thr Arg Pro Cys
65                  70                  75


<210> SEQ ID NO 664
<211> LENGTH: 78
<212> TYPE: PRT
<213> ORGANISM: Nicotiana alata

<400> SEQUENCE: 664

Met Ala Asn Ser Met Arg Phe Phe Ala Thr Val Leu Leu Leu Thr Leu
1               5                   10                  15

Leu Phe Met Ala Thr Glu Met Gly Pro Met Thr Ile Ala Glu Ala Arg
            20                  25                  30

Thr Cys Glu Ser Gln Ser His Arg Phe Lys Gly Pro Cys Ala Arg Asp
        35                  40                  45

Ser Asn Cys Ala Thr Val Cys Leu Thr Glu Gly Phe Ser Gly Gly Asp
    50                  55                  60

Cys Arg Gly Phe Arg Arg Arg Cys Phe Cys Thr Arg Pro Cys
65                  70                  75


<210> SEQ ID NO 665
```

<211> LENGTH: 80
<212> TYPE: PRT
<213> ORGANISM: Avena sativa

<400> SEQUENCE: 665

```
Met Gly Ser Ile Lys Gly Leu Lys Ser Val Val Ile Cys Val Leu Val
1               5                   10                  15

Leu Gly Ile Val Leu Glu Gln Val Gln Val Glu Gly Lys Ser Cys Cys
            20                  25                  30

Lys Asp Ile Met Ala Arg Asn Cys Tyr Asn Val Cys Arg Ile Pro Gly
        35                  40                  45

Thr Pro Arg Pro Val Cys Ala Thr Thr Cys Arg Cys Lys Ile Ile Ser
    50                  55                  60

Gly Asn Lys Cys Pro Lys Asp Tyr Pro Lys Leu His Gly Asp Pro Asp
65                  70                  75                  80
```

<210> SEQ ID NO 666
<211> LENGTH: 80
<212> TYPE: PRT
<213> ORGANISM: Avena sativa

<400> SEQUENCE: 666

```
Met Gly Ser Ile Lys Gly Leu Lys Ser Val Val Ile Cys Val Leu Val
1               5                   10                  15

Leu Gly Ile Val Leu Glu His Val Gln Val Glu Gly Lys Ser Cys Cys
            20                  25                  30

Lys Asp Thr Thr Ala Arg Asn Cys Tyr Asn Val Cys Arg Ile Pro Gly
        35                  40                  45

Thr Pro Arg Pro Val Cys Ala Thr Thr Cys Arg Cys Lys Ile Ile Ser
    50                  55                  60

Gly Asn Lys Cys Pro Lys Asp Tyr Pro Lys Leu His Gly Asp Leu Asp
65                  70                  75                  80
```

<210> SEQ ID NO 667
<211> LENGTH: 112
<212> TYPE: PRT
<213> ORGANISM: Tulipa gesneriana

<400> SEQUENCE: 667

```
Leu Gly Leu Val Val Ala Gln Thr Gln Val Asp Ala Lys Ser Cys Cys
1               5                   10                  15

Pro Ser Thr Ala Ala Arg Asn Cys Tyr Asn Val Cys Arg Phe Pro Gly
            20                  25                  30

Thr Pro Arg Pro Val Cys Ala Ala Thr Cys Gly Cys Lys Ile Ile Thr
        35                  40                  45

Gly Thr Lys Cys Pro Pro Asp Tyr Pro Lys Leu Gly Trp Ser Thr Phe
    50                  55                  60

Gln Asn Ser Asp Val Ala Asp Lys Ala Leu Asp Val Val Asp Glu Ala
65                  70                  75                  80

Leu His Val Ala Lys Glu Val Met Lys Glu Ala Val Glu Arg Cys Asn
                85                  90                  95

Asn Ala Cys Ser Glu Val Cys Thr Lys Gly Ser Tyr Ala Val Thr Ala
            100                 105                 110
```

<210> SEQ ID NO 668
<211> LENGTH: 75
<212> TYPE: PRT
<213> ORGANISM: Vitis vinifera

<400> SEQUENCE: 668

```
Met Glu Arg Lys Ser Leu Gly Phe Phe Phe Phe Leu Leu Leu Ile Leu
1               5                   10                  15

Leu Ala Ser Gln Glu Met Val Val Pro Ser Glu Ala Arg Val Cys Glu
            20                  25                  30

Ser Gln Ser His Lys Phe Glu Gly Ala Cys Met Gly Asp His Asn Cys
        35                  40                  45

Ala Leu Val Cys Arg Asn Glu Gly Phe Ser Gly Gly Lys Cys Lys Gly
    50                  55                  60

Leu Arg Arg Arg Cys Phe Cys Thr Lys Leu Cys
65                  70                  75
```

<210> SEQ ID NO 669
<211> LENGTH: 74
<212> TYPE: PRT
<213> ORGANISM: Vitis vinifera

<400> SEQUENCE: 669

```
Met Glu Arg Lys Ser Leu Gly Phe Phe Phe Phe Leu Leu Leu Ile Leu
1               5                   10                  15

Leu Ala Ser Gln Met Val Val Pro Ser Glu Ala Arg Val Cys Glu Ser
            20                  25                  30

Gln Ser His Lys Phe Glu Gly Ala Cys Met Gly Asp His Asn Cys Ala
        35                  40                  45

Leu Val Cys Arg Asn Glu Gly Phe Ser Gly Gly Lys Cys Lys Gly Leu
    50                  55                  60

Arg Arg Arg Cys Phe Cys Thr Lys Leu Cys
65                  70
```

<210> SEQ ID NO 670
<211> LENGTH: 76
<212> TYPE: PRT
<213> ORGANISM: Citrus sinensis

<400> SEQUENCE: 670

```
Met Glu Arg Ser Val Arg Leu Phe Ser Thr Val Leu Leu Val Leu Leu
1               5                   10                  15

Leu Leu Ala Ser Glu Met Gly Leu Arg Ala Ala Glu Ala Arg Ile Cys
            20                  25                  30

Glu Ser Gln Ser His Arg Phe Lys Gly Pro Cys Val Ser Lys Ser Asn
        35                  40                  45

Cys Ala Ala Val Cys Gln Thr Glu Gly Phe His Gly Gly His Cys Arg
    50                  55                  60

Gly Phe Arg Arg Arg Cys Phe Cys Thr Lys Arg Cys
65                  70                  75
```

<210> SEQ ID NO 671
<211> LENGTH: 50
<212> TYPE: PRT
<213> ORGANISM: Aesculus hippocastanum

<400> SEQUENCE: 671

```
Leu Cys Asn Glu Arg Pro Ser Gln Thr Trp Ser Gly Asn Cys Gly Asn
1               5                   10                  15

Thr Ala His Cys Asp Lys Gln Cys Gln Asp Trp Glu Lys Ala Ser His
            20                  25                  30

Gly Ala Cys His Lys Arg Glu Asn His Trp Lys Cys Phe Cys Tyr Phe
        35                  40                  45
```

Asn Cys
    50

<210> SEQ ID NO 672
<211> LENGTH: 81
<212> TYPE: PRT
<213> ORGANISM: Dacus carota

<400> SEQUENCE: 672

Met Ala Lys Asn Ser Thr Ser Pro Val Ser Leu Phe Ala Ile Ser Leu
1               5                   10                  15

Ile Phe Phe Leu Leu Ala Asn Ser Gly Ser Ile Thr Glu Val Asp Gly
            20                  25                  30

Lys Val Cys Glu Lys Pro Ser Leu Thr Trp Ser Gly Lys Cys Gly Asn
        35                  40                  45

Thr Gln His Cys Asp Lys Gln Cys Gln Asp Trp Glu Gly Ala Lys His
    50                  55                  60

Gly Ala Cys His Ser Arg Gly Gly Trp Lys Cys Phe Cys Tyr Phe Glu
65                  70                  75                  80

Cys

<210> SEQ ID NO 673
<211> LENGTH: 49
<212> TYPE: PRT
<213> ORGANISM: Clitoria ternatea

<400> SEQUENCE: 673

Asn Leu Cys Glu Arg Ala Ser Leu Thr Trp Thr Gly Asn Cys Gly Asn
1               5                   10                  15

Thr Gly His Cys Asp Thr Gln Cys Arg Asn Trp Glu Ser Ala Lys His
            20                  25                  30

Gly Ala Cys His Lys Arg Gly Asn Trp Lys Cys Phe Cys Tyr Phe Asn
        35                  40                  45

Cys

<210> SEQ ID NO 674
<211> LENGTH: 80
<212> TYPE: PRT
<213> ORGANISM: Dacus carota

<400> SEQUENCE: 674

Met Ala Lys Lys Ser Ser Ser Phe Cys Leu Ser Ala Ile Phe Leu Val
1               5                   10                  15

Leu Leu Leu Val Ala Asn Thr Gly Met Val Arg Glu Val Asp Gly Ala
            20                  25                  30

Leu Cys Glu Lys Pro Ser Leu Thr Trp Ser Gly Asn Cys Arg Asn Thr
        35                  40                  45

Gln His Cys Asp Lys Gln Cys Gln Ser Trp Glu Gly Ala Lys His Gly
    50                  55                  60

Ala Cys His Lys Arg Gly Asn Trp Lys Cys Phe Cys Tyr His Ala Cys
65                  70                  75                  80

<210> SEQ ID NO 675
<211> LENGTH: 92
<212> TYPE: PRT
<213> ORGANISM: Bupleurum kaoi

<400> SEQUENCE: 675

-continued

Met Ala Lys Lys Leu Asn Ala Val Thr Val Ser Ala Ile Phe Leu Val
1               5                   10                  15

Val Phe Leu Ile Ala Ser Tyr Ser Val Gly Ala Ala Lys Glu Ala Gly
            20                  25                  30

Ala Glu Gly Glu Val Val Phe Pro Glu Gln Leu Cys Glu Arg Ala Ser
        35                  40                  45

Gln Thr Trp Ser Gly Asp Cys Lys Asn Thr Lys Asn Cys Asp Asn Gln
    50                  55                  60

Cys Ile Gln Trp Glu Lys Ala Arg His Gly Ala Cys His Lys Arg Gly
65                  70                  75                  80

Gly Lys Trp Met Cys Phe Cys Tyr Phe Asp Lys Cys
                85                  90

<210> SEQ ID NO 676
<211> LENGTH: 50
<212> TYPE: PRT
<213> ORGANISM: Dahlia merckii

<400> SEQUENCE: 676

Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
            20                  25                  30

Gly Ala Cys His Val Arg Asn Gly Lys His Met Cys Phe Cys Tyr Phe
        35                  40                  45

Asn Cys
    50

<210> SEQ ID NO 677
<211> LENGTH: 108
<212> TYPE: PRT
<213> ORGANISM: Helianthus annuus

<400> SEQUENCE: 677

Met Ala Lys Ile Ser Val Ala Phe Asn Ala Phe Leu Leu Leu Leu Phe
1               5                   10                  15

Val Leu Ala Ile Ser Glu Ile Gly Ser Val Lys Gly Glu Leu Cys Glu
            20                  25                  30

Lys Ala Ser Gln Thr Trp Ser Gly Thr Cys Gly Lys Thr Lys His Cys
        35                  40                  45

Asp Asp Gln Cys Lys Ser Trp Glu Gly Ala Ala His Gly Ala Cys His
    50                  55                  60

Val Arg Asp Gly Lys His Met Cys Phe Cys Tyr Phe Asn Cys Ser Lys
65                  70                  75                  80

Ala Gln Lys Leu Ala Gln Asp Lys Leu Arg Ala Glu Glu Leu Ala Lys
                85                  90                  95

Glu Lys Ile Glu Pro Glu Lys Ala Thr Ala Lys Pro
            100                 105

<210> SEQ ID NO 678
<211> LENGTH: 117
<212> TYPE: PRT
<213> ORGANISM: Cynara cardunculus

<400> SEQUENCE: 678

Met Ala Lys Asn Ser Val Ala Phe Phe Ala Leu Leu Leu Leu Ile Cys
1               5                   10                  15

Ile Leu Thr Ile Ser Glu Phe Ala Val Val Lys Gly Glu Leu Cys Glu

```
            20                  25                  30

Lys Ala Ser Lys Thr Trp Ser Gly Asn Cys Gly Asn Thr Arg His Cys
        35                  40                  45

Asp Asp Gln Cys Lys Ala Trp Glu Gly Ala Ala His Gly Ala Cys His
    50                  55                  60

Thr Arg Asn Lys Lys His Met Cys Phe Cys Tyr Phe Asn Cys Pro Lys
65                  70                  75                  80

Ala Glu Lys Leu Ala Gln Asp Lys Leu Lys Ala Glu Glu Leu Ala Arg
                85                  90                  95

Asp Lys Val Glu Ala Lys Glu Val Pro His Phe Lys His Pro Ile Glu
            100                 105                 110

Pro Ile His His Pro
        115


<210> SEQ ID NO 679
<211> LENGTH: 117
<212> TYPE: PRT
<213> ORGANISM: Cynara cardunculus

<400> SEQUENCE: 679

Met Ala Lys Gln Trp Val Ser Phe Phe Ala Leu Ala Phe Ile Val Phe
1               5                   10                  15

Val Leu Ala Ile Ser Glu Thr Gln Thr Val Lys Gly Glu Leu Cys Glu
            20                  25                  30

Lys Ala Ser Lys Thr Trp Ser Gly Asn Cys Gly Asn Thr Lys His Cys
        35                  40                  45

Asp Asp Gln Cys Lys Ser Trp Glu Gly Ala Ala His Gly Ala Cys His
    50                  55                  60

Val Arg Asn Gly Lys His Met Cys Phe Cys Tyr Phe Asn Ser Cys Ala
65                  70                  75                  80

Glu Ala Asp Lys Leu Ser Glu Asp Gln Ile Glu Ala Gly Lys Leu Ala
                85                  90                  95

Phe Glu Lys Ala Glu Lys Leu Asp Arg Asp Val Lys Lys Ala Val Pro
            100                 105                 110

Asn Val Asp His Pro
        115


<210> SEQ ID NO 680
<211> LENGTH: 94
<212> TYPE: PRT
<213> ORGANISM: Daucus carota

<400> SEQUENCE: 680

Met Ala Gln Lys Val Asn Ser Ala Leu Ile Phe Ser Ala Ile Phe Val
1               5                   10                  15

Leu Phe Leu Val Ala Ser Tyr Ser Val Thr Val Ala Glu Gly Ala Arg
            20                  25                  30

Ala Gly Ala Glu Gly Glu Val Val Tyr Pro Glu Ala Leu Cys Glu Arg
        35                  40                  45

Ala Ser Gln Thr Trp Thr Gly Lys Cys Gln His Thr Asp His Cys Asp
    50                  55                  60

Asn Gln Cys Ile Gln Trp Glu Asn Ala Arg His Gly Ala Cys His Lys
65                  70                  75                  80

Arg Gly Gly Asn Trp Lys Cys Phe Cys Tyr Phe Asp His Cys
                85                  90
```

<210> SEQ ID NO 681
<211> LENGTH: 78
<212> TYPE: PRT
<213> ORGANISM: Arabidopsis lyrata

<400> SEQUENCE: 681

Met Ala Ser Ser Tyr Thr Leu Met Leu Phe Leu Cys Leu Ser Ile Phe
1 5 10 15

Leu Ile Ala Ser Thr Glu Met Met Ala Val Glu Ala Arg Ile Cys Glu
20 25 30

Arg Arg Ser Lys Thr Trp Thr Gly Phe Cys Gly Asn Thr Arg Gly Cys
35 40 45

Asp Ser Gln Cys Lys Ser Trp Glu Arg Ala Ser His Gly Ala Cys His
50 55 60

Ala Gln Phe Pro Gly Phe Ala Cys Phe Cys Tyr Phe Asn Cys
65 70 75

<210> SEQ ID NO 682
<211> LENGTH: 80
<212> TYPE: PRT
<213> ORGANISM: Parthenium hysterophorus

<400> SEQUENCE: 682

Met Ala Lys Ser Ser Thr Ser Tyr Leu Val Phe Leu Leu Leu Val Leu
1 5 10 15

Val Val Ala Ile Ser Glu Ile Ala Ser Val Asn Gly Lys Val Cys Glu
20 25 30

Lys Pro Ser Lys Thr Trp Phe Gly Asn Cys Lys Asp Thr Glu Lys Cys
35 40 45

Asp Lys Arg Cys Met Glu Trp Glu Gly Ala Lys His Gly Ala Cys His
50 55 60

Gln Arg Glu Ser Lys Tyr Met Cys Phe Cys Tyr Phe Asp Cys Asp Pro
65 70 75 80

<210> SEQ ID NO 683
<211> LENGTH: 78
<212> TYPE: PRT
<213> ORGANISM: Arabidopsis thaliana

<400> SEQUENCE: 683

Met Ala Ser Ser Tyr Thr Leu Met Leu Phe Leu Cys Leu Ser Ile Phe
1 5 10 15

Leu Ile Ala Ser Thr Glu Met Met Ala Val Glu Gly Arg Ile Cys Glu
20 25 30

Arg Arg Ser Lys Thr Trp Thr Gly Phe Cys Gly Asn Thr Arg Gly Cys
35 40 45

Asp Ser Gln Cys Lys Arg Trp Glu Arg Ala Ser His Gly Ala Cys His
50 55 60

Ala Gln Phe Pro Gly Phe Ala Cys Phe Cys Tyr Phe Asn Cys
65 70 75

<210> SEQ ID NO 684
<211> LENGTH: 78
<212> TYPE: PRT
<213> ORGANISM: Eutrema salsugineum

<400> SEQUENCE: 684

Met Ala Ser Ser Tyr Thr Leu Leu Leu Phe Val Cys Leu Ser Ile Phe
1 5 10 15

```
Phe Ile Ala Ser Thr Glu Met Met Met Val Glu Gly Arg Val Cys Glu
            20                  25                  30

Arg Arg Ser Lys Thr Trp Thr Gly Phe Cys Gly Asn Thr Arg Gly Cys
        35                  40                  45

Asp Ser Gln Cys Lys Arg Trp Glu Arg Ala Ser His Gly Ala Cys His
    50                  55                  60

Ala Gln Phe Pro Gly Phe Ala Cys Phe Cys Tyr Phe Asn Cys
65                  70                  75


<210> SEQ ID NO 685
<211> LENGTH: 82
<212> TYPE: PRT
<213> ORGANISM: Vitis vinifera

<400> SEQUENCE: 685

Met Ala Lys Leu Leu Gly Tyr Leu Leu Ser Tyr Ala Leu Ser Phe Leu
1               5                   10                  15

Thr Leu Phe Ala Leu Leu Val Ser Thr Glu Met Val Met Leu Glu Ala
            20                  25                  30

Lys Val Cys Gln Arg Pro Ser Lys Thr Trp Ser Gly Phe Cys Gly Ser
        35                  40                  45

Ser Lys Asn Cys Asp Arg Gln Cys Lys Asn Trp Glu Gly Ala Lys His
    50                  55                  60

Gly Ala Cys His Ala Lys Phe Pro Gly Val Ala Cys Phe Cys Tyr Phe
65                  70                  75                  80

Asn Cys


<210> SEQ ID NO 686
<211> LENGTH: 82
<212> TYPE: PRT
<213> ORGANISM: Corchorus olitorius

<400> SEQUENCE: 686

Met Ala Lys Ser Leu Ser Ser Phe Ala Thr Phe Leu Ala Leu Leu Cys
1               5                   10                  15

Leu Phe Phe Leu Leu Ser Thr Pro Asn Glu Met Lys Met Ala Glu Ala
            20                  25                  30

Lys Ile Cys Glu Lys Arg Ser Gln Thr Trp Ser Gly Trp Cys Gly Asn
        35                  40                  45

Ser Ser His Cys Asp Arg Gln Cys Lys Asn Trp Glu Asn Ala Arg His
    50                  55                  60

Gly Ser Cys His Ala Asp Gly Leu Gly Trp Ala Cys Phe Cys Tyr Phe
65                  70                  75                  80

Asn Cys


<210> SEQ ID NO 687
<211> LENGTH: 58
<212> TYPE: PRT
<213> ORGANISM: Corchorus olitorius

<400> SEQUENCE: 687

Met Glu Met Lys Met Ala Glu Gly Lys Ile Cys Glu Lys Arg Ser Gln
1               5                   10                  15

Thr Trp Ser Gly Trp Cys Gly Asn Ser Ser His Cys Asp Arg Gln Cys
            20                  25                  30

Lys Asn Trp Glu Asn Ala Arg His Gly Ser Cys His Ala Asp Gly Leu
        35                  40                  45
```

Gly Trp Ala Cys Phe Cys Tyr Phe Asn Cys
50 55

<210> SEQ ID NO 688
<211> LENGTH: 78
<212> TYPE: PRT
<213> ORGANISM: Camelina sativa

<400> SEQUENCE: 688

Met Ala Ser Ser Leu Lys Leu Met Leu Phe Leu Cys Leu Ser Ile Phe
1 5 10 15

Leu Ile Ala Ser Thr Glu Met Met Thr Val Glu Gly Arg Thr Cys Glu
20 25 30

Arg Arg Ser Lys Thr Trp Thr Gly Phe Cys Gly Asn Thr Arg Gly Cys
35 40 45

Asp Ser Gln Cys Arg Ser Trp Glu Gly Ala Ser His Gly Ala Cys His
50 55 60

Ala Gln Phe Pro Gly Phe Ala Cys Phe Cys Tyr Phe Asn Cys
65 70 75

<210> SEQ ID NO 689
<211> LENGTH: 84
<212> TYPE: PRT
<213> ORGANISM: Cucumis sativus

<400> SEQUENCE: 689

Met Ala Lys Val Val Gly Asn Ser Ala Lys Met Ile Val Ala Leu Leu
1 5 10 15

Phe Leu Leu Ala Leu Met Leu Ser Met Asn Glu Lys Gln Gly Val Val
20 25 30

Glu Ala Lys Val Cys Glu Arg Arg Ser Lys Thr Trp Ser Gly Trp Cys
35 40 45

Gly Asn Thr Lys His Cys Asp Arg Gln Cys Lys Asn Trp Glu Gly Ala
50 55 60

Thr His Gly Ala Cys His Ala Gln Phe Pro Gly Arg Ala Cys Phe Cys
65 70 75 80

Tyr Phe Asn Cys

<210> SEQ ID NO 690
<211> LENGTH: 80
<212> TYPE: PRT
<213> ORGANISM: Cynara cardunculus

<400> SEQUENCE: 690

Met Ile Asp Ala Phe Asn Tyr Lys Gln Phe Ser Thr Val Lys Gly Lys
1 5 10 15

Ile Cys Glu Lys Pro Ser Lys Thr Trp Phe Gly Lys Cys Gln Asp Thr
20 25 30

Thr Lys Cys Asp Lys Gln Cys Ile Glu Trp Glu Asp Ala Lys His Gly
35 40 45

Ala Cys His Glu Arg Glu Ser Lys Leu Met Cys Phe Cys Tyr Tyr Asn
50 55 60

Cys Gly Pro Pro Lys Asn Thr Pro Pro Gly Thr Pro Pro Ser Pro Pro
65 70 75 80

<210> SEQ ID NO 691
<211> LENGTH: 78
<212> TYPE: PRT
<213> ORGANISM: Capsella rubella

<400> SEQUENCE: 691

Met Ala Ser Ser Tyr Lys Leu Ile Leu Phe Leu Cys Leu Ser Ile Phe
1 5 10 15

Leu Ile Ala Ser Phe Glu Met Met Ala Val Glu Gly Arg Ile Cys Gln
20 25 30

Arg Arg Ser Lys Thr Trp Thr Gly Phe Cys Gly Asn Thr Arg Gly Cys
35 40 45

Asp Ser Gln Cys Lys Arg Trp Glu Arg Ala Ser His Gly Ala Cys His
50 55 60

Ala Gln Phe Pro Gly Phe Ala Cys Phe Cys Tyr Phe Asn Cys
65 70 75

<210> SEQ ID NO 692
<211> LENGTH: 56
<212> TYPE: PRT
<213> ORGANISM: Arabidopsis thaliana

<400> SEQUENCE: 692

Met Met Ala Val Glu Gly Arg Ile Cys Glu Arg Arg Ser Lys Thr Trp
1 5 10 15

Thr Gly Phe Cys Gly Asn Thr Arg Gly Cys Asp Ser Gln Cys Lys Arg
20 25 30

Trp Glu Arg Ala Ser His Gly Ala Cys His Ala Gln Phe Pro Gly Phe
35 40 45

Ala Cys Phe Cys Tyr Phe Asn Cys
50 55

<210> SEQ ID NO 693
<211> LENGTH: 78
<212> TYPE: PRT
<213> ORGANISM: Brassica napus

<400> SEQUENCE: 693

Met Ala Ser Ser Tyr Thr Arg Leu Leu Leu Leu Cys Leu Ser Ile Phe
1 5 10 15

Leu Ile Ala Ser Thr Glu Val Met Met Val Glu Gly Arg Val Cys Gln
20 25 30

Arg Arg Ser Lys Thr Trp Thr Gly Phe Cys Gly Asn Thr Arg Gly Cys
35 40 45

Asp Ser Gln Cys Lys Arg Trp Glu Arg Ala Ser His Gly Ala Cys His
50 55 60

Ala Gln Phe Pro Gly Phe Ala Cys Phe Cys Tyr Phe Asn Cys
65 70 75

<210> SEQ ID NO 694
<211> LENGTH: 78
<212> TYPE: PRT
<213> ORGANISM: Brassica rapa

<400> SEQUENCE: 694

Met Ala Ser Ser Tyr Ala Arg Leu Leu Leu Leu Cys Leu Ser Ile Phe
1 5 10 15

Leu Ile Ala Ser Thr Glu Val Met Met Val Glu Gly Arg Val Cys Gln
20 25 30

Arg Arg Ser Lys Thr Trp Thr Gly Phe Cys Gly Asn Thr Arg Gly Cys
35 40 45

Asp Ser Gln Cys Lys Arg Trp Glu Arg Ala Ser His Gly Ala Cys His

```
    50                  55                  60

Ala Gln Phe Pro Gly Phe Ala Cys Phe Cys Tyr Phe Asn Cys
65                  70                  75


<210> SEQ ID NO 695
<211> LENGTH: 78
<212> TYPE: PRT
<213> ORGANISM: Camelina sativa

<400> SEQUENCE: 695

Met Ala Ser Ser Leu Lys Leu Met Leu Phe Leu Cys Leu Ser Ile Phe
1               5                   10                  15

Leu Ile Ala Ser Thr Glu Met Met Thr Val Glu Gly Arg Thr Cys Glu
            20                  25                  30

Arg Arg Ser Lys Thr Trp Thr Gly Phe Cys Gly Asn Thr Arg Gly Cys
        35                  40                  45

Asp Ser Gln Cys Arg Arg Trp Glu His Ala Ser His Gly Ala Cys His
    50                  55                  60

Ala Gln Phe Pro Gly Phe Ala Cys Phe Cys Tyr Phe Asn Cys
65                  70                  75


<210> SEQ ID NO 696
<211> LENGTH: 77
<212> TYPE: PRT
<213> ORGANISM: Brassica napus

<400> SEQUENCE: 696

Met Ala Ser Tyr Thr Arg Leu Leu Leu Leu Cys Leu Ser Ile Phe Leu
1               5                   10                  15

Ile Ala Ser Thr Glu Val Met Met Val Glu Gly Arg Val Cys Gln Arg
            20                  25                  30

Arg Ser Lys Thr Trp Thr Gly Phe Cys Gly Asn Thr Arg Gly Cys Asp
        35                  40                  45

Ser Gln Cys Lys Arg Trp Glu Arg Ala Ser His Gly Ala Cys His Ala
    50                  55                  60

Gln Phe Pro Gly Phe Ala Cys Phe Cys Tyr Phe Asn Cys
65                  70                  75


<210> SEQ ID NO 697
<211> LENGTH: 56
<212> TYPE: PRT
<213> ORGANISM: Vitis vinifera

<400> SEQUENCE: 697

Met Val Met Leu Glu Ala Lys Val Cys Gln Arg Pro Ser Lys Thr Trp
1               5                   10                  15

Ser Gly Phe Cys Gly Ser Ser Lys Asn Cys Asp Arg Gln Cys Lys Asn
            20                  25                  30

Trp Glu Gly Ala Lys His Gly Ala Cys His Ala Lys Phe Pro Gly Val
        35                  40                  45

Ala Cys Phe Cys Tyr Phe Asn Cys
    50                  55


<210> SEQ ID NO 698
<211> LENGTH: 88
<212> TYPE: PRT
<213> ORGANISM: Brassica napus

<400> SEQUENCE: 698
```

```
Met Thr Lys Ser Phe Ile Leu Val Ala Leu Leu Cys Ile Cys Phe Ile
1               5                   10                  15

Leu Leu Ser Pro Thr Glu Met Arg Leu Thr Leu Asn Ala Cys Leu Lys
            20                  25                  30

Leu Ala Glu Ala Lys Ile Cys Glu Lys Tyr Ser Gln Thr Trp Ser Gly
        35                  40                  45

Arg Cys Thr Lys Thr Ser His Cys Asp Arg Gln Cys Ile Asn Trp Glu
    50                  55                  60

Asp Ala Arg His Gly Ala Cys His Gln Asp Lys His Gly Arg Ala Cys
65                  70                  75                  80

Phe Cys Tyr Phe Asn Cys Lys Lys
                85


<210> SEQ ID NO 699
<211> LENGTH: 78
<212> TYPE: PRT
<213> ORGANISM: Raphanus sativus

<400> SEQUENCE: 699

Met Ala Ser Ser Tyr Thr Val Phe Leu Leu Leu Cys Leu Ser Ile Phe
1               5                   10                  15

Leu Ile Ala Ser Thr Glu Val Met Met Val Glu Gly Arg Val Cys Gln
            20                  25                  30

Arg Arg Ser Lys Thr Trp Thr Gly Phe Cys Gly Asn Thr Arg Gly Cys
        35                  40                  45

Asp Ser Gln Cys Lys Arg Trp Glu His Ala Ser His Gly Ala Cys His
    50                  55                  60

Ala Gln Phe Pro Gly Phe Ala Cys Phe Cys Tyr Phe Asn Cys
65                  70                  75


<210> SEQ ID NO 700
<211> LENGTH: 78
<212> TYPE: PRT
<213> ORGANISM: Arabis alpine

<400> SEQUENCE: 700

Met Ala Ser Ser Tyr Thr Leu Leu Leu Phe Leu Cys Leu Ser Ile Phe
1               5                   10                  15

Leu Ile Val Ser Thr Glu Met Met Met Val Glu Gly Arg Ile Cys Glu
            20                  25                  30

Arg Arg Ser Lys Thr Trp Thr Gly Phe Cys Ala Asn Thr Arg Gly Cys
        35                  40                  45

Asp Ser Gln Cys Lys Arg Trp Glu Arg Ala Ser His Gly Ala Cys His
    50                  55                  60

Ala Gln Phe Pro Gly Val Ala Cys Phe Cys Tyr Phe Asn Cys
65                  70                  75


<210> SEQ ID NO 701
<211> LENGTH: 84
<212> TYPE: PRT
<213> ORGANISM: Cucumis melo

<400> SEQUENCE: 701

Met Ala Lys Val Val Gly Asn Ser Ala Lys Met Ile Val Ala Phe Leu
1               5                   10                  15

Phe Leu Leu Ala Leu Thr Leu Ser Met Asn Glu Lys Gln Gly Val Val
            20                  25                  30

Glu Ala Lys Val Cys Glu Arg Arg Ser Lys Thr Trp Ser Gly Trp Cys
```

35 40 45

Gly Asp Thr Lys His Cys Asp Arg Gln Cys Lys Asn Trp Glu Gly Ala
50 55 60

Lys His Gly Ala Cys His Ala Gln Phe Pro Gly Arg Ala Cys Phe Cys
65 70 75 80

Tyr Phe Asn Cys

<210> SEQ ID NO 702
<211> LENGTH: 82
<212> TYPE: PRT
<213> ORGANISM: Erythranthe guttate

<400> SEQUENCE: 702

Met Ala Ala Ser Leu Val Tyr Arg Leu Ser Ser Val Ile Leu Ile Val
1 5 10 15

Leu Leu Leu Phe Ile Met Leu Asn Asn Glu Val Met Val Val Glu Ser
20 25 30

Arg Leu Cys Glu Arg Arg Ser Lys Thr Trp Thr Gly Phe Cys Gly Ser
35 40 45

Ser Asn Asn Cys Asn Asn Gln Cys Arg Asn Trp Glu Arg Ala Ser His
50 55 60

Gly Ala Cys His Ala Gln Phe Pro Gly Phe Ala Cys Phe Cys Tyr Phe
65 70 75 80

Asn Cys

<210> SEQ ID NO 703
<211> LENGTH: 76
<212> TYPE: PRT
<213> ORGANISM: Sesamum indicum

<400> SEQUENCE: 703

Met Ala Lys Phe Gln Val Ser Ser Thr Ile Phe Phe Ala Leu Phe Phe
1 5 10 15

Cys Phe Leu Leu Leu Ala Ser Asn Glu Ala Lys Ile Cys Gln Arg Met
20 25 30

Ser Lys Thr Trp Ser Gly Val Cys Leu Asn Ser Gly Asn Cys Asp Arg
35 40 45

Gln Cys Arg Asn Trp Glu Arg Ala Gln His Gly Ala Cys His Arg Arg
50 55 60

Gly Leu Gly Phe Ala Cys Leu Cys Tyr Phe Lys Cys
65 70 75

<210> SEQ ID NO 704
<211> LENGTH: 110
<212> TYPE: PRT
<213> ORGANISM: Eclipta prostrata

<400> SEQUENCE: 704

Met Ala Lys Asn Ser Val Ala Phe Phe Ala Phe Leu Leu Ile Leu Phe
1 5 10 15

Val Leu Ala Ile Ser Glu Ile Gly Ser Val Lys Gly Glu Leu Cys Glu
20 25 30

Lys Ala Ser Gln Thr Trp Ser Gly Thr Cys Arg Ile Thr Ser His Cys
35 40 45

Asp Asn Gln Cys Lys Ser Trp Glu Gly Ala Ala His Gly Ala Cys His
50 55 60

Val Arg Gly Gly Lys His Met Cys Phe Cys Tyr Phe Ser His Cys Ala

```
65                  70                  75                  80

Lys Ala Glu Lys Leu Thr Gln Asp Lys Leu Lys Ala Gly His Leu Val
                85                  90                  95

Asn Glu Lys Ser Glu Ala Asp Gln Lys Val Pro Val Thr Pro
            100                 105                 110


<210> SEQ ID NO 705
<211> LENGTH: 105
<212> TYPE: PRT
<213> ORGANISM: Cynara cardunculus

<400> SEQUENCE: 705

Met Ala Lys Asn Thr Lys Val Ser Ala Phe Leu Phe Val Phe Leu Phe
1               5                   10                  15

Val Phe Phe Leu Val Val His Ser Val Thr Ala Phe Ala Ile Arg Phe
            20                  25                  30

Lys Cys Phe Asp Thr Asp Met Leu Leu Lys Val Ile Ala Asp Met Val
        35                  40                  45

Val Gly Met Lys Gly Ile Glu Lys Val Cys Arg Arg Arg Ser Lys Thr
    50                  55                  60

Trp Ser Gly Tyr Cys Gly Asp Ser Lys His Cys Asp Gln Gln Cys Arg
65                  70                  75                  80

Glu Trp Glu Gly Ala Glu His Gly Ala Cys His His Glu Gly Leu Gly
                85                  90                  95

Arg Ala Cys Phe Cys Tyr Phe Asn Cys
            100                 105


<210> SEQ ID NO 706
<211> LENGTH: 110
<212> TYPE: PRT
<213> ORGANISM: Ambrosia artemisiifolia

<400> SEQUENCE: 706

Met Ala Ala Gly Leu Leu Val Phe Val Leu Ala Ile Ser Glu Ile Ala
1               5                   10                  15

Ser Val Lys Gly Lys Leu Cys Glu Lys Pro Ser Val Thr Trp Ser Gly
            20                  25                  30

Lys Cys Lys Val Lys Gln Thr Asp Lys Cys Asp Lys Arg Cys Ile Glu
        35                  40                  45

Trp Glu Gly Ala Lys His Gly Ala Cys His Lys Arg Asp Ser Lys Ala
    50                  55                  60

Ser Cys Phe Cys Tyr Phe Asp Cys Asp Pro Thr Lys Asn Pro Gly Pro
65                  70                  75                  80

Pro Pro Gly Ala Pro Lys Gly Lys Ala Pro Ala Pro Ser Pro Pro Ser
                85                  90                  95

Gly Gly Gly Gly Glu Gly Gly Gly Glu Gly Gly Gly Glu Arg
            100                 105                 110


<210> SEQ ID NO 707
<211> LENGTH: 111
<212> TYPE: PRT
<213> ORGANISM: Ambrosia artemisiifolia

<400> SEQUENCE: 707

Met Ala Ala Gly Leu Leu Val Phe Val Leu Ala Ile Ser Glu Ile Ala
1               5                   10                  15

Ser Val Lys Gly Lys Leu Cys Glu Lys Pro Ser Leu Thr Trp Ser Gly
            20                  25                  30
```

```
Lys Cys Lys Val Lys Gln Thr Asp Lys Cys Asp Lys Arg Cys Ile Glu
        35                  40                  45

Trp Glu Gly Ala Lys His Gly Ala Cys His Lys Arg Asp Ser Lys Ala
    50                  55                  60

Thr Cys Phe Cys Tyr Phe Asp Cys Asp Pro Thr Lys Asn Pro Gly Pro
65                  70                  75                  80

Pro Pro Gly Ala Pro Lys Gly Lys Ala Pro Ala Pro Ser Pro Pro Ser
                85                  90                  95

Gly Gly Gly Ala Pro Pro Pro Ser Gly Gly Glu Gly Gly Glu Arg
            100                 105                 110


<210> SEQ ID NO 708
<211> LENGTH: 79
<212> TYPE: PRT
<213> ORGANISM: Jatropha curcas

<400> SEQUENCE: 708

Met Ala Lys Leu His Ser Ser Ala Leu Cys Phe Leu Ile Ile Phe Leu
1               5                   10                  15

Phe Leu Leu Val Ser Lys Glu Met Ala Val Thr Glu Ala Lys Leu Cys
            20                  25                  30

Gln Arg Arg Ser Lys Thr Trp Ser Gly Phe Cys Gly Asp Pro Gly Lys
        35                  40                  45

Cys Asn Arg Gln Cys Arg Asn Trp Glu Gly Ala Ser His Gly Ala Cys
    50                  55                  60

His Ala Gln Phe Pro Gly Phe Ala Cys Phe Cys Tyr Phe Lys Cys
65                  70                  75


<210> SEQ ID NO 709
<211> LENGTH: 79
<212> TYPE: PRT
<213> ORGANISM: Nelumbo nucifera

<400> SEQUENCE: 709

Met Ala Lys Ala Pro Lys Ser Val Ser Tyr Phe Ala Phe Phe Phe Ile
1               5                   10                  15

Leu Phe Leu Leu Ala Ser Ser Glu Ile Gln Lys Thr Lys Lys Leu Cys
            20                  25                  30

Glu Arg Arg Ser Lys Thr Trp Ser Gly Arg Cys Thr Lys Thr Gln Asn
        35                  40                  45

Cys Asp Lys Gln Cys Lys Asp Trp Glu Tyr Ala Lys His Gly Ala Cys
    50                  55                  60

His Gly Ser Trp Phe Asn Lys Lys Cys Tyr Cys Tyr Phe Asp Cys
65                  70                  75


<210> SEQ ID NO 710
<211> LENGTH: 82
<212> TYPE: PRT
<213> ORGANISM: Pyrus x bretschneideri

<400> SEQUENCE: 710

Met Ala Lys Leu Leu Ser Arg Leu Ser Ile Pro Leu Ile Val Phe Val
1               5                   10                  15

Phe Leu Leu Ile Leu Leu Ala Ser Thr Glu Val Ala Met Val Glu Ala
            20                  25                  30

Arg Ile Cys Gln Arg Arg Ser Lys Thr Trp Ser Gly Phe Cys Ala Asn
        35                  40                  45
```

Thr Gly Asn Cys Asn Arg Gln Cys Thr Asn Trp Glu Gly Ala Leu His
50 55 60

Gly Ala Cys His Ala Gln Phe Pro Gly Val Ala Cys Phe Cys Tyr Phe
65 70 75 80

Arg Cys

<210> SEQ ID NO 711
<211> LENGTH: 83
<212> TYPE: PRT
<213> ORGANISM: Ricinus communis

<400> SEQUENCE: 711

Met Ala Lys Leu His Phe Pro Thr Leu Leu Cys Leu Phe Ile Phe Leu
1 5 10 15

Phe Leu Leu Val Ser Thr Glu Met Gln Val Thr Gln Ala Lys Val Cys
20 25 30

Gln Arg Arg Ser Lys Thr Trp Ser Gly Phe Cys Gly Ser Thr Lys Asn
35 40 45

Cys Asp Arg Gln Cys Lys Asn Trp Glu Gly Ala Leu His Gly Ala Cys
50 55 60

His Ala Gln Phe Pro Gly Val Ala Cys Phe Cys Tyr Phe Lys Cys Gly
65 70 75 80

Gly Glu Arg

<210> SEQ ID NO 712
<211> LENGTH: 91
<212> TYPE: PRT
<213> ORGANISM: Ambrosia artemisiifolia

<400> SEQUENCE: 712

Lys Leu Cys Glu Lys Pro Ser Val Thr Trp Ser Gly Lys Cys Lys Val
1 5 10 15

Lys Gln Thr Asp Lys Cys Asp Lys Arg Cys Ile Glu Trp Glu Gly Ala
20 25 30

Lys His Gly Ala Cys His Lys Arg Asp Ser Lys Ala Ser Cys Phe Cys
35 40 45

Tyr Phe Asp Cys Asp Pro Thr Lys Asn Pro Gly Pro Pro Pro Gly Ala
50 55 60

Pro Lys Gly Lys Ala Pro Ala Pro Ser Pro Pro Ser Gly Gly Gly Ala
65 70 75 80

Pro Pro Pro Ser Gly Gly Glu Gly Gly Gly Asp
85 90

<210> SEQ ID NO 713
<211> LENGTH: 96
<212> TYPE: PRT
<213> ORGANISM: Ambrosia artemisiifolia

<400> SEQUENCE: 713

Lys Leu Cys Glu Lys Pro Ser Val Thr Trp Ser Gly Asn Lys Val Lys
1 5 10 15

Gln Thr Asp Lys Cys Asp Lys Arg Cys Ile Glu Trp Glu Gly Ala Lys
20 25 30

His Gly Ala Cys His Lys Arg Asp Ser Lys Ala Ser Cys Phe Cys Tyr
35 40 45

Phe Asp Cys Asp Pro Thr Lys Asn Pro Gly Pro Pro Pro Gly Ala Pro
50 55 60

Lys Gly Lys Ala Pro Ala Pro Ser Pro Pro Ser Gly Gly Gly Ala Pro
65 70 75 80

Pro Pro Ser Gly Gly Glu Gly Gly Gly Asp Gly Gly Gly Gly Arg Arg
85 90 95

<210> SEQ ID NO 714
<211> LENGTH: 82
<212> TYPE: PRT
<213> ORGANISM: Prunus mume

<400> SEQUENCE: 714

Met Ala Lys Leu Leu Ser His Leu Leu Phe Tyr Pro Ile Leu Phe Leu
1 5 10 15

Phe Leu Phe Ile Phe Leu Ala Ser Thr Glu Val Ala Ile Leu Glu Ala
20 25 30

Arg Ile Cys Gln Arg Arg Ser Lys Thr Trp Ser Gly Phe Cys Gly Asn
35 40 45

Thr Arg Asn Cys Asn Arg Gln Cys Arg Asn Trp Glu Gly Ala Leu Arg
50 55 60

Gly Ala Cys His Ala Gln Phe Pro Gly Phe Ala Cys Phe Cys Tyr Phe
65 70 75 80

Arg Cys

<210> SEQ ID NO 715
<211> LENGTH: 80
<212> TYPE: PRT
<213> ORGANISM: Corchorus olitorius

<400> SEQUENCE: 715

Met Ala Lys Thr Leu Gln Leu Phe Ala Leu Phe Phe Ile Val Ile Leu
1 5 10 15

Leu Ala Asn Gln Glu Ile Pro Val Ala Glu Ala Lys Leu Cys Gln Lys
20 25 30

Arg Ser Lys Thr Trp Thr Gly Ile Cys Ile Lys Thr Lys Asn Cys Asp
35 40 45

Asn Gln Cys Lys Lys Trp Glu Lys Ala Glu His Gly Ala Cys His Arg
50 55 60

Gln Gly Ile Gly Phe Ala Cys Phe Cys Tyr Phe Asn Gln Lys Lys Cys
65 70 75 80

<210> SEQ ID NO 716
<211> LENGTH: 81
<212> TYPE: PRT
<213> ORGANISM: Corchorus olitorius

<400> SEQUENCE: 716

Met Ala Lys Phe Val Ser Thr Val Ala Leu Leu Phe Ala Leu Phe Ile
1 5 10 15

Leu Leu Ala Ser Phe Asp Glu Gly Met Met Pro Met Ala Glu Ala Lys
20 25 30

Val Cys Ser Lys Arg Ser Lys Thr Trp Ser Gly Phe Cys Asn Ser Ser
35 40 45

Ala Asn Cys Asn Lys Gln Cys Arg Glu Trp Glu Asp Ala Lys His Gly
50 55 60

Ala Cys His Phe Glu Phe Pro Gly Phe Ala Cys Phe Cys Tyr Phe Asn
65 70 75 80

Cys

<210> SEQ ID NO 717
<211> LENGTH: 76
<212> TYPE: PRT
<213> ORGANISM: Solanum pennellii

<400> SEQUENCE: 717

Met Asn Ser Lys Val Ile Leu Ala Leu Leu Val Cys Phe Leu Leu Ile
1 5 10 15

Ala Ser Asn Glu Met Gln Gly Gly Glu Ala Lys Val Cys Gly Arg Arg
20 25 30

Ser Ser Thr Trp Ser Gly Leu Cys Leu Asn Thr Gly Asn Cys Asn Thr
35 40 45

Gln Cys Ile Lys Trp Glu His Ala Ser Ser Gly Ala Cys His Arg Asp
50 55 60

Gly Phe Gly Phe Ala Cys Phe Cys Tyr Phe Asn Cys
65 70 75

<210> SEQ ID NO 718
<211> LENGTH: 82
<212> TYPE: PRT
<213> ORGANISM: Fragaria vesca

<400> SEQUENCE: 718

Met Ala Lys Leu Leu Gly Tyr His Leu Val Tyr Pro Ile Leu Phe Leu
1 5 10 15

Phe Ile Phe Leu Leu Leu Ala Ser Thr Glu Met Gly Met Leu Glu Ala
20 25 30

Arg Ile Cys Gln Arg Arg Ser Lys Thr Trp Thr Gly Leu Cys Ala Asn
35 40 45

Thr Gly Asn Cys His Arg Gln Cys Arg Asn Trp Glu Gly Ala Gln Arg
50 55 60

Gly Ala Cys His Ala Gln Phe Pro Gly Phe Ala Cys Phe Cys Tyr Phe
65 70 75 80

Asn Cys

<210> SEQ ID NO 719
<211> LENGTH: 80
<212> TYPE: PRT
<213> ORGANISM: Corchorus capsularis

<400> SEQUENCE: 719

Met Ala Lys Phe Val Ser Val Ala Leu Leu Leu Ala Leu Phe Ile Leu
1 5 10 15

Val Ala Ser Phe Asp Glu Gly Met Val Pro Met Ala Glu Ala Lys Leu
20 25 30

Cys Ser Lys Arg Ser Lys Thr Trp Ser Gly Phe Cys Asn Ser Ser Ala
35 40 45

Asn Cys Asn Arg Gln Cys Arg Glu Trp Glu Asp Ala Lys His Gly Ala
50 55 60

Cys His Phe Glu Phe Pro Gly Phe Ala Cys Phe Cys Tyr Phe Asp Cys
65 70 75 80

<210> SEQ ID NO 720
<211> LENGTH: 56
<212> TYPE: PRT
<213> ORGANISM: Solanum tuberosum

<400> SEQUENCE: 720

-continued

```
Met Gln Gly Gly Glu Ala Arg Val Cys Glu Arg Arg Ser Ser Thr Trp
1               5                   10                  15

Ser Gly Pro Cys Phe Asp Thr Gly Asn Cys Asn Arg Gln Cys Ile Asn
            20                  25                  30

Trp Glu His Ala Ser Ser Gly Ala Cys His Arg Glu Gly Ile Gly Ser
        35                  40                  45

Ala Cys Phe Cys Tyr Phe Asn Cys
    50                  55


<210> SEQ ID NO 721
<211> LENGTH: 80
<212> TYPE: PRT
<213> ORGANISM: Dimocarpus longan

<400> SEQUENCE: 721

Met Ala Lys Thr Leu Lys Ser Val Gln Phe Phe Ala Leu Phe Phe Leu
1               5                   10                  15

Val Ile Leu Leu Ala Gly Ser Glu Met Thr Ala Val Glu Ala Leu Cys
            20                  25                  30

Ser Lys Arg Ser Lys Thr Trp Ser Gly Pro Cys Phe Ile Thr Ser Arg
        35                  40                  45

Cys Asp Arg Gln Cys Lys Arg Trp Glu Asn Ala Lys His Gly Ala Cys
    50                  55                  60

His Arg Ser Gly Trp Gly Phe Ala Cys Phe Cys Tyr Phe Asn Lys Cys
65                  70                  75                  80


<210> SEQ ID NO 722
<211> LENGTH: 80
<212> TYPE: PRT
<213> ORGANISM: Camelina sativa

<400> SEQUENCE: 722

Met Ala Lys Ala Ala Thr Ile Val Thr Leu Leu Phe Ala Ala Leu Val
1               5                   10                  15

Phe Phe Ala Ala Leu Glu Thr Pro Thr Met Val Glu Ala Gln Lys Leu
            20                  25                  30

Cys Glu Arg Pro Ser Gly Thr Trp Ser Gly Val Cys Gly Asn Ser Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80


<210> SEQ ID NO 723
<211> LENGTH: 80
<212> TYPE: PRT
<213> ORGANISM: Arabis alpine

<400> SEQUENCE: 723

Met Ala Lys Phe Ala Ser Ile Ile Ala Phe Leu Phe Ala Ala Leu Val
1               5                   10                  15

Leu Phe Ala Ser Phe Glu Ala Pro Thr Met Val Glu Ala Gln Lys Tyr
            20                  25                  30

Cys Glu Lys Pro Ser Gly Thr Trp Ser Gly Val Cys Gly Asn Ser Asn
        35                  40                  45

Ala Cys Asn Asn Gln Cys Ile Asn Leu Glu Gly Ala Arg His Gly Ser
    50                  55                  60

Cys Asn Tyr Val Phe Pro Tyr Tyr Arg Cys Ile Cys Tyr Phe Gln Cys
```

65 70 75 80

<210> SEQ ID NO 724
<211> LENGTH: 80
<212> TYPE: PRT
<213> ORGANISM: Theobroma cacao

<400> SEQUENCE: 724

Met Ala Met Ser Leu Lys Ser Val His Phe Phe Ala Leu Phe Phe Ile
1 5 10 15

Val Val Leu Leu Ala Asn Gln Glu Met Pro Val Ala Glu Ala Lys Leu
20 25 30

Cys Gln Lys Arg Ser Lys Thr Trp Thr Gly Pro Cys Ile Lys Thr Lys
35 40 45

Asn Cys Asp His Gln Cys Arg Lys Trp Glu Lys Ala Gln His Gly Ala
50 55 60

Cys His Trp Gln Trp Pro Gly Phe Ala Cys Phe Cys Tyr Val Asn Cys
65 70 75 80

<210> SEQ ID NO 725
<211> LENGTH: 80
<212> TYPE: PRT
<213> ORGANISM: Amborella trichopoda

<400> SEQUENCE: 725

Met Ala Lys Leu Val Ser Pro Lys Ala Phe Phe Val Phe Leu Phe Val
1 5 10 15

Phe Leu Leu Ile Ser Ala Ser Glu Phe Ser Gly Ser Glu Ala Lys Leu
20 25 30

Cys Gln Lys Arg Ser Arg Thr Trp Ser Gly Phe Cys Ala Asn Ser Asn
35 40 45

Asn Cys Ser Arg Gln Cys Lys Asn Leu Glu Gly Ala Arg Phe Gly Ala
50 55 60

Cys His Arg Gln Arg Ile Gly Leu Ala Cys Phe Cys Tyr Phe Asn Cys
65 70 75 80

<210> SEQ ID NO 726
<211> LENGTH: 80
<212> TYPE: PRT
<213> ORGANISM: Arabidopsis thaliana

<400> SEQUENCE: 726

Met Ala Lys Ser Ala Thr Ile Val Thr Leu Phe Phe Ala Ala Leu Val
1 5 10 15

Phe Phe Ala Ala Leu Glu Ala Pro Met Val Val Glu Ala Gln Lys Leu
20 25 30

Cys Glu Arg Pro Ser Gly Thr Trp Ser Gly Val Cys Gly Asn Ser Asn
35 40 45

Ala Cys Lys Asn Gln Cys Ile Asn Leu Glu Lys Ala Arg His Gly Ser
50 55 60

Cys Asn Tyr Val Phe Pro Ala His Lys Cys Ile Cys Tyr Phe Pro Cys
65 70 75 80

<210> SEQ ID NO 727
<211> LENGTH: 80
<212> TYPE: PRT
<213> ORGANISM: Arabis alpine

<400> SEQUENCE: 727

-continued

```
Met Ala Lys Phe Ala Ser Ile Ile Thr Leu Leu Phe Ala Ala Leu Val
1               5                   10                  15

Leu Phe Ala Ser Leu Glu Ala Pro Thr Met Val Glu Ala Gln Lys Leu
            20                  25                  30

Cys Gln Arg Pro Ser Gly Thr Trp Ser Gly Val Cys Gly Asn Asn Gly
        35                  40                  45

Ala Cys Lys Asn Gln Cys Ile Asn Leu Glu Lys Ala Arg His Gly Ser
    50                  55                  60

Cys Asn Tyr Val Phe Pro Tyr His Arg Cys Ile Cys Tyr Phe Pro Cys
65                  70                  75                  80


<210> SEQ ID NO 728
<211> LENGTH: 80
<212> TYPE: PRT
<213> ORGANISM: Brassica juncea

<400> SEQUENCE: 728

Met Ala Lys Val Ala Ser Ile Ile Ala Leu Leu Phe Ala Ala Leu Val
1               5                   10                  15

Leu Phe Ala Ala Phe Glu Ala Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80


<210> SEQ ID NO 729
<211> LENGTH: 80
<212> TYPE: PRT
<213> ORGANISM: Brassica oleracea

<400> SEQUENCE: 729

Met Ala Lys Phe Ala Ser Ile Ile Ala Leu Leu Phe Ala Ala Leu Val
1               5                   10                  15

Leu Phe Ala Ala Leu Glu Ala Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80


<210> SEQ ID NO 730
<211> LENGTH: 80
<212> TYPE: PRT
<213> ORGANISM: Camelina sativa

<400> SEQUENCE: 730

Met Ala Lys Pro Ala Thr Ile Val Thr Leu Leu Phe Ala Ala Leu Val
1               5                   10                  15

Phe Phe Ala Ala Leu Glu Thr Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
```

```
    50                  55                  60

Cys Asn Tyr Val Phe Pro Ala His Lys Cys Ile Cys Tyr Phe Pro Cys
65                  70                  75                  80
```

<210> SEQ ID NO 731
<211> LENGTH: 80
<212> TYPE: PRT
<213> ORGANISM: Camelina sativa

<400> SEQUENCE: 731

```
Met Ala Lys Ser Ala Thr Ile Val Thr Leu Leu Phe Ala Ala Leu Val
1               5                   10                  15

Phe Phe Ala Ala Leu Glu Thr Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80
```

<210> SEQ ID NO 732
<211> LENGTH: 80
<212> TYPE: PRT
<213> ORGANISM: Brassica napus

<400> SEQUENCE: 732

```
Met Ala Lys Phe Ala Ser Ile Ile Ala Pro Leu Phe Ala Val Leu Val
1               5                   10                  15

Leu Phe Ala Ala Phe Glu Ala Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80
```

<210> SEQ ID NO 733
<211> LENGTH: 80
<212> TYPE: PRT
<213> ORGANISM: Eutrema salsugineum

<400> SEQUENCE: 733

```
Met Ala Lys Phe Ala Ser Ile Ile Thr Leu Leu Phe Ala Ala Leu Val
1               5                   10                  15

Leu Phe Ala Val Phe Glu Gly Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80
```

<210> SEQ ID NO 734
<211> LENGTH: 80
<212> TYPE: PRT
<213> ORGANISM: Raphanus sativus

<400> SEQUENCE: 734

Met Ala Lys Phe Ala Ser Ile Ile Ala Leu Leu Phe Ala Ala Leu Val
1 5 10 15

Leu Phe Ala Ala Phe Glu Ala Pro Thr Met Val Glu Ala Gln Lys Leu
20 25 30

Cys Glu Arg Pro Ser Gly Thr Trp Ser Gly Val Cys Gly Asn Asn Asn
35 40 45

Ala Cys Lys Asn Gln Cys Ile Asn Leu Glu Lys Ala Arg His Gly Ser
50 55 60

Cys Asn Tyr Val Phe Pro Ala His Lys Cys Ile Cys Tyr Phe Pro Cys
65 70 75 80

<210> SEQ ID NO 735
<211> LENGTH: 80
<212> TYPE: PRT
<213> ORGANISM: Raphanus sativus

<400> SEQUENCE: 735

Met Ala Lys Phe Ala Ser Ile Val Ser Leu Leu Phe Ala Ala Leu Val
1 5 10 15

Leu Phe Thr Ala Phe Glu Ala Pro Ala Met Val Glu Ala Gln Lys Leu
20 25 30

Cys Glu Arg Pro Ser Gly Thr Trp Ser Gly Val Cys Gly Asn Asn Asn
35 40 45

Ala Cys Lys Asn Gln Cys Ile Asn Leu Glu Lys Ala Arg His Gly Ser
50 55 60

Cys Asn Tyr Val Phe Pro Ala His Lys Cys Ile Cys Tyr Phe Pro Cys
65 70 75 80

<210> SEQ ID NO 736
<211> LENGTH: 76
<212> TYPE: PRT
<213> ORGANISM: Raphanus sativus

<400> SEQUENCE: 736

Met Asn Thr Lys Val Ile Leu Ala Leu Leu Phe Cys Phe Leu Leu Val
1 5 10 15

Ala Ser Asn Glu Met Gln Val Gly Glu Ala Lys Val Cys Gln Arg Arg
20 25 30

Ser Lys Thr Trp Ser Gly Pro Cys Ile Asn Thr Gly Asn Cys Ser Arg
35 40 45

Gln Cys Lys Gln Gln Glu Asp Ala Arg Phe Gly Ala Cys His Arg Ser
50 55 60

Gly Phe Gly Phe Ala Cys Phe Cys Tyr Phe Lys Cys
65 70 75

<210> SEQ ID NO 737
<211> LENGTH: 80
<212> TYPE: PRT
<213> ORGANISM: Brassica rapa

<400> SEQUENCE: 737

Met Ala Lys Phe Ala Ser Ile Ile Ala Pro Leu Phe Ala Ala Leu Val
1 5 10 15

Leu Phe Ala Ala Phe Glu Ala Pro Thr Met Val Glu Ala Gln Lys Leu
20 25 30

Cys Glu Arg Pro Ser Gly Thr Trp Ser Gly Val Cys Gly Asn Asn Asn

```
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80


<210> SEQ ID NO 738
<211> LENGTH: 76
<212> TYPE: PRT
<213> ORGANISM: Solanum pennellii

<400> SEQUENCE: 738

Met Asn Thr Lys Leu Ile Leu Ala Leu Met Phe Cys Phe Leu Leu Ile
1               5                   10                  15

Ala Ser Asn Glu Met Gln Val Gly Glu Ala Lys Val Cys Gln Arg Arg
            20                  25                  30

Ser Lys Thr Trp Ser Gly Pro Cys Ile Asn Thr Gly Asn Cys Ser Arg
        35                  40                  45

Gln Cys Lys Gln Gln Glu Asp Ala Arg Phe Gly Ala Cys His Arg Ser
    50                  55                  60

Gly Phe Gly Phe Ala Cys Phe Cys Tyr Phe Lys Cys
65                  70                  75


<210> SEQ ID NO 739
<211> LENGTH: 78
<212> TYPE: PRT
<213> ORGANISM: Citrus clementina

<400> SEQUENCE: 739

Met Ala Lys Phe Thr Thr Thr Phe Ala Leu Leu Phe Ala Phe Phe Ile
1               5                   10                  15

Leu Phe Ala Ala Phe Asp Val Pro Met Ala Glu Ala Lys Val Cys Gln
            20                  25                  30

Arg Arg Ser Lys Thr Trp Ser Gly Leu Cys Leu Asn Thr Gly Asn Cys
        35                  40                  45

Ser Arg Gln Cys Lys Gln Gln Glu Asp Ala Arg Phe Gly Ala Cys His
    50                  55                  60

Arg Gln Gly Ile Gly Phe Ala Cys Phe Cys Tyr Phe Lys Cys
65                  70                  75


<210> SEQ ID NO 740
<211> LENGTH: 80
<212> TYPE: PRT
<213> ORGANISM: Brassica rapa

<400> SEQUENCE: 740

Met Ala Lys Phe Thr Ser Ile Ile Val Leu Leu Phe Ala Ala Leu Val
1               5                   10                  15

Leu Phe Ala Gly Phe Glu Ala Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Arg Leu Glu Lys Ala Arg His Gly Ser
    50                  55                  60

Cys Asn Tyr Val Phe Pro Ala Arg Lys Cys Ile Cys Tyr Phe Pro Cys
65                  70                  75                  80


<210> SEQ ID NO 741
```

<211> LENGTH: 78
<212> TYPE: PRT
<213> ORGANISM: Eutrema salsugineum

<400> SEQUENCE: 741

Met Ala Lys Phe Ala Ser Ile Ile Thr Leu Leu Phe Ala Ala Leu Val
1               5                   10                  15

Leu Phe Ala Thr Phe Ala Pro Thr Met Val Glu Ala Lys Leu Cys Glu
            20                  25                  30

Arg Pro Ser Gly Thr Trp Ser Gly Val Cys Gly Asn Asn Asn Ala Cys
        35                  40                  45

Lys Ser Gln Cys Gln Arg Leu Glu Gly Ala Arg His Gly Ser Cys Asn
    50                  55                  60

Tyr Val Phe Pro Ala His Lys Cys Ile Cys Tyr Phe Pro Cys
65                  70                  75

<210> SEQ ID NO 742
<211> LENGTH: 79
<212> TYPE: PRT
<213> ORGANISM: Eutrema salsugineum

<400> SEQUENCE: 742

Met Ala Lys Phe Ala Ser Ile Ile Thr Leu Leu Phe Ala Ala Leu Val
1               5                   10                  15

Leu Phe Ala Thr Phe Glu Ala Pro Thr Met Val Glu Ala Lys Leu Cys
            20                  25                  30

Glu Arg Pro Ser Gly Thr Trp Ser Gly Val Cys Gly Asn Asn Asn Ala
        35                  40                  45

Cys Lys Ser Gln Cys Gln Arg Leu Glu Gly Ala Arg His Gly Ser Cys
    50                  55                  60

Asn Tyr Val Phe Pro Ala His Lys Cys Ile Cys Tyr Phe Pro Cys
65                  70                  75

<210> SEQ ID NO 743
<211> LENGTH: 80
<212> TYPE: PRT
<213> ORGANISM: Heliophila coronopifolia

<400> SEQUENCE: 743

Met Ala Lys Phe Ala Ser Ile Ile Ala Phe Phe Phe Ala Ala Leu Val
1               5                   10                  15

Leu Phe Ala Ala Phe Glu Ala Pro Thr Ile Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Arg Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80

<210> SEQ ID NO 744
<211> LENGTH: 80
<212> TYPE: PRT
<213> ORGANISM: Brassica oleracea

<400> SEQUENCE: 744

Met Ala Lys Val Ala Ser Ile Val Ala Leu Leu Phe Pro Ala Leu Val
1               5                   10                  15

Ile Phe Ala Ala Phe Glu Ala Pro Thr Met Val Glu Ala Gln Lys Leu

```
            20                  25                  30

Cys Glu Arg Pro Ser Gly Thr Trp Ser Gly Val Cys Gly Asn Asn Asn
        35                  40                  45

Ala Cys Lys Asn Gln Cys Ile Arg Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80


<210> SEQ ID NO 745
<211> LENGTH: 76
<212> TYPE: PRT
<213> ORGANISM: Cicer arietinum

<400> SEQUENCE: 745

Met Ser Lys Phe Tyr Thr Val Phe Met Phe Leu Cys Leu Ala Leu Leu
1               5                   10                  15

Leu Ile Ser Ser Trp Glu Val Glu Ala Lys Leu Cys Gln Arg Arg Ser
            20                  25                  30

Lys Thr Trp Ser Gly Pro Cys Ile Ile Thr Gly Asn Cys Lys Asn Gln
        35                  40                  45

Cys Lys Asn Val Glu His Ala Thr Phe Gly Ala Cys His Arg Gln Gly
    50                  55                  60

Phe Gly Phe Ala Cys Phe Cys Tyr Phe Asn Cys His
65                  70                  75


<210> SEQ ID NO 746
<211> LENGTH: 82
<212> TYPE: PRT
<213> ORGANISM: Citrus clementina

<400> SEQUENCE: 746

Met Ala Lys Ser Val Ala Ser Ile Thr Thr Ala Phe Ala Leu Ile Phe
1               5                   10                  15

Ala Phe Phe Ile Leu Phe Ala Ser Phe Gly Val Pro Met Ala Glu Ala
            20                  25                  30

Lys Val Cys Gln Arg Arg Ser Lys Thr Trp Ser Gly Pro Cys Leu Asn
        35                  40                  45

Thr Gly Lys Cys Ser Arg Gln Cys Lys Gln Gln Glu Tyr Ala Arg Tyr
    50                  55                  60

Gly Ala Cys Tyr Arg Gln Gly Ala Gly Tyr Ala Cys Tyr Cys Tyr Phe
65                  70                  75                  80

Asn Cys


<210> SEQ ID NO 747
<211> LENGTH: 82
<212> TYPE: PRT
<213> ORGANISM: Citrus sinensis

<400> SEQUENCE: 747

Met Ala Lys Ser Val Ala Ser Ile Thr Thr Ala Phe Ala Leu Ile Phe
1               5                   10                  15

Ala Phe Phe Ile Leu Phe Ala Ser Phe Glu Val Pro Met Ala Glu Ala
            20                  25                  30

Lys Val Cys Gln Arg Arg Ser Lys Thr Trp Ser Gly Pro Cys Leu Asn
        35                  40                  45

Thr Gly Lys Cys Ser Arg His Cys Lys Gln Gln Glu Asp Ala Arg Tyr
    50                  55                  60
```

Gly Ala Cys Tyr Arg Gln Gly Thr Gly Tyr Ala Cys Phe Cys Tyr Phe
65 70 75 80

Glu Cys

<210> SEQ ID NO 748
<211> LENGTH: 78
<212> TYPE: PRT
<213> ORGANISM: Citrus sinensis

<400> SEQUENCE: 748

Met Ala Lys Phe Thr Thr Thr Phe Ala Leu Leu Phe Ala Phe Phe Ile
1 5 10 15

Leu Phe Ala Ala Phe Asp Val Pro Met Ala Glu Ala Lys Val Cys Gln
20 25 30

Leu Arg Ser Lys Thr Trp Ser Gly Leu Cys Leu Asn Thr Gly Asn Cys
35 40 45

Ser Arg Gln Cys Lys Gln Gln Glu Asp Ala Arg Phe Gly Ala Cys His
50 55 60

Arg Gln Gly Ile Gly Phe Ala Cys Phe Cys Tyr Phe Lys Cys
65 70 75

<210> SEQ ID NO 749
<211> LENGTH: 76
<212> TYPE: PRT
<213> ORGANISM: Citrus sinensis

<400> SEQUENCE: 749

Met Glu Arg Ser Val Arg Leu Phe Ser Thr Val Leu Leu Val Leu Leu
1 5 10 15

Leu Leu Ala Ser Glu Met Gly Leu Arg Ala Ala Glu Ala Arg Ile Cys
20 25 30

Glu Ser Gln Ser His Arg Phe Lys Gly Pro Cys Val Ser Lys Ser Asn
35 40 45

Cys Ala Ala Val Cys Gln Thr Glu Gly Phe His Gly Gly His Cys Arg
50 55 60

Gly Phe Arg Arg Arg Cys Phe Cys Thr Lys Arg Cys
65 70 75

<210> SEQ ID NO 750
<211> LENGTH: 106
<212> TYPE: PRT
<213> ORGANISM: Artificial Sequence
<220> FEATURE:
<223> OTHER INFORMATION: Synthetic construct

<400> SEQUENCE: 750

Met Ser Thr Ala Thr Phe Val Asp Ile Ile Ile Ala Ile Leu Leu Pro
1 5 10 15

Pro Leu Gly Val Phe Leu Arg Phe Gly Cys Gly Val Glu Phe Trp Ile
20 25 30

Cys Leu Val Leu Thr Leu Leu Gly Tyr Ile Pro Gly Ile Ile Tyr Ala
35 40 45

Ile Tyr Val Leu Thr Lys Arg Thr Cys Glu Ser Gln Ser His Arg Phe
50 55 60

Lys Gly Pro Cys Ser Arg Asp Ser Asn Cys Ala Thr Val Cys Leu Thr
65 70 75 80

Glu Gly Phe Ser Gly Gly Asp Cys Arg Gly Phe Arg Arg Arg Cys Arg
85 90 95

Cys Thr Arg Pro Cys Val Phe Asp Glu Lys
100 105

<210> SEQ ID NO 751
<211> LENGTH: 28
<212> TYPE: PRT
<213> ORGANISM: Pseudomonas syringae

<400> SEQUENCE: 751

Glu Ser Thr Asn Ile Leu Gln Arg Met Arg Glu Leu Ala Val Gln Ser
1 5 10 15

Arg Asn Asp Ser Asn Ser Ala Thr Asp Arg Glu Ala
20 25

<210> SEQ ID NO 752
<211> LENGTH: 15
<212> TYPE: PRT
<213> ORGANISM: Bacillus thuringiensis

<400> SEQUENCE: 752

Arg Ile Asn Ser Ala Lys Asp Asp Ala Ala Gly Leu Ala Ile Ala
1 5 10 15

<210> SEQ ID NO 753
<211> LENGTH: 22
<212> TYPE: PRT
<213> ORGANISM: Bacillus thuringiensis

<400> SEQUENCE: 753

Asp Arg Leu Ser Ser Gly Lys Arg Ile Asn Ser Ala Ser Asp Pro Ala
1 5 10 15

Ala Gly Leu Ala Ile Ala
20

<210> SEQ ID NO 754
<211> LENGTH: 8
<212> TYPE: PRT
<213> ORGANISM: Bacillus thuringiensis

<400> SEQUENCE: 754

Arg Ile Asn Ser Ala Ser Asp Asp
1 5

<210> SEQ ID NO 755
<211> LENGTH: 8
<212> TYPE: PRT
<213> ORGANISM: Bacillus thuringiensis

<400> SEQUENCE: 755

Arg Ile Asn Asn Ala Ser Asp Asp
1 5

<210> SEQ ID NO 756
<211> LENGTH: 8
<212> TYPE: PRT
<213> ORGANISM: Bacillus manliponensis

<400> SEQUENCE: 756

Gln Ile Asn Ser Ala Ser Asp Asp
1 5

<210> SEQ ID NO 757
<211> LENGTH: 8
<212> TYPE: PRT

<213> ORGANISM: Lysinibacillus sp.

<400> SEQUENCE: 757

Arg Ile Asn Ser Ala Ala Asp Asp
1               5

<210> SEQ ID NO 758
<211> LENGTH: 8
<212> TYPE: PRT
<213> ORGANISM: Paenibacillus sp.

<400> SEQUENCE: 758

Arg Ile Asn Gly Ala Ser Asp Asp
1               5

<210> SEQ ID NO 759
<211> LENGTH: 8
<212> TYPE: PRT
<213> ORGANISM: Aneurinibacillus sp.

<400> SEQUENCE: 759

Arg Ile Asn Arg Ala Ser Asp Asp
1               5

<210> SEQ ID NO 760
<211> LENGTH: 8
<212> TYPE: PRT
<213> ORGANISM: Escherichia coli

<400> SEQUENCE: 760

Arg Ile Asn Ser Ala Lys Asp Asp
1               5

<210> SEQ ID NO 761
<211> LENGTH: 8
<212> TYPE: PRT
<213> ORGANISM: Burkholderia ubonensis

<400> SEQUENCE: 761

Arg Ile Asn Thr Ala Ala Asp Asp
1               5

<210> SEQ ID NO 762
<211> LENGTH: 8
<212> TYPE: PRT
<213> ORGANISM: Pseudomonas syringae

<400> SEQUENCE: 762

Lys Ile Asn Ser Ala Lys Asp Asp
1               5

<210> SEQ ID NO 763
<211> LENGTH: 8
<212> TYPE: PRT
<213> ORGANISM: Lysinibacillus spp.

<400> SEQUENCE: 763

Arg Ile Asn Arg Ala Gly Asp Asp
1               5

<210> SEQ ID NO 764
<211> LENGTH: 8
<212> TYPE: PRT
<213> ORGANISM: Lysinibacillus spp.

<400> SEQUENCE: 764

Lys Ile Asn Arg Ala Ser Asp Asp
1 5

<210> SEQ ID NO 765
<211> LENGTH: 8
<212> TYPE: PRT
<213> ORGANISM: Lysinibacillus xylanilyticus

<400> SEQUENCE: 765

Lys Ile Asn Arg Ala Gly Asp Asp
1 5

<210> SEQ ID NO 766
<211> LENGTH: 8
<212> TYPE: PRT
<213> ORGANISM: Bacillus thuringiensis
<220> FEATURE:
<221> NAME/KEY: MISC_FEATURE
<222> LOCATION: (1)..(1)
<223> OTHER INFORMATION: Xaa = Arg or Gln or Lys
<220> FEATURE:
<221> NAME/KEY: MISC_FEATURE
<222> LOCATION: (4)..(4)
<223> OTHER INFORMATION: Xaa = Ser or Asn or Gly or Arg or Thr
<220> FEATURE:
<221> NAME/KEY: MISC_FEATURE
<222> LOCATION: (6)..(6)
<223> OTHER INFORMATION: Xaa = Ser or Ala or Lys or Gly

<400> SEQUENCE: 766

Xaa Ile Asn Xaa Ala Xaa Asp Asp
1 5

<210> SEQ ID NO 767
<211> LENGTH: 15
<212> TYPE: PRT
<213> ORGANISM: Bacillus thuringiensis

<400> SEQUENCE: 767

Ala Ile Ala Leu Gly Ala Ala Asp Asp Lys Ala Ser Asn Ile Arg
1 5 10 15

<210> SEQ ID NO 768
<211> LENGTH: 28
<212> TYPE: PRT
<213> ORGANISM: Pseudomonas syringae

<400> SEQUENCE: 768

Ala Glu Arg Asp Thr Ala Ser Asn Ser Asp Asn Arg Ser Gln Val Ala
1 5 10 15

Leu Glu Arg Met Arg Gln Leu Ile Asn Thr Ser Glu
20 25

<210> SEQ ID NO 769
<211> LENGTH: 31
<212> TYPE: PRT
<213> ORGANISM: Bacillus amyloliquefaciens

<400> SEQUENCE: 769

Met Ile Gln Lys Arg Lys Arg Thr Val Ser Phe Arg Leu Val Leu Met
1 5 10 15

Cys Thr Leu Leu Phe Val Ser Leu Pro Ile Thr Lys Thr Ser Ala
20 25 30

<210> SEQ ID NO 770
<211> LENGTH: 218
<212> TYPE: PRT
<213> ORGANISM: Schistosoma japonicum

<400> SEQUENCE: 770

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys
    210                 215

<210> SEQ ID NO 771
<211> LENGTH: 7
<212> TYPE: PRT
<213> ORGANISM: Artificial Sequence
<220> FEATURE:
<223> OTHER INFORMATION: Synthetic construct

<400> SEQUENCE: 771

Gly Gly Gly Gly Gly Gly Ser
1               5

<210> SEQ ID NO 772
<211> LENGTH: 5
<212> TYPE: PRT
<213> ORGANISM: Artificial Sequence
<220> FEATURE:
<223> OTHER INFORMATION: Synthetic construct

<400> SEQUENCE: 772

Asp Asp Asp Asp Lys
1               5

<210> SEQ ID NO 773
<211> LENGTH: 20
<212> TYPE: DNA

-continued

```
<213> ORGANISM: Artificial Sequence
<220> FEATURE:
<223> OTHER INFORMATION: Synthetic construct (primer)

<400> SEQUENCE: 773

tcgagcgcgt atgcaatacg                                        20


<210> SEQ ID NO 774
<211> LENGTH: 24
<212> TYPE: DNA
<213> ORGANISM: Artificial Sequence
<220> FEATURE:
<223> OTHER INFORMATION: Synthetic construct (primer)

<400> SEQUENCE: 774

gcgttatccc gtagaaaaag gtag                                   24


<210> SEQ ID NO 775
<211> LENGTH: 18
<212> TYPE: PRT
<213> ORGANISM: Artificial Sequence
<220> FEATURE:
<223> OTHER INFORMATION: Synthetic construct (primer)

<400> SEQUENCE: 775

Ala Gly Ala Cys Gly Gly Phe Thr Gly Ala Gly Thr Ala Ala Cys Gly
1               5                   10                  15

Cys Gly
```